(12) United States Patent
Clark et al.

(10) Patent No.: US 11,352,672 B2
(45) Date of Patent: Jun. 7, 2022

(54) METHODS FOR DIAGNOSIS, PROGNOSIS AND MONITORING OF BREAST CANCER AND REAGENTS THEREFOR

(71) Applicant: GARVAN INSTITUTE OF MEDICAL RESEARCH, New South Wales (AU)

(72) Inventors: Susan Clark, New South Wales (AU); Elena Zotenko, New South Wales (AU); Clare Stirzaker, New South Wales (AU); Glenn Francis, Queensland (AU)

(73) Assignee: Garvan Institute of Medical Research, New South Wales (AU)

( * ) Notice: Subject to any disclaimer, the term of this patent is extended or adjusted under 35 U.S.C. 154(b) by 1029 days.

(21) Appl. No.: 15/510,956

(22) PCT Filed: Sep. 15, 2015

(86) PCT No.: PCT/AU2015/050549
§ 371 (c)(1),
(2) Date: Mar. 13, 2017

(87) PCT Pub. No.: WO2016/041010
PCT Pub. Date: Mar. 24, 2016

(65) Prior Publication Data
US 2017/0283886 A1 Oct. 5, 2017

(30) Foreign Application Priority Data
Sep. 15, 2014 (AU) .................. 2014903680

(51) Int. Cl.
*C12Q 1/6886* (2018.01)
(52) U.S. Cl.
CPC ..... *C12Q 1/6886* (2013.01); *C12Q 2600/106* (2013.01); *C12Q 2600/118* (2013.01); *C12Q 2600/154* (2013.01)

(58) Field of Classification Search
CPC .................................................. C12Q 1/6886
USPC ........................................................... 702/19
See application file for complete search history.

(56) References Cited

FOREIGN PATENT DOCUMENTS

| WO | 2001006005 A2 | 1/2001 |
|---|---|---|
| WO | 2012098215 A1 | 7/2012 |
| WO | 2012106559 A2 | 8/2012 |
| WO | 2013012781 A1 | 1/2013 |

OTHER PUBLICATIONS

Branham, M., et al., 'Methylation profile f triple-negative breast carcinomas', Oncoenesis, 2012, vol. 1, e17.
Kowalski, J., et al., 'Methylation signatures specific to triple negative breast cancer subtypes', Cancer Research 2013, vol. 73, No. 13, Supplement 1, Abstract No. B40, Proceedings of the AACR Special Conference on Chromatin and Epigenetics in Cancer, Jun. 19-22, 2013, Atlanta, Georgia, USA. Abstract.
Sharma, P., et al., 'The prognostic value of BRCA1 promoter methylation in early stage triple negative breast cancer', Journal of Cancer Therapeutics & Research, Mar. 19, 2014, vol. 3, pp. 1-11.
Stirzaker, C., et al., 'Methylome sequencing in triple-negative breast cancer reveals distinct methylation clusters with prognostic value', Nature Communications, Feb. 2, 2015, vol. 6, article No. 5899.

*Primary Examiner* — Jerry Lin
(74) *Attorney, Agent, or Firm* — Riverside Law LLP

(57) ABSTRACT

The present disclosure provides methods and reagents for the diagnosis, prognosis or the monitoring of breast cancer, including various subtypes of breast cancer including, for example, estrogen receptor (ER) negative breast cancer, ER positive breast cancer, triple negative breast cancer (TNBC) and other subtypes of breast cancer.

23 Claims, 161 Drawing Sheets
Specification includes a Sequence Listing.

(A)

| | MBDCap-Seq | MBDCap-Seq (≥3 CpGs) | HM450K | HM450K (≥3 CpGs) |
|---|---|---|---|---|
| CpG sites | 5,012,633 (18%) | NA | 482,369 (2%) | NA |
| CpG islands | 25,806 (91%) | 25,772 (91%) | 26,655 (94%) | 22,968 (81%) |
| CpG island shores | 42,936 (84%) | 39,102 (77%) | 45,729 (90%) | 14,511 (28%) |
| RefSeq promoters | 28,840 (72%) | 28,528 (71%) | 36,394 (91%) | 33,200 (83%) |
| RefSeq exons | 119,017 (31%) | 110,756 (28%) | 81,103 (21%) | 18,474 (5%) |
| RefSeq introns | 133,353 (38%) | 111,534 (32%) | 93,921 (27%) | 34,583 (10%) |
| ChromHMM promoters | 28,184 (66%) | 27,422 (64%) | 28,300 (66%) | 18,267 (43%) |
| ChromHMM enhancers | 39,693 (14%) | 35,817 (12%) | 43,203 (15%) | 7,137 (2%) |
| ChromHMM insulators | 4,154 (12%) | 3,734 (11%) | 3,450 (10%) | 336 (1%) |

(B)

(A)

(B)

(C)

(D)

(E)

(A)

(B)

(A)(i)

(A)(ii)

(B)(i)

(B)(ii)

(C)(i)

(C)(ii)

(D)(i)

(D)(ii)

(E)(i)

(E)(ii)

(F)(i)

(F)(ii)

(G)(i)

(G)(ii)

(H)(i)

(H)(ii)

(I)(i)

(I)(ii)

(J)(i)

(J)(ii)

(K)(i)

(K)(ii)

(L)(i)

(L)(ii)

(M)(i)

(M)(ii)

(N)(i)

(N)(ii)

(O)(i)

(O)(ii)

(P)(i)

(P)(ii)

(Q)(i)

(Q)(ii)

(R)(i)

(R)(ii)

(A)

(B)

(C)

(D)

(E)

(F)

(G)

(H)

(I)

(J)

(K)

(L)

(M)

(N)

(O)

A)   B)

A)   B)

SEQUENCE LISTING

<160> NUMBER OF SEQ ID NOS: 50

<210> SEQ ID NO 1
<211> LENGTH: 36
<212> TYPE: DNA
<213> ORGANISM: Artificial sequence
<220> FEATURE:
<223> OTHER INFORMATION: GHSRseq_01F

<400> SEQUENCE: 1
aggaagagag gtttttggt gattattatt ttggtt         36

<210> SEQ ID NO 2
<211> LENGTH: 55
<212> TYPE: DNA
<213> ORGANISM: Artificial sequence
<220> FEATURE:
<223> OTHER INFORMATION: GHSRseq_01R

<400> SEQUENCE: 2
cagtaatacg actcactata gggagaaggc tttcctctac atacccctaa acctc         55

<210> SEQ ID NO 3
<211> LENGTH: 40
<212> TYPE: DNA
<213> ORGANISM: Artificial sequence -continued
<220> FEATURE:
<223> OTHER INFORMATION: GHSRseq_02F

<400> SEQUENCE: 3
aggaagagag gatattatta gtatggtgag taggttgtta          40

<210> SEQ ID NO 4
<211> LENGTH: 54
<212> TYPE: DNA
<213> ORGANISM: Artificial sequence
<220> FEATURE:
<223> OTHER INFORMATION: GHSRseq_02R

<400> SEQUENCE: 4
cagtaatacg actcactata gggagaaggc tacctaaact aaaatacttc cccc          54

<210> SEQ ID NO 5
<211> LENGTH: 39
<212> TYPE: DNA
<213> ORGANISM: Artificial sequence
<220> FEATURE:
<223> OTHER INFORMATION: PLD5seq_01F

<400> SEQUENCE: 5
aggaagagag tgggtttaag tagagaggat tattaattg          39

<210> SEQ ID NO 6
<211> LENGTH: 61
<212> TYPE: DNA
<213> ORGANISM: Artificial sequence
<220> FEATURE:
<223> OTHER INFORMATION: PLD5seq_01R

<400> SEQUENCE: 6
cagtaatacg actcactata gggagaaggc tctattttac tcaatccaaa aactaacaaa          60
t          61

<210> SEQ ID NO 7
<211> LENGTH: 35
<212> TYPE: DNA
<213> ORGANISM: Artificial sequence
<220> FEATURE:
<223> OTHER INFORMATION: PLD5seq_02F

<400> SEQUENCE: 7
aggaagagag tggaggtgtt tgtgtagagt gagta          35

<210> SEQ ID NO 8
<211> LENGTH: 56
<212> TYPE: DNA
<213> ORGANISM: Artificial sequence
<220> FEATURE:
<223> OTHER INFORMATION: PLD5seq_02R

<400> SEQUENCE: 8
cagtaatacg actcactata gggagaaggc tactaaataa acaaccccc aaaaac          56

<210> SEQ ID NO 9
<211> LENGTH: 31
<212> TYPE: DNA
<213> ORGANISM: Artificial sequence
<220> FEATURE:
<223> OTHER INFORMATION: PLD5seq_03F

<400> SEQUENCE: 9
aggaagagag ggaggggagg gtaggttttt t                                31

<210> SEQ ID NO 10
<211> LENGTH: 56
<212> TYPE: DNA
<213> ORGANISM: Artificial sequence
<220> FEATURE:
<223> OTHER INFORMATION: PLD5seq_03R

<400> SEQUENCE: 10
cagtaatacg actcactata gggagaaggc tcactctaca caaacacctc caaaac        56

<210> SEQ ID NO 11
<211> LENGTH: 38
<212> TYPE: DNA
<213> ORGANISM: Artificial sequence
<220> FEATURE:
<223> OTHER INFORMATION: CpG 75seq_01F

<400> SEQUENCE: 11
aggaagagag gttttttat ttttgggat gttataga                               38

<210> SEQ ID NO 12
<211> LENGTH: 56
<212> TYPE: DNA
<213> ORGANISM: Artificial sequence
<220> FEATURE:
<223> OTHER INFORMATION: CpG 75seq_01R

<400> SEQUENCE: 12
cagtaatacg actcactata gggagaaggc taccccacta aaactacttt ccctac         56

<210> SEQ ID NO 13
<211> LENGTH: 35
<212> TYPE: DNA
<213> ORGANISM: Artificial sequence
<220> FEATURE:
<223> OTHER INFORMATION: CpG 75seq_02F

<400> SEQUENCE: 13
aggaagagag tttaagtgag tttgatgttt ttggg                                35

<210> SEQ ID NO 14
<211> LENGTH: 56
<212> TYPE: DNA
<213> ORGANISM: Artificial sequence
<220> FEATURE:
<223> OTHER INFORMATION: CpG 75seq_02R

<400> SEQUENCE: 14
cagtaatacg actcactata gggagaaggc tataaacctt aacttcccat ccaaac         56

<210> SEQ ID NO 15
<211> LENGTH: 37
<212> TYPE: DNA
<213> ORGANISM: Artificial sequence
<220> FEATURE:
<223> OTHER INFORMATION: CpG 245seq_01F

<400> SEQUENCE: 15
aggaagagag gttaggattg ttattattag gaaggtt                              37

<210> SEQ ID NO 16
<211> LENGTH: 57
<212> TYPE: DNA
<213> ORGANISM: Artificial sequence

```
<220> FEATURE:
<223> OTHER INFORMATION: CpG 245seq_01R

<400> SEQUENCE: 16
cagtaatacg actcactata gggagaaggc tcaccatcta tatcctctat accaccc          57

<210> SEQ ID NO 17
<211> LENGTH: 36
<212> TYPE: DNA
<213> ORGANISM: Artificial sequence
<220> FEATURE:
<223> OTHER INFORMATION: CpG 245seq_02F

<400> SEQUENCE: 17
aggaagagag agtagaggtt ggagaaggtg ttgtat                                 36

<210> SEQ ID NO 18
<211> LENGTH: 56
<212> TYPE: DNA
<213> ORGANISM: Artificial sequence
<220> FEATURE:
<223> OTHER INFORMATION: CpG 245seq_02R

<400> SEQUENCE: 18
cagtaatacg actcactata gggagaaggc tacctattca tcctcaacct aaccat           56

<210> SEQ ID NO 19
<211> LENGTH: 35
<212> TYPE: DNA
<213> ORGANISM: Artificial sequence
<220> FEATURE:
<223> OTHER INFORMATION: CpG109seq_01F

<400> SEQUENCE: 19
aggaagagag ttagggtttt ggatttagtg tttgt                                  35

<210> SEQ ID NO 20
<211> LENGTH: 50
<212> TYPE: DNA
<213> ORGANISM: Artificial sequence
<220> FEATURE:
<223> OTHER INFORMATION: CpG109seq_01R

<400> SEQUENCE: 20
cagtaatacg actcactata gggagaaggc ttccctccca aaaccaaaaa                  50

<210> SEQ ID NO 21
<211> LENGTH: 29
<212> TYPE: DNA
<213> ORGANISM: Artificial sequence
<220> FEATURE:
<223> OTHER INFORMATION: CpG 109seq_02F

<400> SEQUENCE: 21
aggaagagag gtagttgggg gttggggag                                         29

<210> SEQ ID NO 22
<211> LENGTH: 54
<212> TYPE: DNA
<213> ORGANISM: Artificial sequence
<220> FEATURE:
<223> OTHER INFORMATION: CpG 109seq_02R

<400> SEQUENCE: 22
cagtaatacg actcactata gggagaaggc taacccctac taccctaaaa accc             54
```

<210> SEQ ID NO 23
<211> LENGTH: 32
<212> TYPE: DNA
<213> ORGANISM: Artificial sequence
<220> FEATURE:
<223> OTHER INFORMATION: CpG 100seq_01F

<400> SEQUENCE: 23
aggaagagag ttgtggattt tgattaatgg gt                          32

<210> SEQ ID NO 24
<211> LENGTH: 52
<212> TYPE: DNA
<213> ORGANISM: Artificial sequence
<220> FEATURE:
<223> OTHER INFORMATION: CpG 100seq_01R

<400> SEQUENCE: 24
cagtaatacg actcactata gggagaaggc taaaaacttt cccaaaaatt cc    52

<210> SEQ ID NO 25
<211> LENGTH: 33
<212> TYPE: DNA
<213> ORGANISM: Artificial sequence
<220> FEATURE:
<223> OTHER INFORMATION: CpG 100seq_02F

<400> SEQUENCE: 25
aggaagagag gttggatatt gggtagtgat gtt                         33

<210> SEQ ID NO 26
<211> LENGTH: 57
<212> TYPE: DNA
<213> ORGANISM: Artificial sequence
<220> FEATURE:
<223> OTHER INFORMATION: CpG 100seq_02R

<400> SEQUENCE: 26
cagtaatacg actcactata gggagaaggc taacctcctt taaaactaaa attctcc  57

<210> SEQ ID NO 27
<211> LENGTH: 34
<212> TYPE: DNA
<213> ORGANISM: Artificial sequence
<220> FEATURE:
<223> OTHER INFORMATION: Cpg 261seq_01F

<400> SEQUENCE: 27
aggaagagag ttgggtaggg atagggttt tatt                         34

<210> SEQ ID NO 28
<211> LENGTH: 56
<212> TYPE: DNA
<213> ORGANISM: Artificial sequence
<220> FEATURE:
<223> OTHER INFORMATION: Cpg 261seq_01R

<400> SEQUENCE: 28
cagtaatacg actcactata gggagaaggc tctctatcaa tttccactcc cctaac  56

<210> SEQ ID NO 29
<211> LENGTH: 35
<212> TYPE: DNA
<213> ORGANISM: Artificial sequence
<220> FEATURE:
<223> OTHER INFORMATION: CpG 24seq_01F

```
<400> SEQUENCE: 29
aggaagagag gttagggagg gaataatgtt aggaa                                   35

<210> SEQ ID NO 30
<211> LENGTH: 57
<212> TYPE: DNA
<213> ORGANISM: Artificial sequence
<220> FEATURE:
<223> OTHER INFORMATION: CpG 24seq_01R

<400> SEQUENCE: 30
cagtaatacg actcactata gggagaaggc taccctaaac tctactctca acacctc          57

<210> SEQ ID NO 31
<211> LENGTH: 36
<212> TYPE: DNA
<213> ORGANISM: Artificial sequence
<220> FEATURE:
<223> OTHER INFORMATION: CpG 24seq_02F

<400> SEQUENCE: 31
aggaagagag ggttgtgaga gtttttttaga gttgaa                                36

<210> SEQ ID NO 32
<211> LENGTH: 52
<212> TYPE: DNA
<213> ORGANISM: Artificial sequence
<220> FEATURE:
<223> OTHER INFORMATION: CpG 24seq_02R

<400> SEQUENCE: 32
cagtaatacg actcactata gggagaaggc tactaaaatc ccccaaccca ac               52

<210> SEQ ID NO 33
<211> LENGTH: 35
<212> TYPE: DNA
<213> ORGANISM: Artificial sequence
<220> FEATURE:
<223> OTHER INFORMATION: CpG 188seq_01F

<400> SEQUENCE: 33
aggaagagag aggttttttag ttttgtttgg ttttg                                 35

<210> SEQ ID NO 34
<211> LENGTH: 55
<212> TYPE: DNA
<213> ORGANISM: Artificial sequence
<220> FEATURE:
<223> OTHER INFORMATION: CpG 188seq_01R

<400> SEQUENCE: 34
cagtaatacg actcactata gggagaaggc taactcttac ccaactactt cccaa            55

<210> SEQ ID NO 35
<211> LENGTH: 35
<212> TYPE: DNA
<213> ORGANISM: Artificial sequence
<220> FEATURE:
<223> OTHER INFORMATION: CpG 272seq_01F

<400> SEQUENCE: 35
aggaagagag tatttgttag ggtagggttt taggg                                  35

<210> SEQ ID NO 36
```

```
<211> LENGTH: 54
<212> TYPE: DNA
<213> ORGANISM: Artificial sequence
<220> FEATURE:
<223> OTHER INFORMATION: CpG 272seq_01R

<400> SEQUENCE: 36
cagtaatacg actcactata gggagaaggc ttaaccttcc tcaaccaaaa ccaa          54

<210> SEQ ID NO 37
<211> LENGTH: 35
<212> TYPE: DNA
<213> ORGANISM: Artificial sequence
<220> FEATURE:
<223> OTHER INFORMATION: C9orf125_01F

<400> SEQUENCE: 37
aggaagagag ttagggtttt ggatttagtg tttgt                              35

<210> SEQ ID NO 38
<211> LENGTH: 50
<212> TYPE: DNA
<213> ORGANISM: Artificial sequence
<220> FEATURE:
<223> OTHER INFORMATION: C9orf125_01R

<400> SEQUENCE: 38
cagtaatacg actcactata gggagaaggc ttccctccca aaaccaaaaa              50

<210> SEQ ID NO 39
<211> LENGTH: 37
<212> TYPE: DNA
<213> ORGANISM: Artificial sequence
<220> FEATURE:
<223> OTHER INFORMATION: NPY_manF

<400> SEQUENCE: 39
aggaagagag gagtttttg tgtttgtaga tgttagg                             37

<210> SEQ ID NO 40
<211> LENGTH: 57
<212> TYPE: DNA
<213> ORGANISM: Artificial sequence
<220> FEATURE:
<223> OTHER INFORMATION: NPY_manR

<400> SEQUENCE: 40
cagtaatacg actcactata gggagaaggc tccraataat atctaaccat atcctcc      57

<210> SEQ ID NO 41
<211> LENGTH: 33
<212> TYPE: DNA
<213> ORGANISM: Artificial sequence
<220> FEATURE:
<223> OTHER INFORMATION: HMX2_05F

<400> SEQUENCE: 41
aggaagagag gttttttggt tgggttattg agt                                33

<210> SEQ ID NO 42
<211> LENGTH: 56
<212> TYPE: DNA
<213> ORGANISM: Artificial sequence
<220> FEATURE:
<223> OTHER INFORMATION: HMX2_05R

<400> SEQUENCE: 42
```
cagtaatacg actcactata gggagaaggc taacacctaa actcccctta aaaatc        56

<210> SEQ ID NO 43
<211> LENGTH: 30
<212> TYPE: DNA
<213> ORGANISM: Artificial sequence
<220> FEATURE:
<223> OTHER INFORMATION: FERD3L_02F

<400> SEQUENCE: 43
aggaagagag ggggaggtta gggataggtt        30

<210> SEQ ID NO 44
<211> LENGTH: 56
<212> TYPE: DNA
<213> ORGANISM: Artificial sequence
<220> FEATURE:
<223> OTHER INFORMATION: FERD3L_02R

<400> SEQUENCE: 44
cagtaatacg actcactata gggagaaggc ttaccccatc aaattcaaaa ctatta        56

<210> SEQ ID NO 45
<211> LENGTH: 35
<212> TYPE: DNA
<213> ORGANISM: Artificial sequence
<220> FEATURE:
<223> OTHER INFORMATION: SATB2__01F

<400> SEQUENCE: 45
aggaagagag gttttttggtt gtagtttttg ggatt        35

<210> SEQ ID NO 46
<211> LENGTH: 58
<212> TYPE: DNA
<213> ORGANISM: Artificial sequence
<220> FEATURE:
<223> OTHER INFORMATION: SATB2__01R

<400> SEQUENCE: 46
cagtaatacg actcactata gggagaaggc tataaacaac ctcccacttt aaaactaa        58

<210> SEQ ID NO 47
<211> LENGTH: 33
<212> TYPE: DNA
<213> ORGANISM: Artificial sequence
<220> FEATURE:
<223> OTHER INFORMATION: CNTD2_01F

<400> SEQUENCE: 47
aggaagagag attttgtaaa ggagagggtt tgg        33

<210> SEQ ID NO 48
<211> LENGTH: 55
<212> TYPE: DNA
<213> ORGANISM: Artificial sequence
<220> FEATURE:
<223> OTHER INFORMATION: CNTD2_01R

<400> SEQUENCE: 48
cagtaatacg actcactata gggagaaggc ttctcttccc ctaactacaa aaatc        55

<210> SEQ ID NO 49
<211> LENGTH: 37
<212> TYPE: DNA

```
<213> ORGANISM: Artificial sequence
<220> FEATURE:
<223> OTHER INFORMATION: RREB1_01F

<400> SEQUENCE: 49
aggaagagag ggagtttttt gagagaaaga gatattg                              37

<210> SEQ ID NO 50
<211> LENGTH: 55
<212> TYPE: DNA
<213> ORGANISM: Artificial sequence
<220> FEATURE:
<223> OTHER INFORMATION: RREB1_01R

<400> SEQUENCE: 50
cagtaatacg actcactata gggagaaggc tacaccccac aaaaaatact tcaac         55
```

METHODS FOR DIAGNOSIS, PROGNOSIS AND MONITORING OF BREAST CANCER AND REAGENTS THEREFOR

CROSS-REFERENCE TO RELATED APPLICATIONS

This application is the U.S. national phase application filed under 35 U.S.C. § 371 claiming benefit to International Patent Application No. PCT/AU2015/50549, filed on Sep. 15, 2015, which is entitled to priority under 35 U.S.C. § 119(e) to Australian Provisional Patent Application No. 2014903680, filed Sep. 15, 2014, the entire disclosures of which are expressly incorporated herein by reference.

TECHNICAL FIELD

The present disclosure generally relates to methods and reagents for the diagnosis, prognosis or the monitoring of breast cancer, including various subtypes of breast cancer including, for example, estrogen receptor (ER) negative breast cancer, ER positive breast cancer, triple negative breast cancer (TNBC) and other subtypes of breast cancer.

BACKGROUND

Cancer is a leading cause of disease worldwide. Breast cancer is one of the most common forms of cancer, affecting both females and males globally. Various subtypes of breast cancer have been distinguished based on a number of factors including the histopathological type of tumor, the grade of the tumor, the stage of the tumor, and the expression of genes which are characteristic of particular subtypes of breast cancer. Determination of the particular subtype of cancer in a patient is often of critical importance in determining the most appropriate course of treatment for the patient.

ER negative (ER-ve) breast cancer and ER positive (ER+ve) breast cancer are two recognised subtypes of breast cancer, defined by the presence or absence of expression of the estrogen receptor gene. Triple negative breast cancer (TNBC) is another recognised subtype of breast cancer. The TNBC subtype is clinically defined by the absence of ER and progesterone receptor (PR) expression, and neither overexpression nor amplification of human epidermal growth factor receptor 2 (HER2). TNBC represents approximately 15-20% of all newly diagnosed breast cancer cases and is generally associated with high risk of disease recurrence and shorter overall survival compared to non-TNBC. Broadly, TNBC patients can be categorized into two distinct groups; those that succumb to their disease within 3-5 years regardless of treatment, and those that remain disease free to the extent that their overall survival exceeds that of non-TNBC patients (i.e. approximately >8 to 10 years post-diagnosis).

Currently, methods by which breast cancer patients are stratified into high- and low-risk subgroups remain limited to staging by clinicopathological factors such as tumor size, level of invasiveness and lymph node infiltration. However, unlike other breast cancer subtypes, TNBC outcome is less closely related to stage. Thus, there is a need to identify a robust method by which TNBC patients can be stratified to enable more informed disease management.

Previous efforts to stratify early breast cancer prognosis have primarily focused on multi-gene expression signatures. In addition to multi-gene expression assays, DNA methylation signatures are being assessed as potential molecular biomarkers of cancer. Despite growing interest in the prognostic significance of DNA methylation in breast cancer, there have been no studies specifically investigating the DNA methylation profile of human breast cancer or human breast cancer subtypes and its association with disease outcome.

There is a need in the art for improved methods for the diagnosis of breast cancer, as well as for the diagnosis of specific subtypes of breast cancer e.g., ER-ve breast cancer, ER+ve breast cancer and TNBC. There is also a need for methods of prognosis, including predicting the likelihood of patient survival for, patients diagnosed with breast cancer.

SUMMARY

The present inventors performed a genome-wide DNA methylation profiling analysis on CpG rich DNA from a number of breast cancer samples. In doing so, the inventors identified novel regions of differential methylation containing one or more CpG dinucleotides, including regional methylation profiles that are specific to breast cancer cells in comparison to healthy cells. The inventors also identified regions of differential methylation which were specific to various subtypes of breast cancer, including ER-ve breast cancer and TNBC. Specific regions of differential methylation were validated for particular subtypes of breast cancer using the cancer genome atlas (TCGA) methylation data. The inventors identified at least 822 hypermethylated and at least 43 hypomethylated, statistically significant, differentially methylated regions (DMRs) harboring 64,005 and 623 CpG sites respectively. Of these, a number of DMRs were shown to be characteristic of particular subtypes of breast cancer, including ER-ve breast cancer and TNBC. These markers have been demonstrated to have significant value in the diagnosis and prognosis of breast cancer, including in the diagnosis and prognosis of ER-ve breast cancer and/or of TNBC.

For example, the inventors identified at least 36 DMRs which were shown to be specific to TNBC samples and which therefore provide significant utility in the diagnosis of TNBC. In addition, amongst these TNBC-specific DMRs, three clusters of DMRs were shown to be reliably predictive of greater or lesser survival outcomes. These DMRs therefore also provide significant utility in the stratification of severity of TNBC during prognosis. Furthermore, a particular subset of CpG sites in any one or more DMRs selected from within a group of 17 particular DMRs have been shown by the inventors to be associated with strong survival outcomes. Therefore, any one or more CpG sites within this subset of DMRs, in any combination, can be used to determine the likelihood of survival of a subject having TNBC.

Particular examples of genes and promoters associated with the DMRs identified in the present disclosure include the WT1 and WT1 antisense (WT1-AS) gene and its bidirectional promoter. Determining the methylation status associated with any one or more of the specific genes and associated promoters disclosed herein (such as the WT1 and WT1-AS genes) is particularly useful in the diagnosis and prognosis of breast cancer, and of particular subtypes of breast cancer such as, for example, ER-ve breast cancer, ER+ve breast cancer and/or TNBC.

Accordingly, the present disclosure provides a method for the diagnosis of breast cancer in a subject, said method comprising:

(i) determining the methylation status of one or more CpG dinucleotide sequences within one or more genomic regions defined in Table 1 in a test sample obtained from the subject; and
(ii) identifying differential methylation of said one or more CpG dinucleotide sequences in the test sample relative to a reference level of methylation for the corresponding one or more CpG dinucleotide sequences, wherein differential methylation of said one or more CpG dinucleotide sequences in the test sample relative to the reference level is indicative of the subject having breast cancer.

In one example increased methylation at one or more CpG dinucleotide sequences within one or more genomic regions defined in Table 1 relative to the reference level may be indicative of a subject having breast cancer; and/or decreased methylation at one or more CpG dinucleotide sequences within one or more genomic regions defined in Table 1 relative to the reference level may be indicative of a subject having breast cancer.

In another example, the identification of differential methylation of one or more CpG dinucleotide sequences within one or more genomic regions defined in Table 1 relative to the reference level is indicative of a subject having breast cancer which is characterised as being estrogen receptor negative (ER−ve) breast cancer.

Alternatively or in addition, the identification of differential methylation at one or more CpG dinucleotide sequences within one or more genomic regions defined in Table 2 and/or Table 3 relative to the reference level of methylation is indicative of the subject having Triple Negative Breast Cancer (TNBC).

The present disclosure also provides a method for prognosis of, predicting the therapeutic outcome of, and/or monitoring the progression of, Triple Negative Breast Cancer (TNBC) in a subject, said method comprising:
(i) determining differential methylation of one or more CpG dinucleotide sequences within one or more genomic regions defined in Table 3 in the subject relative to a reference level of methylation for the corresponding one or more CpG dinucleotide sequences; and
(ii) correlating the differential methylation determined at (i) with a prognosis of the TNBC in the subject.

Again, in one example, differential methylation of one or more CpG dinucleotide sequences within the one or more genomic regions set forth in Table 3 relative to the reference level is associated with a likelihood of survival of the subject.

In another example, differential methylation of one or more CpG dinucleotide sequences within any one or more genomic regions defined in rows 1-14 of Table 3 relative to the reference level of methylation is associated with a decreased likelihood of survival of the subject.

In another example, differential methylation of one or more CpG dinucleotide sequences within any one or more genomic regions defined in rows 15-17 of Table 3 relative to the reference level of methylation is associated with an increased likelihood of survival of the subject.

In another example, differential methylation of one or more CpG dinucleotide sequences within any one or more genomic regions defined in rows 1-14 of Table 3 relative to the reference level of methylation is associated with a decreased likelihood of survival of the subject and differential methylation of one or more CpG dinucleotide sequences within any one or more genomic regions defined in rows 15-17 of Table 3 relative to the reference level of methylation is associated with an increased likelihood of survival of the subject.

In any of the methods disclosed herein, the differential methylation may be increased or decreased methylation relative to the reference level of methylation. In many cases, the differential methylation is increased relative to the reference level of methylation.

In one example of the methods disclosed herein, differential methylation of one or more CpG dinucleotides within the Wilms tumour protein (WT1) gene and/or its antisense counterpart, WT1-AS, is associated with a likelihood of survival of the subject. For example, increased methylation of one or more CpG dinucleotide sequences within the chr11-11623 and/or chr11-1210 genomic regions relative to a reference level of methylation of one or more CpG dinucleotide sequences within those genomic regions may be associated with a decreased likelihood of survival of the subject. In another example, increased methylation of one or more CpG dinucleotide sequences within the chr11-4047 genomic region relative to a reference level of methylation of one or more CpG dinucleotide sequences within that genomic region is associated with an increased likelihood of survival of the subject.

In any of the methods disclosed herein, the likelihood of survival may be determined in accordance with any generally accepted method of determining the likelihood of survival known in the art. In one example, the likelihood of survival is determined as a likelihood that the subject will survive at least 3 years after being diagnosed with TNBC. In another example, the likelihood of survival is determined as a likelihood that the subject will survive at least 5 years after being diagnosed with TNBC.

In any of the methods disclosed herein, methylation status of one or more CpG dinucleotide sequences may be determined according to any suitable method known in the art. For example, methylation status of one or more CpG dinucleotide sequences within the one or more genomic regions analysed may be determined by one or more techniques selected from the group consisting of a nucleic acid amplification, polymerase chain reaction (PCR), methylation specific PCR, bisulfite pyrosequencing, single-strand conformation polymorphism (SSCP) analysis, restriction analysis, microarray technology, and proteomics. For example, methylation status of one or more CpG dinucleotide sequences within the one or more genomic regions in the test sample may be determined by one or more of the following:
(i) performing methylation-sensitive endonuclease digestion of DNA from the subject;
(ii) treating nucleic acid from the subject with an amount of a compound that selectively mutates non-methylated cytosine residues in nucleic acid under conditions sufficient to induce mutagenesis thereof and produce a mutant nucleic acid and amplifying the mutant nucleic acid using at least one primer that selectively hybridizes to the mutant nucleic acid;
(iii) treating nucleic acid from the subject with an amount of a compound that selectively mutates non-methylated cytosine residues in nucleic acid under conditions sufficient to induce mutagenesis thereof and produce a mutant nucleic acid, hybridizing a nucleic acid probe or primer capable of specifically hybridizing to the mutant nucleic acid and detecting the hybridized probe or primer;
(iv) treating nucleic acid from the subject with an amount of a compound that selectively mutates non-methylated cytosine residues in nucleic acid under conditions sufficient to induce mutagenesis thereof and produce a mutant nucleic acid, amplifying the mutant nucleic acid with promoter-tagged primers, transcribing the mutant nucleic acid in vitro to produce a transcript, subjecting the transcript to an enzymatic base-specific cleavage, and determining differences in mass and/or size of any cleaved fragments resulting from mutated cysteine residues, such as by MALDI-TOF mass spectrometry; and (v) treating nucleic acid from the subject with an amount of a compound that selectively mutates non-methylated cytosine residues in nucleic acid under conditions sufficient to induce mutagenesis thereof, thereby producing a mutant nucleic acid, and determining the nucleotide sequence of the mutant nucleic acid.

The compound that selectively mutates non-methylated cytosine residues may be any compound suitable for that purpose, including, for example, a salt of bisulphite.

The methods disclosed herein may be performed on any test sample taken from a subject. For example, the methylation status of one or more CpG dinucleotides sequence within the one or more genomic regions can be determined in a test sample from the subject comprising tissue and/or a body fluid comprising, or suspected of comprising, a breast cancer cell or components of a breast cancer cell. The sample may comprise tissue, a cell and/or an extract thereof taken from a breast or lymph node. When the sample comprises a body fluid, the body fluid may be selected from the group consisting of whole blood, a fraction of blood such as blood serum or plasma, urine, saliva, breast milk, pleural fluid, sweat, tears and mixtures thereof.

In any of the methods disclosed herein, the reference level of methylation may be a level of methylation determined for one or more CpG dinucleotide sequences within a corresponding genomic region of a sample selected from the group consisting of:
(i) a sample from a normal or healthy tissue;
(ii) a sample comprising a non-cancerous cell;
(iii) a sample comprising a cancerous cell other than a TNBC cell;
(iv) an extract of any one of (i) to (iii);
(v) a data set comprising levels of methylation for the one or more CpG dinucleotide sequences within the corresponding genomic region in a normal or healthy individual or a population of normal or healthy individuals;
(vi) a data set comprising levels of methylation for the one or more CpG dinucleotide sequences within the corresponding genomic region in an individual or a population of individuals having cancer of a non-TNBC subtype; and
(vii) a data set comprising levels of methylation for the one or more CpG dinucleotide sequences within the corresponding genomic region in the subject being tested wherein the levels of methylation are determined for a matched sample having normal cells.

In one example, the reference level of methylation may be a level of methylation determined for one or more CpG dinucleotide sequences within a corresponding genomic region of a healthy breast epithelial cell. Thus, the normal or healthy tissue may comprise a breast epithelial cell. In addition, the "non-cancerous cell" may be a breast epithelial cell.

The present disclosure also provides a kit for diagnosing breast cancer in a subject, said kit comprising:
(i) one or more reagents to determine the methylation status of one or more CpG dinucleotide sequences within one or more genomic regions defined in Table 1 in a test sample obtained from the subject; and
(ii) a reference material which provides a reference level of methylation of the corresponding one or more CpG dinucleotide sequences.

The present disclosure also provides a kit for diagnosing estrogen receptor negative (ER−ve) breast cancer in a subject, said kit comprising:
(i) one or more reagents to determine methylation status of one or more CpG dinucleotide sequences within one or more genomic regions defined in Table 1 in a test sample obtained from the subject; and
(ii) a reference material which provides a reference level of methylation of the corresponding one or more CpG dinucleotide sequences.

The present disclosure also provides a kit for diagnosing Triple Negative Breast Cancer (TNBC) in a subject, said kit comprising:
(i) one or more reagents to determine methylation status of one or more CpG dinucleotide sequences within one or more genomic regions defined in Table 2 and/or Table 3 in a test sample obtained from the subject; and
(ii) a reference material which provides a reference level of methylation of the corresponding one or more CpG dinucleotide sequences.

The present disclosure also provides a kit for prognosis of, predicting the therapeutic outcome of, and/or monitoring the progression of, Triple Negative Breast Cancer (TNBC) in a subject; said kit comprising:
(i) one or more reagents to determine methylation status of one or more CpG dinucleotide sequences within one or more genomic regions defined in Table 2 and/or Table 3 in a test sample obtained from the subject; and
(ii) a reference material which provides a reference level of methylation of the corresponding one or more CpG dinucleotide sequences.

In any of the kits disclosed herein, the reference level of methylation may be a level of methylation determined for one or more CpG dinucleotide sequences within a corresponding genomic region of a sample selected from the group consisting of:
(i) a sample from a normal or healthy tissue;
(ii) a sample comprising a non-cancerous cell;
(iii) a sample comprising a cancerous cell other than a TNBC cell;
(iv) an extract of any one of (i) to (iii);
(v) a data set comprising levels of methylation for the one or more CpG dinucleotide sequences within the corresponding genomic region in a normal or healthy individual or a population of normal or healthy individuals;
(vi) a data set comprising levels of methylation for the one or more CpG dinucleotide sequences within the corresponding genomic region in an individual or a population of individuals having cancer of a non-TNBC type; and
(vii) a data set comprising levels of methylation for the one or more CpG dinucleotide sequences within the corresponding genomic region in the subject being tested wherein the levels of methylation are determined for a matched sample having normal cells.

In one example, the reference level of methylation may be a level of methylation determined for one or more CpG dinucleotide sequences within a corresponding genomic region of a healthy breast epithelial cell. Thus, the normal or healthy tissue may comprise a breast epithelial cell. In addition, the "non-cancerous cell" may be a breast epithelial cell.

The present disclosure also provides any one of the kits disclosed herein when used in any one or more of the methods disclosed herein.

In addition, the present disclosure provides the use of one or more reagents in the preparation of a medicament for diagnosing breast cancer in a subject, wherein the one or more reagents is/are configured to determine methylation status of one or more CpG dinucleotide sequences within one or more genomic regions defined in Table 1 in a test sample obtained from the subject.

The present disclosure also provides the use of one or more reagents in the preparation of a medicament for diagnosing estrogen receptor negative (ER−ve) breast cancer in a subject, wherein the one or more reagents is/are configured to determine methylation status of one or more CpG dinucleotide sequences within one or more genomic regions defined in Table 1 in a test sample obtained from the subject.

The present disclosure also provides the use of one or more reagents in the preparation of a medicament for diagnosing Triple Negative Breast Cancer (TNBC) in a subject suspected of having TNBC, wherein the one or more reagents is/are configured to determine methylation status of one or more CpG dinucleotide sequences within one or more genomic regions defined in Table 2 and/or Table 3 in a test sample obtained from the subject.

The present disclosure also provides the use of one or more reagents in the preparation of a medicament for a prognosis of, predicting the therapeutic outcome of, and/or monitoring the progression of Triple Negative Breast Cancer (TNBC) in a subject, wherein the one or more reagents is/are configured to determine methylation status of one or more CpG dinucleotide sequences within one or more genomic regions defined in Table 2 and/or Table 3 in a test sample obtained from the subject.

In addition, any or the methods disclosed herein may further comprise a step of administering a therapeutic treatment to a subject. For example, the determination of the presence of a particular subtype of breast cancer in a subject may lead to the administration of a particular therapeutic treatment to that subject, which therapeutic treatment is particularly tailored to that particular subtype of breast cancer. In another example, the determination of the severity and/or state of progression of a particular subtype of breast cancer in a subject may lead to the administration of a particular therapeutic treatment to that subject, which therapeutic treatment is particularly tailored to that particular level of severity or progression of that particular subtype of breast cancer.

Each feature of any particular aspect or embodiment or example of the present disclosure may be applied mutatis mutandis to any other aspect or embodiment or example of the present disclosure.

BRIEF DESCRIPTION OF DRAWINGS

The following figures form part of the present specification and are included to further demonstrate certain aspects of the present disclosure. The disclosure may be better understood by reference to one or more of these figures in combination with the detailed description of specific embodiments presented herein.

Figure 120:
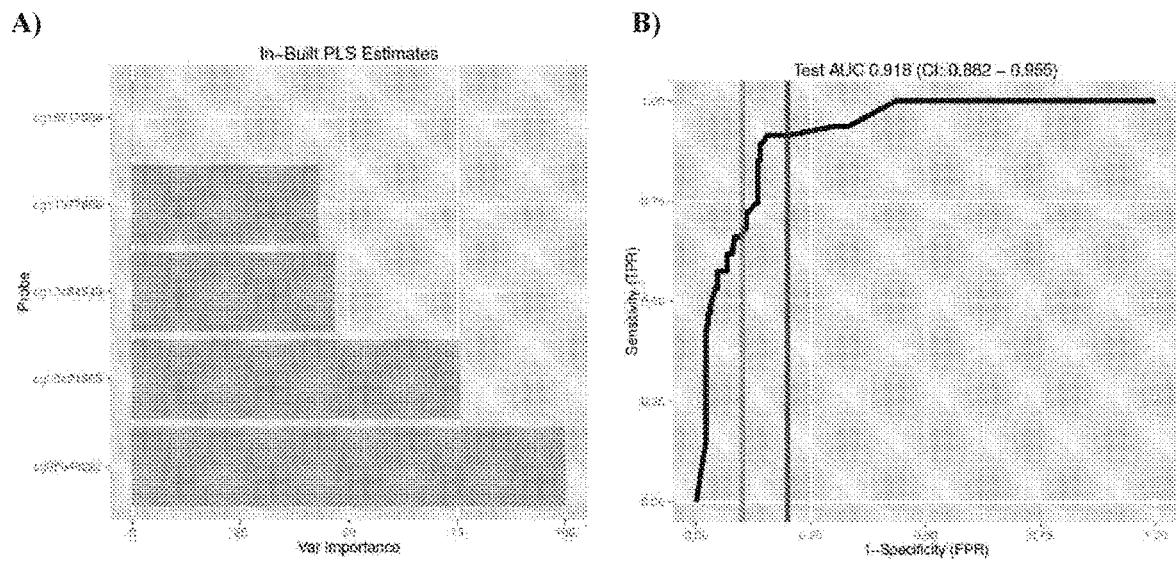

FIG. 120. This figure a) illustrates the distribution of methylation for each of the probes in subset 41 as detailed in Table 13, and b) provides a ROC curve and associated AUC statistics for diagnosing TNBC using probe subset 41.

Figure 121:
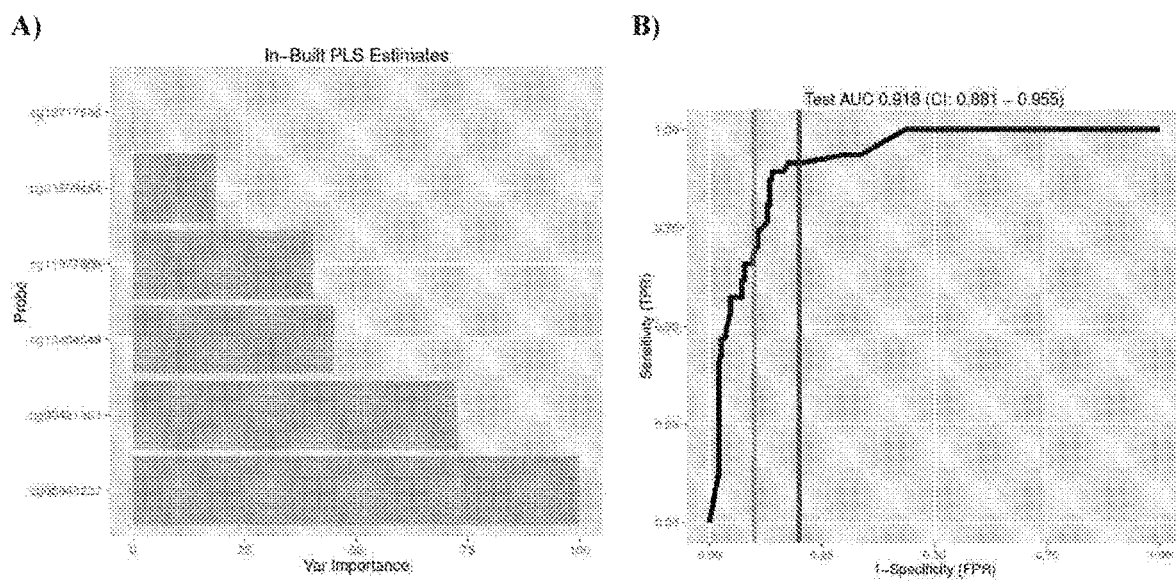

FIG. 121. This figure a) illustrates the distribution of methylation for each of the probes in subset 42 as detailed in Table 13, and b) provides a ROC curve and associated AUC statistics for diagnosing TNBC using probe subset 42.

Figure 122:
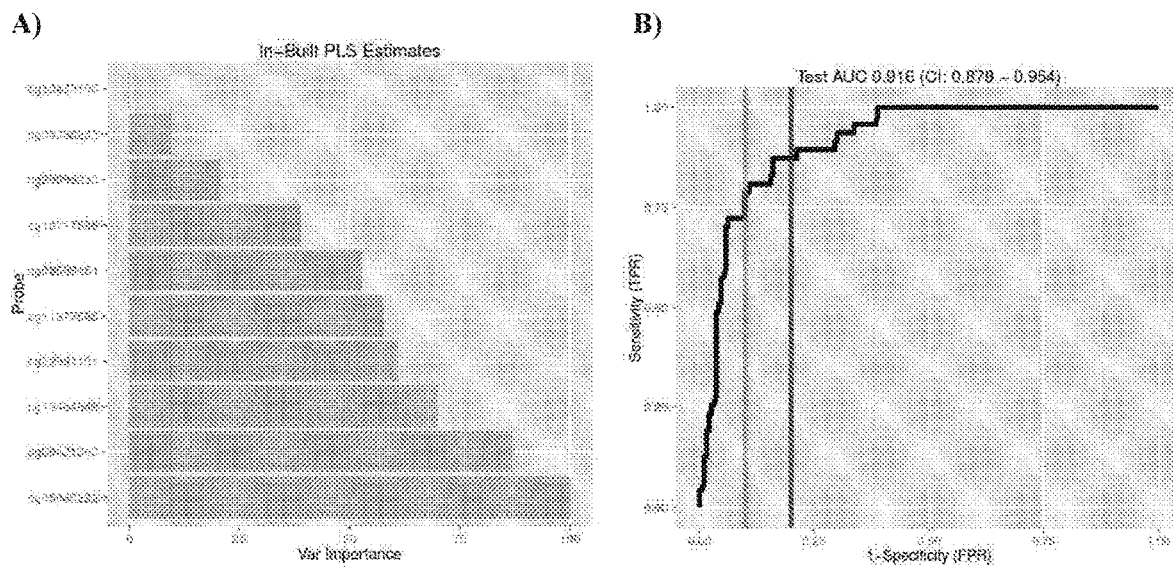

FIG. 122. This figure a) illustrates the distribution of methylation for each of the probes in subset 43 as detailed in Table 13, and b) provides a ROC curve and associated AUC statistics for diagnosing TNBC using probe subset 43.

Figure 123:
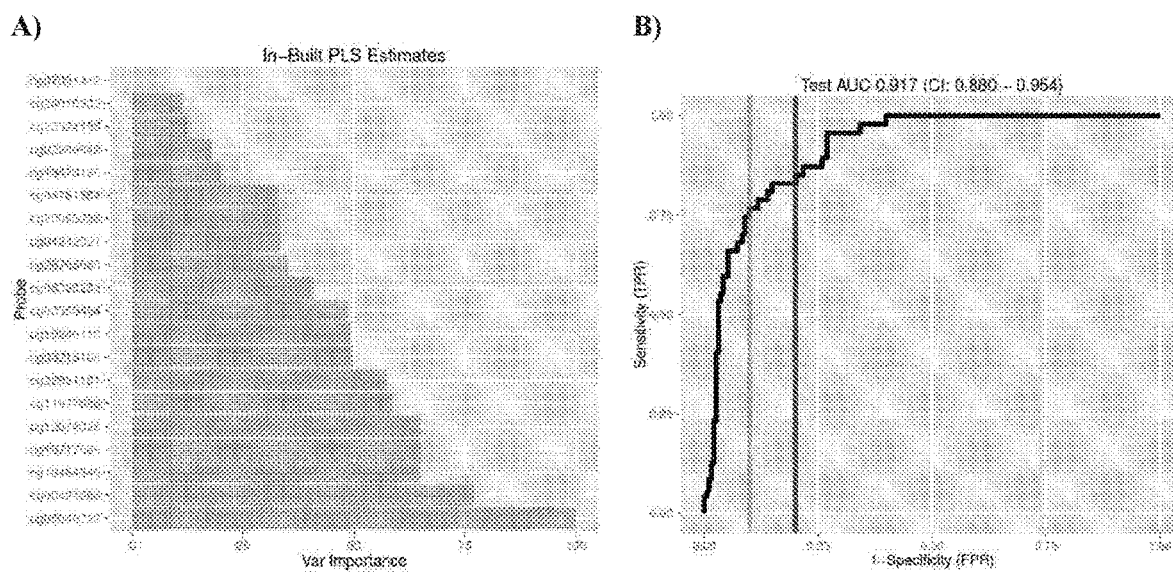

FIG. 123. This figure a) illustrates the distribution of methylation for each of the probes in subset 44 as detailed in Table 13, and b) provides a ROC curve and associated AUC statistics for diagnosing TNBC using probe subset 44.

Figure 124:
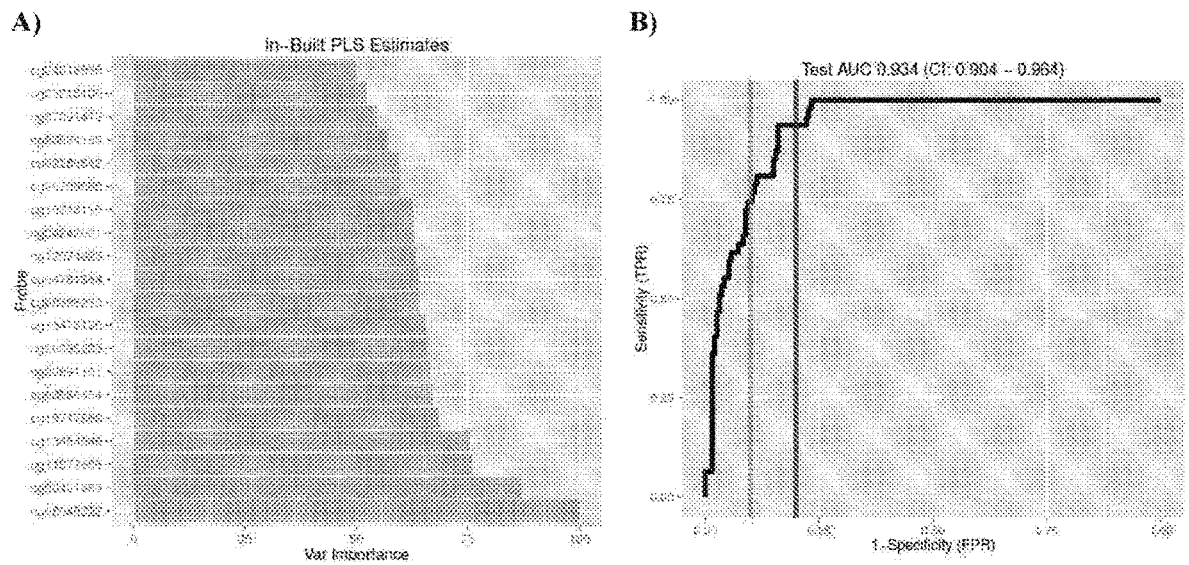

FIG. 124. This figure a) illustrates the distribution of methylation for each of the probes in subset 45 as detailed in Table 13, and b) provides a ROC curve and associated AUC statistics for diagnosing TNBC using probe subset 44.

Figure 125:
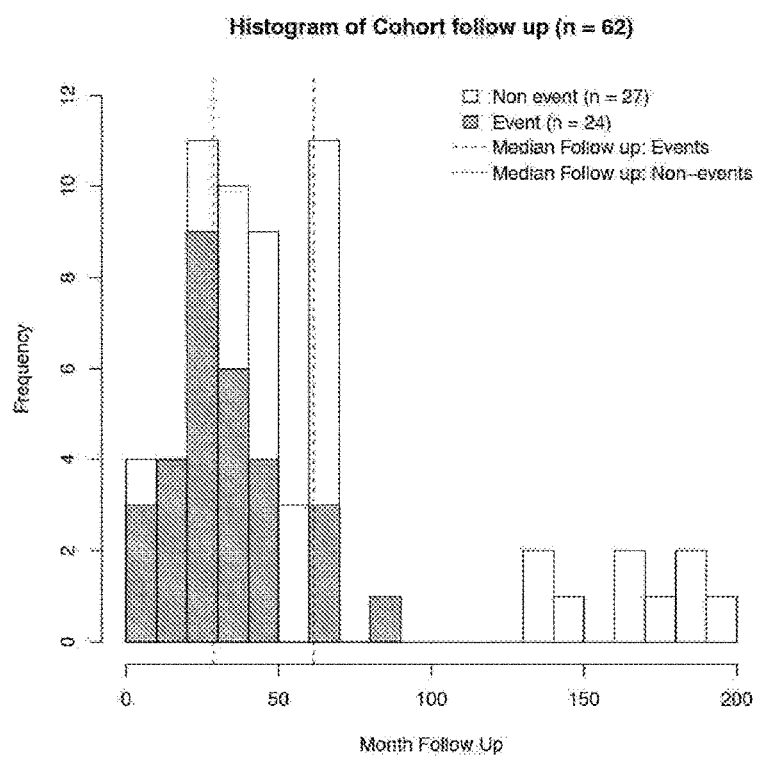

FIG. 125. This figure provides a histogram of NBCF cohort follow up time (months), where shaded regions denote breast cancer specific deaths (events) and white regions denote patients alive at the time of last follow up (non-events).

Figure 126:
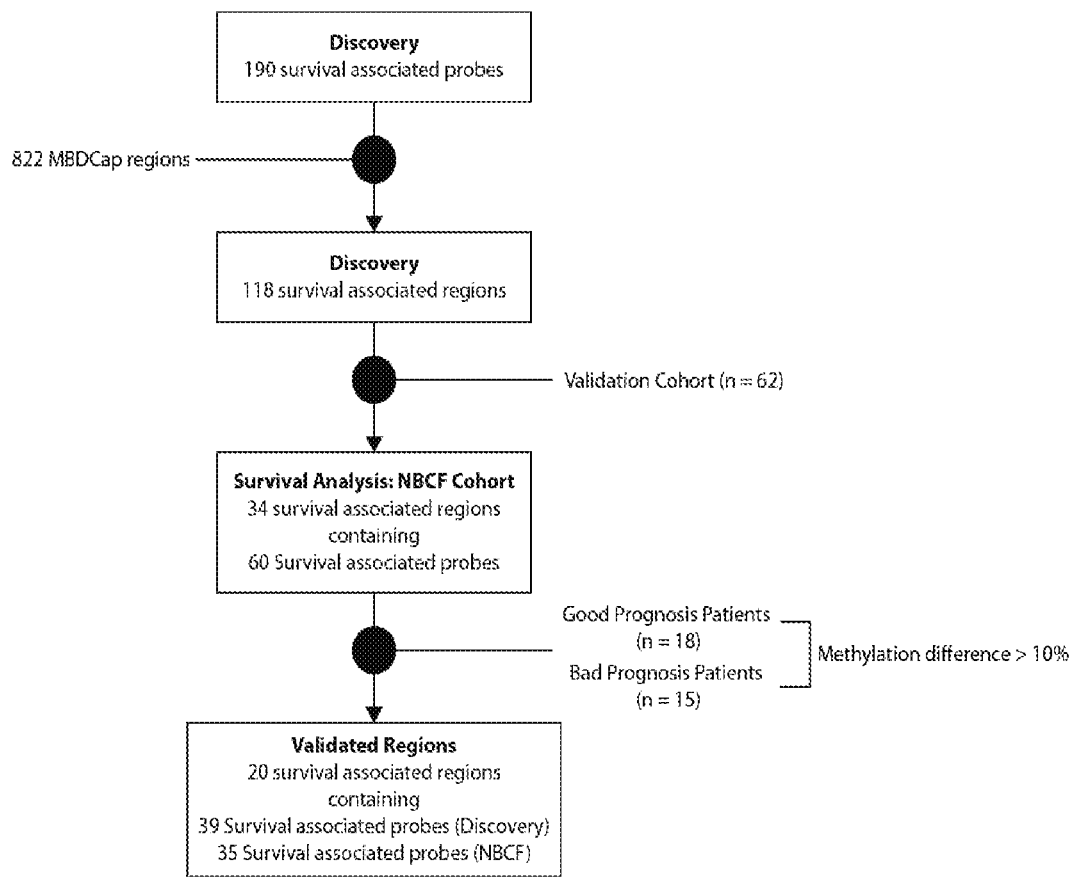

FIG. 126. This figure provides a flowchart illustrating the method used to validate and filter survival regions in the NBCF cohort.

Figure 127:
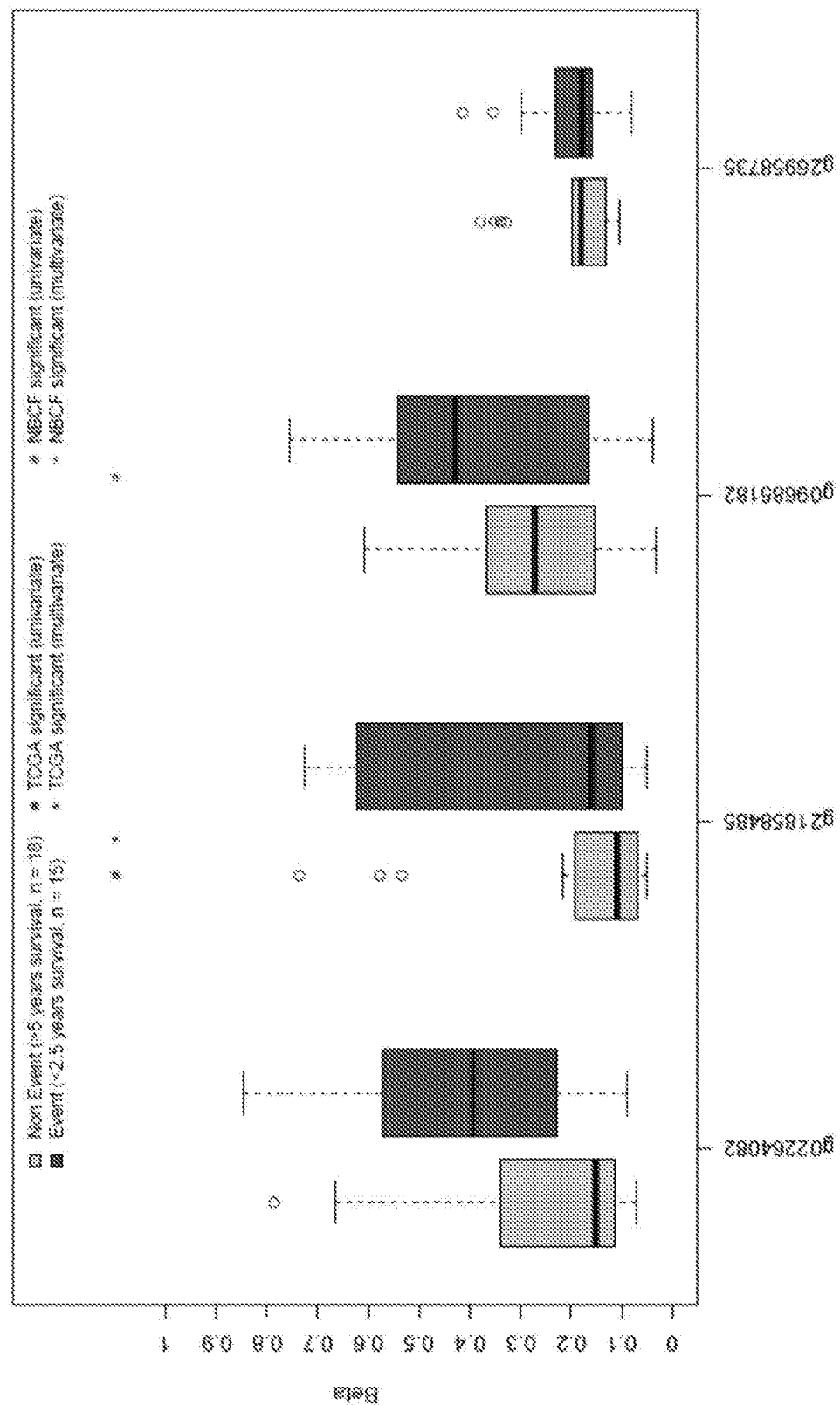

FIG. 127. This figure shows relative levels of methylation for probes in prognostic region designated chr3-1415 (as described in Table 14) for patients in good and poor prognosis groups.

Figure 128:
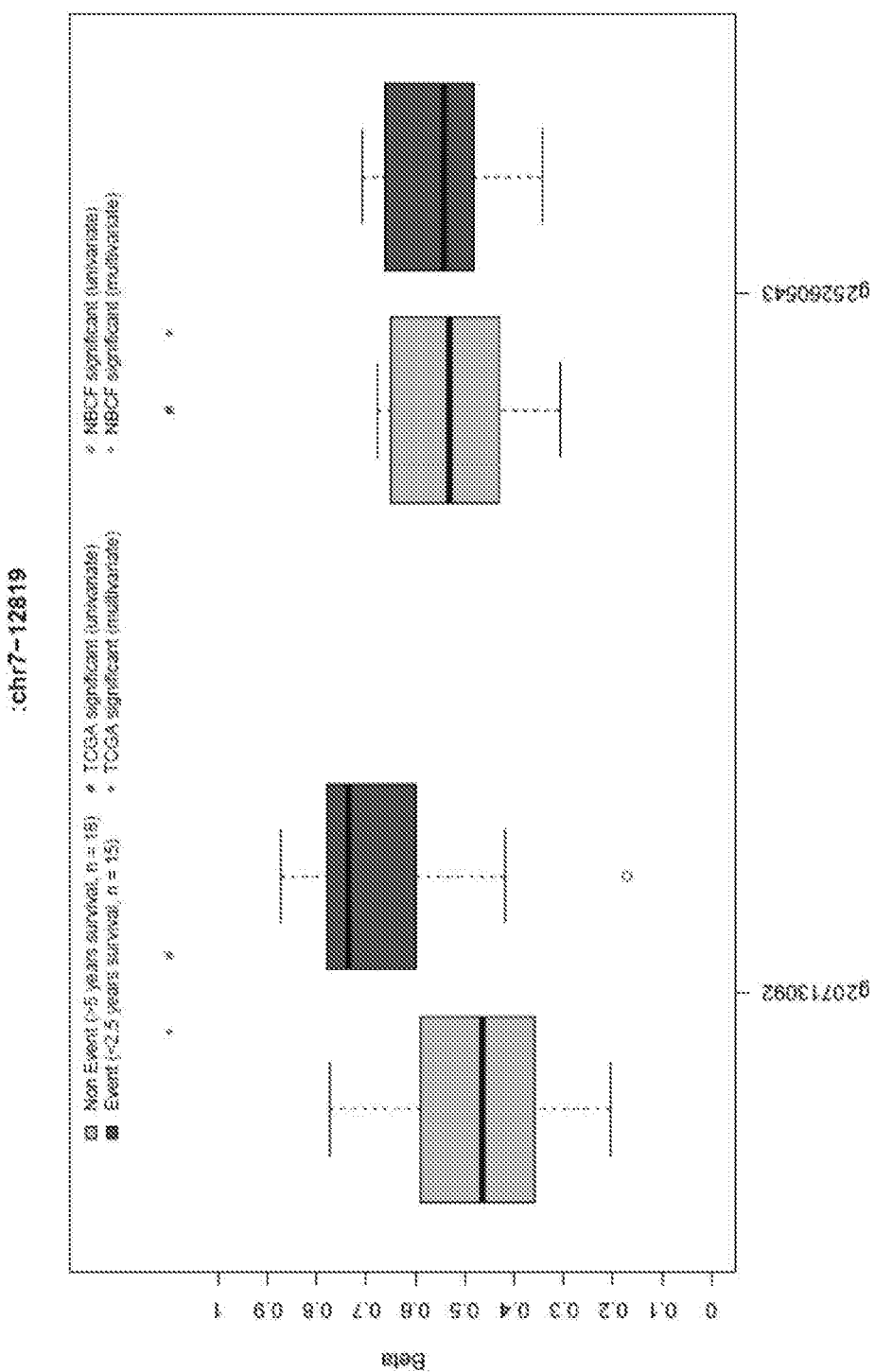

FIG. 128. This figure shows relative levels of methylation for probes in prognostic region designated chr7-12819 (as described in Table 14) for patients in good and poor prognosis groups.

Figure 129:
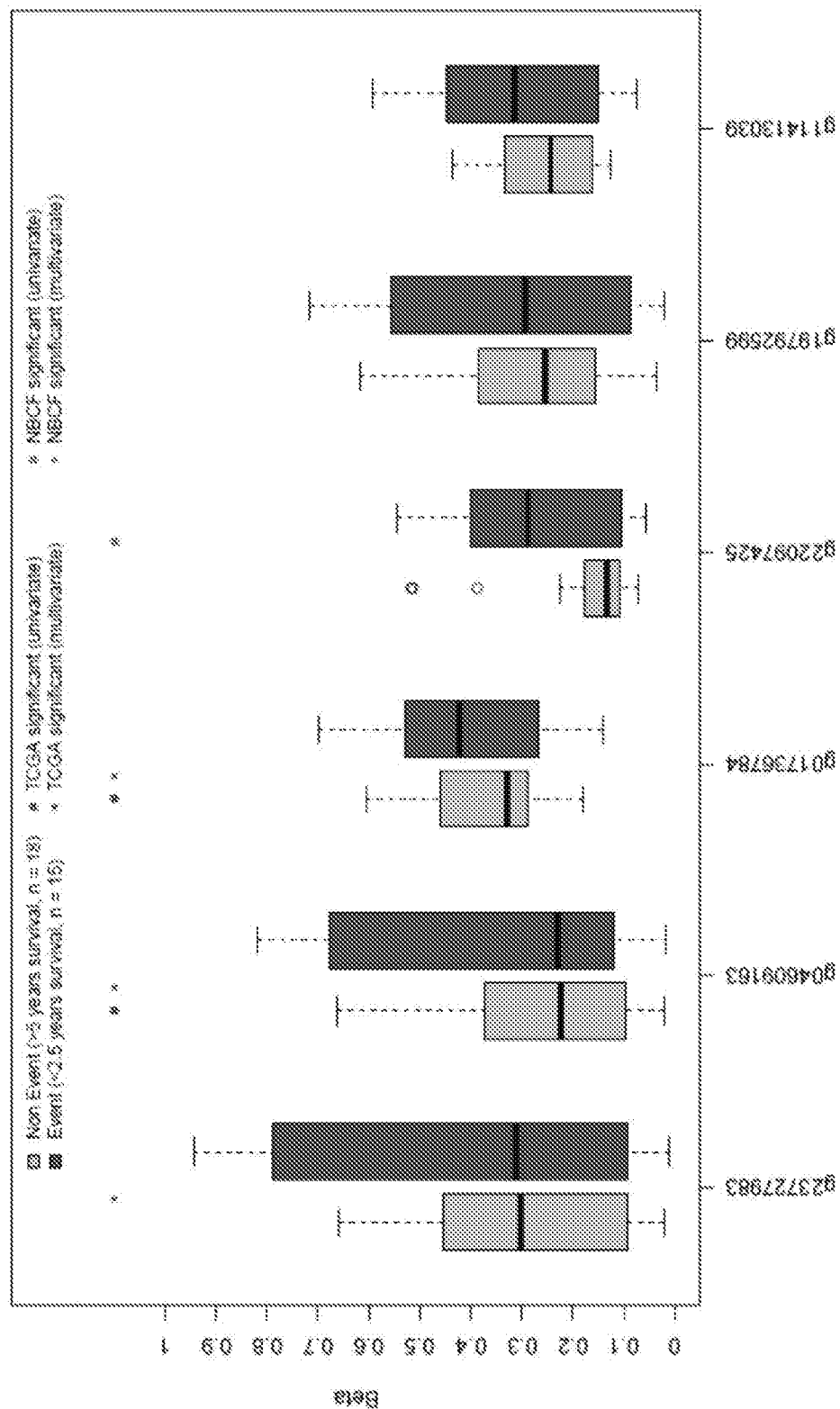

FIG. 129. This figure shows relative levels of methylation for probes in prognostic region designated chr11-24690 (as described in Table 14) for patients in good and poor prognosis groups.

Figure 130:
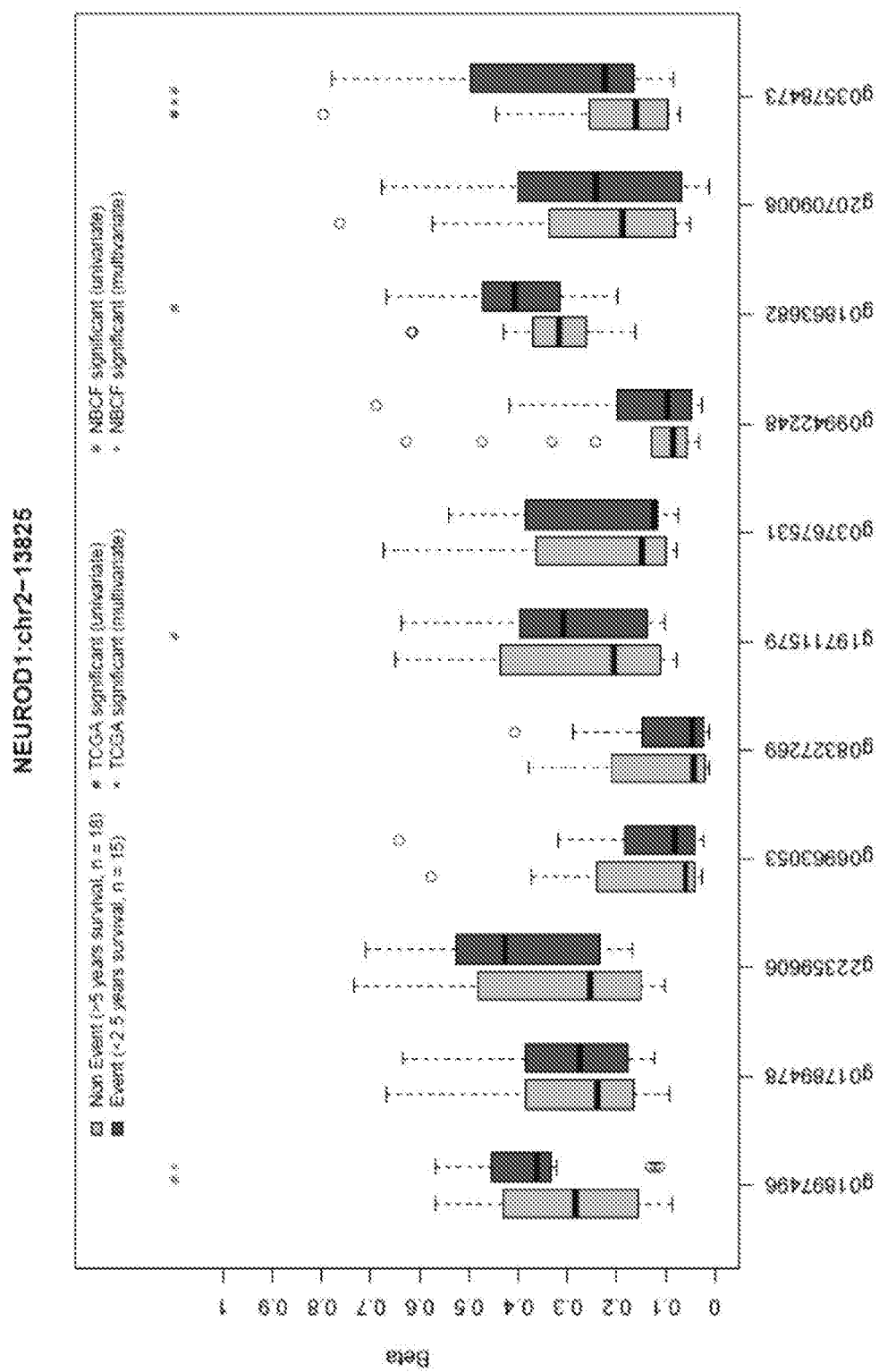

FIG. 130. This figure shows relative levels of methylation for probes in prognostic region designated chr2-13825 (as described in Table 14) for patients in good and poor prognosis groups.

Figure 131:
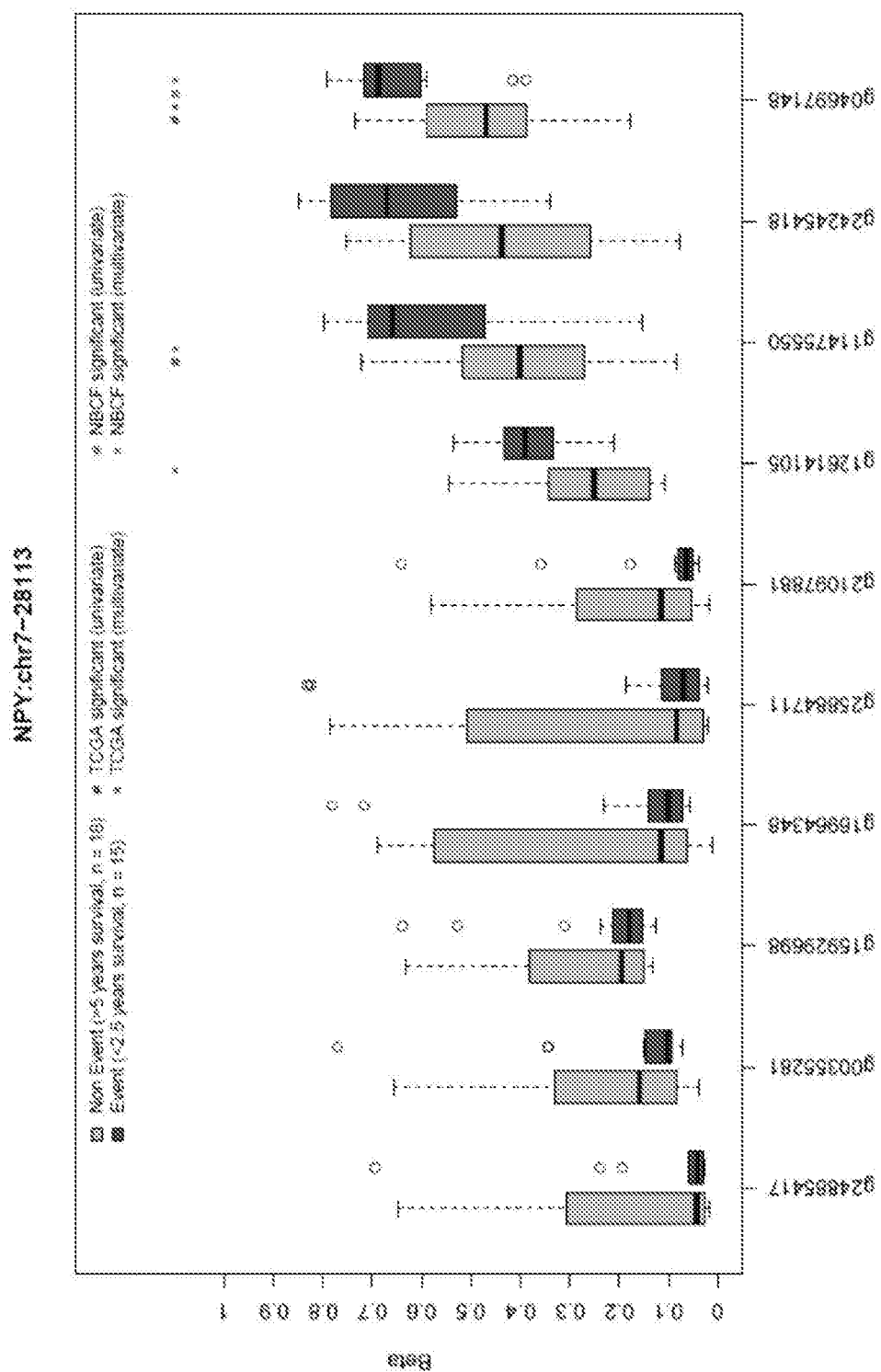

FIG. 131. This figure shows relative levels of methylation for probes in prognostic region designated chr7-28113 (as described in Table 14) for patients in good and poor prognosis groups.

Figure 132:
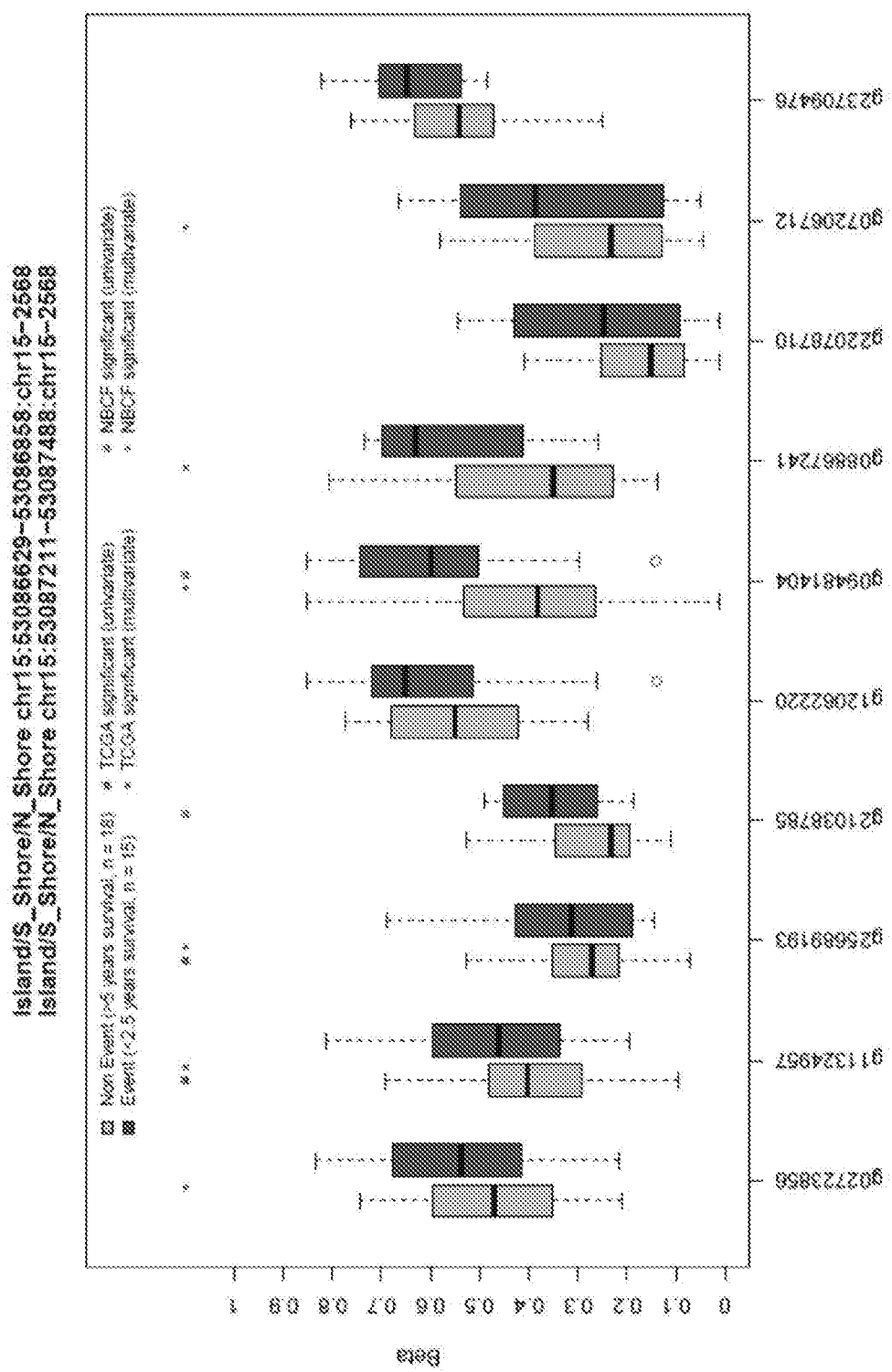

FIG. 132. This figure shows relative levels of methylation for probes in prognostic region designated chr15-2568 (as described in Table 14) for patients in good and poor prognosis groups.

Figure 133:
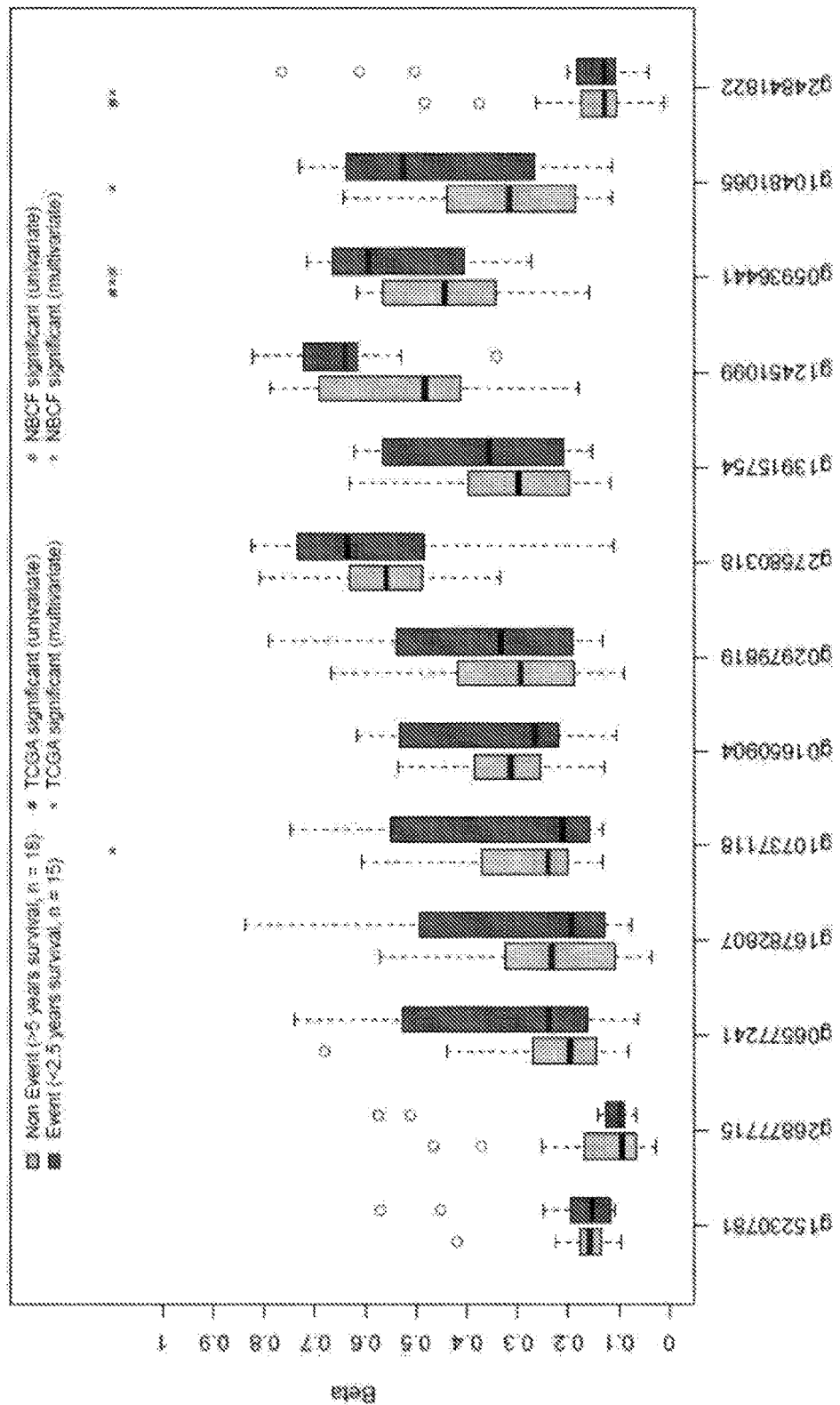

FIG. 133. This figure shows relative levels of methylation for probes in prognostic region designated chr20-11674 (as described in Table 14) for patients in good and poor prognosis groups.

Figure 134:
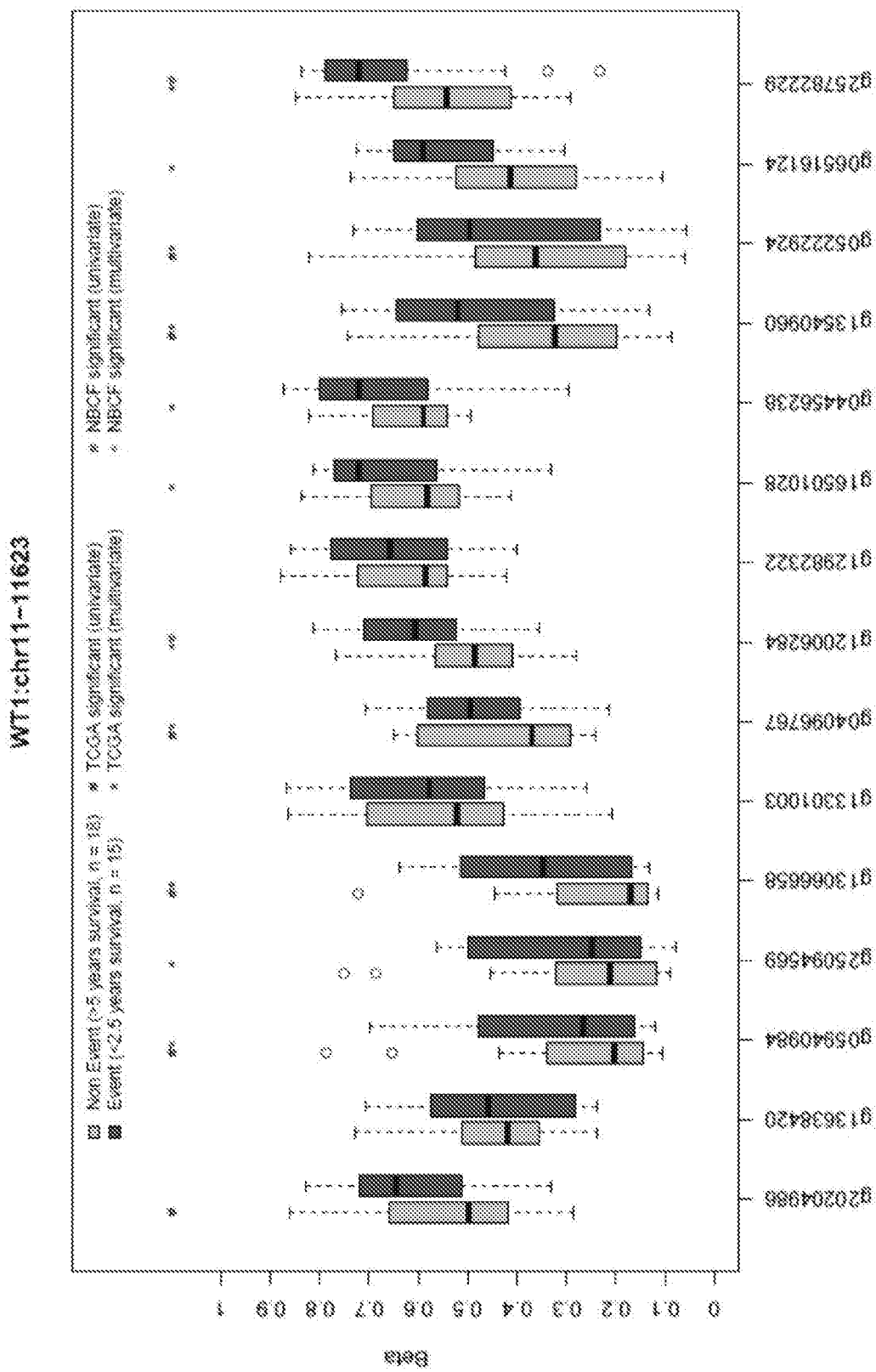

FIG. 134. This figure shows relative levels of methylation for probes in prognostic region designated chr11-11623 (as described in Table 14) for patients in good and poor prognosis groups.

Figure 135:
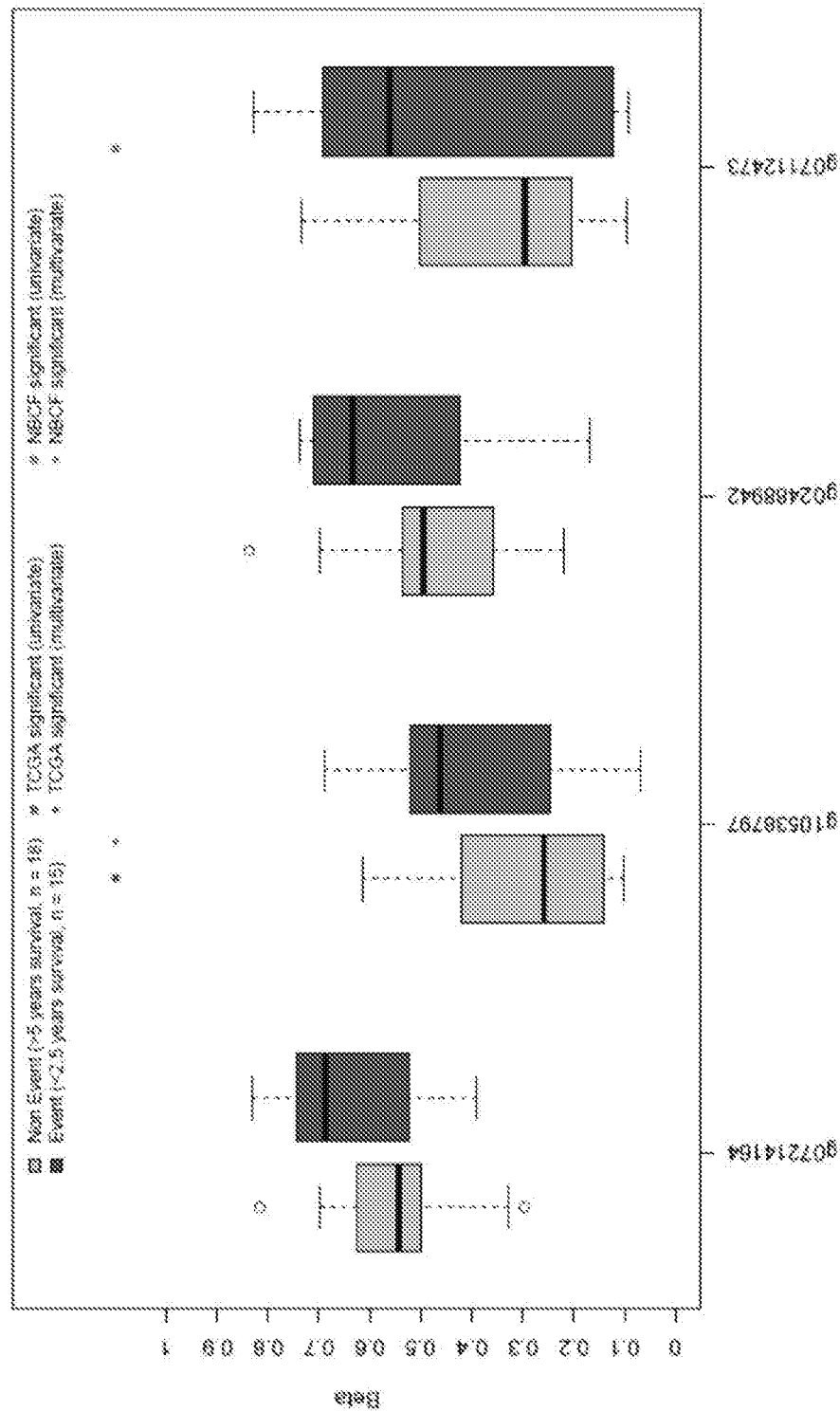

FIG. 135. This figure shows relative levels of methylation for probes in prognostic region designated chr2-26887 (as described in Table 14) for patients in good and poor prognosis groups.

Figure 136:
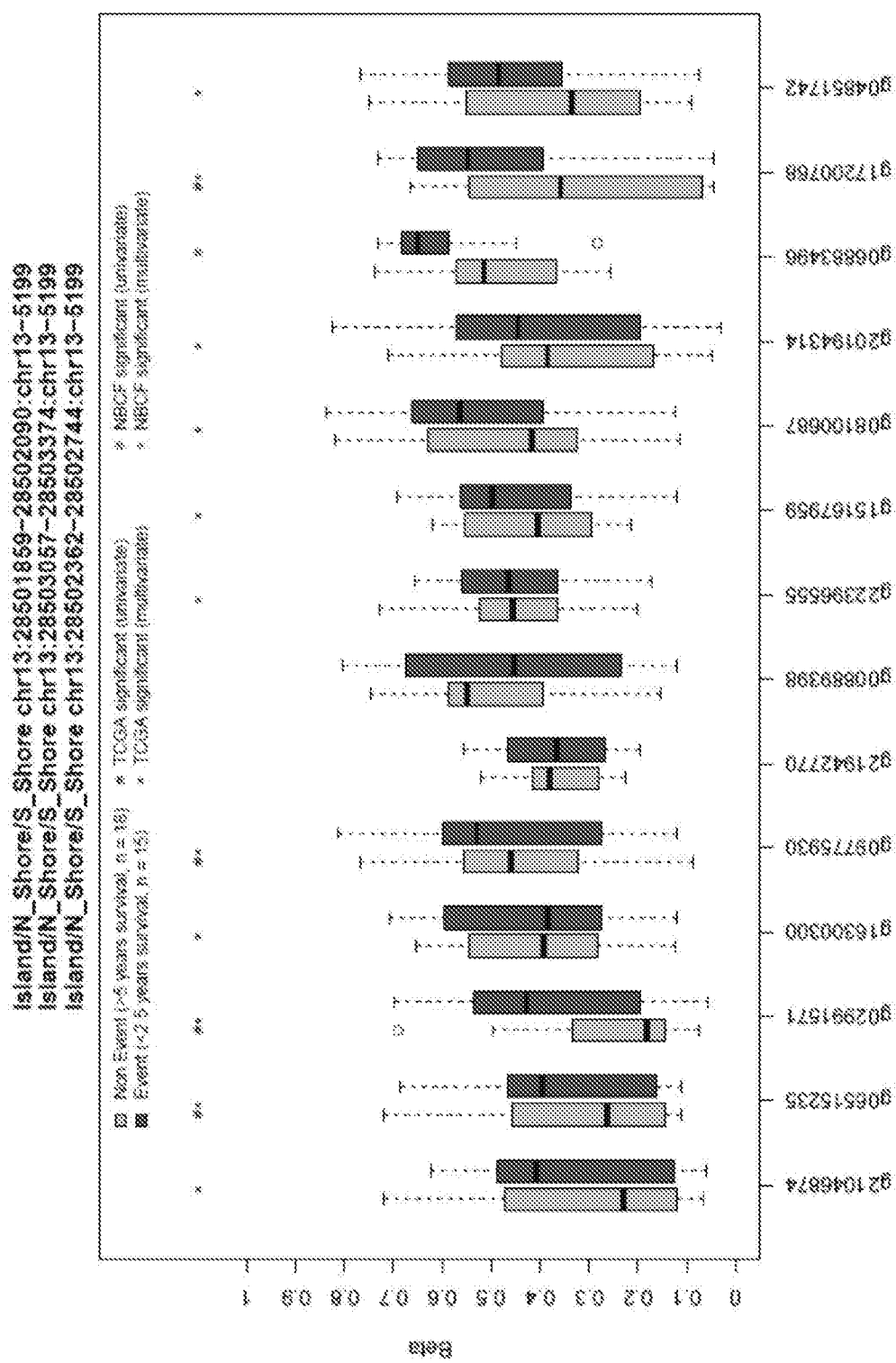

FIG. 136. This figure shows relative levels of methylation for probes in prognostic region designated chr13-5199 (as described in Table 14) for patients in good and poor prognosis groups.

Figure 137:
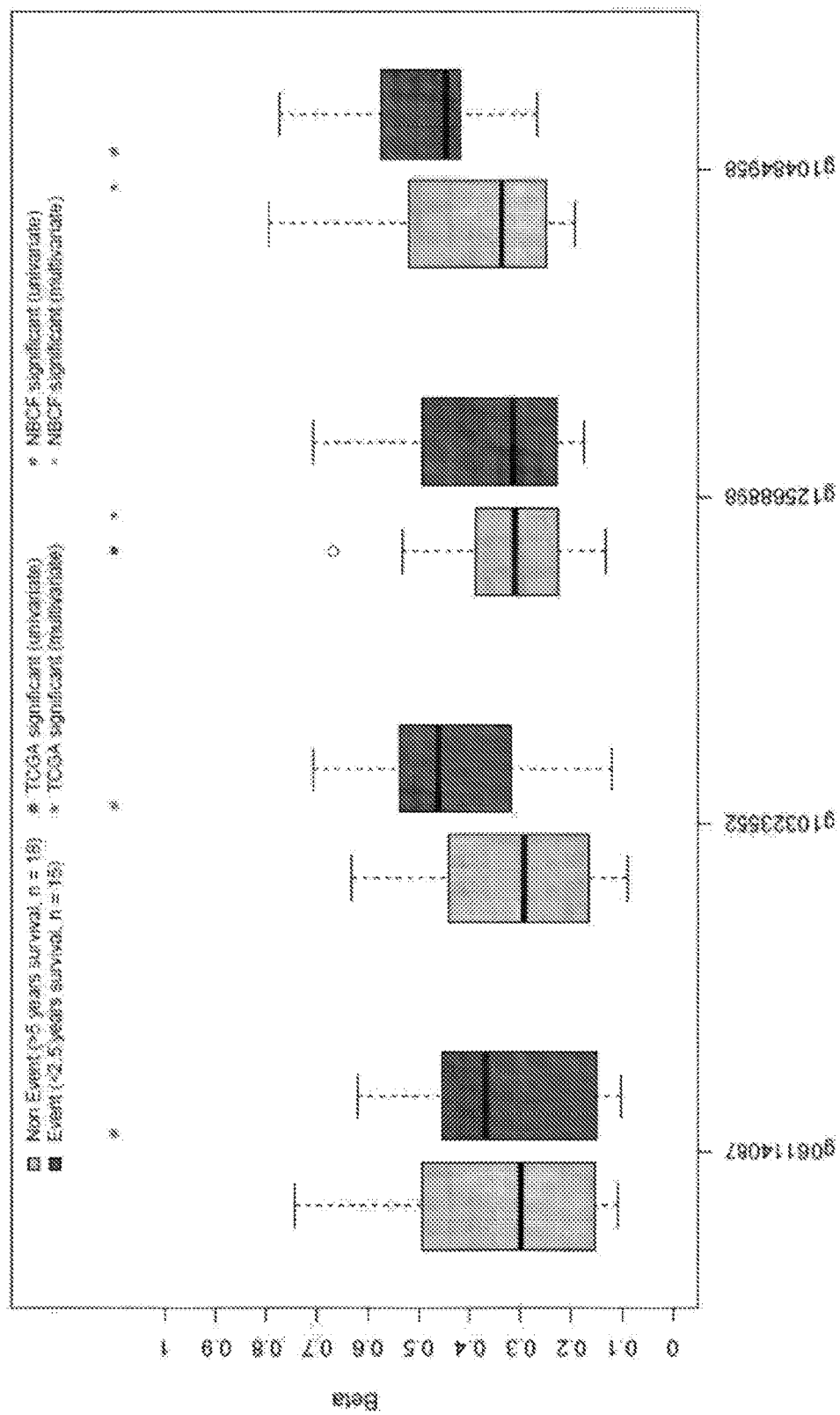

FIG. 137. This figure shows relative levels of methylation for probes in prognostic region designated chr13-5196 (as described in Table 14) for patients in good and poor prognosis groups.

Figure 138:
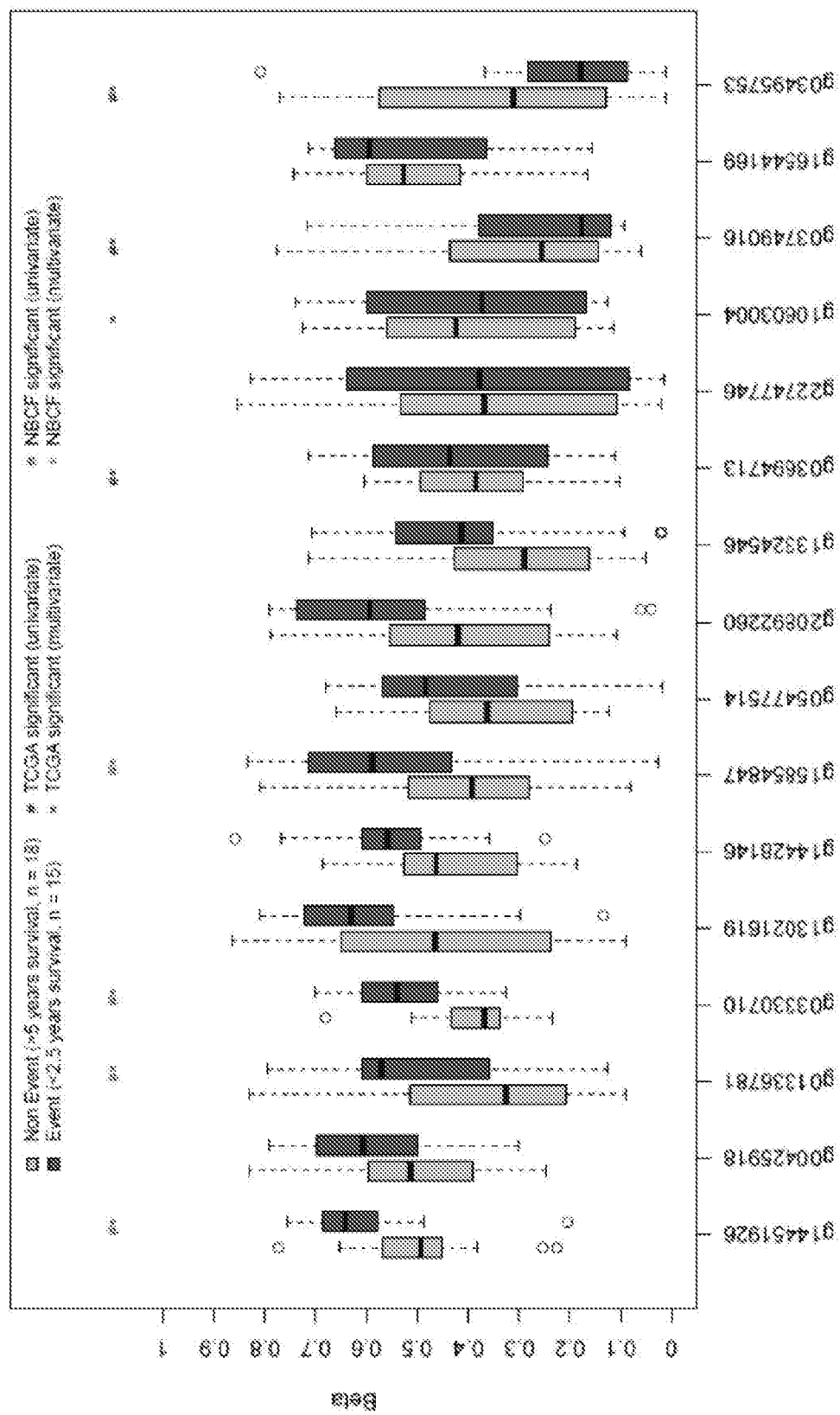

FIG. 138. This figure shows relative levels of methylation for probes in prognostic region designated chr8-13399 (as described in Table 14) for patients in good and poor prognosis groups.

Figure 139:
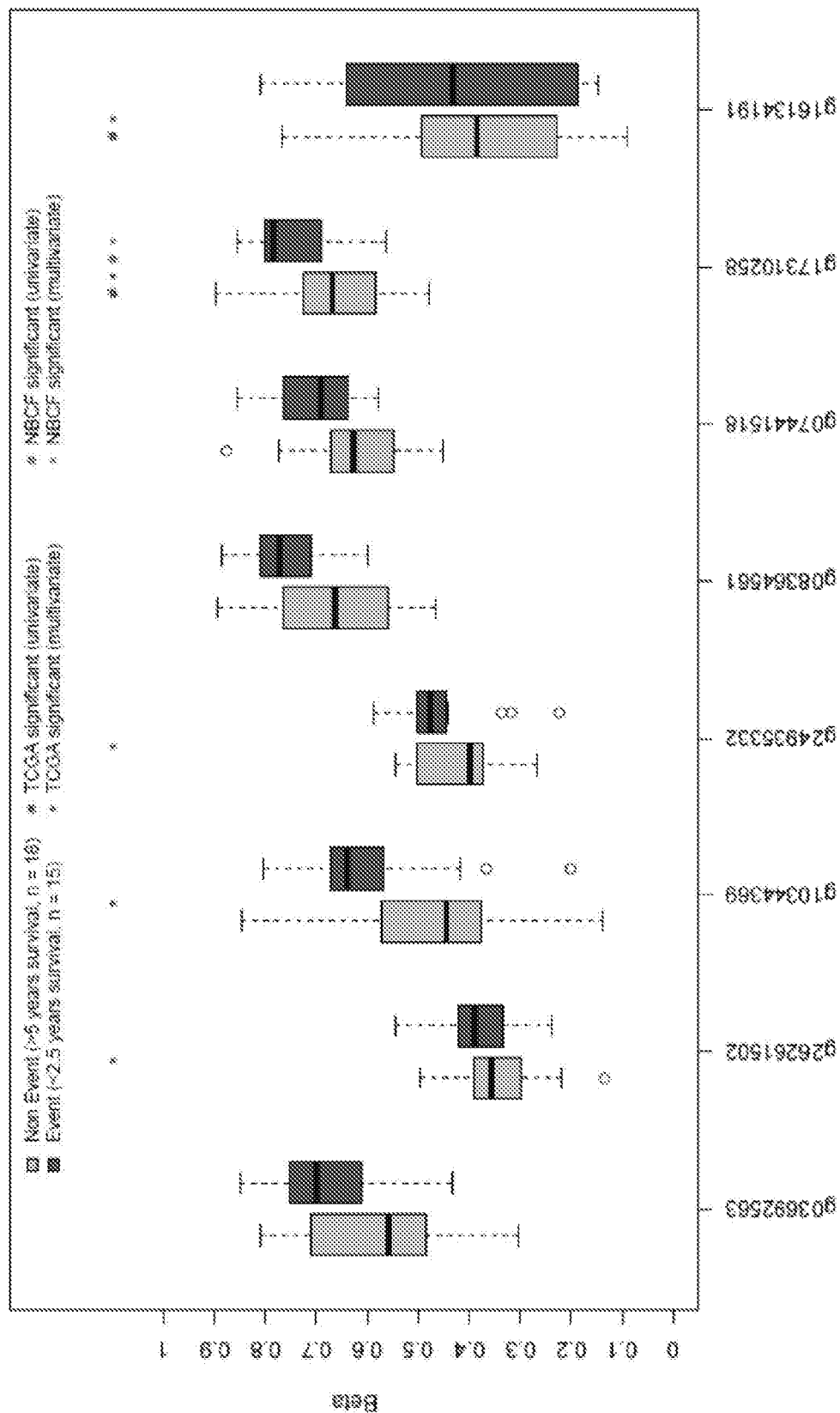

FIG. 139. This figure shows relative levels of methylation for probes in prognostic region designated chr11-18108 (as described in Table 14) for patients in good and poor prognosis groups.

Figure 140:
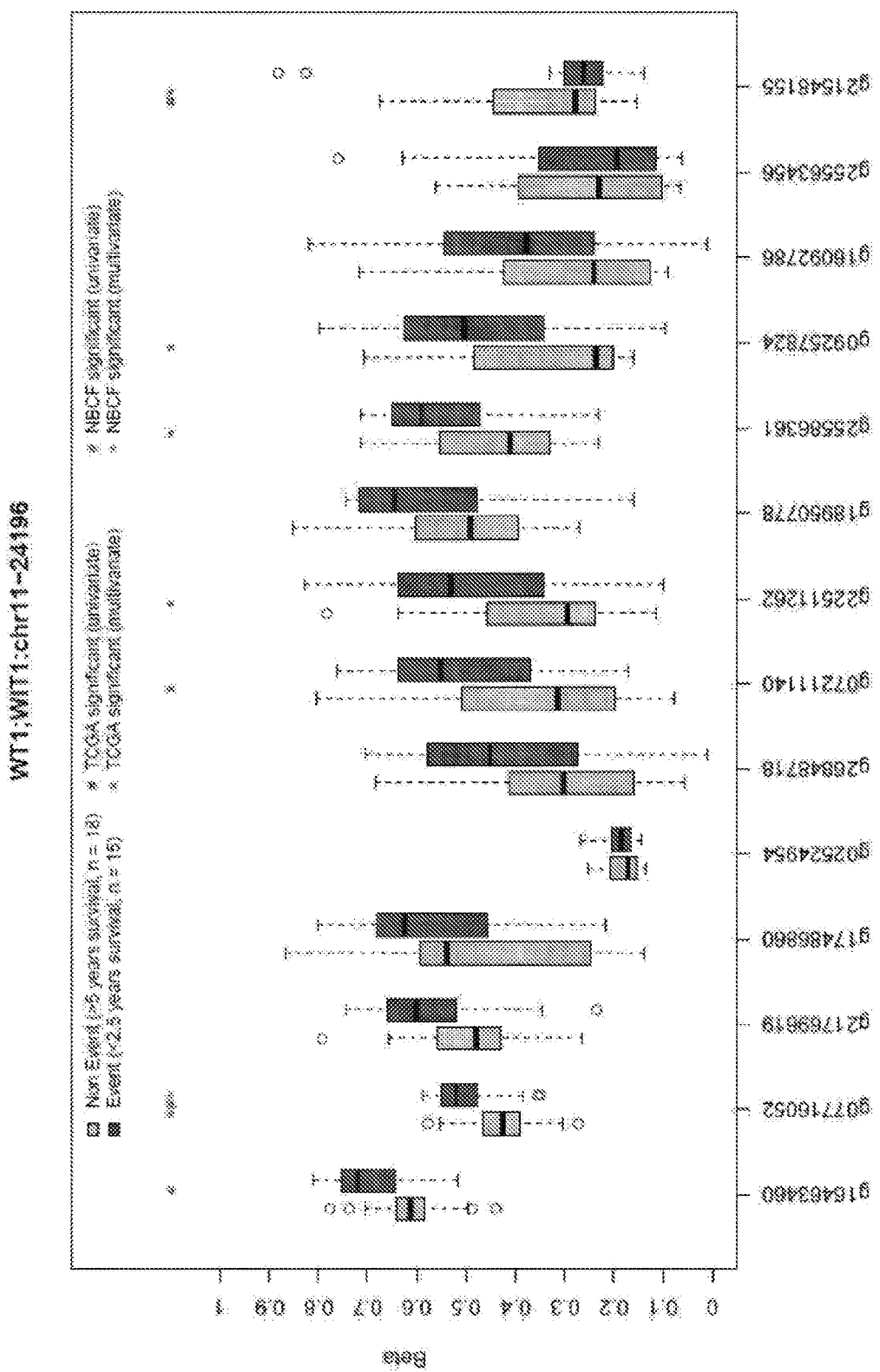

FIG. 140. This figure shows relative levels of methylation for probes in prognostic region designated chr11-24196 (as described in Table 14) for patients in good and poor prognosis groups.

Figure 141:
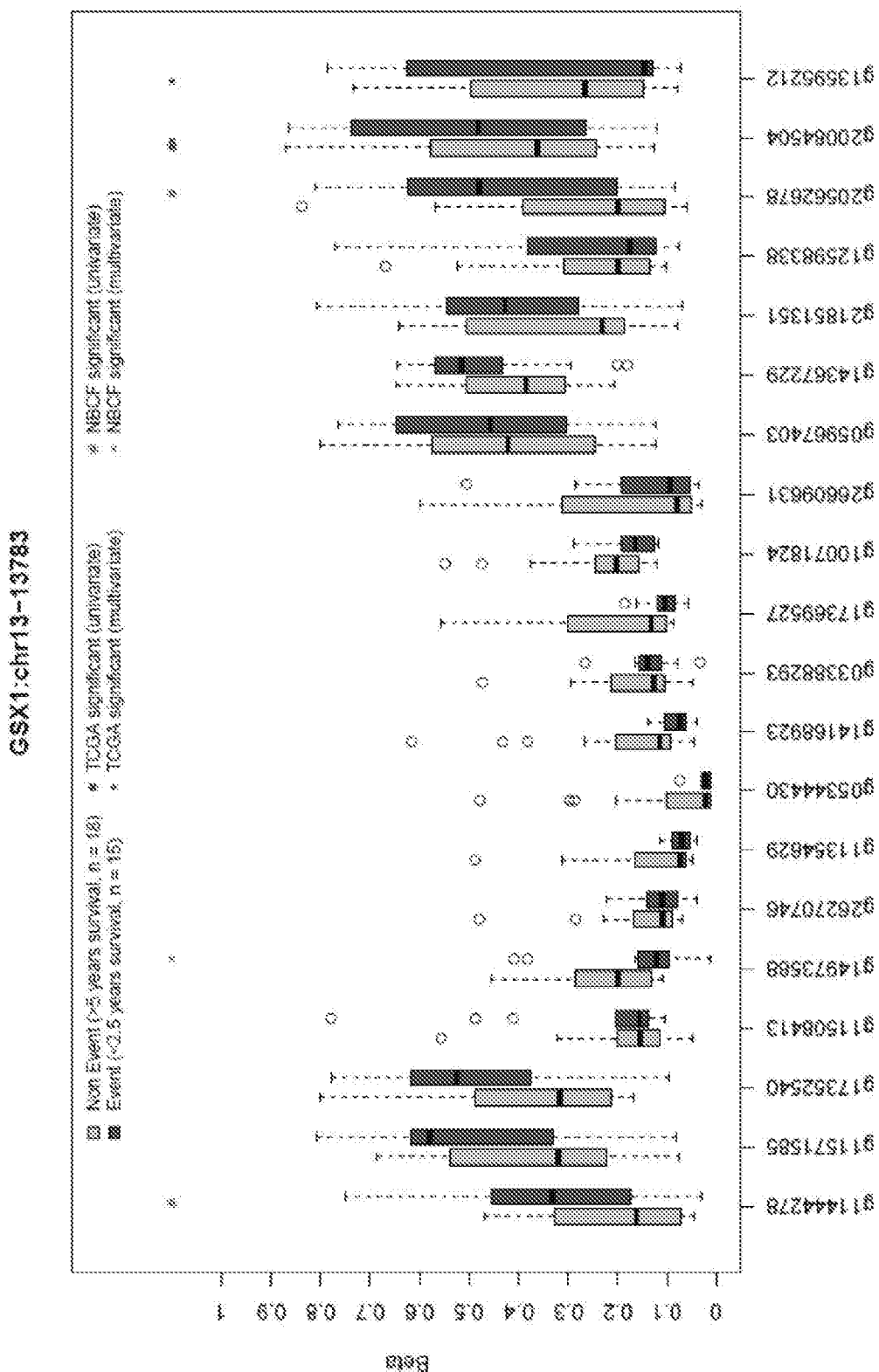

FIG. 141. This figure shows relative levels of methylation for probes in prognostic region designated chr13-13783 (as described in Table 14) for patients in good and poor prognosis groups.

Figure 142:
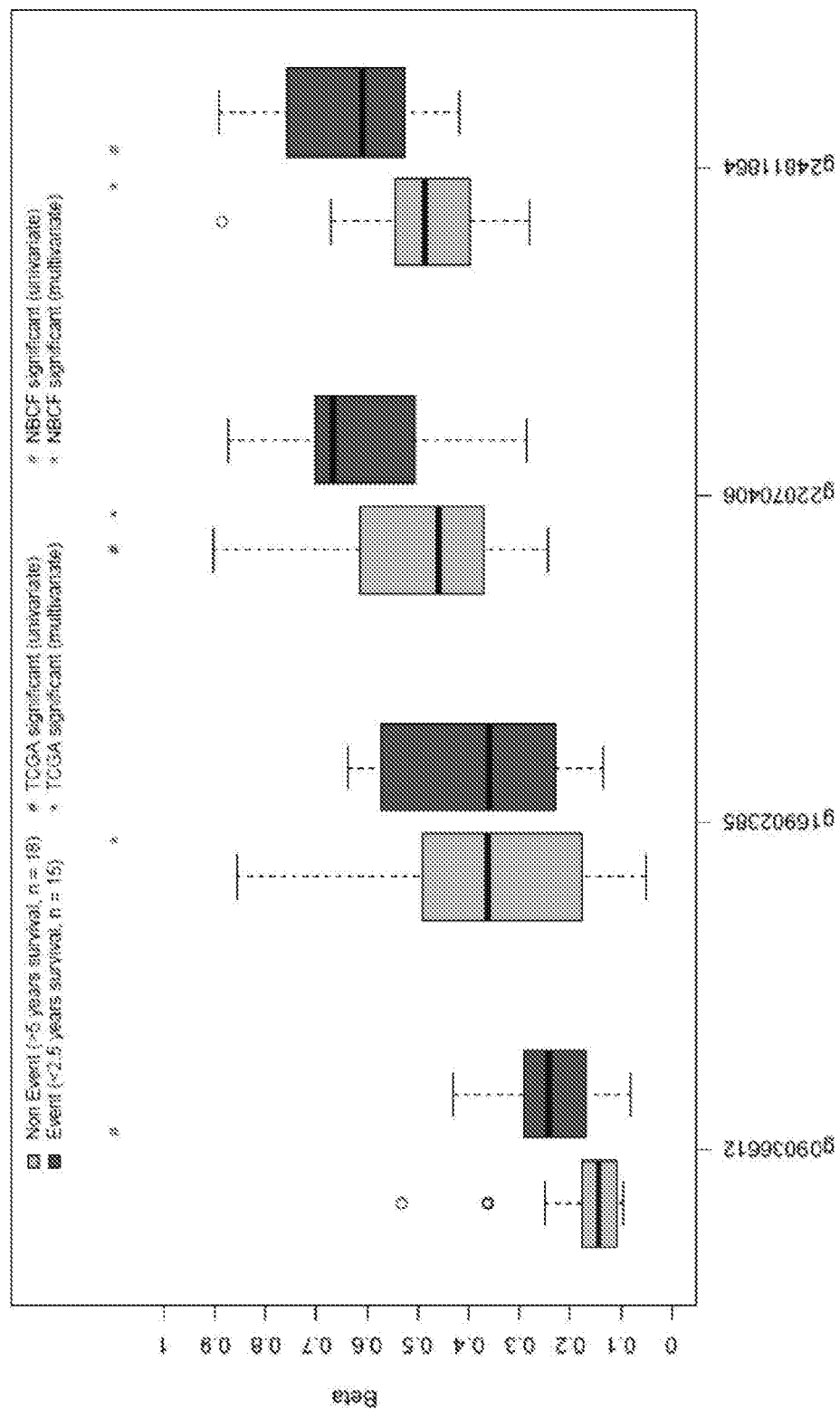

FIG. 142. This figure shows relative levels of methylation for probes in prognostic region designated chr18-11487 (as described in Table 14) for patients in good and poor prognosis groups.

Figure 143:
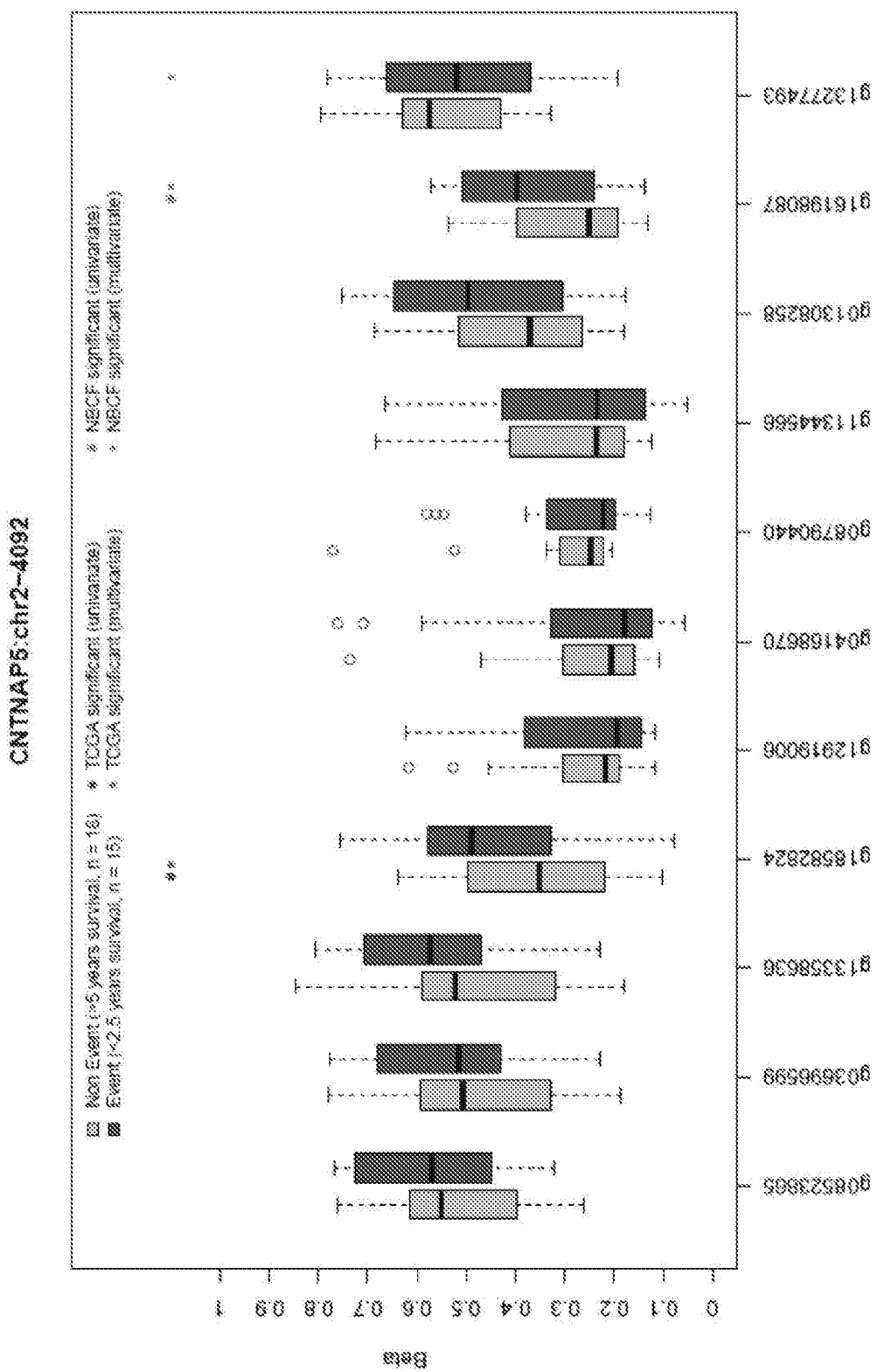

FIG. 143. This figure shows relative levels of methylation for probes in prognostic region designated chr2-4092 (as described in Table 14) for patients in good and poor prognosis groups.

Figure 144:
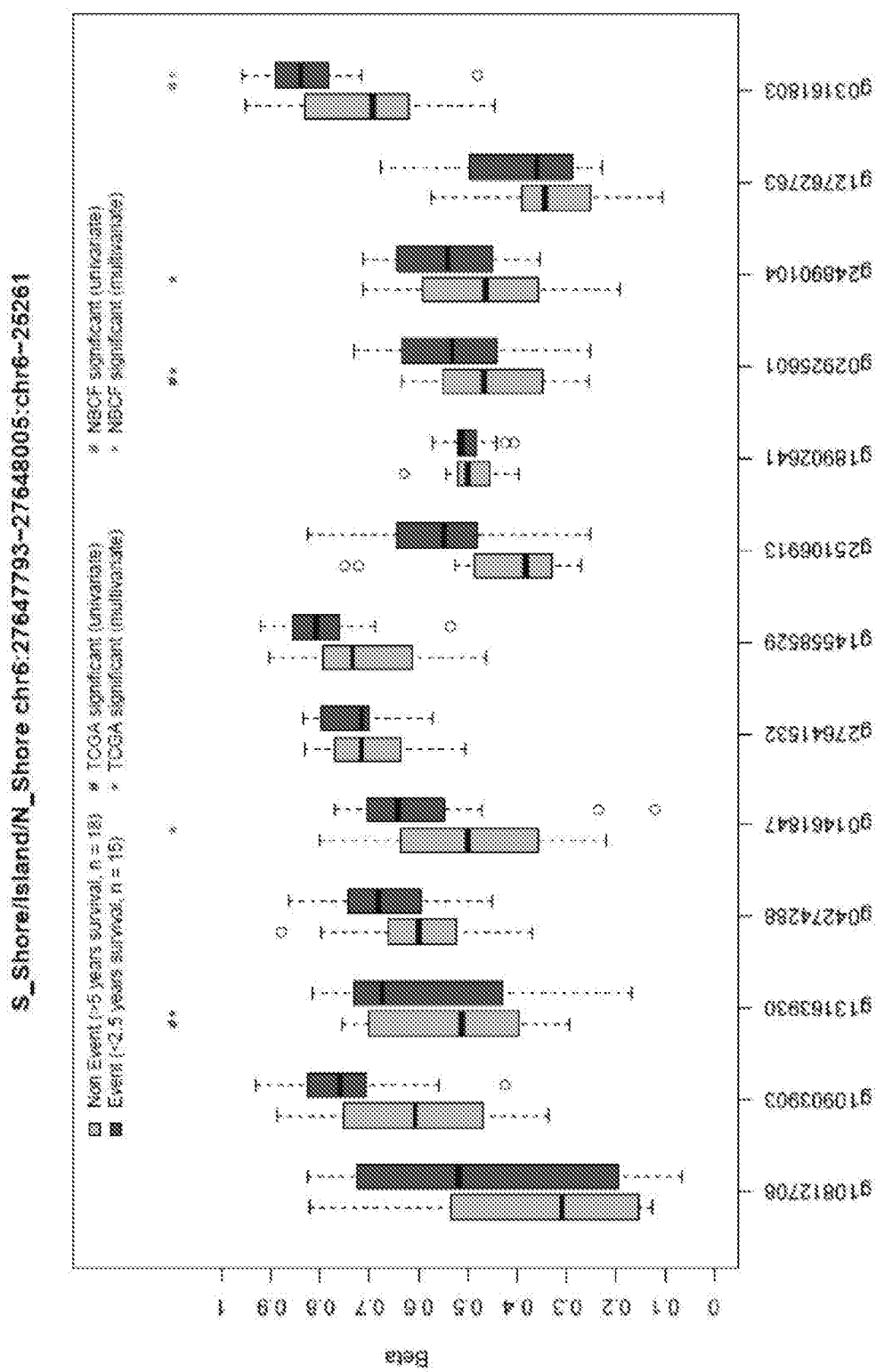

FIG. 144. This figure shows relative levels of methylation for probes in prognostic region designated chr6-25261 (as described in Table 14) for patients in good and poor prognosis groups.

Figure 145:
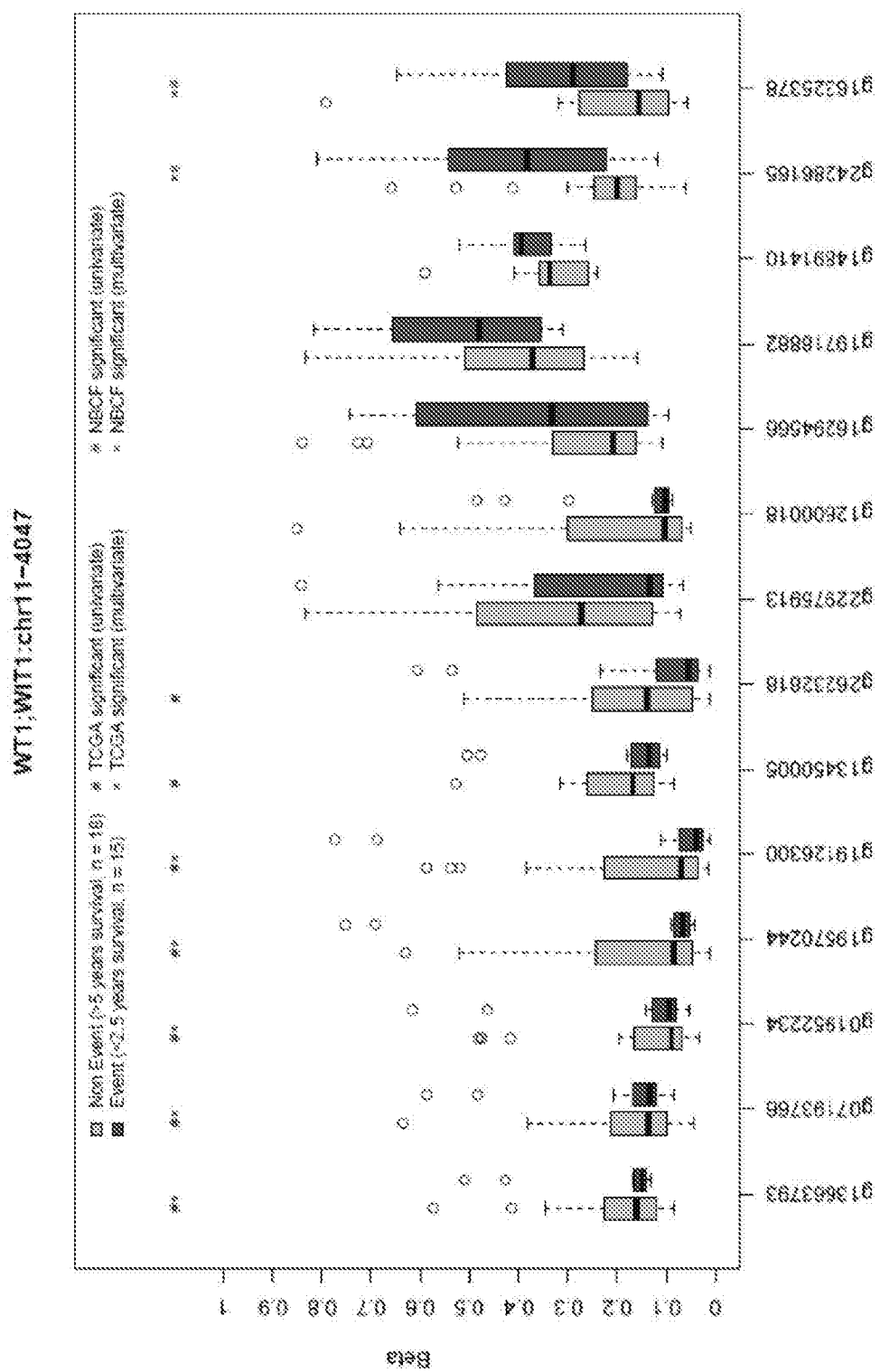

FIG. 145. This figure shows relative levels of methylation for probes in prognostic region designated chr11-4047 (as described in Table 14) for patients in good and poor prognosis groups.

Figure 146:
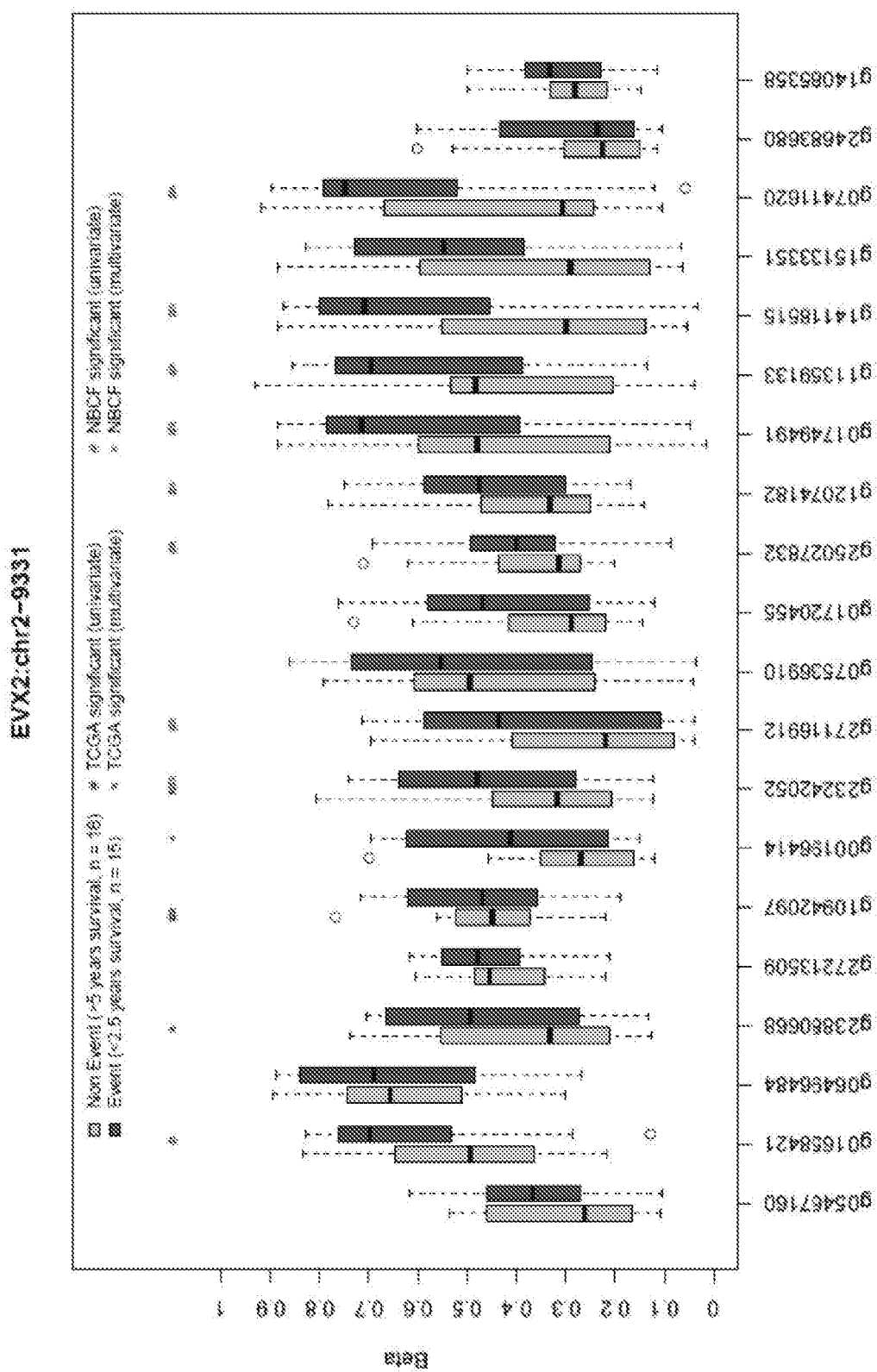

FIG. 146. This figure shows relative levels of methylation for probes in prognostic region designated chr2-9331 (as described in Table 14) for patients in good and poor prognosis groups.

Figure 147:
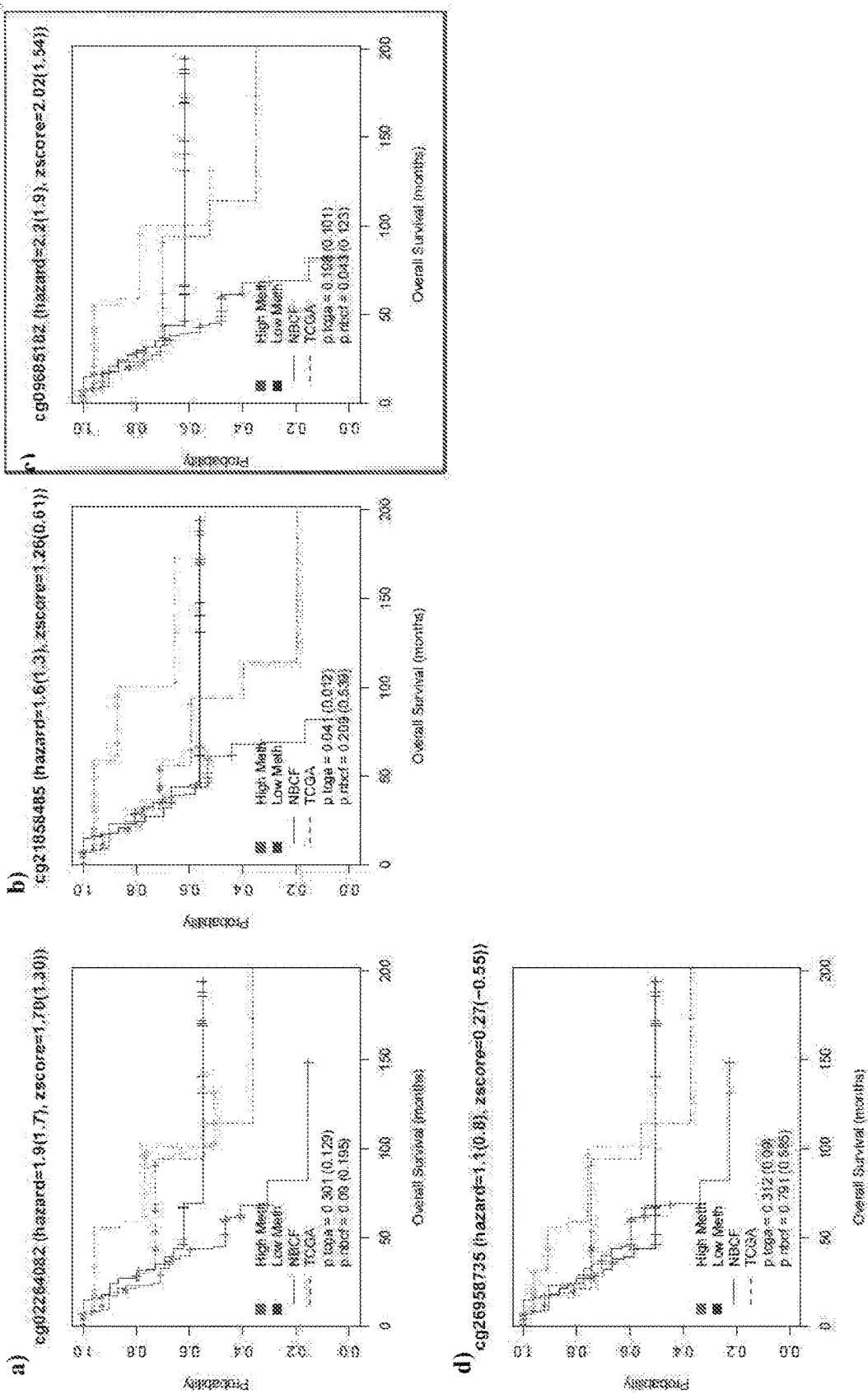

FIG. 147. This figure provides Kaplan Meier plots for each of the probes in prognostic region designated chr3-1415 (as described in Table 14) based on methylation between survival groups in the NBCF cohort. Probes within prognostic region which are statistically significant for predicting patient outcome are boxed.

Figure 148:
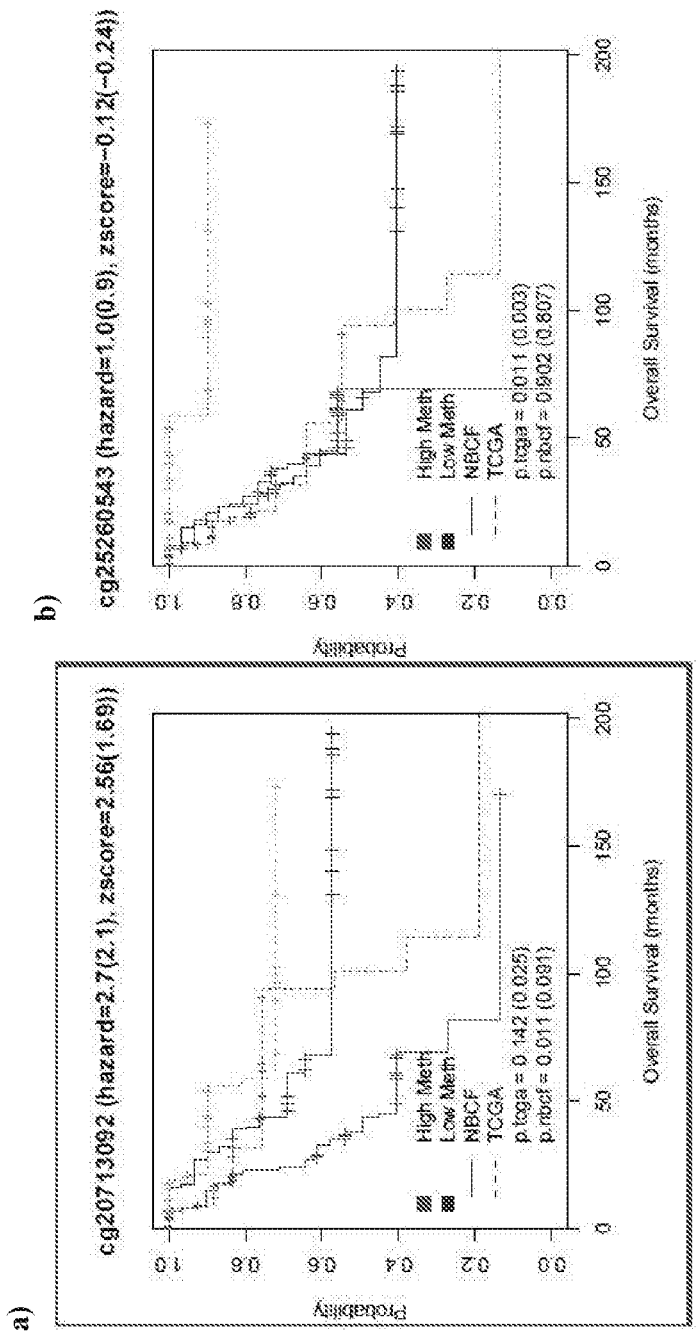

FIG. 148. This figure provides Kaplan Meier plots for each of the probes in prognostic region designated chr7-12819 (as described in Table 14) based on methylation between survival groups in the NBCF cohort. Probes within prognostic region which are statistically significant for predicting patient outcome are boxed.

Figure 149:
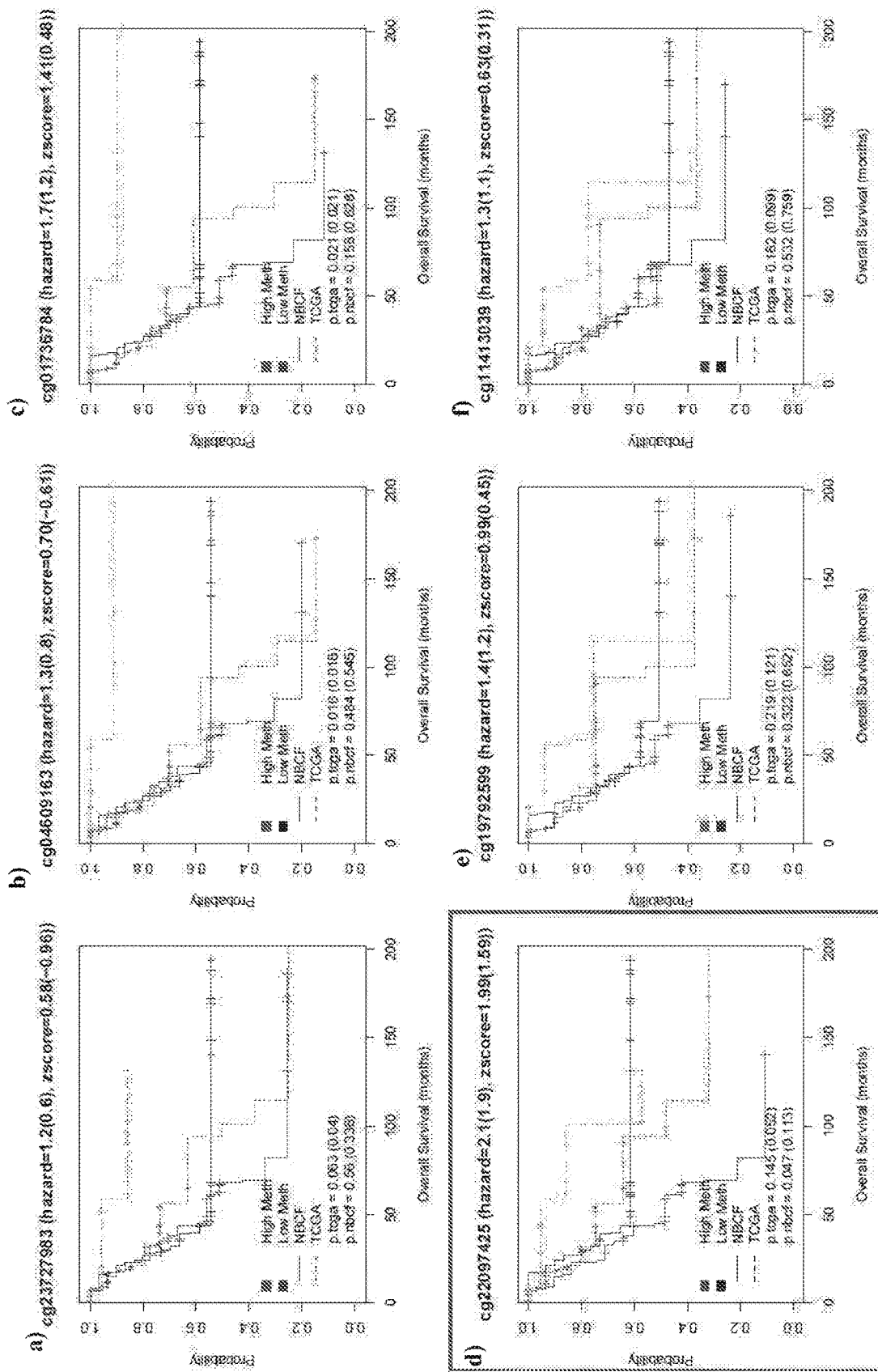

FIG. 149. This figure provides Kaplan Meier plots for each of the probes in prognostic region designated chr11-24690 (as described in Table 14) based on methylation between survival groups in the NBCF cohort. Probes within prognostic region which are statistically significant for predicting patient outcome are boxed.

Figure 150:
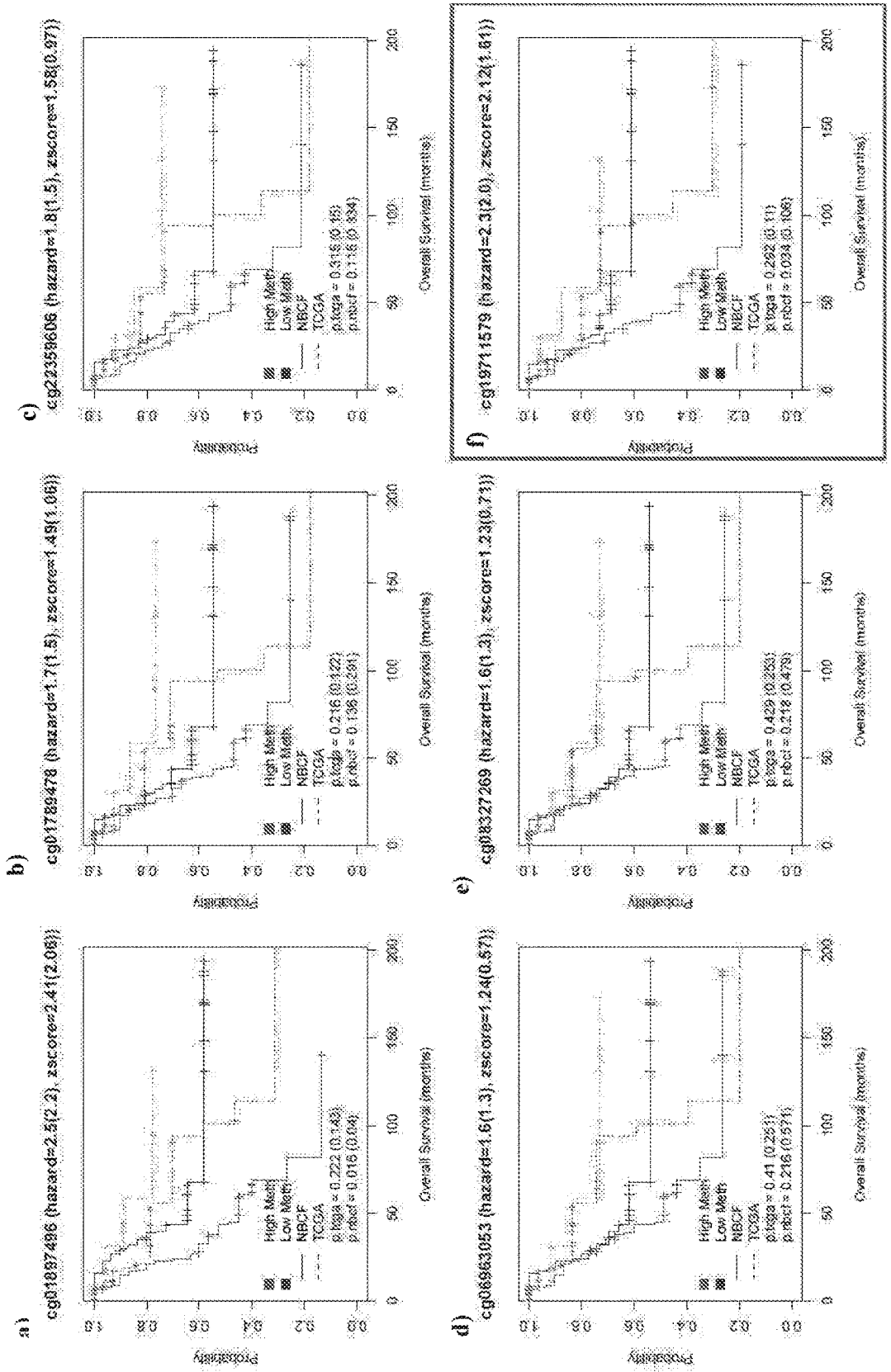
Figure 150:
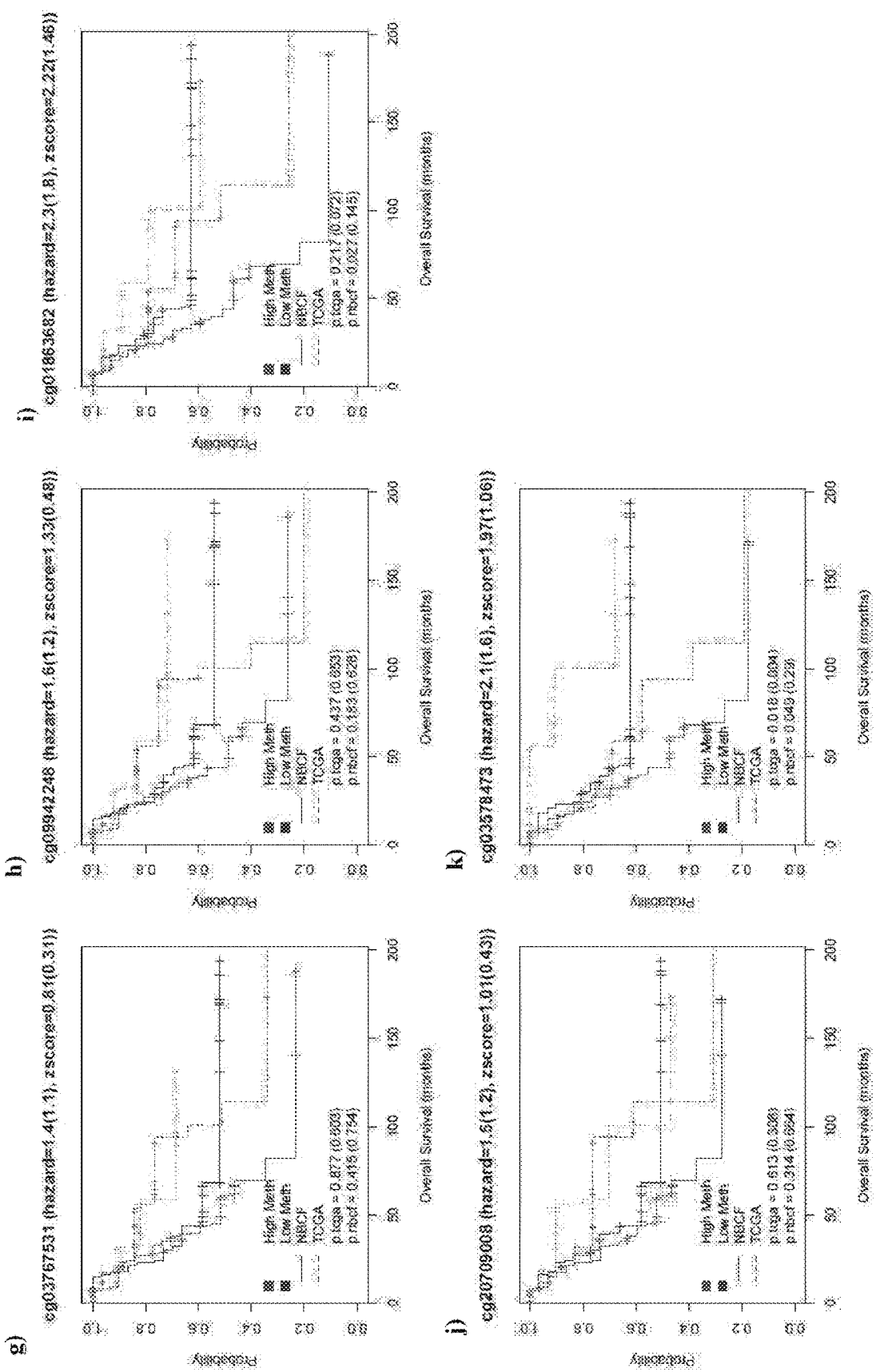

FIG. 150. This figure provides Kaplan Meier plots for each of the probes in prognostic region designated chr2-13825 (as described in Table 14) based on methylation between survival groups in the NBCF cohort. Probes within prognostic region which are statistically significant for predicting patient outcome are boxed.

Figure 151:
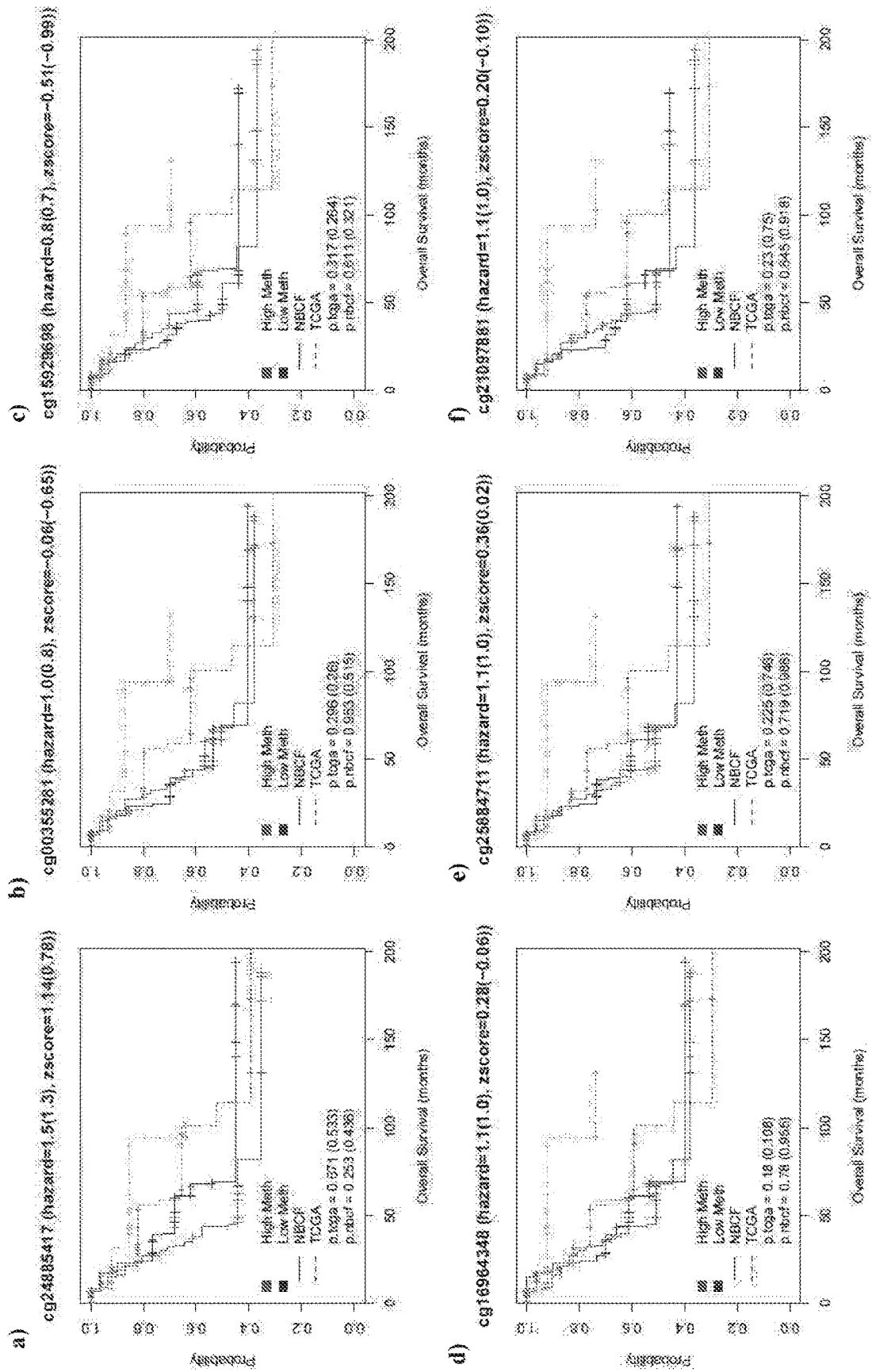
Figure 151:
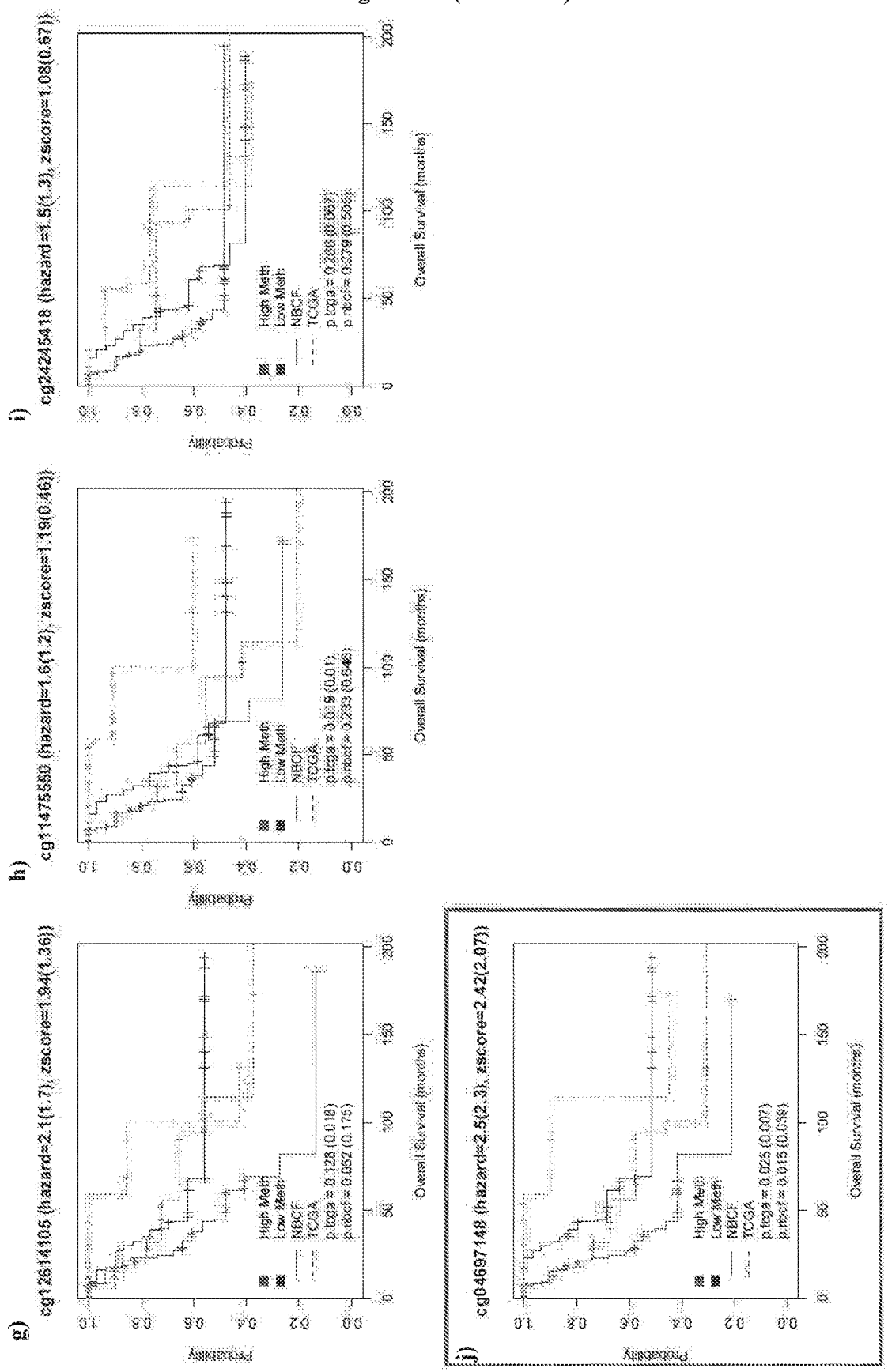

FIG. 151. This figure provides Kaplan Meier plots for each of the probes in prognostic region designated chr7-28113 (as described in Table 14) based on methylation between survival groups in the NBCF cohort. Probes within prognostic region which are statistically significant for predicting patient outcome are boxed.

Figure 152:
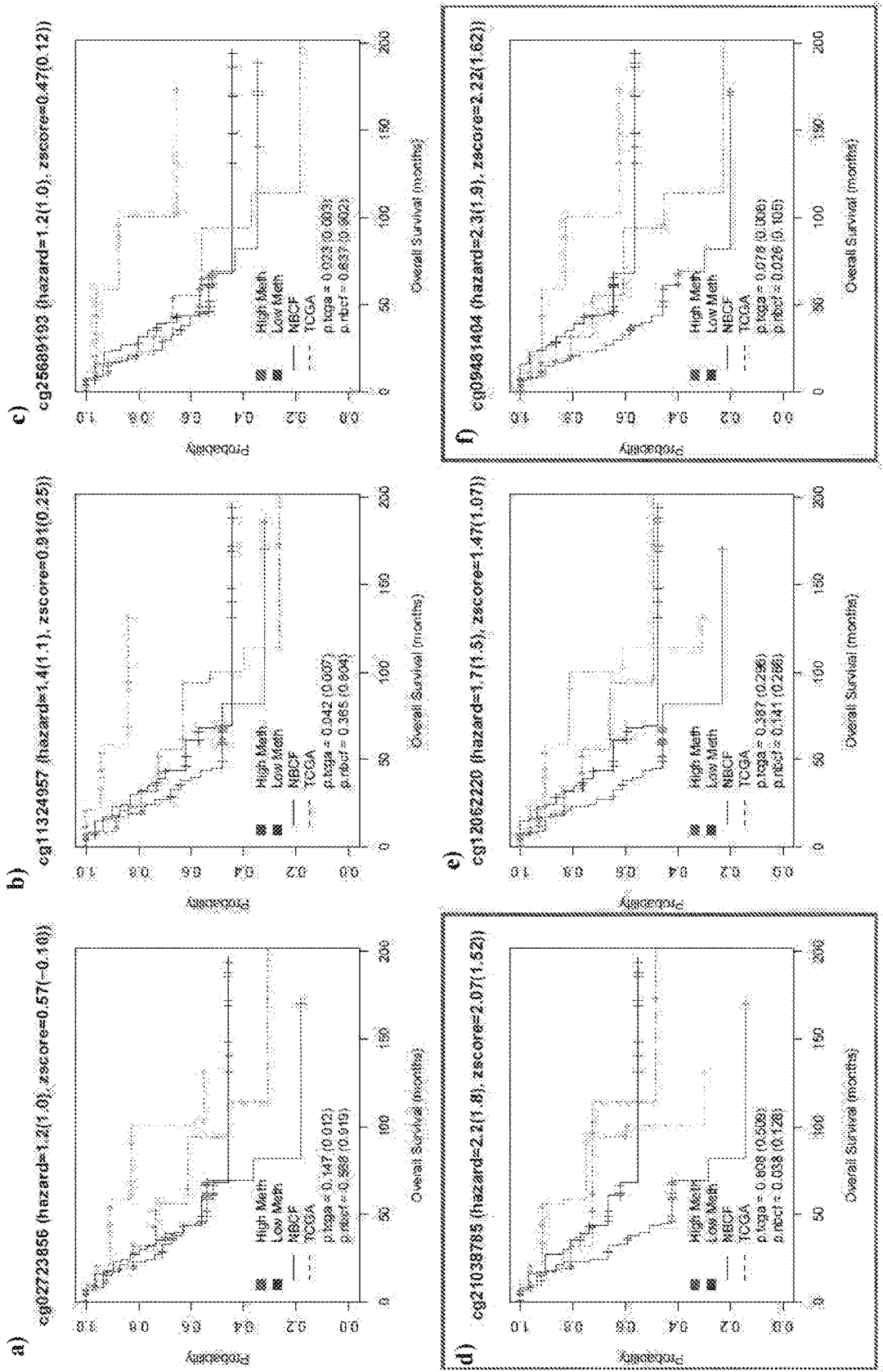
Figure 152:
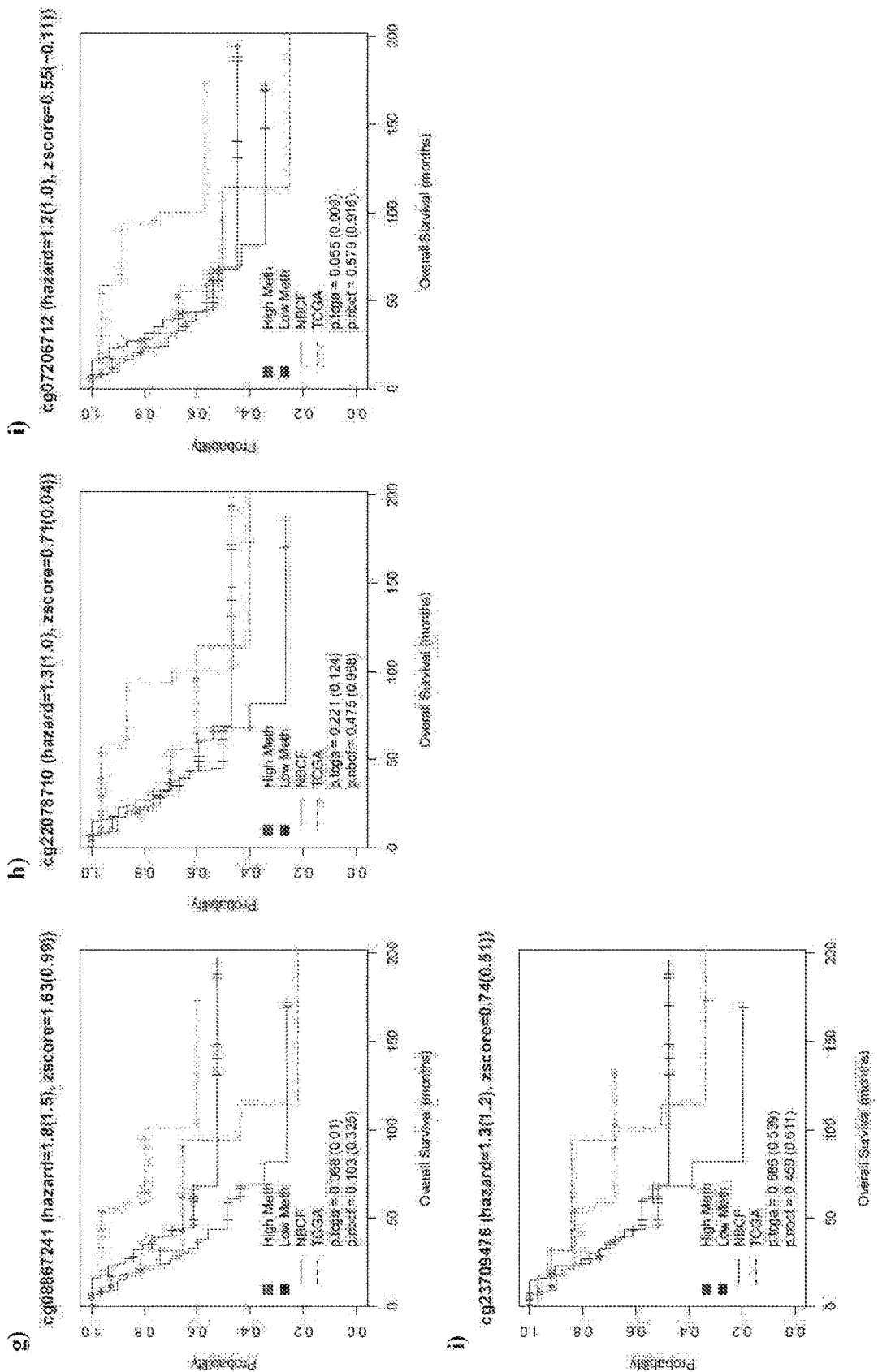

FIG. 152. This figure provides Kaplan Meier plots for each of the probes in prognostic region designated chr15-2568 (as described in Table 14) based on methylation between survival groups in the NBCF cohort. Probes within prognostic region which are statistically significant for predicting patient outcome are boxed.

Figure 153:
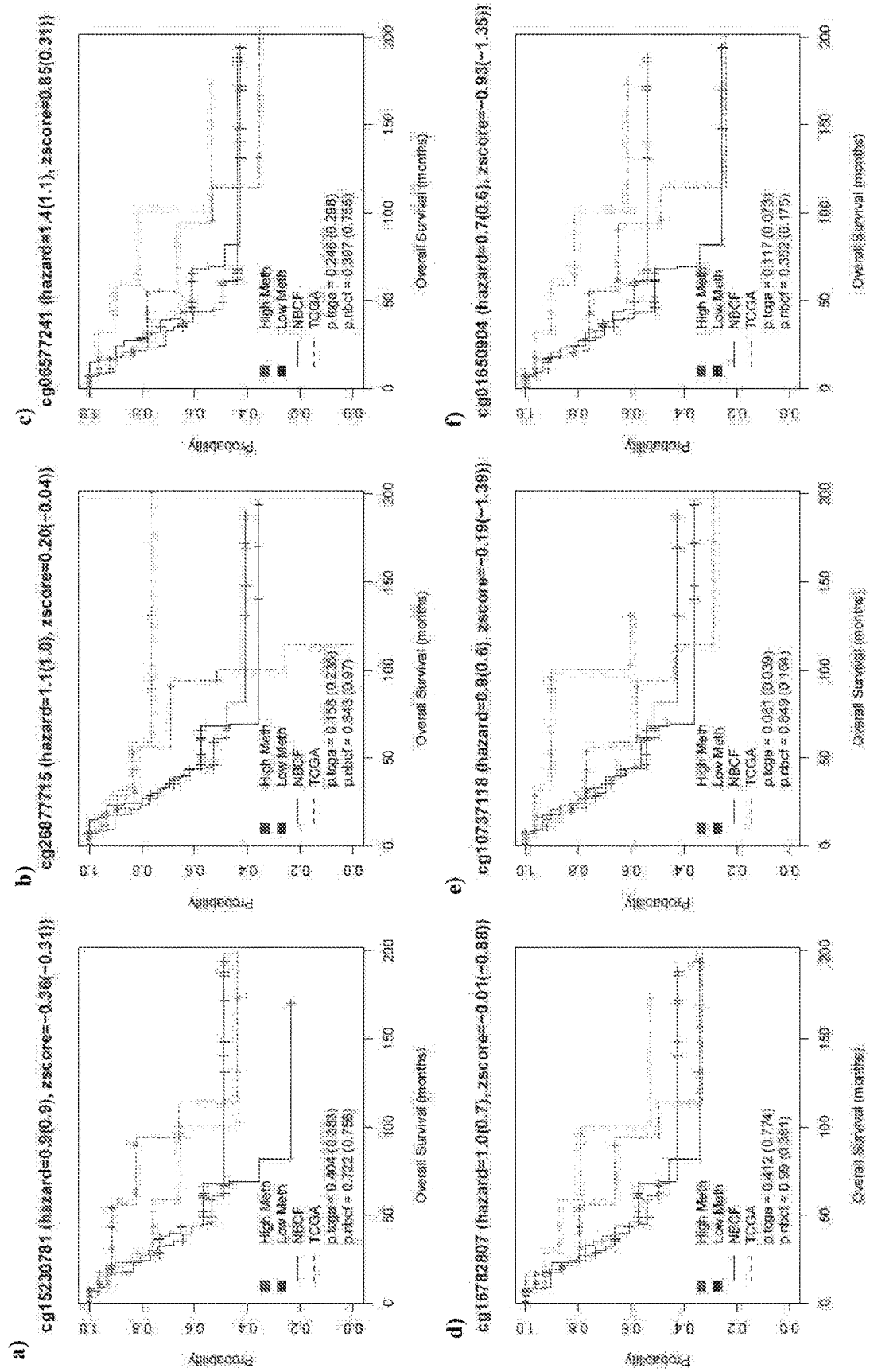
Figure 153:
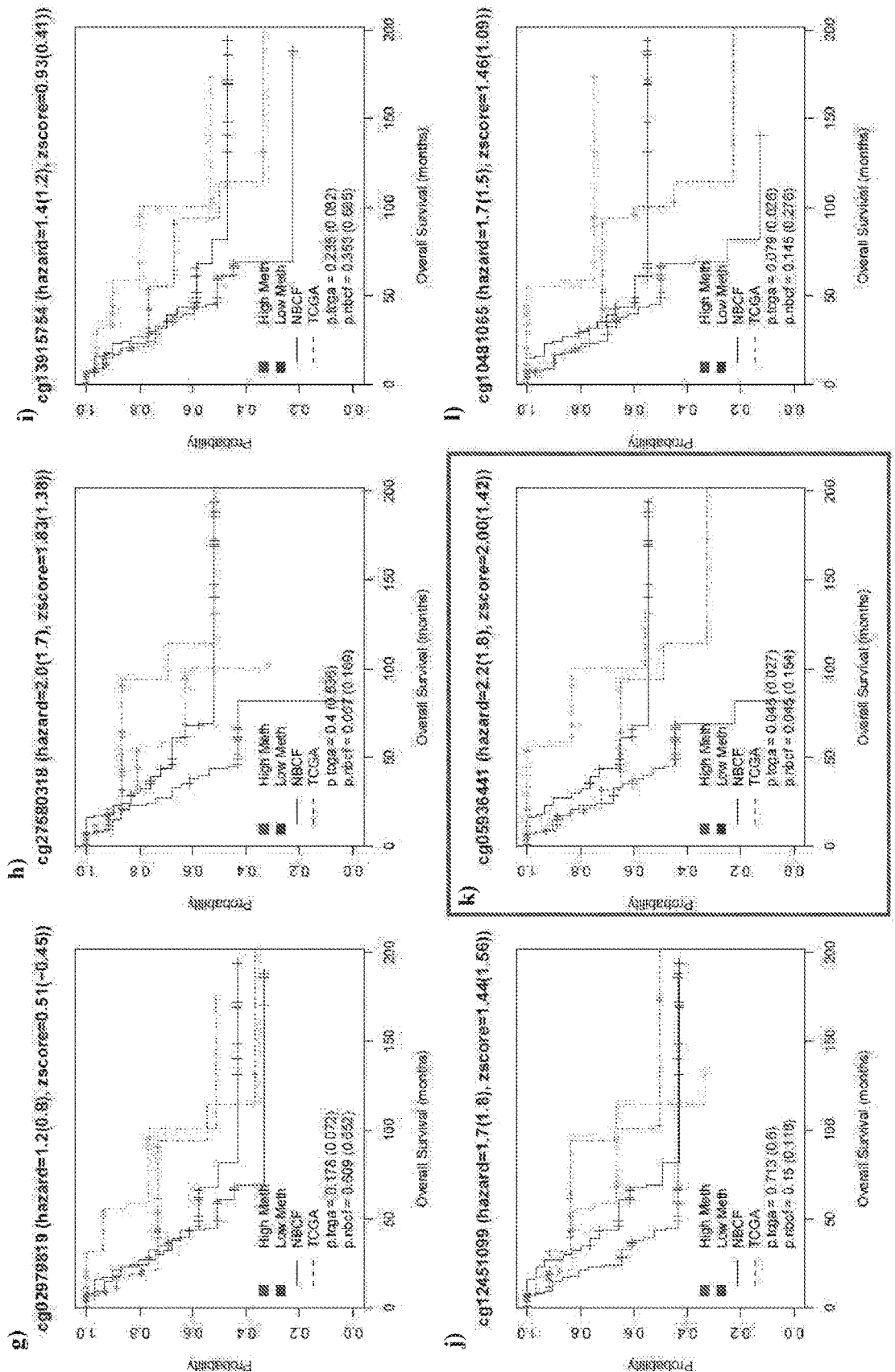
Figure 153:
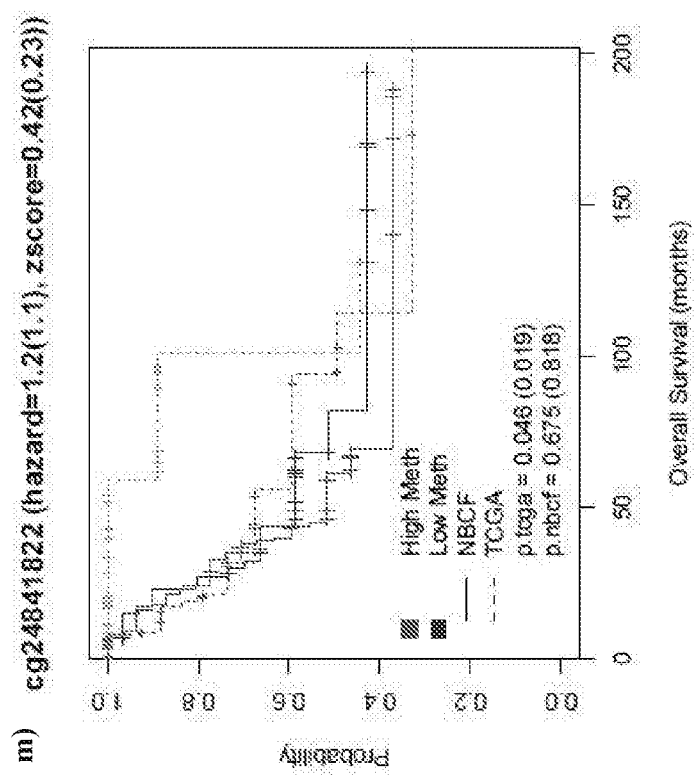

FIG. 153. This figure provides Kaplan Meier plots for each of the probes in prognostic region designated chr20-11674 (as described in Table 14) based on methylation between survival groups in the NBCF cohort. Probes within prognostic region which are statistically significant for predicting patient outcome are boxed.

Figure 154:
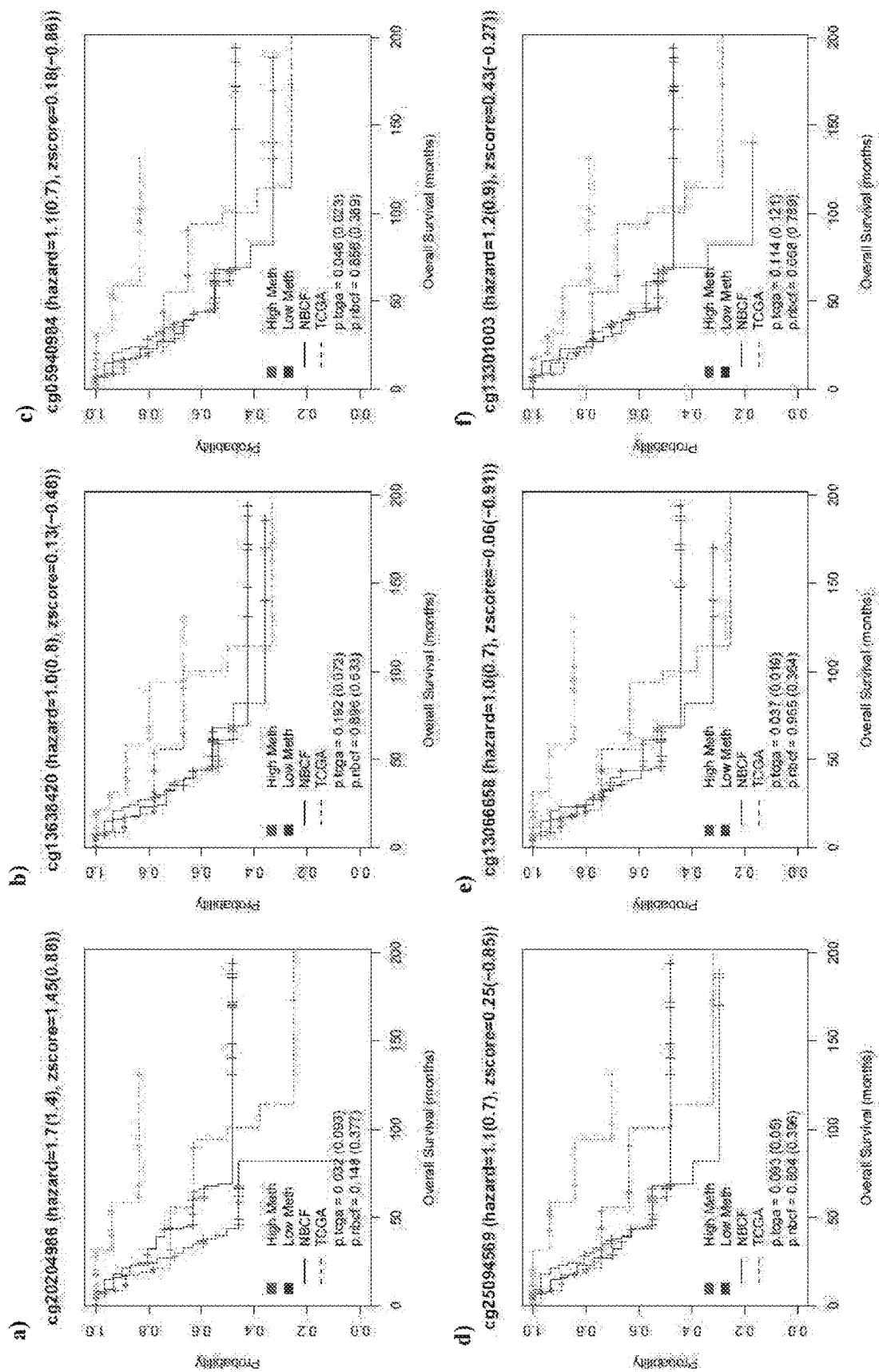
Figure 154:
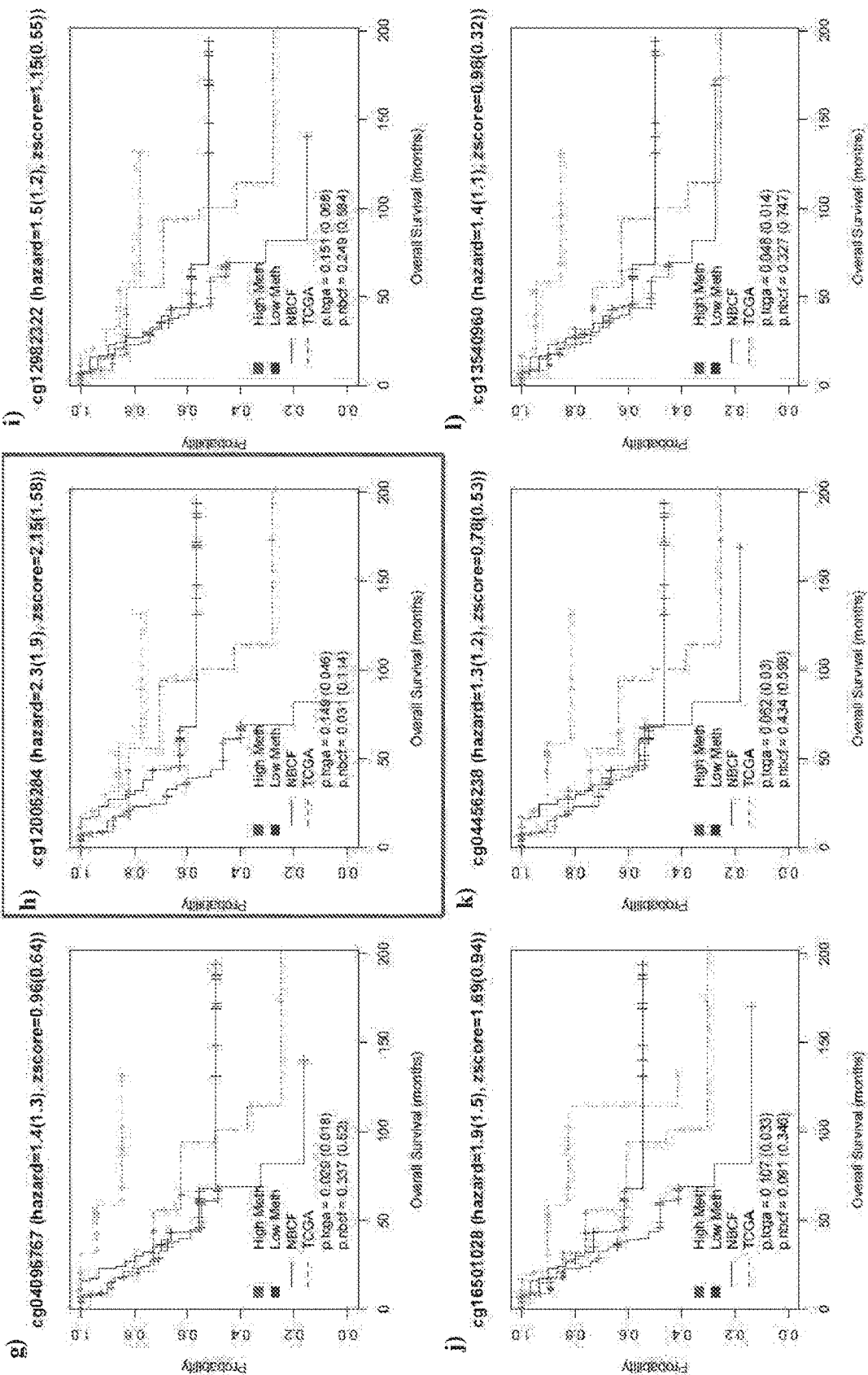
Figure 154:
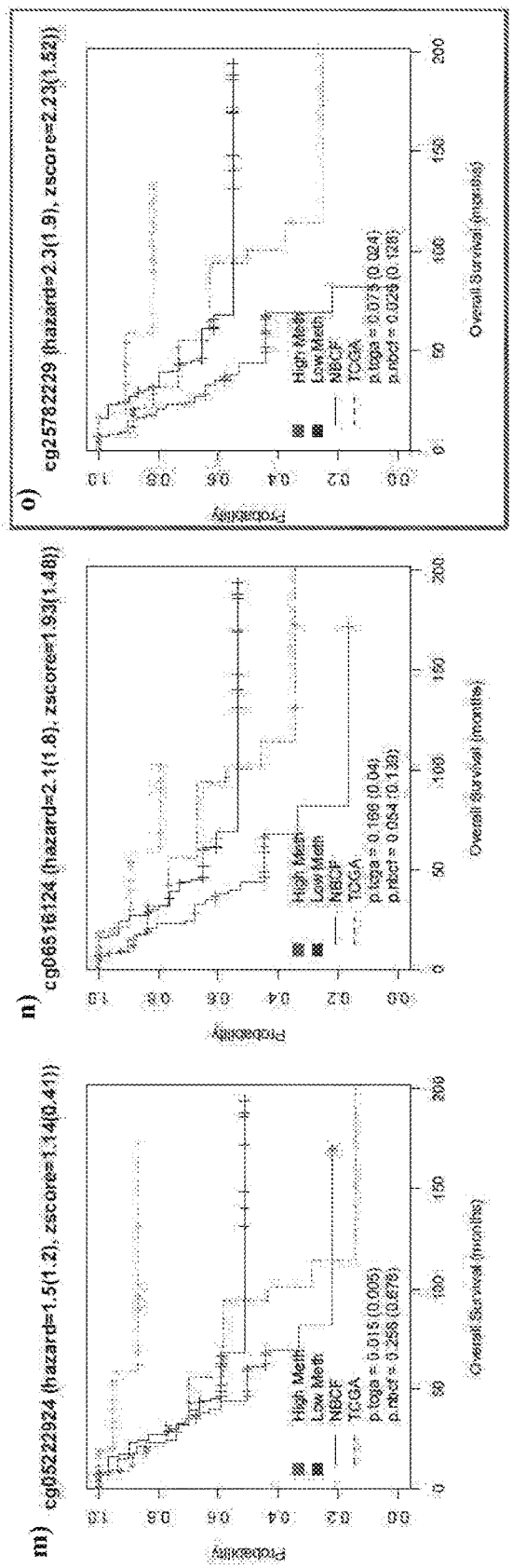

FIG. 154. This figure provides Kaplan Meier plots for each of the probes in prognostic region designated chr11-11623 (as described in Table 14) based on methylation between survival groups in the NBCF cohort. Probes within prognostic region which are statistically significant for predicting patient outcome are boxed.

Figure 155:
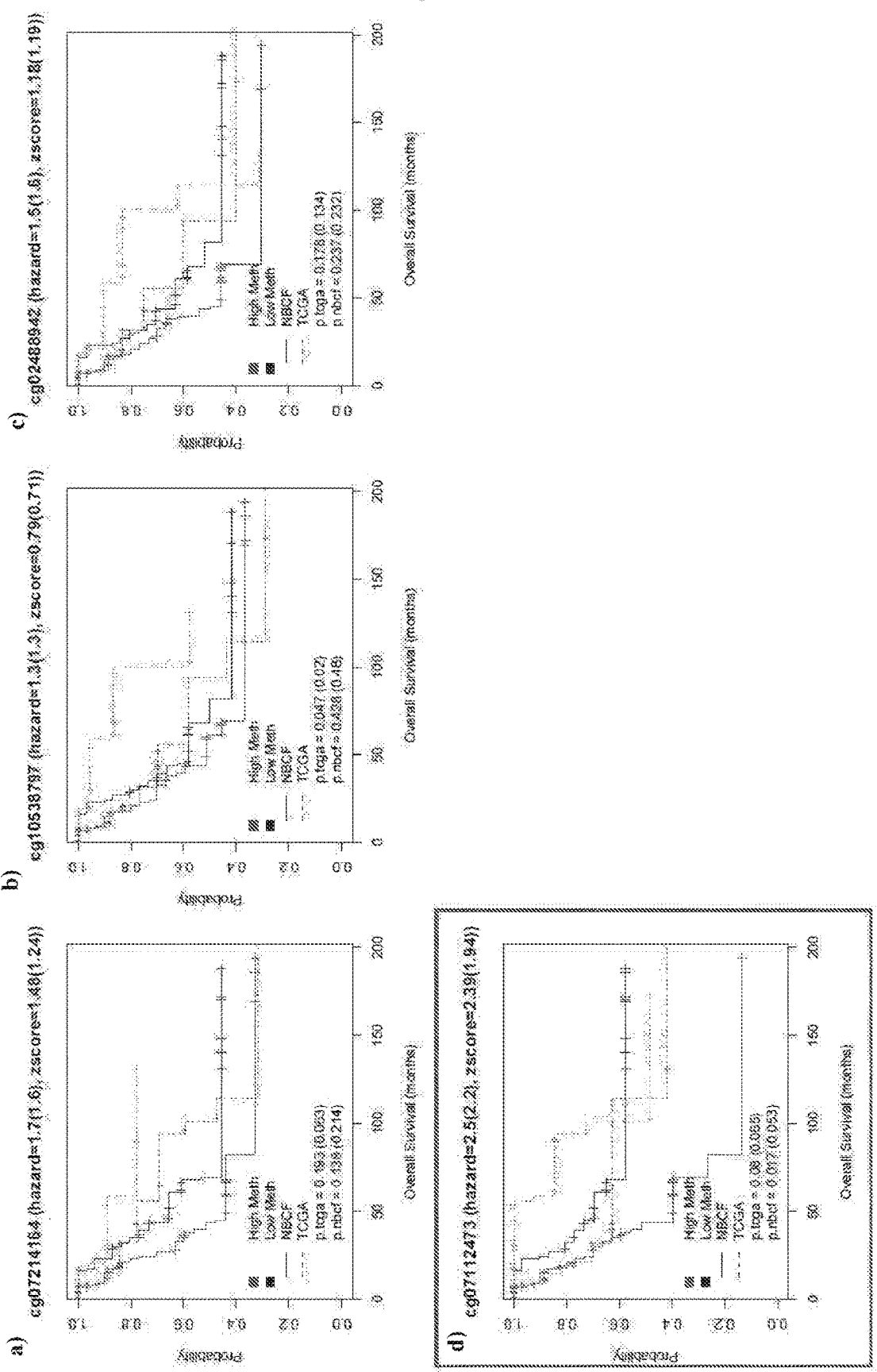

FIG. 155. This figure provides Kaplan Meier plots for each of the probes in prognostic region designated chr2-26887 (as described in Table 14) based on methylation between survival groups in the NBCF cohort. Probes within prognostic region which are statistically significant for predicting patient outcome are boxed.

Figure 156:
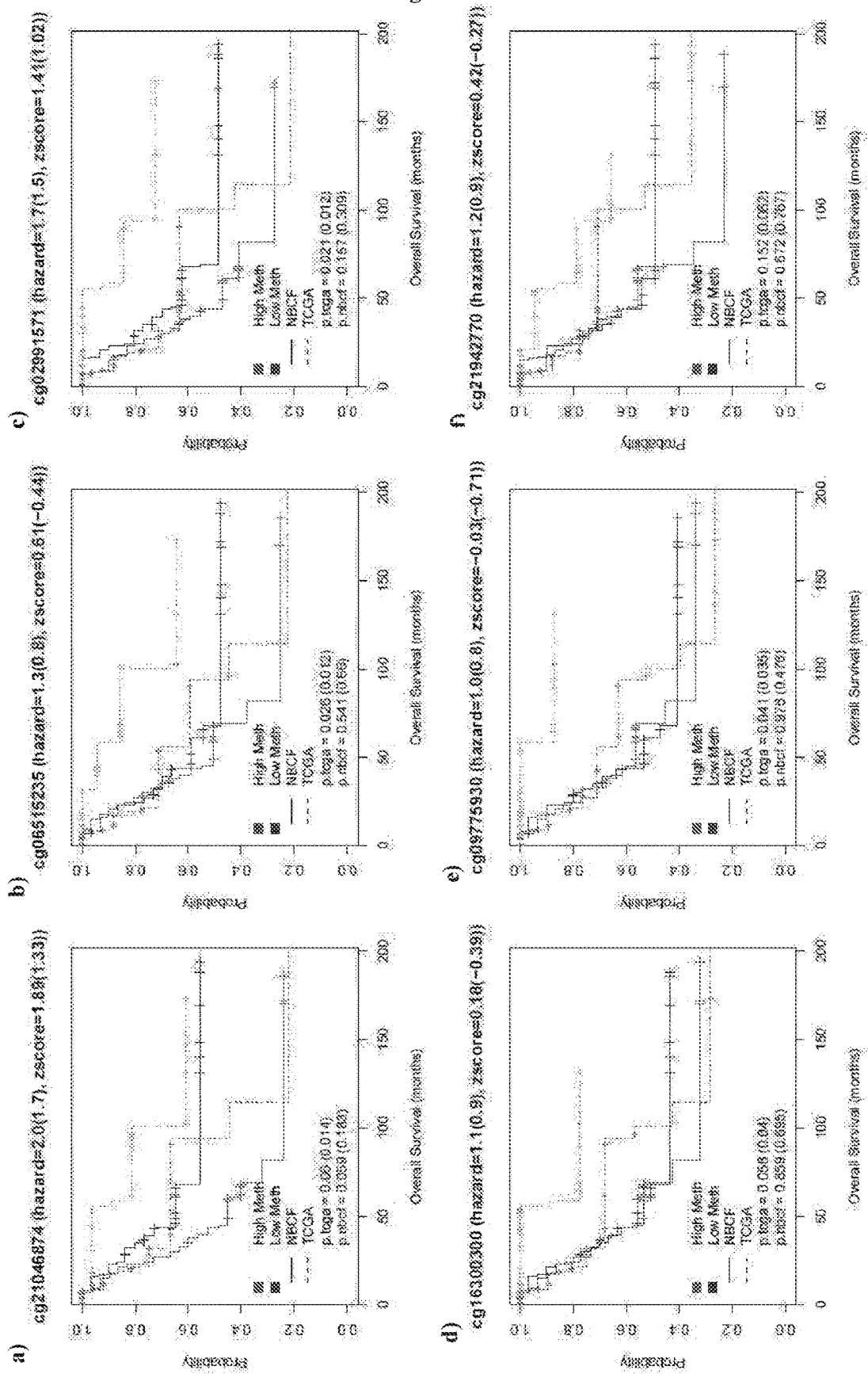
Figure 156:
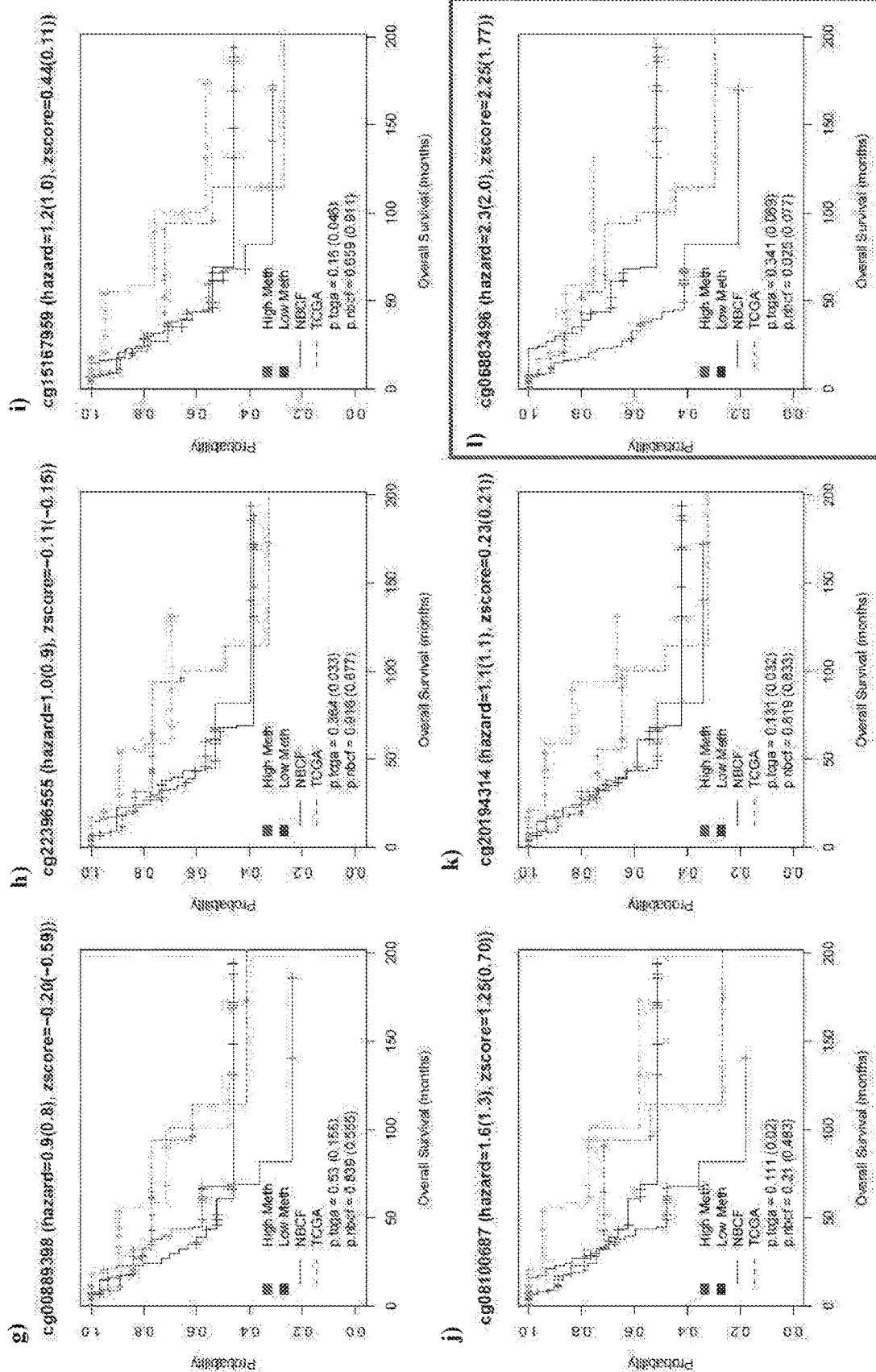
Figure 156:
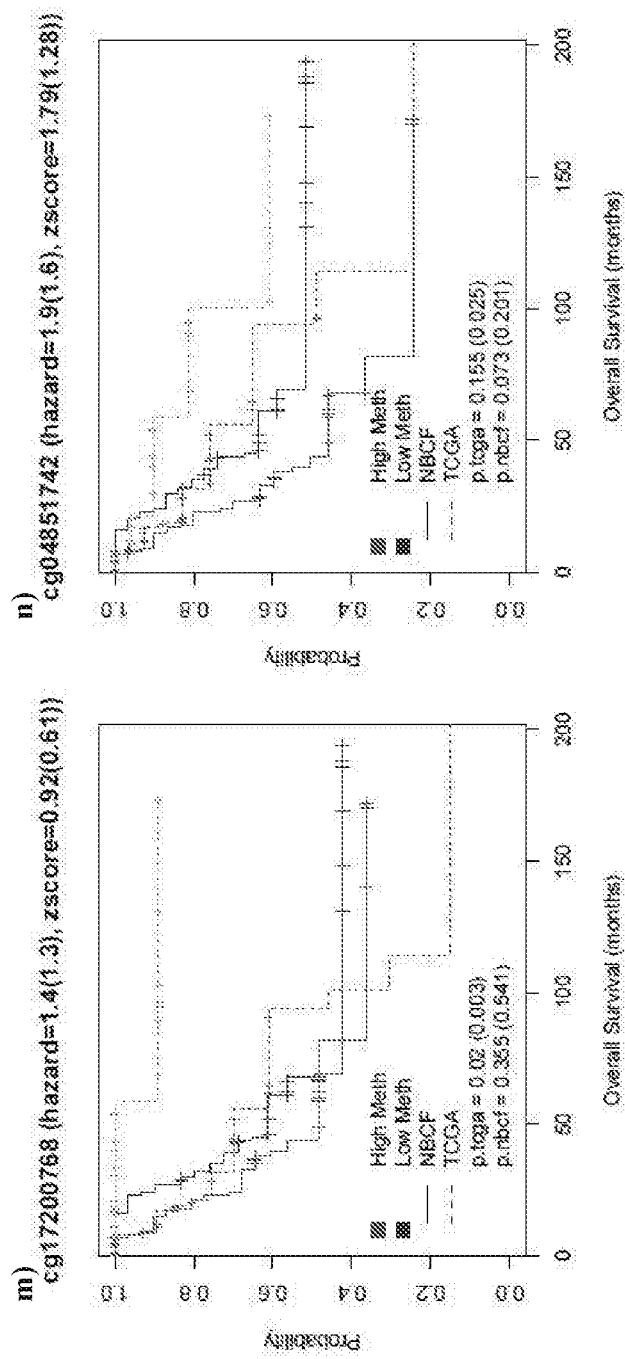

FIG. 156. This figure provides Kaplan Meier plots for each of the probes in prognostic region designated chr13-5199 (as described in Table 14) based on methylation between survival groups in the NBCF cohort. Probes within prognostic region which are statistically significant for predicting patient outcome are boxed.

Figure 157:
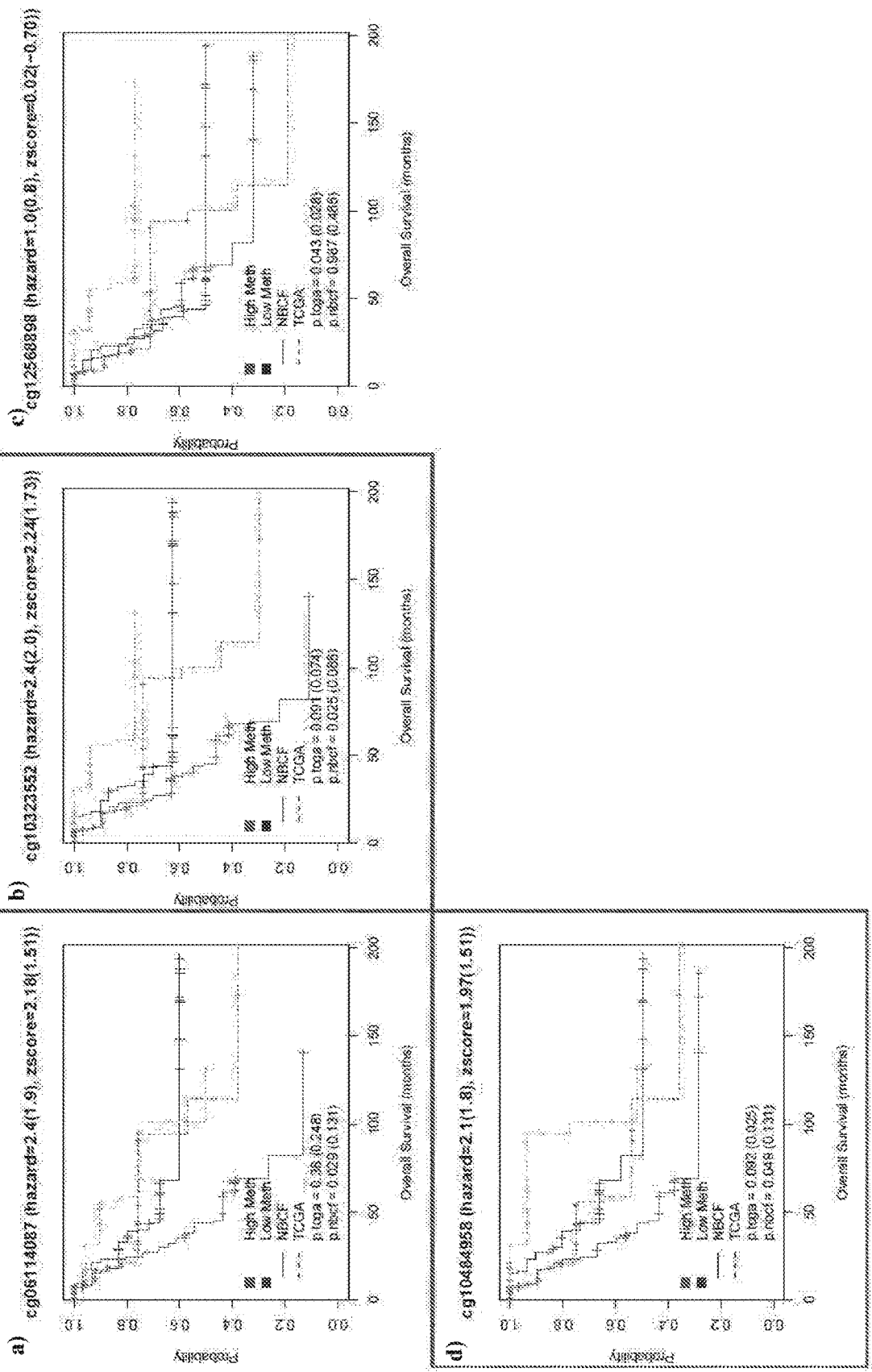

FIG. 157. This figure provides Kaplan Meier plots for each of the probes in prognostic region designated chr13-5196 (as described in Table 14) based on methylation between survival groups in the NBCF cohort. Probes within prognostic region which are statistically significant for predicting patient outcome are boxed.

Figure 158:
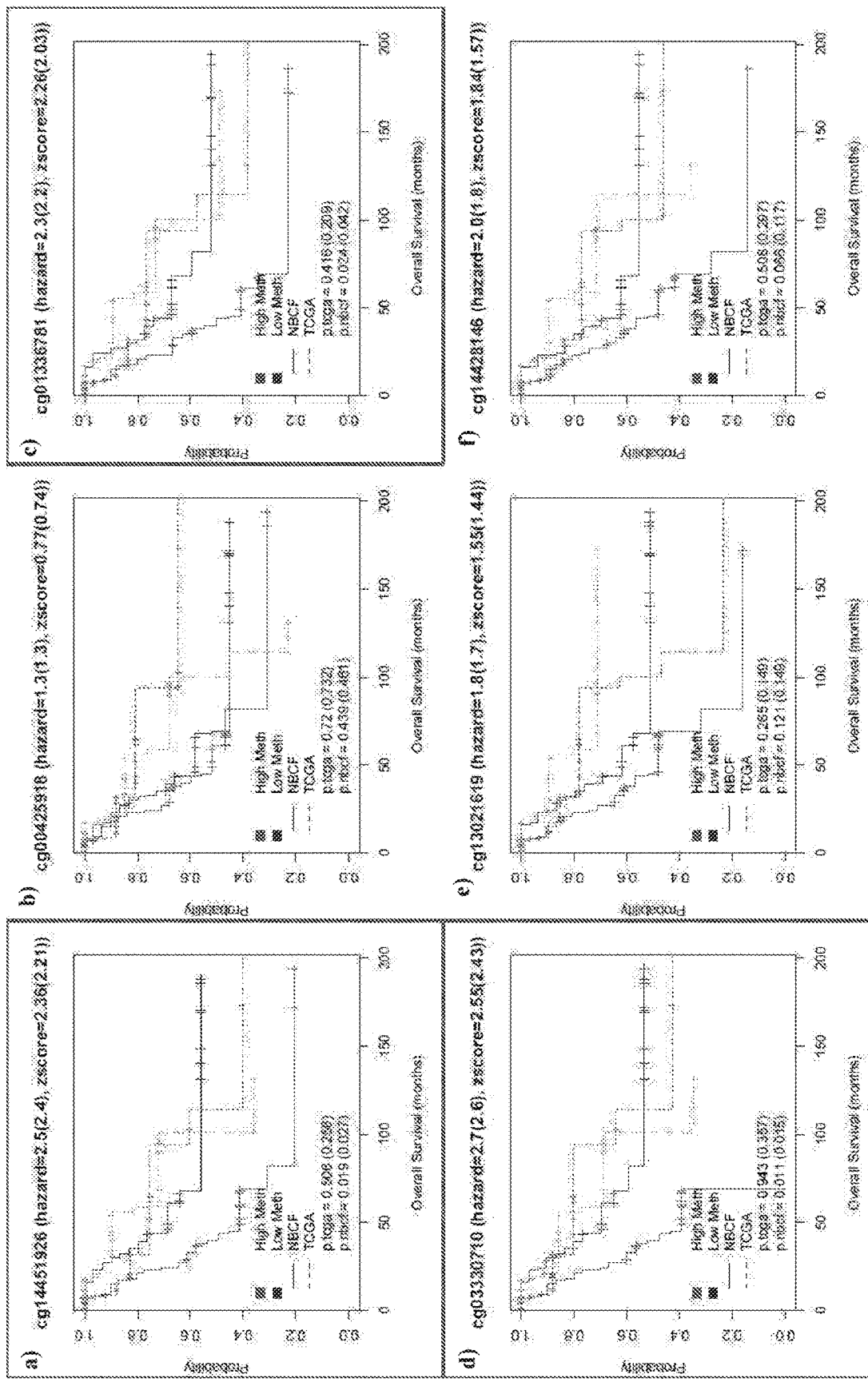
Figure 158:
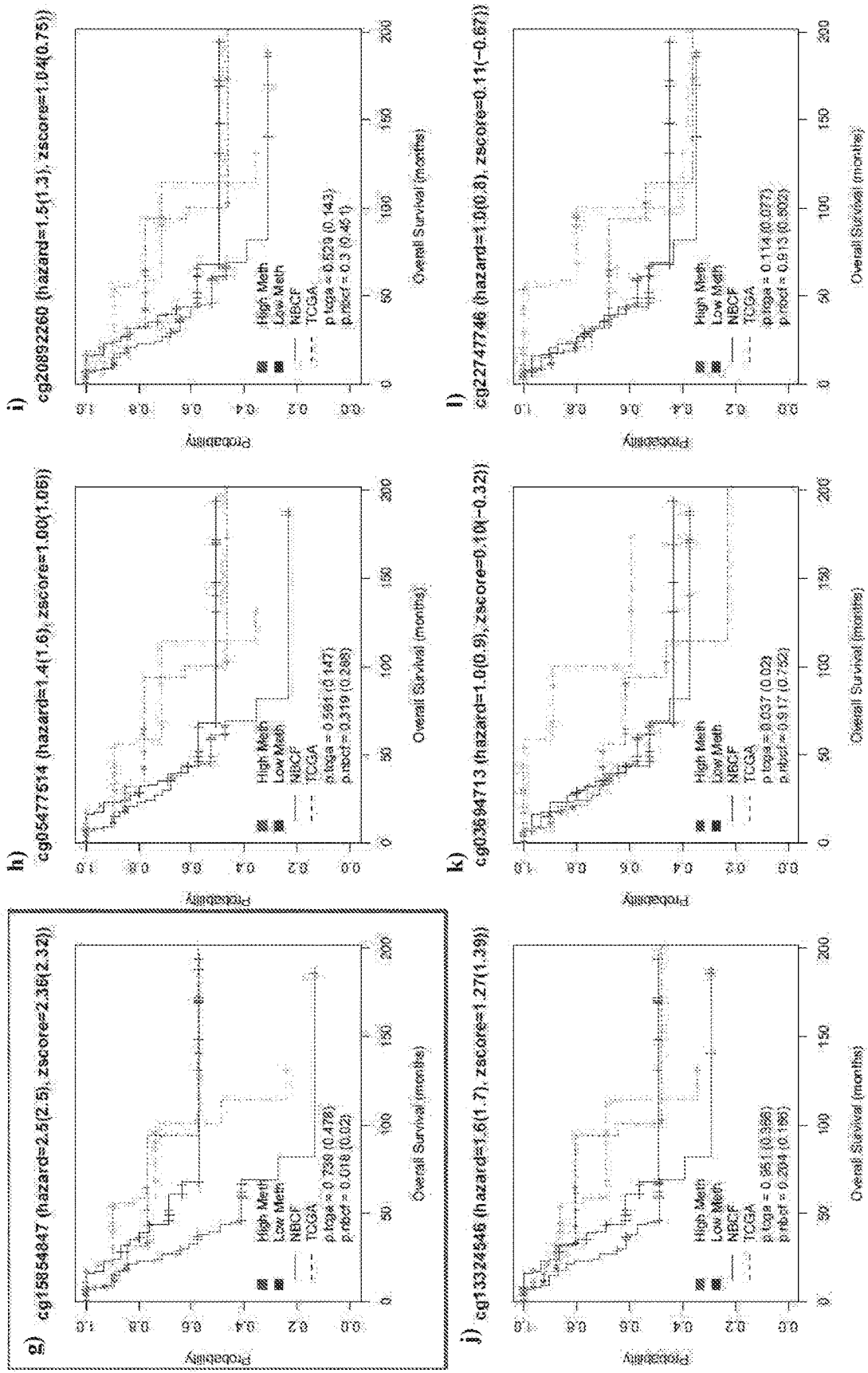
Figure 158:
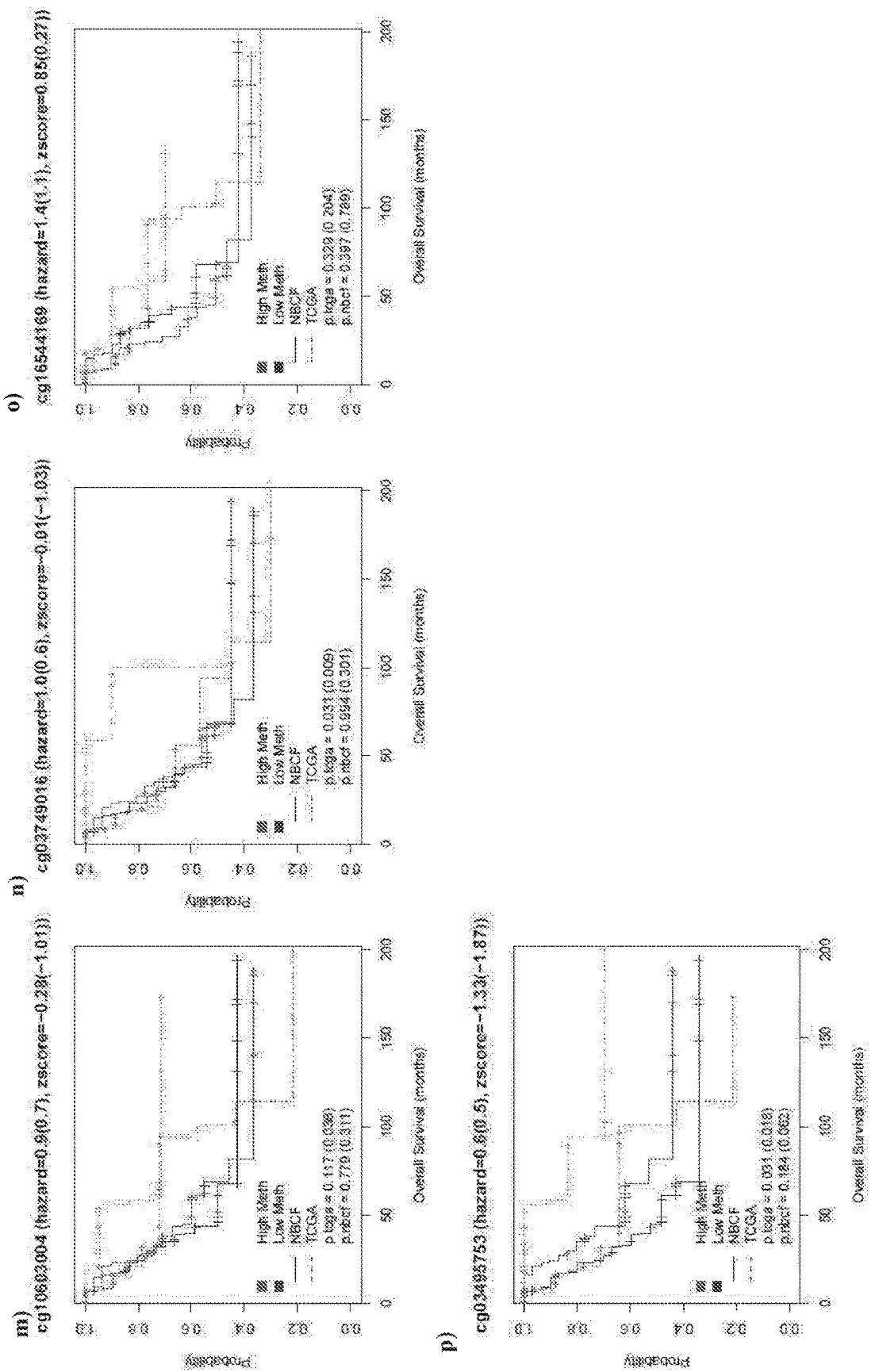

FIG. 158. This figure provides Kaplan Meier plots for each of the probes in prognostic region designated chr8-13399 (as described in Table 14) based on methylation between survival groups in the NBCF cohort. Probes within prognostic region which are statistically significant for predicting patient outcome are boxed.

Figure 159:
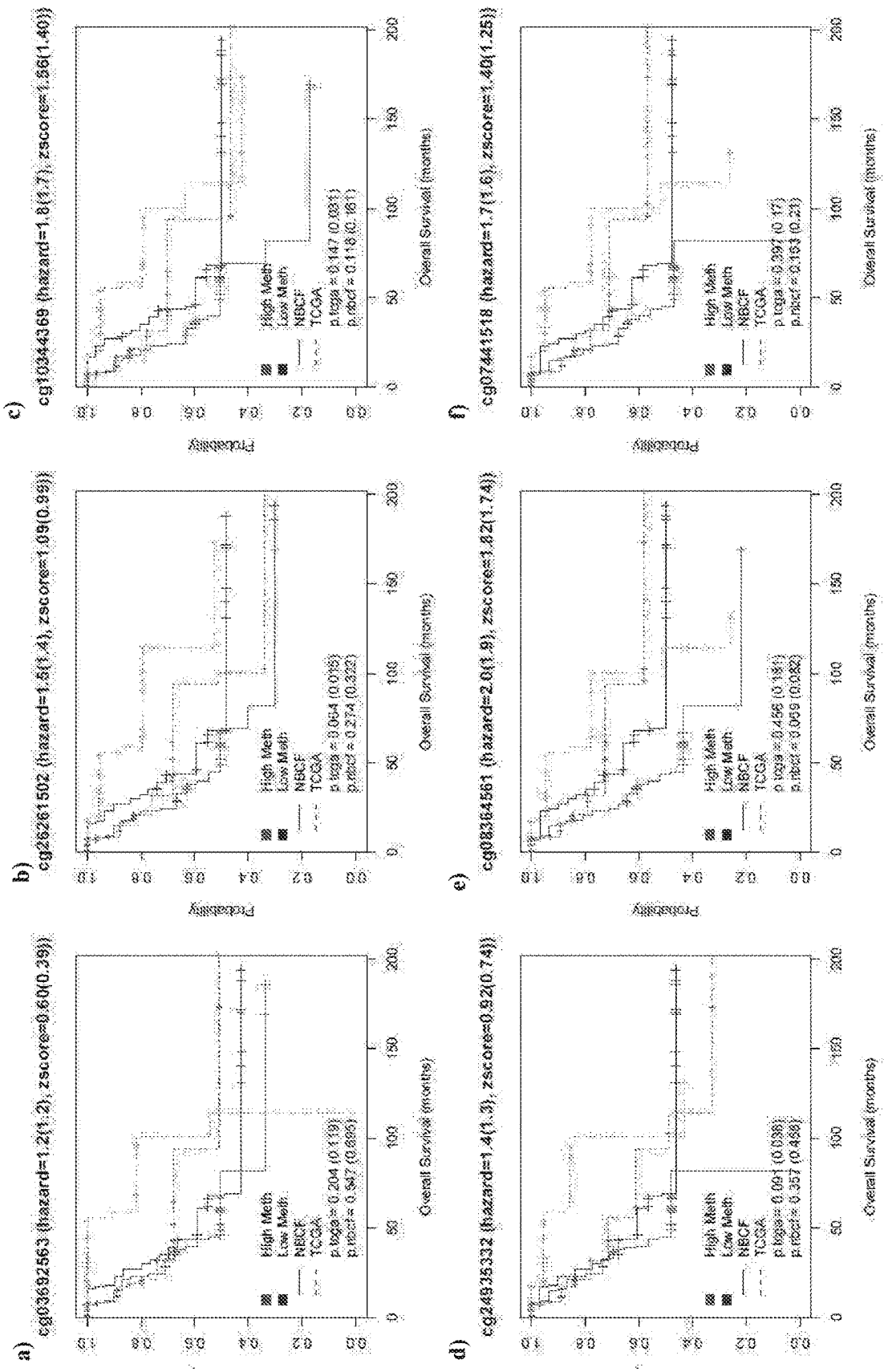
Figure 159:
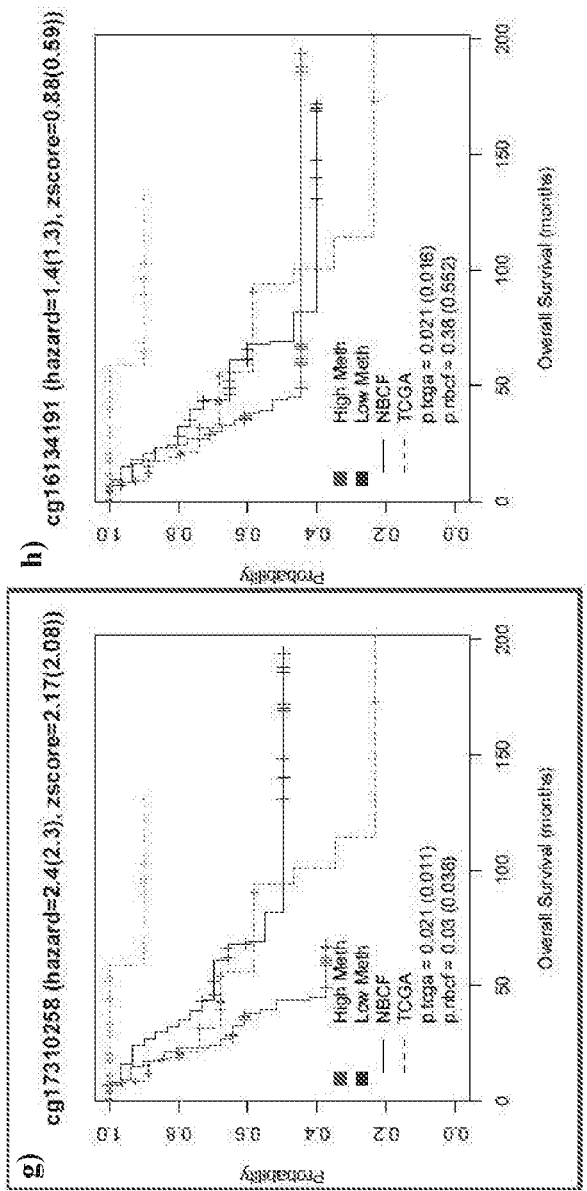

FIG. 159. This figure provides Kaplan Meier plots for each of the probes in prognostic region designated chr11-18108 (as described in Table 14) based on methylation between survival groups in the NBCF cohort. Probes within prognostic region which are statistically significant for predicting patient outcome are boxed.

Figure 160:
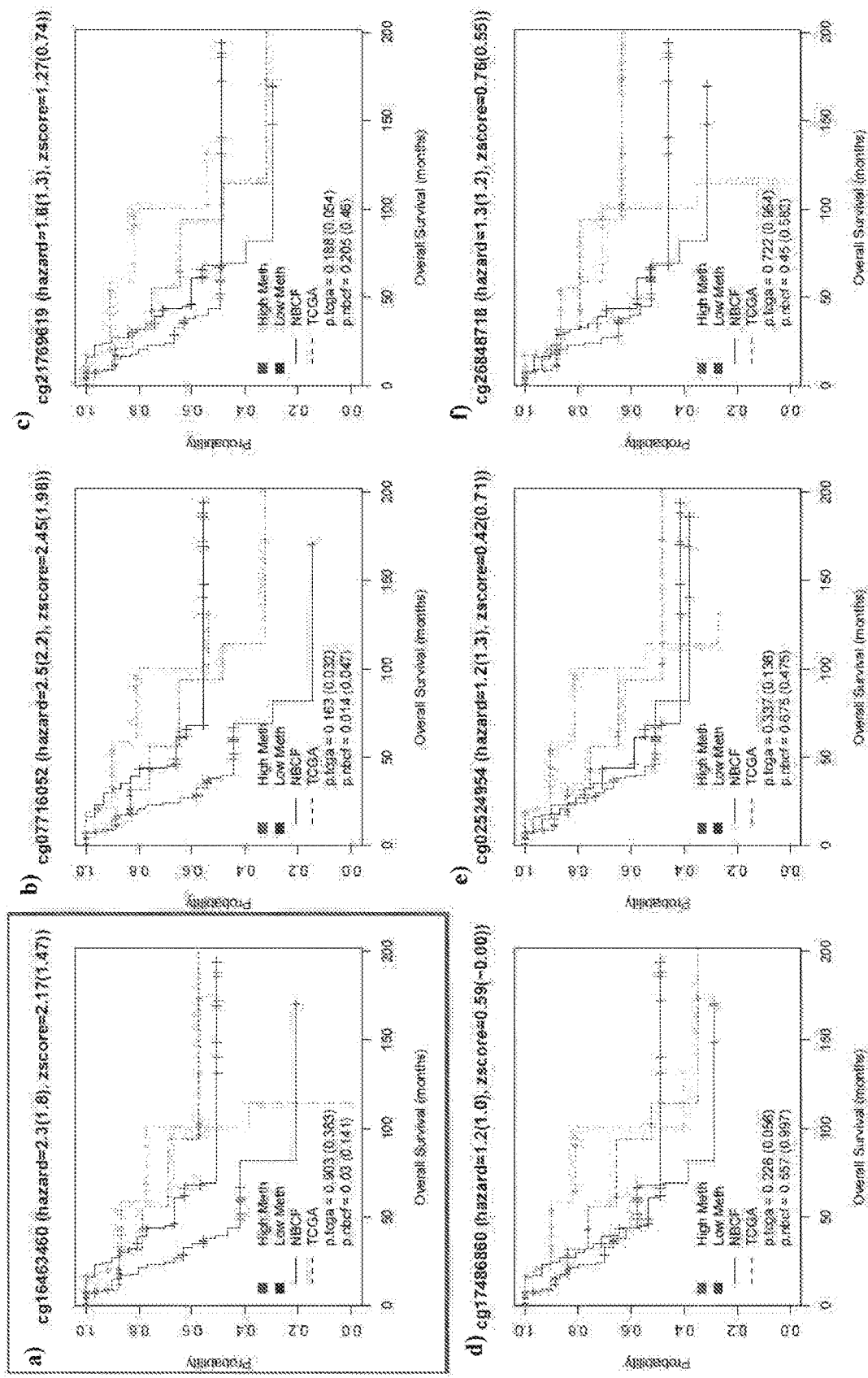
Figure 160:
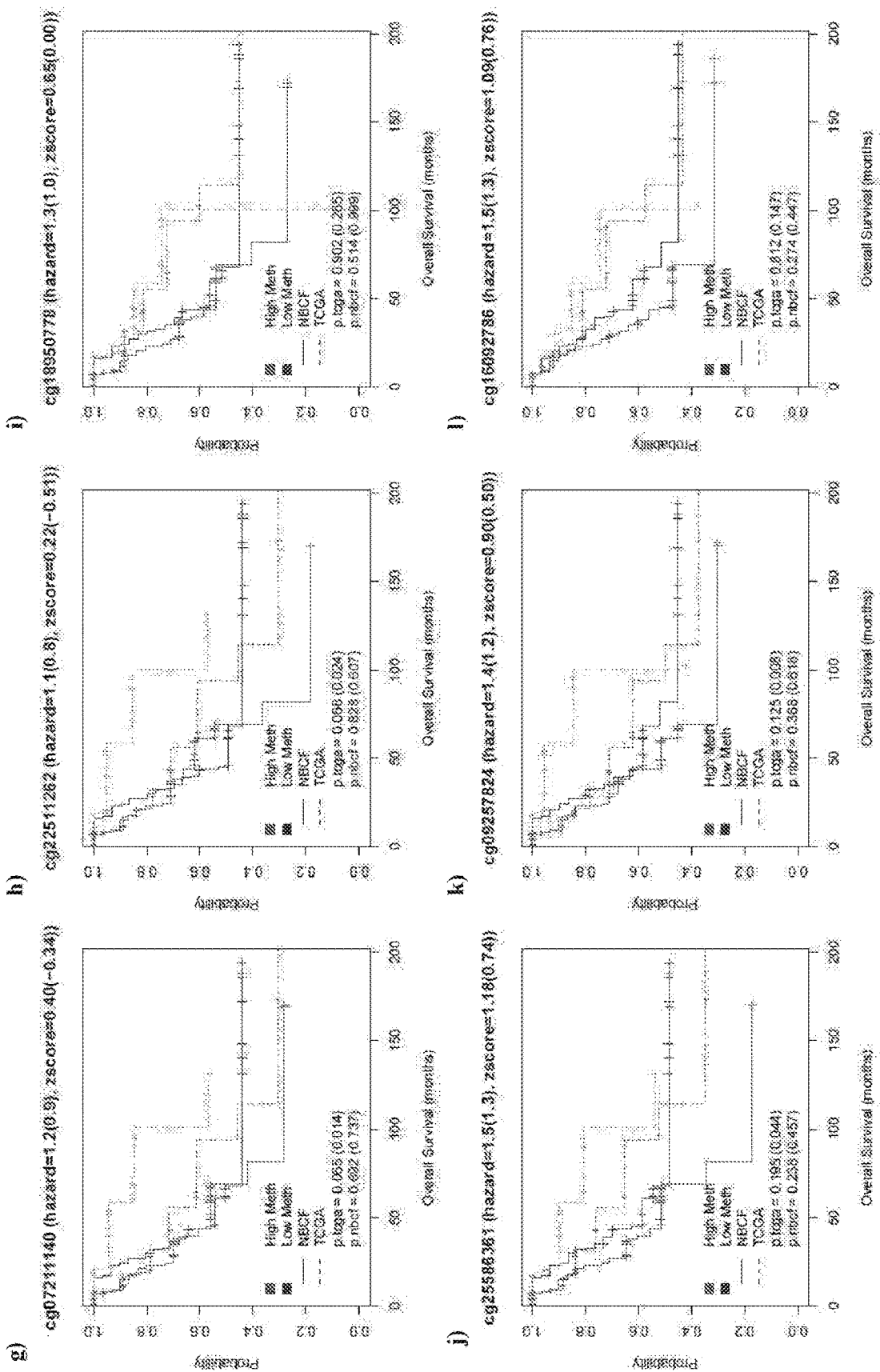
Figure 160:
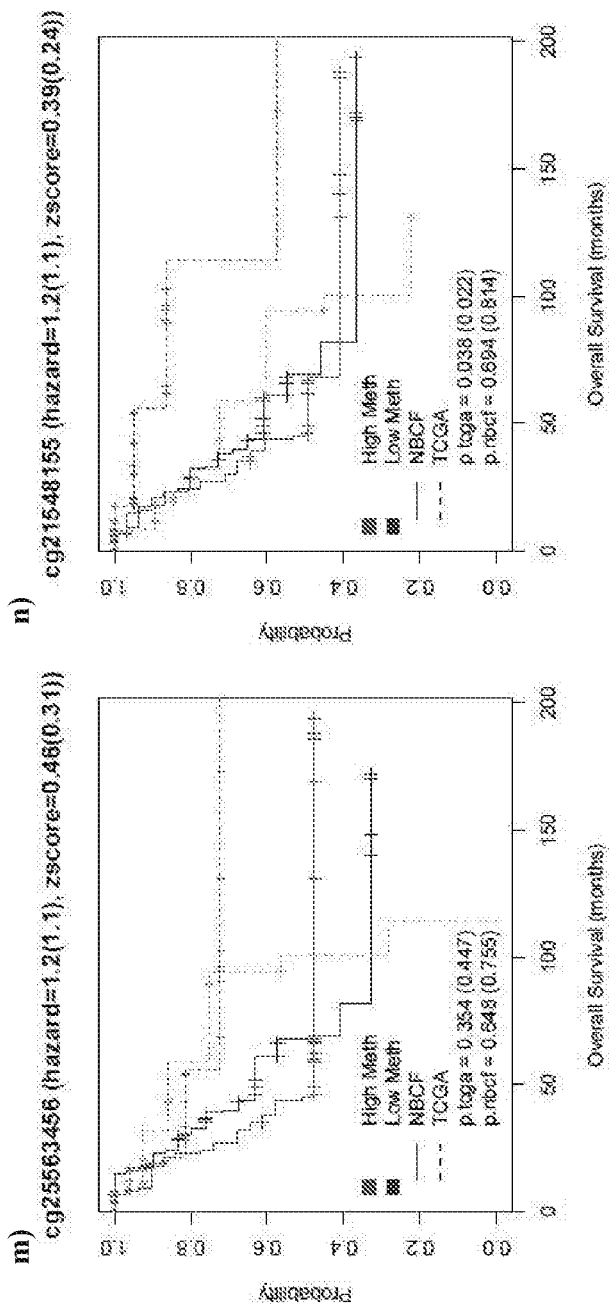

FIG. 160. This figure provides Kaplan Meier plots for each of the probes in prognostic region designated chr11-24196 (as described in Table 14) based on methylation between survival groups in the NBCF cohort. Probes within prognostic region which are statistically significant for predicting patient outcome are boxed.

Figure 161:
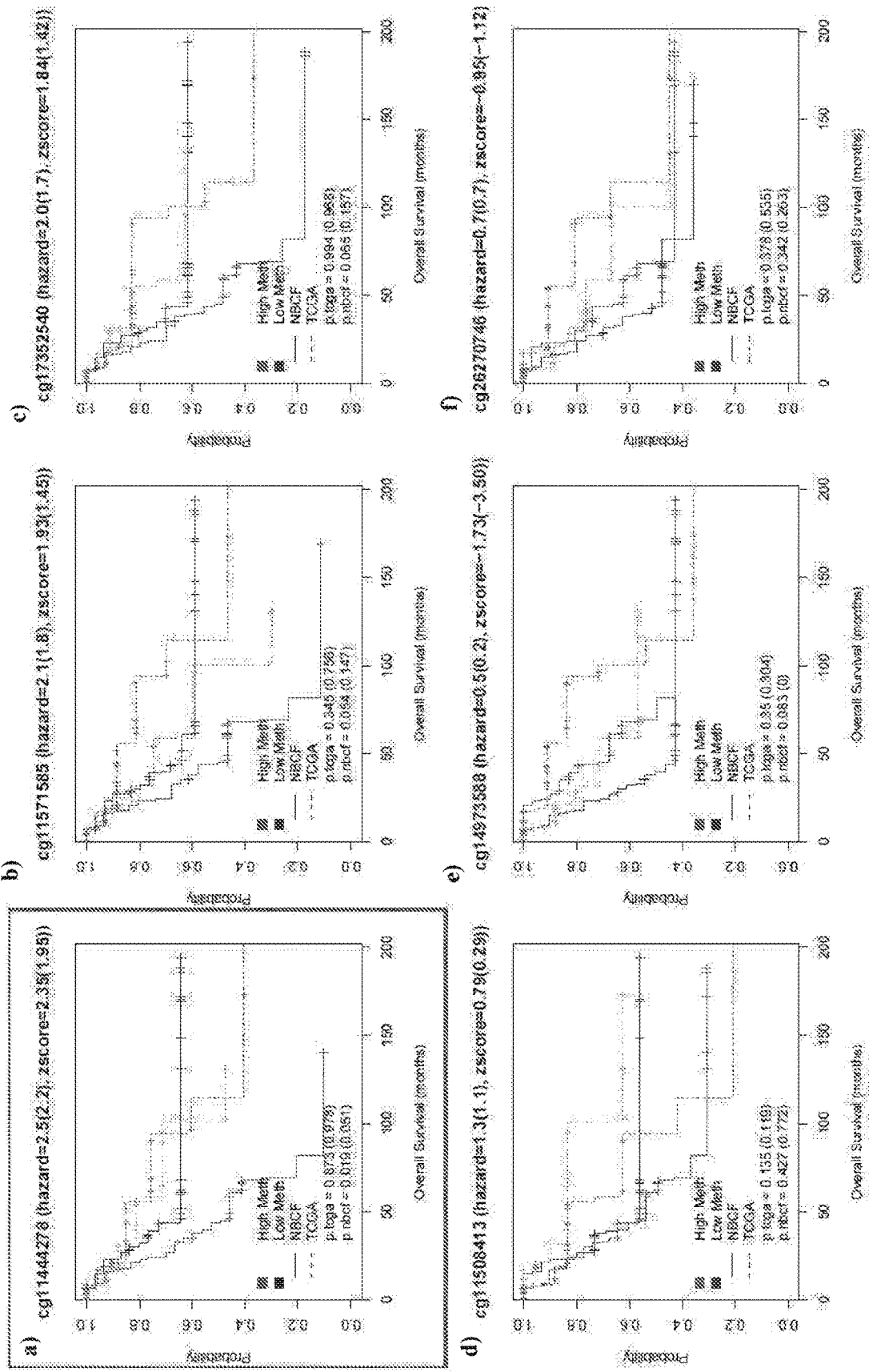
Figure 161:
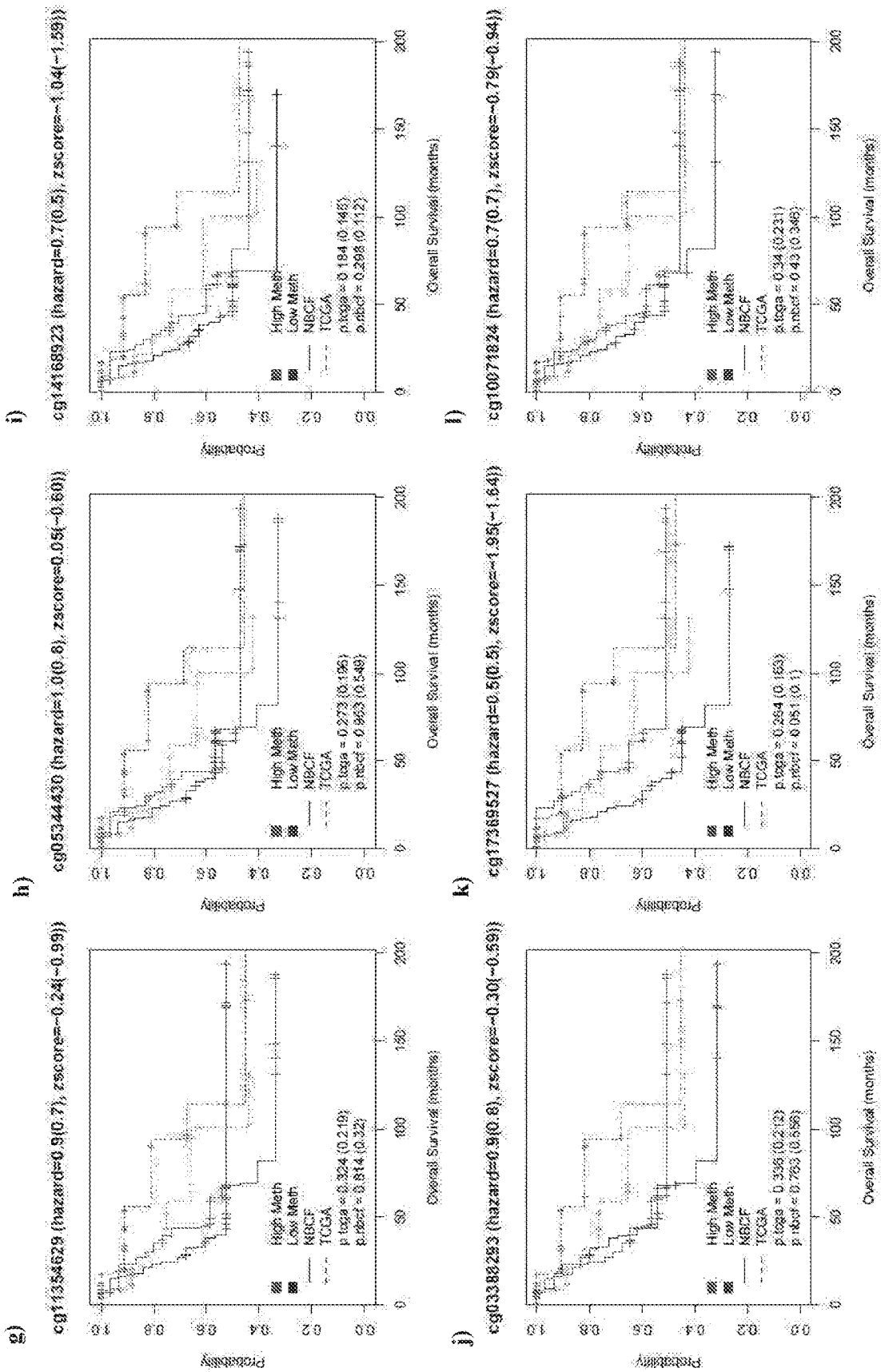
Figure 161:
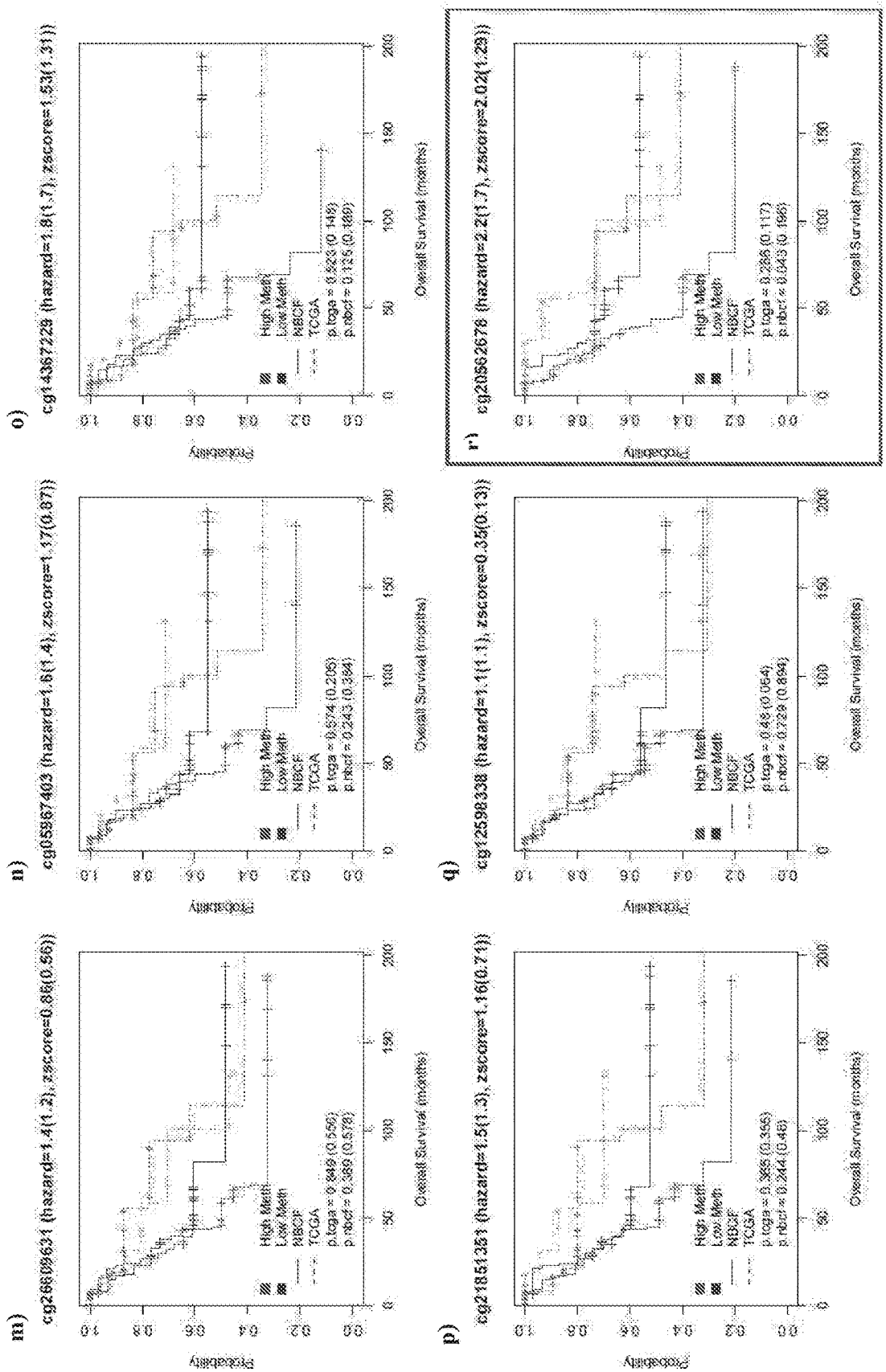
Figure 161:
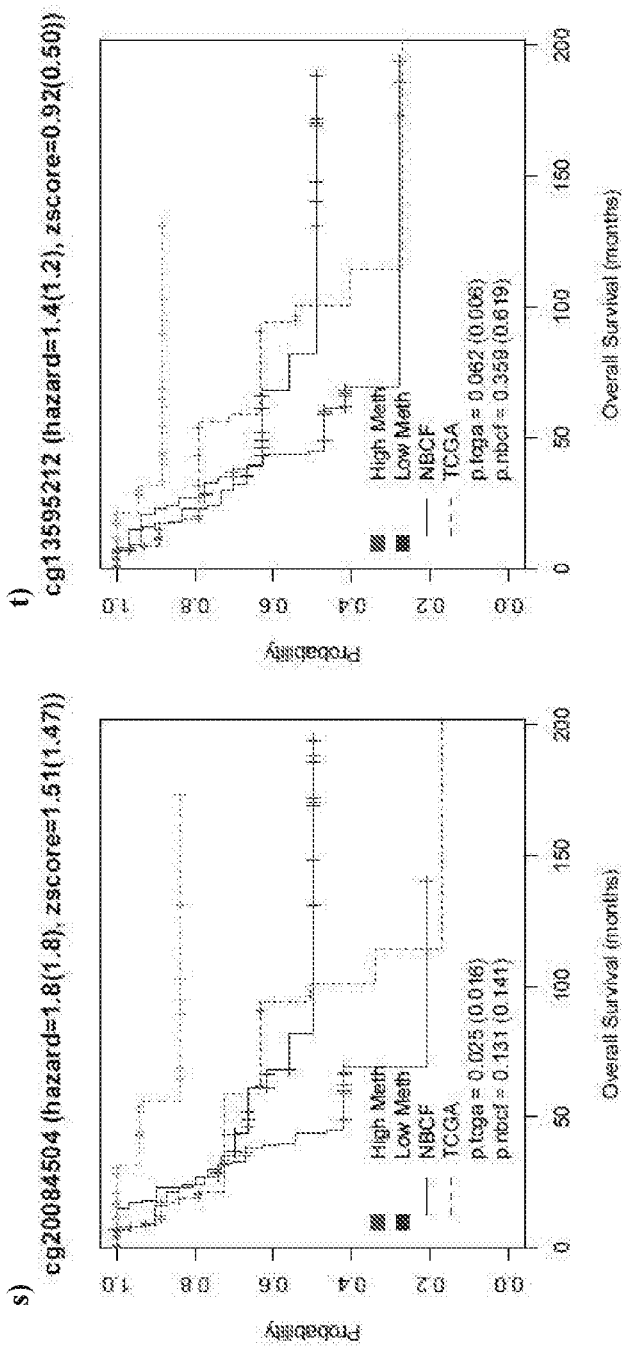

FIG. 161. This figure provides Kaplan Meier plots for each of the probes in prognostic region designated chr13-13783 (as described in Table 14) based on methylation between survival groups in the NBCF cohort. Probes within prognostic region which are statistically significant for predicting patient outcome are boxed.

Figure 162:
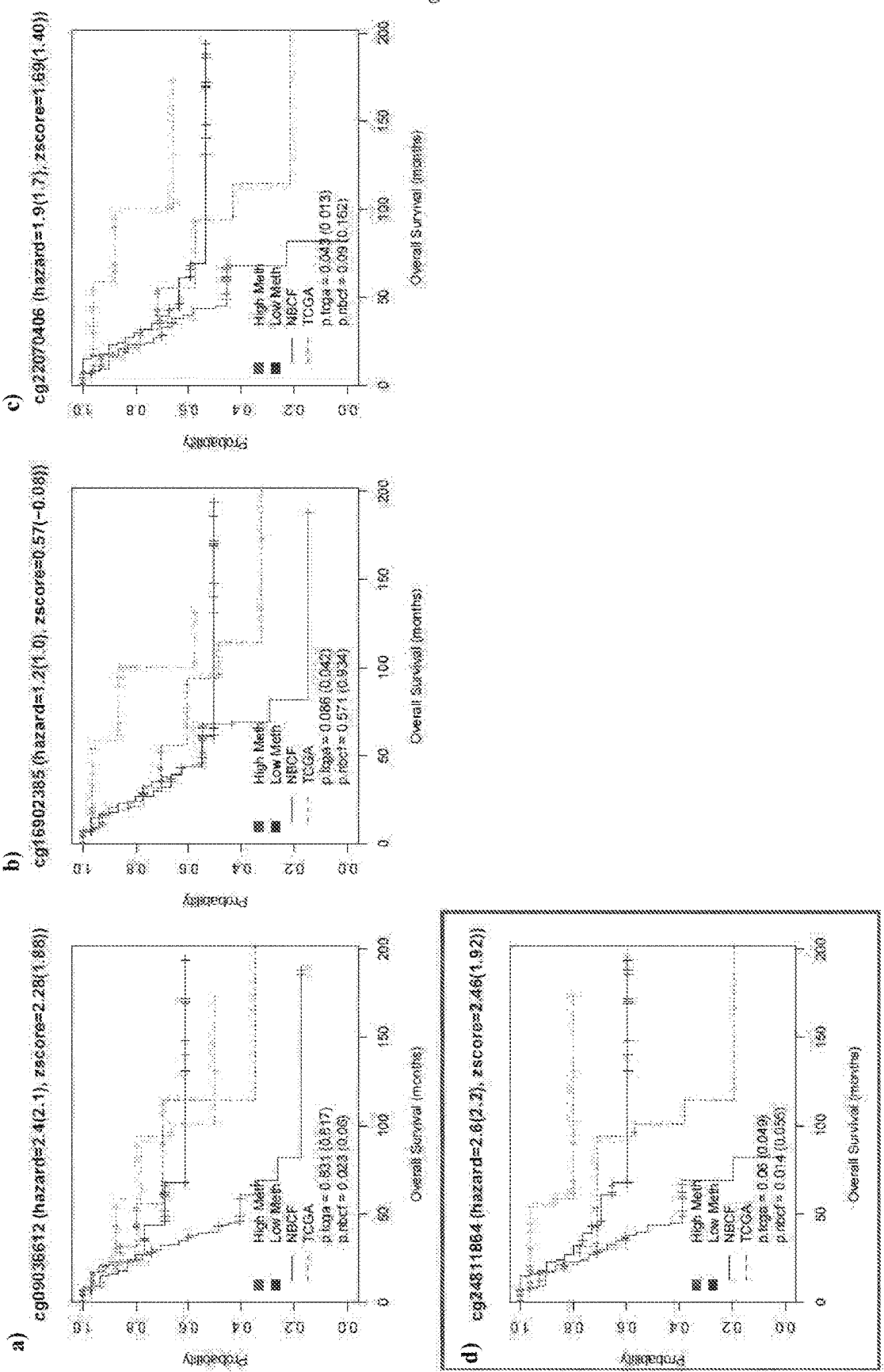

FIG. 162. This figure provides Kaplan Meier plots for each of the probes in prognostic region designated chr18-11487 (as described in Table 14) based on methylation between survival groups in the NBCF cohort. Probes within prognostic region which are statistically significant for predicting patient outcome are boxed.

Figure 163:
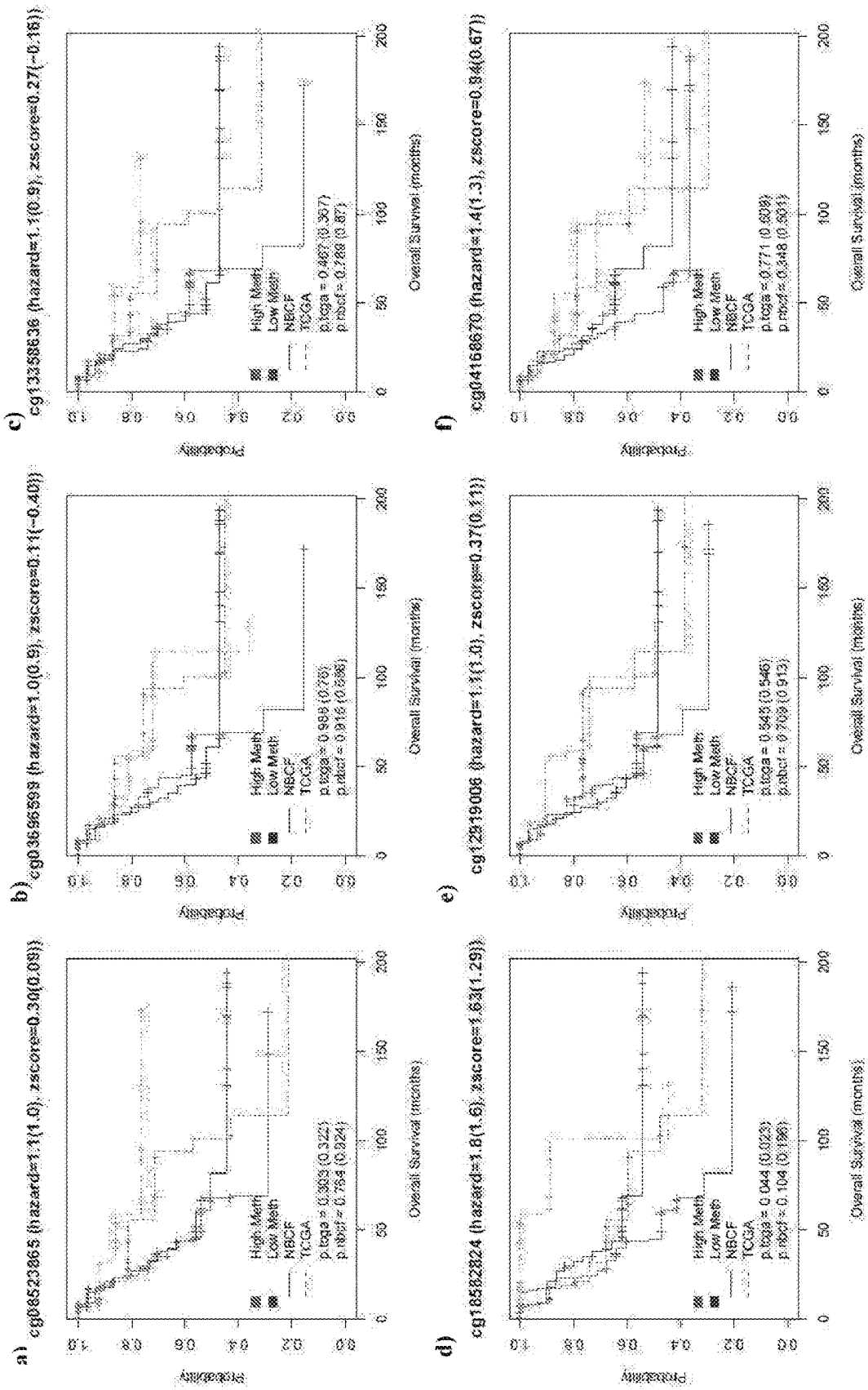
Figure 163:
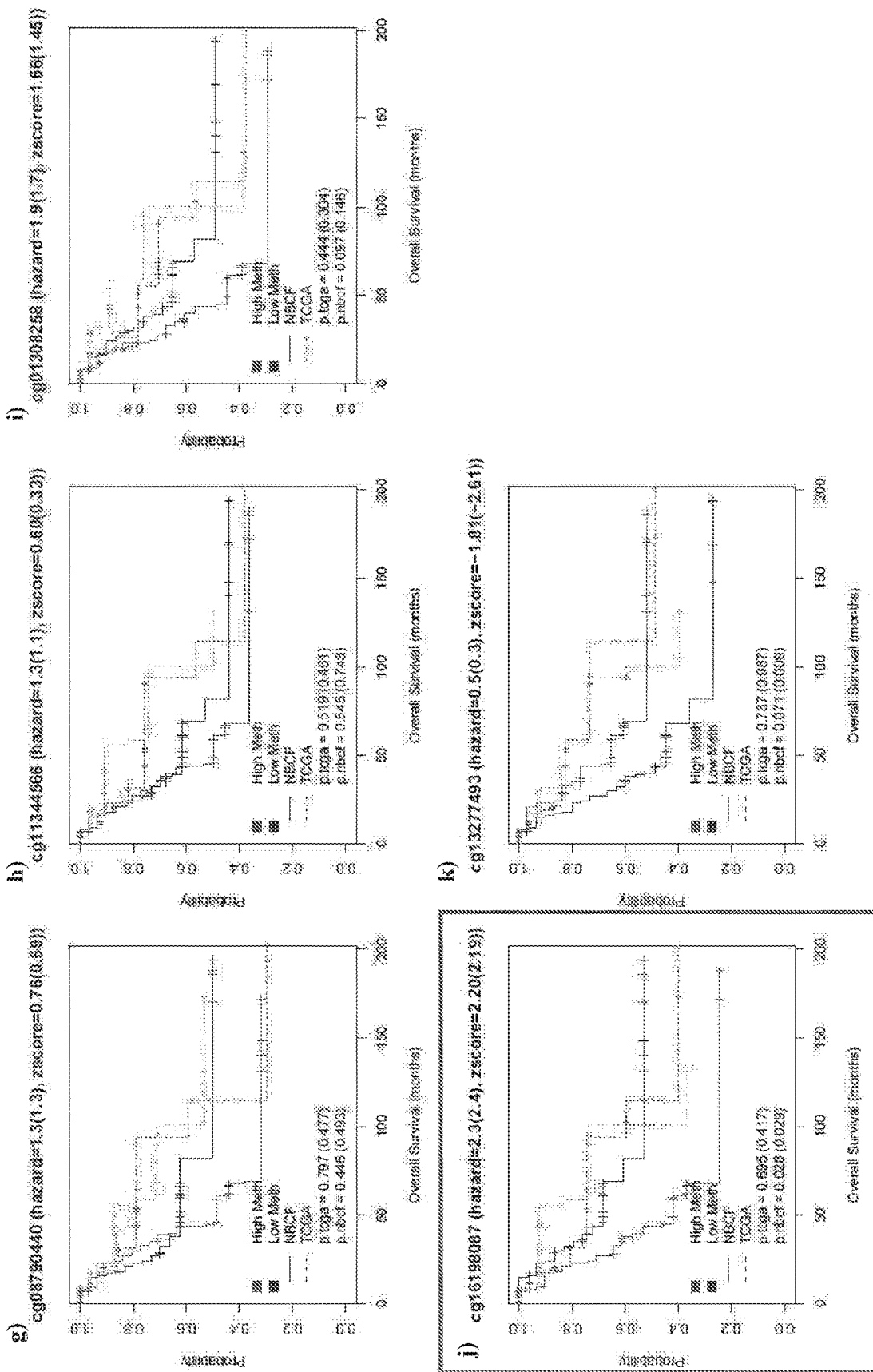

FIG. 163. This figure provides Kaplan Meier plots for each of the probes in prognostic region designated chr2-4092 (as described in Table 14) based on methylation between survival groups in the NBCF cohort. Probes within prognostic region which are statistically significant for predicting patient outcome are boxed.

Figure 164:
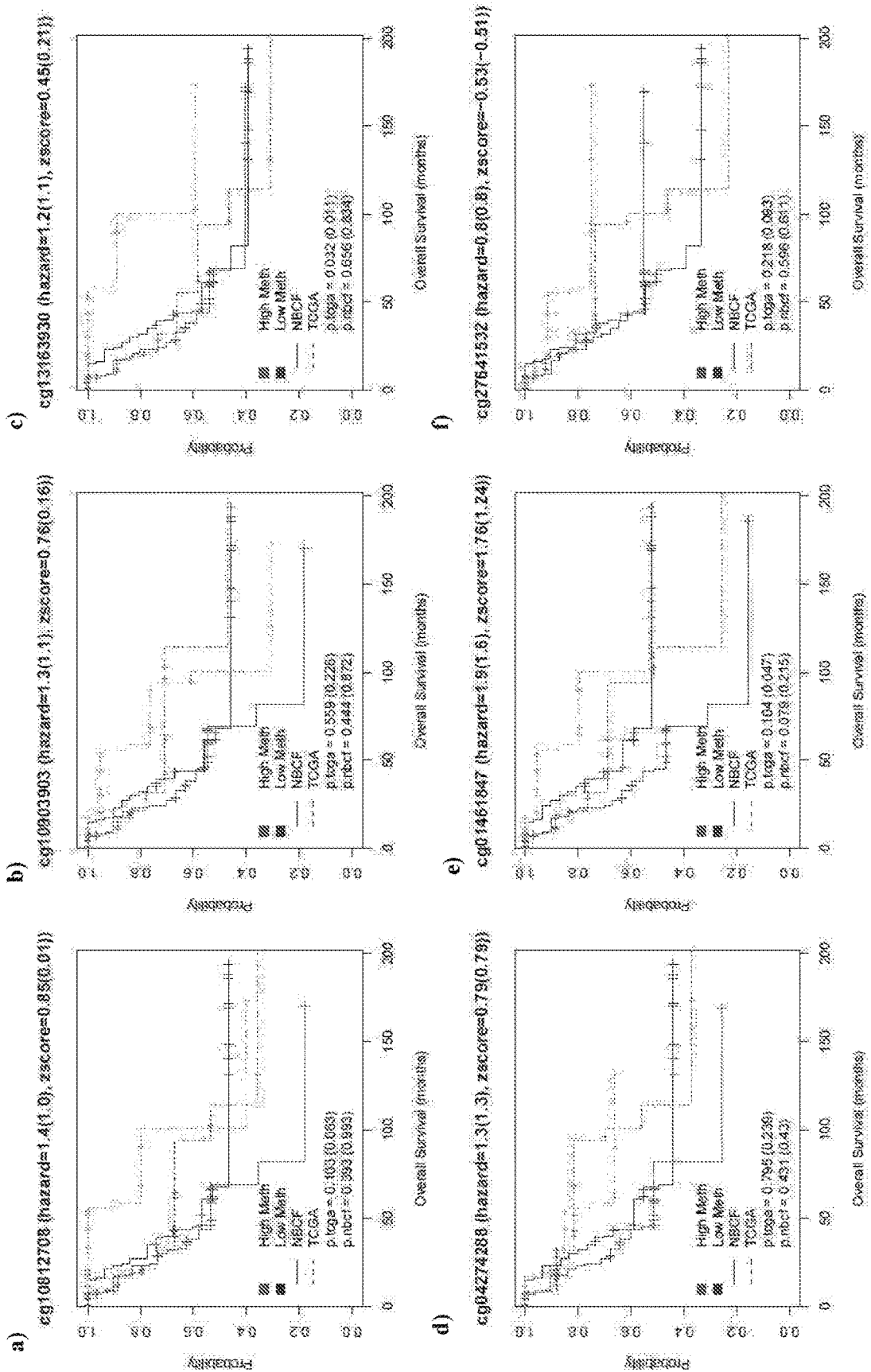
Figure 164:
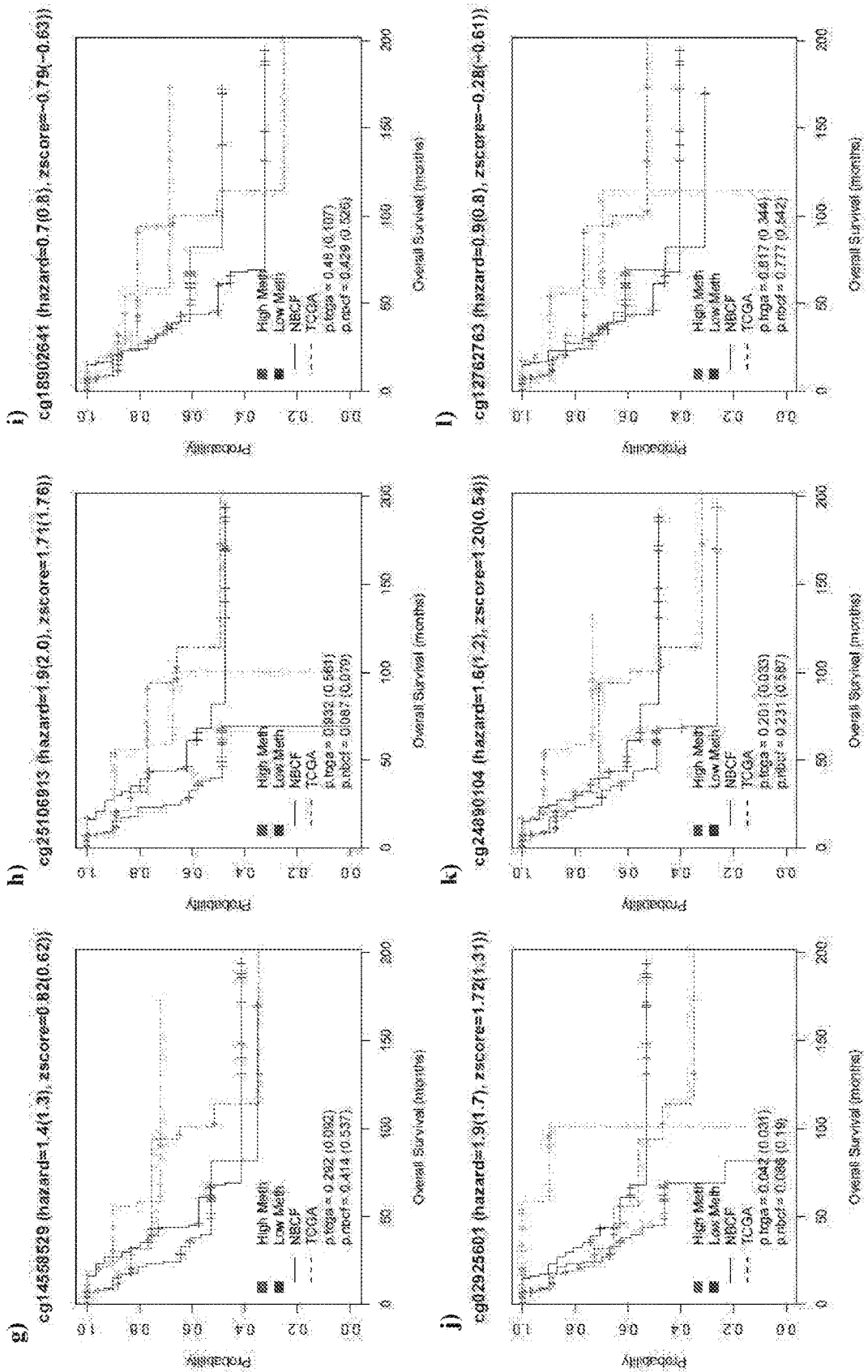
Figure 164:
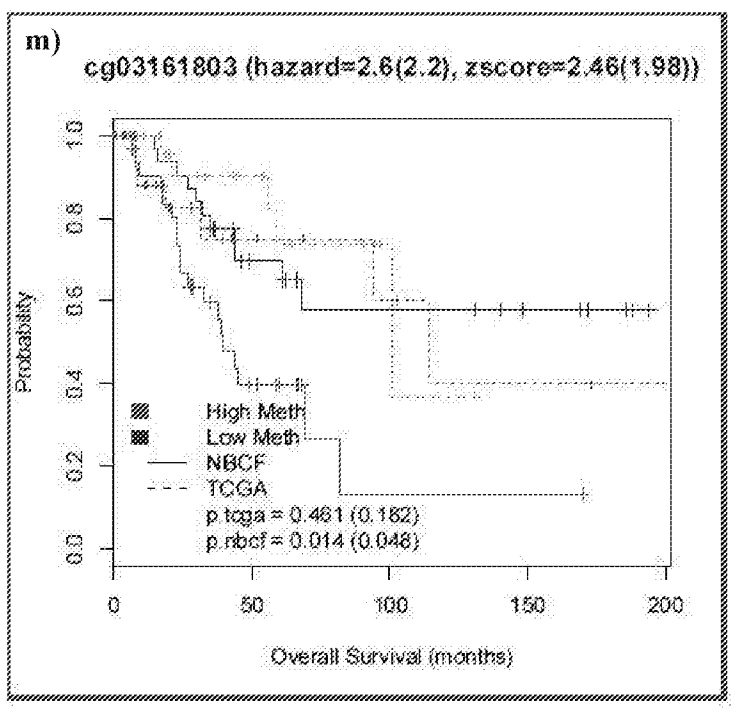

FIG. 164. This figure provides Kaplan Meier plots for each of the probes in prognostic region designated chr6-25261 (as described in Table 14) based on methylation between survival groups in the NBCF cohort. Probes within prognostic region which are statistically significant for predicting patient outcome are boxed.

Figure 165:
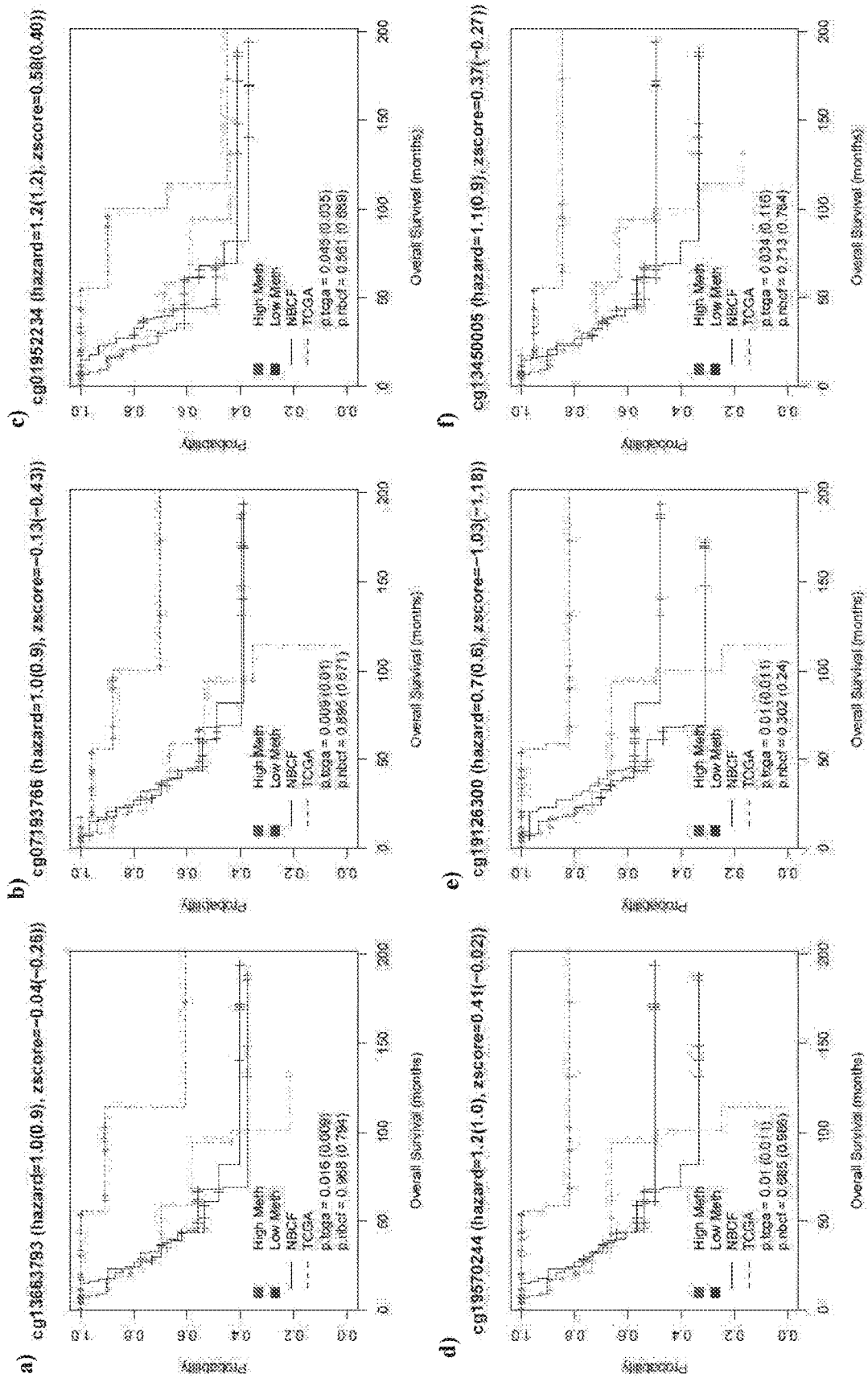
Figure 165:
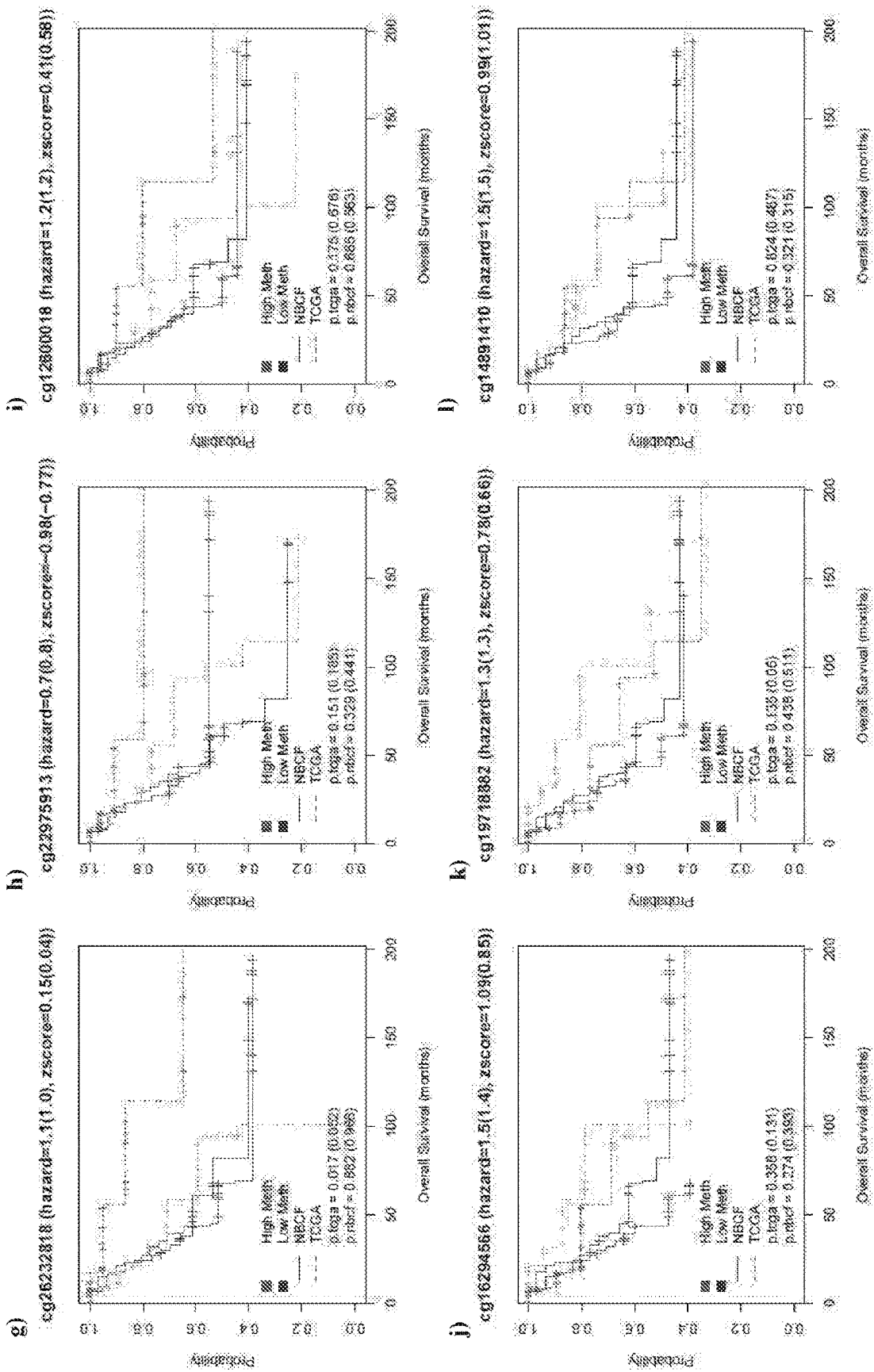
Figure 165:
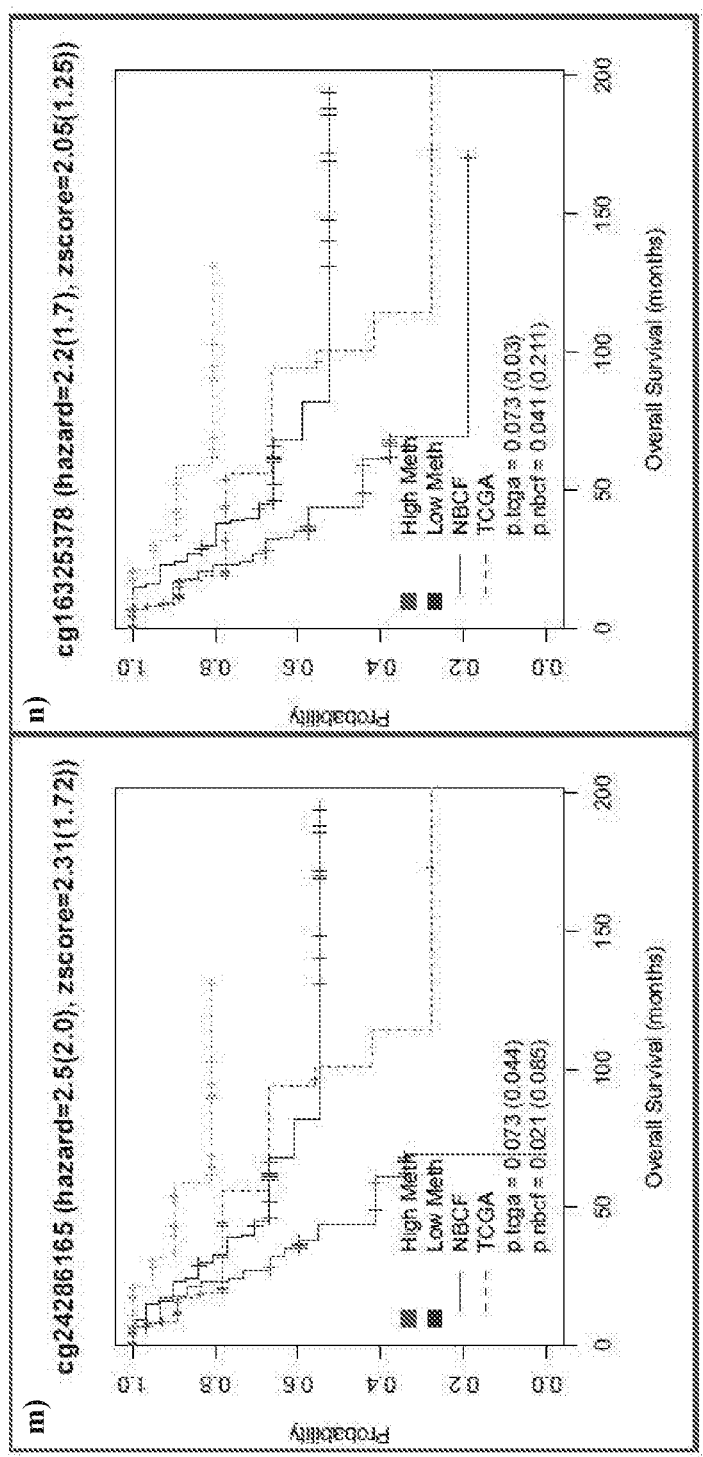

FIG. 165. This figure provides Kaplan Meier plots for each of the probes in prognostic region designated chr11-4047 (as described in Table 14) based on methylation between survival groups in the NBCF cohort. Probes within prognostic region which are statistically significant for predicting patient outcome are boxed.

Figure 166:
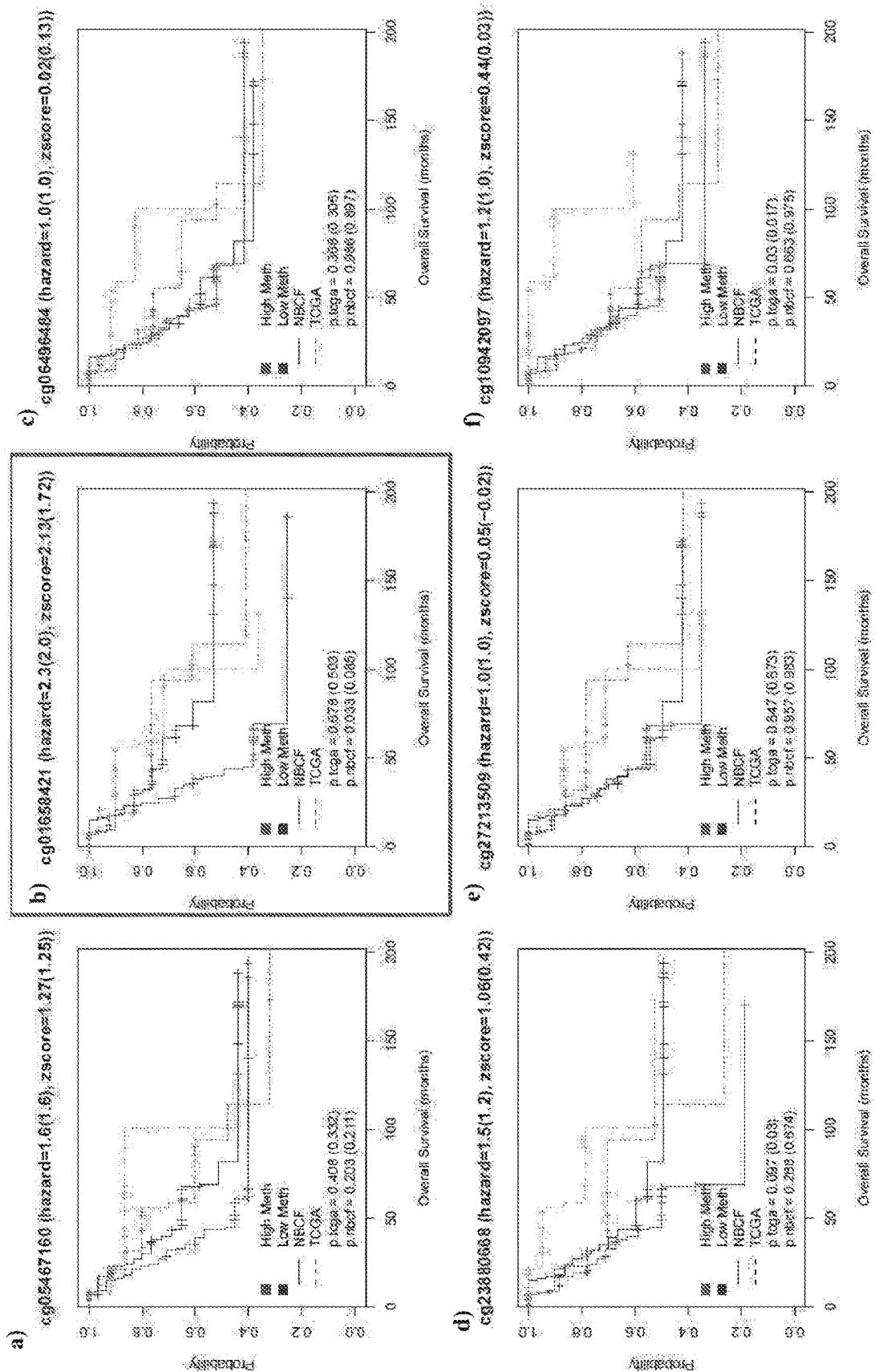
Figure 166:
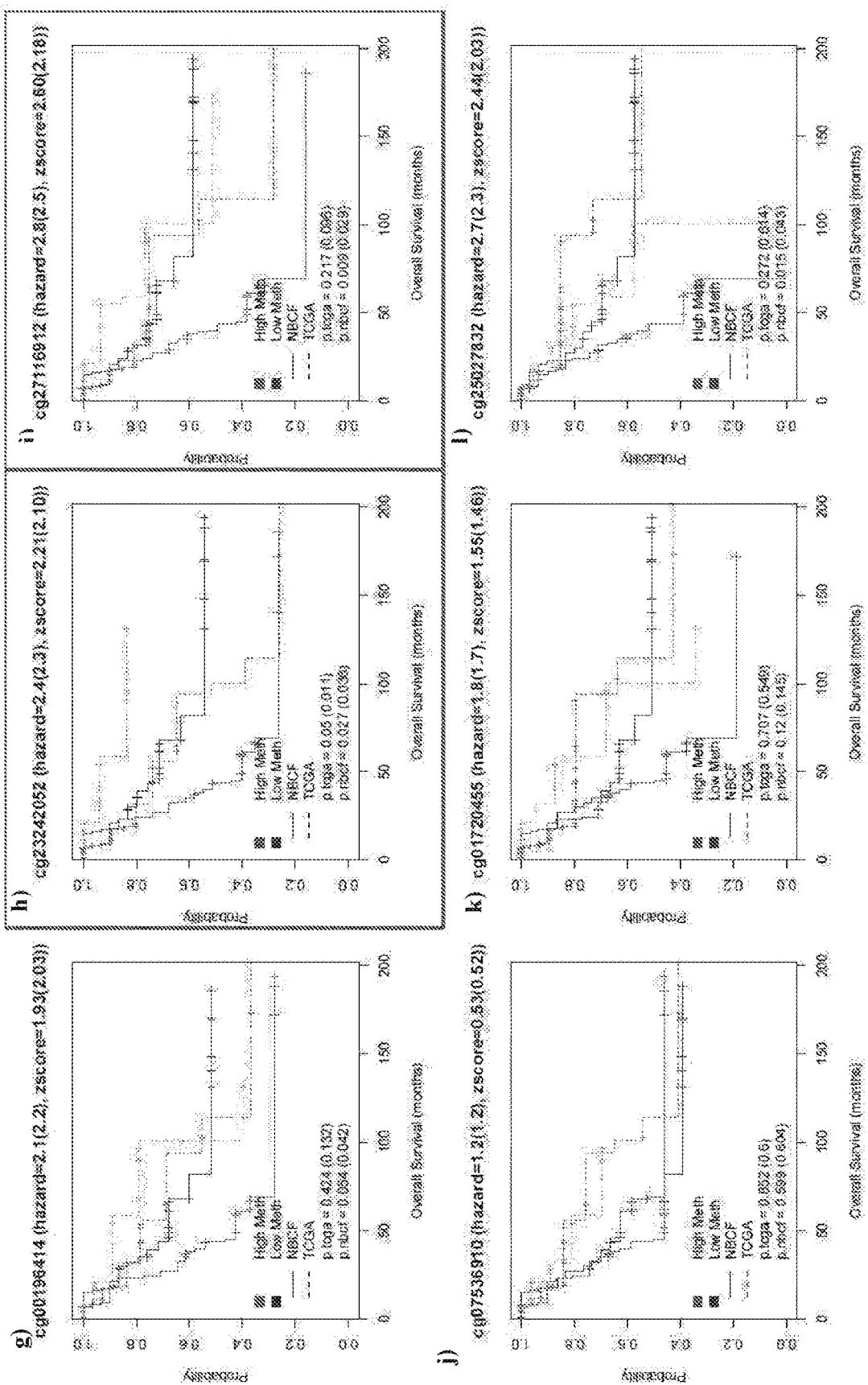
Figure 166:
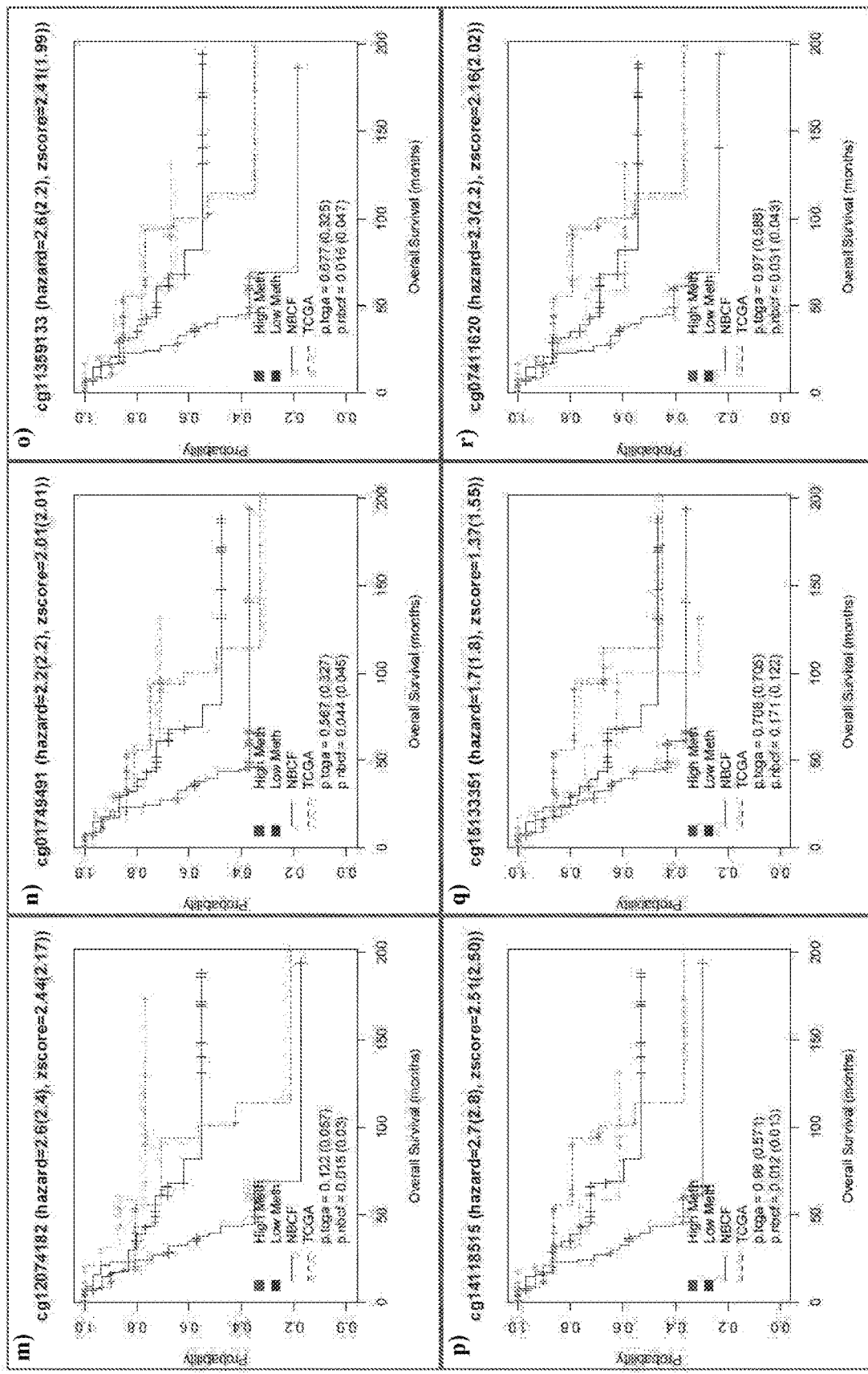
Figure 166:
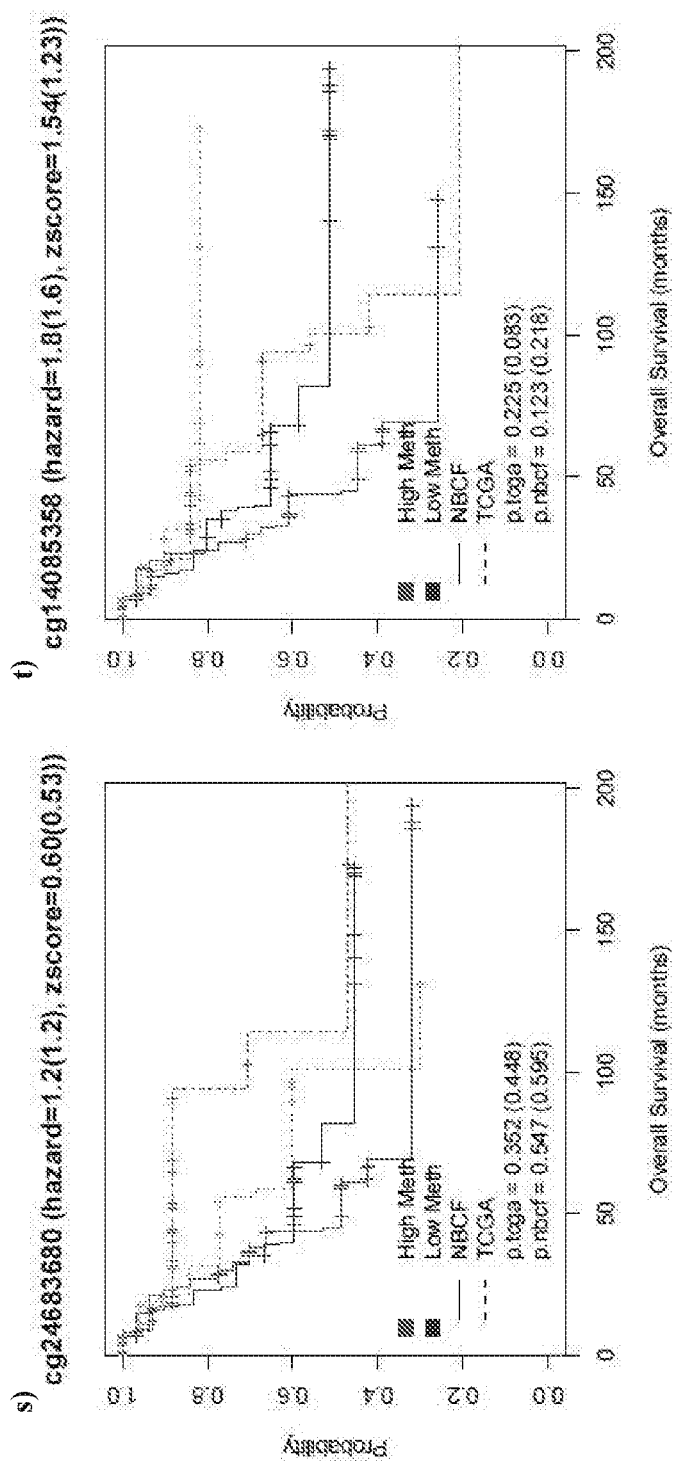

FIG. 166. This figure provides Kaplan Meier plots for each of the probes in prognostic region designated chr2-9331 (as described in Table 14) based on methylation between survival groups in the NBCF cohort. Probes within prognostic region which are statistically significant for predicting patient outcome are boxed.

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

As used herein, the singular forms of "a", "and" and "the" include plural forms of these words, unless the context clearly dictates otherwise.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Selected Definitions

As used herein, the term "diagnosis", and variants thereof, such as, but not limited to "diagnose" or "diagnosing" shall include, but not be limited to, a primary diagnosis of a clinical state or any primary diagnosis of a clinical state. A diagnostic method described herein is also useful for assessing the remission of a subject, or monitoring disease recurrence, or tumor recurrence, such as following surgery, radiation therapy, adjuvant therapy or chemotherapy, or determining the appearance of metastases of a primary tumor. All such uses of the assays described herein are encompassed by the present disclosure.

As used herein, the term "prognosis", and variants thereof, such as, but not limited to "prognosing" shall refer to the prediction of the likelihood that a cancer patient e.g., a breast cancer patient, will have a cancer-attributable death or that the cancer will progress to a worsening stage in the subject, such as recurrence, metastatic spread or drug resistance of the cancer.

As used herein, the term "cancer" shall be taken to include a disease that is characterized by uncontrolled growth of cells within a subject. The term "cancer" shall not be limited to cancer of a specific tissue or cell type. Those skilled in the art will be aware that as a cancer progresses, metastases occur in organs and tissues outside the site of the primary cancer. Accordingly, the term "cancer" as used herein shall be taken to include a metastasis of a cancer in addition to a primary tumor. A particularly preferred cancer in the context of the present disclosure is breast cancer.

As used herein, the term "breast cancer" shall be understood to include a disease that is characterized by uncontrolled growth of cells from breast tissue of a subject.

As used herein, the term "estrogen receptor negative (ER−ve) breast cancer" shall be understood to refer to a breast cancer which is characterised by reduced expression of the ER gene when compared to a non-cancerous sample, or an ER+ve cancerous sample, or which is characterised by a level of expression of the ER gene which is not significantly different from the level of expression of a housekeeping gene, or which is characterised by the absence of a detectable level of expression of the ER gene, or which is characterised by the absence of expression of the ER gene.

As used herein, the term "triple negative breast cancer" or "TNBC" refers to a breast cancer that is characterised as being estrogen receptor (ER) negative, progesterone receptor (PR) negative and human epidermal growth factor receptor 2 (HER-2) negative. Thus, the level of expression of each one of ER, PR and HER-2 may be reduced when compared to a non-cancerous sample, or an ER+ve, PR+ve and HER2+ve cancerous sample, or which is characterised by a level of expression of each one of ER, PR and HER-2 which is not significantly different from the level of expression of a housekeeping gene, or which is characterised by the absence of a detectable level of expression of each one of ER, PR and HER-2, or which is characterised by the absence of expression of each one of ER, PR and HER-2.

The term "tumor" as used herein, refers to all neoplastic cell growth and proliferation, whether malignant or benign, and all pre-cancerous and cancerous cells and tissues. It will also be understood that the term "tumor sample" or similar in the context of a patient having cancer refers to a sample comprising tumor material obtained from a cancer patient. The term encompasses tumor tissue samples, for example, tissue obtained by surgical resection and tissue obtained by biopsy, such as for example, a core biopsy or a fine needle biopsy. In a particular embodiment, the tumor sample is a fixed, wax-embedded tissue sample, such as a formalin-fixed, paraffin-embedded tissue sample. Additionally, the term "tumor sample" encompasses a sample comprising tumor cells obtained from sites other than the primary tumor, e.g., circulating tumor cells.

The term "test sample" as used herein is taken to mean any tissue or body fluid sample taken from a subject having or suspected of having breast cancer. The presence of breast cancer in the subject may therefore already have been determined. Thus, the methods of the present disclosure may be used to determine a particular subtype of breast cancer (such as ER−ve, ER+ve or TNBC) in a subject known to have breast cancer. Thus, the "test sample" may be a "tumor sample" as defined herein. Alternatively, the methods of the present disclosure may be used to determine the presence of breast cancer in a subject in whom the presence of breast cancer has not previously been determined.

As used herein, the term "methylation" will be understood to mean the presence of a methyl group added by the action of a DNA methyl transferase enzyme to a cytosine base or bases in a region of nucleic acid e.g. genomic DNA. Accordingly, the term, "methylation status" as used herein refers to the presence or absence of methylation in a specific nucleic acid region e.g., genomic region. In particular, the present disclosure relates to detection of methylated cytosine (5-methylcytosine). A nucleic acid sequence may comprise one or more CpG methylation sites.

As used herein, the term "differential methylation" shall be taken to mean a change in the relative amount of methylation of a nucleic acid e.g., genomic DNA, in a biological sample e.g., such as a cell or a cell extract, or a body fluid (such as blood), obtained from a subject. In one example, the term "differential methylation" is an increased level of methylation of a nucleic acid. In another example, the term "differential methylation" is a decreased level of methylation of a nucleic acid. In the present disclosure, "differential methylation" is generally determined with reference to a baseline level of methylation for a given genomic region, such as a non-cancerous sample, including a non-cancerous matched sample from a subject known to have cancer e.g., breast cancer. For example, the level of differential methylation may be at least 2% greater or less than a baseline level of methylation, for example at least 5% greater or less than a baseline level of methylation, or at least 10% greater or less than a baseline level of methylation, or at least 15% greater or less than a baseline level of methylation, or at least 20% greater or less than a baseline level of methylation, or at least 25% greater or less than a baseline level of methylation, or at least 30% greater or less than a baseline level of methylation, or at least 40% greater or less than a baseline level of methylation, or at least 50% greater or less than a baseline level of methylation, or at least 60% greater or less than a baseline level of methylation, or at least 70% greater or less than a baseline level of methylation, or at least 80% greater or less than a baseline level of methylation, or at least 90% greater or less than a baseline level of methylation. Thus, the level of differential methylation may be at least 10%, at least 15%, at least 20%, or at least 25% greater than or less than a baseline level of methylation. For example, the level of differential methylation may be at least 10%, at least 15%, at least 20%, or at least 25% greater than a baseline level of methylation.

As used herein, a "CpG dinucleotide", "CpG methylation site" or equivalent, shall be taken to denote a cytosine linked to a guanine by a phosphodiester bond. CpG dinucleotides are targets for methylation of the cytosine residue and may reside within coding or non-coding nucleic acids. Non-coding nucleic acids are understood in the art to include introns, 5'-untranslated regions, 3' untranslated regions, promoter regions of a genomic gene, or intergenic regions.

As used herein, a "reference level of methylation" shall be understood to mean a level of methylation detected in a corresponding nucleic acid from a normal or healthy cell or tissue or body fluid, or a data set produced using information from a normal or healthy cell or tissue or body fluid. For example, a "reference level of methylation" may be a level of methylation in a corresponding nucleic acid from:
(i) a sample comprising a non-cancerous cell;
(ii) a sample from a normal or healthy tissue;
(iii) a sample from a healthy tissue;
(iv) an extract of any one of (i) to (iii);
(v) a data set comprising measurements of methylation for a healthy individual or a population of healthy individuals;
(vi) a data set comprising measurements of methylation for a normal individual or a population of normal individuals; and
(vii) a data set comprising measurements of methylation from the subject being tested wherein the measurements are determined in a matched sample having normal cells. Preferably, the non-cancerous sample is (i) or (ii) or (v) or (vii).

In one example, the reference level of methylation may be a level of methylation determined for one or more CpG dinucleotide sequences within a corresponding genomic region of a healthy breast epithelial cell. Thus, the normal or healthy cell or tissue may comprise a breast epithelial cell. In addition, the "non-cancerous cell" may be a breast epithelial cell. The extract of the normal or healthy cell or tissue, or of the non-cancerous cell may be an extract from a breast epithelial cell.

As used herein, the term "subject" or "patient" shall be taken to mean any animal including a human, preferably a mammal. Exemplary subjects include but are not limited to humans, primates, livestock (e.g. sheep, cows, horses, donkeys, pigs), companion animals (e.g. dogs, cats), laboratory test animals (e.g. mice, rabbits, rats, guinea pigs, hamsters), captive wild animals (e.g. fox, deer). Preferably the mammal is a human or primate. More preferably the mammal is a human.

The term "survival" as used herein refers to survival of a subject having breast cancer for a particular period of time, such as at least 3 years, and preferably 5 years, from the time of diagnosis or prognosis. For example, the term "survival" may refer to survival for at least 3 years, or at least 5 years, or for at least 10 years from the time of diagnosis or prognosis. In another example, the term "survival" may refer to survival of a subject having breast cancer for a particular period of time, such as at least 3 years, or at least 5 years, or at least 10 years following surgery or other treatment associated with breast cancer.

DNA Methylation Biomarkers

The present disclosure provides methods of diagnosing breast cancer comprising detecting the methylation status of one or more CpG dinucleotides within one or more genomic regions set forth in Table 1 in a test sample taken from a subject, and determining differential methylation at said one or more CpG dinucleotides within one or more genomic regions in the test sample relative to a reference level of methylation for the corresponding one or more CpG dinucleotides within one or more corresponding genomic regions, wherein differential methylation at said one or more CpG dinucleotides within one or more genomic regions relative to the reference level of methylation is indicative of the subject having breast cancer. The genomic regions set forth in Table 1 are defined with reference to human genome assembly version 18 ("hg18"). As used herein, "hg18" refers to the March 2006 human reference sequence (NCBI Build 36.1), which was produced by the International Human Genome Sequencing Consortium. Further information about this assembly is provided under the reference NCBI36 in the NCBI Assembly database. Thus, the nucleotide sequences of each of the regions identified in Table 1 (or in any of the Tables disclosed herein) can be identified by reference to hg18, using the "start" and "end" positions described in Table 1 (or in any of the Tables disclosed herein).

The 865 genomic regions listed in Table 1 encompass 822 hypermethylated regions and 43 hypomethylated regions found to be differentially methylated between breast cancer samples and matched normal samples. For each DMR, the following information is provided:
(i) unique DMR identifier (Column 2);
(ii) genomic coordinates of DMR with respect to hg18 (Columns 3-5);
(iii) statistics from statistical analysis with the edgeR package (Columns 6-9);
(iii) overlap (fraction of the region overlapping the element) with various functional elements of the human genome (Columns 10-19); and
(iv) number of overlapping HM450K probes (Column 20).

TABLE 1

Differentially methylated regions (DMRs) associated breast cancer.

| Row No. | DMR identifier | Chromosome | start | end | logCPM | logFC | p-value | adj. p-value | CpG islands: % island | CpG islands: % shore |
|---|---|---|---|---|---|---|---|---|---|---|
| 1 | chr8-27696 | 8 | 92066776 | 92067185 | −19.74 | 8.20 | 1.61E−24 | 3.72E−19 | 0.75 | 0.25 |
| 2 | chr2-45413 | 2 | 279014 | 280443 | −18.72 | 5.96 | 2.70E−21 | 1.50E−16 | 0.76 | 0.24 |

TABLE 1-continued

Differentially methylated regions (DMRs) associated breast cancer.

| | | | | | | | | | |
|---|---|---|---|---|---|---|---|---|---|
| 3 | chr19-49971 | 19 | 34709224 | 34710799 | −18.31 | 5.72 | 1.36E−20 | 5.21E−16 | 1.00 | 0.00 |
| 4 | chr6-28480 | 6 | 170442408 | 170443259 | −20.68 | 8.38 | 1.76E−20 | 5.80E−16 | 0.87 | 0.13 |
| 5 | chr10-29209 | 10 | 134900195 | 134900653 | −19.54 | 6.12 | 6.11E−19 | 1.41E−14 | 1.00 | 0.00 |
| 6 | chr8-26787 | 8 | 72918132 | 72919628 | −18.87 | 5.70 | 3.56E−18 | 6.32E−14 | 0.59 | 0.41 |
| 7 | chr6-6517 | 6 | 30081986 | 30083543 | −18.89 | 5.15 | 5.11E−18 | 7.24E−14 | 0.74 | 0.26 |
| 8 | chr19-24060 | 19 | 36531199 | 36531967 | −20.29 | 6.23 | 9.60E−18 | 1.23E−13 | 0.64 | 0.36 |
| 9 | chr5-29013 | 5 | 1498811 | 1499696 | −17.95 | 4.73 | 1.84E−17 | 2.00E−13 | 0.95 | 0.05 |
| 10 | chr7-23529 | 7 | 27162128 | 27163713 | −18.75 | 4.97 | 2.75E−17 | 2.64E−13 | 0.61 | 0.39 |
| 11 | chr19-6795 | 19 | 42999572 | 43000498 | −17.54 | 4.53 | 5.92E−17 | 5.05E−13 | 0.70 | 0.30 |
| 12 | chr18-12838 | 18 | 75659376 | 75660313 | −20.01 | 5.87 | 1.88E−16 | 1.24E−12 | 0.60 | 0.40 |
| 13 | chr7-5134 | 7 | 133793543 | 133794714 | −19.41 | 5.57 | 2.51E−16 | 1.57E−12 | 0.81 | 0.19 |
| 14 | chr6-2200 | 6 | 84619506 | 84620709 | −19.21 | 4.88 | 4.86E−16 | 2.73E−12 | 0.78 | 0.22 |
| 15 | chr18-4037 | 18 | 73089936 | 73091419 | −18.26 | 4.49 | 6.17E−16 | 3.10E−12 | 0.59 | 0.41 |
| 16 | chr8-15618 | 8 | 100023066 | 100024159 | −18.16 | 4.46 | 8.11E−16 | 3.90E−12 | 0.73 | 0.27 |
| 17 | chr10-33100 | 10 | 11100031 | 11100330 | −33.94 | 32.15 | 1.88E−15 | 8.02E−12 | 1.00 | 0.00 |
| 18 | chr10-2952 | 10 | 124895497 | 124898794 | −17.10 | 4.08 | 2.33E−15 | 9.59E−12 | 0.62 | 0.38 |
| 19 | chr10-17539 | 10 | 134449790 | 134450797 | −18.35 | 4.55 | 2.55E−15 | 1.01E−11 | 1.00 | 0.00 |
| 20 | chr22-16101 | 22 | 44641414 | 44642542 | −18.74 | 4.82 | 2.78E−15 | 1.09E−11 | 0.88 | 0.12 |
| 21 | chr5-23446 | 5 | 3649553 | 3650044 | −20.12 | 5.65 | 2.99E−15 | 1.15E−11 | 1.00 | 0.00 |
| 22 | chr8-20122 | 8 | 92066088 | 92066577 | −19.21 | 5.10 | 3.96E−15 | 1.45E−11 | 0.35 | 0.65 |
| 23 | chr5-19157 | 5 | 179176622 | 179177157 | −21.31 | 7.21 | 5.27E−15 | 1.79E−11 | 0.82 | 0.18 |
| 24 | chr14-10157 | 14 | 36056075 | 36059339 | −16.48 | 3.85 | 5.47E−15 | 1.83E−11 | 0.99 | 0.01 |
| 25 | chr6-10828 | 6 | 26291904 | 26292386 | −21.31 | 7.23 | 6.07E−15 | 1.95E−11 | 0.62 | 0.38 |
| 26 | chr6-14328 | 6 | 336724 | 339195 | −16.77 | 3.99 | 6.09E−15 | 1.95E−11 | 0.84 | 0.16 |
| 27 | chr20-20481 | 20 | 61277034 | 61279412 | −17.94 | 4.27 | 6.86E−15 | 2.17E−11 | 1.00 | 0.00 |
| 28 | chr10-2772 | 10 | 71001436 | 71003609 | −17.41 | 4.06 | 8.97E−15 | 2.72E−11 | 0.79 | 0.21 |
| 29 | chr10-7627 | 10 | 102463030 | 102464122 | −18.74 | 4.32 | 1.11E−14 | 3.32E−11 | 0.75 | 0.25 |
| 30 | chr1-23869 | 1 | 58487792 | 58489026 | −19.18 | 4.87 | 1.14E−14 | 3.36E−11 | 0.67 | 0.33 |
| 31 | chr8-15816 | 8 | 49631324 | 49631776 | −21.22 | 7.30 | 1.15E−14 | 3.37E−11 | 0.42 | 0.58 |
| 32 | chr15-6733 | 15 | 87238541 | 87240007 | −20.87 | 6.16 | 1.78E−14 | 4.64E−11 | 0.46 | 0.54 |
| 33 | chr16-31049 | 16 | 23755027 | 23756125 | −20.65 | 6.38 | 1.84E−14 | 4.71E−11 | 0.53 | 0.47 |
| 34 | chr1-41132 | 1 | 154656571 | 154858487 | −17.87 | 3.95 | 2.20E−14 | 5.41E−11 | 0.61 | 0.39 |
| 35 | chr3-19388 | 3 | 12304623 | 12305653 | −20.76 | 6.22 | 2.69E−14 | 6.46E−11 | 0.69 | 0.31 |
| 36 | chr1-38247 | 1 | 2975045 | 2975421 | −34.06 | 31.91 | 2.87E−14 | 6.69E−11 | 1.00 | 0.00 |
| 37 | chr13-10461 | 13 | 27449406 | 27451115 | −17.89 | 4.11 | 2.84E−14 | 6.69E−11 | 0.85 | 0.15 |
| 38 | chr5-25225 | 5 | 1984151 | 1984908 | −18.71 | 4.53 | 2.86E−14 | 6.69E−11 | 1.00 | 0.00 |
| 39 | chr8-29320 | 8 | 80687184 | 80688436 | −19.78 | 5.37 | 3.50E−14 | 7.84E−11 | 0.91 | 0.09 |
| 40 | chr19-29086 | 19 | 34707398 | 34708614 | −19.17 | 4.81 | 4.05E−14 | 8.74E−11 | 0.82 | 0.18 |
| 41 | chr5-7246 | 5 | 10617612 | 10618776 | −17.61 | 3.95 | 4.24E−14 | 9.06E−11 | 0.92 | 0.08 |
| 42 | chr2-4402 | 2 | 233058433 | 233060592 | −17.28 | 3.81 | 6.03E−14 | 1.25E−10 | 0.96 | 0.04 |
| 43 | chr20-14960 | 20 | 61106610 | 61108291 | −17.11 | 3.79 | 6.14E−14 | 1.26E−10 | 1.00 | 0.00 |
| 44 | chr10-28383 | 10 | 102895469 | 102896935 | −18.19 | 3.92 | 7.21E−14 | 1.46E−10 | 0.67 | 0.33 |
| 45 | chr3-11819 | 3 | 213034 | 214949 | −18.78 | 4.35 | 9.12E−14 | 1.78E−10 | 0.81 | 0.19 |
| 46 | chr1-1238 | 1 | 18835319 | 18835779 | −20.54 | 5.56 | 9.98E−14 | 1.93E−10 | 0.76 | 0.24 |
| 47 | chr2-9305 | 2 | 119248558 | 119249158 | −34.09 | 31.85 | 1.34E−13 | 2.50E−10 | 0.38 | 0.62 |
| 48 | chr18-15120 | 18 | 7106229 | 7107659 | −20.02 | 5.06 | 1.43E−13 | 2.64E−10 | 0.56 | 0.44 |
| 49 | chr8-17019 | 8 | 93182850 | 93185224 | −18.07 | 3.95 | 2.87E−13 | 4.83E−10 | 0.81 | 0.19 |
| 50 | chr9-21502 | 9 | 73954005 | 73954767 | −18.35 | 4.00 | 3.19E−13 | 5.22E−10 | 0.87 | 0.13 |
| 51 | chr19-5700 | 19 | 49403387 | 49403903 | −21.49 | 6.85 | 4.05E−13 | 6.35E−10 | 0.00 | 0.00 |
| 52 | chr8-16712 | 8 | 11596852 | 11598305 | −18.99 | 4.09 | 4.41E−13 | 6.74E−10 | 0.89 | 0.11 |
| 53 | chr2-26540 | 2 | 192767147 | 192769213 | −18.37 | 4.05 | 5.12E−13 | 7.73E−10 | 0.88 | 0.12 |
| 54 | chr6-2258 | 6 | 99385561 | 99386755 | −18.33 | 3.82 | 7.22E−13 | 1.04E−09 | 0.60 | 0.40 |
| 55 | chr19-16607 | 19 | 21449386 | 21450008 | −19.42 | 4.65 | 7.89E−13 | 1.12E−09 | 0.75 | 0.25 |
| 56 | chr16-21410 | 16 | 22731943 | 22733047 | −18.45 | 4.00 | 9.61E−13 | 1.33E−09 | 0.84 | 0.16 |
| 57 | chr12-11186 | 12 | 112397232 | 112399112 | −18.55 | 4.05 | 1.25E−12 | 1.68E−09 | 0.49 | 0.51 |
| 58 | chr20-19800 | 20 | 59261736 | 59262126 | −20.83 | 6.00 | 1.33E−12 | 1.77E−09 | 1.00 | 0.00 |
| 59 | chr13-12381 | 13 | 42046580 | 42047427 | −20.57 | 5.46 | 1.71E−12 | 2.17E−09 | 0.83 | 0.17 |
| 60 | chr3-13141 | 3 | 123385072 | 123386437 | −18.25 | 3.69 | 1.93E−12 | 2.39E−09 | 0.66 | 0.34 |
| 61 | chr20-22169 | 20 | 24398201 | 24400145 | −17.89 | 3.64 | 2.23E−12 | 2.71E−09 | 0.94 | 0.06 |
| 62 | chr1-51037 | 1 | 45024287 | 45025019 | −19.08 | 4.11 | 2.41E−12 | 2.87E−09 | 0.45 | 0.55 |
| 63 | chr8-4616 | 8 | 111055210 | 111056406 | −18.69 | 4.03 | 2.85E−12 | 3.28E−09 | 0.73 | 0.27 |
| 64 | chr6-2768 | 6 | 85528696 | 85531584 | −17.10 | 3.44 | 3.08E−12 | 3.52E−09 | 0.49 | 0.51 |
| 65 | chr6-4563 | 6 | 134258506 | 134259248 | −19.33 | 4.04 | 3.20E−12 | 3.61E−09 | 0.49 | 0.51 |
| 66 | chr15-2506 | 15 | 65914030 | 65915830 | −18.72 | 3.98 | 3.54E−12 | 3.93E−09 | 0.79 | 0.21 |
| 67 | chr17-23838 | 17 | 53589322 | 53590258 | −18.84 | 3.96 | 3.54E−12 | 3.93E−09 | 0.54 | 0.46 |
| 68 | chr2-11562 | 2 | 104827192 | 104828396 | −19.03 | 4.09 | 3.71E−12 | 4.08E−09 | 0.84 | 0.16 |
| 69 | chr19-8158 | 19 | 11550314 | 11551028 | −19.57 | 4.25 | 4.28E−12 | 4.64E−09 | 0.49 | 0.51 |
| 70 | chr1-6349 | 1 | 178470101 | 178471969 | −17.17 | 3.40 | 5.21E−12 | 5.58E−09 | 0.80 | 0.20 |
| 71 | chr10-14823 | 10 | 23527732 | 23529409 | −18.27 | 3.63 | 6.81E−12 | 6.86E−09 | 0.47 | 0.53 |
| 72 | chr1-48080 | 1 | 227635870 | 227837414 | −19.06 | 3.84 | 8.81E−12 | 8.50E−09 | 0.93 | 0.07 |
| 73 | chr8-7644 | 8 | 38705060 | 38705524 | −19.68 | 4.03 | 8.87E−12 | 8.53E−09 | 0.00 | 0.00 |
| 74 | chr7-35552 | 7 | 150736751 | 150738166 | −18.95 | 3.89 | 1.01E−11 | 9.51E−09 | 0.70 | 0.30 |
| 75 | chr1-39600 | 1 | 238321957 | 238322843 | −20.54 | 5.38 | 1.09E−11 | 1.02E−08 | 1.00 | 0.00 |

TABLE 1-continued

Differentially methylated regions (DMRs) associated breast cancer.

| | | | | | | | | | |
|---|---|---|---|---|---|---|---|---|---|
| 76 | chr18-2933 | 18 | 42589839 | 42591235 | −18.79 | 3.81 | 1.15E-11 | 1.06E-08 | 0.66 | 0.34 |
| 77 | chr8-19164 | 8 | 140783597 | 140784422 | −19.22 | 3.98 | 1.19E-11 | 1.09E-08 | 0.79 | 0.21 |
| 78 | chr1-24257 | 1 | 240753295 | 240754308 | −18.52 | 3.71 | 1.27E-11 | 1.14E-08 | 0.55 | 0.45 |
| 79 | chr1-41522 | 1 | 119329995 | 119332779 | −16.74 | 3.21 | 1.28E-11 | 1.15E-08 | 0.32 | 0.68 |
| 80 | chr7-16828 | 7 | 158629179 | 158630121 | −17.39 | 3.27 | 1.60E-11 | 1.40E-08 | 0.90 | 0.10 |
| 81 | chr14-7869 | 14 | 56333447 | 56334854 | −17.70 | 3.19 | 1.87E-11 | 1.59E-08 | 0.33 | 0.67 |
| 82 | chr3-16318 | 3 | 13896785 | 13897673 | −20.50 | 5.44 | 1.87E-11 | 1.59E-08 | 0.62 | 0.38 |
| 83 | chr8-16193 | 8 | 145527618 | 145528086 | −18.88 | 3.61 | 2.62E-11 | 2.11E-08 | 1.00 | 0.00 |
| 84 | chr7-4971 | 7 | 97199969 | 97201481 | −18.63 | 3.61 | 2.67E-11 | 2.15E-08 | 0.65 | 0.35 |
| 85 | chr4-12473 | 4 | 134290693 | 134293738 | −16.94 | 3.20 | 2.73E-11 | 2.19E-08 | 0.65 | 0.35 |
| 86 | chr10-35910 | 10 | 26263333 | 26264042 | −21.10 | 5.61 | 2.76E-11 | 2.20E-08 | 0.98 | 0.02 |
| 87 | chr18-11204 | 18 | 2837112 | 2838477 | −21.56 | 6.65 | 2.76E-11 | 2.20E-08 | 0.78 | 0.22 |
| 88 | chr1-7314 | 1 | 18841892 | 18843502 | −19.39 | 4.27 | 3.16E-11 | 2.46E-08 | 0.74 | 0.26 |
| 89 | chr8-9271 | 8 | 11602545 | 11603549 | −17.78 | 3.34 | 3.30E-11 | 2.55E-08 | 0.92 | 0.08 |
| 90 | chr8-6386 | 8 | 57232090 | 57232767 | −17.69 | 3.30 | 3.35E-11 | 2.58E-08 | 0.60 | 0.40 |
| 91 | chr6-23296 | 6 | 133604035 | 133605961 | −18.59 | 3.61 | 3.41E-11 | 2.62E-08 | 0.75 | 0.25 |
| 92 | chr8-24646 | 8 | 144312844 | 144313143 | −21.22 | 5.39 | 4.03E-11 | 3.01E-08 | 1.00 | 0.00 |
| 93 | chr17-35528 | 17 | 21220609 | 21222242 | −18.47 | 3.69 | 4.66E-11 | 3.40E-08 | 0.95 | 0.05 |
| 94 | chr1-10144 | 1 | 156417196 | 156418247 | −19.76 | 4.03 | 5.35E-11 | 3.81E-08 | 0.84 | 0.16 |
| 95 | chr8-13897 | 8 | 37942231 | 37943375 | −17.53 | 3.31 | 5.33E-11 | 3.81E-08 | 0.82 | 0.18 |
| 96 | chr19-33086 | 19 | 34710844 | 34713600 | −16.04 | 3.06 | 5.39E-11 | 3.82E-08 | 0.86 | 0.14 |
| 97 | chr16-33997 | 16 | 3178206 | 3180403 | −18.27 | 3.44 | 6.33E-11 | 4.41E-08 | 0.17 | 0.83 |
| 98 | chr10-13741 | 10 | 102409068 | 102409766 | −17.59 | 3.21 | 6.93E-11 | 4.77E-08 | 0.75 | 0.25 |
| 99 | chr3-19594 | 3 | 127381204 | 127382027 | −20.85 | 4.97 | 7.29E-11 | 4.96E-08 | 0.82 | 0.18 |
| 100 | chr1-48261 | 1 | 168897582 | 168898339 | −20.84 | 5.01 | 8.33E-11 | 5.60E-08 | 0.00 | 1.00 |
| 101 | chr6-9415 | 6 | 28861643 | 28862262 | −19.68 | 3.84 | 8.55E-11 | 5.71E-08 | 0.43 | 0.57 |
| 102 | chr10-24941 | 10 | 23501946 | 23503503 | −17.07 | 3.16 | 8.81E-11 | 5.84E-08 | 0.82 | 0.18 |
| 103 | chr8-28093 | 8 | 55529318 | 55530316 | −17.98 | 3.37 | 9.28E-11 | 6.12E-08 | 0.86 | 0.14 |
| 104 | chr17-30137 | 17 | 37477869 | 37478517 | −20.87 | 4.91 | 9.52E-11 | 6.26E-08 | 0.80 | 0.20 |
| 105 | chr3-11864 | 3 | 44038270 | 44039120 | −19.04 | 3.63 | 1.15E-10 | 7.48E-08 | 0.61 | 0.39 |
| 106 | chr10-9290 | 10 | 23519886 | 23521695 | −16.93 | 3.02 | 1.28E-10 | 8.13E-08 | 0.55 | 0.45 |
| 107 | chr4-23510 | 4 | 1385469 | 1390166 | −15.36 | 2.94 | 1.33E-10 | 8.33E-08 | 0.82 | 0.18 |
| 108 | chr11-10966 | 11 | 133443978 | 133444518 | −20.27 | 4.57 | 1.37E-10 | 8.52E-08 | 0.85 | 0.15 |
| 109 | chr13-9865 | 13 | 94161892 | 94163404 | −19.16 | 3.79 | 1.77E-10 | 1.08E-07 | 1.00 | 0.00 |
| 110 | chr3-1415 | 3 | 131718242 | 131718973 | −18.24 | 3.25 | 1.88E-10 | 1.14E-07 | 0.29 | 0.71 |
| 111 | chr20-20088 | 20 | 57613692 | 57614327 | −20.68 | 4.47 | 2.32E-10 | 1.36E-07 | 0.77 | 0.23 |
| 112 | chr6-5973 | 6 | 166499687 | 168501552 | −17.48 | 3.01 | 2.37E-10 | 1.38E-07 | 0.85 | 0.15 |
| 113 | chr19-20474 | 19 | 7700739 | 7701731 | −18.84 | 3.60 | 2.64E-10 | 1.51E-07 | 0.94 | 0.06 |
| 114 | chr8-10467 | 8 | 97238897 | 97242187 | −16.49 | 2.95 | 2.66E-10 | 1.51E-07 | 0.39 | 0.61 |
| 115 | chr8-8934 | 8 | 145175158 | 145176215 | −16.93 | 3.04 | 2.90E-10 | 1.64E-07 | 0.89 | 0.11 |
| 116 | chr17-17561 | 17 | 44160443 | 44161169 | −21.18 | 5.38 | 3.30E-10 | 1.85E-07 | 0.82 | 0.18 |
| 117 | chr16-16055 | 16 | 31135270 | 31136018 | −19.76 | 4.08 | 3.35E-10 | 1.87E-07 | 0.66 | 0.34 |
| 118 | chr1-17648 | 1 | 146219219 | 146219619 | −20.51 | 4.67 | 3.51E-10 | 1.95E-07 | 0.34 | 0.66 |
| 119 | chr12-894 | 12 | 112393108 | 112395188 | −17.86 | 3.21 | 3.73E-10 | 2.05E-07 | 0.86 | 0.14 |
| 120 | chr1-39636 | 1 | 235272348 | 235273389 | −16.58 | 2.99 | 3.79E-10 | 2.08E-07 | 0.88 | 0.12 |
| 121 | chr10-26954 | 10 | 94823866 | 94825466 | −17.19 | 2.98 | 3.87E-10 | 2.11E-07 | 0.86 | 0.14 |
| 122 | chr8-13205 | 8 | 11603797 | 11605017 | −18.28 | 3.22 | 4.01E-10 | 2.17E-07 | 0.68 | 0.32 |
| 123 | chr1-36055 | 1 | 227633073 | 227635758 | −15.47 | 2.81 | 4.20E-10 | 2.25E-07 | 0.72 | 0.28 |
| 124 | chr21-7896 | 21 | 33316567 | 33322693 | −15.77 | 2.85 | 4.23E-10 | 2.26E-07 | 0.84 | 0.16 |
| 125 | chr8-18828 | 8 | 55541438 | 55542861 | −16.30 | 2.92 | 4.31E-10 | 2.28E-07 | 0.88 | 0.12 |
| 126 | chr12-11487 | 12 | 93067341 | 93068786 | −19.69 | 4.11 | 4.53E-10 | 2.39E-07 | 0.55 | 0.45 |
| 127 | chr1-32857 | 1 | 242147216 | 242147842 | −21.28 | 5.52 | 4.56E-10 | 2.40E-07 | 0.80 | 0.20 |
| 128 | chr13-7449 | 13 | 78073465 | 78074010 | −18.12 | 3.17 | 4.72E-10 | 2.48E-07 | 0.73 | 0.27 |
| 129 | chr16-27458 | 16 | 3160303 | 3182631 | −17.85 | 3.16 | 4.83E-10 | 2.53E-07 | 0.39 | 0.61 |
| 130 | chr11-27245 | 11 | 77411553 | 77412151 | −18.91 | 3.38 | 5.61E-10 | 2.87E-07 | 0.00 | 0.00 |
| 131 | chr7-28012 | 7 | 103755530 | 103757459 | −19.09 | 3.59 | 6.47E-10 | 3.24E-07 | 0.61 | 0.39 |
| 132 | chr7-40429 | 7 | 1243450 | 1244528 | −19.27 | 3.62 | 6.61E-10 | 3.30E-07 | 1.00 | 0.00 |
| 133 | chr20-4787 | 20 | 5244160 | 5246038 | −18.50 | 3.28 | 7.04E-10 | 3.49E-07 | 0.82 | 0.18 |
| 134 | chr9-27388 | 9 | 29203497 | 29205489 | −18.33 | 3.13 | 7.09E-10 | 3.50E-07 | 0.12 | 0.88 |
| 135 | chr19-11834 | 19 | 8562642 | 8563981 | −19.58 | 3.81 | 7.28E-10 | 3.57E-07 | 0.84 | 0.16 |
| 136 | chr7-25883 | 7 | 154863002 | 154863839 | −20.46 | 4.68 | 7.78E-10 | 3.78E-07 | 0.38 | 0.62 |
| 137 | chr1-40004 | 1 | 226312674 | 226315609 | −16.17 | 2.83 | 7.84E-10 | 3.81E-07 | 0.19 | 0.81 |
| 138 | chr16-16067 | 16 | 31120490 | 31122067 | −18.87 | 3.21 | 8.02E-10 | 3.87E-07 | 0.46 | 0.54 |
| 139 | chr11-13529 | 11 | 20646986 | 20847555 | −20.85 | 4.84 | 8.29E-10 | 3.99E-07 | 0.70 | 0.30 |
| 140 | chr12-17914 | 12 | 118515687 | 118517758 | −19.03 | 3.43 | 8.80E-10 | 4.20E-07 | 0.83 | 0.17 |
| 141 | chr19-46269 | 19 | 6541010 | 6542269 | −19.82 | 3.98 | 9.13E-10 | 4.34E-07 | 0.58 | 0.42 |
| 142 | chr20-2803 | 20 | 41250974 | 41251609 | −34.54 | 30.96 | 1.08E-09 | 4.99E-07 | 1.00 | 0.00 |
| 143 | chr19-7319 | 19 | 35408061 | 35408437 | −20.33 | 4.34 | 1.10E-09 | 5.03E-07 | 0.71 | 0.29 |
| 144 | chr7-11150 | 7 | 154866571 | 154868288 | −18.31 | 3.26 | 1.14E-09 | 5.20E-07 | 0.65 | 0.35 |
| 145 | chr1-20056 | 1 | 90948898 | 90949502 | −20.58 | 4.52 | 1.18E-09 | 5.37E-07 | 0.49 | 0.51 |
| 146 | chr12-28277 | 12 | 4252918 | 4254496 | −20.06 | 4.25 | 1.23E-09 | 5.57E-07 | 0.66 | 0.34 |
| 147 | chr6-3358 | 6 | 117697858 | 117699053 | −18.64 | 3.23 | 1.31E-09 | 5.89E-07 | 0.62 | 0.38 |
| 148 | chr8-3384 | 8 | 65454075 | 65455349 | −18.61 | 3.13 | 1.33E-09 | 5.96E-07 | 0.00 | 1.00 |
| 149 | chr11-27664 | 11 | 64749540 | 64750291 | −18.52 | 3.29 | 1.39E-09 | 6.20E-07 | 0.27 | 0.73 |
| 150 | chr7-24732 | 7 | 121737427 | 121738331 | −18.41 | 2.97 | 1.41E-09 | 6.30E-07 | 0.75 | 0.25 |
| 151 | chr19-49834 | 19 | 21985098 | 21985686 | −20.31 | 4.00 | 1.43E-09 | 6.35E-07 | 0.43 | 0.57 |
| 152 | chr6-17652 | 6 | 28662601 | 28663625 | −20.58 | 4.56 | 1.62E-09 | 7.13E-07 | 0.25 | 0.75 |
| 153 | chr1-18702 | 1 | 146242078 | 146242459 | −20.87 | 4.81 | 1.64E-09 | 7.21E-07 | 0.34 | 0.66 |

TABLE 1-continued

Differentially methylated regions (DMRs) associated breast cancer.

| | | | | | | | | | |
|---|---|---|---|---|---|---|---|---|---|
| 154 | chr8-27831 | 8 | 109162559 | 109165258 | −16.74 | 2.74 | 1.67E−09 | 7.33E−07 | 0.51 | 0.49 |
| 155 | chr1-31174 | 1 | 150754436 | 150755138 | −20.15 | 4.18 | 1.72E−09 | 7.51E−07 | 0.42 | 0.58 |
| 156 | chr7-39912 | 7 | 45094906 | 45095877 | −19.46 | 3.83 | 1.78E−09 | 7.71E−07 | 0.37 | 0.63 |
| 157 | chr8-25495 | 8 | 11591837 | 11593200 | −19.02 | 3.28 | 1.90E−09 | 8.22E−07 | 0.37 | 0.63 |
| 158 | chr1-32633 | 1 | 159542085 | 159542934 | −18.60 | 3.32 | 2.05E−09 | 8.74E−07 | 0.00 | 0.00 |
| 159 | chr22-15317 | 22 | 25383018 | 25383912 | −19.99 | 3.98 | 2.05E−09 | 8.74E−07 | 0.61 | 0.39 |
| 160 | chr1-24072 | 1 | 240754763 | 240755457 | −21.78 | 6.19 | 2.12E−09 | 9.00E−07 | 0.78 | 0.22 |
| 161 | chr16-19848 | 16 | 85098394 | 85099853 | −17.86 | 2.94 | 2.85E−09 | 1.17E−06 | 0.63 | 0.37 |
| 162 | chr18-13032 | 18 | 11139121 | 11140070 | −18.40 | 2.99 | 2.97E−09 | 1.21E−06 | 0.86 | 0.14 |
| 163 | chr9-25007 | 9 | 93752490 | 93752945 | −22.08 | 5.74 | 2.98E−09 | 1.21E−06 | 0.89 | 0.11 |
| 164 | chr13-14276 | 13 | 94417645 | 94419167 | −19.32 | 3.47 | 3.34E−09 | 1.34E−06 | 0.72 | 0.28 |
| 165 | chr4-20909 | 4 | 1390317 | 1391758 | −16.59 | 2.71 | 3.37E−09 | 1.35E−06 | 0.98 | 0.02 |
| 166 | chr13-8091 | 13 | 109235458 | 109235911 | −18.83 | 3.34 | 3.43E−09 | 1.37E−06 | 1.00 | 0.00 |
| 167 | chr8-19479 | 8 | 105547717 | 105548686 | −16.39 | 2.69 | 3.74E−09 | 1.47E−06 | 0.69 | 0.31 |
| 168 | chr20-7936 | 20 | 44575280 | 44575737 | −19.62 | 3.81 | 3.86E−09 | 1.51E−06 | 0.72 | 0.28 |
| 169 | chr1-22437 | 1 | 147404036 | 147405091 | −17.34 | 2.69 | 3.91E−09 | 1.53E−06 | 0.81 | 0.19 |
| 170 | chr7-14832 | 7 | 126678417 | 126680079 | −19.29 | 3.54 | 4.00E−09 | 1.56E−06 | 0.93 | 0.07 |
| 171 | chr8-17320 | 8 | 145895909 | 145896990 | −17.61 | 2.79 | 4.06E−09 | 1.58E−06 | 0.64 | 0.36 |
| 172 | chr6-12570 | 6 | 100173498 | 100174098 | −17.52 | 2.80 | 4.26E−09 | 1.65E−06 | 0.83 | 0.17 |
| 173 | chr1-1764 | 1 | 226718035 | 226719183 | −17.09 | 2.69 | 4.38E−09 | 1.69E−06 | 0.94 | 0.06 |
| 174 | chr21-5935 | 21 | 38209736 | 38211169 | −18.41 | 2.87 | 4.62E−09 | 1.77E−06 | 0.92 | 0.08 |
| 175 | chr1-18828 | 1 | 205909091 | 205910115 | −17.48 | 2.73 | 4.79E−09 | 1.81E−06 | 0.44 | 0.56 |
| 176 | chr19-47954 | 19 | 22506840 | 22507427 | −19.42 | 3.23 | 5.53E−09 | 2.06E−06 | 0.53 | 0.47 |
| 177 | chr20-15341 | 20 | 21634216 | 21635840 | −17.42 | 2.80 | 5.71E−09 | 2.13E−06 | 0.91 | 0.09 |
| 178 | chr5-17366 | 5 | 158459878 | 158460825 | −19.90 | 3.80 | 5.80E−09 | 2.16E−06 | 0.64 | 0.36 |
| 179 | chr3-16920 | 3 | 129690745 | 129692733 | −20.64 | 4.41 | 6.00E−09 | 2.22E−06 | 1.00 | 0.00 |
| 180 | chr6-6670 | 6 | 12858176 | 12858647 | −19.16 | 3.39 | 6.11E−09 | 2.26E−06 | 0.66 | 0.34 |
| 181 | chr19-45411 | 19 | 56535026 | 56535791 | −20.70 | 3.87 | 6.47E−09 | 2.37E−06 | 0.93 | 0.07 |
| 182 | chr20-11215 | 20 | 21033980 | 21035294 | −18.86 | 3.03 | 7.13E−09 | 2.58E−06 | 0.79 | 0.21 |
| 183 | chr1-34837 | 1 | 198270644 | 198272124 | −18.05 | 2.88 | 7.18E−09 | 2.59E−06 | 0.31 | 0.69 |
| 184 | chr21-8209 | 21 | 36989873 | 36993170 | −16.22 | 2.61 | 7.36E−09 | 2.65E−06 | 0.94 | 0.06 |
| 185 | chr5-27730 | 5 | 9597561 | 9598916 | −18.55 | 3.12 | 7.60E−09 | 2.73E−06 | 0.90 | 0.10 |
| 186 | chr1-30464 | 1 | 16892517 | 16893245 | −17.29 | 2.65 | 7.64E−09 | 2.73E−06 | 1.00 | 0.00 |
| 187 | chr15-7466 | 15 | 46957300 | 46958277 | −21.34 | 5.10 | 7.63E−09 | 2.73E−06 | 0.58 | 0.42 |
| 188 | chr17-12235 | 17 | 32371653 | 32372627 | −18.57 | 2.96 | 8.12E−09 | 2.88E−06 | 1.00 | 0.00 |
| 189 | chr3-17474 | 3 | 126558531 | 126559202 | −18.61 | 3.03 | 8.12E−09 | 2.88E−06 | 0.84 | 0.16 |
| 190 | chr11-7178 | 11 | 113435550 | 113437712 | −19.88 | 3.58 | 8.17E−09 | 2.89E−06 | 0.86 | 0.14 |
| 191 | chr7-12819 | 7 | 100732591 | 100733729 | −17.06 | 2.72 | 8.45E−09 | 2.97E−06 | 0.00 | 0.00 |
| 192 | chr1-33177 | 1 | 239653649 | 239653948 | −34.68 | 30.67 | 8.64E−09 | 3.01E−06 | 0.00 | 1.00 |
| 193 | chr6-23289 | 6 | 27408690 | 27409294 | −34.64 | 30.76 | 8.64E−09 | 3.01E−06 | 0.00 | 0.00 |
| 194 | chr18-12432 | 18 | 65219359 | 65220459 | −18.00 | 2.93 | 9.24E−09 | 3.20E−06 | 0.72 | 0.28 |
| 195 | chr11-24690 | 11 | 125278717 | 125279989 | −17.24 | 2.76 | 9.50E−09 | 3.28E−06 | 0.25 | 0.75 |
| 196 | chr1-20728 | 1 | 151917440 | 151919117 | −17.61 | 2.83 | 1.00E−08 | 3.45E−06 | 0.92 | 0.08 |
| 197 | chr3-1158 | 3 | 173648106 | 173650702 | −15.48 | 2.52 | 1.05E−08 | 3.60E−06 | 0.64 | 0.36 |
| 198 | chr21-5864 | 21 | 38953773 | 38955606 | −16.80 | 2.68 | 1.05E−08 | 3.61E−06 | 0.78 | 0.22 |
| 199 | chr6-15257 | 6 | 7672425 | 7674161 | −20.92 | 4.13 | 1.06E−08 | 3.64E−06 | 0.55 | 0.45 |
| 200 | chr3-11179 | 3 | 62333852 | 62335905 | −17.27 | 2.69 | 1.09E−08 | 3.72E−06 | 0.47 | 0.53 |
| 201 | chr2-13825 | 2 | 182253383 | 182254903 | −17.84 | 2.71 | 1.10E−08 | 3.73E−06 | 0.00 | 0.52 |
| 202 | chr9-17404 | 9 | 34568108 | 34568587 | −19.30 | 3.43 | 1.17E−08 | 3.95E−06 | 0.31 | 0.69 |
| 203 | chr7-28113 | 7 | 24290275 | 24291795 | −17.19 | 2.72 | 1.18E−08 | 3.96E−06 | 0.88 | 0.12 |
| 204 | chr19-10652 | 19 | 49644032 | 49644762 | −20.07 | 3.62 | 1.20E−08 | 4.00E−06 | 0.54 | 0.46 |
| 205 | chr8-4283 | 8 | 86537557 | 86538509 | −17.13 | 2.66 | 1.24E−08 | 4.11E−06 | 0.45 | 0.55 |
| 206 | chr1-32204 | 1 | 235271550 | 235271938 | −19.40 | 3.47 | 1.43E−08 | 4.69E−06 | 0.49 | 0.51 |
| 207 | chr5-18793 | 5 | 9599452 | 9600097 | −19.32 | 3.32 | 1.49E−08 | 4.87E−06 | 0.41 | 0.59 |
| 208 | chr14-18299 | 14 | 56353014 | 56354411 | −17.12 | 2.65 | 1.53E−08 | 4.97E−06 | 0.42 | 0.58 |
| 209 | chr7-8996 | 7 | 154951647 | 154953283 | −17.73 | 2.73 | 1.58E−08 | 5.11E−06 | 1.00 | 0.00 |
| 210 | chr9-7772 | 9 | 103288066 | 103289677 | −16.49 | 2.58 | 1.62E−08 | 5.25E−06 | 0.78 | 0.22 |
| 211 | chr19-10697 | 19 | 62309101 | 62309842 | −18.10 | 2.80 | 1.69E−08 | 5.43E−06 | 0.58 | 0.42 |
| 212 | chr1-25380 | 1 | 154096691 | 154097077 | −21.27 | 5.14 | 1.71E−08 | 5.48E−06 | 0.67 | 0.33 |
| 213 | chr8-7773 | 8 | 69026539 | 69027642 | −18.13 | 2.96 | 1.78E−08 | 5.66E−06 | 0.33 | 0.67 |
| 214 | chr14-18459 | 14 | 100993460 | 100995003 | −16.86 | 2.59 | 1.94E−08 | 6.13E−06 | 1.00 | 0.00 |
| 215 | chr6-26510 | 6 | 78228763 | 78231120 | −16.41 | 2.53 | 1.94E−08 | 6.13E−06 | 0.79 | 0.21 |
| 216 | chr6-16375 | 6 | 31890480 | 31891670 | −20.55 | 4.02 | 1.95E−08 | 6.14E−06 | 0.69 | 0.31 |
| 217 | chr10-15047 | 10 | 1768602 | 1770120 | −20.00 | 3.64 | 2.00E−08 | 6.27E−06 | 0.81 | 0.19 |
| 218 | chr4-2412 | 4 | 172970178 | 172971846 | −18.71 | 2.93 | 2.02E−08 | 6.30E−06 | 0.83 | 0.17 |
| 219 | chr8-13432 | 8 | 65455535 | 65456036 | −18.59 | 2.80 | 2.04E−08 | 6.36E−06 | 0.00 | 0.00 |
| 220 | chr7-4850 | 7 | 8439552 | 8442214 | −17.13 | 2.61 | 2.15E−08 | 6.64E−06 | 0.77 | 0.23 |
| 221 | chr7-30884 | 7 | 127459174 | 127459558 | −21.53 | 4.88 | 2.18E−08 | 6.74E−06 | 1.00 | 0.00 |
| 222 | chr4-7057 | 4 | 13138180 | 13139150 | −18.70 | 3.12 | 2.19E−08 | 6.77E−06 | 0.63 | 0.37 |
| 223 | chr19-22107 | 19 | 44446457 | 44447692 | −16.49 | 2.56 | 2.22E−08 | 6.81E−06 | 0.71 | 0.29 |
| 224 | chr5-23479 | 5 | 36026653 | 36027313 | −19.55 | 3.27 | 2.25E−08 | 6.89E−06 | 0.00 | 0.00 |
| 225 | chr6-7762 | 6 | 43384179 | 43384892 | −21.93 | 5.89 | 2.30E−08 | 6.99E−06 | 0.34 | 0.66 |
| 226 | chr8-14986 | 8 | 145532810 | 145533610 | −20.04 | 3.87 | 2.39E−08 | 7.27E−06 | 0.64 | 0.36 |
| 227 | chr2-26142 | 2 | 167858796 | 167859492 | −20.22 | 4.03 | 2.52E−08 | 7.62E−06 | 0.36 | 0.64 |
| 228 | chr1-8996 | 1 | 18844034 | 18844768 | −19.84 | 3.44 | 2.53E−08 | 7.62E−06 | 0.50 | 0.50 |
| 229 | chr10-8209 | 10 | 26543645 | 26547703 | −16.52 | 2.49 | 2.81E−08 | 8.36E−06 | 0.75 | 0.25 |
| 230 | chr1-17872 | 1 | 50658646 | 50659783 | −16.87 | 2.57 | 2.89E−08 | 8.58E−06 | 1.00 | 0.00 |
| 231 | chr15-2568 | 15 | 50873927 | 50875994 | −18.15 | 2.67 | 2.91E−08 | 8.62E−06 | 0.24 | 0.76 |

TABLE 1-continued

Differentially methylated regions (DMRs) associated breast cancer.

| | | | | | | | | | |
|---|---|---|---|---|---|---|---|---|---|
| 232 | chr8-10864 | 8 | 56176559 | 56177228 | −18.46 | 2.89 | 3.06E-08 | 9.03E-06 | 1.00 | 0.00 |
| 233 | chr8-5843 | 8 | 57520576 | 57521847 | −15.93 | 2.47 | 3.28E-08 | 9.58E-06 | 0.92 | 0.08 |
| 234 | chr9-16770 | 9 | 37019348 | 37020844 | −18.38 | 2.88 | 3.44E-08 | 9.99E-06 | 0.24 | 0.76 |
| 235 | chr15-15389 | 15 | 46725135 | 46725818 | −21.02 | 4.49 | 3.48E-08 | 1.01E-05 | 1.00 | 0.00 |
| 236 | chr6-23012 | 6 | 137858031 | 137859078 | −17.58 | 2.62 | 3.68E-08 | 1.06E-05 | 0.71 | 0.29 |
| 237 | chr3-9567 | 3 | 148561647 | 148561946 | −20.47 | 3.70 | 3.74E-08 | 1.07E-05 | 0.00 | 1.00 |
| 238 | chr7-38902 | 7 | 98084470 | 98085748 | −16.42 | 2.51 | 3.73E-08 | 1.07E-05 | 0.96 | 0.04 |
| 239 | chr17-668 | 17 | 40399881 | 40401028 | −19.48 | 3.18 | 3.88E-08 | 1.10E-05 | 0.99 | 0.01 |
| 240 | chr10-6509 | 10 | 102478872 | 102480011 | −21.29 | 4.15 | 3.96E-08 | 1.12E-05 | 0.59 | 0.41 |
| 241 | chr11-7826 | 11 | 91597095 | 91599952 | −18.55 | 2.85 | 4.00E-08 | 1.13E-05 | 0.93 | 0.07 |
| 242 | chr8-21750 | 8 | 38746617 | 38747410 | −17.48 | 2.62 | 4.08E-08 | 1.15E-05 | 0.00 | 0.00 |
| 243 | chr9-28705 | 9 | 78823050 | 78824812 | −17.02 | 2.56 | 4.10E-08 | 1.15E-05 | 0.94 | 0.06 |
| 244 | chr10-32739 | 10 | 25504311 | 25505823 | −18.14 | 2.79 | 4.17E-08 | 1.17E-05 | 0.88 | 0.12 |
| 245 | chr1-42850 | 1 | 6401196 | 6402156 | −19.45 | 3.15 | 4.66E-08 | 1.29E-05 | 0.53 | 0.47 |
| 246 | chr9-31429 | 9 | 36248189 | 36249110 | −20.51 | 4.04 | 4.72E-08 | 1.30E-05 | 0.76 | 0.24 |
| 247 | chr6-3985 | 6 | 7051996 | 7052718 | −20.85 | 4.07 | 4.80E-08 | 1.32E-05 | 0.89 | 0.11 |
| 248 | chr8-10122 | 8 | 65448362 | 65448976 | −17.96 | 2.56 | 4.81E-08 | 1.32E-05 | 0.58 | 0.42 |
| 249 | chr9-33298 | 9 | 95750508 | 95751903 | −17.69 | 2.58 | 4.98E-08 | 1.36E-05 | 0.65 | 0.35 |
| 250 | chr17-22392 | 17 | 44184869 | 44185763 | −21.04 | 4.48 | 5.21E-08 | 1.41E-05 | 0.00 | 0.73 |
| 251 | chr1-18644 | 1 | 198275935 | 198278813 | −16.29 | 2.41 | 5.40E-08 | 1.46E-05 | 0.31 | 0.69 |
| 252 | chr2-3750 | 2 | 137238538 | 137240987 | −19.40 | 3.13 | 5.59E-08 | 1.51E-05 | 0.50 | 0.50 |
| 253 | chr7-12114 | 7 | 154856923 | 154860744 | −16.04 | 2.40 | 5.64E-08 | 1.52E-05 | 0.86 | 0.14 |
| 254 | chr18-8326 | 18 | 68359872 | 68360921 | −18.86 | 3.00 | 5.88E-08 | 1.58E-05 | 0.92 | 0.08 |
| 255 | chr19-45799 | 19 | 56521875 | 56522920 | −18.31 | 2.81 | 5.95E-08 | 1.59E-05 | 1.00 | 0.00 |
| 256 | chr9-33335 | 9 | 95148049 | 95148890 | −17.51 | 2.57 | 6.00E-08 | 1.60E-05 | 0.62 | 0.38 |
| 257 | chr18-245 | 18 | 53255803 | 53260282 | −16.04 | 2.42 | 6.14E-08 | 1.63E-05 | 0.90 | 0.10 |
| 258 | chr8-3960 | 8 | 24868578 | 24871425 | −16.71 | 2.50 | 6.14E-08 | 1.63E-05 | 0.48 | 0.52 |
| 259 | chr20-4500 | 20 | 25011764 | 25013922 | −16.64 | 2.44 | 6.45E-08 | 1.70E-05 | 0.78 | 0.22 |
| 260 | chr10-9549 | 10 | 50272881 | 50273274 | −21.37 | 4.92 | 6.66E-08 | 1.74E-05 | 0.71 | 0.29 |
| 261 | chr1-4629 | 1 | 222869931 | 222872599 | −16.52 | 2.41 | 6.92E-08 | 1.80E-05 | 0.80 | 0.20 |
| 262 | chr8-5807 | 8 | 144232946 | 144234345 | −18.61 | 2.88 | 6.96E-08 | 1.81E-05 | 0.00 | 0.00 |
| 263 | chr13-8202 | 13 | 99439503 | 99440212 | −19.12 | 3.00 | 7.35E-08 | 1.89E-05 | 0.97 | 0.03 |
| 264 | chr1-15009 | 1 | 239586266 | 239586643 | −22.25 | 5.38 | 7.67E-08 | 1.97E-05 | 0.00 | 1.00 |
| 265 | chr20-11329 | 20 | 22507549 | 22508115 | −19.98 | 3.09 | 7.80E-08 | 2.00E-05 | 0.79 | 0.21 |
| 266 | chr8-5087 | 8 | 65445829 | 65446662 | −17.60 | 2.46 | 7.83E-08 | 2.00E-05 | 0.00 | 1.00 |
| 267 | chr7-40510 | 7 | 19150608 | 19151892 | −17.52 | 2.51 | 7.87E-08 | 2.01E-05 | 0.53 | 0.47 |
| 268 | chr3-13959 | 3 | 27747702 | 27748100 | −19.07 | 2.74 | 8.25E-08 | 2.09E-05 | 0.00 | 1.00 |
| 269 | chr7-24792 | 7 | 103416300 | 103417009 | −20.27 | 3.87 | 8.81E-08 | 2.22E-05 | 0.35 | 0.65 |
| 270 | chr8-16413 | 8 | 120720021 | 120720320 | −21.33 | 4.11 | 9.00E-08 | 2.25E-05 | 0.00 | 0.00 |
| 271 | chr10-23344 | 10 | 124891388 | 124893492 | −17.17 | 2.45 | 9.46E-08 | 2.34E-05 | 0.34 | 0.66 |
| 272 | chr11-30051 | 11 | 20647654 | 20649654 | −19.15 | 2.88 | 9.71E-08 | 2.38E-05 | 0.38 | 0.62 |
| 273 | chr19-8563 | 19 | 49147040 | 49147610 | −34.79 | 30.44 | 9.79E-08 | 2.40E-05 | 0.74 | 0.26 |
| 274 | chr3-4075 | 3 | 63238878 | 63240098 | −19.45 | 3.07 | 1.07E-07 | 2.58E-05 | 0.18 | 0.82 |
| 275 | chr8-29409 | 8 | 79740841 | 79741568 | −20.78 | 4.18 | 1.07E-07 | 2.59E-05 | 0.52 | 0.48 |
| 276 | chr1-27293 | 1 | 152741716 | 152742254 | −16.47 | 2.40 | 1.14E-07 | 2.73E-05 | 1.00 | 0.00 |
| 277 | chr10-16430 | 10 | 132998977 | 132999442 | −18.48 | 2.72 | 1.14E-07 | 2.73E-05 | 0.56 | 0.44 |
| 278 | chr14-12954 | 14 | 91859637 | 91860687 | −18.93 | 2.85 | 1.21E-07 | 2.90E-05 | 0.79 | 0.21 |
| 279 | chr7-37359 | 7 | 71439704 | 71441020 | −17.17 | 2.49 | 1.25E-07 | 2.98E-05 | 0.76 | 0.24 |
| 280 | chr20-11674 | 20 | 36786620 | 36791737 | −15.32 | 2.32 | 1.26E-07 | 3.00E-05 | 0.81 | 0.19 |
| 281 | chr8-2210 | 8 | 65451687 | 65453842 | −16.49 | 2.39 | 1.28E-07 | 3.03E-05 | 0.39 | 0.61 |
| 282 | chr10-10042 | 10 | 102870703 | 102871609 | −18.28 | 2.48 | 1.29E-07 | 3.06E-05 | 0.00 | 0.71 |
| 283 | chr10-28832 | 10 | 102498899 | 102499830 | −19.04 | 3.04 | 1.35E-07 | 3.19E-05 | 0.79 | 0.21 |
| 284 | chr6-3486 | 6 | 26853218 | 26853781 | −19.52 | 2.96 | 1.37E-07 | 3.22E-05 | 0.00 | 0.00 |
| 285 | chr13-12246 | 13 | 111759028 | 111761130 | −16.01 | 2.34 | 1.37E-07 | 3.22E-05 | 0.78 | 0.22 |
| 286 | chr4-8602 | 4 | 177223716 | 177224452 | −22.13 | 5.57 | 1.37E-07 | 3.22E-05 | 0.60 | 0.40 |
| 287 | chr3-19000 | 3 | 131176181 | 131177707 | −16.42 | 2.39 | 1.41E-07 | 3.29E-05 | 0.88 | 0.12 |
| 288 | chr20-22989 | 20 | 61108502 | 61108900 | −34.83 | 30.37 | 1.42E-07 | 3.31E-05 | 1.00 | 0.00 |
| 289 | chr1-47207 | 1 | 75368128 | 75368976 | −18.44 | 2.52 | 1.54E-07 | 3.56E-05 | 0.41 | 0.59 |
| 290 | chr20-1414 | 20 | 20292251 | 20294265 | −17.48 | 2.48 | 1.58E-07 | 3.65E-05 | 0.93 | 0.07 |
| 291 | chr7-14221 | 7 | 87067400 | 87068467 | −19.47 | 3.14 | 1.60E-07 | 3.69E-05 | 0.51 | 0.49 |
| 292 | chr6-15406 | 6 | 27913755 | 27915100 | −20.72 | 4.18 | 1.68E-07 | 3.85E-05 | 0.75 | 0.25 |
| 293 | chr6-20418 | 6 | 28885462 | 28886854 | −19.13 | 2.89 | 1.69E-07 | 3.87E-05 | 0.00 | 0.00 |
| 294 | chr19-30142 | 19 | 57564768 | 57565451 | −20.69 | 3.82 | 1.71E-07 | 3.92E-05 | 0.71 | 0.29 |
| 295 | chr19-48169 | 19 | 62309903 | 62310319 | −18.86 | 2.73 | 1.75E-07 | 3.98E-05 | 0.86 | 0.14 |
| 296 | chr12-16245 | 12 | 131991417 | 131991716 | −19.63 | 3.11 | 1.76E-07 | 4.00E-05 | 0.00 | 0.00 |
| 297 | chr2-25081 | 2 | 171386257 | 171388430 | −18.47 | 2.67 | 1.83E-07 | 4.14E-05 | 0.75 | 0.25 |
| 298 | chr16-43212 | 16 | 85088677 | 85089077 | −20.08 | 3.42 | 1.85E-07 | 4.18E-05 | 1.00 | 0.00 |
| 299 | chr8-9764 | 8 | 57394577 | 57395494 | −18.26 | 2.57 | 1.87E-07 | 4.21E-05 | 0.46 | 0.54 |
| 300 | chr5-10265 | 5 | 145705002 | 145706101 | −17.62 | 2.42 | 1.91E-07 | 4.29E-05 | 0.51 | 0.49 |
| 301 | chr5-14304 | 5 | 452636 | 453644 | −17.49 | 2.43 | 1.91E-07 | 4.29E-05 | 0.00 | 0.00 |
| 302 | chr19-41383 | 19 | 35408947 | 35409765 | −19.86 | 3.23 | 1.93E-07 | 4.33E-05 | 1.00 | 0.00 |
| 303 | chr6-18714 | 6 | 26854543 | 26855628 | −20.08 | 3.67 | 1.93E-07 | 4.33E-05 | 0.00 | 0.00 |
| 304 | chr10-18957 | 10 | 133000272 | 133001373 | −17.01 | 2.38 | 1.99E-07 | 4.43E-05 | 0.70 | 0.30 |
| 305 | chr11-25281 | 11 | 124240101 | 124242276 | −18.44 | 2.50 | 2.00E-07 | 4.44E-05 | 0.64 | 0.36 |
| 306 | chr6-6380 | 6 | 28475091 | 28475975 | −19.12 | 2.78 | 2.07E-07 | 4.58E-05 | 0.60 | 0.40 |
| 307 | chr10-11832 | 10 | 23523652 | 23524551 | −16.63 | 2.32 | 2.12E-07 | 4.68E-05 | 0.67 | 0.33 |
| 308 | chr1-40817 | 1 | 178468989 | 178469844 | −17.42 | 2.47 | 2.15E-07 | 4.74E-05 | 1.00 | 0.00 |
| 309 | chr12-30179 | 12 | 109611561 | 109612145 | −21.14 | 4.29 | 2.18E-07 | 4.80E-05 | 0.29 | 0.71 |

TABLE 1-continued

Differentially methylated regions (DMRs) associated breast cancer.

| | | | | | | | | | | |
|---|---|---|---|---|---|---|---|---|---|---|
| 310 | chr16-38440 | 16 | 66120313 | 66122195 | −19.92 | 3.05 | 2.21E-07 | 4.86E-05 | 0.45 | 0.55 |
| 311 | chr18-7308 | 18 | 74837592 | 74839685 | −16.79 | 2.37 | 2.22E-07 | 4.86E-05 | 0.81 | 0.19 |
| 312 | chr7-34695 | 7 | 6536641 | 6537912 | −20.75 | 4.15 | 2.25E-07 | 4.91E-05 | 0.50 | 0.50 |
| 313 | chr17-32969 | 17 | 47591129 | 47592954 | −18.83 | 2.74 | 2.30E-07 | 5.02E-05 | 0.18 | 0.82 |
| 314 | chr3-9862 | 3 | 148609673 | 148611987 | −15.54 | 2.26 | 2.42E-07 | 5.23E-05 | 0.87 | 0.13 |
| 315 | chr18-4595 | 18 | 19071802 | 19072183 | −21.06 | 3.80 | 2.50E-07 | 5.40E-05 | 0.00 | 0.00 |
| 316 | chr19-20838 | 19 | 20974468 | 20975124 | −20.74 | 3.76 | 2.55E-07 | 5.48E-05 | 0.00 | 0.00 |
| 317 | chr20-21706 | 20 | 238489 | 239288 | −18.87 | 2.61 | 2.89E-07 | 6.16E-05 | 0.00 | 0.00 |
| 318 | chr19-22015 | 19 | 20398075 | 20398528 | −19.56 | 3.17 | 2.92E-07 | 6.19E-05 | 0.00 | 0.00 |
| 319 | chr12-4418 | 12 | 101882694 | 101883147 | −21.25 | 4.18 | 3.04E-07 | 6.40E-05 | 0.00 | 1.00 |
| 320 | chr19-31732 | 19 | 62702907 | 62703289 | −22.35 | 5.19 | 3.05E-07 | 6.40E-05 | 0.92 | 0.08 |
| 321 | chr9-18934 | 9 | 132805164 | 132805693 | −22.41 | 5.08 | 3.05E-07 | 6.40E-05 | 0.83 | 0.17 |
| 322 | chr3-3854 | 3 | 188870124 | 188871016 | −18.09 | 2.45 | 3.14E-07 | 6.59E-05 | 0.29 | 0.71 |
| 323 | chr13-8627 | 13 | 69579522 | 69580526 | −18.59 | 2.57 | 3.15E-07 | 6.61E-05 | 0.48 | 0.52 |
| 324 | chr1-11343 | 1 | 177978096 | 177979141 | −18.99 | 2.59 | 3.20E-07 | 6.69E-05 | 0.55 | 0.45 |
| 325 | chr13-16458 | 13 | 111764441 | 111766059 | −17.26 | 2.34 | 3.27E-07 | 6.81E-05 | 0.18 | 0.82 |
| 326 | chr9-13838 | 9 | 99649709 | 99650308 | −21.40 | 3.94 | 3.28E-07 | 6.82E-05 | 0.00 | 1.00 |
| 327 | chr14-17061 | 14 | 100613465 | 100614257 | −19.40 | 3.10 | 3.29E-07 | 6.83E-05 | 0.00 | 0.00 |
| 328 | chr7-12415 | 7 | 72675186 | 72676378 | −19.84 | 3.40 | 3.42E-07 | 7.05E-05 | 0.77 | 0.23 |
| 329 | chr6-7903 | 6 | 336105 | 336557 | −19.30 | 3.01 | 3.53E-07 | 7.23E-05 | 0.81 | 0.19 |
| 330 | chr15-5377 | 15 | 32833697 | 32834284 | −19.87 | 2.97 | 3.60E-07 | 7.35E-05 | 0.93 | 0.07 |
| 331 | chr19-33708 | 19 | 55852950 | 55854597 | −18.10 | 2.42 | 3.62E-07 | 7.37E-05 | 0.36 | 0.64 |
| 332 | chr8-1848 | 8 | 55544961 | 55545861 | −16.92 | 2.30 | 3.62E-07 | 7.37E-05 | 0.61 | 0.39 |
| 333 | chr20-22464 | 20 | 21436219 | 21437286 | −18.21 | 2.41 | 3.63E-07 | 7.39E-05 | 1.00 | 0.00 |
| 334 | chr14-13812 | 14 | 56347638 | 58348186 | −18.82 | 2.52 | 3.68E-07 | 7.47E-05 | 0.40 | 0.60 |
| 335 | chr7-18218 | 7 | 117299526 | 117300618 | −19.47 | 2.84 | 3.75E-07 | 7.56E-05 | 0.40 | 0.60 |
| 336 | chr18-10939 | 18 | 53246045 | 53247374 | −16.25 | 2.27 | 3.84E-07 | 7.70E-05 | 0.95 | 0.05 |
| 337 | chr1-49613 | 1 | 85300309 | 85300783 | −34.93 | 30.17 | 3.95E-07 | 7.88E-05 | 0.00 | 0.00 |
| 338 | chr8-4423 | 3 | 114513510 | 114514431 | −17.52 | 2.26 | 3.94E-07 | 7.88E-05 | 0.28 | 0.72 |
| 339 | chr9-21477 | 9 | 123538279 | 123538578 | −20.48 | 3.56 | 3.95E-07 | 7.88E-05 | 0.81 | 0.19 |
| 340 | chr7-10468 | 7 | 71438612 | 71439608 | −18.01 | 2.49 | 4.03E-07 | 8.02E-05 | 0.92 | 0.08 |
| 341 | chr7-36589 | 7 | 20789757 | 20791421 | −16.82 | 2.32 | 4.06E-07 | 8.08E-05 | 0.95 | 0.05 |
| 342 | chr3-8813 | 3 | 37008980 | 37010487 | −21.65 | 4.52 | 4.11E-07 | 8.15E-05 | 0.75 | 0.25 |
| 343 | chr5-8897 | 5 | 1938336 | 1940120 | −17.69 | 2.49 | 4.14E-07 | 8.20E-05 | 1.00 | 0.00 |
| 344 | chr8-19800 | 8 | 65443925 | 65445545 | −16.28 | 2.25 | 4.21E-07 | 8.33E-05 | 0.67 | 0.33 |
| 345 | chr10-3695 | 10 | 106389441 | 106390669 | −18.82 | 2.69 | 4.34E-07 | 8.56E-05 | 0.90 | 0.10 |
| 346 | chr7-36476 | 7 | 19149605 | 19150556 | −18.55 | 2.36 | 4.40E-07 | 8.67E-05 | 0.00 | 1.00 |
| 347 | chr15-2485 | 15 | 58083248 | 58086233 | −16.29 | 2.25 | 4.43E-07 | 8.72E-05 | 0.80 | 0.20 |
| 348 | chr13-3613 | 13 | 78067586 | 78069656 | −16.23 | 2.21 | 4.62E-07 | 9.00E-05 | 0.54 | 0.46 |
| 349 | chr10-6953 | 10 | 22673906 | 22675235 | −15.71 | 2.19 | 4.73E-07 | 9.15E-05 | 0.65 | 0.35 |
| 350 | chr7-15475 | 7 | 97198854 | 97199710 | −17.08 | 2.27 | 4.90E-07 | 9.41E-05 | 0.75 | 0.25 |
| 351 | chr7-38573 | 7 | 154944311 | 154945854 | −17.99 | 2.39 | 5.01E-07 | 9.57E-05 | 0.26 | 0.74 |
| 352 | chr6-17667 | 6 | 28851357 | 28851980 | −19.57 | 2.68 | 5.33E-07 | 1.01E-04 | 0.00 | 0.00 |
| 353 | chr4-7295 | 4 | 21558920 | 21559523 | −19.46 | 2.88 | 5.42E-07 | 1.02E-04 | 0.43 | 0.57 |
| 354 | chr1-13372 | 1 | 147422212 | 147423512 | −17.77 | 2.35 | 5.47E-07 | 1.03E-04 | 0.43 | 0.57 |
| 355 | chr8-30753 | 8 | 72631179 | 72633837 | −15.64 | 2.17 | 5.51E-07 | 1.03E-04 | 0.35 | 0.65 |
| 356 | chr19-36061 | 19 | 12166237 | 12167686 | −17.29 | 2.35 | 5.54E-07 | 1.04E-04 | 0.52 | 0.48 |
| 357 | chr7-22735 | 7 | 121726837 | 121728266 | −16.98 | 2.26 | 5.57E-07 | 1.04E-04 | 0.45 | 0.55 |
| 358 | chr8-11127 | 8 | 11574986 | 11576514 | −16.85 | 2.26 | 5.58E-07 | 1.04E-04 | 0.91 | 0.09 |
| 359 | chr19-28047 | 19 | 46223609 | 46223985 | −19.44 | 2.67 | 5.60E-07 | 1.05E-04 | 0.66 | 0.34 |
| 360 | chr7-15663 | 7 | 128124636 | 128125186 | −18.19 | 2.38 | 5.85E-07 | 1.09E-04 | 0.00 | 0.00 |
| 361 | chr7-7163 | 7 | 35263434 | 35264855 | −16.39 | 2.23 | 5.98E-07 | 1.11E-04 | 0.91 | 0.09 |
| 362 | chr8-16602 | 8 | 55533048 | 55535238 | −15.35 | 2.17 | 5.99E-07 | 1.11E-04 | 0.93 | 0.07 |
| 363 | chr14-2517 | 14 | 60046946 | 60048179 | −16.89 | 2.24 | 6.33E-07 | 1.16E-04 | 0.80 | 0.20 |
| 364 | chr1-4928 | 1 | 13712100 | 13712644 | −19.66 | 2.91 | 6.43E-07 | 1.18E-04 | 1.00 | 0.00 |
| 365 | chr4-2246 | 4 | 5103783 | 5104235 | −22.46 | 5.33 | 6.47E-07 | 1.18E-04 | 0.23 | 0.77 |
| 366 | chr8-10610 | 8 | 61355732 | 61356545 | −22.19 | 5.45 | 6.47E-07 | 1.18E-04 | 0.83 | 0.17 |
| 367 | chr2-27090 | 2 | 200042979 | 200044725 | −17.88 | 2.37 | 6.50E-07 | 1.19E-04 | 0.52 | 0.48 |
| 368 | chr17-30111 | 17 | 24964666 | 24965386 | −18.13 | 2.49 | 6.61E-07 | 1.20E-04 | 0.32 | 0.68 |
| 369 | chr6-12472 | 6 | 28710444 | 28711481 | −18.90 | 2.49 | 6.62E-07 | 1.20E-04 | 0.43 | 0.57 |
| 370 | chr1-38532 | 1 | 246086842 | 246087566 | −17.39 | 2.39 | 6.76E-07 | 1.22E-04 | 0.85 | 0.15 |
| 371 | chr7-29879 | 7 | 154953416 | 154954284 | −19.04 | 2.53 | 6.93E-07 | 1.25E-04 | 0.86 | 0.14 |
| 372 | chr19-46712 | 19 | 33976573 | 33976980 | −17.59 | 2.35 | 6.97E-07 | 1.25E-04 | 0.68 | 0.32 |
| 373 | chr10-22147 | 10 | 118022736 | 118024248 | −19.36 | 2.86 | 7.26E-07 | 1.30E-04 | 0.98 | 0.02 |
| 374 | chr12-18252 | 12 | 97813217 | 97813685 | −21.35 | 4.60 | 7.50E-07 | 1.34E-04 | 0.62 | 0.38 |
| 375 | chr13-15234 | 13 | 107946265 | 107947449 | −18.45 | 2.63 | 7.55E-07 | 1.34E-04 | 0.64 | 0.36 |
| 376 | chr18-13866 | 18 | 55085532 | 55087379 | −18.11 | 2.37 | 7.67E-07 | 1.36E-04 | 0.85 | 0.15 |
| 377 | chr19-6109 | 19 | 62930239 | 62930957 | −17.70 | 2.37 | 7.70E-07 | 1.37E-04 | 0.62 | 0.38 |
| 378 | chr17-34151 | 17 | 69150577 | 69151641 | −20.49 | 3.84 | 7.86E-07 | 1.39E-04 | 0.96 | 0.04 |
| 379 | chr3-9548 | 3 | 182925623 | 182926260 | −19.49 | 2.55 | 7.96E-07 | 1.40E-04 | 0.00 | 1.00 |
| 380 | chr2-35810 | 2 | 182252321 | 182252798 | −18.97 | 2.43 | 8.43E-07 | 1.48E-04 | 0.00 | 0.00 |
| 381 | chr12-693 | 12 | 61829916 | 61832308 | −16.49 | 2.17 | 8.51E-07 | 1.49E-04 | 0.55 | 0.45 |
| 382 | chr18-1832 | 18 | 71756971 | 71757548 | −19.89 | 2.69 | 8.64E-07 | 1.51E-04 | 1.00 | 0.00 |
| 383 | chr6-24682 | 6 | 127881341 | 127882455 | −18.26 | 2.40 | 8.66E-07 | 1.51E-04 | 0.00 | 0.05 |
| 384 | chr19-26515 | 19 | 42733848 | 42734723 | −16.85 | 2.24 | 9.08E-07 | 1.58E-04 | 0.00 | 0.44 |
| 385 | chr7-8399 | 7 | 120755995 | 120758043 | −17.62 | 2.29 | 9.34E-07 | 1.61E-04 | 0.56 | 0.44 |
| 386 | chr5-19148 | 5 | 31229537 | 31230816 | −19.80 | 2.99 | 9.37E-07 | 1.62E-04 | 0.36 | 0.64 |
| 387 | chr13-16371 | 13 | 111806052 | 111808603 | −15.74 | 2.14 | 9.44E-07 | 1.63E-04 | 0.74 | 0.26 |

TABLE 1-continued

Differentially methylated regions (DMRs) associated breast cancer.

| | | | | | | | | | |
|---|---|---|---|---|---|---|---|---|---|
| 388 | chr8-3407 | 8 | 132120752 | 132124250 | −15.21 | 2.12 | 9.60E-07 | 1.65E-04 | 0.73 | 0.27 |
| 389 | chr19-24064 | 19 | 61846398 | 61847156 | −17.66 | 2.30 | 9.80E-07 | 1.68E-04 | 0.57 | 0.43 |
| 390 | chr8-18281 | 8 | 145528408 | 145528889 | −20.60 | 3.77 | 1.00E-06 | 1.71E-04 | 1.00 | 0.00 |
| 391 | chr11-11472 | 11 | 118697004 | 118697486 | −35.05 | 29.94 | 1.01E-06 | 1.72E-04 | 0.81 | 0.19 |
| 392 | chr19-31043 | 19 | 56788808 | 56789998 | −20.89 | 3.46 | 1.01E-06 | 1.72E-04 | 0.63 | 0.37 |
| 393 | chr8-4176 | 8 | 16928527 | 16928982 | −21.66 | 4.47 | 1.02E-06 | 1.73E-04 | 0.54 | 0.46 |
| 394 | chr19-5544 | 19 | 59137025 | 59138496 | −18.48 | 2.47 | 1.03E-06 | 1.74E-04 | 0.35 | 0.65 |
| 395 | chr5-23290 | 5 | 6740085 | 6740486 | −22.28 | 5.29 | 1.03E-06 | 1.74E-04 | 0.00 | 0.00 |
| 396 | chr5-7502 | 5 | 15553610 | 15554084 | −21.75 | 4.39 | 1.03E-06 | 1.74E-04 | 0.66 | 0.34 |
| 397 | chr18-5039 | 18 | 55082452 | 55084373 | −17.58 | 2.33 | 1.03E-06 | 1.75E-04 | 0.32 | 0.68 |
| 398 | chr11-11623 | 11 | 32404535 | 32407465 | −16.44 | 2.15 | 1.04E-06 | 1.77E-04 | 0.51 | 0.49 |
| 399 | chr6-9424 | 6 | 50797741 | 50798040 | −20.15 | 2.79 | 1.08E-06 | 1.82E-04 | 0.00 | 0.00 |
| 400 | chr5-13092 | 5 | 1940356 | 1941066 | −20.18 | 3.10 | 1.11E-06 | 1.85E-04 | 0.55 | 0.45 |
| 401 | chr12-24670 | 12 | 4249005 | 4250035 | −19.14 | 2.45 | 1.12E-06 | 1.87E-04 | 1.00 | 0.00 |
| 402 | chr1-53988 | 1 | 75369036 | 75371706 | −17.40 | 2.18 | 1.14E-06 | 1.91E-04 | 0.08 | 0.92 |
| 403 | chr19-44228 | 19 | 3385736 | 3386568 | −17.43 | 2.23 | 1.16E-06 | 1.94E-04 | 0.59 | 0.41 |
| 404 | chr9-9221 | 9 | 94609232 | 94612099 | −17.54 | 2.25 | 1.23E-06 | 2.03E-04 | 0.99 | 0.01 |
| 405 | chr3-12106 | 3 | 171785722 | 171786096 | −17.86 | 2.28 | 1.24E-06 | 2.06E-04 | 0.96 | 0.04 |
| 406 | chr3-22823 | 3 | 61522661 | 61524867 | −18.62 | 2.32 | 1.30E-06 | 2.14E-04 | 0.93 | 0.07 |
| 407 | chr11-20709 | 11 | 716315 | 716939 | −18.48 | 2.45 | 1.30E-06 | 2.15E-04 | 0.89 | 0.11 |
| 408 | chr8-13120 | 8 | 77756536 | 77757627 | −17.64 | 2.30 | 1.33E-06 | 2.18E-04 | 0.55 | 0.45 |
| 409 | chr19-5399 | 19 | 45006599 | 45007416 | −20.87 | 3.49 | 1.34E-06 | 2.20E-04 | 0.27 | 0.73 |
| 410 | chr4-14651 | 4 | 147780313 | 147781689 | −16.48 | 2.12 | 1.37E-06 | 2.23E-04 | 0.75 | 0.25 |
| 411 | chr1-55770 | 1 | 57660234 | 57662326 | −19.18 | 2.81 | 1.43E-06 | 2.33E-04 | 0.85 | 0.15 |
| 412 | chr13-10642 | 13 | 111771075 | 111771643 | −17.27 | 2.21 | 1.43E-06 | 2.34E-04 | 0.89 | 0.11 |
| 413 | chr19-13959 | 19 | 61571120 | 61571844 | −20.04 | 3.02 | 1.45E-06 | 2.35E-04 | 0.80 | 0.20 |
| 414 | chr9-31375 | 9 | 29202550 | 29202931 | −21.22 | 4.15 | 1.48E-06 | 2.39E-04 | 0.71 | 0.29 |
| 415 | chr7-16609 | 7 | 154942132 | 154942742 | −20.61 | 3.37 | 1.54E-06 | 2.48E-04 | 1.00 | 0.00 |
| 416 | chr6-21066 | 6 | 146391658 | 146392926 | −18.05 | 2.19 | 1.54E-06 | 2.49E-04 | 0.20 | 0.80 |
| 417 | chr18-3786 | 18 | 43040367 | 43044918 | −15.82 | 2.07 | 1.55E-06 | 2.49E-04 | 0.30 | 0.70 |
| 418 | chr9-24850 | 9 | 22436668 | 22437704 | −22.10 | 5.56 | 1.55E-06 | 2.50E-04 | 0.98 | 0.02 |
| 419 | chr12-2820 | 12 | 30839655 | 30841565 | −17.79 | 2.35 | 1.57E-06 | 2.53E-04 | 0.63 | 0.37 |
| 420 | chr7-12265 | 7 | 121743462 | 121744765 | −16.43 | 2.11 | 1.59E-06 | 2.56E-04 | 0.61 | 0.39 |
| 421 | chr9-16243 | 9 | 78826045 | 78826344 | −20.90 | 3.42 | 1.63E-06 | 2.60E-04 | 0.00 | 1.00 |
| 422 | chr22-24548 | 22 | 47264373 | 47264866 | −22.24 | 5.28 | 1.65E-06 | 2.64E-04 | 1.00 | 0.00 |
| 423 | chr7-6402 | 7 | 8447245 | 8450849 | −15.53 | 2.06 | 1.66E-06 | 2.65E-04 | 0.38 | 0.62 |
| 424 | chr10-18190 | 10 | 57057212 | 57058581 | −18.16 | 2.17 | 1.67E-06 | 2.66E-04 | 0.34 | 0.66 |
| 425 | chr17-16808 | 17 | 58969065 | 58989919 | −20.06 | 2.81 | 1.68E-06 | 2.66E-04 | 0.75 | 0.25 |
| 426 | chr12-16783 | 12 | 113369423 | 113370090 | −19.47 | 2.67 | 1.69E-06 | 2.68E-04 | 0.47 | 0.53 |
| 427 | chr6-21444 | 6 | 28522662 | 28523159 | −18.71 | 2.41 | 1.70E-06 | 2.69E-04 | 0.00 | 0.00 |
| 428 | chr18-1098 | 18 | 5186191 | 5187783 | −17.51 | 2.17 | 1.77E-06 | 2.79E-04 | 0.72 | 0.28 |
| 429 | chr19-11665 | 19 | 62786387 | 62787669 | −17.69 | 2.22 | 1.79E-06 | 2.81E-04 | 0.80 | 0.20 |
| 430 | chr4-25870 | 4 | 46689372 | 46691121 | −17.85 | 2.21 | 1.84E-06 | 2.88E-04 | 0.43 | 0.57 |
| 431 | chr13-11476 | 13 | 111763091 | 111764344 | −18.00 | 2.23 | 1.97E-06 | 3.04E-04 | 0.70 | 0.30 |
| 432 | chr16-21001 | 16 | 67101292 | 67102016 | −18.85 | 2.37 | 1.97E-06 | 3.05E-04 | 0.52 | 0.48 |
| 433 | chr9-11097 | 9 | 78818499 | 78820515 | −17.42 | 2.23 | 1.98E-06 | 3.06E-04 | 0.35 | 0.65 |
| 434 | chr6-15498 | 6 | 50799906 | 50800777 | −18.48 | 2.39 | 2.01E-06 | 3.09E-04 | 0.26 | 0.74 |
| 435 | chr8-14169 | 8 | 56596097 | 56596396 | −35.00 | 30.04 | 2.03E-06 | 3.12E-04 | 0.00 | 0.00 |
| 436 | chr12-10547 | 12 | 73889129 | 73889832 | −18.50 | 2.26 | 2.03E-06 | 3.13E-04 | 0.50 | 0.50 |
| 437 | chr3-13593 | 3 | 182923564 | 182924686 | −17.77 | 2.18 | 2.04E-06 | 3.13E-04 | 0.00 | 0.00 |
| 438 | chr3-22674 | 3 | 171786097 | 171786716 | −18.67 | 2.44 | 2.06E-06 | 3.16E-04 | 0.59 | 0.41 |
| 439 | chr4-6479 | 4 | 6251718 | 6252521 | −21.05 | 4.11 | 2.09E-06 | 3.19E-04 | 0.97 | 0.03 |
| 440 | chr8-6273 | 8 | 56177470 | 56178405 | −17.12 | 2.19 | 2.09E-06 | 3.19E-04 | 0.90 | 0.10 |
| 441 | chr17-1165 | 17 | 5915052 | 5915590 | −22.29 | 5.24 | 2.11E-06 | 3.21E-04 | 0.23 | 0.77 |
| 442 | chr19-16291 | 19 | 63137956 | 63138704 | −19.93 | 3.10 | 2.12E-06 | 3.23E-04 | 0.62 | 0.38 |
| 443 | chr10-18652 | 10 | 102311731 | 102312878 | −17.20 | 2.16 | 2.19E-06 | 3.32E-04 | 0.67 | 0.33 |
| 444 | chr8-8079 | 3 | 50984817 | 50986296 | −17.23 | 2.11 | 2.21E-06 | 3.35E-04 | 0.40 | 0.60 |
| 445 | chr10-28230 | 10 | 50273292 | 50274913 | −18.01 | 2.29 | 2.22E-06 | 3.36E-04 | 1.00 | 0.00 |
| 446 | chr18-5240 | 18 | 43030844 | 43032407 | −17.75 | 2.16 | 2.28E-06 | 3.43E-04 | 0.29 | 0.71 |
| 447 | chr8-27248 | 8 | 13468321 | 13488959 | −20.23 | 3.43 | 2.28E-06 | 3.43E-04 | 0.00 | 0.00 |
| 448 | chr1-29954 | 1 | 37271442 | 37272343 | −20.23 | 3.15 | 2.30E-06 | 3.45E-04 | 1.00 | 0.00 |
| 449 | chr7-14720 | 7 | 154939048 | 154939576 | −21.11 | 3.69 | 2.39E-06 | 3.56E-04 | 0.80 | 0.20 |
| 450 | chr1-20269 | 1 | 32486433 | 32486893 | −19.92 | 3.19 | 2.40E-06 | 3.58E-04 | 0.58 | 0.42 |
| 451 | chr8-11517 | 8 | 80685816 | 80686115 | −19.22 | 2.42 | 2.51E-06 | 3.71E-04 | 0.00 | 1.00 |
| 452 | chr10-35571 | 10 | 50488303 | 50490800 | −14.96 | 2.01 | 2.60E-06 | 3.82E-04 | 0.82 | 0.18 |
| 453 | chr2-22578 | 2 | 176664645 | 176665958 | −17.73 | 2.17 | 2.61E-06 | 3.82E-04 | 0.66 | 0.34 |
| 454 | chr19-28214 | 19 | 19792999 | 19793698 | −21.30 | 3.95 | 2.64E-06 | 3.86E-04 | 0.00 | 0.00 |
| 455 | chr7-10560 | 7 | 155297155 | 155298044 | −20.54 | 3.40 | 2.65E-06 | 3.87E-04 | 0.42 | 0.58 |
| 456 | chr4-6334 | 4 | 154362897 | 154364005 | −18.76 | 2.46 | 2.66E-06 | 3.88E-04 | 0.48 | 0.52 |
| 457 | chr15-12559 | 15 | 73791768 | 73792265 | −21.57 | 3.59 | 2.69E-06 | 3.92E-04 | 0.00 | 0.00 |
| 458 | chr8-15117 | 3 | 57521886 | 57522799 | −17.62 | 2.10 | 2.70E-06 | 3.93E-04 | 0.33 | 0.67 |
| 459 | chr22-14473 | 22 | 17518170 | 17519064 | −17.77 | 2.16 | 2.71E-06 | 3.94E-04 | 0.38 | 0.62 |
| 460 | chr7-7931 | 7 | 35259480 | 35261331 | −16.85 | 2.10 | 2.72E-06 | 3.94E-04 | 0.91 | 0.09 |
| 461 | chr11-3267 | 11 | 27699682 | 27701500 | −18.04 | 2.08 | 2.72E-06 | 3.94E-04 | 0.60 | 0.40 |
| 462 | chr2-6335 | 2 | 219881210 | 219882684 | −18.40 | 2.32 | 2.77E-06 | 4.01E-04 | 0.45 | 0.55 |
| 463 | chr6-7514 | 8 | 26865279 | 26866569 | −17.90 | 2.13 | 2.86E-06 | 4.12E-04 | 0.00 | 0.00 |
| 464 | chr7-25866 | 7 | 153214115 | 153216681 | −15.75 | 2.02 | 2.93E-06 | 4.22E-04 | 0.92 | 0.08 |
| 465 | chr8-3477 | 8 | 57188104 | 57189264 | −17.30 | 2.08 | 3.21E-06 | 4.57E-04 | 0.86 | 0.14 |

TABLE 1-continued

Differentially methylated regions (DMRs) associated breast cancer.

| | | | | | | | | | | |
|---|---|---|---|---|---|---|---|---|---|---|
| 466 | chr18-7963 | 18 | 43311867 | 43312590 | −20.15 | 2.78 | 3.41E−06 | 4.83E−04 | 0.00 | 0.00 |
| 467 | chr2-26887 | 2 | 104846206 | 104847327 | −16.82 | 2.04 | 3.41E−06 | 4.83E−04 | 0.50 | 0.50 |
| 468 | chr5-28475 | 5 | 140685836 | 140686523 | −19.78 | 2.62 | 3.42E−06 | 4.83E−04 | 0.00 | 0.00 |
| 469 | chr7-27744 | 7 | 158630723 | 158631338 | −17.89 | 2.24 | 3.48E−06 | 4.90E−04 | 0.86 | 0.14 |
| 470 | chr7-34758 | 7 | 8442749 | 8443535 | −21.60 | 4.48 | 3.54E−06 | 4.97E−04 | 0.00 | 1.00 |
| 471 | chr19-43568 | 19 | 1400800 | 1401099 | −35.13 | 29.75 | 3.61E−06 | 5.07E−04 | 0.14 | 0.86 |
| 472 | chr13-5199 | 13 | 27398788 | 27401867 | −16.69 | 2.02 | 3.65E−06 | 5.11E−04 | 0.30 | 0.70 |
| 473 | chr2-17703 | 2 | 182255228 | 182256746 | −18.07 | 2.21 | 3.85E−06 | 5.37E−04 | 0.41 | 0.59 |
| 474 | chr6-6788 | 8 | 28889818 | 28890404 | −17.71 | 2.12 | 3.90E−06 | 5.41E−04 | 0.76 | 0.24 |
| 475 | chr9-14636 | 9 | 132797997 | 132798853 | −20.74 | 3.23 | 3.90E−06 | 5.41E−04 | 0.00 | 0.00 |
| 476 | chr14-13134 | 14 | 56330541 | 58332135 | −16.87 | 2.03 | 3.95E−06 | 5.46E−04 | 0.78 | 0.22 |
| 477 | chr9-21296 | 9 | 103538968 | 103541083 | −16.91 | 2.04 | 3.99E−06 | 5.51E−04 | 0.58 | 0.42 |
| 478 | chr10-27138 | 10 | 23501139 | 23501763 | −19.03 | 2.45 | 4.03E−06 | 5.55E−04 | 0.50 | 0.50 |
| 479 | chr18-7873 | 18 | 75367913 | 75389070 | −17.23 | 2.09 | 4.09E−06 | 5.63E−04 | 0.00 | 0.00 |
| 480 | chr16-37738 | 16 | 87279246 | 87279545 | −21.70 | 4.39 | 4.11E−06 | 5.65E−04 | 0.00 | 1.00 |
| 481 | chr9-15898 | 9 | 128200681 | 128201070 | −19.29 | 2.56 | 4.13E−06 | 5.67E−04 | 0.00 | 0.00 |
| 482 | chr10-20648 | 10 | 15800657 | 15801822 | −18.16 | 2.19 | 4.20E−06 | 5.75E−04 | 0.34 | 0.66 |
| 483 | chr20-19966 | 20 | 61275517 | 61276082 | −20.18 | 2.85 | 4.24E−06 | 5.80E−04 | 0.00 | 1.00 |
| 484 | chr22-16452 | 22 | 48450232 | 48451665 | −18.60 | 2.27 | 4.27E−06 | 5.84E−04 | 0.23 | 0.77 |
| 485 | chr9-8617 | 9 | 76302527 | 76305004 | −18.17 | 2.15 | 4.30E−06 | 5.87E−04 | 0.44 | 0.56 |
| 486 | chr9-8090 | 9 | 17124673 | 17125832 | −20.74 | 2.90 | 4.32E−06 | 5.88E−04 | 0.76 | 0.24 |
| 487 | chr7-9575 | 7 | 35267289 | 35288488 | −17.05 | 2.05 | 4.38E−06 | 5.94E−04 | 0.48 | 0.52 |
| 488 | chr6-28662 | 6 | 117691091 | 117691644 | −18.21 | 2.21 | 4.41E−06 | 5.97E−04 | 0.42 | 0.58 |
| 489 | chr2-33315 | 2 | 98330298 | 98331540 | −18.09 | 2.10 | 4.53E−06 | 6.10E−04 | 0.26 | 0.74 |
| 490 | chr1-19681 | 1 | 154860239 | 154861211 | −20.55 | 3.39 | 4.55E−06 | 6.12E−04 | 0.96 | 0.04 |
| 491 | chr6-7421 | 6 | 100167235 | 100168199 | −17.46 | 2.10 | 4.60E−06 | 6.17E−04 | 0.52 | 0.48 |
| 492 | chr10-23988 | 10 | 23503516 | 23504392 | −18.13 | 2.07 | 4.64E−06 | 6.20E−04 | 0.43 | 0.57 |
| 493 | chr1-33096 | 1 | 75374659 | 75375886 | −17.46 | 2.14 | 4.67E−06 | 6.24E−04 | 0.66 | 0.34 |
| 494 | chr13-14599 | 13 | 111756947 | 111759018 | −16.76 | 2.04 | 4.69E−06 | 6.25E−04 | 0.55 | 0.45 |
| 495 | chr1-29436 | 1 | 50662305 | 50664209 | −17.08 | 2.04 | 4.85E−06 | 6.45E−04 | 0.92 | 0.08 |
| 496 | chr13-5185 | 13 | 111755582 | 111758946 | −17.12 | 2.04 | 4.87E−06 | 6.46E−04 | 0.65 | 0.35 |
| 497 | chr10-19113 | 10 | 118889398 | 118890307 | −17.17 | 2.07 | 4.87E−06 | 6.47E−04 | 1.00 | 0.00 |
| 498 | chr8-18053 | 3 | 110772419 | 110773490 | −18.40 | 2.27 | 4.89E−06 | 6.48E−04 | 0.46 | 0.54 |
| 499 | chr16-10222 | 16 | 81217864 | 81218691 | −20.60 | 3.30 | 4.92E−06 | 6.52E−04 | 0.65 | 0.35 |
| 500 | chr8-8662 | 8 | 65449063 | 65449743 | −18.49 | 2.13 | 5.03E−06 | 6.65E−04 | 0.22 | 0.78 |
| 501 | chr9-29496 | 9 | 137746214 | 137746513 | −21.49 | 3.67 | 5.14E−06 | 6.77E−04 | 0.96 | 0.04 |
| 502 | chr10-21536 | 10 | 111206790 | 111207168 | −18.82 | 2.34 | 5.18E−06 | 6.82E−04 | 0.75 | 0.25 |
| 503 | chr3-9248 | 3 | 79899047 | 79900065 | −20.04 | 2.74 | 5.18E−06 | 6.82E−04 | 0.00 | 1.00 |
| 504 | chr18-14616 | 18 | 68686390 | 68687284 | −17.67 | 2.16 | 5.25E−06 | 6.89E−04 | 1.00 | 0.00 |
| 505 | chr18-4761 | 18 | 68684752 | 68685778 | −17.67 | 2.17 | 5.26E−06 | 6.91E−04 | 0.81 | 0.19 |
| 506 | chr14-7997 | 14 | 60021645 | 60022784 | −17.05 | 2.01 | 5.28E−06 | 6.93E−04 | 0.85 | 0.15 |
| 507 | chr1-52773 | 1 | 165156276 | 165157660 | −16.45 | 1.99 | 5.31E−06 | 6.96E−04 | 0.63 | 0.37 |
| 508 | chr3-19953 | 3 | 169449828 | 169451332 | −20.39 | 3.04 | 5.33E−06 | 6.96E−04 | 0.59 | 0.41 |
| 509 | chr6-9636 | 6 | 12857279 | 12857578 | −20.42 | 2.98 | 5.33E−06 | 6.96E−04 | 0.00 | 1.00 |
| 510 | chr1-48028 | 1 | 179719201 | 179719802 | −20.01 | 2.83 | 5.40E−06 | 7.06E−04 | 0.61 | 0.39 |
| 511 | chr16-43017 | 16 | 6009572 | 6010985 | −17.79 | 2.08 | 5.45E−06 | 7.11E−04 | 0.59 | 0.41 |
| 512 | chr6-10546 | 6 | 74081214 | 74081830 | −17.04 | 2.04 | 5.59E−06 | 7.26E−04 | 0.86 | 0.14 |
| 513 | chr11-25392 | 11 | 20185641 | 20186213 | −19.46 | 2.50 | 5.64E−06 | 7.31E−04 | 0.00 | 0.00 |
| 514 | chr1-11916 | 1 | 147194313 | 147195312 | −16.49 | 1.98 | 5.67E−06 | 7.34E−04 | 0.00 | 0.00 |
| 515 | chr8-12141 | 8 | 67507023 | 67507666 | −18.55 | 2.42 | 5.83E−06 | 7.51E−04 | 0.76 | 0.24 |
| 516 | chr5-12906 | 5 | 145698009 | 145700619 | −16.65 | 2.00 | 6.03E−06 | 7.71E−04 | 0.69 | 0.31 |
| 517 | chr6-16814 | 6 | 58255054 | 58255979 | −18.59 | 2.25 | 6.09E−06 | 7.78E−04 | 0.00 | 0.00 |
| 518 | chr12-22778 | 12 | 106692971 | 106693781 | −18.60 | 2.29 | 6.29E−06 | 8.00E−04 | 0.72 | 0.28 |
| 519 | chr20-4865 | 20 | 21449236 | 21452072 | −17.37 | 2.07 | 6.31E−06 | 8.01E−04 | 0.69 | 0.31 |
| 520 | chr11-24352 | 11 | 113434777 | 113435377 | −22.31 | 5.14 | 6.46E−06 | 8.18E−04 | 0.89 | 0.11 |
| 521 | chr17-35096 | 17 | 43127241 | 43128186 | −19.21 | 2.32 | 6.59E−06 | 8.33E−04 | 0.79 | 0.21 |
| 522 | chr14-2805 | 14 | 36061285 | 36062365 | −17.10 | 2.00 | 6.94E−06 | 8.72E−04 | 0.83 | 0.17 |
| 523 | chr3-18149 | 3 | 148569747 | 148570426 | −18.95 | 2.21 | 7.10E−06 | 8.90E−04 | 0.00 | 0.00 |
| 524 | chr6-12241 | 6 | 28850875 | 28851174 | −21.13 | 3.14 | 7.20E−06 | 8.99E−04 | 0.00 | 0.00 |
| 525 | chr9-11022 | 9 | 32772588 | 32773890 | −17.61 | 2.10 | 7.25E−06 | 9.05E−04 | 0.53 | 0.47 |
| 526 | chr11-31615 | 11 | 131285836 | 131287061 | −17.66 | 2.06 | 7.28E−06 | 9.08E−04 | 0.74 | 0.26 |
| 527 | chr20-17172 | 20 | 34603307 | 34803606 | −20.48 | 2.87 | 7.31E−06 | 9.11E−04 | 0.00 | 1.00 |
| 528 | chr11-1210 | 11 | 32416010 | 32417947 | −17.12 | 2.03 | 7.35E−06 | 9.14E−04 | 0.45 | 0.55 |
| 529 | chr13-15917 | 13 | 27395919 | 27396699 | −18.25 | 2.12 | 7.39E−06 | 9.18E−04 | 0.61 | 0.39 |
| 530 | chr5-12543 | 5 | 37876045 | 37876600 | −21.03 | 3.68 | 7.43E−06 | 9.22E−04 | 0.79 | 0.21 |
| 531 | chr12-24630 | 12 | 45760774 | 45761158 | −35.14 | 29.75 | 7.59E−06 | 9.39E−04 | 0.00 | 1.00 |
| 532 | chr18-12033 | 18 | 5618866 | 5620739 | −18.49 | 2.38 | 7.69E−06 | 9.48E−04 | 1.00 | 0.00 |
| 533 | chr1-35819 | 1 | 34401107 | 34403040 | −19.90 | 2.91 | 7.69E−06 | 9.48E−04 | 0.86 | 0.14 |
| 534 | chr3-13473 | 3 | 140140990 | 140141890 | −17.58 | 2.07 | 7.85E−06 | 9.67E−04 | 0.89 | 0.11 |
| 535 | chr14-4809 | 14 | 41148725 | 41149233 | −20.05 | 2.65 | 7.87E−06 | 9.67E−04 | 0.00 | 0.00 |
| 536 | chr8-6564 | 8 | 114514742 | 114515804 | −17.44 | 1.96 | 7.87E−06 | 9.67E−04 | 0.00 | 1.00 |
| 537 | chr4-2028 | 4 | 36921605 | 36923906 | −17.92 | 2.12 | 7.92E−06 | 9.72E−04 | 0.75 | 0.25 |
| 538 | chr6-13773 | 6 | 166341901 | 166342916 | −18.37 | 2.26 | 7.96E−06 | 9.76E−04 | 0.33 | 0.67 |
| 539 | chr9-17317 | 9 | 99650551 | 99651573 | −17.19 | 1.98 | 8.06E−06 | 9.87E−04 | 0.77 | 0.23 |
| 540 | chr19-26183 | 19 | 17658705 | 17660538 | −19.92 | 2.74 | 8.10E−06 | 9.91E−04 | 0.38 | 0.62 |
| 541 | chr9-32778 | 9 | 832501 | 833578 | −16.77 | 1.97 | 8.33E−06 | 1.01E−03 | 0.80 | 0.20 |
| 542 | chr1-20354 | 1 | 90954471 | 90955463 | −17.67 | 2.05 | 8.75E−06 | 1.06E−03 | 0.62 | 0.38 |
| 543 | chr19-36386 | 19 | 22781128 | 22782049 | −18.26 | 2.10 | 8.76E−06 | 1.06E−03 | 0.22 | 0.78 |

TABLE 1-continued

Differentially methylated regions (DMRs) associated breast cancer.

| | | | | | | | | | |
|---|---|---|---|---|---|---|---|---|---|
| 544 | chr9-9261 | 9 | 16716795 | 16717470 | −22.56 | 4.76 | 8.84E−06 | 1.06E−03 | 0.61 | 0.39 |
| 545 | chr1-28592 | 1 | 210939995 | 210941410 | −21.03 | 3.62 | 8.97E−06 | 1.08E−03 | 0.48 | 0.52 |
| 546 | chr6-27327 | 6 | 28282873 | 28284334 | −17.06 | 1.95 | 9.09E−06 | 1.09E−03 | 0.22 | 0.78 |
| 547 | chr13-5914 | 13 | 27268702 | 27269918 | −20.00 | 2.87 | 9.19E−06 | 1.10E−03 | 0.21 | 0.79 |
| 548 | chr19-36571 | 19 | 24061637 | 24062272 | −20.74 | 3.48 | 9.30E−06 | 1.11E−03 | 0.00 | 0.00 |
| 549 | chr17-8384 | 17 | 32377397 | 32377860 | −18.94 | 2.21 | 9.32E−06 | 1.11E−03 | 0.62 | 0.38 |
| 550 | chr18-12335 | 18 | 43027885 | 43028280 | −18.54 | 2.25 | 9.41E−06 | 1.12E−03 | 1.00 | 0.00 |
| 551 | chr1-19649 | 1 | 20682759 | 20684507 | −19.80 | 2.69 | 9.74E−06 | 1.15E−03 | 0.83 | 0.17 |
| 552 | chr1-6836 | 1 | 38002381 | 38003734 | −17.94 | 2.05 | 9.76E−06 | 1.16E−03 | 0.78 | 0.22 |
| 553 | chr2-4079 | 2 | 176639782 | 176641943 | −16.41 | 1.92 | 9.85E−06 | 1.17E−03 | 0.65 | 0.35 |
| 554 | chr2-42491 | 2 | 118783832 | 118784739 | −20.85 | 3.32 | 1.05E−05 | 1.24E−03 | 0.00 | 0.00 |
| 555 | chr6-6376 | 6 | 101956346 | 101957787 | −16.51 | 1.91 | 1.12E−05 | 1.30E−03 | 0.81 | 0.19 |
| 556 | chr13-11038 | 13 | 83350909 | 83352653 | −16.71 | 1.92 | 1.13E−05 | 1.31E−03 | 0.13 | 0.87 |
| 557 | chr8-2655 | 8 | 77747628 | 77748201 | −18.52 | 2.03 | 1.13E−05 | 1.31E−03 | 0.00 | 0.00 |
| 558 | chr20-12429 | 20 | 22510293 | 22512770 | −16.53 | 1.93 | 1.17E−05 | 1.35E−03 | 0.82 | 0.18 |
| 559 | chr16-33967 | 16 | 49704874 | 49705374 | −19.16 | 2.31 | 1.19E−05 | 1.37E−03 | 0.76 | 0.24 |
| 560 | chr3-23796 | 3 | 61524948 | 61525699 | −18.00 | 2.07 | 1.21E−05 | 1.38E−03 | 0.31 | 0.69 |
| 561 | chr12-23224 | 12 | 127317974 | 127319200 | −17.94 | 1.98 | 1.22E−05 | 1.39E−03 | 0.92 | 0.08 |
| 562 | chr20-4778 | 20 | 54013046 | 54014804 | −16.63 | 1.90 | 1.22E−05 | 1.39E−03 | 0.59 | 0.41 |
| 563 | chr11-27538 | 11 | 8146412 | 8147571 | −18.72 | 2.24 | 1.28E−05 | 1.44E−03 | 0.38 | 0.62 |
| 564 | chr13-5196 | 13 | 52321726 | 52322229 | −20.41 | 2.76 | 1.29E−05 | 1.45E−03 | 0.00 | 1.00 |
| 565 | chr9-19031 | 9 | 23821077 | 23821585 | −20.55 | 3.25 | 1.30E−05 | 1.46E−03 | 0.00 | 0.00 |
| 566 | chr14-16431 | 14 | 56340466 | 56341025 | −19.44 | 2.13 | 1.33E−05 | 1.49E−03 | 0.00 | 0.00 |
| 567 | chr16-31470 | 16 | 86192406 | 86193085 | −21.37 | 3.88 | 1.33E−05 | 1.49E−03 | 0.00 | 1.00 |
| 568 | chr3-7330 | 3 | 44728954 | 44729579 | −20.72 | 3.18 | 1.37E−05 | 1.53E−03 | 0.48 | 0.52 |
| 569 | chr12-13086 | 12 | 112513962 | 112514340 | −35.19 | 29.64 | 1.40E−05 | 1.56E−03 | 0.46 | 0.54 |
| 570 | chr2-11853 | 2 | 127498721 | 127500096 | −18.21 | 2.07 | 1.40E−05 | 1.56E−03 | 0.32 | 0.68 |
| 571 | chr9-28476 | 9 | 16861414 | 16862101 | −22.64 | 4.60 | 1.40E−05 | 1.56E−03 | 0.88 | 0.12 |
| 572 | chr8-9961 | 8 | 55528201 | 55529158 | −17.37 | 1.94 | 1.42E−05 | 1.57E−03 | 0.44 | 0.56 |
| 573 | chr1-26841 | 1 | 219131024 | 219132359 | −16.30 | 1.87 | 1.44E−05 | 1.59E−03 | 0.53 | 0.47 |
| 574 | chr12-26855 | 12 | 103221159 | 103222245 | −17.32 | 1.94 | 1.46E−05 | 1.61E−03 | 0.59 | 0.41 |
| 575 | chr8-13399 | 8 | 23618273 | 23621219 | −15.89 | 1.85 | 1.57E−05 | 1.72E−03 | 0.92 | 0.08 |
| 576 | chr7-33041 | 7 | 136203783 | 138208921 | −17.18 | 1.95 | 1.59E−05 | 1.74E−03 | 0.75 | 0.25 |
| 577 | chr7-3549 | 7 | 93041451 | 93043195 | −19.64 | 2.71 | 1.60E−05 | 1.75E−03 | 0.17 | 0.83 |
| 578 | chr11-5813 | 11 | 17696719 | 17699162 | −16.86 | 1.92 | 1.60E−05 | 1.75E−03 | 0.74 | 0.26 |
| 579 | chr3-20990 | 3 | 113534558 | 113534857 | −21.79 | 4.21 | 1.62E−05 | 1.76E−03 | 0.92 | 0.08 |
| 580 | chr5-15770 | 5 | 170677426 | 170678175 | −21.79 | 4.15 | 1.62E−05 | 1.76E−03 | 0.00 | 1.00 |
| 581 | chr9-33024 | 9 | 70978335 | 70978728 | −35.20 | 29.63 | 1.64E−05 | 1.78E−03 | 0.49 | 0.51 |
| 582 | chr20-11499 | 20 | 61055725 | 61056352 | −19.10 | 2.33 | 1.70E−05 | 1.84E−03 | 0.00 | 1.00 |
| 583 | chr9-31522 | 9 | 36729494 | 36730076 | −17.91 | 1.98 | 1.78E−05 | 1.91E−03 | 0.43 | 0.57 |
| 584 | chr12-29205 | 12 | 127316828 | 127317529 | −18.39 | 2.06 | 1.78E−05 | 1.92E−03 | 0.76 | 0.24 |
| 585 | chr10-20181 | 10 | 70998508 | 70998807 | −21.40 | 3.77 | 1.83E−05 | 1.96E−03 | 0.00 | 0.00 |
| 586 | chr8-13946 | 8 | 116729607 | 116729987 | −17.79 | 1.96 | 1.84E−05 | 1.96E−03 | 0.83 | 0.17 |
| 587 | chr10-22036 | 10 | 106388504 | 106389138 | −20.63 | 2.89 | 1.96E−05 | 2.08E−03 | 0.00 | 1.00 |
| 588 | chr19-41265 | 19 | 1082598 | 1083086 | −20.62 | 2.74 | 1.96E−05 | 2.08E−03 | 0.00 | 0.00 |
| 589 | chr1-23365 | 1 | 226723970 | 226724548 | −17.91 | 1.98 | 1.98E−05 | 2.10E−03 | 0.37 | 0.63 |
| 590 | chr9-2514 | 9 | 23814089 | 23815144 | −18.12 | 2.02 | 1.99E−05 | 2.11E−03 | 0.00 | 0.55 |
| 591 | chr18-12277 | 18 | 53171722 | 53172797 | −17.33 | 1.92 | 2.03E−05 | 2.15E−03 | 0.82 | 0.18 |
| 592 | chr1-40928 | 1 | 167662928 | 167663578 | −18.38 | 1.95 | 2.07E−05 | 2.18E−03 | 0.38 | 0.62 |
| 593 | chr5-22310 | 5 | 140767601 | 140767900 | −19.05 | 2.21 | 2.11E−05 | 2.21E−03 | 0.90 | 0.10 |
| 594 | chr1-52163 | 1 | 147168367 | 147168845 | −17.24 | 1.92 | 2.17E−05 | 2.27E−03 | 1.00 | 0.00 |
| 595 | chr3-13919 | 3 | 62330759 | 62332438 | −16.49 | 1.83 | 2.17E−05 | 2.27E−03 | 0.48 | 0.52 |
| 596 | chr16-40286 | 16 | 49725701 | 49726347 | −18.38 | 2.07 | 2.17E−05 | 2.27E−03 | 0.90 | 0.10 |
| 597 | chr11-5662 | 11 | 46367350 | 46369651 | −20.42 | 2.83 | 2.23E−05 | 2.32E−03 | 0.94 | 0.06 |
| 598 | chr19-31963 | 19 | 23445448 | 23446281 | −18.12 | 2.02 | 2.24E−05 | 2.33E−03 | 0.66 | 0.34 |
| 599 | chr17-40131 | 17 | 76929312 | 76930082 | −17.33 | 1.92 | 2.28E−05 | 2.36E−03 | 0.68 | 0.32 |
| 600 | chr6-1289 | 8 | 28848985 | 28849457 | −20.47 | 2.78 | 2.30E−05 | 2.38E−03 | 0.00 | 0.00 |
| 601 | chr3-22112 | 3 | 148624151 | 148625148 | −18.01 | 1.93 | 2.37E−05 | 2.44E−03 | 0.21 | 0.79 |
| 602 | chr18-4284 | 18 | 53265397 | 53265773 | −22.45 | 4.91 | 2.41E−05 | 2.47E−03 | 0.00 | 0.00 |
| 603 | chr11-23138 | 11 | 31780750 | 31781049 | −19.74 | 2.36 | 2.45E−05 | 2.51E−03 | 0.00 | 1.00 |
| 604 | chr17-38402 | 17 | 17567720 | 17569033 | −19.53 | 2.40 | 2.46E−05 | 2.52E−03 | 1.00 | 0.00 |
| 605 | chr8-20019 | 8 | 121206240 | 121207734 | −16.97 | 1.88 | 2.50E−05 | 2.56E−03 | 0.55 | 0.45 |
| 606 | chr19-14446 | 19 | 22260848 | 22261568 | −17.99 | 1.93 | 2.52E−05 | 2.57E−03 | 0.44 | 0.56 |
| 607 | chr19-26167 | 19 | 61517339 | 61518102 | −35.21 | 29.62 | 2.64E−05 | 2.67E−03 | 0.68 | 0.32 |
| 608 | chr6-1806 | 6 | 58256334 | 58257651 | −17.62 | 1.87 | 2.75E−05 | 2.77E−03 | 0.00 | 0.00 |
| 609 | chr10-22333 | 10 | 106430554 | 106431167 | −21.24 | 3.36 | 2.81E−05 | 2.82E−03 | 0.00 | 0.00 |
| 610 | chr20-17950 | 20 | 62181948 | 62182625 | −20.60 | 2.94 | 2.96E−05 | 2.95E−03 | 0.36 | 0.64 |
| 611 | chr9-22655 | 9 | 70978942 | 70979510 | −20.80 | 3.30 | 2.96E−05 | 2.95E−03 | 0.74 | 0.26 |
| 612 | chr10-26762 | 10 | 118880706 | 118881322 | −17.83 | 1.94 | 3.03E−05 | 3.01E−03 | 0.00 | 1.00 |
| 613 | chr11-34612 | 11 | 31805046 | 31805901 | −18.01 | 2.00 | 3.03E−05 | 3.01E−03 | 0.34 | 0.66 |
| 614 | chr14-10016 | 14 | 37747939 | 37750251 | −15.87 | 1.77 | 3.05E−05 | 3.03E−03 | 0.97 | 0.03 |
| 615 | chr19-30352 | 19 | 9469636 | 9470723 | −17.89 | 1.92 | 3.10E−05 | 3.07E−03 | 0.50 | 0.50 |
| 616 | chr8-21157 | 8 | 93176592 | 93176969 | −20.08 | 2.61 | 3.14E−05 | 3.10E−03 | 0.00 | 0.00 |
| 617 | chr6-25890 | 8 | 10990659 | 10991273 | −17.74 | 1.95 | 3.14E−05 | 3.10E−03 | 0.36 | 0.64 |
| 618 | chr4-18262 | 4 | 5942748 | 5943766 | −18.33 | 1.90 | 3.16E−05 | 3.12E−03 | 0.58 | 0.42 |
| 619 | chr7-37861 | 7 | 157173808 | 157176308 | −16.08 | 1.77 | 3.19E−05 | 3.14E−03 | 1.00 | 0.00 |
| 620 | chr2-45508 | 2 | 232959226 | 232950738 | −15.58 | 1.76 | 3.26E−05 | 3.20E−03 | 0.75 | 0.25 |
| 621 | chr8-20522 | 8 | 145131929 | 145132492 | −21.56 | 3.56 | 3.31E−05 | 3.24E−03 | 0.00 | 0.00 |

TABLE 1-continued

Differentially methylated regions (DMRs) associated breast cancer.

| | | | | | | | | | |
|---|---|---|---|---|---|---|---|---|---|
| 622 | chr16-23007 | 16 | 86179871 | 86180426 | −20.60 | 2.72 | 3.37E−05 | 3.30E−03 | 0.00 | 0.00 |
| 623 | chr12-10548 | 12 | 70952716 | 70954501 | −18.07 | 1.99 | 3.38E−05 | 3.30E−03 | 0.62 | 0.38 |
| 624 | chr6-21369 | 5 | 12857751 | 12858050 | −21.47 | 3.60 | 3.49E−05 | 3.40E−03 | 0.62 | 0.38 |
| 625 | chr19-17643 | 19 | 10489290 | 10490623 | −20.44 | 2.80 | 3.58E−05 | 3.48E−03 | 0.10 | 0.90 |
| 626 | chr7-21508 | 7 | 104372640 | 104373101 | −22.69 | 4.50 | 3.65E−05 | 3.53E−03 | 0.00 | 0.00 |
| 627 | chr1-19467 | 1 | 145010595 | 145011162 | −17.35 | 1.79 | 3.67E−05 | 3.55E−03 | 0.80 | 0.20 |
| 628 | chr11-5760 | 11 | 29994166 | 29994552 | −19.17 | 2.08 | 3.87E−05 | 3.72E−03 | 0.70 | 0.30 |
| 629 | chr3-6248 | 3 | 14826633 | 14827091 | −20.27 | 2.51 | 3.88E−05 | 3.72E−03 | 0.78 | 0.22 |
| 630 | chr16-39747 | 16 | 12901915 | 12902840 | −21.10 | 3.07 | 3.90E−05 | 3.73E−03 | 0.83 | 0.17 |
| 631 | chr3-18012 | 3 | 27740141 | 27741506 | −16.80 | 1.76 | 4.06E−05 | 3.86E−03 | 0.35 | 0.65 |
| 632 | chr1-29703 | 1 | 78284385 | 78285128 | −16.87 | 1.79 | 4.21E−05 | 3.97E−03 | 0.49 | 0.51 |
| 633 | chr10-23192 | 10 | 57060264 | 57061520 | −17.88 | 1.83 | 4.32E−05 | 4.06E−03 | 0.69 | 0.31 |
| 634 | chr20-5927 | 20 | 22504911 | 22507274 | −16.74 | 1.77 | 4.43E−05 | 4.15E−03 | 0.73 | 0.27 |
| 635 | chr7-12439 | 7 | 154941358 | 154941912 | −20.90 | 3.25 | 4.45E−05 | 4.17E−03 | 1.00 | 0.00 |
| 636 | chr6-21729 | 6 | 27620848 | 27621582 | −18.02 | 1.90 | 4.64E−05 | 4.33E−03 | 0.00 | 0.00 |
| 637 | chr1-43361 | 1 | 227609391 | 227610531 | −16.58 | 1.78 | 4.66E−05 | 4.34E−03 | 0.72 | 0.28 |
| 638 | chr19-29813 | 19 | 21560949 | 21562012 | −19.39 | 2.17 | 4.73E−05 | 4.40E−03 | 0.56 | 0.44 |
| 639 | chr17-9298 | 17 | 55581827 | 55582219 | −22.34 | 5.06 | 4.78E−05 | 4.43E−03 | 0.50 | 0.50 |
| 640 | chr18-14140 | 18 | 57151481 | 57151856 | −21.47 | 3.63 | 4.86E−05 | 4.49E−03 | 0.51 | 0.49 |
| 641 | chr8-14671 | 8 | 79740337 | 79740799 | −21.44 | 3.67 | 4.86E−05 | 4.49E−03 | 0.29 | 0.71 |
| 642 | chr4-3545 | 4 | 66216516 | 66217347 | −20.90 | 3.20 | 4.88E−05 | 4.51E−03 | 0.00 | 1.00 |
| 643 | chr21-15309 | 21 | 39905342 | 39905737 | −19.92 | 2.45 | 4.89E−05 | 4.51E−03 | 0.00 | 0.00 |
| 644 | chr11-10407 | 11 | 122355001 | 122355564 | −18.13 | 1.93 | 4.93E−05 | 4.55E−03 | 0.00 | 1.00 |
| 645 | chr9-12742 | 9 | 97264393 | 97265064 | −19.83 | 2.11 | 5.02E−05 | 4.62E−03 | 0.00 | 0.00 |
| 646 | chr16-6800 | 16 | 47870657 | 47872951 | −17.83 | 1.88 | 5.06E−05 | 4.64E−03 | 0.62 | 0.38 |
| 647 | chr19-28830 | 19 | 22977311 | 22978162 | −17.33 | 1.81 | 5.20E−05 | 4.75E−03 | 0.57 | 0.43 |
| 648 | chr3-18921 | 3 | 161239255 | 161239880 | −20.78 | 2.69 | 5.21E−05 | 4.76E−03 | 0.58 | 0.42 |
| 649 | chr7-20736 | 7 | 154933652 | 154937288 | −16.16 | 1.72 | 5.21E−05 | 4.76E−03 | 0.75 | 0.25 |
| 650 | chr11-5754 | 11 | 31782242 | 31783996 | −16.93 | 1.78 | 5.26E−05 | 4.79E−03 | 0.70 | 0.30 |
| 651 | chr11-26384 | 11 | 124243246 | 124244782 | −17.75 | 1.80 | 5.29E−05 | 4.81E−03 | 0.19 | 0.81 |
| 652 | chr6-10449 | 6 | 27343730 | 27344104 | −18.05 | 1.86 | 5.33E−05 | 4.84E−03 | 0.00 | 0.00 |
| 653 | chr17-34300 | 17 | 70178657 | 70179522 | −17.37 | 1.81 | 5.36E−05 | 4.87E−03 | 0.59 | 0.41 |
| 654 | chr7-31210 | 7 | 154995248 | 154996216 | −17.09 | 1.76 | 5.38E−05 | 4.88E−03 | 0.69 | 0.31 |
| 655 | chr3-1810 | 3 | 132563160 | 132564028 | −16.80 | 1.76 | 5.81E−05 | 5.22E−03 | 0.71 | 0.29 |
| 656 | chr12-2151 | 12 | 128953476 | 128954156 | −18.07 | 1.88 | 5.86E−05 | 5.26E−03 | 0.87 | 0.13 |
| 657 | chr10-2387 | 10 | 6282716 | 6283428 | −35.25 | 29.52 | 5.99E−05 | 5.35E−03 | 0.63 | 0.37 |
| 658 | chr11-33859 | 11 | 117171063 | 117172707 | −18.39 | 1.92 | 6.02E−05 | 5.37E−03 | 0.52 | 0.48 |
| 659 | chr2-24491 | 2 | 219905312 | 219905929 | −19.21 | 2.10 | 6.27E−05 | 5.56E−03 | 0.00 | 1.00 |
| 660 | chr3-9414 | 3 | 148557064 | 148557363 | −21.78 | 3.25 | 6.37E−05 | 5.63E−03 | 0.00 | 0.00 |
| 661 | chr6-1661 | 6 | 63053409 | 63054691 | −17.48 | 1.81 | 6.51E−05 | 5.94E−03 | 0.29 | 0.71 |
| 662 | chr11-13605 | 11 | 20137690 | 20138947 | −17.28 | 1.77 | 6.77E−05 | 5.94E−03 | 0.89 | 0.11 |
| 663 | chr13-9261 | 13 | 48692492 | 48693637 | −16.34 | 1.71 | 6.78E−05 | 5.94E−03 | 0.92 | 0.08 |
| 664 | chr1-55159 | 1 | 243396381 | 243396680 | −20.63 | 2.85 | 7.01E−05 | 6.12E−03 | 0.00 | 0.00 |
| 665 | chr13-8903 | 13 | 95092320 | 95092694 | −18.35 | 1.96 | 7.09E−05 | 6.16E−03 | 0.76 | 0.24 |
| 666 | chr19-35894 | 19 | 62302287 | 62302885 | −18.71 | 1.99 | 7.10E−05 | 6.17E−03 | 0.42 | 0.58 |
| 667 | chr18-11477 | 18 | 53248374 | 53249217 | −20.74 | 2.73 | 7.11E−05 | 6.18E−03 | 0.00 | 1.00 |
| 668 | chr19-6899 | 19 | 58503272 | 58503954 | −18.92 | 1.90 | 7.50E−05 | 6.46E−03 | 0.57 | 0.43 |
| 669 | chr6-16690 | 6 | 28749581 | 28750455 | −19.98 | 2.49 | 7.70E−05 | 6.61E−03 | 0.00 | 0.00 |
| 670 | chr3-10180 | 3 | 174597694 | 174598312 | −22.41 | 4.93 | 7.86E−05 | 6.73E−03 | 0.35 | 0.65 |
| 671 | chr5-10230 | 5 | 63290659 | 63291554 | −19.64 | 2.32 | 7.90E−05 | 6.76E−03 | 0.41 | 0.59 |
| 672 | chr19-19483 | 19 | 60850975 | 60851445 | −20.33 | 2.80 | 7.94E−05 | 6.78E−03 | 0.80 | 0.20 |
| 673 | chr12-7564 | 12 | 46863133 | 46865076 | −17.48 | 1.75 | 8.50E−05 | 7.20E−03 | 0.62 | 0.38 |
| 674 | chr11-24671 | 11 | 133332035 | 133333054 | −19.10 | 1.88 | 8.64E−05 | 7.31E−03 | 0.62 | 0.38 |
| 675 | chr19-19145 | 19 | 63301076 | 63301887 | −21.63 | 3.40 | 8.92E−05 | 7.51E−03 | 0.80 | 0.20 |
| 676 | chr7-9141 | 7 | 96470160 | 96471563 | −17.32 | 1.72 | 9.24E−05 | 7.74E−03 | 0.00 | 1.00 |
| 677 | chr3-23572 | 3 | 148596152 | 148597503 | −15.95 | 1.65 | 9.24E−05 | 7.75E−03 | 0.64 | 0.36 |
| 678 | chr11-25406 | 11 | 31775677 | 31779112 | −16.36 | 1.67 | 9.26E−05 | 7.75E−03 | 0.39 | 0.61 |
| 679 | chr17-5347 | 17 | 55573396 | 55573950 | −19.19 | 2.12 | 9.46E−05 | 7.90E−03 | 0.54 | 0.46 |
| 680 | chr11-22903 | 11 | 62315518 | 62316198 | −21.30 | 3.18 | 9.56E−05 | 7.97E−03 | 0.67 | 0.33 |
| 681 | chr6-16740 | 6 | 28518900 | 28519531 | −18.79 | 1.83 | 9.67E−05 | 8.05E−03 | 0.00 | 0.00 |
| 682 | chr6-12588 | 6 | 12400479 | 12400778 | −18.87 | 1.92 | 9.77E−05 | 8.13E−03 | 0.00 | 0.00 |
| 683 | chr1-24925 | 1 | 147490921 | 147491510 | −19.11 | 1.90 | 9.90E−05 | 8.22E−03 | 0.48 | 0.52 |
| 684 | chr1-42512 | 1 | 199729768 | 199730067 | −19.61 | 2.20 | 9.93E−05 | 8.23E−03 | 0.00 | 0.00 |
| 685 | chr19-47868 | 19 | 3161711 | 3162010 | −35.33 | 29.38 | 9.95E−05 | 8.24E−03 | 0.00 | 0.00 |
| 686 | chr19-31544 | 19 | 62911410 | 62912734 | −16.73 | 1.71 | 1.01E−04 | 8.33E−03 | 0.32 | 0.68 |
| 687 | chr11-15137 | 11 | 45333436 | 45333891 | −22.44 | 4.86 | 1.01E−04 | 8.36E−03 | 0.68 | 0.32 |
| 688 | chr18-5740 | 18 | 73740881 | 73741255 | −21.13 | 3.34 | 1.04E−04 | 8.57E−03 | 0.60 | 0.40 |
| 689 | chr20-19704 | 20 | 61840600 | 61841345 | −20.06 | 2.43 | 1.07E−04 | 8.77E−03 | 1.00 | 0.00 |
| 690 | chr7-10983 | 7 | 35460718 | 35461475 | −16.75 | 1.66 | 1.11E−04 | 9.01E−03 | 0.65 | 0.35 |
| 691 | chr13-11675 | 13 | 94453413 | 94453712 | −20.28 | 2.36 | 1.14E−04 | 9.25E−03 | 0.35 | 0.65 |
| 692 | chr8-7098 | 8 | 143702377 | 143702833 | −19.52 | 2.21 | 1.15E−04 | 9.30E−03 | 0.00 | 0.00 |
| 693 | chr3-24896 | 3 | 148590966 | 148592290 | −16.05 | 1.63 | 1.15E−04 | 9.30E−03 | 0.82 | 0.18 |
| 694 | chr11-18108 | 11 | 31802820 | 31804364 | −17.07 | 1.70 | 1.17E−04 | 9.44E−03 | 0.42 | 0.58 |
| 695 | chr2-31496 | 2 | 241408904 | 241409558 | −22.80 | 4.29 | 1.18E−04 | 9.51E−03 | 0.84 | 0.16 |
| 696 | chr17-25891 | 17 | 39338985 | 39340161 | −21.49 | 3.53 | 1.19E−04 | 9.55E−03 | 0.41 | 0.59 |
| 697 | chr3-13418 | 3 | 148573160 | 148573538 | −21.09 | 2.96 | 1.19E−04 | 9.55E−03 | 0.00 | 0.00 |
| 698 | chr16-15120 | 16 | 84877272 | 84878635 | −18.80 | 1.92 | 1.19E−04 | 9.57E−03 | 0.84 | 0.16 |
| 699 | chr13-9410 | 13 | 107317793 | 107319138 | −18.71 | 2.02 | 1.22E−04 | 9.76E−03 | 0.95 | 0.05 |

TABLE 1-continued

Differentially methylated regions (DMRs) associated breast cancer.

| | | | | | | | | | |
|---|---|---|---|---|---|---|---|---|---|
| 700 | chr11-23818 | 11 | 19691771 | 19693088 | −20.31 | 2.46 | 1.23E−04 | 9.84E−03 | 0.10 | 0.90 |
| 701 | chr6-12015 | 6 | 27628983 | 27629386 | −20.25 | 2.52 | 1.23E−04 | 9.85E−03 | 0.00 | 0.00 |
| 702 | chr19-9802 | 19 | 41026611 | 41027335 | −18.18 | 1.82 | 1.24E−04 | 9.91E−03 | 0.45 | 0.55 |
| 703 | chr19-26240 | 19 | 58232322 | 58233098 | −18.00 | 1.77 | 1.26E−04 | 1.00E−02 | 0.64 | 0.36 |
| 704 | chr22-14234 | 22 | 43784756 | 43785475 | −22.13 | 3.61 | 1.31E−04 | 1.04E−02 | 0.39 | 0.61 |
| 705 | chr9-25922 | 9 | 98679294 | 98679924 | −17.17 | 1.69 | 1.35E−04 | 1.06E−02 | 0.74 | 0.26 |
| 706 | chr3-2993 | 3 | 149898092 | 149899204 | −18.66 | 1.87 | 1.35E−04 | 1.06E−02 | 0.44 | 0.56 |
| 707 | chr16-3077 | 16 | 47868513 | 47870198 | −17.66 | 1.68 | 1.37E−04 | 1.08E−02 | 0.53 | 0.47 |
| 708 | chr1-45365 | 1 | 81652725 | 81653024 | −20.73 | 2.45 | 1.39E−04 | 1.09E−02 | 0.00 | 0.00 |
| 709 | chr8-21185 | 8 | 142446426 | 142446725 | −35.31 | 29.41 | 1.41E−04 | 1.10E−02 | 0.00 | 0.00 |
| 710 | chr17-22033 | 17 | 44159065 | 44159578 | −17.98 | 1.71 | 1.41E−04 | 1.10E−02 | 0.41 | 0.59 |
| 711 | chr19-46114 | 19 | 54337512 | 54338223 | −18.61 | 1.99 | 1.45E−04 | 1.13E−02 | 0.30 | 0.70 |
| 712 | chr11-24196 | 11 | 32410931 | 32413157 | −16.92 | 1.64 | 1.51E−04 | 1.17E−02 | 0.77 | 0.23 |
| 713 | chr7-18563 | 7 | 2527436 | 2527812 | −21.86 | 3.98 | 1.52E−04 | 1.17E−02 | 0.00 | 1.00 |
| 714 | chr19-31045 | 19 | 22396428 | 22397198 | −19.11 | 1.94 | 1.56E−04 | 1.20E−02 | 0.00 | 0.00 |
| 715 | chr13-13783 | 13 | 27263290 | 27268058 | −15.85 | 1.58 | 1.57E−04 | 1.21E−02 | 0.46 | 0.54 |
| 716 | chr16-10570 | 16 | 19991910 | 19993697 | −18.29 | 1.84 | 1.58E−04 | 1.22E−02 | 0.33 | 0.67 |
| 717 | chr8-17537 | 8 | 23615270 | 23616687 | −18.04 | 1.80 | 1.61E−04 | 1.23E−02 | 0.53 | 0.47 |
| 718 | chr1-11022 | 1 | 26360354 | 26360829 | −20.03 | 2.19 | 1.63E−04 | 1.25E−02 | 0.91 | 0.09 |
| 719 | chr3-10449 | 3 | 148557618 | 148558026 | −18.75 | 1.73 | 1.67E−04 | 1.27E−02 | 0.00 | 0.55 |
| 720 | chr3-19059 | 3 | 9568824 | 9569550 | −18.92 | 1.96 | 1.71E−04 | 1.30E−02 | 0.36 | 0.64 |
| 721 | chr19-35922 | 19 | 55520704 | 55521725 | −19.73 | 2.27 | 1.72E−04 | 1.30E−02 | 0.32 | 0.68 |
| 722 | chr8-26677 | 8 | 141676464 | 141676763 | −22.12 | 3.69 | 1.76E−04 | 1.33E−02 | 0.00 | 0.00 |
| 723 | chr11-27829 | 11 | 22318966 | 22320078 | −17.37 | 1.63 | 1.85E−04 | 1.38E−02 | 0.46 | 0.54 |
| 724 | chr14-8228 | 14 | 21074297 | 21075104 | −19.09 | 1.92 | 1.85E−04 | 1.38E−02 | 0.00 | 0.00 |
| 725 | chr8-4443 | 8 | 24826766 | 24828794 | −15.79 | 1.58 | 1.86E−04 | 1.39E−02 | 0.81 | 0.19 |
| 726 | chr7-24476 | 7 | 127047249 | 127047992 | −21.36 | 3.69 | 1.87E−04 | 1.39E−02 | 0.00 | 0.00 |
| 727 | chr8-19833 | 8 | 143356659 | 143356958 | −19.31 | 1.87 | 1.89E−04 | 1.41E−02 | 0.00 | 1.00 |
| 728 | chr11-12951 | 11 | 6904062 | 6904897 | −19.03 | 1.83 | 1.93E−04 | 1.44E−02 | 0.83 | 0.17 |
| 729 | chr10-3216 | 10 | 79066063 | 79067359 | −19.57 | 2.31 | 1.99E−04 | 1.48E−02 | 0.97 | 0.03 |
| 730 | chr8-18358 | 8 | 144588313 | 144589359 | −16.73 | 1.60 | 2.03E−04 | 1.50E−02 | 0.00 | 0.00 |
| 731 | chr16-31613 | 16 | 83728346 | 83728886 | −22.62 | 4.58 | 2.04E−04 | 1.51E−02 | 0.56 | 0.44 |
| 732 | chr3-2228 | 3 | 148621006 | 148622296 | −16.18 | 1.56 | 2.06E−04 | 1.52E−02 | 0.50 | 0.50 |
| 733 | chr2-9342 | 2 | 176688986 | 176689871 | −17.28 | 1.65 | 2.08E−04 | 1.53E−02 | 0.74 | 0.26 |
| 734 | chr6-10441 | 6 | 27358632 | 27360245 | −16.76 | 1.58 | 2.21E−04 | 1.61E−02 | 0.00 | 0.00 |
| 735 | chr6-22508 | 6 | 29628870 | 29629928 | −15.88 | 1.56 | 2.37E−04 | 1.71E−02 | 0.68 | 0.32 |
| 736 | chr10-11960 | 10 | 112421814 | 112422487 | −21.86 | 3.04 | 2.37E−04 | 1.71E−02 | 0.88 | 0.12 |
| 737 | chr8-25433 | 8 | 124242036 | 124243002 | −18.08 | 1.76 | 2.41E−04 | 1.73E−02 | 0.71 | 0.29 |
| 738 | chr8-23865 | 8 | 143710429 | 143711017 | −20.82 | 2.81 | 2.47E−04 | 1.77E−02 | 0.00 | 0.00 |
| 739 | chr1-38653 | 1 | 63556809 | 63559083 | −15.73 | 1.52 | 2.48E−04 | 1.77E−02 | 1.00 | 0.00 |
| 740 | chr8-27810 | 8 | 145468821 | 145469864 | −17.74 | 1.68 | 2.48E−04 | 1.77E−02 | 0.25 | 0.75 |
| 741 | chr9-23405 | 9 | 95749855 | 95750434 | −21.73 | 3.25 | 2.52E−04 | 1.79E−02 | 0.00 | 1.00 |
| 742 | chr13-8897 | 13 | 42464009 | 42464693 | −18.00 | 1.66 | 2.52E−04 | 1.79E−02 | 0.63 | 0.37 |
| 743 | chr17-10321 | 17 | 72893521 | 72893820 | −18.78 | 1.73 | 2.53E−04 | 1.80E−02 | 0.00 | 0.00 |
| 744 | chr1-4856 | 1 | 103346188 | 103347175 | −17.42 | 1.63 | 2.58E−04 | 1.83E−02 | 0.00 | 0.00 |
| 745 | chr6-14517 | 6 | 35587318 | 35587692 | −18.17 | 1.76 | 2.60E−04 | 1.84E−02 | 0.77 | 0.23 |
| 746 | chr6-6486 | 6 | 28888677 | 28889053 | −19.06 | 1.76 | 2.63E−04 | 1.86E−02 | 0.00 | 1.00 |
| 747 | chr6-9437 | 6 | 43720677 | 43721056 | −17.67 | 1.72 | 2.74E−04 | 1.92E−02 | 0.96 | 0.04 |
| 748 | chr10-27233 | 10 | 101280559 | 101281416 | −17.97 | 1.71 | 2.74E−04 | 1.92E−02 | 0.64 | 0.36 |
| 749 | chr17-18721 | 17 | 72933896 | 72934270 | −18.96 | 1.73 | 2.75E−04 | 1.92E−02 | 0.00 | 0.00 |
| 750 | chr11-17573 | 11 | 68822506 | 68822892 | −22.62 | 4.53 | 2.76E−04 | 1.93E−02 | 0.00 | 0.00 |
| 751 | chr12-9653 | 12 | 106821502 | 106821877 | −35.42 | 29.20 | 2.85E−04 | 1.98E−02 | 0.84 | 0.16 |
| 752 | chr22-23171 | 22 | 22882253 | 22883195 | −35.41 | 29.21 | 2.85E−04 | 1.98E−02 | 0.47 | 0.53 |
| 753 | chr10-10203 | 10 | 101279569 | 101280477 | −18.01 | 1.65 | 2.96E−04 | 2.05E−02 | 0.34 | 0.66 |
| 754 | chr16-17571 | 16 | 9014474 | 9015029 | −18.61 | 1.73 | 2.99E−04 | 2.06E−02 | 0.00 | 0.00 |
| 755 | chr13-14820 | 13 | 97926663 | 97927038 | −20.85 | 2.59 | 3.07E−04 | 2.11E−02 | 0.00 | 1.00 |
| 756 | chr8-5741 | 8 | 56919297 | 56919906 | −20.83 | 2.52 | 3.07E−04 | 2.11E−02 | 0.00 | 0.00 |
| 757 | chr11-34050 | 11 | 122355856 | 122356563 | −21.30 | 3.12 | 3.12E−04 | 2.14E−02 | 0.00 | 1.00 |
| 758 | chr3-15060 | 3 | 66931170 | 66931701 | −18.49 | 1.70 | 3.14E−04 | 2.15E−02 | 0.00 | 0.00 |
| 759 | chr9-26649 | 9 | 99656732 | 99657696 | −16.31 | 1.52 | 3.14E−04 | 2.15E−02 | 0.62 | 0.38 |
| 760 | chr13-7948 | 13 | 27396809 | 27397199 | −19.27 | 1.89 | 3.17E−04 | 2.17E−02 | 0.61 | 0.39 |
| 761 | chr14-5903 | 14 | 76669824 | 76670283 | −35.45 | 29.14 | 3.42E−04 | 2.30E−02 | 0.00 | 0.00 |
| 762 | chr18-8094 | 18 | 10443675 | 10444423 | −18.00 | 1.64 | 3.46E−04 | 2.33E−02 | 0.29 | 0.71 |
| 763 | chr12-16201 | 12 | 109957155 | 109958601 | −20.97 | 3.02 | 3.58E−04 | 2.39E−02 | 0.54 | 0.46 |
| 764 | chr8-16621 | 8 | 145718161 | 145719871 | −15.79 | 1.51 | 3.58E−04 | 2.39E−02 | 0.69 | 0.31 |
| 765 | chr8-15516 | 8 | 65446926 | 65447225 | −19.85 | 1.86 | 3.61E−04 | 2.40E−02 | 0.00 | 1.00 |
| 766 | chr1-17428 | 1 | 90950424 | 90950882 | −19.24 | 1.72 | 3.68E−04 | 2.45E−02 | 0.00 | 1.00 |
| 767 | chr18-11487 | 18 | 53170434 | 53170733 | −20.60 | 2.50 | 3.71E−04 | 2.46E−02 | 0.09 | 0.91 |
| 768 | chr11-28585 | 11 | 108798003 | 108800346 | −17.39 | 1.54 | 3.76E−04 | 2.48E−02 | 0.62 | 0.38 |
| 769 | chr7-18939 | 7 | 150573094 | 150573546 | −22.19 | 3.44 | 3.74E−04 | 2.48E−02 | 0.68 | 0.32 |
| 770 | chr7-2510 | 7 | 4888353 | 4889381 | −18.99 | 1.89 | 3.75E−04 | 2.48E−02 | 0.14 | 0.86 |
| 771 | chr7-11427 | 7 | 86812365 | 86813417 | −21.60 | 3.31 | 3.92E−04 | 2.57E−02 | 0.33 | 0.67 |
| 772 | chr11-30995 | 11 | 132319281 | 132320002 | −18.72 | 1.68 | 4.01E−04 | 2.62E−02 | 0.45 | 0.55 |
| 773 | chr19-49418 | 19 | 59172707 | 59173789 | −18.02 | 1.67 | 4.07E−04 | 2.66E−02 | 0.50 | 0.50 |
| 774 | chr6-19743 | 6 | 117692358 | 117693371 | −19.90 | 2.15 | 4.10E−04 | 2.67E−02 | 0.19 | 0.81 |
| 775 | chr8-8451 | 8 | 139995655 | 139996047 | −35.41 | 29.21 | 4.11E−04 | 2.67E−02 | 0.00 | 0.00 |
| 776 | chr16-27356 | 16 | 47873886 | 47875016 | −18.78 | 1.84 | 4.16E−04 | 2.70E−02 | 0.78 | 0.22 |
| 777 | chr2-4712 | 2 | 182250696 | 182252163 | −17.26 | 1.52 | 4.16E−04 | 2.70E−02 | 0.00 | 0.00 |

TABLE 1-continued

Differentially methylated regions (DMRs) associated breast cancer.

| | | | | | | | | | | |
|---|---|---|---|---|---|---|---|---|---|---|
| 778 | chr11-6782 | 11 | 46339498 | 46339953 | −20.09 | 2.09 | 4.16E−04 | 2.70E−02 | 0.00 | 0.00 |
| 779 | chr10-20530 | 10 | 50557375 | 50557969 | −17.66 | 1.56 | 4.19E−04 | 2.72E−02 | 0.50 | 0.50 |
| 780 | chr11-12271 | 11 | 46804641 | 46805127 | −20.75 | 2.54 | 4.32E−04 | 2.79E−02 | 0.00 | 0.00 |
| 781 | chr11-29093 | 11 | 17673651 | 17673950 | −21.19 | 2.72 | 4.33E−04 | 2.79E−02 | 0.00 | 1.00 |
| 782 | chr12-2463 | 12 | 125776431 | 125778625 | −16.35 | 1.49 | 4.34E−04 | 2.80E−02 | 0.51 | 0.49 |
| 783 | chr9-26765 | 9 | 137117535 | 137119363 | −19.16 | 1.76 | 4.35E−04 | 2.81E−02 | 0.39 | 0.61 |
| 784 | chr19-41652 | 19 | 22507612 | 22507911 | −21.33 | 2.63 | 4.42E−04 | 2.83E−02 | 0.00 | 1.00 |
| 785 | chr16-39788 | 16 | 29982494 | 29983133 | −19.75 | 2.07 | 4.59E−04 | 2.92E−02 | 0.00 | 1.00 |
| 786 | chr18-249 | 18 | 43028812 | 43029683 | −16.12 | 1.48 | 4.60E−04 | 2.93E−02 | 0.88 | 0.12 |
| 787 | chr3-6105 | 3 | 148588462 | 148589450 | −16.94 | 1.48 | 4.67E−04 | 2.96E−02 | 0.00 | 0.25 |
| 788 | chr7-19417 | 7 | 86110997 | 86112738 | −18.09 | 1.58 | 4.79E−04 | 3.03E−02 | 0.00 | 0.00 |
| 789 | chr2-4092 | 2 | 124498663 | 124500373 | −17.23 | 1.48 | 4.87E−04 | 3.07E−02 | 0.59 | 0.41 |
| 790 | chr1-10651 | 1 | 196155374 | 196156447 | −16.55 | 1.48 | 4.92E−04 | 3.09E−02 | 0.00 | 1.00 |
| 791 | chr11-2782 | 11 | 118797889 | 118798265 | −22.08 | 3.59 | 4.92E−04 | 3.09E−02 | 0.54 | 0.46 |
| 792 | chr5-172 | 5 | 6502005 | 6502716 | −21.55 | 2.79 | 4.92E−04 | 3.09E−02 | 0.88 | 0.12 |
| 793 | chr13-10897 | 13 | 57103538 | 57107350 | −14.63 | 1.43 | 4.98E−04 | 3.12E−02 | 0.63 | 0.37 |
| 794 | chr9-20659 | 9 | 21959647 | 21959946 | −21.30 | 2.72 | 4.99E−04 | 3.12E−02 | 0.00 | 1.00 |
| 795 | chr16-33015 | 16 | 1357709 | 1358087 | −18.58 | 1.60 | 5.06E−04 | 3.15E−02 | 0.00 | 0.00 |
| 796 | chr10-13508 | 10 | 50646183 | 50646772 | −17.61 | 1.55 | 5.21E−04 | 3.23E−02 | 0.71 | 0.29 |
| 797 | chr6-10868 | 6 | 44000049 | 44000348 | −20.20 | 1.86 | 5.27E−04 | 3.26E−02 | 0.00 | 0.00 |
| 798 | chr18-3706 | 18 | 33319509 | 33319999 | −21.33 | 3.06 | 5.41E−04 | 3.33E−02 | 0.08 | 0.92 |
| 799 | chr18-5056 | 18 | 72336354 | 72336986 | −21.23 | 2.60 | 5.41E−04 | 3.33E−02 | 1.00 | 0.00 |
| 800 | chr1-10203 | 1 | 21773561 | 21774294 | −19.42 | 1.75 | 5.45E−04 | 3.35E−02 | 0.00 | 0.00 |
| 801 | chr17-29531 | 17 | 44073871 | 44075510 | −16.40 | 1.45 | 5.57E−04 | 3.42E−02 | 0.53 | 0.47 |
| 802 | chr19-39407 | 19 | 52434946 | 52435401 | −22.06 | 3.64 | 5.64E−04 | 3.45E−02 | 0.10 | 0.90 |
| 803 | chr8-29731 | 8 | 145092002 | 145092688 | −17.63 | 1.53 | 5.69E−04 | 3.47E−02 | 0.00 | 1.00 |
| 804 | chr6-25261 | 6 | 27755606 | 27757375 | −16.08 | 1.43 | 5.92E−04 | 3.59E−02 | 0.12 | 0.88 |
| 805 | chr12-15097 | 12 | 61115300 | 61115599 | −35.48 | 29.06 | 5.94E−04 | 3.60E−02 | 0.00 | 0.00 |
| 806 | chr7-36853 | 7 | 92299813 | 92302446 | −20.57 | 2.66 | 6.13E−04 | 3.69E−02 | 0.88 | 0.12 |
| 807 | chr8-8438 | 8 | 38391353 | 38391733 | −18.16 | 1.51 | 6.16E−04 | 3.71E−02 | 0.00 | 0.00 |
| 808 | chr1-46192 | 1 | 199775112 | 199775968 | −21.94 | 3.80 | 6.38E−04 | 3.82E−02 | 0.97 | 0.03 |
| 809 | chr1-18402 | 1 | 110474178 | 110475057 | −17.88 | 1.53 | 6.41E−04 | 3.83E−02 | 0.60 | 0.40 |
| 810 | chr11-24335 | 11 | 74119235 | 74120026 | −19.35 | 1.91 | 6.51E−04 | 3.88E−02 | 0.15 | 0.85 |
| 811 | chr5-5052 | 5 | 63291787 | 63293760 | −16.39 | 1.44 | 6.72E−04 | 3.99E−02 | 0.68 | 0.32 |
| 812 | chr9-19431 | 9 | 66083242 | 66083541 | −18.87 | 1.68 | 6.74E−04 | 4.00E−02 | 0.73 | 0.27 |
| 813 | chr22-25789 | 22 | 44038255 | 44038641 | −20.65 | 2.49 | 6.88E−04 | 4.07E−02 | 0.00 | 0.00 |
| 814 | chr1-21514 | 1 | 26423939 | 26424890 | −17.43 | 1.51 | 7.52E−04 | 4.39E−02 | 0.71 | 0.29 |
| 815 | chr4-2115 | 4 | 5944225 | 5945132 | −18.41 | 1.57 | 7.61E−04 | 4.43E−02 | 0.18 | 0.82 |
| 816 | chr10-8149 | 10 | 44108655 | 44109163 | −18.27 | 1.53 | 7.79E−04 | 4.51E−02 | 0.61 | 0.39 |
| 817 | chr11-4047 | 11 | 32413697 | 32415714 | −18.12 | 1.63 | 7.97E−04 | 4.60E−02 | 0.09 | 0.91 |
| 818 | chr16-28483 | 16 | 60625710 | 60628552 | −17.03 | 1.43 | 8.05E−04 | 4.64E−02 | 0.53 | 0.47 |
| 819 | chr10-14177 | 10 | 102885581 | 102886942 | −17.02 | 1.45 | 8.36E−04 | 4.77E−02 | 0.24 | 0.76 |
| 820 | chr2-9331 | 2 | 176653510 | 176657430 | −15.22 | 1.36 | 8.77E−04 | 4.95E−02 | 0.81 | 0.19 |
| 821 | chr9-17475 | 9 | 94922180 | 94922561 | −19.55 | 1.78 | 8.77E−04 | 4.95E−02 | 0.00 | 0.00 |
| 822 | chr8-25100 | 8 | 145530028 | 145530950 | −17.82 | 1.56 | 8.88E−04 | 4.99E−02 | 1.00 | 0.00 |
| 823 | chr1-46896 | 1 | 9522331 | 9523130 | −20.78 | −2.77 | 6.72E−07 | 1.22E−04 | 0.88 | 0.12 |
| 824 | chr10-1806 | 10 | 121291154 | 121291996 | −19.51 | −2.30 | 9.54E−07 | 1.64E−04 | 0.63 | 0.37 |
| 825 | chr6-7206 | 6 | 2968391 | 2969638 | −18.35 | −1.86 | 9.57E−07 | 1.65E−04 | 0.00 | 0.00 |
| 826 | chr2-24638 | 2 | 237127007 | 237127306 | −19.90 | −1.93 | 3.47E−06 | 4.90E−04 | 0.00 | 0.00 |
| 827 | chr1-22430 | 1 | 166675449 | 166675833 | −21.89 | −3.13 | 4.74E−06 | 6.32E−04 | 0.00 | 0.00 |
| 828 | chr16-21721 | 16 | 5572196 | 5572575 | −19.74 | −1.94 | 6.34E−06 | 8.04E−04 | 0.00 | 0.00 |
| 829 | chr16-41361 | 16 | 72135367 | 72135666 | −21.14 | −2.40 | 1.55E−05 | 1.70E−03 | 0.00 | 0.00 |
| 830 | chr11-20041 | 11 | 129112952 | 129113251 | −20.05 | −1.97 | 1.56E−05 | 1.71E−03 | 0.00 | 0.00 |
| 831 | chr11-33860 | 11 | 122375007 | 122375306 | −19.99 | −2.05 | 1.96E−05 | 2.08E−03 | 0.00 | 0.00 |
| 832 | chr13-2085 | 13 | 35902497 | 35903099 | −19.09 | −1.80 | 2.19E−05 | 2.28E−03 | 0.00 | 1.00 |
| 833 | chr12-24790 | 12 | 128204248 | 128204547 | −20.63 | −2.32 | 2.22E−05 | 2.31E−03 | 0.00 | 0.00 |
| 834 | chr10-25116 | 10 | 129960630 | 129960929 | −19.27 | −1.77 | 2.53E−05 | 2.58E−03 | 0.00 | 0.00 |
| 835 | chr13-14938 | 13 | 43118830 | 43119129 | −19.94 | −1.86 | 2.90E−05 | 2.91E−03 | 0.00 | 0.00 |
| 836 | chr8-14802 | 8 | 3088897 | 3089196 | −19.25 | −1.78 | 2.92E−05 | 2.92E−03 | 0.00 | 0.00 |
| 837 | chr16-34470 | 16 | 82084464 | 82084763 | −19.72 | −1.76 | 4.01E−05 | 3.83E−03 | 0.00 | 0.00 |
| 838 | chr15-11755 | 15 | 90661465 | 90661764 | −20.89 | −2.30 | 4.34E−05 | 4.08E−03 | 0.00 | 0.00 |
| 839 | chr2-36107 | 2 | 2033286 | 2033661 | −19.64 | −1.75 | 6.14E−05 | 5.46E−03 | 0.00 | 0.00 |
| 840 | chr16-40307 | 16 | 49508539 | 49508838 | −19.70 | −1.81 | 6.45E−05 | 5.69E−03 | 0.00 | 0.00 |
| 841 | chr15-17372 | 15 | 86294813 | 86295112 | −19.75 | −1.77 | 9.23E−05 | 7.74E−03 | 0.00 | 0.00 |
| 842 | chr17-5864 | 17 | 9965973 | 9966347 | −19.93 | −1.73 | 1.41E−04 | 1.10E−02 | 0.00 | 0.00 |
| 843 | chr11-34899 | 11 | 130368453 | 130368752 | −21.20 | −2.23 | 1.52E−04 | 1.17E−02 | 0.00 | 0.00 |
| 844 | chr8-24061 | 8 | 9792346 | 9792645 | −20.66 | −1.97 | 1.53E−04 | 1.18E−02 | 0.00 | 1.00 |
| 845 | chr20-8094 | 20 | 29283035 | 29283661 | −15.86 | −1.30 | 1.70E−04 | 1.29E−02 | 0.00 | 0.00 |
| 846 | chr10-25783 | 10 | 38849376 | 38849756 | −16.32 | −1.33 | 1.84E−04 | 1.38E−02 | 0.00 | 0.00 |
| 847 | chr12-12927 | 12 | 5712122 | 5712421 | −19.61 | −1.62 | 2.09E−04 | 1.54E−02 | 0.00 | 0.00 |
| 848 | chr20-10013 | 20 | 59441617 | 59441916 | −19.82 | −1.66 | 3.14E−04 | 2.15E−02 | 0.00 | 0.00 |
| 849 | chr10-30301 | 10 | 38910740 | 38911411 | −15.69 | −1.24 | 3.35E−04 | 2.27E−02 | 0.00 | 0.00 |
| 850 | chr8-20311 | 8 | 23530788 | 23531087 | −19.76 | −1.61 | 3.66E−04 | 2.43E−02 | 0.00 | 0.00 |
| 851 | chr4-23273 | 4 | 23439030 | 23439329 | −19.78 | −1.60 | 3.94E−04 | 2.58E−02 | 0.00 | 0.00 |
| 852 | chr5-29351 | 5 | 68374685 | 68374984 | −21.95 | −2.87 | 4.40E−04 | 2.83E−02 | 0.00 | 0.00 |
| 853 | chr5-18842 | 5 | 54562689 | 54563650 | −19.70 | −1.69 | 4.53E−04 | 2.89E−02 | 0.46 | 0.54 |
| 854 | chr8-2027 | 8 | 4517707 | 4518006 | −17.81 | −1.31 | 4.67E−04 | 2.96E−02 | 0.00 | 0.00 |
| 855 | chr17-27731 | 17 | 10433681 | 10433980 | −20.21 | −1.83 | 4.99E−04 | 3.12E−02 | 0.00 | 0.00 |

TABLE 1-continued

Differentially methylated regions (DMRs) associated breast cancer.

| | | | | | | | | | |
|---|---|---|---|---|---|---|---|---|---|
| 856 | chr16-37866 | 16 | 6632034 | 6632333 | −22.22 | −2.79 | 5.05E-04 | 3.15E-02 | 0.00 | 0.00 |
| 857 | chr14-12411 | 14 | 75867409 | 75867708 | −20.27 | −1.60 | 5.42E-04 | 3.34E-02 | 0.00 | 0.00 |
| 858 | chr8-21088 | 8 | 2800314 | 2800783 | −19.01 | −1.38 | 6.66E-04 | 3.96E-02 | 0.00 | 0.00 |
| 859 | chr21-14737 | 21 | 35345487 | 35345786 | −20.00 | −1.52 | 7.59E-04 | 4.42E-02 | 0.00 | 0.00 |
| 860 | chr11-10804 | 11 | 258741 | 259538 | −19.18 | −1.38 | 8.00E-04 | 4.61E-02 | 0.00 | 0.00 |
| 861 | chr6-18690 | 6 | 137778131 | 137778782 | −19.99 | −1.65 | 8.05E-04 | 4.64E-02 | 0.00 | 0.00 |
| 862 | chr12-25577 | 12 | 130026153 | 130026452 | −19.25 | −1.41 | 8.30E-04 | 4.74E-02 | 0.00 | 0.00 |
| 863 | chr8-26072 | 8 | 10928026 | 10928325 | −18.71 | −1.29 | 8.71E-04 | 4.92E-02 | 0.00 | 0.00 |
| 864 | chr12-16106 | 12 | 129620053 | 129620352 | −20.46 | −1.81 | 8.80E-04 | 4.96E-02 | 0.00 | 0.00 |
| 865 | chr2-27025 | 2 | 2494857 | 2495156 | −20.40 | −1.70 | 8.80E-04 | 4.96E-02 | 0.00 | 0.00 |

| Row No. | RefSeq: % promoter | RefSeq: % exon | RefSeq: % intron | RefSeq: % intergenic | ChromHMM HMEC: % promoter | ChromHMM HMEC: % enhancer | ChromHMM HMEC: % insulator | ChromHMM HMEC: % polycomb | HM450K: number of probes |
|---|---|---|---|---|---|---|---|---|---|
| 1 | 1.00 | 0.00 | 0.00 | 0.00 | 1.00 | 0.00 | 0.00 | 0.00 | 2 |
| 2 | 0.91 | 0.00 | 0.00 | 0.09 | 0.84 | 0.00 | 0.03 | 0.13 | 8 |
| 3 | 0.81 | 0.17 | 0.76 | 0.00 | 0.51 | 0.00 | 0.00 | 0.49 | 4 |
| 4 | 1.00 | 0.00 | 0.00 | 0.00 | 0.70 | 0.30 | 0.00 | 0.00 | 3 |
| 5 | 1.00 | 0.00 | 0.00 | 0.00 | 1.00 | 0.00 | 0.00 | 0.00 | 7 |
| 6 | 0.88 | 0.77 | 0.83 | 0.00 | 0.69 | 0.31 | 0.00 | 0.00 | 13 |
| 7 | 0.00 | 0.32 | 1.00 | 0.00 | 0.91 | 0.09 | 0.00 | 0.00 | 46 |
| 8 | 0.05 | 0.05 | 0.95 | 0.00 | 1.00 | 0.00 | 0.00 | 0.00 | 3 |
| 9 | 1.00 | 0.00 | 0.00 | 0.00 | 0.00 | 0.00 | 0.00 | 1.00 | 4 |
| 10 | 0.62 | 0.32 | 0.12 | 0.00 | 0.55 | 0.45 | 0.00 | 0.00 | 15 |
| 11 | 0.45 | 0.31 | 0.34 | 0.00 | 0.86 | 0.00 | 0.00 | 0.00 | 5 |
| 12 | 0.00 | 0.00 | 0.00 | 1.00 | 0.43 | 0.00 | 0.00 | 0.57 | 3 |
| 13 | 0.33 | 0.12 | 0.64 | 0.00 | 0.73 | 0.27 | 0.00 | 0.00 | 13 |
| 14 | 0.25 | 0.32 | 0.51 | 0.00 | 1.00 | 0.00 | 0.00 | 0.00 | 12 |
| 15 | 0.78 | 0.29 | 0.00 | 0.00 | 0.54 | 0.00 | 0.00 | 0.46 | 27 |
| 16 | 0.32 | 0.00 | 0.00 | 0.68 | 0.67 | 0.33 | 0.00 | 0.00 | 4 |
| 17 | 0.00 | 0.34 | 1.00 | 0.00 | 1.00 | 0.00 | 0.00 | 0.00 | 3 |
| 18 | 0.64 | 0.16 | 0.19 | 0.04 | 0.54 | 0.00 | 0.00 | 0.46 | 20 |
| 19 | 1.00 | 0.00 | 0.00 | 0.00 | 0.00 | 0.00 | 0.00 | 1.00 | 24 |
| 20 | 0.00 | 0.00 | 0.00 | 1.00 | 0.87 | 0.00 | 0.00 | 0.13 | 7 |
| 21 | 0.00 | 0.00 | 1.00 | 0.00 | 1.00 | 0.00 | 0.00 | 0.00 | 2 |
| 22 | 0.03 | 0.12 | 0.88 | 0.00 | 1.00 | 0.00 | 0.00 | 0.00 | 2 |
| 23 | 0.00 | 0.00 | 1.00 | 0.00 | 0.00 | 0.00 | 0.00 | 0.00 | 2 |
| 24 | 0.24 | 0.55 | 0.50 | 0.00 | 0.47 | 0.00 | 0.00 | 0.53 | 18 |
| 25 | 0.41 | 0.79 | 0.00 | 0.00 | 1.00 | 0.00 | 0.00 | 0.00 | 3 |
| 26 | 0.05 | 0.14 | 0.96 | 0.00 | 0.84 | 0.00 | 0.00 | 0.16 | 8 |
| 27 | 0.47 | 0.00 | 0.00 | 0.53 | 0.32 | 0.00 | 0.00 | 0.68 | 8 |
| 28 | 0.23 | 0.58 | 0.08 | 0.00 | 0.37 | 0.00 | 0.00 | 0.63 | 14 |
| 29 | 0.00 | 0.00 | 0.00 | 1.00 | 0.00 | 0.00 | 0.00 | 1.00 | 4 |
| 30 | 0.26 | 0.24 | 0.57 | 0.00 | 0.97 | 0.00 | 0.00 | 0.03 | 11 |
| 31 | 0.00 | 0.00 | 0.00 | 1.00 | 1.00 | 0.00 | 0.00 | 0.00 | 4 |
| 32 | 0.23 | 0.05 | 0.79 | 0.00 | 0.82 | 0.00 | 0.18 | 0.00 | 10 |
| 33 | 0.00 | 0.13 | 0.87 | 0.00 | 0.34 | 0.00 | 0.00 | 0.66 | 6 |
| 34 | 0.91 | 0.05 | 1.00 | 0.00 | 0.94 | 0.05 | 0.00 | 0.02 | 11 |
| 35 | 0.89 | 0.19 | 1.00 | 0.00 | 0.95 | 0.00 | 0.00 | 0.05 | 6 |
| 36 | 1.00 | 0.00 | 0.00 | 0.00 | 1.00 | 0.00 | 0.00 | 0.00 | 4 |
| 37 | 0.00 | 0.20 | 0.31 | 0.00 | 0.23 | 0.00 | 0.00 | 0.77 | 4 |
| 38 | 0.00 | 0.00 | 0.00 | 1.00 | 0.00 | 1.00 | 0.00 | 0.00 | 5 |
| 39 | 0.00 | 0.00 | 1.00 | 0.00 | 0.96 | 0.00 | 0.00 | 0.04 | 4 |
| 40 | 1.00 | 0.27 | 0.64 | 0.00 | 0.00 | 0.00 | 0.00 | 1.00 | 6 |
| 41 | 0.00 | 0.29 | 0.71 | 0.00 | 1.00 | 0.00 | 0.00 | 0.00 | 3 |
| 42 | 0.00 | 0.41 | 0.59 | 0.00 | 0.37 | 0.00 | 0.00 | 0.63 | 10 |
| 43 | 0.00 | 0.31 | 0.00 | 0.00 | 0.00 | 0.00 | 0.00 | 1.00 | 5 |
| 44 | 0.00 | 0.00 | 0.00 | 1.00 | 1.00 | 0.00 | 0.00 | 0.00 | 7 |
| 45 | 0.73 | 0.48 | 0.63 | 0.00 | 0.81 | 0.00 | 0.00 | 0.19 | 15 |
| 46 | 0.00 | 0.29 | 0.72 | 0.00 | 0.00 | 0.00 | 0.00 | 1.00 | 1 |
| 47 | 0.00 | 0.00 | 0.00 | 1.00 | 1.00 | 0.00 | 0.00 | 0.00 | 6 |
| 48 | 0.00 | 0.00 | 1.00 | 0.00 | 1.00 | 0.00 | 0.00 | 0.00 | 4 |
| 49 | 0.39 | 0.16 | 0.59 | 0.00 | 0.84 | 0.00 | 0.00 | 0.16 | 13 |
| 50 | 0.24 | 0.43 | 1.00 | 0.00 | 1.00 | 0.00 | 0.00 | 0.00 | 5 |
| 51 | 0.00 | 0.00 | 0.00 | 1.00 | 1.00 | 0.00 | 0.00 | 0.00 | 0 |
| 52 | 0.81 | 0.00 | 0.00 | 0.19 | 0.00 | 0.00 | 0.00 | 1.00 | 15 |
| 53 | 0.69 | 0.27 | 0.09 | 0.00 | 0.88 | 0.00 | 0.00 | 0.12 | 7 |
| 54 | 0.00 | 0.00 | 0.00 | 1.00 | 0.63 | 0.00 | 0.00 | 0.37 | 7 |
| 55 | 0.00 | 0.00 | 0.00 | 1.00 | 0.00 | 0.00 | 0.00 | 0.00 | 5 |
| 56 | 1.00 | 0.00 | 0.00 | 0.00 | 1.00 | 0.00 | 0.00 | 0.00 | 6 |
| 57 | 0.00 | 0.00 | 0.00 | 1.00 | 0.00 | 0.00 | 0.00 | 1.00 | 7 |
| 58 | 0.00 | 0.00 | 1.00 | 0.00 | 1.00 | 0.00 | 0.00 | 0.00 | 1 |
| 59 | 0.00 | 0.09 | 1.00 | 0.00 | 1.00 | 0.00 | 0.00 | 0.00 | 7 |
| 60 | 0.66 | 0.24 | 0.80 | 0.00 | 0.83 | 0.00 | 0.00 | 0.17 | 11 |
| 61 | 0.00 | 0.10 | 0.90 | 0.00 | 1.00 | 0.00 | 0.00 | 0.00 | 12 |
| 62 | 0.00 | 0.53 | 0.47 | 0.00 | 0.82 | 0.18 | 0.00 | 0.00 | 2 |
| 63 | 0.31 | 0.67 | 0.10 | 0.00 | 1.00 | 0.00 | 0.00 | 0.00 | 6 |

TABLE 1-continued

Differentially methylated regions (DMRs) associated breast cancer.

| | | | | | | | | | |
|---|---|---|---|---|---|---|---|---|---|
| 64 | 0.37 | 0.17 | 0.49 | 0.00 | 0.83 | 0.00 | 0.00 | 0.17 | 17 |
| 65 | 0.00 | 0.00 | 0.00 | 0.00 | 0.54 | 0.00 | 0.00 | 0.46 | 4 |
| 66 | 0.00 | 0.00 | 0.00 | 0.33 | 0.98 | 0.00 | 0.02 | 0.00 | 7 |
| 67 | 0.10 | 1.00 | 0.00 | 0.00 | 0.72 | 0.00 | 0.00 | 0.28 | 3 |
| 68 | 0.00 | 0.00 | 1.00 | 0.00 | 0.00 | 0.00 | 0.00 | 1.00 | 6 |
| 69 | 1.00 | 0.47 | 0.48 | 0.00 | 0.96 | 0.00 | 0.00 | 0.00 | 12 |
| 70 | 0.00 | 0.00 | 1.00 | 0.00 | 0.00 | 0.00 | 0.00 | 1.00 | 9 |
| 71 | 0.00 | 0.00 | 0.00 | 1.00 | 0.00 | 0.00 | 0.00 | 1.00 | 6 |
| 72 | 0.68 | 0.06 | 0.33 | 0.00 | 0.00 | 0.00 | 0.00 | 0.99 | 15 |
| 73 | 0.00 | 0.00 | 0.62 | 0.38 | 0.00 | 0.73 | 0.27 | 0.00 | 3 |
| 74 | 0.57 | 0.53 | 1.00 | 0.00 | 0.96 | 0.04 | 0.00 | 0.00 | 5 |
| 75 | 0.00 | 1.00 | 0.00 | 0.00 | 0.05 | 0.00 | 0.00 | 0.95 | 6 |
| 76 | 0.21 | 0.50 | 0.36 | 0.00 | 0.45 | 0.00 | 0.00 | 0.55 | 2 |
| 77 | 0.05 | 0.35 | 0.65 | 0.00 | 0.27 | 0.00 | 0.00 | 0.73 | 5 |
| 78 | 0.00 | 0.29 | 0.71 | 0.00 | 1.00 | 0.00 | 0.00 | 0.00 | 5 |
| 79 | 0.00 | 0.00 | 1.00 | 0.00 | 0.43 | 0.00 | 0.00 | 0.57 | 15 |
| 80 | 0.00 | 0.00 | 1.00 | 0.00 | 0.00 | 0.00 | 0.00 | 1.00 | 5 |
| 81 | 0.00 | 0.00 | 0.00 | 1.00 | 0.00 | 0.00 | 0.00 | 1.00 | 7 |
| 82 | 1.00 | 0.00 | 0.00 | 0.00 | 0.69 | 0.31 | 0.00 | 0.00 | 6 |
| 83 | 0.00 | 1.00 | 0.00 | 0.00 | 0.43 | 0.00 | 0.00 | 0.57 | 1 |
| 84 | 0.00 | 0.07 | 0.92 | 0.00 | 0.68 | 0.00 | 0.00 | 0.32 | 4 |
| 85 | 0.00 | 1.00 | 0.12 | 0.00 | 0.66 | 0.00 | 0.00 | 0.34 | 5 |
| 86 | 0.00 | 0.00 | 1.00 | 0.00 | 0.00 | 0.00 | 0.00 | 0.00 | 1 |
| 87 | 0.01 | 0.24 | 0.76 | 0.00 | 0.65 | 0.00 | 0.00 | 0.35 | 7 |
| 88 | 0.00 | 0.00 | 1.00 | 0.00 | 0.50 | 0.00 | 0.00 | 0.50 | 4 |
| 89 | 0.00 | 0.77 | 0.23 | 0.00 | 0.00 | 0.00 | 0.00 | 1.00 | 5 |
| 90 | 0.00 | 0.00 | 0.00 | 1.00 | 0.75 | 0.00 | 0.00 | 0.25 | 3 |
| 91 | 0.13 | 0.20 | 0.72 | 0.00 | 0.50 | 0.00 | 0.00 | 0.50 | 18 |
| 92 | 1.00 | 0.47 | 0.76 | 0.00 | 0.00 | 0.00 | 0.00 | 1.00 | 0 |
| 93 | 0.00 | 0.13 | 0.87 | 0.00 | 0.97 | 0.00 | 0.00 | 0.03 | 10 |
| 94 | 0.00 | 0.58 | 0.42 | 0.00 | 0.96 | 0.00 | 0.00 | 0.00 | 8 |
| 95 | 0.12 | 0.97 | 0.00 | 0.00 | 1.00 | 0.00 | 0.00 | 0.00 | 6 |
| 96 | 0.00 | 0.18 | 0.82 | 0.00 | 0.22 | 0.00 | 0.00 | 0.78 | 9 |
| 97 | 0.00 | 0.00 | 0.00 | 1.00 | 0.63 | 0.37 | 0.00 | 0.00 | 7 |
| 98 | 0.00 | 0.00 | 0.00 | 1.00 | 0.00 | 0.00 | 0.00 | 1.00 | 6 |
| 99 | 0.00 | 0.02 | 0.98 | 0.00 | 1.00 | 0.00 | 0.00 | 0.00 | 4 |
| 100 | 0.53 | 0.00 | 0.00 | 0.47 | 1.00 | 0.00 | 0.00 | 0.00 | 2 |
| 101 | 0.00 | 0.00 | 0.00 | 1.00 | 0.58 | 0.00 | 0.00 | 0.42 | 5 |
| 102 | 0.00 | 0.00 | 0.00 | 1.00 | 0.00 | 0.00 | 0.00 | 1.00 | 7 |
| 103 | 0.00 | 0.00 | 0.00 | 1.00 | 0.48 | 0.00 | 0.00 | 0.52 | 5 |
| 104 | 0.00 | 0.00 | 0.00 | 1.00 | 0.82 | 0.00 | 0.00 | 0.18 | 3 |
| 105 | 0.00 | 0.00 | 0.00 | 1.00 | 0.00 | 1.00 | 0.00 | 0.00 | 6 |
| 106 | 0.93 | 0.13 | 0.00 | 0.00 | 0.00 | 0.00 | 0.00 | 1.00 | 13 |
| 107 | 0.00 | 0.00 | 0.00 | 1.00 | 0.00 | 0.00 | 0.00 | 1.00 | 13 |
| 108 | 0.28 | 0.43 | 0.47 | 0.00 | 1.00 | 0.00 | 0.00 | 0.00 | 5 |
| 109 | 0.74 | 0.33 | 0.00 | 0.00 | 1.00 | 0.00 | 0.00 | 0.00 | 13 |
| 110 | 0.00 | 0.00 | 0.00 | 1.00 | 0.00 | 0.00 | 0.00 | 1.00 | 4 |
| 111 | 0.00 | 0.00 | 1.00 | 0.00 | 0.00 | 0.00 | 0.00 | 1.00 | 2 |
| 112 | 0.00 | 0.35 | 0.65 | 0.00 | 0.00 | 0.00 | 0.00 | 1.00 | 8 |
| 113 | 0.00 | 0.41 | 0.58 | 0.00 | 0.00 | 0.00 | 0.00 | 1.00 | 4 |
| 114 | 0.03 | 0.15 | 0.85 | 0.00 | 0.24 | 0.00 | 0.00 | 0.76 | 16 |
| 115 | 0.00 | 0.00 | 0.00 | 0.14 | 0.58 | 0.00 | 0.00 | 0.42 | 4 |
| 116 | 0.22 | 0.92 | 0.00 | 0.00 | 0.78 | 0.00 | 0.00 | 0.22 | 6 |
| 117 | 0.30 | 0.44 | 1.00 | 0.00 | 0.71 | 0.00 | 0.00 | 0.29 | 8 |
| 118 | 0.00 | 0.00 | 0.00 | 1.00 | 1.00 | 0.00 | 0.00 | 0.00 | 3 |
| 119 | 0.49 | 0.36 | 0.20 | 0.00 | 0.00 | 0.00 | 0.00 | 1.00 | 10 |
| 120 | 0.07 | 0.14 | 0.86 | 0.00 | 0.24 | 0.00 | 0.00 | 0.76 | 5 |
| 121 | 0.00 | 0.42 | 0.58 | 0.00 | 0.83 | 0.00 | 0.00 | 0.17 | 6 |
| 122 | 0.00 | 0.04 | 0.96 | 0.00 | 0.00 | 0.00 | 0.00 | 1.00 | 3 |
| 123 | 0.00 | 0.52 | 0.27 | 0.00 | 0.45 | 0.00 | 0.00 | 0.55 | 12 |
| 124 | 0.34 | 0.30 | 0.13 | 0.25 | 0.00 | 0.00 | 0.00 | 1.00 | 28 |
| 125 | 0.00 | 0.00 | 0.00 | 1.00 | 0.96 | 0.00 | 0.00 | 0.04 | 8 |
| 126 | 0.00 | 0.41 | 0.58 | 0.00 | 0.46 | 0.00 | 0.00 | 0.54 | 7 |
| 127 | 0.34 | 0.20 | 0.62 | 0.00 | 1.00 | 0.00 | 0.00 | 0.00 | 6 |
| 128 | 0.00 | 1.00 | 0.00 | 0.00 | 0.00 | 0.00 | 0.00 | 1.00 | 1 |
| 129 | 0.00 | 0.00 | 0.00 | 1.00 | 0.26 | 0.69 | 0.00 | 0.00 | 8 |
| 130 | 0.47 | 0.19 | 1.00 | 0.00 | 0.25 | 0.75 | 0.00 | 0.00 | 4 |
| 131 | 0.47 | 0.29 | 0.28 | 0.00 | 0.52 | 0.00 | 0.00 | 0.48 | 8 |
| 132 | 1.00 | 0.00 | 0.00 | 0.00 | 0.00 | 0.00 | 0.00 | 1.00 | 7 |
| 133 | 0.46 | 0.00 | 0.00 | 0.54 | 0.64 | 0.00 | 0.00 | 0.36 | 5 |
| 134 | 0.00 | 0.00 | 0.00 | 1.00 | 0.96 | 0.04 | 0.00 | 0.00 | 1 |
| 135 | 0.00 | 0.24 | 0.76 | 0.00 | 0.00 | 0.00 | 0.00 | 0.00 | 5 |
| 136 | 0.00 | 0.00 | 0.00 | 1.00 | 0.72 | 0.00 | 0.00 | 0.28 | 3 |
| 137 | 0.00 | 0.78 | 0.22 | 0.00 | 0.75 | 0.00 | 0.00 | 0.25 | 9 |
| 138 | 0.36 | 0.37 | 0.36 | 0.00 | 1.00 | 0.00 | 0.00 | 0.00 | 13 |
| 139 | 1.00 | 0.00 | 0.00 | 0.00 | 0.62 | 0.00 | 0.00 | 0.38 | 7 |
| 140 | 0.03 | 0.26 | 0.74 | 0.00 | 0.00 | 0.00 | 0.00 | 1.00 | 9 |
| 141 | 0.16 | 0.27 | 0.64 | 0.00 | 1.00 | 0.00 | 0.00 | 0.00 | 5 |

TABLE 1-continued

Differentially methylated regions (DMRs) associated breast cancer.

| | | | | | | | | | |
|---|---|---|---|---|---|---|---|---|---|
| 142 | 0.00 | 0.00 | 1.00 | 0.00 | 0.00 | 0.00 | 0.00 | 1.00 | 2 |
| 143 | 0.00 | 0.00 | 0.00 | 1.00 | 0.00 | 0.00 | 0.00 | 1.00 | 2 |
| 144 | 0.00 | 0.00 | 0.00 | 1.00 | 0.58 | 0.00 | 0.00 | 0.42 | 8 |
| 145 | 0.00 | 0.00 | 0.00 | 0.00 | 0.00 | 0.00 | 0.00 | 1.00 | 5 |
| 146 | 0.22 | 0.32 | 0.53 | 0.00 | 1.00 | 0.00 | 0.00 | 0.00 | 12 |
| 147 | 0.00 | 0.44 | 1.00 | 0.00 | 0.67 | 0.00 | 0.00 | 0.33 | 6 |
| 148 | 0.22 | 0.08 | 0.00 | 0.00 | 0.00 | 0.00 | 0.00 | 1.00 | 11 |
| 149 | 0.00 | 0.68 | 1.00 | 0.00 | 0.00 | 1.00 | 0.00 | 0.00 | 4 |
| 150 | 0.00 | 0.00 | 0.00 | 0.00 | 0.63 | 0.00 | 0.00 | 0.37 | 8 |
| 151 | 0.34 | 0.26 | 0.57 | 0.00 | 0.00 | 0.00 | 0.00 | 0.00 | 6 |
| 152 | 0.62 | 0.48 | 0.00 | 0.00 | 0.98 | 0.02 | 0.00 | 0.00 | 24 |
| 153 | 0.00 | 0.00 | 0.00 | 1.00 | 0.15 | 0.85 | 0.00 | 0.00 | 3 |
| 154 | 0.10 | 0.28 | 0.66 | 0.00 | 0.44 | 0.00 | 0.00 | 0.56 | 19 |
| 155 | 0.00 | 0.91 | 0.04 | 0.00 | 0.80 | 0.20 | 0.00 | 0.00 | 8 |
| 156 | 0.99 | 0.07 | 0.05 | 0.00 | 0.72 | 0.21 | 0.00 | 0.00 | 7 |
| 157 | 0.00 | 0.00 | 0.00 | 1.00 | 0.00 | 0.00 | 0.00 | 1.00 | 4 |
| 158 | 0.00 | 0.59 | 0.40 | 0.00 | 1.00 | 0.00 | 0.00 | 0.00 | 2 |
| 159 | 0.59 | 0.19 | 0.33 | 0.00 | 0.87 | 0.00 | 0.00 | 0.13 | 14 |
| 160 | 1.00 | 0.00 | 0.00 | 0.00 | 0.05 | 0.95 | 0.00 | 0.00 | 6 |
| 161 | 0.15 | 0.06 | 0.94 | 0.00 | 0.04 | 0.00 | 0.00 | 0.96 | 4 |
| 162 | 1.00 | 0.00 | 0.00 | 0.00 | 0.00 | 0.00 | 0.00 | 0.00 | 5 |
| 163 | 1.00 | 0.00 | 0.00 | 0.00 | 1.00 | 0.00 | 0.00 | 0.00 | 2 |
| 164 | 0.00 | 0.00 | 0.00 | 1.00 | 0.66 | 0.00 | 0.00 | 0.34 | 5 |
| 165 | 0.00 | 0.00 | 0.00 | 1.00 | 0.00 | 0.00 | 0.00 | 1.00 | 3 |
| 166 | 0.00 | 1.00 | 0.00 | 0.00 | 1.00 | 0.00 | 0.00 | 0.00 | 2 |
| 167 | 0.34 | 0.40 | 0.35 | 0.00 | 0.82 | 0.00 | 0.00 | 0.18 | 9 |
| 168 | 0.51 | 0.70 | 0.38 | 0.00 | 1.00 | 0.00 | 0.00 | 0.00 | 6 |
| 169 | 0.00 | 0.00 | 0.00 | 1.00 | 0.72 | 0.19 | 0.00 | 0.00 | 6 |
| 170 | 0.31 | 0.15 | 0.60 | 0.00 | 0.89 | 0.00 | 0.00 | 0.11 | 6 |
| 171 | 0.00 | 0.00 | 0.00 | 1.00 | 0.37 | 0.18 | 0.00 | 0.00 | 8 |
| 172 | 0.00 | 0.00 | 0.00 | 1.00 | 0.84 | 0.00 | 0.00 | 0.16 | 1 |
| 173 | 0.00 | 0.00 | 0.00 | 0.62 | 0.84 | 0.16 | 0.00 | 0.00 | 7 |
| 174 | 0.49 | 0.35 | 0.22 | 0.00 | 0.56 | 0.00 | 0.00 | 0.44 | 10 |
| 175 | 0.00 | 0.00 | 1.00 | 0.00 | 0.89 | 0.00 | 0.00 | 0.11 | 4 |
| 176 | 0.00 | 0.00 | 0.00 | 1.00 | 0.00 | 0.00 | 0.00 | 0.00 | 4 |
| 177 | 0.11 | 0.60 | 0.35 | 0.00 | 0.36 | 0.00 | 0.00 | 0.64 | 11 |
| 178 | 1.00 | 0.00 | 0.00 | 0.00 | 0.76 | 0.00 | 0.00 | 0.24 | 9 |
| 179 | 0.66 | 0.00 | 1.00 | 0.00 | 0.63 | 0.00 | 0.00 | 0.37 | 6 |
| 180 | 0.00 | 0.00 | 1.00 | 0.00 | 0.00 | 0.00 | 0.00 | 1.00 | 2 |
| 181 | 0.00 | 0.75 | 0.24 | 0.00 | 0.75 | 0.25 | 0.00 | 0.00 | 2 |
| 182 | 0.00 | 0.00 | 0.00 | 1.00 | 0.76 | 0.00 | 0.00 | 0.24 | 7 |
| 183 | 0.00 | 0.00 | 1.00 | 0.00 | 0.41 | 0.00 | 0.00 | 0.59 | 10 |
| 184 | 0.40 | 0.00 | 0.00 | 0.60 | 0.11 | 0.00 | 0.00 | 0.89 | 20 |
| 185 | 1.00 | 0.16 | 0.84 | 0.00 | 1.00 | 0.00 | 0.00 | 0.00 | 5 |
| 186 | 0.00 | 0.00 | 1.00 | 0.00 | 1.00 | 0.00 | 0.00 | 0.00 | 3 |
| 187 | 0.39 | 0.71 | 1.00 | 0.00 | 1.00 | 0.00 | 0.00 | 0.00 | 14 |
| 188 | 0.00 | 0.52 | 0.48 | 0.00 | 0.41 | 0.00 | 0.00 | 0.59 | 3 |
| 189 | 0.00 | 0.00 | 1.00 | 0.00 | 1.00 | 0.00 | 0.00 | 0.00 | 5 |
| 190 | 0.48 | 0.09 | 0.88 | 0.00 | 0.95 | 0.00 | 0.00 | 0.05 | 9 |
| 191 | 0.00 | 0.00 | 0.00 | 1.00 | 0.00 | 0.00 | 0.00 | 1.00 | 2 |
| 192 | 0.00 | 0.00 | 0.00 | 1.00 | 1.00 | 0.00 | 0.00 | 0.00 | 3 |
| 193 | 0.00 | 0.00 | 0.00 | 1.00 | 0.82 | 0.18 | 0.00 | 0.00 | 3 |
| 194 | 0.00 | 0.15 | 0.85 | 0.00 | 0.76 | 0.00 | 0.00 | 0.24 | 2 |
| 195 | 1.00 | 0.16 | 0.24 | 0.00 | 1.00 | 0.00 | 0.00 | 0.00 | 6 |
| 196 | 0.27 | 0.68 | 0.11 | 0.00 | 0.93 | 0.00 | 0.00 | 0.07 | 15 |
| 197 | 0.72 | 0.32 | 0.00 | 0.00 | 0.35 | 0.00 | 0.00 | 0.65 | 16 |
| 198 | 0.68 | 0.15 | 0.92 | 0.00 | 0.87 | 0.00 | 0.00 | 0.13 | 4 |
| 199 | 0.00 | 0.25 | 0.75 | 0.00 | 0.91 | 0.00 | 0.00 | 0.09 | 5 |
| 200 | 0.86 | 0.11 | 0.07 | 0.00 | 0.49 | 0.00 | 0.00 | 0.51 | 14 |
| 201 | 0.90 | 0.12 | 0.05 | 0.00 | 0.66 | 0.00 | 0.00 | 0.34 | 11 |
| 202 | 0.00 | 0.00 | 1.00 | 0.00 | 0.00 | 0.00 | 0.00 | 1.00 | 0 |
| 203 | 0.10 | 0.18 | 0.78 | 0.00 | 0.48 | 0.00 | 0.00 | 0.52 | 10 |
| 204 | 0.49 | 0.23 | 0.42 | 0.00 | 0.50 | 0.50 | 0.00 | 0.00 | 10 |
| 205 | 0.89 | 0.12 | 0.09 | 0.00 | 0.00 | 0.89 | 0.00 | 0.00 | 12 |
| 206 | 1.00 | 0.00 | 0.00 | 0.00 | 0.35 | 0.00 | 0.00 | 0.65 | 3 |
| 207 | 1.00 | 0.30 | 0.70 | 0.00 | 1.00 | 0.00 | 0.00 | 0.00 | 2 |
| 208 | 0.00 | 0.00 | 1.00 | 0.00 | 0.00 | 0.00 | 0.00 | 1.00 | 8 |
| 209 | 0.00 | 0.00 | 0.00 | 0.61 | 0.00 | 0.00 | 0.00 | 1.00 | 6 |
| 210 | 0.30 | 0.15 | 0.61 | 0.00 | 0.95 | 0.05 | 0.00 | 0.00 | 3 |
| 211 | 0.00 | 0.00 | 0.00 | 1.00 | 0.00 | 0.00 | 0.00 | 0.00 | 2 |
| 212 | 0.00 | 0.00 | 1.00 | 0.00 | 0.00 | 0.72 | 0.00 | 0.28 | 2 |
| 213 | 0.65 | 0.15 | 0.29 | 0.00 | 0.72 | 0.00 | 0.00 | 0.28 | 13 |
| 214 | 0.00 | 0.00 | 0.00 | 1.00 | 0.00 | 0.00 | 0.00 | 1.00 | 5 |
| 215 | 0.59 | 0.46 | 0.00 | 0.00 | 1.00 | 0.00 | 0.00 | 0.00 | 12 |
| 216 | 1.00 | 0.48 | 0.14 | 0.00 | 0.90 | 0.10 | 0.00 | 0.00 | 29 |
| 217 | 0.36 | 0.28 | 0.42 | 0.00 | 0.39 | 0.00 | 0.00 | 0.61 | 13 |
| 218 | 0.64 | 0.34 | 0.08 | 0.00 | 0.96 | 0.00 | 0.00 | 0.04 | 11 |
| 219 | 0.00 | 0.00 | 0.00 | 0.00 | 0.00 | 0.00 | 0.00 | 1.00 | 1 |

TABLE 1-continued

Differentially methylated regions (DMRs) associated breast cancer.

| | | | | | | | | | |
|---|---|---|---|---|---|---|---|---|---|
| 220 | 0.25 | 0.36 | 0.43 | 0.00 | 0.00 | 0.00 | 0.00 | 1.00 | 11 |
| 221 | 1.00 | 0.00 | 1.00 | 0.00 | 1.00 | 0.00 | 0.00 | 0.00 | 3 |
| 222 | 0.00 | 0.55 | 0.45 | 0.00 | 0.98 | 0.00 | 0.00 | 0.02 | 5 |
| 223 | 0.00 | 0.00 | 0.00 | 1.00 | 0.32 | 0.00 | 0.00 | 0.68 | 5 |
| 224 | 0.18 | 0.43 | 1.00 | 0.00 | 0.00 | 0.00 | 0.00 | 1.00 | 3 |
| 225 | 0.68 | 0.06 | 0.40 | 0.00 | 0.97 | 0.03 | 0.00 | 0.00 | 9 |
| 226 | 0.00 | 0.00 | 0.00 | 1.00 | 0.49 | 0.00 | 0.00 | 0.51 | 3 |
| 227 | 0.00 | 0.00 | 0.00 | 1.00 | 1.00 | 0.00 | 0.00 | 0.00 | 4 |
| 228 | 0.00 | 0.00 | 1.00 | 0.00 | 0.00 | 0.00 | 0.00 | 1.00 | 4 |
| 229 | 0.42 | 0.19 | 0.41 | 0.00 | 0.00 | 0.00 | 0.00 | 1.00 | 21 |
| 230 | 0.00 | 0.48 | 0.52 | 0.00 | 0.34 | 0.00 | 0.00 | 0.66 | 7 |
| 231 | 0.00 | 0.00 | 0.00 | 1.00 | 0.00 | 0.00 | 0.00 | 1.00 | 10 |
| 232 | 1.00 | 0.00 | 0.00 | 0.00 | 1.00 | 0.00 | 0.00 | 0.00 | 2 |
| 233 | 0.63 | 0.34 | 0.71 | 0.00 | 0.63 | 0.00 | 0.00 | 0.37 | 12 |
| 234 | 0.00 | 0.00 | 1.00 | 0.00 | 0.84 | 0.00 | 0.00 | 0.16 | 5 |
| 235 | 0.94 | 0.21 | 0.00 | 0.00 | 0.97 | 0.03 | 0.00 | 0.00 | 5 |
| 236 | 1.00 | 0.00 | 0.00 | 0.00 | 0.00 | 0.00 | 0.00 | 1.00 | 6 |
| 237 | 0.00 | 0.00 | 0.00 | 1.00 | 0.00 | 0.00 | 0.00 | 1.00 | 1 |
| 238 | 0.13 | 0.47 | 0.48 | 0.00 | 0.42 | 0.00 | 0.00 | 0.58 | 4 |
| 239 | 0.00 | 0.59 | 0.41 | 0.00 | 1.00 | 0.00 | 0.00 | 0.00 | 9 |
| 240 | 0.00 | 0.00 | 0.00 | 1.00 | 1.00 | 0.00 | 0.00 | 0.00 | 3 |
| 241 | 0.00 | 0.00 | 0.00 | 1.00 | 0.63 | 0.00 | 0.00 | 0.37 | 12 |
| 242 | 0.00 | 0.00 | 1.00 | 0.00 | 0.00 | 1.00 | 0.00 | 0.00 | 2 |
| 243 | 0.82 | 0.24 | 0.00 | 0.00 | 0.91 | 0.00 | 0.00 | 0.09 | 6 |
| 244 | 0.53 | 0.63 | 0.57 | 0.00 | 0.19 | 0.00 | 0.00 | 0.81 | 14 |
| 245 | 0.00 | 0.73 | 0.26 | 0.00 | 0.58 | 0.42 | 0.00 | 0.00 | 4 |
| 246 | 0.77 | 0.19 | 1.00 | 0.00 | 1.00 | 0.00 | 0.00 | 0.00 | 6 |
| 247 | 1.00 | 0.00 | 0.00 | 0.00 | 0.99 | 0.01 | 0.00 | 0.00 | 3 |
| 248 | 0.11 | 0.49 | 0.51 | 0.00 | 0.00 | 0.00 | 0.00 | 1.00 | 6 |
| 249 | 0.00 | 0.00 | 0.00 | 0.88 | 0.00 | 0.00 | 0.00 | 1.00 | 3 |
| 250 | 0.00 | 0.00 | 0.00 | 1.00 | 0.00 | 0.00 | 0.00 | 1.00 | 2 |
| 251 | 0.00 | 0.00 | 1.00 | 0.00 | 0.37 | 0.00 | 0.00 | 0.63 | 18 |
| 252 | 0.00 | 0.00 | 0.00 | 1.00 | 0.76 | 0.00 | 0.00 | 0.24 | 8 |
| 253 | 0.00 | 0.00 | 0.00 | 1.00 | 0.77 | 0.00 | 0.00 | 0.23 | 21 |
| 254 | 0.00 | 0.50 | 0.50 | 0.00 | 0.00 | 0.00 | 0.00 | 1.00 | 2 |
| 255 | 0.00 | 0.32 | 0.68 | 0.00 | 0.31 | 0.00 | 0.00 | 0.69 | 4 |
| 256 | 0.56 | 0.40 | 0.15 | 0.00 | 0.82 | 0.00 | 0.00 | 0.18 | 2 |
| 257 | 0.00 | 0.00 | 1.00 | 0.00 | 0.45 | 0.00 | 0.00 | 0.55 | 15 |
| 258 | 0.52 | 0.40 | 0.11 | 0.00 | 0.99 | 0.00 | 0.00 | 0.01 | 13 |
| 259 | 0.58 | 0.00 | 0.00 | 0.42 | 0.00 | 0.00 | 0.00 | 1.00 | 9 |
| 260 | 0.00 | 0.00 | 0.00 | 1.00 | 0.00 | 0.00 | 0.00 | 1.00 | 1 |
| 261 | 0.36 | 0.29 | 0.38 | 0.00 | 0.97 | 0.03 | 0.00 | 0.00 | 14 |
| 262 | 0.00 | 0.00 | 0.00 | 1.00 | 0.00 | 0.00 | 0.00 | 1.00 | 3 |
| 263 | 0.00 | 0.00 | 0.00 | 1.00 | 0.00 | 0.00 | 0.00 | 1.00 | 6 |
| 264 | 0.00 | 0.00 | 1.00 | 0.00 | 0.64 | 0.00 | 0.00 | 0.36 | 2 |
| 265 | 1.00 | 0.00 | 0.00 | 0.00 | 0.80 | 0.00 | 0.00 | 0.20 | 3 |
| 266 | 0.40 | 0.00 | 0.00 | 0.60 | 0.00 | 0.00 | 0.00 | 1.00 | 2 |
| 267 | 0.33 | 0.50 | 0.00 | 0.00 | 0.00 | 0.00 | 0.00 | 1.00 | 10 |
| 268 | 0.00 | 0.00 | 0.00 | 1.00 | 0.00 | 0.00 | 0.00 | 0.75 | 2 |
| 269 | 0.00 | 0.27 | 0.72 | 0.00 | 0.58 | 0.00 | 0.00 | 0.42 | 3 |
| 270 | 0.44 | 0.39 | 0.49 | 0.00 | 1.00 | 0.00 | 0.00 | 0.00 | 1 |
| 271 | 0.00 | 0.00 | 0.00 | 1.00 | 0.00 | 0.00 | 0.00 | 1.00 | 11 |
| 272 | 0.07 | 0.10 | 0.88 | 0.00 | 0.27 | 0.00 | 0.00 | 0.73 | 11 |
| 273 | 0.52 | 0.27 | 0.38 | 0.00 | 0.98 | 0.02 | 0.00 | 0.00 | 7 |
| 274 | 0.14 | 0.31 | 0.62 | 0.00 | 0.16 | 0.00 | 0.00 | 0.84 | 5 |
| 275 | 0.13 | 0.16 | 0.84 | 0.00 | 1.00 | 0.00 | 0.00 | 0.00 | 5 |
| 276 | 1.00 | 0.77 | 0.23 | 0.00 | 0.00 | 0.00 | 0.00 | 1.00 | 3 |
| 277 | 0.00 | 0.00 | 1.00 | 0.00 | 0.00 | 0.00 | 0.00 | 0.00 | 3 |
| 278 | 0.35 | 0.14 | 1.00 | 0.00 | 0.35 | 0.00 | 0.00 | 0.65 | 7 |
| 279 | 0.74 | 0.33 | 1.00 | 0.00 | 0.00 | 0.00 | 0.00 | 0.98 | 3 |
| 280 | 0.00 | 0.48 | 0.46 | 0.00 | 0.19 | 0.00 | 0.00 | 0.81 | 13 |
| 281 | 1.00 | 0.38 | 0.69 | 0.00 | 0.00 | 0.00 | 0.00 | 1.00 | 8 |
| 282 | 0.00 | 0.00 | 1.00 | 0.00 | 0.99 | 0.00 | 0.00 | 0.01 | 7 |
| 283 | 0.00 | 0.18 | 0.82 | 0.00 | 0.00 | 0.00 | 0.00 | 1.00 | 5 |
| 284 | 0.00 | 0.00 | 0.00 | 1.00 | 0.68 | 0.00 | 0.00 | 0.32 | 3 |
| 285 | 0.00 | 0.00 | 0.00 | 1.00 | 0.00 | 0.00 | 0.00 | 1.00 | 9 |
| 286 | 0.49 | 0.33 | 1.00 | 0.00 | 1.00 | 0.00 | 0.00 | 0.00 | 12 |
| 287 | 0.00 | 0.26 | 0.74 | 0.00 | 0.13 | 0.00 | 0.00 | 0.87 | 9 |
| 288 | 0.42 | 0.83 | 0.00 | 0.00 | 0.00 | 0.00 | 0.00 | 1.00 | 3 |
| 289 | 0.00 | 0.56 | 0.44 | 0.00 | 0.00 | 0.00 | 0.00 | 1.00 | 4 |
| 290 | 0.00 | 0.00 | 0.00 | 1.00 | 0.10 | 0.00 | 0.00 | 0.90 | 6 |
| 291 | 0.00 | 0.34 | 0.65 | 0.00 | 1.00 | 0.00 | 0.00 | 0.00 | 9 |
| 292 | 1.00 | 0.59 | 0.00 | 0.00 | 1.00 | 0.00 | 0.00 | 0.00 | 14 |
| 293 | 0.00 | 0.00 | 0.00 | 1.00 | 1.00 | 0.00 | 0.00 | 0.00 | 9 |
| 294 | 0.46 | 0.09 | 0.60 | 0.00 | 1.00 | 0.00 | 0.00 | 0.00 | 9 |
| 295 | 0.00 | 0.00 | 0.00 | 1.00 | 0.00 | 0.00 | 0.00 | 0.00 | 2 |
| 296 | 0.00 | 0.00 | 0.00 | 1.00 | 0.00 | 0.00 | 1.00 | 0.00 | 3 |
| 297 | 0.00 | 0.03 | 0.97 | 0.00 | 1.00 | 0.00 | 0.00 | 0.00 | 8 |

TABLE 1-continued

Differentially methylated regions (DMRs) associated breast cancer.

| | | | | | | | | | |
|---|---|---|---|---|---|---|---|---|---|
| 298 | 0.00 | 0.00 | 1.00 | 0.00 | 0.00 | 0.00 | 0.00 | 1.00 | 0 |
| 299 | 0.00 | 0.35 | 0.65 | 0.00 | 1.00 | 0.00 | 0.00 | 0.00 | 5 |
| 300 | 0.00 | 0.00 | 0.00 | 1.00 | 0.00 | 0.00 | 0.00 | 1.00 | 2 |
| 301 | 0.00 | 0.00 | 1.00 | 0.00 | 0.00 | 1.00 | 0.00 | 0.00 | 5 |
| 302 | 0.00 | 0.00 | 0.00 | 1.00 | 0.69 | 0.00 | 0.00 | 0.31 | 5 |
| 303 | 0.00 | 0.00 | 0.00 | 1.00 | 0.79 | 0.00 | 0.00 | 0.21 | 3 |
| 304 | 1.00 | 0.00 | 0.00 | 0.00 | 0.00 | 0.00 | 0.00 | 0.00 | 4 |
| 305 | 0.24 | 0.15 | 0.66 | 0.00 | 0.92 | 0.00 | 0.00 | 0.08 | 16 |
| 306 | 0.62 | 0.12 | 0.36 | 0.00 | 1.00 | 0.00 | 0.00 | 0.00 | 9 |
| 307 | 0.00 | 0.00 | 0.00 | 0.00 | 0.00 | 0.00 | 0.00 | 1.00 | 3 |
| 308 | 0.00 | 0.00 | 1.00 | 0.00 | 0.47 | 0.00 | 0.00 | 0.53 | 4 |
| 309 | 1.00 | 0.15 | 0.60 | 0.00 | 0.07 | 0.00 | 0.00 | 0.93 | 2 |
| 310 | 0.44 | 0.12 | 1.00 | 0.00 | 0.15 | 0.85 | 0.00 | 0.00 | 5 |
| 311 | 0.20 | 0.00 | 0.00 | 0.80 | 0.00 | 0.00 | 0.00 | 1.00 | 5 |
| 312 | 0.00 | 0.00 | 1.00 | 0.00 | 0.63 | 0.00 | 0.00 | 0.37 | 7 |
| 313 | 1.00 | 0.34 | 0.63 | 0.00 | 0.59 | 0.00 | 0.00 | 0.41 | 13 |
| 314 | 0.13 | 0.73 | 0.18 | 0.00 | 0.43 | 0.00 | 0.00 | 0.57 | 16 |
| 315 | 0.00 | 0.00 | 1.00 | 0.00 | 1.00 | 0.00 | 0.00 | 0.00 | 0 |
| 316 | 0.00 | 0.00 | 0.00 | 1.00 | 0.80 | 0.20 | 0.00 | 0.00 | 0 |
| 317 | 0.00 | 0.00 | 0.00 | 1.00 | 0.00 | 1.00 | 0.00 | 0.00 | 0 |
| 318 | 0.00 | 0.00 | 1.00 | 0.00 | 1.00 | 0.00 | 0.00 | 0.00 | 0 |
| 319 | 0.00 | 0.00 | 0.00 | 1.00 | 0.32 | 0.00 | 0.00 | 0.68 | 6 |
| 320 | 0.82 | 0.44 | 0.00 | 0.00 | 0.75 | 0.00 | 0.00 | 0.00 | 6 |
| 321 | 1.00 | 0.00 | 0.00 | 0.00 | 0.00 | 0.82 | 0.00 | 0.00 | 2 |
| 322 | 0.25 | 0.29 | 0.57 | 0.00 | 0.00 | 0.00 | 0.00 | 1.00 | 10 |
| 323 | 0.00 | 1.00 | 0.65 | 0.00 | 0.00 | 0.00 | 0.00 | 1.00 | 6 |
| 324 | 0.88 | 0.21 | 0.00 | 0.00 | 0.52 | 0.00 | 0.00 | 0.48 | 11 |
| 325 | 0.00 | 0.00 | 0.00 | 1.00 | 0.00 | 0.00 | 0.00 | 1.00 | 7 |
| 326 | 0.00 | 0.00 | 0.00 | 1.00 | 0.18 | 0.00 | 0.00 | 0.82 | 0 |
| 327 | 0.00 | 0.00 | 0.00 | 1.00 | 0.00 | 0.25 | 0.00 | 0.00 | 3 |
| 328 | 0.00 | 0.00 | 1.00 | 0.00 | 0.99 | 0.00 | 0.00 | 0.01 | 3 |
| 329 | 1.00 | 0.00 | 0.00 | 0.00 | 0.79 | 0.00 | 0.00 | 0.21 | 4 |
| 330 | 0.68 | 0.12 | 0.36 | 0.00 | 0.82 | 0.00 | 0.00 | 0.18 | 4 |
| 331 | 0.00 | 0.30 | 0.56 | 0.00 | 0.00 | 0.76 | 0.00 | 0.00 | 5 |
| 332 | 0.00 | 0.00 | 0.00 | 1.00 | 0.96 | 0.00 | 0.00 | 0.04 | 4 |
| 333 | 0.00 | 0.00 | 0.00 | 1.00 | 0.00 | 0.00 | 0.00 | 1.00 | 1 |
| 334 | 1.00 | 0.00 | 0.00 | 0.00 | 0.00 | 0.00 | 0.00 | 1.00 | 3 |
| 335 | 0.00 | 0.00 | 1.00 | 0.00 | 1.00 | 0.00 | 0.00 | 0.00 | 5 |
| 336 | 0.00 | 0.00 | 0.00 | 1.00 | 0.00 | 0.00 | 0.00 | 1.00 | 5 |
| 337 | 0.78 | 0.37 | 0.05 | 0.00 | 1.00 | 0.00 | 0.00 | 0.00 | 5 |
| 338 | 0.00 | 0.00 | 1.00 | 0.00 | 0.00 | 0.00 | 0.00 | 1.00 | 5 |
| 339 | 0.00 | 0.00 | 1.00 | 0.00 | 0.00 | 1.00 | 0.00 | 0.00 | 1 |
| 340 | 0.00 | 0.00 | 1.00 | 0.00 | 0.00 | 0.00 | 0.00 | 0.21 | 2 |
| 341 | 0.00 | 1.00 | 0.00 | 0.00 | 0.49 | 0.51 | 0.00 | 0.00 | 4 |
| 342 | 1.00 | 0.83 | 0.22 | 0.00 | 1.00 | 0.00 | 0.00 | 0.00 | 38 |
| 343 | 0.00 | 0.00 | 0.00 | 1.00 | 1.00 | 0.00 | 0.00 | 0.00 | 9 |
| 344 | 0.00 | 0.00 | 0.00 | 1.00 | 0.00 | 0.00 | 0.00 | 1.00 | 9 |
| 345 | 1.00 | 0.00 | 0.00 | 0.00 | 0.49 | 0.00 | 0.00 | 0.51 | 8 |
| 346 | 0.00 | 0.00 | 0.00 | 0.00 | 0.00 | 0.00 | 0.00 | 1.00 | 7 |
| 347 | 0.19 | 0.49 | 0.09 | 0.00 | 1.00 | 0.00 | 0.00 | 0.00 | 18 |
| 348 | 0.00 | 0.00 | 0.00 | 0.79 | 0.00 | 0.00 | 0.00 | 1.00 | 15 |
| 349 | 0.43 | 0.28 | 0.43 | 0.00 | 0.45 | 0.00 | 0.00 | 0.55 | 14 |
| 350 | 0.53 | 0.28 | 0.31 | 0.00 | 1.00 | 0.00 | 0.00 | 0.00 | 9 |
| 351 | 0.00 | 0.13 | 0.86 | 0.00 | 0.19 | 0.00 | 0.00 | 0.81 | 8 |
| 352 | 0.00 | 0.00 | 0.00 | 1.00 | 0.00 | 0.00 | 0.00 | 1.00 | 3 |
| 353 | 0.25 | 0.30 | 0.62 | 0.00 | 1.00 | 0.00 | 0.00 | 0.00 | 4 |
| 354 | 0.00 | 0.00 | 0.00 | 1.00 | 0.31 | 0.09 | 0.00 | 0.46 | 7 |
| 355 | 0.00 | 0.00 | 0.00 | 1.00 | 0.00 | 0.00 | 0.00 | 1.00 | 13 |
| 356 | 0.00 | 0.00 | 0.00 | 1.00 | 0.89 | 0.00 | 0.00 | 0.00 | 7 |
| 357 | 0.00 | 0.00 | 0.00 | 0.00 | 0.00 | 0.00 | 0.00 | 1.00 | 8 |
| 358 | 0.00 | 0.00 | 0.00 | 1.00 | 0.00 | 0.00 | 0.00 | 1.00 | 5 |
| 359 | 0.00 | 0.00 | 0.00 | 1.00 | 0.00 | 0.00 | 0.00 | 1.00 | 3 |
| 360 | 0.00 | 0.00 | 0.00 | 1.00 | 1.00 | 0.00 | 0.00 | 0.00 | 3 |
| 361 | 0.00 | 0.00 | 0.00 | 1.00 | 0.00 | 0.00 | 0.00 | 1.00 | 5 |
| 362 | 0.05 | 0.72 | 0.28 | 0.00 | 0.89 | 0.00 | 0.00 | 0.11 | 10 |
| 363 | 0.00 | 0.51 | 0.49 | 0.00 | 0.00 | 0.00 | 0.00 | 1.00 | 7 |
| 364 | 0.00 | 1.00 | 0.00 | 0.00 | 0.00 | 0.00 | 0.00 | 0.00 | 3 |
| 365 | 1.00 | 0.00 | 0.00 | 0.00 | 1.00 | 0.00 | 0.00 | 0.00 | 2 |
| 366 | 0.17 | 0.43 | 0.53 | 0.00 | 0.92 | 0.00 | 0.00 | 0.08 | 5 |
| 367 | 0.34 | 1.00 | 0.57 | 0.00 | 0.19 | 0.00 | 0.00 | 0.81 | 10 |
| 368 | 0.00 | 1.00 | 0.00 | 0.00 | 0.00 | 0.28 | 0.19 | 0.00 | 0 |
| 369 | 0.00 | 0.00 | 0.00 | 1.00 | 1.00 | 0.00 | 0.00 | 0.00 | 35 |
| 370 | 0.53 | 0.61 | 0.00 | 0.00 | 0.00 | 0.00 | 0.00 | 0.00 | 9 |
| 371 | 0.00 | 0.00 | 0.00 | 1.00 | 0.69 | 0.00 | 0.00 | 0.31 | 5 |
| 372 | 0.00 | 0.00 | 0.00 | 1.00 | 0.00 | 0.00 | 0.00 | 0.00 | 2 |
| 373 | 1.00 | 0.25 | 0.00 | 0.00 | 0.70 | 0.00 | 0.00 | 0.30 | 15 |
| 374 | 1.00 | 0.00 | 1.00 | 0.00 | 0.00 | 0.00 | 0.00 | 1.00 | 2 |
| 375 | 0.00 | 0.00 | 0.00 | 1.00 | 0.28 | 0.00 | 0.00 | 0.72 | 3 |

TABLE 1-continued

Differentially methylated regions (DMRs) associated breast cancer.

| | | | | | | | | | |
|---|---|---|---|---|---|---|---|---|---|
| 376 | 0.00 | 1.00 | 0.00 | 0.00 | 0.85 | 0.00 | 0.00 | 0.15 | 5 |
| 377 | 0.35 | 0.33 | 0.46 | 0.00 | 1.00 | 0.00 | 0.00 | 0.00 | 7 |
| 378 | 0.00 | 0.00 | 1.00 | 0.00 | 1.00 | 0.00 | 0.00 | 0.00 | 3 |
| 379 | 0.00 | 0.00 | 1.00 | 0.00 | 0.00 | 0.00 | 0.00 | 1.00 | 1 |
| 380 | 0.00 | 0.00 | 1.00 | 0.00 | 0.00 | 0.00 | 0.00 | 1.00 | 3 |
| 381 | 0.00 | 1.00 | 0.00 | 0.00 | 0.80 | 0.00 | 0.00 | 0.20 | 10 |
| 382 | 0.00 | 0.00 | 0.00 | 1.00 | 0.00 | 0.95 | 0.00 | 0.00 | 1 |
| 383 | 0.32 | 0.70 | 0.07 | 0.00 | 0.18 | 0.00 | 0.00 | 0.82 | 11 |
| 384 | 0.42 | 0.34 | 1.00 | 0.00 | 0.86 | 0.00 | 0.14 | 0.00 | 7 |
| 385 | 0.21 | 0.29 | 0.88 | 0.00 | 0.90 | 0.00 | 0.00 | 0.10 | 13 |
| 386 | 0.06 | 0.17 | 0.83 | 0.00 | 0.95 | 0.00 | 0.00 | 0.05 | 10 |
| 387 | 0.00 | 0.00 | 0.00 | 1.00 | 0.00 | 0.00 | 0.00 | 0.71 | 10 |
| 388 | 0.60 | 0.35 | 0.01 | 0.07 | 0.91 | 0.00 | 0.00 | 0.09 | 14 |
| 389 | 0.05 | 0.00 | 1.00 | 0.00 | 0.00 | 0.00 | 0.00 | 0.00 | 3 |
| 390 | 0.00 | 0.37 | 0.63 | 0.00 | 0.00 | 0.00 | 0.00 | 1.00 | 2 |
| 391 | 0.00 | 0.00 | 0.00 | 1.00 | 1.00 | 0.00 | 0.00 | 0.00 | 3 |
| 392 | 0.55 | 0.36 | 0.17 | 0.00 | 1.00 | 0.00 | 0.00 | 0.00 | 5 |
| 393 | 1.00 | 0.00 | 0.00 | 0.00 | 1.00 | 0.00 | 0.00 | 0.00 | 6 |
| 394 | 0.00 | 0.95 | 0.05 | 0.00 | 0.00 | 0.00 | 0.00 | 0.00 | 3 |
| 395 | 0.00 | 0.00 | 0.00 | 1.00 | 0.00 | 0.79 | 0.00 | 0.00 | 4 |
| 396 | 0.00 | 0.45 | 0.55 | 0.00 | 0.82 | 0.00 | 0.00 | 0.18 | 3 |
| 397 | 0.00 | 0.00 | 0.00 | 0.41 | 0.91 | 0.00 | 0.00 | 0.09 | 7 |
| 398 | 0.00 | 0.08 | 0.92 | 0.00 | 0.00 | 0.00 | 0.00 | 1.00 | 15 |
| 399 | 0.00 | 0.00 | 1.00 | 0.00 | 0.00 | 0.00 | 0.00 | 1.00 | 0 |
| 400 | 0.00 | 0.00 | 0.00 | 1.00 | 0.06 | 0.94 | 0.00 | 0.00 | 2 |
| 401 | 0.00 | 0.00 | 0.00 | 1.00 | 1.00 | 0.00 | 0.00 | 0.00 | 4 |
| 402 | 0.21 | 0.00 | 1.00 | 0.00 | 0.00 | 0.00 | 0.00 | 1.00 | 10 |
| 403 | 0.00 | 0.15 | 0.85 | 0.00 | 0.20 | 0.80 | 0.00 | 0.00 | 4 |
| 404 | 0.73 | 0.09 | 0.04 | 0.17 | 1.00 | 0.00 | 0.00 | 0.00 | 12 |
| 405 | 0.00 | 0.00 | 1.00 | 0.00 | 1.00 | 0.00 | 0.00 | 0.00 | 4 |
| 406 | 0.00 | 0.19 | 0.81 | 0.00 | 1.00 | 0.00 | 0.00 | 0.00 | 4 |
| 407 | 0.00 | 0.54 | 0.45 | 0.00 | 0.00 | 1.00 | 0.00 | 0.00 | 2 |
| 408 | 0.00 | 0.00 | 1.00 | 0.00 | 1.00 | 0.00 | 0.00 | 0.00 | 5 |
| 409 | 0.00 | 0.00 | 0.00 | 0.00 | 0.98 | 0.02 | 0.00 | 0.00 | 6 |
| 410 | 0.00 | 0.89 | 0.11 | 0.00 | 0.00 | 0.00 | 0.00 | 1.00 | 6 |
| 411 | 0.00 | 0.00 | 1.00 | 0.00 | 0.63 | 0.00 | 0.00 | 0.37 | 11 |
| 412 | 0.00 | 1.00 | 0.00 | 0.00 | 0.00 | 0.00 | 0.00 | 1.00 | 4 |
| 413 | 0.39 | 0.50 | 0.61 | 0.00 | 1.00 | 0.00 | 0.00 | 0.00 | 11 |
| 414 | 0.00 | 0.00 | 0.00 | 1.00 | 1.00 | 0.00 | 0.00 | 0.00 | 1 |
| 415 | 1.00 | 0.00 | 0.00 | 0.00 | 0.56 | 0.00 | 0.00 | 0.44 | 6 |
| 416 | 0.00 | 0.71 | 0.29 | 0.00 | 0.11 | 0.00 | 0.00 | 0.89 | 10 |
| 417 | 0.00 | 0.00 | 0.00 | 1.00 | 0.00 | 0.00 | 0.00 | 1.00 | 10 |
| 418 | 0.26 | 0.83 | 0.00 | 0.00 | 1.00 | 0.00 | 0.00 | 0.00 | 3 |
| 419 | 0.17 | 0.28 | 0.60 | 0.00 | 0.61 | 0.39 | 0.00 | 0.00 | 11 |
| 420 | 0.00 | 0.00 | 0.00 | 0.19 | 0.00 | 0.00 | 0.00 | 1.00 | 7 |
| 421 | 0.00 | 0.00 | 0.00 | 0.00 | 0.00 | 0.00 | 0.00 | 1.00 | 0 |
| 422 | 0.00 | 0.00 | 1.00 | 0.00 | 0.81 | 0.00 | 0.00 | 0.19 | 1 |
| 423 | 0.00 | 0.00 | 1.00 | 0.00 | 0.00 | 0.00 | 0.00 | 0.82 | 16 |
| 424 | 0.00 | 0.00 | 0.00 | 1.00 | 0.72 | 0.00 | 0.00 | 0.28 | 9 |
| 425 | 0.00 | 0.53 | 0.47 | 0.00 | 0.86 | 0.00 | 0.00 | 0.14 | 4 |
| 426 | 0.00 | 0.00 | 0.00 | 1.00 | 0.00 | 0.00 | 0.00 | 1.00 | 4 |
| 427 | 0.00 | 0.00 | 0.00 | 1.00 | 1.00 | 0.00 | 0.00 | 0.00 | 3 |
| 428 | 0.39 | 0.14 | 0.53 | 0.00 | 0.00 | 0.00 | 0.00 | 0.25 | 11 |
| 429 | 0.90 | 0.10 | 0.08 | 0.00 | 0.68 | 0.18 | 0.00 | 0.00 | 10 |
| 430 | 0.54 | 0.64 | 0.39 | 0.00 | 0.64 | 0.00 | 0.00 | 0.36 | 13 |
| 431 | 0.00 | 0.00 | 0.00 | 1.00 | 0.00 | 0.00 | 0.00 | 1.00 | 4 |
| 432 | 0.00 | 0.00 | 0.00 | 1.00 | 0.00 | 0.83 | 0.00 | 0.00 | 4 |
| 433 | 0.00 | 0.00 | 0.00 | 1.00 | 0.50 | 0.00 | 0.00 | 0.50 | 4 |
| 434 | 0.00 | 0.00 | 1.00 | 0.00 | 0.46 | 0.00 | 0.00 | 0.54 | 6 |
| 435 | 0.00 | 0.00 | 1.00 | 0.00 | 0.00 | 1.00 | 0.00 | 0.00 | 4 |
| 436 | 0.22 | 0.74 | 0.18 | 0.00 | 0.85 | 0.00 | 0.00 | 0.15 | 5 |
| 437 | 0.00 | 0.00 | 1.00 | 0.00 | 0.00 | 0.00 | 0.00 | 1.00 | 8 |
| 438 | 0.42 | 0.26 | 0.48 | 0.00 | 0.81 | 0.00 | 0.00 | 0.19 | 5 |
| 439 | 1.00 | 0.00 | 1.00 | 0.00 | 0.00 | 0.00 | 0.00 | 1.00 | 3 |
| 440 | 0.21 | 0.89 | 0.00 | 0.00 | 0.99 | 0.00 | 0.00 | 0.01 | 5 |
| 441 | 0.00 | 0.00 | 1.00 | 0.00 | 0.00 | 0.00 | 0.00 | 1.00 | 4 |
| 442 | 0.34 | 0.28 | 0.51 | 0.00 | 1.00 | 0.00 | 0.00 | 0.00 | 9 |
| 443 | 0.00 | 0.00 | 0.00 | 1.00 | 0.00 | 0.87 | 0.13 | 0.00 | 4 |
| 444 | 0.77 | 0.00 | 0.00 | 0.23 | 1.00 | 0.00 | 0.00 | 0.00 | 10 |
| 445 | 0.00 | 0.00 | 0.00 | 1.00 | 0.25 | 0.00 | 0.00 | 0.75 | 7 |
| 446 | 0.00 | 0.00 | 0.00 | 1.00 | 0.00 | 0.00 | 0.00 | 1.00 | 6 |
| 447 | 0.79 | 0.37 | 0.00 | 0.00 | 1.00 | 0.00 | 0.00 | 0.00 | 8 |
| 448 | 0.01 | 0.18 | 0.82 | 0.00 | 0.00 | 0.00 | 0.00 | 1.00 | 5 |
| 449 | 0.00 | 0.00 | 1.00 | 0.00 | 0.00 | 0.00 | 0.00 | 1.00 | 2 |
| 450 | 0.00 | 0.72 | 0.27 | 0.00 | 0.00 | 1.00 | 0.00 | 0.00 | 4 |
| 451 | 0.00 | 0.63 | 0.37 | 0.00 | 0.00 | 0.00 | 0.00 | 1.00 | 4 |
| 452 | 0.72 | 0.97 | 1.00 | 0.00 | 0.60 | 0.00 | 0.00 | 0.40 | 7 |
| 453 | 0.94 | 0.14 | 0.00 | 0.00 | 0.12 | 0.00 | 0.00 | 0.88 | 8 |

TABLE 1-continued

Differentially methylated regions (DMRs) associated breast cancer.

| | | | | | | | | | |
|---|---|---|---|---|---|---|---|---|---|
| 454 | 0.34 | 0.21 | 0.59 | 0.00 | 1.00 | 0.00 | 0.00 | 0.00 | 7 |
| 455 | 0.47 | 0.51 | 0.14 | 0.00 | 1.00 | 0.00 | 0.00 | 0.00 | 8 |
| 456 | 0.00 | 0.00 | 1.00 | 0.00 | 0.91 | 0.09 | 0.00 | 0.00 | 4 |
| 457 | 0.24 | 0.36 | 0.59 | 0.00 | 0.93 | 0.07 | 0.00 | 0.00 | 6 |
| 458 | 1.00 | 0.00 | 0.00 | 0.00 | 0.00 | 0.00 | 0.00 | 1.00 | 7 |
| 459 | 1.00 | 0.00 | 0.00 | 0.00 | 0.00 | 0.00 | 0.00 | 1.00 | 5 |
| 460 | 0.64 | 0.33 | 0.08 | 0.00 | 0.43 | 0.00 | 0.00 | 0.57 | 14 |
| 461 | 1.00 | 0.27 | 0.00 | 0.00 | 0.95 | 0.00 | 0.00 | 0.05 | 15 |
| 462 | 0.55 | 0.33 | 0.66 | 0.00 | 0.41 | 0.40 | 0.00 | 0.19 | 7 |
| 463 | 0.00 | 0.00 | 0.00 | 1.00 | 1.00 | 0.00 | 0.00 | 0.00 | 6 |
| 464 | 0.52 | 0.16 | 0.36 | 0.00 | 0.00 | 0.00 | 0.00 | 0.00 | 11 |
| 465 | 0.23 | 0.85 | 0.00 | 0.00 | 0.60 | 0.00 | 0.00 | 0.40 | 5 |
| 466 | 0.00 | 0.00 | 0.00 | 1.00 | 0.00 | 0.00 | 0.00 | 1.00 | 0 |
| 467 | 0.00 | 0.00 | 0.00 | 1.00 | 0.00 | 0.00 | 0.00 | 1.00 | 4 |
| 468 | 0.00 | 0.00 | 0.00 | 1.00 | 0.76 | 0.24 | 0.00 | 0.00 | 5 |
| 469 | 1.00 | 0.00 | 0.00 | 0.00 | 0.00 | 0.00 | 0.00 | 0.00 | 4 |
| 470 | 0.00 | 0.00 | 1.00 | 0.00 | 0.00 | 0.00 | 0.76 | 0.07 | 4 |
| 471 | 1.00 | 0.00 | 0.00 | 0.00 | 0.00 | 0.00 | 0.00 | 1.00 | 5 |
| 472 | 0.00 | 0.00 | 0.00 | 0.46 | 0.00 | 0.00 | 0.00 | 1.00 | 14 |
| 473 | 0.27 | 0.00 | 0.00 | 0.73 | 0.26 | 0.00 | 0.00 | 0.74 | 4 |
| 474 | 0.00 | 0.00 | 0.00 | 1.00 | 0.99 | 0.01 | 0.00 | 0.00 | 2 |
| 475 | 0.00 | 0.00 | 1.00 | 0.00 | 0.00 | 1.00 | 0.00 | 0.00 | 0 |
| 476 | 0.00 | 0.00 | 0.00 | 1.00 | 0.00 | 0.00 | 0.00 | 1.00 | 8 |
| 477 | 0.24 | 0.61 | 0.20 | 0.00 | 0.28 | 0.00 | 0.00 | 0.72 | 7 |
| 478 | 0.00 | 0.00 | 0.00 | 1.00 | 0.00 | 0.00 | 0.00 | 1.00 | 3 |
| 479 | 0.00 | 0.00 | 1.00 | 0.00 | 0.35 | 0.58 | 0.00 | 0.00 | 1 |
| 480 | 0.00 | 0.00 | 1.00 | 0.00 | 0.48 | 0.52 | 0.00 | 0.00 | 1 |
| 481 | 0.00 | 0.00 | 1.00 | 0.00 | 0.00 | 0.00 | 0.82 | 0.00 | 0 |
| 482 | 0.12 | 0.29 | 0.67 | 0.00 | 0.19 | 0.00 | 0.00 | 0.81 | 6 |
| 483 | 0.00 | 0.00 | 0.00 | 1.00 | 0.00 | 0.00 | 0.00 | 1.00 | 0 |
| 484 | 0.00 | 0.00 | 0.00 | 1.00 | 0.00 | 0.00 | 0.00 | 0.56 | 5 |
| 485 | 0.00 | 0.08 | 0.92 | 0.00 | 0.84 | 0.00 | 0.00 | 0.16 | 3 |
| 486 | 0.40 | 0.33 | 0.35 | 0.00 | 0.72 | 0.28 | 0.00 | 0.00 | 2 |
| 487 | 0.00 | 0.00 | 0.00 | 1.00 | 0.00 | 0.00 | 0.00 | 1.00 | 4 |
| 488 | 0.42 | 0.00 | 0.00 | 0.58 | 0.00 | 0.00 | 0.00 | 1.00 | 4 |
| 489 | 0.00 | 0.00 | 1.00 | 0.00 | 0.00 | 0.00 | 0.00 | 1.00 | 3 |
| 490 | 0.00 | 0.65 | 0.34 | 0.00 | 1.00 | 0.00 | 0.00 | 0.00 | 3 |
| 491 | 0.00 | 0.59 | 0.41 | 0.00 | 0.41 | 0.00 | 0.00 | 0.59 | 5 |
| 492 | 0.00 | 0.00 | 0.00 | 1.00 | 0.00 | 0.00 | 0.00 | 1.00 | 4 |
| 493 | 0.00 | 0.20 | 0.80 | 0.00 | 0.28 | 0.00 | 0.00 | 0.72 | 6 |
| 494 | 0.00 | 0.00 | 0.00 | 1.00 | 0.00 | 0.00 | 0.00 | 1.00 | 8 |
| 495 | 0.74 | 0.00 | 0.00 | 0.26 | 0.16 | 0.00 | 0.00 | 0.84 | 9 |
| 496 | 0.00 | 0.00 | 0.00 | 1.00 | 0.00 | 0.00 | 0.00 | 1.00 | 2 |
| 497 | 0.45 | 0.00 | 0.00 | 0.55 | 0.00 | 0.00 | 0.00 | 1.00 | 3 |
| 498 | 0.37 | 0.43 | 0.30 | 0.00 | 0.75 | 0.00 | 0.00 | 0.25 | 8 |
| 499 | 0.16 | 0.41 | 0.54 | 0.00 | 0.83 | 0.17 | 0.00 | 0.00 | 11 |
| 500 | 0.00 | 0.00 | 1.00 | 0.00 | 0.00 | 0.00 | 0.00 | 1.00 | 5 |
| 501 | 0.00 | 0.48 | 0.52 | 0.00 | 0.00 | 0.00 | 0.00 | 1.00 | 0 |
| 502 | 0.00 | 0.00 | 0.00 | 1.00 | 0.00 | 0.00 | 0.00 | 1.00 | 3 |
| 503 | 0.41 | 0.15 | 0.53 | 0.00 | 0.00 | 0.00 | 0.00 | 1.00 | 7 |
| 504 | 1.00 | 0.00 | 0.00 | 0.00 | 1.00 | 0.00 | 0.00 | 0.00 | 1 |
| 505 | 1.00 | 0.29 | 0.71 | 0.00 | 0.76 | 0.00 | 0.00 | 0.24 | 5 |
| 506 | 0.32 | 0.09 | 0.68 | 0.00 | 0.69 | 0.00 | 0.00 | 0.31 | 8 |
| 507 | 0.00 | 0.49 | 0.51 | 0.00 | 0.72 | 0.00 | 0.00 | 0.28 | 7 |
| 508 | 0.18 | 0.34 | 0.55 | 0.00 | 0.91 | 0.00 | 0.00 | 0.09 | 8 |
| 509 | 0.00 | 0.00 | 1.00 | 0.00 | 0.00 | 0.00 | 0.00 | 1.00 | 2 |
| 510 | 0.35 | 0.76 | 0.05 | 0.00 | 0.00 | 0.00 | 0.00 | 1.00 | 5 |
| 511 | 0.00 | 0.30 | 0.70 | 0.00 | 0.00 | 0.00 | 0.00 | 0.00 | 5 |
| 512 | 0.00 | 0.00 | 0.00 | 1.00 | 0.63 | 0.00 | 0.00 | 0.37 | 3 |
| 513 | 0.00 | 0.00 | 0.00 | 1.00 | 0.00 | 0.00 | 0.00 | 1.00 | 3 |
| 514 | 0.98 | 0.10 | 0.30 | 0.00 | 0.31 | 0.69 | 0.00 | 0.00 | 2 |
| 515 | 0.54 | 0.14 | 0.47 | 0.00 | 0.59 | 0.41 | 0.00 | 0.00 | 9 |
| 516 | 0.33 | 0.45 | 0.12 | 0.00 | 0.15 | 0.00 | 0.00 | 0.85 | 12 |
| 517 | 0.00 | 0.00 | 0.00 | 1.00 | 1.00 | 0.00 | 0.00 | 0.00 | 3 |
| 518 | 0.00 | 1.00 | 0.00 | 0.00 | 0.00 | 0.00 | 0.00 | 1.00 | 4 |
| 519 | 0.00 | 0.00 | 0.00 | 1.00 | 0.42 | 0.00 | 0.00 | 0.58 | 9 |
| 520 | 1.00 | 0.00 | 0.00 | 0.00 | 0.29 | 0.00 | 0.00 | 0.71 | 2 |
| 521 | 0.52 | 0.59 | 0.00 | 0.00 | 0.80 | 0.20 | 0.00 | 0.00 | 7 |
| 522 | 0.00 | 0.00 | 0.00 | 1.00 | 0.00 | 0.00 | 0.00 | 1.00 | 2 |
| 523 | 0.00 | 0.00 | 0.00 | 1.00 | 0.00 | 0.00 | 0.00 | 1.00 | 4 |
| 524 | 0.00 | 0.00 | 0.00 | 1.00 | 0.00 | 0.00 | 0.00 | 1.00 | 2 |
| 525 | 0.77 | 0.23 | 0.07 | 0.00 | 0.61 | 0.00 | 0.00 | 0.39 | 4 |
| 526 | 0.15 | 0.68 | 0.93 | 0.00 | 1.00 | 0.00 | 0.00 | 0.00 | 3 |
| 527 | 0.31 | 0.24 | 0.76 | 0.00 | 0.00 | 1.00 | 0.00 | 0.00 | 0 |
| 528 | 0.00 | 1.00 | 0.00 | 0.00 | 0.00 | 0.00 | 0.00 | 1.00 | 10 |
| 529 | 0.00 | 0.39 | 0.61 | 0.00 | 0.00 | 0.00 | 0.00 | 1.00 | 6 |
| 530 | 1.00 | 0.00 | 0.00 | 0.00 | 1.00 | 0.00 | 0.00 | 0.00 | 3 |
| 531 | 1.00 | 0.00 | 0.00 | 0.00 | 0.59 | 0.41 | 0.00 | 0.00 | 1 |

TABLE 1-continued

Differentially methylated regions (DMRs) associated breast cancer.

| | | | | | | | | | |
|---|---|---|---|---|---|---|---|---|---|
| 532 | 0.00 | 0.00 | 0.00 | 1.00 | 0.82 | 0.00 | 0.00 | 0.18 | 9 |
| 533 | 0.00 | 0.00 | 1.00 | 0.00 | 0.95 | 0.00 | 0.00 | 0.05 | 9 |
| 534 | 0.00 | 0.00 | 0.00 | 1.00 | 0.46 | 0.00 | 0.00 | 0.54 | 7 |
| 535 | 0.00 | 0.00 | 1.00 | 0.00 | 0.00 | 0.00 | 0.00 | 1.00 | 2 |
| 536 | 0.00 | 0.00 | 1.00 | 0.00 | 0.00 | 0.00 | 0.00 | 1.00 | 6 |
| 537 | 0.69 | 0.07 | 0.29 | 0.00 | 0.00 | 0.00 | 0.00 | 0.87 | 11 |
| 538 | 0.00 | 0.00 | 0.00 | 1.00 | 0.00 | 0.00 | 0.00 | 0.00 | 6 |
| 539 | 0.00 | 0.00 | 0.00 | 1.00 | 0.64 | 0.00 | 0.00 | 0.36 | 1 |
| 540 | 0.34 | 0.01 | 0.70 | 0.00 | 0.67 | 0.00 | 0.00 | 0.33 | 8 |
| 541 | 0.00 | 0.00 | 1.00 | 0.00 | 0.00 | 0.00 | 0.00 | 1.00 | 3 |
| 542 | 0.18 | 0.67 | 0.25 | 0.00 | 0.00 | 0.00 | 0.00 | 1.00 | 9 |
| 543 | 0.00 | 0.00 | 0.00 | 1.00 | 0.00 | 0.00 | 0.00 | 0.00 | 1 |
| 544 | 0.00 | 0.00 | 1.00 | 0.00 | 1.00 | 0.00 | 0.00 | 0.00 | 1 |
| 545 | 1.00 | 0.00 | 0.00 | 0.00 | 0.85 | 0.00 | 0.00 | 0.15 | 9 |
| 546 | 0.00 | 0.00 | 0.00 | 1.00 | 1.00 | 0.00 | 0.00 | 0.00 | 10 |
| 547 | 0.00 | 0.00 | 0.00 | 1.00 | 0.66 | 0.00 | 0.00 | 0.34 | 6 |
| 548 | 0.44 | 0.26 | 0.46 | 0.00 | 1.00 | 0.00 | 0.00 | 0.00 | 5 |
| 549 | 0.00 | 0.00 | 0.00 | 0.00 | 0.00 | 0.00 | 0.00 | 1.00 | 4 |
| 550 | 0.00 | 0.00 | 0.00 | 1.00 | 0.00 | 0.00 | 0.00 | 1.00 | 3 |
| 551 | 0.00 | 0.15 | 0.85 | 0.00 | 1.00 | 0.00 | 0.00 | 0.00 | 8 |
| 552 | 0.31 | 0.14 | 0.62 | 0.00 | 0.00 | 0.00 | 0.00 | 1.00 | 10 |
| 553 | 0.00 | 0.00 | 0.00 | 1.00 | 0.71 | 0.00 | 0.00 | 0.29 | 10 |
| 554 | 0.00 | 0.00 | 0.00 | 1.00 | 0.81 | 0.00 | 0.00 | 0.19 | 8 |
| 555 | 0.00 | 0.00 | 1.00 | 0.00 | 0.83 | 0.00 | 0.00 | 0.17 | 4 |
| 556 | 0.00 | 1.00 | 0.00 | 0.00 | 0.83 | 0.00 | 0.00 | 0.17 | 6 |
| 557 | 0.00 | 0.34 | 0.66 | 0.00 | 0.00 | 0.00 | 0.00 | 1.00 | 4 |
| 558 | 0.00 | 0.61 | 0.39 | 0.00 | 0.88 | 0.00 | 0.00 | 0.12 | 6 |
| 559 | 0.00 | 0.00 | 0.00 | 1.00 | 0.00 | 0.00 | 0.00 | 1.00 | 5 |
| 560 | 0.00 | 0.00 | 1.00 | 0.00 | 1.00 | 0.00 | 0.00 | 0.00 | 3 |
| 561 | 0.02 | 0.01 | 0.99 | 0.00 | 0.00 | 0.00 | 0.00 | 0.49 | 7 |
| 562 | 0.84 | 0.21 | 0.00 | 0.00 | 0.00 | 0.00 | 0.00 | 1.00 | 7 |
| 563 | 0.43 | 0.15 | 0.50 | 0.00 | 1.00 | 0.00 | 0.00 | 0.00 | 11 |
| 564 | 1.00 | 0.00 | 0.00 | 0.00 | 0.00 | 0.00 | 0.00 | 1.00 | 4 |
| 565 | 0.00 | 0.00 | 0.00 | 1.00 | 0.00 | 0.00 | 0.00 | 1.00 | 0 |
| 566 | 0.00 | 0.31 | 0.73 | 0.00 | 0.00 | 0.00 | 0.00 | 1.00 | 1 |
| 567 | 1.00 | 0.00 | 0.00 | 0.00 | 0.00 | 0.00 | 0.00 | 1.00 | 3 |
| 568 | 0.46 | 0.16 | 0.55 | 0.00 | 1.00 | 0.00 | 0.00 | 0.00 | 8 |
| 569 | 0.00 | 0.00 | 0.00 | 1.00 | 0.63 | 0.00 | 0.00 | 0.37 | 2 |
| 570 | 0.00 | 0.00 | 0.00 | 1.00 | 0.80 | 0.15 | 0.00 | 0.00 | 7 |
| 571 | 1.00 | 0.00 | 0.00 | 0.00 | 0.85 | 0.00 | 0.00 | 0.15 | 0 |
| 572 | 0.00 | 0.00 | 0.00 | 1.00 | 0.00 | 0.00 | 0.00 | 1.00 | 2 |
| 573 | 0.00 | 0.00 | 0.00 | 1.00 | 0.00 | 0.00 | 0.00 | 1.00 | 6 |
| 574 | 0.53 | 0.56 | 1.00 | 0.00 | 0.00 | 1.00 | 0.00 | 0.00 | 13 |
| 575 | 0.43 | 0.09 | 0.51 | 0.00 | 0.27 | 0.00 | 0.00 | 0.73 | 16 |
| 576 | 0.27 | 0.19 | 0.79 | 0.00 | 0.19 | 0.00 | 0.00 | 0.81 | 21 |
| 577 | 0.75 | 0.15 | 0.15 | 0.00 | 0.00 | 0.00 | 0.00 | 1.00 | 22 |
| 578 | 0.44 | 0.38 | 0.22 | 0.00 | 0.00 | 0.00 | 0.00 | 1.00 | 10 |
| 579 | 0.49 | 0.52 | 0.32 | 0.00 | 1.00 | 0.00 | 0.00 | 0.00 | 3 |
| 580 | 0.00 | 0.00 | 0.00 | 1.00 | 0.00 | 0.00 | 0.00 | 1.00 | 1 |
| 581 | 1.00 | 0.00 | 1.00 | 0.00 | 0.32 | 0.68 | 0.00 | 0.00 | 2 |
| 582 | 0.00 | 0.00 | 1.00 | 0.00 | 0.00 | 1.00 | 0.00 | 0.00 | 0 |
| 583 | 0.00 | 0.00 | 0.00 | 1.00 | 0.00 | 0.53 | 0.00 | 0.00 | 1 |
| 584 | 1.00 | 0.00 | 0.00 | 0.00 | 0.00 | 0.00 | 0.00 | 0.00 | 4 |
| 585 | 0.00 | 0.00 | 0.00 | 1.00 | 0.00 | 0.00 | 0.00 | 1.00 | 0 |
| 586 | 0.00 | 0.00 | 1.00 | 0.00 | 0.00 | 1.00 | 0.00 | 0.00 | 3 |
| 587 | 0.46 | 0.00 | 0.00 | 0.54 | 0.85 | 0.00 | 0.00 | 0.15 | 3 |
| 588 | 0.00 | 0.00 | 1.00 | 0.00 | 0.00 | 1.00 | 0.00 | 0.00 | 0 |
| 589 | 0.00 | 0.00 | 0.00 | 1.00 | 0.00 | 0.00 | 0.00 | 1.00 | 4 |
| 590 | 0.00 | 0.00 | 1.00 | 0.00 | 0.89 | 0.11 | 0.00 | 0.00 | 1 |
| 591 | 0.00 | 0.11 | 0.88 | 0.00 | 0.00 | 0.00 | 0.00 | 1.00 | 3 |
| 592 | 0.59 | 0.22 | 0.34 | 0.00 | 0.89 | 0.00 | 0.00 | 0.11 | 9 |
| 593 | 1.00 | 0.00 | 1.00 | 0.00 | 0.33 | 0.00 | 0.67 | 0.00 | 4 |
| 594 | 0.00 | 0.00 | 0.00 | 1.00 | 0.51 | 0.00 | 0.00 | 0.49 | 0 |
| 595 | 0.00 | 0.34 | 0.66 | 0.00 | 0.00 | 0.00 | 0.00 | 1.00 | 7 |
| 596 | 0.00 | 0.00 | 0.00 | 0.00 | 0.77 | 0.00 | 0.00 | 0.23 | 4 |
| 597 | 0.00 | 0.00 | 0.00 | 1.00 | 0.74 | 0.00 | 0.00 | 0.26 | 5 |
| 598 | 0.00 | 0.00 | 0.00 | 1.00 | 0.72 | 0.10 | 0.00 | 0.00 | 5 |
| 599 | 0.00 | 0.00 | 0.00 | 1.00 | 0.00 | 1.00 | 0.00 | 0.00 | 1 |
| 600 | 0.00 | 0.00 | 0.00 | 1.00 | 0.00 | 0.00 | 0.00 | 1.00 | 2 |
| 601 | 0.00 | 0.00 | 0.00 | 1.00 | 0.00 | 0.00 | 0.00 | 1.00 | 8 |
| 602 | 0.00 | 0.00 | 1.00 | 0.00 | 0.00 | 0.00 | 0.00 | 0.00 | 1 |
| 603 | 0.00 | 0.43 | 0.56 | 0.00 | 0.00 | 0.00 | 0.00 | 1.00 | 2 |
| 604 | 0.00 | 0.10 | 0.90 | 0.00 | 0.00 | 0.79 | 0.00 | 0.00 | 2 |
| 605 | 0.26 | 0.15 | 0.65 | 0.00 | 0.64 | 0.00 | 0.00 | 0.36 | 8 |
| 606 | 0.48 | 0.15 | 0.51 | 0.00 | 0.00 | 0.00 | 0.00 | 0.00 | 3 |
| 607 | 0.00 | 0.00 | 0.00 | 1.00 | 0.92 | 0.08 | 0.00 | 0.00 | 4 |
| 608 | 0.00 | 0.00 | 0.00 | 1.00 | 0.96 | 0.00 | 0.00 | 0.04 | 6 |
| 609 | 0.00 | 0.00 | 1.00 | 0.00 | 0.92 | 0.00 | 0.00 | 0.08 | 3 |

TABLE 1-continued

Differentially methylated regions (DMRs) associated breast cancer.

| | | | | | | | | | |
|---|---|---|---|---|---|---|---|---|---|
| 610 | 1.00 | 0.30 | 0.70 | 0.00 | 0.67 | 0.00 | 0.00 | 0.00 | 4 |
| 611 | 0.00 | 0.40 | 1.00 | 0.00 | 1.00 | 0.00 | 0.00 | 0.00 | 2 |
| 612 | 0.00 | 1.00 | 0.00 | 0.00 | 0.52 | 0.00 | 0.00 | 0.48 | 3 |
| 613 | 0.00 | 0.00 | 1.00 | 0.00 | 0.00 | 0.00 | 0.00 | 1.00 | 8 |
| 614 | 0.00 | 0.97 | 0.03 | 0.00 | 0.00 | 0.00 | 0.00 | 0.46 | 9 |
| 615 | 0.50 | 0.14 | 0.45 | 0.00 | 0.00 | 0.74 | 0.00 | 0.00 | 12 |
| 616 | 1.00 | 0.78 | 1.00 | 0.00 | 0.00 | 0.00 | 0.00 | 1.00 | 5 |
| 617 | 1.00 | 0.00 | 0.00 | 0.00 | 0.00 | 0.00 | 0.00 | 1.00 | 4 |
| 618 | 0.46 | 0.00 | 1.00 | 0.00 | 0.00 | 0.00 | 0.00 | 1.00 | 6 |
| 619 | 0.00 | 0.00 | 1.00 | 0.00 | 0.00 | 0.00 | 0.00 | 1.00 | 8 |
| 620 | 0.55 | 0.51 | 0.00 | 0.00 | 0.64 | 0.00 | 0.00 | 0.36 | 5 |
| 621 | 0.00 | 0.68 | 0.32 | 0.00 | 1.00 | 0.00 | 0.00 | 0.00 | 0 |
| 622 | 0.00 | 0.00 | 0.00 | 1.00 | 0.00 | 0.00 | 0.59 | 0.00 | 2 |
| 623 | 0.69 | 0.50 | 0.56 | 0.00 | 1.00 | 0.00 | 0.00 | 0.00 | 10 |
| 624 | 0.00 | 0.49 | 0.51 | 0.00 | 0.00 | 0.00 | 0.00 | 1.00 | 2 |
| 625 | 1.00 | 0.13 | 0.16 | 0.00 | 0.53 | 0.45 | 0.00 | 0.00 | 5 |
| 626 | 0.00 | 0.00 | 0.00 | 1.00 | 0.00 | 1.00 | 0.00 | 0.00 | 1 |
| 627 | 0.00 | 0.00 | 0.00 | 1.00 | 0.99 | 0.00 | 0.00 | 0.01 | 4 |
| 628 | 0.00 | 0.00 | 1.00 | 0.00 | 0.00 | 0.00 | 0.00 | 1.00 | 3 |
| 629 | 0.00 | 0.00 | 0.00 | 1.00 | 0.00 | 0.00 | 0.00 | 1.00 | 4 |
| 630 | 1.00 | 0.00 | 0.00 | 0.00 | 0.86 | 0.14 | 0.00 | 0.00 | 6 |
| 631 | 0.48 | 0.00 | 0.00 | 0.52 | 0.59 | 0.04 | 0.00 | 0.37 | 11 |
| 632 | 0.00 | 0.30 | 0.70 | 0.00 | 0.83 | 0.00 | 0.00 | 0.17 | 3 |
| 633 | 0.00 | 0.00 | 0.00 | 1.00 | 0.90 | 0.00 | 0.00 | 0.10 | 6 |
| 634 | 0.04 | 0.05 | 0.95 | 0.00 | 0.71 | 0.00 | 0.00 | 0.29 | 4 |
| 635 | 0.59 | 0.00 | 0.00 | 0.41 | 0.00 | 0.00 | 0.00 | 1.00 | 2 |
| 636 | 0.00 | 0.00 | 0.00 | 1.00 | 0.75 | 0.00 | 0.00 | 0.00 | 8 |
| 637 | 0.00 | 0.00 | 0.00 | 1.00 | 0.53 | 0.29 | 0.00 | 0.18 | 6 |
| 638 | 0.00 | 0.00 | 0.00 | 1.00 | 0.00 | 0.00 | 0.00 | 0.00 | 4 |
| 639 | 0.91 | 0.34 | 0.00 | 0.00 | 1.00 | 0.00 | 0.00 | 0.00 | 4 |
| 640 | 0.00 | 0.00 | 0.00 | 1.00 | 0.00 | 0.00 | 0.00 | 1.00 | 2 |
| 641 | 1.00 | 0.00 | 0.00 | 0.00 | 1.00 | 0.00 | 0.00 | 0.00 | 7 |
| 642 | 1.00 | 0.00 | 1.00 | 0.00 | 0.48 | 0.00 | 0.00 | 0.52 | 4 |
| 643 | 0.00 | 0.00 | 1.00 | 0.00 | 0.00 | 0.00 | 0.00 | 0.35 | 0 |
| 644 | 0.00 | 0.35 | 0.65 | 0.00 | 0.00 | 0.00 | 0.00 | 1.00 | 2 |
| 645 | 1.00 | 0.00 | 1.00 | 0.00 | 0.60 | 0.39 | 0.00 | 0.00 | 0 |
| 646 | 0.00 | 0.35 | 0.64 | 0.00 | 0.15 | 0.00 | 0.00 | 0.85 | 6 |
| 647 | 0.00 | 0.00 | 0.00 | 1.00 | 0.00 | 0.00 | 0.00 | 0.00 | 3 |
| 648 | 0.00 | 0.00 | 0.00 | 1.00 | 0.87 | 0.00 | 0.00 | 0.13 | 6 |
| 649 | 0.00 | 0.00 | 0.00 | 1.00 | 0.00 | 0.00 | 0.00 | 1.00 | 11 |
| 650 | 0.00 | 0.00 | 1.00 | 0.00 | 0.46 | 0.00 | 0.00 | 0.54 | 8 |
| 651 | 0.00 | 0.31 | 0.68 | 0.00 | 0.52 | 0.00 | 0.00 | 0.48 | 8 |
| 652 | 0.00 | 0.00 | 0.00 | 1.00 | 0.00 | 1.00 | 0.00 | 0.00 | 4 |
| 653 | 0.34 | 0.62 | 0.15 | 0.00 | 0.00 | 0.00 | 0.00 | 0.40 | 6 |
| 654 | 0.00 | 0.00 | 1.00 | 0.00 | 0.00 | 0.00 | 0.00 | 1.00 | 3 |
| 655 | 0.40 | 0.69 | 1.00 | 0.00 | 0.97 | 0.00 | 0.00 | 0.00 | 9 |
| 656 | 0.13 | 0.58 | 0.42 | 0.00 | 0.00 | 0.00 | 0.00 | 0.00 | 3 |
| 657 | 0.82 | 0.00 | 1.00 | 0.00 | 1.00 | 0.00 | 0.00 | 0.00 | 2 |
| 658 | 0.00 | 0.00 | 1.00 | 0.00 | 0.67 | 0.00 | 0.00 | 0.33 | 5 |
| 659 | 0.00 | 0.35 | 0.65 | 0.00 | 0.00 | 0.00 | 0.00 | 1.00 | 2 |
| 660 | 0.00 | 0.00 | 0.00 | 1.00 | 0.00 | 0.00 | 0.00 | 1.00 | 2 |
| 661 | 0.57 | 0.26 | 0.24 | 0.00 | 0.00 | 0.00 | 0.00 | 0.62 | 14 |
| 662 | 0.48 | 0.29 | 0.31 | 0.00 | 0.00 | 0.00 | 0.00 | 1.00 | 10 |
| 663 | 0.07 | 0.77 | 0.23 | 0.00 | 0.79 | 0.00 | 0.00 | 0.21 | 3 |
| 664 | 0.00 | 0.00 | 1.00 | 0.00 | 0.00 | 1.00 | 0.00 | 0.00 | 1 |
| 665 | 0.00 | 0.00 | 0.47 | 0.53 | 0.00 | 1.00 | 0.00 | 0.00 | 1 |
| 666 | 0.00 | 0.00 | 0.00 | 1.00 | 0.00 | 0.00 | 0.67 | 0.00 | 5 |
| 667 | 0.00 | 0.00 | 0.00 | 1.00 | 0.00 | 0.00 | 0.00 | 1.00 | 1 |
| 668 | 0.00 | 0.00 | 0.00 | 1.00 | 0.00 | 0.29 | 0.29 | 0.00 | 4 |
| 669 | 0.00 | 0.00 | 0.00 | 1.00 | 1.00 | 0.00 | 0.00 | 0.00 | 15 |
| 670 | 1.00 | 0.00 | 0.00 | 0.00 | 0.83 | 0.00 | 0.00 | 0.17 | 4 |
| 671 | 0.00 | 0.00 | 0.00 | 0.00 | 0.00 | 0.00 | 0.00 | 1.00 | 4 |
| 672 | 0.00 | 1.00 | 0.00 | 0.00 | 1.00 | 0.00 | 0.00 | 0.00 | 3 |
| 673 | 0.31 | 0.74 | 0.00 | 0.00 | 0.96 | 0.00 | 0.00 | 0.04 | 10 |
| 674 | 1.00 | 0.05 | 0.00 | 0.00 | 0.75 | 0.20 | 0.00 | 0.00 | 7 |
| 675 | 0.55 | 0.53 | 1.00 | 0.00 | 0.65 | 0.35 | 0.00 | 0.00 | 14 |
| 676 | 0.24 | 0.00 | 1.00 | 0.00 | 0.00 | 0.00 | 0.00 | 1.00 | 8 |
| 677 | 0.00 | 0.46 | 1.00 | 0.00 | 0.00 | 0.00 | 0.00 | 1.00 | 5 |
| 678 | 0.00 | 0.05 | 0.95 | 0.00 | 0.23 | 0.00 | 0.00 | 0.77 | 22 |
| 679 | 0.00 | 0.00 | 0.00 | 1.00 | 1.00 | 0.00 | 0.00 | 0.00 | 4 |
| 680 | 0.35 | 0.53 | 0.31 | 0.00 | 1.00 | 0.00 | 0.00 | 0.00 | 6 |
| 681 | 0.59 | 0.16 | 0.40 | 0.00 | 1.00 | 0.00 | 0.00 | 0.00 | 9 |
| 682 | 0.00 | 0.56 | 0.44 | 0.00 | 0.00 | 1.00 | 0.00 | 0.00 | 1 |
| 683 | 0.00 | 0.00 | 0.00 | 1.00 | 0.00 | 1.00 | 0.00 | 0.00 | 4 |
| 684 | 0.00 | 0.00 | 1.00 | 0.00 | 0.00 | 1.00 | 0.00 | 0.00 | 0 |
| 685 | 0.00 | 0.00 | 0.00 | 0.00 | 0.00 | 0.00 | 0.97 | 0.00 | 0 |
| 686 | 0.33 | 0.21 | 0.54 | 0.00 | 1.00 | 0.00 | 0.00 | 0.00 | 11 |
| 687 | 0.00 | 0.00 | 0.00 | 1.00 | 0.44 | 0.58 | 0.00 | 0.00 | 4 |

TABLE 1-continued

Differentially methylated regions (DMRs) associated breast cancer.

| | | | | | | | | | |
|---|---|---|---|---|---|---|---|---|---|
| 688 | 0.00 | 0.00 | 0.00 | 1.00 | 0.00 | 1.00 | 0.00 | 0.00 | 3 |
| 689 | 1.00 | 0.41 | 0.00 | 0.00 | 0.00 | 0.73 | 0.00 | 0.00 | 3 |
| 690 | 0.00 | 0.00 | 0.00 | 1.00 | 0.00 | 0.00 | 0.00 | 1.00 | 4 |
| 691 | 0.00 | 0.00 | 0.00 | 1.00 | 0.63 | 0.00 | 0.00 | 0.37 | 2 |
| 692 | 0.00 | 0.00 | 0.00 | 1.00 | 0.00 | 0.00 | 0.95 | 0.00 | 0 |
| 693 | 0.00 | 0.24 | 0.76 | 0.00 | 0.00 | 0.00 | 0.00 | 1.00 | 5 |
| 694 | 0.00 | 0.00 | 1.00 | 0.00 | 0.00 | 0.00 | 0.00 | 1.00 | 8 |
| 695 | 1.00 | 0.00 | 0.00 | 0.00 | 0.00 | 0.00 | 0.00 | 1.00 | 3 |
| 696 | 0.00 | 0.00 | 1.00 | 0.00 | 1.00 | 0.00 | 0.00 | 0.00 | 4 |
| 697 | 0.00 | 0.00 | 0.00 | 1.00 | 0.00 | 0.00 | 0.00 | 1.00 | 0 |
| 698 | 0.27 | 0.09 | 0.72 | 0.00 | 0.00 | 0.00 | 0.00 | 1.00 | 5 |
| 699 | 1.00 | 0.00 | 0.00 | 0.00 | 1.00 | 0.00 | 0.00 | 0.00 | 10 |
| 700 | 0.30 | 0.78 | 1.00 | 0.00 | 0.00 | 1.00 | 0.00 | 0.00 | 8 |
| 701 | 0.00 | 0.00 | 0.00 | 1.00 | 1.00 | 0.00 | 0.00 | 0.00 | 5 |
| 702 | 0.00 | 0.39 | 0.61 | 0.00 | 0.00 | 0.00 | 0.00 | 1.00 | 3 |
| 703 | 0.00 | 0.00 | 0.00 | 1.00 | 0.77 | 0.23 | 0.00 | 0.00 | 3 |
| 704 | 1.00 | 0.00 | 0.00 | 0.00 | 0.90 | 0.00 | 0.00 | 0.10 | 4 |
| 705 | 0.00 | 0.00 | 0.00 | 1.00 | 0.00 | 0.80 | 0.00 | 0.00 | 2 |
| 706 | 0.32 | 0.23 | 0.54 | 0.00 | 0.64 | 0.00 | 0.00 | 0.36 | 8 |
| 707 | 0.00 | 0.51 | 0.00 | 0.00 | 0.00 | 0.00 | 0.00 | 1.00 | 10 |
| 708 | 0.00 | 0.00 | 0.00 | 1.00 | 0.00 | 0.00 | 0.92 | 0.00 | 0 |
| 709 | 0.92 | 0.21 | 0.19 | 0.00 | 0.00 | 1.00 | 0.00 | 0.00 | 5 |
| 710 | 0.00 | 0.66 | 0.34 | 0.00 | 0.00 | 0.00 | 0.00 | 1.00 | 4 |
| 711 | 0.00 | 0.28 | 0.72 | 0.00 | 0.59 | 0.41 | 0.00 | 0.00 | 5 |
| 712 | 0.59 | 0.15 | 0.85 | 0.00 | 0.52 | 0.00 | 0.00 | 0.48 | 14 |
| 713 | 0.00 | 0.00 | 1.00 | 0.00 | 1.00 | 0.00 | 0.00 | 0.00 | 3 |
| 714 | 0.40 | 0.20 | 0.53 | 0.00 | 0.00 | 0.00 | 0.00 | 0.00 | 5 |
| 715 | 0.33 | 0.18 | 0.10 | 0.00 | 0.23 | 0.00 | 0.00 | 0.77 | 20 |
| 716 | 0.67 | 0.16 | 0.23 | 0.00 | 0.00 | 0.00 | 0.00 | 0.34 | 7 |
| 717 | 0.00 | 0.44 | 0.10 | 0.00 | 0.42 | 0.00 | 0.00 | 0.58 | 5 |
| 718 | 0.00 | 1.00 | 0.00 | 0.00 | 0.48 | 0.42 | 0.00 | 0.00 | 3 |
| 719 | 0.00 | 0.00 | 0.00 | 1.00 | 0.00 | 0.00 | 0.00 | 1.00 | 3 |
| 720 | 0.00 | 0.79 | 0.21 | 0.00 | 0.00 | 0.00 | 0.00 | 0.00 | 4 |
| 721 | 0.00 | 0.00 | 1.00 | 0.00 | 0.00 | 0.00 | 0.00 | 0.00 | 3 |
| 722 | 0.00 | 0.00 | 1.00 | 0.00 | 0.00 | 1.00 | 0.00 | 0.00 | 0 |
| 723 | 0.00 | 0.23 | 0.77 | 0.00 | 0.00 | 0.00 | 0.00 | 1.00 | 4 |
| 724 | 0.03 | 0.35 | 0.65 | 0.00 | 0.87 | 0.00 | 0.00 | 0.13 | 3 |
| 725 | 0.83 | 0.72 | 0.25 | 0.00 | 0.98 | 0.02 | 0.00 | 0.00 | 16 |
| 726 | 0.00 | 0.00 | 0.00 | 1.00 | 0.00 | 0.00 | 0.00 | 1.00 | 4 |
| 727 | 0.00 | 0.00 | 1.00 | 0.00 | 0.00 | 0.00 | 0.00 | 0.00 | 0 |
| 728 | 0.32 | 0.31 | 0.48 | 0.00 | 1.00 | 0.00 | 0.00 | 0.00 | 12 |
| 729 | 0.00 | 0.25 | 0.74 | 0.00 | 0.74 | 0.26 | 0.00 | 0.00 | 6 |
| 730 | 0.00 | 0.00 | 0.00 | 0.63 | 0.00 | 0.00 | 0.08 | 0.00 | 1 |
| 731 | 0.02 | 0.00 | 1.00 | 0.00 | 0.00 | 1.00 | 0.00 | 0.00 | 4 |
| 732 | 0.00 | 0.00 | 0.00 | 1.00 | 0.00 | 0.00 | 0.00 | 1.00 | 3 |
| 733 | 0.96 | 0.15 | 0.00 | 0.00 | 0.45 | 0.00 | 0.00 | 0.55 | 7 |
| 734 | 0.00 | 0.00 | 0.00 | 1.00 | 0.00 | 0.35 | 0.00 | 0.00 | 0 |
| 735 | 0.00 | 0.00 | 0.00 | 0.47 | 1.00 | 0.00 | 0.00 | 0.00 | 36 |
| 736 | 0.00 | 0.00 | 1.00 | 0.00 | 1.00 | 0.00 | 0.00 | 0.00 | 7 |
| 737 | 0.00 | 0.00 | 0.00 | 1.00 | 0.58 | 0.21 | 0.00 | 0.00 | 6 |
| 738 | 0.00 | 0.00 | 0.00 | 1.00 | 0.00 | 0.00 | 0.29 | 0.00 | 0 |
| 739 | 0.30 | 0.00 | 0.00 | 0.70 | 0.00 | 0.00 | 0.00 | 1.00 | 11 |
| 740 | 0.00 | 0.00 | 1.00 | 0.00 | 0.00 | 0.25 | 0.00 | 0.00 | 0 |
| 741 | 0.00 | 0.00 | 0.00 | 1.00 | 0.00 | 0.00 | 0.00 | 1.00 | 0 |
| 742 | 0.61 | 0.38 | 0.15 | 0.00 | 0.43 | 0.57 | 0.00 | 0.00 | 12 |
| 743 | 0.00 | 0.00 | 1.00 | 0.00 | 0.00 | 1.00 | 0.00 | 0.00 | 0 |
| 744 | 0.64 | 0.43 | 0.03 | 0.00 | 0.00 | 0.22 | 0.00 | 0.00 | 8 |
| 745 | 0.00 | 0.42 | 0.57 | 0.00 | 0.00 | 0.00 | 0.00 | 0.00 | 3 |
| 746 | 0.00 | 0.00 | 0.00 | 1.00 | 0.00 | 1.00 | 0.00 | 0.00 | 0 |
| 747 | 0.44 | 0.78 | 0.04 | 0.00 | 0.00 | 1.00 | 0.00 | 0.00 | 4 |
| 748 | 0.86 | 0.00 | 0.00 | 0.14 | 0.28 | 0.00 | 0.00 | 0.72 | 5 |
| 749 | 0.00 | 0.00 | 1.00 | 0.00 | 0.00 | 1.00 | 0.00 | 0.00 | 1 |
| 750 | 0.00 | 0.00 | 0.00 | 0.00 | 0.00 | 1.00 | 0.00 | 0.00 | 0 |
| 751 | 0.79 | 0.47 | 0.00 | 0.00 | 1.00 | 0.00 | 0.00 | 0.00 | 3 |
| 752 | 0.00 | 0.00 | 1.00 | 0.00 | 0.79 | 0.21 | 0.00 | 0.00 | 3 |
| 753 | 0.00 | 0.00 | 0.00 | 1.00 | 0.08 | 0.00 | 0.00 | 0.92 | 4 |
| 754 | 0.00 | 0.00 | 0.00 | 1.00 | 0.00 | 0.72 | 0.00 | 0.00 | 1 |
| 755 | 0.00 | 0.00 | 1.00 | 0.00 | 0.00 | 1.00 | 0.00 | 0.00 | 0 |
| 756 | 0.00 | 0.00 | 0.00 | 1.00 | 1.00 | 0.00 | 0.00 | 0.00 | 3 |
| 757 | 0.00 | 0.00 | 1.00 | 0.00 | 0.00 | 0.00 | 0.00 | 1.00 | 3 |
| 758 | 0.00 | 0.00 | 0.00 | 1.00 | 0.00 | 0.75 | 0.00 | 0.00 | 3 |
| 759 | 0.00 | 1.00 | 0.00 | 0.00 | 0.00 | 0.00 | 0.00 | 1.00 | 2 |
| 760 | 0.00 | 1.00 | 0.00 | 0.00 | 0.00 | 0.00 | 0.00 | 1.00 | 3 |
| 761 | 0.00 | 0.48 | 0.52 | 0.00 | 0.00 | 0.00 | 0.00 | 1.00 | 1 |
| 762 | 1.00 | 0.00 | 0.00 | 0.00 | 0.30 | 0.00 | 0.00 | 0.70 | 2 |
| 763 | 0.00 | 0.00 | 1.00 | 0.00 | 0.00 | 0.00 | 0.00 | 1.00 | 8 |
| 764 | 0.00 | 1.00 | 0.16 | 0.00 | 0.86 | 0.14 | 0.00 | 0.00 | 5 |
| 765 | 1.00 | 0.00 | 0.00 | 0.00 | 0.00 | 0.00 | 0.00 | 1.00 | 4 |

TABLE 1-continued

Differentially methylated regions (DMRs) associated breast cancer.

| | | | | | | | | | |
|---|---|---|---|---|---|---|---|---|---|
| 766 | 0.00 | 0.75 | 0.24 | 0.00 | 0.00 | 0.00 | 0.00 | 1.00 | 0 |
| 767 | 1.00 | 0.05 | 0.00 | 0.00 | 0.00 | 0.00 | 0.00 | 1.00 | 4 |
| 768 | 0.07 | 0.50 | 0.47 | 0.00 | 0.94 | 0.00 | 0.00 | 0.06 | 14 |
| 769 | 0.00 | 0.15 | 0.85 | 0.00 | 0.76 | 0.00 | 0.00 | 0.24 | 1 |
| 770 | 0.00 | 0.00 | 1.00 | 0.00 | 0.76 | 0.00 | 0.00 | 0.24 | 6 |
| 771 | 1.00 | 0.49 | 0.38 | 0.00 | 0.60 | 0.40 | 0.00 | 0.00 | 16 |
| 772 | 1.00 | 0.00 | 1.00 | 0.00 | 0.44 | 0.00 | 0.00 | 0.55 | 4 |
| 773 | 0.00 | 0.08 | 0.92 | 0.00 | 0.00 | 0.00 | 0.00 | 0.73 | 5 |
| 774 | 1.00 | 0.00 | 0.00 | 0.00 | 1.00 | 0.00 | 0.00 | 0.00 | 6 |
| 775 | 1.00 | 0.00 | 0.00 | 0.00 | 0.88 | 0.00 | 0.12 | 0.00 | 2 |
| 776 | 1.00 | 0.00 | 0.00 | 0.00 | 0.28 | 0.00 | 0.00 | 0.72 | 5 |
| 777 | 0.00 | 0.78 | 0.22 | 0.00 | 0.00 | 0.00 | 0.00 | 1.00 | 5 |
| 778 | 0.71 | 0.24 | 1.00 | 0.00 | 0.00 | 1.00 | 0.00 | 0.00 | 4 |
| 779 | 0.70 | 0.26 | 0.21 | 0.00 | 0.00 | 1.00 | 0.00 | 0.00 | 10 |
| 780 | 0.00 | 0.00 | 1.00 | 0.00 | 0.00 | 1.00 | 0.00 | 0.00 | 3 |
| 781 | 0.00 | 0.00 | 0.00 | 1.00 | 0.00 | 0.00 | 0.00 | 1.00 | 1 |
| 782 | 0.00 | 0.00 | 0.00 | 1.00 | 0.00 | 0.00 | 0.00 | 0.64 | 6 |
| 783 | 0.00 | 0.00 | 1.00 | 0.00 | 0.00 | 0.00 | 0.11 | 0.75 | 4 |
| 784 | 0.00 | 0.00 | 0.00 | 1.00 | 0.00 | 0.00 | 0.00 | 0.00 | 0 |
| 785 | 1.00 | 0.86 | 0.19 | 0.00 | 0.00 | 1.00 | 0.00 | 0.00 | 5 |
| 786 | 0.00 | 0.00 | 0.00 | 1.00 | 0.00 | 0.00 | 0.00 | 1.00 | 5 |
| 787 | 0.00 | 0.88 | 0.11 | 0.00 | 0.00 | 0.00 | 0.00 | 1.00 | 6 |
| 788 | 0.15 | 0.55 | 0.35 | 0.00 | 0.00 | 0.00 | 0.00 | 1.00 | 8 |
| 789 | 0.45 | 0.26 | 0.35 | 0.00 | 0.00 | 0.00 | 0.00 | 0.57 | 11 |
| 790 | 0.00 | 0.19 | 0.81 | 0.00 | 0.56 | 0.00 | 0.00 | 0.44 | 5 |
| 791 | 0.00 | 0.00 | 1.00 | 0.00 | 1.00 | 0.00 | 0.00 | 0.00 | 3 |
| 792 | 0.00 | 0.50 | 0.50 | 0.00 | 0.56 | 0.00 | 0.00 | 0.44 | 4 |
| 793 | 0.09 | 0.91 | 0.03 | 0.00 | 0.28 | 0.00 | 0.00 | 0.72 | 10 |
| 794 | 0.00 | 0.00 | 1.00 | 0.00 | 0.00 | 0.00 | 0.00 | 0.00 | 0 |
| 795 | 0.00 | 0.40 | 0.60 | 0.00 | 0.00 | 0.00 | 0.00 | 0.00 | 1 |
| 796 | 0.00 | 0.00 | 0.00 | 1.00 | 0.00 | 0.00 | 0.00 | 1.00 | 3 |
| 797 | 0.00 | 0.00 | 1.00 | 0.00 | 0.00 | 1.00 | 0.00 | 0.00 | 0 |
| 798 | 0.00 | 0.12 | 0.88 | 0.00 | 0.00 | 0.59 | 0.00 | 0.41 | 0 |
| 799 | 1.00 | 0.00 | 0.00 | 0.00 | 1.00 | 0.00 | 0.00 | 0.00 | 2 |
| 800 | 0.00 | 0.00 | 1.00 | 0.00 | 0.00 | 1.00 | 0.00 | 0.00 | 3 |
| 801 | 0.00 | 0.00 | 0.00 | 1.00 | 0.00 | 0.00 | 0.00 | 1.00 | 7 |
| 802 | 0.00 | 0.00 | 0.00 | 1.00 | 0.00 | 1.00 | 0.00 | 0.00 | 0 |
| 803 | 1.00 | 0.00 | 1.00 | 0.00 | 0.00 | 1.00 | 0.00 | 0.00 | 2 |
| 804 | 0.00 | 0.00 | 0.00 | 1.00 | 0.22 | 0.78 | 0.00 | 0.00 | 13 |
| 805 | 0.00 | 0.00 | 0.00 | 1.00 | 1.00 | 0.00 | 0.00 | 0.00 | 1 |
| 806 | 0.52 | 0.24 | 0.77 | 0.00 | 0.85 | 0.15 | 0.00 | 0.00 | 16 |
| 807 | 0.00 | 0.32 | 0.67 | 0.00 | 0.00 | 0.00 | 0.00 | 0.00 | 0 |
| 808 | 0.00 | 0.00 | 0.00 | 1.00 | 1.00 | 0.00 | 0.00 | 0.00 | 5 |
| 809 | 0.00 | 0.00 | 0.00 | 1.00 | 0.45 | 0.00 | 0.00 | 0.55 | 6 |
| 810 | 0.37 | 0.42 | 0.33 | 0.00 | 0.29 | 0.00 | 0.00 | 0.71 | 2 |
| 811 | 0.28 | 0.64 | 0.00 | 0.00 | 0.00 | 0.00 | 0.00 | 1.00 | 14 |
| 812 | 0.00 | 0.00 | 0.00 | 1.00 | 0.47 | 0.00 | 0.00 | 0.53 | 1 |
| 813 | 0.00 | 0.00 | 0.00 | 1.00 | 0.00 | 1.00 | 0.00 | 0.00 | 1 |
| 814 | 0.00 | 0.00 | 0.00 | 1.00 | 0.72 | 0.21 | 0.00 | 0.00 | 5 |
| 815 | 0.00 | 0.00 | 1.00 | 0.00 | 0.00 | 0.00 | 0.00 | 1.00 | 1 |
| 816 | 0.00 | 0.00 | 0.00 | 1.00 | 0.00 | 0.00 | 0.00 | 0.00 | 4 |
| 817 | 0.97 | 0.05 | 0.86 | 0.00 | 0.15 | 0.00 | 0.00 | 0.85 | 14 |
| 818 | 0.14 | 0.27 | 0.62 | 0.00 | 0.84 | 0.10 | 0.00 | 0.05 | 15 |
| 819 | 0.00 | 0.39 | 0.63 | 0.00 | 0.00 | 0.00 | 0.00 | 1.00 | 7 |
| 820 | 0.15 | 0.30 | 0.57 | 0.00 | 0.13 | 0.00 | 0.00 | 0.87 | 20 |
| 821 | 0.00 | 0.00 | 0.00 | 0.00 | 0.00 | 1.00 | 0.00 | 0.00 | 0 |
| 822 | 0.32 | 0.24 | 0.54 | 0.00 | 0.00 | 0.00 | 0.00 | 1.00 | 2 |
| 823 | 0.00 | 0.08 | 0.92 | 0.00 | 1.00 | 0.00 | 0.00 | 0.00 | 3 |
| 824 | 0.00 | 0.00 | 1.00 | 0.00 | 1.00 | 0.00 | 0.00 | 0.00 | 2 |
| 825 | 0.00 | 0.00 | 0.00 | 1.00 | 0.17 | 0.83 | 0.00 | 0.00 | 6 |
| 826 | 0.00 | 0.00 | 0.00 | 1.00 | 0.00 | 0.00 | 0.00 | 0.00 | 0 |
| 827 | 0.00 | 0.00 | 0.00 | 1.00 | 0.00 | 1.00 | 0.00 | 0.00 | 0 |
| 828 | 0.00 | 0.00 | 0.00 | 1.00 | 0.00 | 0.00 | 0.00 | 0.00 | 0 |
| 829 | 0.00 | 0.00 | 0.00 | 1.00 | 0.00 | 0.00 | 0.00 | 0.00 | 0 |
| 830 | 0.00 | 0.00 | 0.00 | 1.00 | 0.00 | 0.00 | 0.00 | 0.00 | 0 |
| 831 | 0.00 | 0.00 | 0.00 | 1.00 | 0.00 | 0.00 | 0.00 | 0.00 | 1 |
| 832 | 1.00 | 0.00 | 0.00 | 0.00 | 0.00 | 0.00 | 0.00 | 0.00 | 16 |
| 833 | 0.00 | 0.00 | 1.00 | 0.00 | 0.00 | 0.00 | 0.00 | 0.00 | 0 |
| 834 | 0.00 | 0.00 | 0.00 | 1.00 | 0.00 | 0.00 | 0.00 | 0.00 | 0 |
| 835 | 0.00 | 0.00 | 1.00 | 0.00 | 0.00 | 0.00 | 0.00 | 0.00 | 0 |
| 836 | 0.00 | 0.00 | 1.00 | 0.00 | 0.00 | 0.00 | 0.00 | 0.00 | 0 |
| 837 | 0.00 | 0.00 | 1.00 | 0.00 | 0.00 | 0.00 | 0.00 | 0.00 | 0 |
| 838 | 0.00 | 0.00 | 0.00 | 1.00 | 0.00 | 0.00 | 0.00 | 0.00 | 0 |
| 839 | 0.00 | 0.00 | 0.00 | 1.00 | 0.00 | 0.00 | 0.00 | 0.00 | 0 |
| 840 | 0.00 | 0.00 | 0.00 | 1.00 | 0.00 | 0.87 | 0.13 | 0.00 | 0 |
| 841 | 0.00 | 0.00 | 1.00 | 0.00 | 0.00 | 0.00 | 0.00 | 0.00 | 0 |
| 842 | 0.00 | 0.00 | 1.00 | 0.00 | 0.00 | 0.00 | 0.00 | 0.00 | 0 |
| 843 | 0.00 | 0.00 | 0.00 | 1.00 | 0.00 | 0.00 | 0.00 | 0.00 | 0 |

TABLE 1-continued

Differentially methylated regions (DMRs) associated breast cancer.

| | | | | | | | | | |
|---|---|---|---|---|---|---|---|---|---|
| 844 | 0.00 | 0.00 | 0.00 | 1.00 | 0.00 | 0.00 | 0.00 | 1.00 | 0 |
| 845 | 0.00 | 0.00 | 0.00 | 1.00 | 0.00 | 0.00 | 0.00 | 0.00 | 0 |
| 846 | 0.00 | 0.00 | 0.00 | 1.00 | 0.00 | 0.00 | 0.00 | 0.00 | 0 |
| 847 | 0.00 | 0.04 | 0.96 | 0.00 | 0.00 | 0.74 | 0.00 | 0.00 | 0 |
| 848 | 0.00 | 0.00 | 1.00 | 0.00 | 0.00 | 0.00 | 0.00 | 0.00 | 0 |
| 849 | 0.00 | 0.00 | 0.00 | 1.00 | 0.00 | 0.00 | 0.00 | 0.00 | 0 |
| 850 | 0.00 | 0.00 | 0.00 | 1.00 | 0.00 | 0.00 | 0.00 | 0.00 | 0 |
| 851 | 0.00 | 0.68 | 0.31 | 0.00 | 0.00 | 0.00 | 0.00 | 0.00 | 0 |
| 852 | 0.00 | 0.00 | 0.00 | 1.00 | 0.00 | 0.61 | 0.39 | 0.00 | 0 |
| 853 | 0.00 | 0.73 | 0.21 | 0.00 | 0.88 | 0.00 | 0.00 | 0.00 | 4 |
| 854 | 0.00 | 0.00 | 1.00 | 0.00 | 0.00 | 0.00 | 0.00 | 0.00 | 0 |
| 855 | 0.00 | 0.00 | 0.00 | 1.00 | 0.00 | 0.00 | 0.00 | 0.00 | 0 |
| 856 | 0.00 | 0.00 | 1.00 | 0.00 | 0.00 | 0.00 | 0.00 | 0.00 | 1 |
| 857 | 0.00 | 0.00 | 0.00 | 1.00 | 0.00 | 0.00 | 0.00 | 0.00 | 0 |
| 858 | 0.00 | 0.38 | 0.61 | 0.00 | 0.00 | 0.00 | 0.00 | 0.00 | 0 |
| 859 | 0.00 | 0.00 | 0.00 | 1.00 | 0.00 | 1.00 | 0.00 | 0.00 | 0 |
| 860 | 0.00 | 0.00 | 0.00 | 1.00 | 0.00 | 0.00 | 0.00 | 0.00 | 5 |
| 861 | 0.00 | 0.00 | 0.00 | 1.00 | 0.72 | 0.00 | 0.28 | 0.00 | 3 |
| 862 | 0.00 | 0.00 | 1.00 | 0.00 | 0.00 | 0.00 | 0.00 | 0.00 | 0 |
| 863 | 0.00 | 0.00 | 1.00 | 0.00 | 0.00 | 0.00 | 0.00 | 0.00 | 0 |
| 864 | 0.00 | 0.00 | 0.00 | 1.00 | 0.00 | 0.00 | 0.00 | 0.00 | 0 |
| 865 | 0.00 | 0.00 | 0.00 | 1.00 | 0.00 | 0.00 | 0.00 | 0.00 | 0 |

In one example, detecting increased methylation at any one or more of the DMRs set forth in rows 1-822 of Table 1 in a test sample relative to a reference level of methylation for the corresponding one or more DMRs is indicative of the subject having breast cancer. Alternatively, or in addition, detecting decreased methylation at any one or more of the DMRs set forth in rows 823-865 of Table 1 in a test sample relative to a reference level of methylation for the corresponding one or more DMRs is indicative of the subject having breast cancer.

Detecting differential methylation at a single CpG dinucleotide sequence within any one of the genomic regions defined in Table 1 may be indicative of the subject having breast cancer.

Alternatively, detecting differential methylation at two or more CpG dinucleotides within any genomic region defined in Table 1 may be indicative of the subject having breast cancer. For example, detecting differential methylation at two or more CpG dinucleotides, or three or more CpG dinucleotides, or four or more CpG dinucleotides, or five or more CpG dinucleotides, or six or more CpG dinucleotides, or seven or more CpG dinucleotides, or eight or more CpG dinucleotides, or nine or more CpG dinucleotides, or 10 or more CpG dinucleotides, or 20 or more CpG dinucleotides, or 30 or more CpG dinucleotides, or 40 or more CpG dinucleotides, or 50 or more CpG dinucleotides within a genomic region set forth in Table 1 may be indicative of the subject having breast cancer. The two or more CpG dinucleotides may be consecutive (i.e., contiguous) within a genomic region. Alternatively, the two or more CpG dinucleotides may not be consecutive (i.e., may not be contiguous) within any genomic region.

Detecting differential methylation of at least one CpG dinucleotide within two or more different genomic regions set forth in Table 1 may be indicative of the subject having breast cancer. For example, detecting differential methylation at a CpG dinucleotide within two or more, or three or more, or four or more, or five or more, or six or more, or seven or more, or eight or more, or nine or more, or 10 or more different genomic regions set forth in Table 1 may be indicative of the subject having breast cancer.

In one example, detecting differential methylation of at least one CpG dinucleotide residing within a CpG island defined in Table 1 is indicative of the subject having breast cancer. In this regard, Table 1 provides details of genomic regions residing in, or overlapping with, one or more CpG islands. Such genomic regions will be recognised by a person skilled in the art.

In another example, detecting differential methylation of at least one CpG dinucleotide residing within a CpG shore defined in Table 1 is indicative of the subject having breast cancer. In this regard, Table 1 provides details of genomic regions residing in, or overlapping with, a CpG shore. Such genomic regions will be recognised by a person skilled in the art.

In another example, detecting differential methylation of at least one CpG dinucleotide within one or more genomic regions defined in Table 1 associated with, or spanning, a promoter region e.g., such as a CpG island promoter of NPY, FERD3L, HMX2, SATB2 and/or C9orf125, is indicative of the subject having breast cancer.

In another example, detecting differential methylation of at least one CpG dinucleotide within one or more genomic regions defined in Table 1 associated with, or spanning, a transcription factor e.g., such as BARHL2, DLX6, OTX2, RUNX1T1 and/or TAC1, is indicative of the subject having breast cancer.

In another example, detecting differential methylation of at least one CpG dinucleotide within one or more genomic regions defined in Table 1 associated with, or spanning, a signalling pathway gene e.g., such as BADRB3, GHSR, NPY and/or ROBO3, is indicative of the subject having breast cancer.

In another example, detecting differential methylation of at least one CpG dinucleotide within one or more genomic regions defined in Table 1 associated with, or spanning, a promoter region e.g., such as in C9orf125, COL14A1, ENPP2, ERG2, PLD5, ROBO3, RUNX1T1, SEMA5A, TBX18, TSHZ3, ZBTB16, and/or ZNF208, is indicative of the subject having breast cancer. In certain examples, the promoter includes a mutation and is downregulated.

In another example, detecting differential methylation of at least one CpG dinucleotide within one or more genomic regions defined in Table 1 associated with, or spanning, a gene involved in the axon guidance pathway e.g., such as CRMP1, GDNF, GFRA1, MYL9, ROBO1, ROBO3 and/or SEMA5A, is indicative of the subject having breast cancer. For example, detecting hypermethylation of at least one CpG dinucleotide within one or more genomic regions defined in Table 1 associated with, or spanning, a gene involved in the axon guidance pathway e.g., such as CRMP1, GDNF, GFRA1, MYL9, ROBO1, ROBO3 and/or SEMA5A, is indicative of the subject having breast cancer.

It will be understood that the methods described herein encompass determining methylation status of any combination of CpG dinucleotide sequences in any combination of genomic regions set forth in Table 1, in any permutation. For example, the methods disclosed herein may comprise determining the methylation status of any one or more CpG dinucleotide sequences in any 2 or more, 3 or more, 4 or more, 5 or more, 10 or more, 20 or more, 30 or more, 40 or more, 50 or more, 60 or more, 70 or more, 80 or more, 90 or more, or 100 or more genomic regions set forth in Table 1, in any permutation. In this regard, the inventors have shown e.g., in Examples 5 and 6 herein, that small subsets of probes configured to detect differential methylation at CpG dinucleotide sequences within genomic regions set forth in Table 1 e.g., 2 or 3 or 4 or 5 probes, are capable of discriminating TNBC from non-TNBC with high sensitivity and specificity.

For example, a subset of probes configured to detect differential methylation at CpG dinucleotide sequences within the 2 or more, 3 or more, 4 or more, 5 or more, 10 or more, 20 or more, 30 or more, 40 or more, 50 or more, 60 or more, 70 or more, 80 or more, 90 or more, or 100 or more genomic regions set forth in Table 1 may include 1 or more, or 2 or more, or 3 or more, or 4 or more, or 5 or more, or 6 or more, or 7 or more or all probes selected from:
  cg0804822—promoter of ZNF671;
  cg09368188—intronic region of KIF26B;
  cg00421363—promoter region of PPFIA3;
  cg04781584—promoter region of PPFIA3;
  cg03559454—promoter region of PPFIA3;
  cg01926238—distant promoter of VGLL2;
  cg05650260—intronic region of TFAP2D; and
  cg04416734—exonic region of ALDOA.

Alternatively, or in addition, probes configured to detect differential methylation at CpG dinucleotide sequences within the 2 or more, 3 or more, 4 or more, 5 or more, 10 or more, 20 or more, 30 or more, 40 or more, 50 or more, 60 or more, 70 or more, 80 or more, 90 or more, or 100 or more genomic regions set forth in Table 1 may include 1 or more, or 2 or more, or 3 or more, or 4 or more, or 5 or more, or 6 or more, or 7 or more or all probes selected from:
  cg11977686—promoter of ZNF671
  cg13484549—promoter of PPFIA3
  cg08048222—promoter of ZNF671
  cg00421363—promoter of PPFIA3
  cg01926238—distant promoter of VGLL2
  cg08398233—intronic region of CAMK2N1
  cg07802350—distant promoter of HOXD13
  cg20095233—distant promoter of GFRA1
  cg13473196—intronic region of CKAP5

Generally, the greater the number of CpG dinucleotides assessed for methylation status, the more reliable the diagnosis and/or prognosis of the subject. Thus, the greater the number of genomic regions defined in Table 1 for which methylation status is determined in the methods disclosed herein, the more reliable the diagnosis or prognosis of the subject.

Particular individual CpG dinucleotides within any of the genomic regions identified in Table 1 may be particularly strong predictors of the presence of breast cancer, or of the presence of a particular subtype of breast cancer e.g., such as ER negative breast cancer or TNBC. For example, detecting differential methylation of a CpG dinucleotide sequence within the Wilms tumour protein (WT1) gene and/or its antisense counterpart, WT1-AS, e.g., such as within one or more of the DMRs designated chr11-1163, chr11-1210 and/or chr11-4047 (see, e.g., FIG. 3F), is predictive of the presence of breast cancer, including the presence of a TNBC.

Differential methylation of one or more CpG dinucleotides in any one of more of the genomic regions defined in Table 1 may alter expression of a gene within which a CpG resides. Accordingly, expression levels of genes associated with any of the genomic regions defined in Table 1 may be used as a predictor of the presence of breast cancer, or of the presence of a particular subtype of breast cancer e.g., such as ER negative breast cancer or TNBC.

The present disclosure also provides methods of diagnosing ER–ve breast cancer specifically, involving determining the methylation status of one or more CpG dinucleotide sequences within one or more genomic regions set forth in Table 1 in a test sample obtained from a subject, and identifying differential methylation at said one or more CpG dinucleotide sequences within one or more genomic regions in the test sample relative to a reference level of methylation for the corresponding one or more CpG dinucleotide sequences.

The present disclosure also provides methods of diagnosing triple negative breast cancer (TNBC) specifically, involving determining the methylation status of one or more CpG dinucleotides within one or more genomic regions set forth in Table 2 and/or Table 3 in a test sample obtained from a subject, and determining differential methylation of said one or more CpG dinucleotides at said one or more genomic regions in the test sample relative to a reference level of methylation for the corresponding one or more CpG dinucleotides at said one or more genomic regions.

Differential methylation of said one or more CpG dinucleotides within one or more of the genomics regions set forth in Table 2 relative to the reference level is indicative of the subject having TNBC. In this regard, Table 2 provides a list of 36 regions identified to be more methylated in tumours of TNBC breast cancer subtype as compared to tumours in other breast cancer subtypes. The genomic regions set forth in Table 2 are defined with reference to human genome assembly version 18 (hg18). For each DMR, the following information is provided in Table 2:
  (i) unique DMR identifier (Column 1);
  (ii) genomic coordinates of DMR with respect to hg18 (Columns 2-4);
  (iii) transcript IDs and gene names for regions overlapping RefSeq promoter and transcript body regions (Columns 5-6);
  (iv) whether the corresponding gene is up-/down-regulated in TNBC (Column 7);
  (v) expression percentile of the corresponding gene in normal samples (Column 8);
  (vi) overlap (fraction of the region overlapping the element) with various functional elements of the human genome (Columns 9-15);
  (vii) number of overlapping TNBC specific HM450K probes, probes showing statistically significant hypermethylation in TNBC tumours as compared to tumours of other breast cancer subtypes (Column 16);
  (viii) number of HM450K probes which are TNBC specific (Column 17); and (ix) number of HM450K probes with statistically significant association with poor/good prognosis in subjects with TNBC (Columns 18-19).

In one example, detecting differential methylation of at least one CpG dinucleotide residing within a CpG island defined in Table 2 is indicative of the subject having TNBC specifically, as opposed to other breast cancer subtypes. For example, Table 2 provides details of genomic regions residing in, or overlapping with, zinc finger proteins e.g., such as ZNF154 and/or ZNF671. Such genomic regions may be silenced as a result of methylation of the one or more CpG dinucleotides.

The present disclosure also provides methods of prognosis of, predicting the therapeutic outcome of, and/or monitoring progression of, triple negative breast cancer (TNBC) in a subject, comprising detecting the methylation status of one or more CpG dinucleotides within one or more genomic regions set forth in Table 3 in a test sample obtained from the subject, and determining differential methylation at said one or more genomic regions in the test sample relative to a reference level of methylation for the corresponding one or more CpG dinucleotides, wherein differential methylation at said one or more CpG dinucleotides within the genomic regions set forth in Table 3 relative to the reference level of methylation is correlated with a prognosis and/or a prediction of the therapeutic outcome of the TNBC.

For example, the prognosis performed in the methods disclosed herein may comprise determining a disease outcome in a subject suffering from TNBC. In this regard, Table 3 provides a list of 17 DMRs identified as being associated with disease outcome, such as an increased or decreased likelihood of survival, in TNBC. The genomic regions set forth in Table 3 are defined with reference to human genome assembly version 18 (hg18). For each DMR, the following information is provided in Table 3:
(i) DMR number and unique identifier (Columns 1-2);
(ii) genomic coordinates of DMR with respect to hg18 (Columns 3-5);
(iii) transcript IDs and gene names for regions overlapping RefSeq promoter and transcript body regions (Columns 6-7);
(iv) overlap (fraction of the region overlapping the element) with various functional elements of the human genome (Columns 8-17);
(v) number of overlapping TNBC specific HM450K probes, probes showing statistically significant hypermethylation in TNBC tumours as compared to tumours of other breast cancer subtypes (Column 18); and
(vi) number of HM450K probes with statistically significant association with poor/good prognosis in subjects with TNBC (Columns 19-20).

In one example, detecting differential methylation of at least one CpG dinucleotide within one or more genomic regions defined in Table 3 associated with or spanning a promoter e.g., such as a promoter of SLC6A3, C6orf174, WT1-AS and/or ZNF254, and/or associated with or spanning a gene body e.g., DMRTA2, LHX8, WT1, WT1-AS, HOXB13, ECEL1 and/or SOX2-OT, and/or associated with or spanning an intergenic region, is associated disease outcome, such as an increased or decreased likelihood of survival, in TNBC.

Table 14 provides an alternative list of 20 DMRs identified as being associated with disease outcome, such as an increased or decreased likelihood of survival, in TNBC. The genomic regions set forth in Table 14 are defined with reference to human genome assembly version 18 (hg18). For each DMR, the following information is provided in Table 3:
(i) chromosome (Column 1);
(ii) genomic coordinates of DMR with respect to hg18 (Columns 2-3);
(iii) region name (Column 4); and
(iv) associated Figure.

Accordingly, any of the methods disclosed herein may comprise detecting methylation status at one or more CpG dinucleotides within one or more regions set forth in Table 14.

TABLE 2

Differentially methylated regions (DMRs) associated with Triple Negative Breast Cancer (TN-BC).

| DMR unique identifier | Chromosome | start | end | RefSeq Promoter | RefSeq Body | Agilent TNBC Normal vs Tumor | Agilent TNBC Normal Percentile | RefSeq: % exon | RefSeq: % intron |
|---|---|---|---|---|---|---|---|---|---|
| chr1-19649 | 1 | 20,682,759 | 20,684,507 | | CAMK2N1 | No change | 75-100 | 0.15 | 0.85 |
| chr1-4856 | 1 | 103,346,188 | 103,347,175 | COL11A1 | COL11A1 | Up | 50-75 | 0.43 | 0.03 |
| chr1-38532 | 1 | 246,086,842 | 246,087,566 | TRIM58 | TRIM58 | No change | 0-25 | 0.61 | 0.00 |
| chr11-25406 | 11 | 31,775,677 | 31,779,112 | | PAX6 | No change | 0-25 | 0.05 | 0.95 |
| chr11-18108 | 11 | 31,802,820 | 31,804,364 | | RCN1 | No change | 50-75 | 0.00 | 1.00 |
| chr11-1210 | 11 | 32,416,010 | 32,417,947 | | WT1-AS | NA | NA | 1.00 | 0.00 |
| chr13-14599 | 13 | 111,756,947 | 111,759,018 | | | | | 0.00 | 0.00 |
| chr13-12246 | 13 | 111,759,028 | 111,761,130 | | | | | 0.00 | 0.00 |
| chr13-16458 | 13 | 111,764,441 | 111,766,059 | | | | | 0.00 | 0.00 |
| chr13-16371 | 13 | 111,806,052 | 111,808,603 | | | | | 0.00 | 0.00 |
| chr16-43017 | 16 | 6,009,572 | 6,010,985 | | RBFOX1 | NA | NA | 0.30 | 0.70 |
| chr18-245 | 18 | 53,255,803 | 53,260,282 | | ONECUT2 | Up | 0-25 | 0.00 | 1.00 |
| chr19-44228 | 19 | 3,385,736 | 3,386,568 | | NFIC | No change | 50-75 | 0.15 | 0.85 |
| chr19-36061 | 19 | 12,166,237 | 12,167,686 | | | | | 0.00 | 0.00 |
| chr19-14446 | 19 | 22,260,848 | 22,261,568 | ZNF729 | ZNF729 | NA | NA | 0.15 | 0.51 |
| chr19-36571 | 19 | 24,061,637 | 24,062,272 | ZNF254 | ZNF254 | No change | 50-75 | 0.26 | 0.46 |
| chr19-46114 | 19 | 54,337,512 | 54,338,223 | | PPFIA3 | Up | 0-25 | 0.28 | 0.72 |
| chr19-31544 | 19 | 62,911,410 | 62,912,734 | ZNF154 | ZNF154 | Down | 50-75 | 0.21 | 0.54 |
| chr19-6109 | 19 | 62,930,239 | 62,930,957 | ZNF671 | ZNF671 | Down | 75-100 | 0.33 | 0.46 |
| chr21-8209 | 21 | 36,989,873 | 36,993,170 | SIM2 | | up | 0-25 | 0.00 | 0.00 |
| chr3-18012 | 3 | 27,740,141 | 27,741,506 | EOMES | | No change | 75-100 | 0.00 | 0.00 |
| chr3-1810 | 3 | 132,563,160 | 132,564,028 | NR_002949 NR_027766 | NR_002949 NR_027766 NR_038976 | NA | NA | 0.69 | 1.00 |

TABLE 2-continued

Differentially methylated regions (DMRs) associated with Triple Negative Breast Cancer (TN-BC).

| DMR unique identifier | Chr | start | end | RefSeq Promoter | RefSeq Gene Body | Expression | Methylation | CpG Islands: % Island | CpG Islands: % shore |
|---|---|---|---|---|---|---|---|---|---|
| chr3-22112 | 3 | 148,624,151 | 148,625,148 | | | | | 0.00 | 0.00 |
| chr3-1158 | 3 | 173,648,106 | 173,650,702 | GHSR | GHSR | No change | 50-75 | 0.32 | 0.00 |
| chr6-3486 | 6 | 26,853,218 | 26,853,781 | | | | | 0.00 | 0.00 |
| chr6-7514 | 6 | 26,865,279 | 26,866,569 | | | | | 0.00 | 0.00 |
| chr6-25261 | 6 | 27,755,606 | 27,757,375 | | | | | 0.00 | 0.00 |
| chr6-15498 | 6 | 50,799,906 | 50,800,777 | | TFAP2D | NA | NA | 0.00 | 1.00 |
| chr6-1806 | 6 | 53,256,334 | 58,257,651 | | | | | 0.00 | 0.00 |
| chr6-28662 | 6 | 117,691,091 | 117,691,644 | VGLL2 | | Down | 50-75 | 0.00 | 0.00 |
| chr7-23113 | 7 | 24,290,275 | 24,291,795 | NPY | NPY | No change | 0-25 | 0.18 | 0.78 |
| chr8-19800 | 8 | 65,443,925 | 65,445,545 | | | | | 0.00 | 0.00 |
| chr8-15516 | 8 | 65,446,926 | 65,447,225 | NR_034102 | NR_034102 | NA | NA | 0.00 | 0.00 |
| chr8-8662 | 8 | 65,449,063 | 65,449,743 | | NR_034102 | NA | NA | 0.00 | 1.00 |
| chr8-3384 | 8 | 65,454,075 | 65,455,349 | MIR124-2 | MIR124-2 | NA | NA | 0.08 | 0.00 |
| chr8-17320 | 8 | 145,395,909 | 145,896,990 | | | | | 0.00 | 0.00 |

| DMR unique identifier | RefSeq: % intergenic | ChromHMM HMEC: % promoter | ChromHMM HMEC: % enhancer | ChromHMM HMEC: % insulator | ChromHMM HMEC: % polycomb | HM450K: number of probes | HM450K: TNBC Specific | HM450K: Bad Prognosis | HM450K: Good Prognosis |
|---|---|---|---|---|---|---|---|---|---|
| chr1-19649 | 0.00 | 1.00 | 0.00 | 0.00 | 0.00 | 8 | 3 | 0 | 0 |
| chr1-4856 | 0.00 | 0.00 | 0.22 | 0.00 | 0.00 | 8 | 3 | 0 | 0 |
| chr1-38532 | 0.00 | 0.00 | 0.00 | 0.00 | 0.00 | 9 | 6 | 0 | 0 |
| chr11-25406 | 0.00 | 0.23 | 0.00 | 0.00 | 0.77 | 22 | 5 | 0 | 0 |
| chr11-18108 | 0.00 | 0.00 | 0.00 | 0.00 | 1.00 | 8 | 3 | 2 | 0 |
| chr11-1210 | 0.00 | 0.00 | 0.00 | 0.00 | 1.00 | 10 | 3 | 4 | 0 |
| chr13-14599 | 1.00 | 0.00 | 0.00 | 0.00 | 1.00 | 8 | 3 | 0 | 0 |
| chr13-12246 | 1.00 | 0.00 | 0.00 | 0.00 | 1.00 | 9 | 4 | 0 | 0 |
| chr13-16458 | 1.00 | 0.00 | 0.00 | 0.00 | 1.00 | 7 | 4 | 0 | 0 |
| chr13-16371 | 1.00 | 0.00 | 0.00 | 0.00 | 0.71 | 10 | 3 | 0 | 0 |
| chr16-43017 | 0.00 | 0.00 | 0.00 | 0.00 | 0.00 | 5 | 3 | 0 | 0 |
| chr18-245 | 0.00 | 0.45 | 0.00 | 0.00 | 0.55 | 15 | 5 | 0 | 0 |
| chr19-44228 | 0.00 | 0.20 | 0.80 | 0.00 | 0.00 | 4 | 4 | 0 | 0 |
| chr19-36061 | 1.00 | 0.89 | 0.00 | 0.00 | 0.00 | 7 | 5 | 0 | 0 |
| chr19-14446 | 0.00 | 0.00 | 0.00 | 0.00 | 0.00 | 3 | 3 | 0 | 0 |
| chr19-36571 | 0.00 | 1.00 | 0.00 | 0.00 | 0.00 | 5 | 3 | 0 | 4 |
| chr19-46114 | 0.00 | 0.59 | 0.41 | 0.00 | 0.00 | 5 | 5 | 0 | 0 |
| chr19-31544 | 0.00 | 1.00 | 0.00 | 0.00 | 0.00 | 11 | 8 | 0 | 0 |
| chr19-6109 | 0.00 | 1.00 | 0.00 | 0.00 | 0.00 | 7 | 7 | 0 | 0 |
| chr21-8209 | 0.60 | 0.11 | 0.00 | 0.00 | 0.89 | 20 | 3 | 0 | 0 |
| chr3-18012 | 0.52 | 0.59 | 0.04 | 0.00 | 0.37 | 11 | 5 | 1 | 0 |
| chr3-1810 | 0.00 | 0.97 | 0.00 | 0.00 | 0.00 | 9 | 6 | 0 | 0 |
| chr3-22112 | 1.00 | 0.00 | 0.00 | 0.00 | 1.00 | 8 | 5 | 2 | 0 |
| chr3-1158 | 0.00 | 0.35 | 0.00 | 0.00 | 0.65 | 16 | 3 | 2 | 0 |
| chr6-3486 | 1.00 | 0.68 | 0.00 | 0.00 | 0.32 | 3 | 3 | 0 | 0 |
| chr6-7514 | 1.00 | 1.00 | 0.00 | 0.00 | 0.00 | 6 | 3 | 0 | 0 |
| chr6-25261 | 1.00 | 0.22 | 0.78 | 0.00 | 0.00 | 13 | 4 | 2 | 0 |
| chr6-15498 | 0.00 | 0.46 | 0.00 | 0.00 | 0.54 | 6 | 3 | 1 | 0 |
| chr6-1806 | 1.00 | 0.96 | 0.00 | 0.00 | 0.04 | 6 | 5 | 0 | 0 |
| chr6-28662 | 0.58 | 0.00 | 0.00 | 0.00 | 1.00 | 4 | 3 | 1 | 0 |
| chr7-23113 | 0.00 | 0.48 | 0.00 | 0.00 | 0.52 | 10 | 3 | 2 | 0 |
| chr8-19800 | 1.00 | 0.00 | 0.00 | 0.00 | 1.00 | 9 | 3 | 0 | 0 |
| chr8-15516 | 0.00 | 0.00 | 0.00 | 0.00 | 1.00 | 4 | 4 | 0 | 0 |
| chr8-8662 | 0.00 | 0.00 | 0.00 | 0.00 | 1.00 | 5 | 5 | 0 | 0 |
| chr8-3384 | 0.00 | 0.00 | 0.00 | 0.00 | 1.00 | 11 | 11 | 0 | 0 |
| chr8-17320 | 1.00 | 0.37 | 0.18 | 0.00 | 0.00 | 8 | 3 | 0 | 0 |

TABLE 3

Differentially methylated regions (DMRs) associated with overall survival in Triple Negative Breast Cancer (TNBC)

| Row No. | DMR unique identifier | Chromosome | start | end | RefSeq Promoter | RefSeq Gene Body | CpG Islands: % Island | CpG Islands: % shore |
|---|---|---|---|---|---|---|---|---|
| 1 | chr1-17872 | 1 | 50,658,646 | 50,659,783 | | DMRTA2 | 1.00 | 0.00 |
| 2 | chr1-47207 | 1 | 75,368,128 | 75,368,976 | | LHX8 | 0.41 | 0.59 |
| 3 | chr10-13741 | 10 | 102,409,068 | 102,409,766 | | | 0.75 | 0.25 |
| 4 | chr11-11623 | 11 | 32,404,535 | 32,407,465 | | WT1 | 0.51 | 0.49 |
| 5 | chr11-1210 | 11 | 32,416,010 | 32,417,947 | | WT1-AS | 0.45 | 0.55 |
| 6 | chr13-5199 | 13 | 27,398,788 | 27,401,867 | | | 0.30 | 0.70 |
| 7 | chr14-13134 | 14 | 56,330,541 | 56,332,135 | | | 0.78 | 0.22 |
| 8 | chr17-22033 | 17 | 44,159,065 | 44,159,578 | | HOXB13 | 0.41 | 0.59 |
| 9 | chr2-4402 | 2 | 233,058,433 | 233,060,592 | | ECEL1 | 0.96 | 0.04 |

TABLE 3-continued

Differentially methylated regions (DMRs) associated with overall survival in Triple Negative Breast Cancer (TNBC)

| | | | | | | | |
|---|---|---|---|---|---|---|---|
| 10 | chr3-13593 | 3 | 182,923,564 | 182,924,686 | | SOX2-OT | 0.00 0.00 |
| 11 | chr5-29013 | 5 | 1,498,811 | 1,499,696 | SLC6A3 | | 0.95 0.05 |
| 12 | chr6-21729 | 6 | 27,620,848 | 27,621,582 | | | 0.00 0.00 |
| 13 | chr6-24682 | 6 | 127,881,341 | 127,882,455 | C6orf174 | C6orf174 | 0.00 0.05 |
| 14 | chr7-22735 | 7 | 121,726,837 | 121,728,266 | | | 0.45 0.55 |
| 15 | chr11-4047 | chr11 | 32,413,697 | 32,415,714 | WT1 WT1-AS | WT1-AS | 0.09 0.91 |
| 16 | chr19-36571 | chr19 | 24,061,637 | 24,062,272 | ZNF254 | ZNF254 | 0.00 0.00 |
| 17 | chr22-16101 | chr22 | 44,641,414 | 44,642,542 | | | 0.88 0.12 |

| Row No. | RefSeq: % promoter | RefSeq: % exon | RefSeq: % intron | RefSeq: % intergenic | ChromHMM HMEC: % promoter | ChromHMM HMEC: % enhancer | ChromHMM HMEC: % insulator | ChromHMM HMEC: % polycomb | HM450K: Number of Probes | HM450K: Poor Prognosis | HM450K: Good Prognosis |
|---|---|---|---|---|---|---|---|---|---|---|---|
| 1 | 0.00 | 0.48 | 0.52 | 0.00 | 0.34 | 0.00 | 0.00 | 0.66 | 7 | 3 | |
| 2 | 0.00 | 0.56 | 0.44 | 0.00 | 0.00 | 0.00 | 0.00 | 1.00 | 4 | 3 | |
| 3 | 0.00 | 0.00 | 0.00 | 1.00 | 0.00 | 0.00 | 0.00 | 1.00 | 6 | 5 | |
| 4 | 0.00 | 0.08 | 0.92 | 0.00 | 0.00 | 0.00 | 0.00 | 1.00 | 15 | 5 | |
| 5 | 0.00 | 1.00 | 0.00 | 0.00 | 0.00 | 0.00 | 0.00 | 1.00 | 10 | 4 | |
| 6 | 0.00 | 0.00 | 0.00 | 0.46 | 0.00 | 0.00 | 0.00 | 1.00 | 14 | 4 | |
| 7 | 0.00 | 0.00 | 0.00 | 1.00 | 0.00 | 0.00 | 0.00 | 1.00 | 6 | 3 | |
| 8 | 0.00 | 0.66 | 0.34 | 0.00 | 0.00 | 0.00 | 0.00 | 1.00 | 4 | 3 | |
| 9 | 0.00 | 0.41 | 0.59 | 0.00 | 0.37 | 0.00 | 0.00 | 0.63 | 10 | 3 | |
| 10 | 0.00 | 0.00 | 1.00 | 0.00 | 0.00 | 0.00 | 0.00 | 1.00 | 8 | 4 | |
| 11 | 1.00 | 0.00 | 0.00 | 0.00 | 0.00 | 0.00 | 0.00 | 1.00 | 4 | 3 | |
| 12 | 0.00 | 0.00 | 0.00 | 1.00 | 0.75 | 0.00 | 0.00 | 0.00 | 8 | 3 | |
| 13 | 0.32 | 0.70 | 0.07 | 0.00 | 0.18 | 0.00 | 0.00 | 0.82 | 11 | 6 | |
| 14 | 0.00 | 0.00 | 0.00 | 0.00 | 0.00 | 0.00 | 0.00 | 1.00 | 8 | 4 | |
| 15 | 0.97 | 0.05 | 0.86 | 0.00 | 0.15 | 0.00 | 0.00 | 0.85 | 14 | | 5 |
| 16 | 0.44 | 0.26 | 0.46 | 0.00 | 1.00 | 0.00 | 0.00 | 0.00 | 5 | | 4 |
| 17 | 0.00 | 0.00 | 0.00 | 1.00 | 0.87 | 0.00 | 0.00 | 0.13 | 7 | | 3 |

Detecting differential methylation at a single CpG dinucleotide sequence within any one of the genomic regions defined in Table 3 may be predictive of an increased or a decreased likelihood of survival of the subject.

Similarly, detecting differential methylation at a single CpG dinucleotide sequence within any one of the genomic regions defined in Table 14 may be predictive of an increased or a decreased likelihood of survival of the subject. Examples of CpG dinucleotide sequences within the genomic regions defined in Table 14 which may be predictive of an increased or a decreased likelihood of survival of the subject are provided in Table 15. Thus, a method of predicting increased or a decreased likelihood of survival of a subject may comprise detecting methylation status of a single CpG dinucleotide sequence set forth in Table 15.

Alternatively, detecting differential methylation at any two or more CpG dinucleotides within any genomic region set forth in Table 3 may be predictive of an increased or a decreased likelihood of survival of the subject. For example, detecting differential methylation at two or more CpG dinucleotides, or three or more CpG dinucleotides, or four or more CpG dinucleotides, or five or more CpG dinucleotides, or six or more CpG dinucleotides, or seven or more CpG dinucleotides, or eight or more CpG dinucleotides, or nine or more CpG dinucleotides, or 10 or more CpG dinucleotides with a genomic region set forth in Table 3 may be predictive of an increased or a decreased likelihood of survival of the subject.

Similarly, detecting differential methylation at two or more CpG dinucleotide sequence within any one of the genomic regions defined in Table 14 may be predictive of an increased or a decreased likelihood of survival of the subject. For example, detecting differential methylation at two or more CpG dinucleotides, or three or more CpG dinucleotides, or four or more CpG dinucleotides, or five or more CpG dinucleotides, or six or more CpG dinucleotides, or seven or more CpG dinucleotides, or eight or more CpG dinucleotides, or nine or more CpG dinucleotides, or 10 or more CpG dinucleotides with a genomic region set forth in Table 14 may be predictive of an increased or a decreased likelihood of survival of the subject. Thus, a method of predicting increased or a decreased likelihood of survival of a subject may comprise detecting methylation status of two or more CpG dinucleotide sequences set forth in Table 15.

Alternatively or in addition, detecting differential methylation of at least one CpG dinucleotide within two or more different genomic regions set forth in Table 3 can be predictive of an increased or a decreased likelihood of survival of the subject. For example, detecting differential methylation at a CpG dinucleotide within two or more, or three or more, or four or more, or five or more, or six or more, or seven or more, or eight or more, or nine or more, or 10 or more different genomic regions set forth in Table 3 is predictive of an increased or a decreased likelihood of survival of the subject.

Alternatively or in addition, detecting differential methylation of at least one CpG dinucleotide within two or more different genomic regions set forth in Table 14 can be predictive of an increased or a decreased likelihood of survival of the subject. For example, detecting differential methylation at a CpG dinucleotide within two or more, or three or more, or four or more, or five or more, or six or more, or seven or more, or eight or more, or nine or more, or 10 or more different genomic regions set forth in Table 14 is predictive of an increased or a decreased likelihood of survival of the subject.

Generally, the greater the number of CpG dinucleotides assessed for methylation status, the more reliable the prognosis of the subject. Thus, the greater the number of genomic regions defined in Table 3 for which methylation status is determined in the methods disclosed herein, the more reliable the prognosis of the subject. Similarly, the greater the number of genomic regions defined in Table 14 for which methylation status is determined in the methods disclosed herein, the more reliable the prognosis of the subject.

Differential methylation of one or more CpG dinucleotides in any one of more of the genomics regions defined in Table 3 may alter expression of a gene within which a CpG resides. Accordingly, expression levels of genes associated with any of the genomic regions defined in Table 3 may be used to predict of an increased or a decreased likelihood of survival of the subject.

Similarly, differential methylation of one or more CpG dinucleotides in any one of more of the genomics regions defined in Table 14 may alter expression of a gene within which a CpG resides. Accordingly, expression levels of genes associated with any of the genomic regions defined in Table 14 may be used to predict of an increased or a decreased likelihood of survival of the subject.

In one example, detecting increased methylation e.g., such as hypermethylation, at one or more of the DMRs set forth in rows 1-14 of Table 3 for a test sample relative to a reference level of methylation for the corresponding one or more DMRs is predictive that the subject will have a decreased likelihood of survival relative to a subject in which the corresponding DMR(s) do not show increased methylation.

In another example, detecting decreased methylation e.g., such as hypomethylation, at one or more of the DMRs set forth in rows 15-17 of Table 3 for a test sample relative to a reference level of methylation for the corresponding one or more DMRs is predictive that the subject will have an increased likelihood of survival relative to a subject in which the corresponding DMR(s) do not show decreased methylation.

In a particularly preferred example, the method of prognosis disclosed herein comprises detecting differential methylation of a CpG dinucleotide sequence within the Wilms tumour protein (WT1) gene and/or its antisense counterpart, WT1-AS, For example, detecting increased methylation of a CpG dinucleotide sequence within one or more of the DMRs designated chr11-1163 and/or chr11-1210 relative to the reference levels of methylation for those genomic regions is predictive of a decreased likelihood of survival. Alternatively, detecting decreased methylation of a CpG dinucleotide sequence within the DMRs designated chr11-4047 relative to the reference level of methylation for that genomic region is predictive of an increased likelihood of survival.

Breast Cancer Subtypes

The present disclosure provides the diagnosis, prognosis, or prediction of therapeutic outcome of any breast cancer, or cancer caused by a malignant cell derived from a breast. Exemplary breast cancers include basal breast cancer, Her2 positive breast cancer, progesterone receptor positive breast cancer, estrogen receptor positive breast cancer, ductal carcinoma in situ, lobular carcinoma in situ, early breast cancer, invasive breast cancer, Paget's disease of the nipple, inflammatory breast cancer, locally advanced breast cancer and secondary breast cancer. Breast cancer may also be characterised according to various molecular subtypes which are typically categorized on an immunohistochemical basis. Exemplary molecular subtypes of breast cancer are as follows:
  (i) normal (ER+, PR+, HER2+, cytokeratin 5/6+, and HER1+);
  (ii) luminal A (ER+ and/or PR+, HER2-);
  (iii) luminal B (ER+ and/or PR+, HER2+);
  (iv) triple-negative (ER-, PR-, HER2-);
  (v) HER2+/ER- (ER-, PR-, and HER2+); and
  (vi) unclassified (ER-, PR-, HER2-, cytokeratin 5/6-, and HER1-).

Particular combinations of the DMRs identified herein may be particularly useful in the identification of any one or more of these known subtypes of breast cancer.

Diagnostic and/or Prognostic Assay Formats

1. Detection of Methylation of Nucleic Acid and Methods Therefor

The present inventors have identified differentially methylated regions (DMRs) in breast cancer cells compared to non-cancerous cells. The present inventors have also identified specific DMRs in breast cancer cells characterised as being ER-ve or TNBC compared to other breast cancer cells. Furthermore, the present inventors have demonstrated that a subset of DMRs identified in TNBC cells are capable of stratifying TNBC subtypes associated with distinct prognostic profiles e.g., populations of TNBC patients with high, medium or low risk disease outcomes. Accordingly, a method for detecting DMRs as described herein shall be taken to include detecting methylation status of CpG dinucleotide sequences in one or more genomic regions i.e., to determine whether or not a genomic region is differentially methylated relative to a reference level of methylation for the genomic region. Suitable methods for the detection of methylation status are known in the art and/or described herein.

The term "methylation" shall be taken to mean the addition of a methyl group by the action of a DNA methyl transferase enzyme to a CpG island of nucleic acid, e.g., genomic DNA. As described herein, there are several methods known to those skilled in the art for determining the level or degree of methylation of nucleic acid. By "differential methylation" of a nucleic acid it is meant that there is a deviation in the number of methylated CpG dinucleotides at a genomic region within the subject diagnosed compared to that detected within a corresponding genomic region in a suitable control sample i.e., which provides a reference level of methylation for that genomic region. The differentially methylated nucleic acid may have an increased level of methylation within a specific or defined region of nucleic acid e.g., such as hypermethylation, or a decreased level of methylation within a specific or defined region of nucleic acid e.g., such as hypomethylation.

The term "hypermethylation" shall be taken to mean that a plurality of CpG dinucleotides in a specific or defined region of nucleic acid are methylated relative to a reference level.

The term "hypomethylation" shall be taken to mean that a plurality of CpG dinucleotides in a specific or defined region of nucleic acid are unmethylated relative to a reference level.

The present disclosure is not to be limited by a precise number of methylated residues that are considered to be diagnostic of cancer in a subject or predictive of its outcome, because some variation between patient samples will occur. The present disclosure is also not limited by the specific positioning of the methylated residue within a DMR In one example, the degree of methylation in a subject is determined for one or more genomic regions set forth in Tables 1-3. In one example, the degree of methylation in a subject is determined for one or more genomic regions set forth in Table 1. In one example, the degree of methylation in a subject is determined for one or more genomic regions set forth in Table 2. In one example, the degree of methylation in a subject is determined for one or more genomic regions set forth in Table 3.

a) Probe or Primer Design and/or Production

Several methods described herein for the diagnosis and/or prognosis of breast cancer e.g., such as ER−ve breast cancer or TNBC, use one or more probes and/or primers to detect methylation at a genomic region. Methods for designing probes and/or primers for use in, for example, PCR or hybridization are known in the art and described, for example, in Dieffenbach and Dveksler (Eds) (In: PCR Primer: A Laboratory Manual, Cold Spring Harbor Laboratories, NY, 1995). Furthermore, several software packages are publicly available that design optimal probes and/or primers for a variety of assays, e.g. Primer 3 available from the Center for Genome Research, Cambridge, Mass., USA.

The potential use of the probe or primer should be considered during its design. For example, should the probe or primer be produced for use in, for example, a methylation specific PCR or ligase chain reaction (LCR) assay the nucleotide at the 3' end (or 5' end in the case of LCR) should correspond to a methylated nucleotide in a nucleic acid.

Probes and/or primers useful for detection of a marker associated with a cancer are assessed, for example, to determine those that do not form hairpins, self-prime or form primer dimers (e.g. with another probe or primer used in a detection assay).

Methods for producing/synthesizing a probe or primer of the present disclosure are known in the art. For example, oligonucleotide synthesis is described, in Gait (Ed) (In: Oligonucleotide Synthesis: A Practical Approach, IRL Press, Oxford, 1984). For example, a probe or primer may be obtained by biological synthesis (e.g. by digestion of a nucleic acid with a restriction endonuclease) or by chemical synthesis. For short sequences (up to about 100 nucleotides) chemical synthesis is preferable.

Other methods for oligonucleotide synthesis include, for example, phosphotriester and phosphodiester methods (Narang, et al. *Meth. Enzymol* 68: 90, 1979) and synthesis on a support (Beaucage, et al *Tetrahedron Letters* 22: 1859-1862, 1981) as well as phosphoramidate technique, Caruthers, M. H., et al., "Methods in Enzymology," Vol. 154, pp. 287-314 (1988), and others described in "Synthesis and Applications of DNA and RNA," S. A. Narang, editor, Academic Press, New York, 1987, and the references cited therein.

Probes comprising locked nucleic acid (LNA) are synthesized as described, for example, in Nielsen et al, *J. Chem. Soc. Perkin Trans.*, 1: 3423, 1997; Singh and Wengel, *Chem. Commun.* 1247, 1998. While, probes comprising peptide-nucleic acid (PNA) are synthesized as described, for example, in Egholm et al., *Am. Chem. Soc.*, 114: 1895, 1992; Egholm et al., *Nature*, 365: 566, 1993; and Orum et al., *Nucl. Acids Res.*, 21: 5332, 1993.

b) Methylation-Sensitive Endonuclease Digestion of DNA

In one example, the methylation status of one or more genomic regions in a sample is determined using a process comprising treating the nucleic acid with an amount of a methylation-sensitive restriction endonuclease enzyme under conditions sufficient for nucleic acid to be digested and then detecting the fragments produced. Exemplary methylation-sensitive endonucleases include, for example, HpaI or HpaII.

In one example, the digestion of nucleic acid is detected by selective hybridization of a probe or primer to the undigested nucleic acid. Alternatively, the probe selectively hybridizes to both digested and undigested nucleic acid but facilitates differentiation between both forms, e.g., by electrophoresis. Suitable detection methods for achieving selective hybridization to a hybridization probe include, for example, Southern or other nucleic acid hybridization (Kawai et al., *Mol. Cell. Biol.* 14, 7421-7427, 1994; Gonzalgo et al., *Cancer Res.* 57, 594-599, 1997).

The term "selectively hybridizable" means that the probe is used under conditions where a target nucleic acid hybridizes to the probe to produce a signal that is significantly above background (i.e., a high signal-to-noise ratio). The intensity of hybridization is measured, for example, by radiolabeling the probe, e.g. by incorporating $[\alpha\text{-}^{35}S]$ and/or $[\alpha\text{-}^{32}P]$dNTPs, $[\gamma\text{-}^{32}P]$ATP, biotin, a dye ligand (e.g., FAM or TAMRA), a fluorophore, or other suitable ligand into the probe prior to use and then detecting the ligand following hybridization.

The skilled artisan will be aware that optimum hybridization reaction conditions should be determined empirically for each probe, although some generalities can be applied. Preferably, hybridizations employing short oligonucleotide probes are performed at low to medium stringency.

For the purposes of defining the level of stringency to be used in these diagnostic assays, a low stringency is defined herein as being a hybridization and/or a wash carried out in about 6×SSC buffer and/or about 0.1% (w/v) SDS at about 28° C. to about 40° C., or equivalent conditions. A moderate stringency is defined herein as being a hybridization and/or washing carried out in about 2×SSC buffer and/or about 0.1% (w/v) SDS at a temperature in the range of about 45° C. to about 65° C., or equivalent conditions.

In the case of a GC rich probe or primer or a longer probe or primer a high stringency hybridization and/or wash is preferred. A high stringency is defined herein as being a hybridization and/or wash carried out in about 0.1×SSC buffer and/or about 0.1% (w/v) SDS, or lower salt concentration, and/or at a temperature of at least 65° C., or equivalent conditions. Reference herein to a particular level of stringency encompasses equivalent conditions using wash/hybridization solutions other than SSC known to those skilled in the art.

Generally, the stringency is increased by reducing the concentration of SSC buffer, and/or increasing the concentration of SDS and/or increasing the temperature of the hybridization and/or wash. Those skilled in the art will be aware that the conditions for hybridization and/or wash may vary depending upon the nature of the hybridization matrix used to support the sample DNA, and/or the type of hybridization probe used and/or constituents of any buffer used in a hybridization. For example, formamide reduces the melting temperature of a probe or primer in a hybridization or an amplification reaction.

Conditions for specifically hybridizing nucleic acid, and conditions for washing to remove non-specific hybridizing nucleic acid, are understood by those skilled in the art. For the purposes of further clarification only, reference to the parameters affecting hybridization between nucleic acid molecules is found in Ausubel et al. (Current Protocols in Molecular Biology, Wiley Interscience, ISBN 047150338, 1992), which is herein incorporated by reference.

In accordance with the present example, a difference in the fragments produced for the test sample and a control sample is indicative of the subject having breast cancer. Similarly, in cases where the control sample comprises data from a tumor, cancer tissue, a cancerous cell or pre-cancerous cell e.g., such as from a subject having breast cancer, similarity, albeit not necessarily absolute identity, between the test sample and the control sample is indicative of a positive diagnosis i.e. breast cancer.

In an alternative example, the fragments produced by the restriction enzyme are detected using an amplification system, such as, for example, polymerase chain reaction (PCR), rolling circle amplification (RCA), inverse polymerase chain reaction (iPCR), in situ PCR (Singer-Sam et al., *Nucl. Acids Res.* 18, 687,1990), strand displacement amplification (SDA) or cycling probe technology.

Methods of PCR are known in the art and described, for example, by McPherson et al., PCR: A Practical Approach. (series eds, D. Rickwood and B. D. Hames), IRL Press Limited, Oxford. pp1-253, 1991 and by Dieffenbach (ed) and Dveksler (ed) (In: PCR Primer: A Laboratory Manual, Cold Spring Harbour Laboratories, NY, 1995), the contents of which are each incorporated in their entirety by way of reference. Generally, for PCR two non-complementary nucleic acid primer molecules comprising at least about 18 nucleotides in length, and more preferably at least 20-30 nucleotides in length are hybridized to different strands of a nucleic acid template molecule at their respective annealing sites, and specific nucleic acid molecule copies of the template that intervene the annealing sites are amplified enzymatically. Amplification products may be detected, for example, using electrophoresis and detection with a detectable marker that binds nucleic acids. Alternatively, one or more of the oligonucleotides are labeled with a detectable marker (e.g. a fluorophore) and the amplification product detected using, for example, a lightcycler (Perkin Elmer, Wellesley, Mass., USA).

Strand displacement amplification (SDA) utilizes oligonucleotide primers, a DNA polymerase and a restriction endonuclease to amplify a target sequence. The oligonucleotides are hybridized to a target nucleic acid and the polymerase is used to produce a copy of the region intervening the primer annealing sites. The duplexes of copied nucleic acid and target nucleic acid are then nicked with an endonuclease that specifically recognizes a sequence at the beginning of the copied nucleic acid. The DNA polymerase recognizes the nicked DNA and produces another copy of the target region at the same time displacing the previously generated nucleic acid. The advantage of SDA is that it occurs in an isothermal format, thereby facilitating high-throughput automated analysis.

Cycling Probe Technology uses a chimeric synthetic primer that comprises DNA-RNA-DNA that is capable of hybridizing to a target sequence. Upon hybridization to a target sequence the RNA-DNA duplex formed is a target for RNaseH thereby cleaving the primer. The cleaved primer is then detected, for example, using mass spectrometry or electrophoresis.

For primers that flank, or which are adjacent tom a methylation-sensitive endonuclease recognition site, it is preferred that such primers flank only those sites that are hypermethylated in the cancer to ensure that a diagnostic and/or prognostic amplification product is produced. In this regard, an amplification product will only be produced when the restriction site is not cleaved i.e., when it is methylated. Accordingly, detection of an amplification product indicates that the CpG dinucleotide/s of interest is/are methylated.

This form of analysis may be used to determine the methylation status of a plurality of CpG dinucleotides within a genomic region provided that each dinucleotide is within a methylation sensitive restriction endonuclease site.

In these methods, one or more of the primers may be labeled with a detectable marker to facilitate rapid detection of amplified nucleic acid, for example, a fluorescent label (e.g. Cy5 or Cy3) or a radioisotope (e.g. $^{32}$P).

The amplified nucleic acids are generally analyzed using, for example, non-denaturing agarose gel electrophoresis, non-denaturing polyacrylamide gel electrophoresis, mass spectrometry, liquid chromatography (e.g. HPLC or dHPLC), or capillary electrophoresis. (e.g. MALDI-TOF). High throughput detection methods, such as, for example, matrix-assisted laser desorption/ionization time of flight (MALDI-TOF), electrospray ionization (ESI), mass spectrometry (including tandem mass spectrometry, e.g. LC MS/MS), biosensor technology, evanescent fiber-optics technology or DNA chip technology (e.g., WO98/49557; WO 96/17958; Fodor et al., *Science* 767-773, 1991; U.S. Pat. Nos. 5,143,854; and 5,837,832, the contents of which are all incorporated herein by reference).

Alternatively, amplification of a nucleic acid may be continuously monitored using a melting curve analysis method as described herein and/or in, for example, U.S. Pat. No. 6,174,670, which is incorporated herein by reference.

c) Selective Mutagenesis of Non-Methylated DNA

In an alternative example of the present disclosure, the methylation status of a genomic region in a subject sample is determined using a process comprising treating the nucleic acid with an amount of a compound that selectively mutates a non-methylated cytosine residue within a CpG dinucleotide under conditions sufficient to induce mutagenesis.

Exemplary compounds mutate cytosine to uracil or thymidine, such as, for example, a salt of bisulfite, e.g., sodium bisulfite or potassium bisulfite (Frommer et al., *Proc. Natl. Acad. Sci. USA* 89, 1827-1831, 1992). Bisulfite treatment of DNA is known to distinguish methylated from non-methylated cytosine residues, by mutating cytosine residues that are not protected by methylation, including cytosine residues that are not within a CpG dinucleotide or that are positioned within a CpG dinucleotide that is not subject to methylation.

(i) Sequence Based Detection

In one example, the presence of one or more mutated nucleotides in a genomic region or the number of mutated sequences in a sample is determined by sequencing mutated DNA. One form of analysis comprises amplifying mutated nucleic acid or methylated nucleic acid using an amplification reaction described herein, for example, PCR. The amplified product is then directly sequenced or cloned and the cloned product sequenced. Methods for sequencing DNA are known in the art and include for example, the dideoxy chain termination method or the Maxam-Gilbert method (see Sambrook et al., Molecular Cloning, A Laboratory Manual (2nd Ed., CSHP, New York 1989) or Zyskind et al., Recombinant DNA Laboratory Manual, (Acad. Press, 1988)).

As the treatment of nucleic acid with a compound, such as, for example, bisulfite results in non-methylated cytosines being mutated to uracil or thymidine, analysis of the sequence determines the presence or absence of a methylated nucleotide. For example, by comparing the sequence obtained using a control sample or a sample that has not been treated with bisulfite, or the known nucleotide sequence of the region of interest with a treated sample facilitates the detection of differences in the nucleotide sequence. Any thymine residue detected at the site of a cytosine in the treated sample compared to a control or untreated sample may be considered to be caused by mutation as a result of bisulfite treatment. Suitable methods for the detection of methylation using sequencing of bisulfite treated nucleic acid are described, for example, in Frommer et al., *Proc. Natl. Acad. Sci. USA* 89: 1827-1831, 1992 or Clark et al., *Nucl. Acids Res.* 22: 2990-2997, 1994. One example of a commercially available kit for carrying out such methods is the CpGenome™ DNA modification Kit (Millipore). Other suitable kits are available from MDX Health SA (Belgium).

In another example, the presence of a mutated or non-mutated nucleotide in a bisulfite treated sample is detected using pyrosequencing, such as, for example, as described in Uhlmann et al., *Electrophoresis,* 23: 4072-4079, 2002. Essentially this method is a form of real-time sequencing that uses a primer that hybridizes to a site adjacent or close to the site of a cytosine that is methylated in a cancer cell. Following hybridization of the primer and template in the presence of a DNA polymerase each of four modified deoxynucleotide triphosphates are added separately according to a predetermined dispensation order. Only an added nucleotide that is complementary to the bisulfite treated sample is incorporated and inorganic pyrophosphate (PPi) is liberated. The PPi then drives a reaction resulting in production of detectable levels of light. Such a method allows determination of the identity of a specific nucleotide adjacent to the site of hybridization of the primer.

A related method for determining the sequence of a bisulfite treated nucleotide is methylation-sensitive single nucleotide primer extension (Me-SnuPE) or SNaPmeth. Suitable methods are described, for example, in Gonzalgo and Jones *Nucl. Acids Res.,* 25: 2529-2531 or Uhlmann et al., *Electrophoresis,* 23: 4072-4079, 2002.

Clearly other high throughput sequencing methods are encompassed by the present disclosure. Such methods include, for example, solid phase minisequencing (as described, for example, in Syvämen et al, *Genomics,* 13: 1008-1017, 1992), or minisequencing with FRET (as described, for example, in Chen and Kwok, *Nucleic Acids Res.* 25: 347-353, 1997).

(ii) Restriction Endonuclease-Based Assay Format

In one example, the presence of a non-mutated nucleic sequence is detected using combined bisulfite restriction analysis (COBRA) essentially as described in Xiong and Laird, *Nucl. Acids Res.,* 25: 2532-2534, 2001. This method exploits the differences in restriction enzyme recognition sites between methylated and unmethylated nucleic acid after treatment with a compound that selectively mutates a non-methylated cytosine residue, e.g., bisulfite.

Following bisulfite treatment a region of interest comprising one or more CpG dinucleotides that are methylated in a cancer cell and are included in a restriction endonuclease recognition sequence is amplified using an amplification reaction described herein, e.g., PCR. The amplified product is then contacted with the restriction enzyme that cleaves at the site of the CpG dinucleotide for a time and under conditions sufficient for cleavage to occur. A restriction site may be selected to indicate the presence or absence of methylation. For example, the restriction endonuclease TaqI cleaves the sequence TCGA, following bisulfite treatment of a non-methylated nucleic acid the sequence will be TTGA and, as a consequence, will not be cleaved. The digested and/or non-digested nucleic acid is then detected using a detection means known in the art, such as, for example, electrophoresis and/or mass spectrometry. The cleavage or non-cleavage of the nucleic acid is indicative of cancer in a subject.

Clearly, this method may be employed in either a positive read-out or negative read-out system for the diagnosis of a cancer.

(iii) Positive Read-Out Assay Format

In one example, the assay format of the disclosure comprises a positive read-out system in which DNA from a cancer sample e.g., breast cancer, that has been treated, for example, with bisulfite is detected as a positive signal. For example, the non-hypermethylated DNA from a healthy or normal control subject is not detected or only weakly detected.

In one example, the enhanced methylation in a subject sample is determined using a process comprising:
(i) treating the nucleic acid with an amount of a compound that selectively mutates a non-methylated cytosine residue under conditions sufficient to induce mutagenesis thereby producing a mutated nucleic acid;
(ii) hybridizing a nucleic acid to a probe or primer comprising a nucleotide sequence that is complementary to a sequence comprising a methylated cytosine residue under conditions such that selective hybridization to the non-mutated nucleic acid occurs; and
(iii) detecting the selective hybridization.

In this context, the term "selective hybridization" means that hybridization of a probe or primer to the non-mutated nucleic acid occurs at a higher frequency or rate, or has a higher maximum reaction velocity, than hybridization of the same probe or primer to the corresponding mutated sequence. Preferably, the probe or primer does not hybridize or detectably hybridize (e.g., does not hybridize at a level significantly above background) to the non-methylated sequence carrying the mutation(s) under the reaction conditions used.

In one example, the hybridization is detected using Southern, dot blot, slot blot or other nucleic acid hybridization means (Kawai et al., *Mol. Cell. Biol.* 14, 7421-7427, 1994; Gonzalgo et al., *Cancer Res.* 57, 594-599, 1997). Subject to appropriate probe selection, such assay formats are generally described herein above and apply mutatis mutandis to the presently described selective mutagenesis approach.

In one example, a ligase chain reaction format is employed to distinguish between a mutated and non-mutated nucleic acid. Ligase chain reaction (described in EP 320,308 and U.S. Pat. No. 4,883,750) uses at least two oligonucleotide probes that anneal to a target nucleic acid in such a way that they are juxtaposed on the target nucleic acid such that they can be linked using a ligase. The probes that are not ligated are removed by modifying the hybridization stringency. In this respect, probes that have not been ligated will selectively hybridize under lower stringency hybridization conditions than probes that have been ligated. Accordingly, the stringency of the hybridization can be increased to a stringency that is at least as high as the stringency used to hybridize the longer probe, and preferably at a higher stringency due to the increased length contributed by the shorter probe following ligation. One exemplary method melts the target-probe duplex, elute the dissociated probe and confirm that is has been ligated, e.g., by determining its length using electrophoresis, mass spectrometry, nucleotide sequence analysis, gel filtration, or other means known to the skilled artisan.

Methylation specific microarrays (MSO) are also useful for differentiating between a mutated and non-mutated sequence. A suitable method is described, for example, in Adorján et al, *Nucl. Acids Res.,* 30: e21, 2002. MSO uses nucleic acid that has been treated with a compound that selectively mutates a non-methylated cytosine residue (e.g., bisulfite) as template for an amplification reaction that amplifies both mutant and non-mutated nucleic acid. The amplification is performed with at least one primer that comprises a detectable label, such as, for example, a fluorophore, e.g., Cy3 or Cy5. The labeled amplification products are then hybridized to oligonucleotides on the microarray under conditions that enable detection of single nucleotide differences. Following washing to remove unbound amplification product, hybridization is detected using, for example, a microarray scanner. Not only does this method allow for determination of the methylation status of a large number of CpG dinucleotides, it is also semi-quantitative, enabling determination of the degree of methylation at each CpG dinucleotide analyzed. As there may be some degree of heterogeneity of methylation in a single sample, such quantification may assist in the diagnosis of cancer.

In an alternative example, the hybridization is detected using an amplification system. In methylation-specific PCR formats (MSP; Herman et al. *Proc. Natl. Acad. Sci. USA* 93: 9821-9826, 1992), the hybridization is detection using a process comprising amplifying the bisulfite-treated DNA. By using one or more probe or primer that anneals specifically to the unmutated sequence under moderate and/or high stringency conditions an amplification product is only produced using a sample comprising a methylated nucleotide.

Any amplification assay format described herein can be used, such as, for example, polymerase chain reaction (PCR), rolling circle amplification (RCA), inverse polymerase chain reaction (iPCR), in situ PCR (Singer-Sam et al., Nucl. Acids Res. 18, 687, 1990), strand displacement amplification, or cycling probe technology.

PCR techniques have been developed for detection of gene mutations (Kuppuswamy et al., *Proc. Natl. Acad. Sci. USA* 88:1143-1147, 1991) and quantitation of allelic-specific expression (Szabo and Mann, *Genes Dev.* 9: 3097-3108, 1995; and Singer-Sam et al., *PCR Methods Appl.* 1: 160-163, 1992). Such techniques use internal primers, which anneal to a PCR-generated template and terminate immediately 5' of the single nucleotide to be assayed. Such as format is readily combined with ligase chain reaction as described herein above.

Methylation-specific melting-curve analysis (essentially as described in Worm et al., *Clin. Chem.*, 47: 1183-1189, 2001) is also contemplated by the present disclosure. This process exploits the difference in melting temperature in amplification products produced using bisulfite treated methylated or unmethylated nucleic acid. In essence, non-discriminatory amplification of a bisulfite treated sample is performed in the presence of a fluorescent dye that specifically binds to double stranded DNA (e.g., SYBR Green I). By increasing the temperature of the amplification product while monitoring fluorescence the melting properties and thus the sequence of the amplification product is determined. A decrease in the fluorescence reflects melting of at least a domain in the amplification product. The temperature at which the fluorescence decreases is indicative of the nucleotide sequence of the amplified nucleic acid, thereby permitting the nucleotide at the site of one or more CpG dinucleotides to be determined. As the sequence of the nucleic acids amplified using the present disclosure The present disclosure also encompasses the use of real-time quantitative forms of PCR, such as, for example, TaqMan (Holland et al., Proc. Natl Acad. Sci. USA, 88, 7276-7280, 1991; Lee et al., Nucleic Acid Res. 21, 3761-3766, 1993) to perform this embodiment. For example, the MethylLight method of Eads et al., Nucl. Acids Res. 28: E32, 2000 uses a modified TaqMan assay to detect methylation of a CpG dinucleotide.

Alternatively, rather than using a labeled probe that requires cleavage, a probe, such as, for example, a Molecular Beacon™ is used (see, for example, Mhlang and Malmberg, *Methods* 25: 463-471, 2001). Molecular beacons are single stranded nucleic acid molecules with a stem-and-loop structure. The loop structure is complementary to the region surrounding the one or more CpG dinucleotides that are methylated in a cancer sample and not in a control sample. The stem structure is formed by annealing two "arms" complementary to each other, which are on either side of the probe (loop). A fluorescent moiety is bound to one arm and a quenching moiety that suppresses any detectable fluorescence when the molecular beacon is not bound to a target sequence is bound to the other arm. Upon binding of the loop region to its target nucleic acid the arms are separated and fluorescence is detectable. However, even a single base mismatch significantly alters the level of fluorescence detected in a sample. Accordingly, the presence or absence of a particular base is determined by the level of fluorescence detected. Such an assay facilitates detection of one or more unmutated sites (i.e. methylated nucleotides) in a nucleic acid.

As exemplified herein, another amplification based assay useful for the detection of a methylated nucleic acid following treatment with a compound that selectively mutates a non-methylated cytosine residue makes use of headloop PCR technology (e.g., as described in published PCT Application No. PCT/AU03/00244; WO 03/072810). This form of amplification uses a probe or primer that comprises a region that binds to a nucleic acid and is capable of amplifying nucleic acid in an amplification reaction whether the nucleic acid is methylated or not. The primer additionally comprises a region that is complementary to a portion of the amplified nucleic acid enabling this region of the primer to hybridize to the amplified nucleic acid incorporating the primer thereby forming a hairpin. The now 3' terminal nucleotide/s of the annealed region (i.e. the most 5° nucleotide's of the primer) hybridize to the site of one or more mutated cytosine residues (i.e., unmethylated in nucleic acid from a cancer subject). Accordingly, this facilitates self priming of amplification products from unmethylated nucleic acid, the thus formed hairpin structure blocking further amplification of this nucleic acid. In contrast, the complementary region may or may not by capable of hybridizing to an amplification product from methylated (mutated) nucleic acid, but is unable to "self prime" thereby enabling further amplification of this nucleic acid (e.g., by the inability of the now 3' nucleotide to hybridize to the amplification product). This method may be performed using a melting curve analysis method to determine the amount of methylated nucleic acid in a biological sample from a subject.

Other amplification based methods for detecting methylated nucleic acid following treatment with a compound that selectively mutates a non-methylated cytosine residue include, for example, methylation-specific single stranded conformation analysis (MS-SSCA) (Bianco et al., *Hum. Mutat.*, 14: 289-293, 1999), methylation-specific denaturing gradient gel electrophoresis (MS-DGGE) (Abrams and Stanton, *Methods Enzymol.*, 212: 71-74, 1992) and methylation-specific denaturing high-performance liquid chromatography (MS-DHPLC) (Deng et al, *Chin. J. Cancer Res.*, 12: 171-191, 2000). Each of these methods use different techniques for detecting nucleic acid differences in an amplification product based on differences in nucleotide sequence and/or secondary structure. Such methods are clearly contemplated by the present disclosure.

(iv) Negative Read-Out Assays

In an alternative example, the assay format comprises a negative read-out system in which reduced methylation of DNA from a healthy/normal control sample is detected as a positive signal and preferably, methylated DNA from a cancer sample e.g., a breast cancer sample, is not detected or is only weakly detected.

In one example, the reduced methylation is determined using a process comprising:
(i) treating the nucleic acid with an amount of a compound that selectively mutates a non-methylated cytosine residue within a CpG island under conditions sufficient to induce mutagenesis thereby producing a mutated nucleic acid;
(ii) hybridizing the nucleic acid to a probe or primer comprising a nucleotide sequence that is complementary to a sequence comprising the mutated cytosine residue under conditions such that selective hybridization to the mutated nucleic acid occurs; and
(iii) detecting the selective hybridization.

In this context, the term "selective hybridization" means that hybridization of a probe or primer to the mutated nucleic acid occurs at a higher frequency or rate, or has a higher maximum reaction velocity, than hybridization of the same probe or primer to the corresponding non-mutated sequence. In one example, the probe or primer does not hybridize or detectably hybridize to the methylated sequence (or non-mutated sequence) under the reaction conditions used.

The skilled artisan will be able to adapt a positive read-out assay described above to a negative read-out assay, e.g., by producing a probe or primer that selectively hybridizes to non-mutated DNA rather than mutated DNA.

d) Additional Method Steps

The methods disclosed herein may further comprise one or more steps of enriching methylated DNA in a sample. Thus, the methods disclosed herein may further comprise one or more steps of isolating methylated DNA from a sample. The enrichment/isolation step may be performed prior to or concomitant with any other step in the method for detecting the level of methylation of a marker as disclosed herein.

Any suitable enriching/isolating step known in the art may be used. For example, the methods disclosed herein may comprise a step of enriching methylated DNA in a sample using a commercially available kit such as the CpG MethylQuest DNA Isolation Kit (Millipore), which provides a recombinant protein comprising the methyl binding domain (MBD) of the mouse MBD2b protein fused to a glutathione-S-transferase (GST) protein from *S. japonicum* via a linker containing a thrombin cleavage site, the recombinant protein being immobilized to a magnetic bead. The MBD binds to methylated CpG sites with high affinity and in a sequence-independent manner, thereby allowing enrichment of methylated DNA in a sample.

It will be appreciated that alternative or additional methods known in the art for enrichment/isolation of methylated DNA in a sample can be used in the methods disclosed herein. For example, methods of enrichment/isolation of methylated DNA in a sample are described in Hsu et al., (2014) *Methods Mol Biol*, 1105:61-70, Serre et al., (2010) *Nucleic Acids Res*, 38:391-399, Rauch and Pfeifer (2005) *Lab Invest*, 85:1172-1180, Nair et al., (2011) *Epigenetics*, 6:34-44; and Robinson et al., (2010) *Genome Res*, 20:1719-1729.

A method disclosed herein according to any example may also comprise selecting a patient based on the result of a method disclosed herein and performing an additional diagnostic method or recommending performance of an additional diagnostic method. For example, for a patient diagnosed as suffering from breast cancer, the additional diagnostic method may be an ultrasound or a biopsy.

2. Detection of Reduced Gene Expression

Since methylation of a nucleic acid sequence affects its expression, the present inventors have also demonstrated that the level of expression of nucleic acids within any of a number of genomic regions described herein is varied (e.g., reduced or increased) in breast cancer subjects and in breast cancer cell lines. Thus, the methods disclosed herein may additionally or alternatively comprise determining the level of expression of any polynucleotides within any of the genomic regions identified in any of the Tables herein.

a) Nucleic Acid Detection

In one example, the level of expression of a nucleic acid is determined by detecting the level of mRNA transcribed from genomic region described herein.

In one example, the mRNA is detected by hybridizing a nucleic acid probe or primer capable of specifically hybridizing to a transcript of a genomic region described herein to a nucleic acid in a biological sample derived from a subject and detecting the hybridization by a detection means. Preferably, the detection means is an amplification reaction, or a nucleic acid hybridization reaction, such as, for example, as described herein.

In this context, the term "selective hybridization" means that hybridization of a probe or primer to the transcript occurs at a higher frequency or rate, or has a higher maximum reaction velocity, than hybridization of the same probe or primer to any other nucleic acid. Preferably, the probe or primer does not hybridize to another nucleic acid at a detectable level under the reaction conditions used.

As transcripts of a gene or pseudogene described herein are detected using mRNA or cDNA derived therefrom, assays that detect changes in mRNA are preferred (e.g. Northern hybridization, RT-PCR, NASBA, TMA or ligase chain reaction).

Methods of RT-PCR are known in the art and described, for example, in Dieffenbach (ed) and Dveksler (ed) (In: PCR Primer: A Laboratory Manual, Cold Spring Harbour Laboratories, NY, 1995). Essentially, this method comprises performing a PCR reaction using cDNA produced by reverse transcribing mRNA from a cell using a reverse transcriptase. Methods of PCR described supra are to be taken to apply mutatis mutandis to this embodiment of the disclosure.

Similarly LCR may be performed using cDNA. Preferably, one or more of the probes or primers used in the reaction specifically hybridize to the transcript of interest. Method of LCR are described supra and are to be taken to apply mutatis mutandis to this embodiment of the disclosure.

Methods of TMA or self-sustained sequence replication (3SR) use two or more oligonucleotides that flank a target sequence, a RNA polymerase, RNase H and a reverse transcriptase. One oligonucleotide (that also comprises a RNA polymerase binding site) hybridizes to an RNA molecule that comprises the target sequence and the reverse transcriptase produces cDNA copy of this region. RNase H is used to digest the RNA in the RNA-DNA complex, and the second oligonucleotide used to produce a copy of the cDNA. The RNA polymerase is then used to produce a RNA copy of the cDNA, and the process repeated.

NASBA systems relies on the simultaneous activity of three enzymes (a reverse transcriptase, RNase H and RNA polymerase) to selectively amplify target mRNA sequences. The mRNA template is transcribed to cDNA by reverse transcription using an oligonucleotide that hybridizes to the target sequence and comprises a RNA polymerase binding site at its 5' end. The template RNA is digested with RNase H and double stranded DNA is synthesized. The RNA polymerase then produces multiple RNA copies of the cDNA and the process is repeated.

The present disclosure also contemplates the use of a microarray to determine the level of expression of one or more nucleic acids described herein. Such a method enables the detection of a number of different nucleic acids, thereby providing a multi-analyte test and improving the sensitivity and/or accuracy of the diagnostic assay of the disclosure.

b) Polypeptide Detection

In an alternative example, the level of expression of a genomic region is determined by detecting the level of a protein encoded by a nucleic acid within a genomic region described herein.

In this respect, the present disclosure is not necessarily limited to the detection of a protein comprising the specific amino acid sequence recited herein. Rather, the present disclosure encompasses the detection of variant sequences (e.g., having at least about 80% or 90% or 95% or 98% amino acid sequence identity) or the detection of an immunogenic fragment or epitope of said protein.

The amount, level or presence of a polypeptide is determined using any of a variety of techniques known to the skilled artisan such as, for example, a technique selected from the group consisting of, immunohistochemistry, immunofluorescence, an immunoblot, a Western blot, a dot blot, an enzyme linked immunosorbent assay (ELISA), radioimmunoassay (RIA), enzyme immunoassay, fluorescence resonance energy transfer (FRET), matrix-assisted laser desorption/ionization time of flight (MALDI-TOF), electrospray ionization (ESI), mass spectrometry (including tandem mass spectrometry, e.g. LC MS/MS), biosensor technology, evanescent fiber-optics technology or protein chip technology.

In one example, the assay used to determine the amount or level of a protein is a semi-quantitative assay. In another example, the assay used to determine the amount or level of a protein in a quantitative assay. As will be apparent from the preceding description, such an assay may require the use of a suitable control, e.g. from a normal individual or matched normal control.

Standard solid-phase ELISA or FLISA formats are particularly useful in determining the concentration of a protein from a variety of samples.

In one form such an assay involves immobilizing a biological sample onto a solid matrix, such as, for example a polystyrene or polycarbonate microwell or dipstick, a membrane, or a glass support (e.g. a glass slide). An antibody that specifically binds to a protein described herein is brought into direct contact with the immobilized biological sample, and forms a direct bond with any of its target protein present in said sample. This antibody is generally labeled with a detectable reporter molecule, such as for example, a fluorescent label (e.g. FITC or Texas Red) or a fluorescent semiconductor nanocrystal (as described in U.S. Pat. No. 6,306,610) in the case of a FLISA or an enzyme (e.g. horseradish peroxidase (HRP), alkaline phosphatase (AP) or β-galactosidase) in the case of an ELISA, or alternatively a second labeled antibody can be used that binds to the first antibody. Following washing to remove any unbound antibody the label is detected either directly, in the case of a fluorescent label, or through the addition of a substrate, such as for example hydrogen peroxide, TMB, or toluidine, or 5-bromo-4-chloro-3-indol-beta-D-galaotopyranoside (x-gal) in the case of an enzymatic label.

In another form, an ELISA or FLISA comprises immobilizing an antibody or ligand that specifically binds a protein described supra on a solid matrix, such as, for example, a membrane, a polystyrene or polycarbonate microwell, a polystyrene or polycarbonate dipstick or a glass support. A sample is then brought into physical relation with said antibody, and the polypeptide is bound or 'captured'. The bound protein is then detected using a labeled antibody. For example, a labeled antibody that binds to an epitope that is distinct from the first (capture) antibody is used to detect the captured protein. Alternatively, a third labeled antibody can be used that binds the second (detecting) antibody.

In another example, the presence or level of a protein is detected in a body fluid using, for example, a biosensor instrument (e.g., BIAcore™, Pharmacia Biosensor, Piscataway, N.J.). In such an assay, an antibody or ligand that specifically binds a protein is immobilized onto the surface of a receptor chip. For example, the antibody or ligand is covalently attached to dextran fibers that are attached to gold film within the flow cell of the biosensor device. A test sample is passed through the cell. Any antigen present in the body fluid sample, binds to the immobilized antibody or ligand, causing a change in the refractive index of the medium over the gold film, which is detected as a change in surface plasmon resonance of the gold film.

In another example, the presence or level of a protein or a fragment or epitope thereof is detected using a protein and/or antibody chip. To produce such a chip, an antibody or ligand that binds to the antigen of interest is bound to a solid support such as, for example glass, polycarbonate, polytetrafluoroethylene, polystyrene, silicon oxide, gold or silicon nitride. This immobilization is either direct (e.g. by covalent linkage, such as, for example, Schiff's base formation, disulfide linkage, or amide or urea bond formation) or indirect.

To bind a protein to a solid support it is often necessary to treat the solid support so as to create chemically reactive groups on the surface, such as, for example, with an aldehyde-containing silane reagent or the calixcrown derivatives described in Lee et al, Proteomics, 3: 2289-2304, 2003. A streptavidin chip is also useful for capturing proteins and/or peptides and/or nucleic acid and/or cells that have been conjugated with biotin (e.g. as described in Pavlickova et al., *Biotechniques,* 34: 124-130, 2003). Alternatively, a peptide is captured on a microfabricated polyacrylamide gel pad and accelerated into the gel using microelectrophoresis as described in, Arenkov et al. *Anal. Biochem.* 278:123-131, 2000.

Other assay formats are also contemplated, such as flow-trough immunoassays (PCT/AU2002/01684), a lateral flow immunoassay (US20040228761, US20040248322 or US20040265926), a fluorescence polarization immunoassay (FPIA) (U.S. Pat. Nos. 4,593,089, 4,492,762, 4,668,640, and 4,751,190), a homogeneous microparticles immunoassay ("HMI") (e.g., U.S. Pat. Nos. 5,571,728, 4,847,209, 6,514,770, and 6,248,597) or a chemiluminescent microparticle immunoassay ("CMIA").

3 Multiplex Assay Formats

The present disclosure also contemplates multiplex or multianalyte format assays to improve the accuracy or specificity of a diagnosis or prognosis of breast cancer. Such assays may also improve the population coverage by an assay.

Methods for determining the sensitivity of an assay will be apparent to the skilled artisan. For example, an assay described herein is used to analyze a population of test subjects to determine those that will develop cancer. Postmortem analysis is then used to determine those subjects that did actually determine breast cancer. The number of "true positives" (i.e., subjects that developed breast cancer and were positively identified using the method of the disclosure) and "true negatives" (i.e., subjects that did not develop breast cancer and were not identified using the method of the disclosure) are determined.

Sensitivity of the assay is then determined by the following formula:

No. of true positives/(No. of true positives+No. of false negatives).

In one example, a method of the disclosure has a high degree of sensitivity in detecting of subjects developing or suffering from breast cancer. For example, in a test population of individuals, the assay detects at least about 50% of subjects developing or suffering from breast cancer, for example, at least about 60% of subjects developing or suffering from breast cancer, for example, at least about 65% of subjects developing or suffering from breast cancer, for example, at least about 70% of subjects developing or suffering from breast cancer, for example, at least about 75% of subjects developing or suffering from breast cancer, for example, at least about 80% of subjects developing or suffering from breast cancer, for example, at least about 85% of subjects developing or suffering from breast cancer, for example, at least about 90% of subjects developing or suffering from breast cancer, for example, at least about 95% of subjects developing or suffering from breast cancer.

In a more specific example, a method of the disclosure has a high degree of sensitivity in detecting of subjects developing or suffering from ER−ve breast cancer and/or TNBC. For example, in a test population of individuals, the assay detects at least about 50% of subjects developing or suffering from ER−ve breast cancer and/or TNBC, for example, at least about 60% of subjects developing or suffering from ER−ve breast cancer and/or TNBC, for example, at least about 65% of subjects developing or suffering from ER−ve breast cancer and/or TNBC, for example, at least about 70% of subjects developing or suffering from ER−ve breast cancer and/or TNBC, for example, at least about 75% of subjects developing or suffering from ER−ve breast cancer and/or TNBC, for example, at least about 80% of subjects developing or suffering from ER−ve breast cancer and/or TNBC, for example, at least about 85% of subjects developing or suffering from ER−ve breast cancer and/or TNBC, for example, at least about 90% of subjects developing or suffering from ER−ve breast cancer and/or TNBC, for example, at least about 95% of subjects developing or suffering from ER−ve breast cancer and/or TNBC.

In another example, a method of the disclosure has a high degree of sensitivity in stratifying TNBC subtypes associated with distinct prognostic profiles e.g., such as populations of TNBC patients with high, medium or low risk disease outcomes. For example, in a test population of individuals having TNBC, the assay stratifies at least about 50% of subjects having TNBC according to a disease outcome, for example, at least about 60% of subjects having TNBC according to a disease outcome, for example, at least about 70% of subjects having TNBC according to a disease outcome, for example, at least about 80% of subjects having TNBC according to a disease outcome, for example, at least about 85% of subjects having TNBC according to a disease outcome, for example, at least about 90% of subjects having TNBC according to a disease outcome, for example, at least about 95% of subjects having TNBC according to a disease outcome. A disease outcome in accordance with this example is a likelihood that the breast cancer patient will survive at least 3 years from the time or diagnosis/prognosis, for example, at least 5 years from the time or diagnosis/prognosis, for example, at least 10 years from the time or diagnosis/prognosis.

Specificity is determined by the following formula:

No. of true negatives/(No. of true negatives+No. of false positives).

An exemplary multiplex assay comprises, for example, detecting differential methylation of one or more CpG dinucleotides in a plurality of DMRs set forth in Tables 1-3. In one example, the method comprises detecting the level of methylation of one or more CpG dinucleotides in a plurality of DMRs set forth in Table 1 to diagnose breast cancer. In another example, the method comprises detecting the level of methylation of one or more CpG dinucleotides in a plurality of DMRs set forth in Table 2 to diagnose ER−ve breast cancer and/or TNBC. In yet another example, the method comprises detecting the level of methylation of one or more CpG dinucleotides in a plurality of DMRs set forth in Table 3 to stratify and/or predict disease outcome in a patient suffering from TNBC.

The multiplex assay of the disclosure is not to be limited to the detection of methylation at a single CpG dinucleotide within a region of interest i.e., each DMR. Rather, the present disclosure contemplates detection of methylation at a sufficient number of CpG dinucleotides in each nucleic acid to provide a diagnosis/prognosis. For example, the disclosure contemplates detection of methylation at 1 or 2 or 3 or 4 or 5 or 7 or 9 or 10 or 15 or 20 or 25 or 30 CpG dinculeotides in each nucleic acid i.e., each DMR. Preferably, the disclosure contemplates detection of methylation at more than 1 CpG dinculeotide in each nucleic acid i.e., each DMR.

As will be apparent from the foregoing description, a methylation specific microarray is amenable to such high density analysis. Previously, up to 232 CpG dinucleotides have been analyzed using such a microarray (Adorján et al., *Nucl. Acids Res.* 30: e21, 2002).

In another example, the method determines the level of expression of a gene comprising, or comprised in, at least one DMR set forth in Tables 1-3 to diagnose/prognose breast cancer. For example, the method determines the level of expression of a gene comprising, or comprised in, at least one DMR set forth in Table 1 to diagnose breast cancer. In another example, the method determines the level of expression of a gene comprising, or comprised in, at least one DMR set forth in Table 2 to diagnose ER−ve and/or TNBC. In another example, the method determines the level of expression of a gene comprising, or comprised in, at least one DMR set forth in Table 3 to stratify and/or predict disease outcome in a patient suffering from TNBC. The level of mRNA or protein may be detected. Alternatively, the level of mRNA transcribed from one or more genes and the level of one or more proteins expressed by the same or different genes may be determined.

Each of the previously described detection techniques can be used independently of one another to diagnose cancer. Accordingly, a single sample may be analyzed to determine the level of methylation of one or more CpG dinculeotides in one or more nucleic acids and the level of expression of one or more nucleic acids and/or proteins is also determined. In accordance with this example, enhanced methylation and reduced gene expression is indicative of cancer.

Based on the teachings provided herein, a variety of combinations of assays will be apparent to the skilled artisan.

The present disclosure also contemplates the use of a known diagnostic assay in combination with an assay described herein. For example, detection of a mutation in a BRCA gene using an assay described herein may be used to diagnose breast cancer.

Samples

A sample useful for the method of the present disclosure is, for example, from a tissue suspected of comprising a breast cancer or breast cancer cell. For example, the cell is from a region of a tissue thought to comprise a breast cancer or breast cancer cell. This does not exclude cells that have originated in a particular tissue but are isolated from a remote source.

The sample may be taken from a subject suspected of having or being at risk of developing breast cancer. For example, the subject may have a family history of cancer, may have been subjected to tests identifying elevated levels of BRCA gene (which, in one example, may be deemed to indicate an increased likelihood of having or being susceptible to developing breast cancer), or may have been subjected to any other test for detecting and/or determining the likelihood of developing any form of breast cancer. The sample may be taken from a subject who has been subjected to any combination of any known test for detecting and/or determining the likelihood of developing any form of breast cancer. Alternatively, the sample may be taken from a subject not previously suspected of having breast cancer.

In one example, the sample comprises a body fluid or a derivative of a body fluid or a body secretion. For example, the body fluid is selected from the group consisting of whole blood, urine, saliva, breast milk, pleural fluid, sweat, tears and mixtures thereof. An example of a derivative of a body fluid is selected from the group consisting of plasma, serum or buffy coat fraction. In one example, the sample comprises a whole blood sample, a serum sample or a plasma sample.

In one example DNA is isolated from either; whole blood, plasma, serum, peripheral blood mononucleated cells (PBMC) or enriched epithelial cells derived from the blood of patients diagnosed with breast cancer or healthy controls. DNA may then be bisulfite converted and gene-specific methylated sequences may be detected by either; methylation specific headloop suppression PCR, MALDI-TOF mass spectrometry (sequenom) or other bisulfite based PCR assay.

Preferably, the sample comprises a nucleated cell or an extract thereof. More preferably, the sample comprises a breast cancer cell or an extract thereof.

In another example, the sample comprises nucleic acid and/or protein from a breast cancer cell. The nucleic acid and/or protein may be separate need not be isolated with a cell, but rather may be from, for example, a lysed cell.

As the present disclosure is particularly useful for the early detection of breast cancer in the medium to long term, the term breast cancer cell is not to be limited by the stage of a cancer in the subject from which said breast cancer cell is derived (i.e. whether or not the patient is in remission or undergoing disease recurrence or whether or not the breast cancer is a primary tumor or the consequence of metastases). Nor is the term "breast cancer cell", "cancer cell" or similar to be limited by the stage of the cell cycle of said cancer cell.

In one example, the sample comprises a cell or a plurality of cells derived from a breast.

In one example, the biological sample has been isolated previously from the subject. In accordance with this example, a method of the present disclosure is performed ex vivo. In such cases, the sample may be processed or partially processed into a nucleic acid sample that is substantially free of contaminating protein. All such examples are encompassed by the present disclosure.

Methods for isolating a sample from a subject are known in the art and include, for example, surgery, biopsy, collection of a body fluid, for example, by paracentesis or thoracentesis or collection of, for example, blood or a fraction thereof. All such methods for isolating a biological sample shall be considered to be within the scope of providing or obtaining a sample.

For example, in the case of a breast cancer, a sample is collected, for example, using a fine needle aspiration biopsy, a core needle biopsy, or a surgical biopsy.

It will be apparent from the preceding description that methods provided by the present disclosure involve a degree of quantification to determine elevated or enhanced methylation of nucleic acid in tissue that is suspected of comprising a cancer cell or metastases thereof, or reduced gene expression in tissue that is suspected of comprising a cancer cell or metastases thereof. Such quantification is readily provided by the inclusion of appropriate control samples in the assays as described below.

As will be apparent to the skilled artisan, when internal controls are not included in each assay conducted, the control may be derived from an established data set.

Data pertaining to the control subjects are selected from the group consisting of:
1. a data set comprising measurements of the degree of methylation and/or gene expression for a typical population of subjects known to have breast cancer, or a particular form of breast cancer e.g., such as TNBC, that is currently being tested or a typical population of subjects known to have breast cancer generally;
2. a data set comprising measurements of the degree of methylation and/or gene expression for the subject being tested wherein said measurements have been made previously, such as, for example, when the subject was known to be healthy or, in the case of a subject having breast cancer, when the subject was diagnosed or at an earlier stage in disease progression;
3. a data set comprising measurements of the degree of methylation and/or gene expression for a healthy individual or a population of healthy individuals;
4. a data set comprising measurements of the degree of methylation and/or gene expression for a normal individual or a population of normal individuals; and
5. a data set comprising measurements of the degree of methylation and/or gene expression from the subject being tested wherein the measurements are determined in a matched sample.

In a preferred example, the data comprising measurements of the degree of methylation and/or gene expression for a healthy subject, individual or population pertains to healthy breast epithelial cell(s) from the subject, individual or population.

Those skilled in the art are readily capable of determining the baseline for comparison in any diagnostic/prognostic assay of the present disclosure without undue experimentation, based upon the teaching provided herein.

In the present context, the term "typical population" with respect to subjects known to have breast cancer shall be taken to refer to a population or sample of subjects diagnosed with a specific form of breast cancer that is representative of the spectrum of subjects suffering from breast cancer. This is not to be taken as requiring a strict normal distribution of morphological or clinicopathopathological parameters in the population, since some variation in such a distribution is permissible. Preferably, a "typical population" will exhibit a spectrum of subtypes of breast cancers at different stages of disease progression and with tumors at different stages and having different morphologies or degrees of differentiation.

In the present context, the term "healthy individual" shall be taken to mean an individual who is known not to suffer from breast cancer, such knowledge being derived from clinical data on the individual. It is preferred that the healthy individual is asymptomatic with respect to the any symptoms associated with breast cancer.

The term "normal individual" shall be taken to mean an individual having a normal level of methylation at a genomic region and/or gene expression as described herein in a particular sample derived from said individual.

As will be known to those skilled in the art, data obtained from a sufficiently large sample of the population will normalize, allowing the generation of a data set for determining the average level of a particular parameter. Accordingly, the level of methylation and/or gene expression as described herein can be determined for any population of individuals, and for any sample derived from said individual, for subsequent comparison to levels determined for a sample being assayed. Where such normalized data sets are relied upon, internal controls are preferably included in each assay conducted to control for variation.

The term "matched sample" shall be taken to mean that a control sample is derived from the same subject as the test sample is derived, at approximately the same point in time. In one example, the control sample provides little or no morphological and/or pathological indications of cancer. Matched samples are not applicable to blood-based or serum-based assays. Accordingly, it is preferable that the matched sample is from a region of the same tissue as the test sample e.g., breast tissue, such as breast epithelial tissue, however does not appear to comprise a cancer cell. For example, the matched sample does not include malignant cells or exhibit any symptom of the disease. For example, the sample comprises less than about 20% malignant cells, such as less than about 10% malignant cells, for example less than about 5% malignant cells, e.g., less than about 1% malignant cells. Morphological and pathological indications of malignant cells are known in the art and/or described herein.

For example, the differential methylation of one or more DMRs set forth in Tables 1-3 relative to the methylation status of a corresponding one or more DMRs of a control is indicative of a subject having breast cancer. Alternatively, or in addition, differential methylation of one or more DMRs set forth in Tables 1-3 relative to the methylation status a corresponding one or more DMRs of a control is indicative of a breast cancer patient's response to therapy or the progression or recurrence of disease or metastasis.

In an alternative example, the differential expression of a gene associated with one or more DMRs set forth in Tables 1-3 e.g., a gene comprised within the DMR or comprising the DMR, relative to a corresponding gene expression of a control is indicative of a subject having breast cancer. Alternatively, or in addition, differential expression of a gene associated with one or more DMRs set forth in Tables 1-3 e.g., a gene comprised within one of the DMR or comprising the DMR, relative to a corresponding gene expression of a control is indicative of a breast cancer patient's response to therapy or the progression or recurrence of disease or metastasis.

In one example, the level(s) of differential methylation of the one or more DMRs set forth in Tables 1-3 are subjected to multivariate analysis to create an algorithm which enables the determination of an index of probability of the presence or absence of breast cancer, or metastasis or progression of breast cancer or response to treatment. For example, the level(s) of differential methylation of the one or more DMRs set forth in Table 1 are subjected to multivariate analysis to create an algorithm which enables the determination of an index of probability of the presence or absence of breast cancer, or metastasis or progression of breast cancer or response to treatment. For example, the level(s) of differential methylation of the one or more DMRs set forth in Table 2 are subjected to multivariate analysis to create an algorithm which enables the determination of an index of probability of the presence or absence of ER-ve breast cancer and/or TNBC, or metastasis or progression of ER-ve breast cancer and/or TNBC. For example, the level(s) of differential methylation of the one or more DMRs set forth in Table 3 are subjected to multivariate analysis to create an algorithm which enables determination of an index of probability of the presence or absence of TNBC, stratification of TNBC subtypes according to prognostic risk profiles, determination or prediction of metastasis or prediction of progression of TNBC to a worsening stage. Hence, in one example, the present disclosure provides a rule based on the application of a comparison of levels of methylation biomarkers to control samples. In another example, the rule is based on application of statistical and machine learning algorithms. Such an algorithm uses the relationships between methylation biomarkers and disease status observed in training data (with known disease status) to infer relationships which are then used to predict the status of patients with unknown status. Practitioners skilled in the art of data analysis recognize that many different forms of inferring relationships in the training data may be used without materially changing the present disclosure.

The term "status" shall be taken to include whether or not a subject suffers from breast cancer (i.e., diagnostic status), including breast cancer subtype (e.g., ER-ve breast cancer or TNBC), whether or not a breast cancer has progressed, whether or not a cancer has metastasized, and/or whether or not a subject is responding to treatment for a breast cancer.

Analysis as described in the preceding paragraphs can also consider clinical parameters or traditional laboratory risk factors.

Information as discussed above can be combined and made more clinically useful through the use of various formulae, including statistical classification algorithms and others, combining and in many cases extending the performance characteristics of the combination beyond that of any individual data point. These specific combinations show an acceptable level of diagnostic/prognostic accuracy, and, when sufficient information from multiple markers is combined in a trained formula, often reliably achieve a high level of diagnostic/prognostic accuracy transportable from one population to another.

Several statistical and modeling algorithms known in the art can be used to both assist in biomarker selection choices and optimize the algorithms combining these choices. Statistical tools such as factor and cross-biomarker correlation/covariance analyses allow more rational approaches to panel construction. Mathematical clustering and classification tree showing the Euclidean standardized distance between the biomarkers can be advantageously used. Pathway informed seeding of such statistical classification techniques also may be employed, as may rational approaches based on the selection of individual biomarkers (e.g., such as those DMRs set forth in Tables 1-3) based on their participation across in particular pathways or physiological functions or individual performance.

Ultimately, formulae such as statistical classification algorithms can be directly used to both select methylation biomarkers and to generate and train the optimal formula necessary to combine the results from multiple methylation biomarkers into a single index. Often techniques such as forward (from zero potential explanatory parameters) and backwards selection (from all available potential explanatory parameters) are used, and information criteria are used to quantify the tradeoff between the performance and diagnostic/prognostic accuracy of the panel and the number of methylation biomarkers used. The position of the individual methylation biomarkers on a forward or backwards selected panel can be closely related to its provision of incremental information content for the algorithm, so the order of contribution is highly dependent on the other constituent biomarkers in the panel.

Any formula may be used to combine methylation biomarker results into indices or indexes useful in the practice of the disclosure. As indicated herein, and without limitation, such indices may indicate, among the various other indications, the probability, likelihood, absolute or relative risk, time to or rate of disease, conversion from one to another disease states, or make predictions of future biomarker measurements of cancer. This may be for a specific time period or horizon, or for remaining lifetime risk, or simply be provided as an index relative to another reference subject population.

The actual model type or formula used may itself be selected from the field of potential models based on the performance and diagnostic accuracy characteristics of its results in a training population. The specifics of the formula itself may commonly be derived from biomarker results in the relevant training population. Amongst other uses, such formula may be intended to map the feature space derived from one or more biomarker inputs to a set of subject classes (e.g. useful in predicting class membership of subjects as normal, at risk for having breast cancer, recurrence or metastasis thereof or responding/not-responding to treatment), to derive an estimation of a probability function of risk using a Bayesian approach (e.g. the risk of breast cancer or a metastatic or recurrence event), or to estimate the class-conditional probabilities, then use Bayes' rule to produce the class probability function as in the previous case.

Following analysis and determination of an index of probability of the presence or absence of breast cancer (e.g., ER-ve breast cancer and/or TNBC), or metastasis or progression of breast cancer or response to treatment, the index can be transmitted or provided to a third party, e.g., a medical practitioner for assessment. The index may be used by the practitioner to assess whether or not additional diagnostic methods are required, e.g., biopsy and histological analysis and/or other assays, or a change in treatment or commencement of treatment.

Monitoring the Progression of Cancer

As the level of a biomarker of breast cancer varies with the progression of cancer, the methods described herein are useful for monitoring the progression of breast cancer in a subject suffering therefrom. In this regard, the term "determining the progression of cancer" includes determining the stage or grade of the breast cancer. For example, the method comprises determining differential methylation of one or more genomic regions set forth in Table 1, Table 2 and/or Table 3 in a sample from a subject relative to a reference level of methylation for the corresponding one or more genomic regions previously determined for the subject or a control sample. Enhanced differential methylation i.e., a further increased or further reduced level of methylation, of a genomic region in the sample compared to the previously obtained sample indicates that the disease has progressed, e.g., the disease may have progressed to a more advanced stage or may have advanced from pre-clinical to clinical. In a particularly preferred example, the method comprises determining differential methylation of one or more genomic regions set forth in Table 3 in a sample from a subject suffering from TNBC relative to a reference level of methylation for the corresponding one or more genomic regions previously determined for the subject or a control sample. Comparison to a control sample from a subject having a specific stage or grade permits identification of the stage or grade of the breast cancer e.g., such as TNBC, in the subject.

The present disclosure is also useful for determining the degree or risk of metastasis of breast cancer, for example, by determining the stage of the breast cancer. For example, the present disclosure is useful for determining metastasis of a breast cancer to a tissue, such as, for example, a lymph node, bone or lung.

Clearly, the detection of one or more additional biomarkers other than those set forth in Tables 1-3 is encompassed by this example of the disclosure.

Methods for detecting markers are described herein and are to be taken to apply mutatis mutandis to this example of the disclosure.

Monitoring the Efficacy of Treatment

As the method of the disclosure is useful for monitoring or determining the progression (e.g., stage) of breast cancer, it is also useful for determining the efficacy of a therapy for said disease.

For example, a method described herein is used to determine methylation status of one or more CpG dinucleotides within one or more genomic regions set forth in Table 1-3 in sample from a subject receiving treatment for breast cancer. This methylation status is then compared to, for example, methylation status for a healthy or control subject. Detection of differential methylation of one or more CpG dinucleotides within one or more genomic regions set forth in Table 1-3 in the test sample relative to a level of methylation for the corresponding genomic regions in the healthy or control sample is indicative that the subject is not responding to treatment. A similar level of methylation in the test sample and a healthy or control sample indicates that the subject is responding to or has responded to treatment for said disease.

In another example, the control sample is derived from a subject suffering from breast cancer or from the subject prior to commencing treatment or from a point in time earlier in the treatment. In this respect, a reduced level of differential methylation of the one or more CpG dinucleotides within one or more genomic regions set forth in Table 1-3 in the test sample compared to the control sample indicates that the subject is responding to or has responded to treatment. An enhanced or similar level of differential methylation of the one or more CpG dinucleotides within one or more genomic regions set forth in Table 1-3 in the test sample compared to the control sample indicates that the subject is not or has not responded to treatment.

Determining the Time to an Event

The method of the present disclosure is also useful for determining, for example, the risk of an event occurring, or the timing to an event occurring. For example, the present disclosure is useful for determining the risk of a patient dying early as a result of breast cancer e.g., as a result of TNBC, or determining the risk of metastasis or the timing to metastasis.

Such methods are also applicable to determining, for example, the risk of or time to development of one or more of the following:

(i) onset of clinical breast cancer;
(ii) the progression of breast cancer from one stage to another; or
(iii) the likelihood of response of a subject to a therapeutic or prophylactic agent.

To determine the time to an event or the risk of an event, e.g., the time to death of a subject, the level of a methylation biomarker of the disclosure is determined in a series of subjects for which survival data is known. A Cox Proportional Hazards model (see, e.g. Cox and Oakes (1984), Analysis of Survival Data, Chapman and Hall, London, N.Y.) is defined with time to death or early death as the dependent variable, and the level of the marker detected as the independent variable. The Cox model provides the relative risk (RR) of death for a unit change in the level of the marker. The subjects may then be partitioned into subgroups at any threshold value of the level of the marker (on the CT scale), where all subjects with levels above the threshold have higher risk, and all patients with levels below the threshold have lower risk of death or time to death, or vice versa, depending on whether the marker is an indicator of bad (RR>1.01) or good (RR<1.01) prognosis. Thus, any threshold value will define subgroups of patients with respectively increased or decreased risk.

The Cox proportional hazard model is the most general of the regression models because it is not based on any assumptions concerning the nature or shape of the underlying survival distribution. The model assumes that the underlying hazard rate (rather than survival time) is a function of the independent variables (covariates); no assumptions are made about the nature or shape of the hazard function.

In another embodiment, a Cox's Proportional Hazard Model with Time-Dependent Covariates is used to determine the time to or risk of an event in cancer based on a marker described herein in a sample from a subject. An assumption of the proportional hazard model is that the hazard function for an individual (i.e., observation in the analysis) depends on the values of the covariates and the value of the baseline hazard. Given two individuals with particular values for the covariates, the ratio of the estimated hazards over time will be constant.

Other methods for determining the time to or risk of an event will be apparent to the skilled artisan and include, for example, exponential regression, normal regression, log-normal regression or stratified analysis.

Using any of these forms of analysis a level of detection of a methylation biomarker is determined that is predictive of the risk or time to an event. For example, a level of differential methylation of one or more CpG dinucleotides within one or more genomic regions set forth in Table 3 in a TNBC sample relative to a reference level of methylation for the respective genomic regions, is predictive that a subject is likely to live for fewer than a predetermined number of years. For example, fewer than 5 years from the time of diagnosis/prognosis, or fewer than 3 years from the time of diagnosis/prognosis. In one example, a level of differential methylation of one or more CpG dinucleotides within one or more genomic regions set forth in rows 1-14 of Table 3 in a TNBC sample relative to a reference level of methylation for the respective genomic regions, is predictive that a subject is likely to live for fewer than 5 years from the time of diagnosis/prognosis, such as fewer than 3 years from the time of diagnosis/prognosis. In another example, a level of differential methylation of one or more CpG dinucleotides within one or more genomic regions set forth in rows 15-17 of Table 3 in a TNBC sample relative to a reference level of methylation for the respective genomic regions, is predictive that a subject is likely to live for greater than 3 years from the time of diagnosis/prognosis, such as greater than 5 years from the time of diagnosis/prognosis.

This form of analysis is useful for determining the risk of an event occurring in a subject or the time to an event occurring in a subject.

Accordingly, one example of the disclosure provides a method of determining a time to an event in breast cancer e.g., TNBC, or the risk of an event occurring in a breast cancer subject e.g., a TNBC subject, by determining a level of differential methylation of one or more CpG dinucleotides within one or more genomic regions set forth in Table 3 in a TNBC sample relative to a reference level of methylation for the respective genomic regions, wherein an enhanced level methylation or reduced level of methylation relative to the reference level is indicative of the time to an event in the breast cancer.

Methods of Treatment

The present disclosure additionally provides a method of treatment of breast cancer. Such a method comprises, for example diagnosing breast cancer using a method of the disclosure described in any one or more examples described herein and administering a suitable therapeutic and/or prophylactic compound or performing surgery or recommending treatment with a suitable therapeutic/prophylactic agent or recommending performance of surgery.

Kits

The present disclosure additionally provides a kit for use in a method of the disclosure. In one embodiment, the kit comprises:

(i) one or more probes or primers (or isolated antibodies or ligands) that specifically hybridize to a biomarker described herein according to any example; and
(ii) detection means.

In another example, a kit additionally comprises a reference sample. Such a reference sample may for example, be a polynucleotide sample derived from a sample isolated from one or more subjects suffering from breast cancer. Alternatively, a reference sample may comprise a sample isolated from one or more normal healthy individuals.

In one example, the kit comprises a probe or primer. In one example, the probe or primer that is capable of selectively hybridizing to a CpG dinucleotide of a genomic region described herein according to any example.

In those cases where the probe is not already available, they must be produced. Apparatus for such synthesis is presently available commercially, such as the Applied Biosystems 380A DNA synthesizer and techniques for synthesis of various nucleic acids are available in the literature. Methods for producing probes or primers are known in the art and/or described herein.

In one example, a probe or primer selectively hybridizes to a CpG dinucleotide of a genomic region set forth in Tables 1-3 that is selectively mutated by, for example, bisulphite treatment if the residue is not methylated. In another example, a probe or primer selectively hybridizes to a CpG dinucleotide of a genomic region set forth in Tables 1-3 that can be methylated in a breast cancer cell.

The kit may further comprise instructions for the detection of methylation levels of any of the target genes disclosed herein and for the comparison of those methylation levels with a reference level. The instructions may provide one or a series of cut-off values demarcating the likelihood of risk of a subject having, or being predisposed to breast cancer.

The present disclosure additionally provides a kit or an article of manufacture comprising a compound for therapeutic or prophylactic treatment of breast cancer packaged with instructions to perform a method substantially as described herein according to any example of the disclosure.

Knowledge-Based Systems

Knowledge-based computer software and hardware for implementing an algorithm of the disclosure also form part of the present disclosure. Such computer software and/or hardware are useful for performing a method of the disclosure. Thus, the present disclosure also provides software or hardware programmed to implement an algorithm that processes data obtained by performing the method of the disclosure via an univariate or multivariate analysis to provide a disease index value and provide or permit a diagnosis of cancer and/or determine progression or status of a breast cancer or determine whether or not a breast cancer has progressed or determine whether or not a subject is responding to treatment for breast cancer in accordance with the results of the disease index value in comparison with predetermined values.

In one example, a method of the disclosure may be used in existing knowledge-based architecture or platforms associated with pathology services. For example, results from a method described herein are transmitted via a communications network (e.g. the Internet) to a processing system in which an algorithm is stored and used to generate a predicted posterior probability value which translates to the index of disease probability or risk of recurrence or metastasis or responsiveness to treatment which is then forwarded to an end user in the form of a diagnostic or predictive report.

The method of the disclosure may, therefore, be in the form of a kit or computer-based system which comprises the reagents necessary to detect the concentration of the biomarkers and the computer hardware and/or software to facilitate determination and transmission of reports to a clinician.

The assay of the present disclosure permits integration into existing or newly developed pathology architecture or platform systems. For example, the present disclosure contemplates a method of allowing a user to determine the status of a subject with respect to a breast cancer, the method including:
(a) receiving data in the form of levels of differential methylation of one or more CpG dinucleotides within one or more genomic regions set forth in Tables 1-3 for a test sample relative to a reference level of methylation, optionally in combination with another marker of breast cancer;
(b) processing the subject data via univariate and/or multivariate analysis to provide a disease index value;
(c) determining the status of the subject in accordance with the results of the disease index value in comparison with predetermined values; and
(d) transferring an indication of the status of the subject to the user via the communications network reference to the multivariate analysis includes an algorithm which performs the multivariate analysis function.

In one example, the method additionally includes:
(a) having the user determine the data using a remote end station; and
(b) transferring the data from the end station to the base station via the communications network.

The base station can include first and second processing systems, in which case the method can include:
(a) transferring the data to the first processing system;
(b) transferring the data to the second processing system; and
(c) causing the first processing system to perform the univariate or multivariate analysis function to generate the disease index value.

The method may also include:
(a) transferring the results of the univariate or multivariate analysis function to the first processing system; and
(b) causing the first processing system to determine the status of the subject.

In this case, the method also includes at least one of:
(a) transferring the data between the communications network and the first processing system through a first firewall; and
(b) transferring the data between the first and the second processing systems through a second firewall.

The second processing system may be coupled to a database adapted to store predetermined data and/or the univariate or multivariate analysis function, the method include: (a) querying the database to obtain at least selected predetermined data or access to the multivariate analysis function from the database; and
(b) comparing the selected predetermined data to the subject data or generating a predicted probability index.

The second processing system can be coupled to a database, the method including storing the data in the database.

The method can also include having the user determine the data using a secure array, the secure array of elements capable of determining the level of biomarker and having a number of features each located at respective position(s) on the respective code. In this case, the method typically includes causing the base station to:
(a) determine the code from the data;
(b) determine a layout indicating the position of each feature on the array; and
(c) determine the parameter values in accordance with the determined layout, and the data.

The method can also include causing the base station to:
(a) determine payment information, the payment information representing the provision of payment by the user; and
(b) perform the comparison in response to the determination of the payment information.

The present disclosure also provides a base station for determining the status of a subject with respect to a cancer, the base station including:
(a) a store method;
(b) a processing system, the processing system being adapted to:
(i) receive subject data from the user via a communications network;
(iii) determining the status of the subject in accordance with the results of the algorithmic function including the comparison; and
(c) output an indication of the status of the subject to the user via the communications network.

The processing system can be adapted to receive data from a remote end station adapted to determine the data.

The processing system may include:
(a) a first processing system adapted to:
(i) receive the data; and
(ii) determine the status of the subject in accordance with the results of the univariate or multivariate analysis function including comparing the data; and
(b) a second processing system adapted to:
(i) receive the data from the processing system;
(ii) perform the univariate or multivariate analysis function including the comparison; and
(iii) transfer the results to the first processing system.

The base station typically includes:
(a) a first firewall for coupling the first processing system to the communications network; and
(b) a second firewall for coupling the first and the second processing systems.

The processing system can be coupled to a database, the processing system being adapted to store the data in the database.

The present disclosure is now described further in the following non-limiting examples.

Example 1: Markers of Breast Cancer 1.1 Methods
1.1.1 Breast Cancer Tissue Samples DNA was extracted from cells microdissected from human tissue samples representing normal breast and tumor breast. Fresh frozen (FF) and formalin fixed paraffin embedded (FFPE) tissue were obtained. Samples were classified as triple negative Grade 3 ductal adenocarcinomas. Details of the sample are presented in Table 4.

1.1.2 DNA Isolation
1.1.2.1 Formalin Fixed Paraffin Embedded (FFPE) Tissue Samples DNA isolation from formalin fixed paraffin embedded (FFPE) tissue was performed using the Gentra Puregene Genomic DNA purification tissue kit according to the manufacturer's instructions (Qiagen). 5×1 mm cores or 5×10 um full faced sections were used for each extraction. The de-paraffinization step was carried out as follows: the paraffin samples was cut into small piece, 500 ul Xylene was added and incubated at 55° C. for 5 mins, and the tissue was pelleted at 16,000 g for 3 mins, discarding the Xylene. After repeating this step, 500 ul 100% EtOH was added for 5 mins at room temperature with constant mixing and the tissue collected by centrifugation @16,000 g for 3 mins. The EtOH step was repeated and the tissue pellet dried for 10 mins. 300 ul of cell lysis solution was added and the tube incubated for 70° C. for 10 mins, followed by addition of 20 ul Proteinase K (20 mg/ml) to each sample and vortexing for 20 secs and incubation in a 55° C. block overnight with constant vortexing. The following day a further 10 ul proteinase K was added, vortexed for 20 secs and further incubated at 55° C. until the samples appear clear. 1 ul RNase A solution (100 mg/ml) was added, mixed by inverting 25 times and incubated at 37° C. for 1 hr. The sample was placed on ice to quickly cool it. 100 ul protein precipitation solution was added to the cell lysates, which was then vortexed for 20 secs, incubated on ice for 5 mins, and centrifuged at full speed for 5 mins at 4° C. to pellet the protein precipitate. The supernatant containing the DNA was carefully removed into a clean microcentrifuge tube. The DNA was precipitated with 300 ul 100% isopropanol and 2 ul glycogen (20 mg/ml) were added if low yield was expected (<1 ug). The solutions were mixed by inversion (50 times) followed by centrifugation for 10 mins at 4° C. The DNA pellet was washed with 70% EtOH, air-dried and dissolved in 20 ul $H_2O$. To dissolve the pellet it was incubated for 1 hr at 65° C. with constant vortexing.

1.1.2.2 Formalin Fixed Paraffin Embedded (FETE) Tissue Samples

DNA from fresh frozen (FE) tissue was isolated using the Gentra Puregene Genomic DNA purification tissue kit according to the manufacturer's instructions (Qiagen). 5×1 mm cores or 5×10 um full faced sections were used for each extraction. Each sample was ground in a 1.5 ml tube. 300 ul of cell lysis solution was added and the tube incubated for 70° C. for 10 mins, followed by addition of 20 ul Proteinase K (20 mg/ml) to each sample and vortexing for 20 secs and incubation in a 55° C. block overnight with constant vortexing. The following day a further 10 ul proteinase K was added, vortexed for 20 secs and further incubated at 55° C. until the samples appear clear. 1 ul RNase A solution (100 mg/ml) was added, mixed by inverting 25 times and incubated at 37° C. for 1 hr. The sample was placed on ice to quickly cool it. 100 ul protein precipitation solution was added to the cell lysates, which was then vortexed for 20 secs, incubated on ice for 5 mins, and centrifuged at full speed for 5 mins at 4° C. to pellet the protein precipitate. The supernatant containing the DNA was carefully removed into a clean microcentrifuge tube. The DNA was precipitated with 300 ul 100% isopropanol and 2 ul glycogen (20 mg/ml) were added if low yield was expected (<1 ug). The solutions were mixed by inversion (50 times) followed by centrifugation for 10 mins at 4° C. The DNA pellet was washed with 70% EtOH, air-dried and dissolved in 20 ul $H_2O$. To dissolve the pellet it was incubated for 1 hr at 65° C. with constant vortexing.

TABLE 4

Summary of Discovery Cohort—A list of patient samples used in the discovery of DMRs associated with breast cancer.

| Sample Code | Sample Type | ER | PR | HER2 | Grade | AGE | Year | DOB | LN Status | Status/Outcome |
|---|---|---|---|---|---|---|---|---|---|---|
| 17420*** | normal | NEG | NEG | NEG | 3 | 47 | 2008 | Aug. 31, 1961 | Neg | Unknown |
| 17420*** | tumour | NEG | NEG | NEG |   | 47 | 2008 | Aug. 31, 1961 | Neg | Alive |
| 16693*** | normal | NEG | NEG | NEG | 3 | 54 | 2008 | Dec. 6, 1954 | Neg | Unknown |
| 16693*** | tumour | NEG | NEG | NEG |   | 54 | 2008 | Dec. 6, 1954 | Neg | Alive |
| 23622*** | normal | NEG | NEG | NEG | 3 | 68 | 2009 | Sep. 22, 1941 | Neg | Unknown |
| 23622*** | tumour | NEG | NEG | NEG |   | 68 | 2009 | Sep. 22, 1941 | Neg | Unknown |
| 20578*** | normal | NEG | NEG | NEG | 3 | Unknown | 2008 | Unknown | Pos | Unknown |
| 20578*** | tumour FF | NEG | NEG | NEG | 3 | Unknown | 2008 | Unknown | Pos | Unknown |
| 20578*** | tumour | NEG | NEG | NEG |   | Unknown | 2008 | Unknown | Pos | Unknown |
| 2850*** | normal | NEG | NEG | NEG | 3 | 30 | 1992 | Sep. 7, 1962 | Pos | Alive |
| 2850*** | tumour | NEG | NEG | NEG |   | 30 | 1992 | Sep. 7, 1962 | Pos |   |
| 14906*** | normal | NEG | NEG | NEG | 3 | 48 | 2002 | Jan. 23, 1954 | Pos | Alive |
| 14906*** | tumour | NEG | NEG | NEG | 3 | 48 | 2002 | Jan. 23, 1954 | Pos |   |
| 4537 | tumour | NEG | NEG | NEG | 3 | 73 | 2002 | Jun. 27, 1929 | Neg | Alive |
| 7700 | tumour | NEG | NEG | NEG | 3 | 40 | 2002 | Dec. 13, 1962 | Neg | Alive |
| 19038 | tumour | NEG | NEG | NEG | 3 | 33 | 1999 | Jul. 14, 1966 | Neg | Alive |
| 2319 | tumour | NEG | NEG | NEG | 3 | 60 | 1998 | Sep. 15, 1938 | Neg | Alive |
| 8948 | tumour | NEG | NEG | NEG | 3 | 48 | 2003 | Mar. 21, 1955 | Neg | Alive |
| 19328 | tumour | NEG | NEG | NEG | 3 | 27 | 1999 | Nov. 28, 1972 | Neg | Alive |
| 12627 | tumour | NEG | NEG | NEG | 3 | 50 | 1996 | Nov. 2, 1946 | Pos | Feb. 28, 1999 |

TABLE 4-continued

Summary of Discovery Cohort—A list of patient samples used in the discovery of DMRs associated with breast cancer.

| Sample Code | Sample Type | ER | PR | HER2 | Grade | AGE | Year | DOB | LN Status | Status/Outcome |
|---|---|---|---|---|---|---|---|---|---|---|
| 2532 | tumour | NEG | NEG | NEG | 3 | Unknown | unknown | Apr. 11, 1935 | Pos | Sep. 4, 1999 |
| 1138 | tumour | NEG | NEG | NEG | 3 | 62 | 1997 | Mar. 19, 1935 | Pos | Alive |
| 214 | tumour | NEG | NEG | NEG | 3 | 66 | 2003 | Mar. 31, 1937 | Pos | Alive |
| 3050 | tumour | NEG | NEG | NEG | 3 | 48 | 2002 | Sep. 16, 1954 | Pos | Alive |
| 4488 | tumour | NEG | NEG | NEG | 3 | unknown | unknown | May 31, 1927 | Unknown | Aug. 16, 1996 |
| 2032 | tumour | NEG | NEG | NEG |  | 39 | 2002 | Dec. 11, 1963 | Neg | Alive |

***denotes paired normal/tumour samples where the sample code is the same 1.1.3 Enrichment of Methylated DNA by MBDCap The MethylMiner™ Methylated DNA Enrichment Kit (Invitrogen) was used to isolate methylated DNA. 500 ng-1 µg of the genomic DNA previously isolated from tissue samples was sonicated to 100-500 bp. MBD-Biotin Protein (3.5 µg) was coupled to 10 µl of Dynabeads M-280 Streptavidin according to the manufacturer's instructions. The MBD-magnetic bead conjugates were washed three times and resuspended in 1 volume of 1× Bind/Wash buffer. The capture reaction was performed by the addition of 500 ng-1 µg sonicated DNA to the MBD-magnetic beads on a rotating mixer for 1 h at room temperature. All capture reactions were done in duplicate. The beads were washed three times with 1× Bind/Wash buffer. The bound methylated DNA was eluted as a single fraction with a single High Salt Elution Buffer (2,000 mM NaCl). Each fraction was concentrated by ethanol precipitation using 1 µl glycogen (20 µg/µl), 1/10 volume of 3 M sodium acetate, pH 5.2 and 2 sample volumes of 100% ethanol and resuspended in 60 µl H2O.

Figure 4:
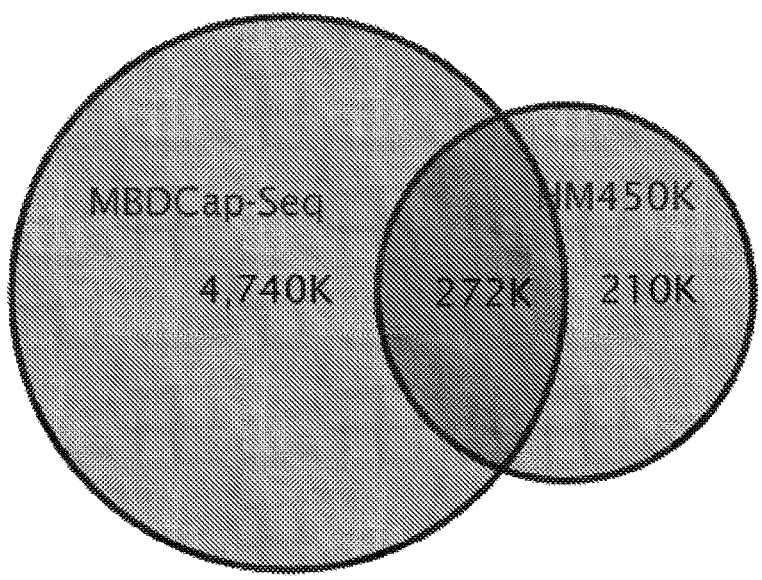
FIG. 4. Coverage of CpG sites and functional elements in the human genome by MBDCap-Seq and Illumina HumanMethylation450K platforms. (A) A table summarizing the number of functional/regulatory elements overlapping CpG sites covered by the MBDCap-Seq and HM450K platforms. For each platform two sets of numbers are shown with the second set (>=3 CpGs column) corresponding to elements overlapping 3 or more covered CpG sites. In both cases the fraction of covered elements is given in parentheses. (B) A Venn diagram showing overlap between CpG sites covered by MBDCap-Seq and HM450K platforms; for MBDCap-Seq covered CpGs are those overlapping SssI regions.

Enrichment of methylated DNA after capture was assessed by quantitative PCR of control genes of known methylation status; namely EN1 (heavily methylated) and GAPDH (unmethylated) (Perou et al., (2000) Nature, 406: 747-752) and both showed enrichment (FIG. 4). In particular, FIG. 4(A) summarises the number of functional/regulatory elements overlapping CpG sites covered by the MBDCap-Seq and HM450K platforms. For each platform two sets of numbers are shown with the second set (>=3 CpGs column) corresponding to elements overlapping 3 or more covered CpG sites. In both cases the fraction of covered elements is given in parentheses. Computational analysis of SssI MBDCap-Seq revealed that MBDCap-Seq can robustly assess the methylation status of 230,655 regions spanning a total of 1.1.6 Mbp, comprising 5,012,633 CpG dinucleotides, or approximately 18% of the total number of CpG sites in the human genome. The assayed CpG sites span 91% of all CpG islands; 84% CpG island shores; 72% RefSeq promoters; 38% introns and 31% exons. To assess CpG methylation coverage of additional functional elements in human mammary epithelial cells (HMEC), computationally derived annotation were used (Ernst et al., (2011) Nature, 473:43-49) to determine the extent of interrogation of HMEC promoters, enhancers and insulators. As a result, it was found that MBDCap-Seq interrogates approximately 66% HMEC promoters; 14% HMEC enhancers, and 12% HMEC insulators. Next, coverage of MBDCap-Seq was compared with coverage of the Illumina HumanMethylation450K (HM450K) array, and it was found that MBDCap-Seq interrogates an additional 4,740,327 CpG sites as compared to the high-density HM450K array. A major advantage of the MBDCap-Seq method is the ability to interrogate regional blocks of hypermethylation, that is methylation spanning consecutive CpG sites, which commonly occurs in cancer. Regional MBDCap-Seq coverage was therefore compared to coverage of HM450K arrays, by requiring that each functional element is covered by 3 or more assayed CpG sites. Interestingly, while MBDCap-Seq and HM450K arrays have similar regional coverage of CpG islands (91% vs. 81%) and RefSeq promoters (71% vs. 83%), MBDCap-Seq regional coverage of shores (77% vs. 28%), enhancers (12% vs. 2%) and insulators (11% vs. 1%) is much greater, highlighting the potential advantage of MBDCap-Seq in screening novel functional regions of the cancer methylome. FIG. 4(B) illustrates the overlap between CpG sites covered by MBDCap-Seq and HM450K platforms; for MBDCap-Seq covered CpGs are those overlapping SssI regions.

1.1.4 Preparation of MBDCap-Seq Libraries and Illumina Sequencing

To enable comparison of genome-wide analysis for the affinity captured methylated DNA from FF and FFPET DNA, libraries were prepared and Illumina sequencing performed.

10 ng DNA of MBDCap enriched DNA was prepared for Ilumina sequencing using the Illumina ChIP-Seq DNA sample prep kit (IP-102-1001) according to the manufacturer's instructions. The library preparation was analyzed on Agilent High Sensitivity DNA 1000 Chip. Each sample was sequenced on one lane of the GA11x.

1.1.5 Sequenom Quantitative MassARRAY Methylation Analysis

Sequenom MassARRAY methylation analysis was performed as described previously in Perou CM: (2011) Oncologist, 16 Suppl 1:61-70. 500 ng of FFPET clinical sample DNA was extracted and bisulphite treated using the standard bisulphite protocol (Blows et al., (2010) PLoS Med., 7:e1000279). As controls for the methylation analysis, whole genome amplified (WGA) DNA (0% methylated) and M.SssI treated DNA (100% methylated) were bisulphite treated in parallel. The primers were designed using the EpiDesignerBETA software from Sequenom (See Tables 5A-5C). Each reverse primer has a T7-promoter tag (5-CAG TAA TAC GAC TCA CTA TAG GGA GAA GGC T-3) and each forward primer has a 10-mer tag (5-AGG AAG AGA G-3). Upon testing these primers on bisulphite treated DNA, all the primers gave specific PCR products at a Tm of 60° C. In order to check for potential PCR bias towards methylated or non-methylated sequences, serological DNA (Millipore) was used as a 100% methylated control and Whole Genome Amplified human blood DNA used as a 0% methylated control. The PCRs were optimized and performed in triplicate using the conditions: 95° C. for 2 min, 45 cycles of 95° C. for 40 sec, 60° C. for 1 min and 72° C. for 1 min 30 sec and final extension at 72° C. for 5 min. After PCR amplification, the triplicates were pooled and a Shrimp Alkaline Phosphatase (SAP) treatment was performed using 5 µl of the PCR product as template. 2 µl of the SAP-treated PCR product was taken and subjected to in vitro transcription and RNaseA Cleavage for the T-cleavage reaction. The samples were purified by resin treatment and spotted on a 384-well SpectroCHIP by a MassARRAY Nanodispenser. This was followed by spectral acquisition on a MassARRAY Analyser Compact matrix-assisted laser desorption/ionisation time-of-flight mass spectrometry. The results were then analysed by the EpiTYPER software V 1.0 which gives quantitative methylation levels for individual CpG sites. The average methylation ratio was calculated by averaging the ratios obtained from each CpG site.

For the Sequenom validation, sample sizes were determined for a two sample t-test with a 2-sided alpha of 0.01, assuming 5 regions were to be investigated. Assuming the difference in average methylation levels is 0.25 (tumors: SD=0.2, normals: SD=0.05), in order to have 90% power to establish a significant difference between tumor and normal samples, 15 samples per group were required.

TABLE 5(A)-(C)

Sequenom MassARRAY methylation analysis:
A list of primers used for technical and independent validations with Sequenom.

| Primer Name | Position | Primer Sequence 5'-3' | SEQ ID NO |
|---|---|---|---|
| (A) Sequenom primers for validation of MBDCap.Seq data | | | |
| GHSRseq_01F | chr3: 173648423-173648622 | aggaagagagGTTTTTTGGTGATTATTATTTTGGT | 1 |
| GHSRseq_01R | | cagtaatacgactcactatagggagaaggctTTCCTCTACATACCCCTAAACCTC | 2 |
| GHSRseq_02F | Cbr3: 173648692-173648846 | aggaagagagGATATTATTAGTATGGTGAGTAGGTTGTTA | 3 |
| GHSRseq_02R | | cagtaatacgactcactatagggagaaggctACCTAAACTAAAATACTTCCCCC | 4 |
| PLD5seq_01F | chr1: 240753468-240753604 | aggaagagagTGGGTTTAAGTAGAGAGGATTATTAATTG | 5 |
| PLD5seq_02R | | cagtaatacgactcactatagggagaaggctCTATTTTACTCAATCCAAAAACTAACAAAT | 6 |
| PLD5seq_02F | chr1: 240753604-240751733 | aggaagagagTGGAGGTGTTTGTGTAGAGTGAGTA | 7 |
| PLD5seq_02R | | cagtaatacgactcactatagggagaaggctACTAAATAAAACAACCCCCAAAAAC | 8 |
| PLD5seq_03F | chr1: 240751712-240751827 | aggaagagagGGAGGGGAGGGTAGGTTTTTT | 9 |
| PLD5seq_03R | | cagtaatacgactcactatagggagaaggctCACTCTACACAAACACCTCCAAAAC | 10 |
| CpG 75seq_01F | chr1: 147404239-147404367 | aggaagagagGTTTTTTTATTTTTTGGGATGTTATAGA | 11 |
| CpG 75seq_01R | | cagtaatacgactcactatagggagaaggctACCCCACTAAAACTACTTTCCCTAC | 12 |
| CpG 75seq_02F | chr1: 147404516-147404624 | aggaagagagTTTAAGTGAGTTTGATGTTTTTGGG | 13 |
| CpG 75seq_02R | | cagtaatacgactcactatagggagaaggctATAAACCTTAACTTCCCATCCAAAC | 14 |
| CpG 245seq_01F | chr8: 54015671-54015794 | aggaagagagGTTAGGATTGTTATTATTAGGAAGGTT | 15 |
| CpG 245seq_01R | | cagtaatacgactcactatagggagaaggctCACCATCTATATCCTCTATACCACCC | 16 |
| CpG 245seq_02F | chr8: 54015238-54015397 | aggaagagagAGTAGAGGTTGGAGAAGGTGTTGTAT | 17 |
| CpG 245seq_02R | | cagtaatacgactcactatagggagaaggctACCTATTCATCCTCAACCTAACCAT | 18 |
| CpG 109seq_01F | chr9: 103288127-103288472 | aggaagagagTTAGGGTTTTGGATTTAGTGTTTGT | 19 |
| CpG 109seq_01R | | cagtaatacgactcactatagggagaaggctTCCCTCCCAAAACCAAAAA | 20 |
| CpG 109seq_02F | chr9: 101288784-101288140 | aggaagagagGTAGTTGGGGGTTGGGGAG | 21 |
| CpG 109seq_02R | | cagtaatacgactcactatagggagaaggctAACCCCTACTACCCTAAAAACCC | 22 |
| CpG 100seq_01F | chr16: 84489852-84490026 | aggaagagagTTGTGGATTTTGATTAATGGGT | 23 |
| CpG 100seq_01R | | cagtaatacgactcactatagggagaaggctAAAAACTTTCCCAAAAATTCC | 24 |

TABLE 5(A)-(C)-continued

Sequenom MassARRAY methylation analysis:
A list of primers used for technical and
independent validations with Sequenom.

| Primer Name | Position | Primer Sequence 5'-3' | SEQ ID NO |
|---|---|---|---|
| CpG 100seq_02F | chr16: 84489673-84489812 | aggaagagagGTTGGATATTGGGTAGTGATGTT | 25 |
| CpG 100seq_02R | | cagtaatacgactcactatagggagaaggctAACCTCCTTTAAAACTAAAATTCTCC | 26 |
| Cpg 261seq_01F | chr6: 337531-337687 | aggaagagagTTGGGTAGGGATAGGGGTTTTATT | 27 |
| Cpg 261seq_01R | | cagtaatacgactcactatagggagaaggctCTCTATCAATTTCCACTCCCCTAAC | 28 |
| CpG 24seq_01F | chr1: 198276357-198276524 | aggaagagagGTTAGGGAGGGAATAATGTTAGGAA | 29 |
| CpG 24seq_01R | | cagtaatacgactcactatagggagaaggctACCCTAAACTCTACTCTCAACACCTC | 30 |
| CpG 24seq_02F | chr1: 198276693-198276861 | aggaagagagGGTTGTGAGAGTTTTTTAGAGTTGAA | 31 |
| CpG 24seq_02R | | cagtaatacgactcactatagggagaaggctACTAAAATCCCCAACCCAAC | 32 |
| CpG 188seq_01F | chr11: 32412596-32412728 | aggaagagagAGGTTTTTAGTTTTGTTTGGTTTTG | 33 |
| CpG 188seq_01R | | cagtaatacgactcactatagggagaaggctAACTCTTACCCAACTACTTCCCAA | 34 |
| CpG 272seq_01F | chr20: 61107904-61108031 | aggaagagagTATTTGTTAGGGTAGGGTTTTAGGG | 35 |
| CpG 272seq_01R | | cagtaatacgactcactatagggagaaggctTAACCTTCCTCAACCAAAACCAA | 36 |
| (B) Sequenom Primers: for N vs T Validation ||||
| C9orf125_01F | chr9: 103288327-103288472 | aggaagagagTTAGGGTTTTGGATTTAGTGTTTGT | 37 |
| C9orf125_01R | | cagtaatacgactcactatagggagaaggctTCCCTCCCAAAACCAAAA | 38 |
| NPY_manF | chr7: 24291366-24291534 | aggaagagagGAGTTTTTTGTGTTTGTAGATGTTAGG | 39 |
| NPY_manR | | cagtaatacgactcactatagggagaaggctCCRAATAATATCTAACCATATCCTCC | 40 |
| HMX2_05F | chr10: 124892242-124892377 | aggaagagagGTTTTTTGGTTGGGTTATTGAGT | 41 |
| HMX2_05R | | cagtaatacgactcactatagggagaaggctAACACCTAAACTCCCCTTAAAAATC | 42 |
| FFRD3L_02F | chr7: 19151437-19151604 | aggaagagagGGGGAGGTTAGGGATAGGTT | 43 |
| FERD3L_02R | | cagtaatacgactcactatagggagaaggctTACCCCATCAAATTCAAAACTATTA | 44 |
| SATB2_01F | chr2: 200043840-200043962 | aggaagagagGTTTTTGGTTGTAGTTTTTGGGATT | 45 |
| SATB2_01R | | cagtaatacgactcactatagggagaaggctATAAACAACCTCCCACTTTAAAACTAA | 46 |
| (C) Sequenom Primers: for T Technical Validation ||||
| CNTD2_01F | Chr19: 45424298-45424447 | aggaagagagATTTTGTAAAGGAGAGGGTTTGG | 47 |
| CNTD2_01R | | cagtaatacgactcactatagggagaaggctTCTCTTCCCCTAACTACAAAAATC | 48 |
| RREB1_01F | Chr6: 7052019-7052195 | aggaagagagGGAGTTTTTTGAGAGAAAGAGATATTG | 49 |
| RRKB1_01R | | cagtaatacgactcactatagggagaaggctACACCCCACAAAAAATACTTCAAC | 50 |

1.1.6 Computational Analysis of MBDCap-Seq Data
1.1.6.1 Alignment

MBDCap-Seq sequenced reads were aligned to the hg18 version of the human genome with BOWTIE v1.0. Reads with more than three mismatches and reads mapping to multiple positions were removed. Finally, multiple reads mapping to exactly the same genomic coordinate were eliminated and only one read was retained for downstream analysis to remove redundancy. Alignment statistics for samples used in this study are provided in Table 6.

TABLE 6

Alignment statistics: for each sample the (i) total number of reads in the library, (ii) number of aligned reads, and (iii) number of unique reads are provided.

| Sample ID | Total reads | Aligned reads | Unique reads |
|---|---|---|---|
| 17420 Normal | 41,214,252 | 21,396,042 | 16,524,012 |
| 17420 Tumor | 40,818,983 | 24,232,321 | 18,884,159 |
| 16693 Normal | 41,096,580 | 20,734,837 | 15,979,081 |
| 16693 Tumor | 39,360,609 | 22,063,794 | 16,031,831 |
| 23622 Normal | 38,285,502 | 20,153,788 | 16,611,821 |
| 23622 Tumor | 37,404,722 | 21,637,499 | 16,547,504 |
| 2032 Tumor | 40,053,141 | 17,688,522 | 10,537,184 |
| 4537 Tumor | 40,806,884 | 19,252,828 | 13,006,143 |
| 7700 Tumor | 40,245,430 | 22,013,746 | 15,838,961 |
| 19038 Tumor | 39,025,015 | 19,543,733 | 14,041,729 |
| 2319 Tumor | 36,864,046 | 18,406,242 | 13,986,362 |
| 8948 Tumor | 38,280,170 | 17,047,988 | 11,506,247 |
| 19328 Tumor | 38,497,959 | 16,647,038 | 10,707,102 |
| 20578 Normal | 41,850,776 | 19,673,402 | 13,675,555 |
| 20578 Tumor FF | 12,635,126 | 7,344,021 | 6,645,009 |
| 20578 Tumor | 11,105,400 | 6,164,585 | 5,345,885 |
| 2850 Normal | 39,184,148 | 15,936,763 | 11,542,100 |
| 2850 Tumor | 17,615,232 | 10,002,313 | 7,787,875 |
| 14906 Normal | 41,562,010 | 16,405,617 | 9,099,153 |
| 14906 Tumor | 40,430,984 | 17,411,629 | 11,818,921 |
| 12627 Tumor | 16,283,374 | 8,432,654 | 6,159,450 |
| 2532 Tumor | 37,558,382 | 17,567,682 | 13,898,084 |
| 1138 Tumor | 23,312,671 | 10,738,212 | 5,892,046 |
| 214 Tumor | 22,290,885 | 10,776,952 | 7,835,497 |
| 3050 Tumor | 26,040,883 | 10,929,464 | 7,563,843 |
| 4488 Tumor | 39,937,701 | 20,672,983 | 14,388,291 |
| Roche Blood | 37,445,060 | 28,126,429 | 23,155,761 |
| Roche Blood SssI | 33,374,082 | 21,324,538 | 19,131,929 |

1.1.6.2 Identification of Differentially Methylated Regions (DMRs)

In order to accurately delineate regions of the genome assayable by MBDCap-Seq, a fully methylated sample (SssI blood sample) was used to guide us to the genomic regions attracting sequenced tags. More specifically, the findPeaks peak calling utility from HOMER suite of programs (Jatoi et al., (2011) *Journal of Clinical Oncology* 29:2301-2304) was applied to the fully methylated sample (with parameter settings of—style histone—size 300—minDist 300—tag Threshold 18) to identify 230,655 regions covering approximately 116 Mbp of the genome. These regions are interchangeably referred to as regions of interest or SssI regions.

For each MBDCap-Seq sample to be analyzed, the number of sequenced tags overlapping SssI regions were computed, which resulted in table of counts where columns are samples and rows are SssI regions. The edgeR Bioconductor package (Park et al., (2011) *Annals of Oncology*, 22:1554-1560), available at URL http://www.bioconductor.org/packages/release/bioc/html/edgeR.html, was used to model distribution of reads between normal (n=6) and tumor (n=19) group of samples in the discovery cohort. Since the edgeR package does not support modelling of paired and unpaired data simultaneously, two separate analyses were performed, a paired analysis with 6 normal/tumor pairs and unpaired analysis with all the samples, and then intersected the results.

1.1.6.3 Clustering of MBDCap-Seq Data

The number of reads mapping to a particular region of a genome does not depend solely on the average level of methylation in the region, but also on other factors, such as density of methylated CpG nucleotides. In order to compare MBDCap-Seq readout to other more quantitative technologies, such as HM450K and Sequenom, a fully methylated MBDCap-Seq sample was used to normalize MBDCap-Seq readouts for samples in the discovery cohort. More specifically, let $X_i$ be the number of tags overlapping region i and N be the total number of tags overlapping SssI regions in the sample to be normalized and $Y_i$ and M be the corresponding numbers in the control sample. Then, the normalized number of tags overlapping the region i is given by $$\log(X_i/N \cdot M/Y_i + 1)$$

Figure 1:
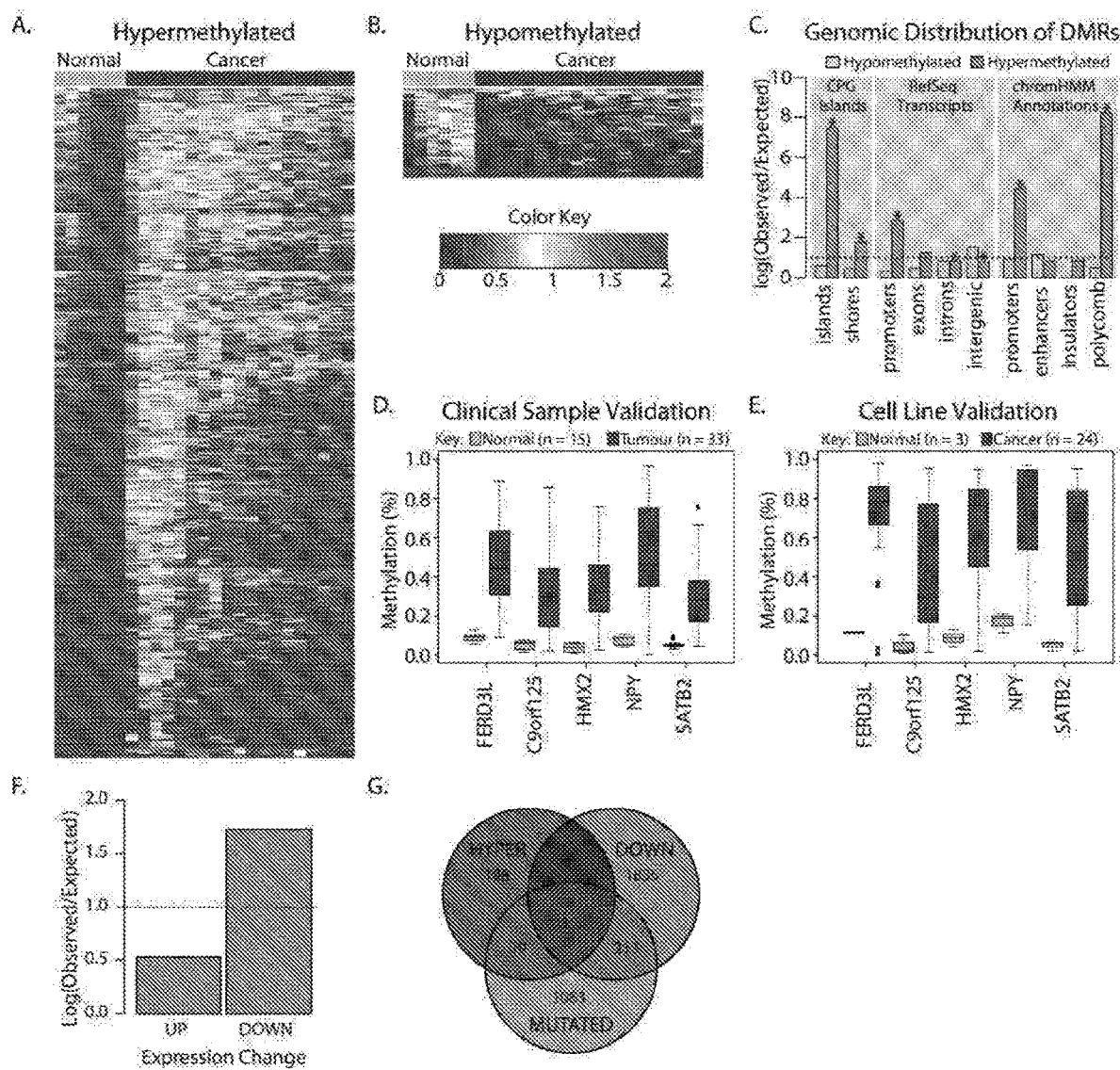
FIG. 1. MBDCap-seq identifies DMRs in a discovery cohort. (A) A heatmap showing methylation profile of 822 hypermethylated regions across a cohort of 19 tumour and 6 matched normal samples in the discovery cohort. The columns are samples and the rows are regions. The level of methylation (number of reads normalized with respect to fully methylated sample) is represented by a colour scale— blue for low levels and red for high levels of methylation. (B) A heatmap showing methylation profile of 43 hypomethylated regions across a cohort of 19 tumour and 6 matched normal samples in the discovery cohort. The columns are samples and the rows are regions. The level of methylation (number of reads normalized with respect to fully methylated sample) is represented by a colour scale— blue for low levels and red for high levels of methylation. (C) A bar plot showing location of DMRs across functional/regulatory regions of the genome—(i) CpG islands and shores, (ii) RefSeq transcripts, and (iii) Broad ChromHMM HMEC annotation. The height of the bars represents the level of enrichment measured as ratio between the number of hypermethylated (pink) or hypomethylated (blue) regions overlapping a functional element to the expected number of such regions. Statistically significant enrichments (p-value<0.05; hyper-geometric test) are marked with asterisks. (D) Sequenom validation of five hypermethylated regions—FERD3L, C9orf125, HMX2, NPY and SATB2— is shown for an independent cohort of TNBC samples. For each region average methylation levels are shown in grey/blue for normal/tumour samples. (E) Sequenom validation of five hypermethylated regions—FERD3L, C9orf125, HMX2, NPY and SATB2—is shown for a panel of breast cancer cell lines. For each region average methylation levels are shown in grey/blue for normal/tumour cell lines. (F) A bar plot showing enrichment of genes with promoter hypermethylation in sets of genes that are up-/down-regulated in the TCGA cohort of TNBC tumour as compared to matched normal samples. The height of the bars represents the level of enrichment measured as a ratio between the observed number of up-/down-regulated genes with promoter hypermethylation to the expected number of such genes. (G) A Venn diagram showing overlap between genes with promoter hypermethylation, genes down-regulated in TCGA TNBC cohort and genes with two or more mutation in TCGA breast cancer cohort.
Figure 5:
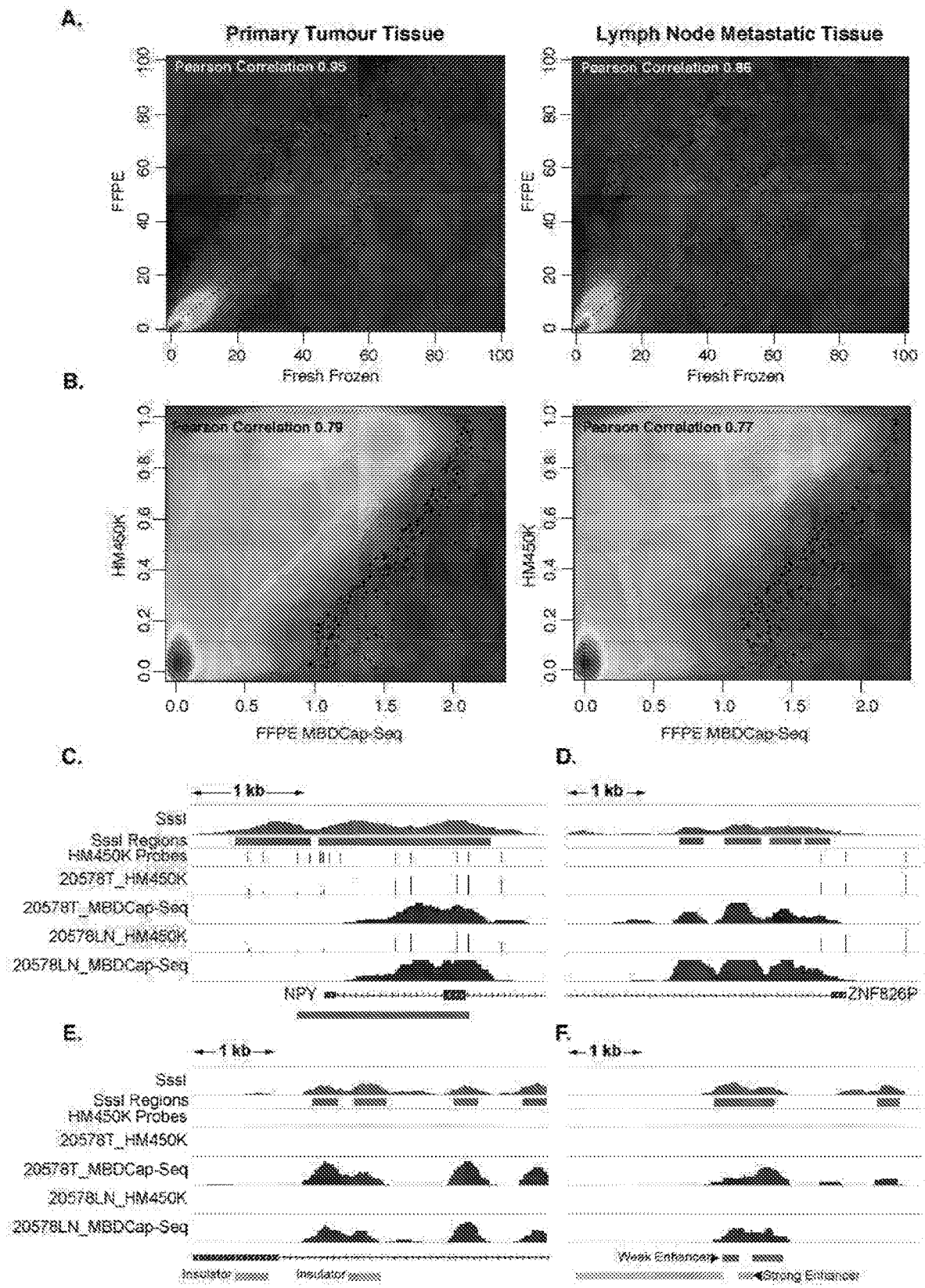
FIG. 5. Technological assessment of MBDCap-seq platform. (A) A scatter plot showing correlation between MBDCap-Seq readout (number of tags across SssI regions) generated from high quality fresh frozen tissue and archival FFPE samples for both primary tumour and lymph node metastatic tissue. (B) A scatter plot showing agreement between MBDCap-seq readout (number of tags overlapping a region normalized to the number of overlapping tags in SssI sample) and HM450K array readout (average beta value of HM450K probes overlapping a region) over 75,020 SssI regions that contain at least one HM450K probe. At these commonly interrogated loci, HM450K and MBDCap-seq readouts correlated highly (pearson's $r>0.77$). (C) The NPY promoter assayed by both MBDCap-Seq and HM450K array with high concordance. (D) This figure illustrates that the promoter region of ZNF826P contains few HM450K probes, however, MBDCap-Seq demonstrates that the region immediately downstream is heavily methylated in a region not assayed by HM450K. (E) This figure illustrates that MBDCap-Seq interrogates functionally important insulator elements that are missed by the HM450K array. (F) This figure illustrates that MBDCap-Seq interrogates functionally important enhancers that are missed by the HM450K array.
Figure 7:
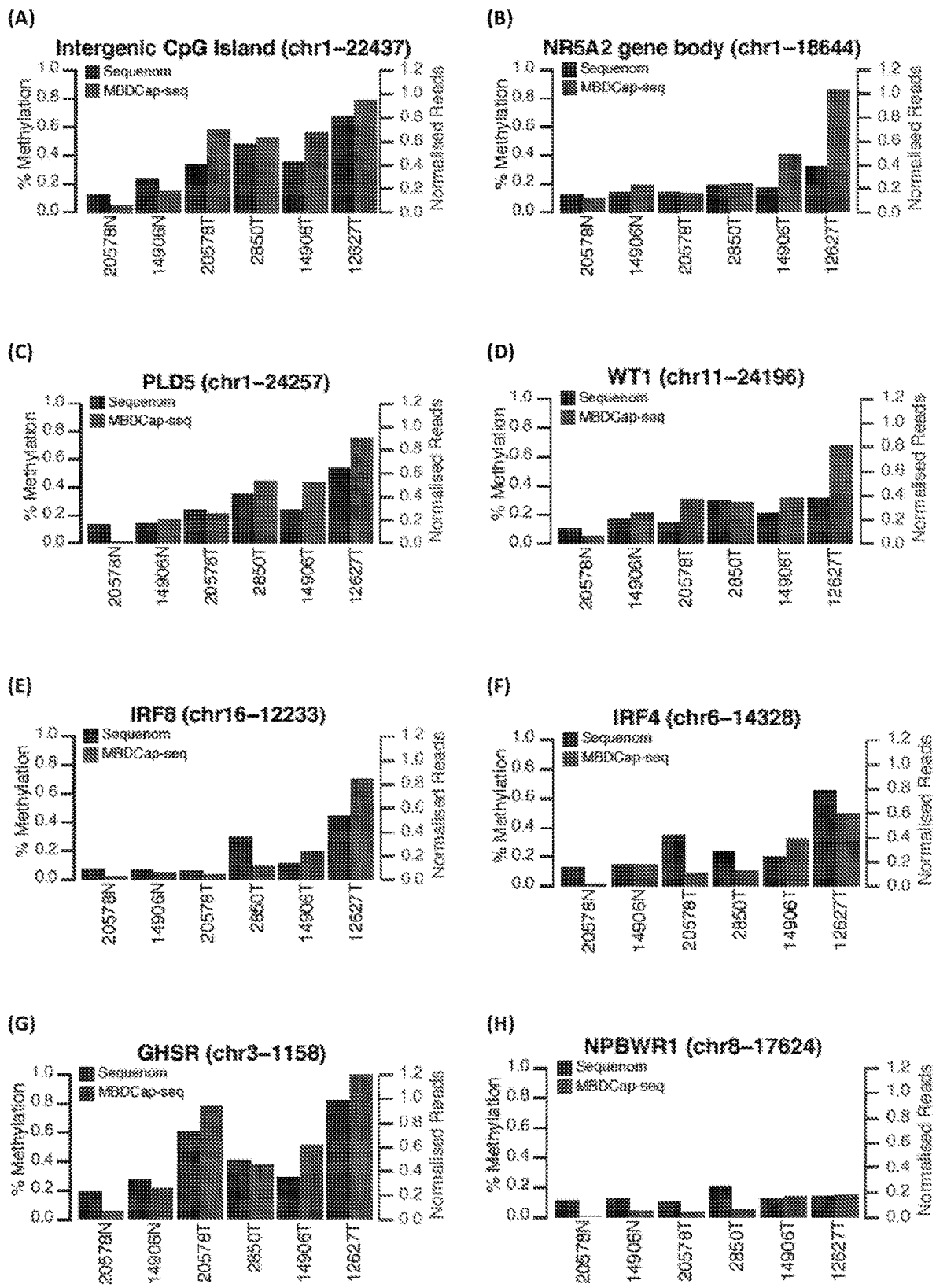
FIG. 7. Technical validation of MBDCap-Seq with Sequenom methylation analysis. Eight SssI regions were selected to validate the methylation levels reported by MBDCap-Seq using Sequenom on the same DNA samples. These regions included an intergenic CpG Island and the genes NR5A2, PLD5, WT1, IRF8, IRF4, GHSR and NPBWR1. Validation data for each of these Sssi regions is represented in A-H respectively. For each region, mean CpG methylation by Sequenom (purple bars, left axis) is shown alongside MBDCap-Seq readout (number of tags overlapping the region normalized to the number of overlapping tags in SssI sample; red bars, right axis) across 2 normal and 4 tumour samples from the discovery cohort. This validation shows that regions of high methylation detected by MBDCap-Seq also show corresponding elevated cancer-specific methylation levels by Sequenom analysis, while samples with no MBDCap-Seq enrichment were unmethylated in corresponding patient DNA.
Figure 8:
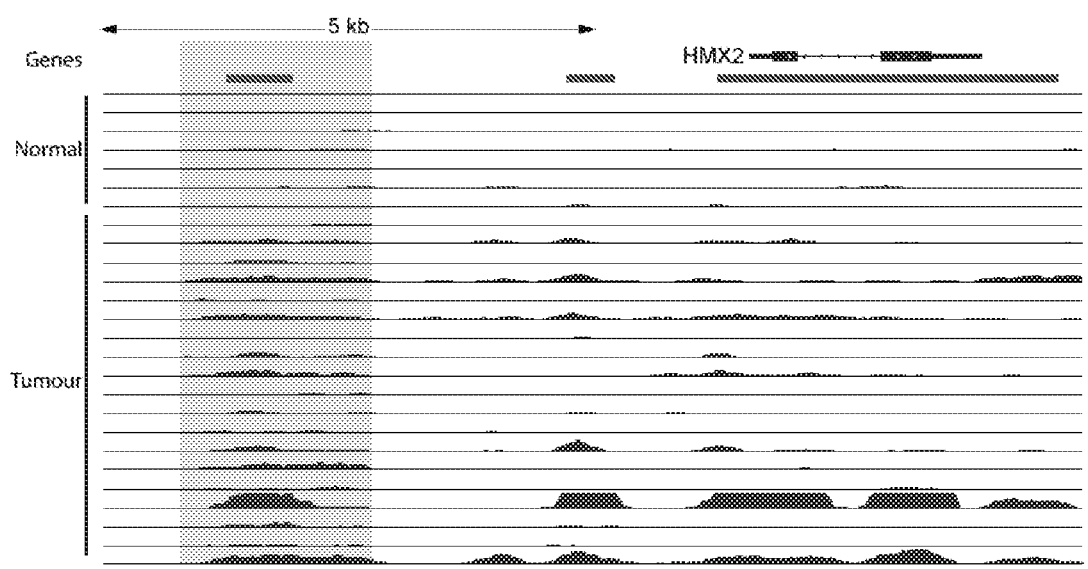
FIG. 8. MBDCap-Seq methylation profiles of candidate DMRs selected for Sequenom validation in an independent cohort of TNBC samples. The methylation profiles for genomic loci associated with HMX2, FERD31, SATB2, NPY and C9orf125 (illustrated in A-E respectively) exhibit low normal and high tumour methylation in the discovery cohort.
Figure 8:
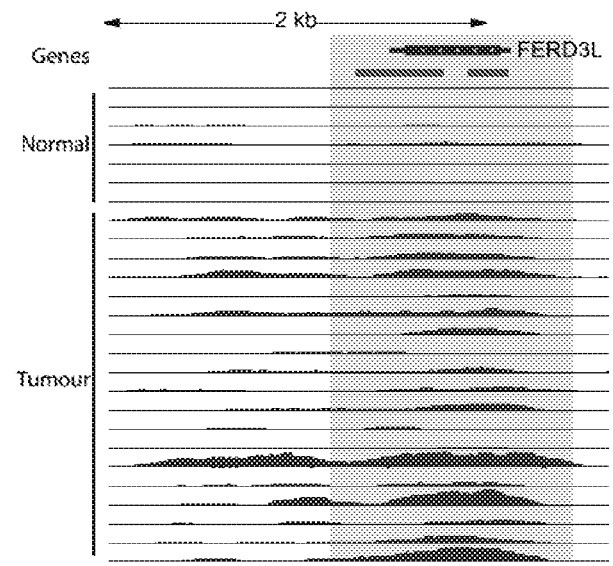
Figure 8:
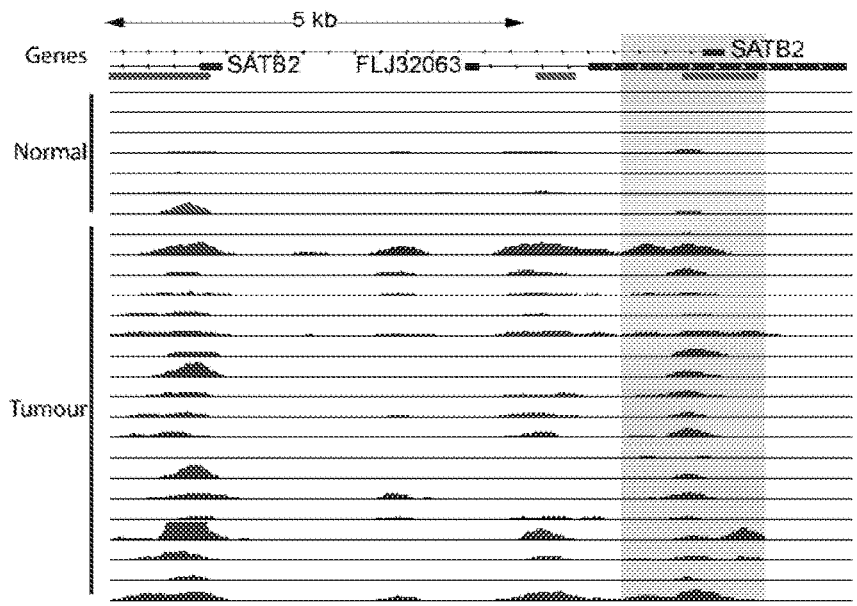
Figure 8:
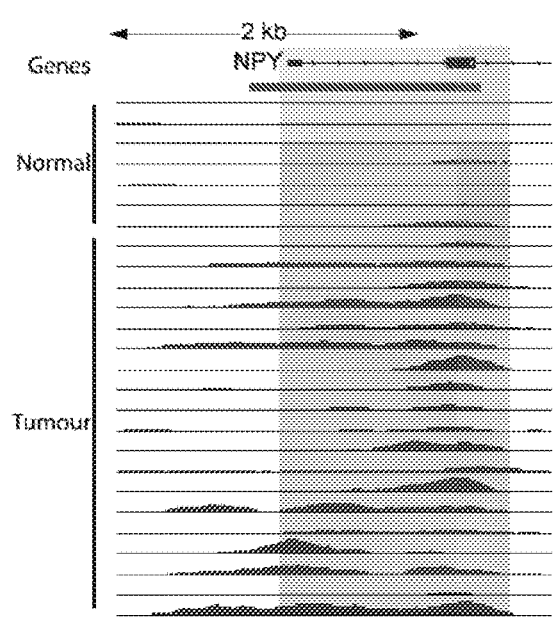
Figure 8:
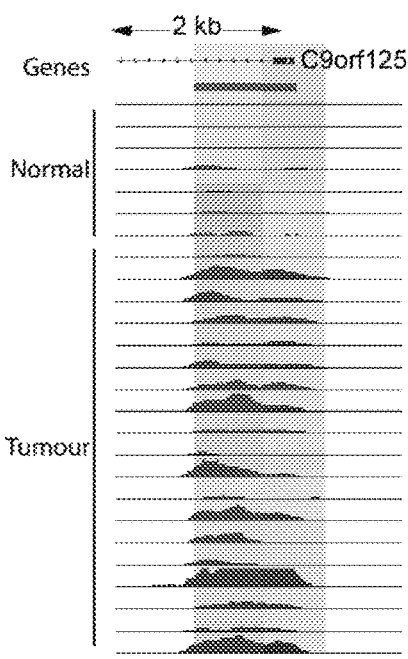

The normalized tag counts were used for heatmap visualization in FIG. 1, for comparison to HM450K in FIG. 5 and for comparison to Sequenom in FIG. 7.

1.1.7 Functional Annotations of the Genome 1.1.7.1 CpG Islands and Shores

CpG island annotation for hg18 was obtained from UCSC genome browser. The location of CpG island shores was derived from CpG islands by taking +/−2 Kb flanking regions and removing any overlaps with CpG islands.

1.1.7.2 RefSeq Transcripts

RefSeq transcript annotation for hg18 was obtained from UCSC genome browser. Promoters were defined as +2000/−100 bp around transcription start site (TSS). Intergenic regions were defined as regions complementing transcript regions extended to +/−2 Kb around the transcripts.

1.1.7.3 HMEC ChromHMM

HMEC ChromHMM annotations for hg18 were downloaded from ENCODE. The original annotation partitions the HMEC genome into 15 functional states (see FIG. 1b in Reis-Filho and Pusztai, (2011) *The Lancet*, 378:1812-1823). For the sake of brevity, the three original promoter states were collapsed into one promoter state and the four original enhancer states collapsed into one enhancer state (FIG. 1C and FIG. 4B).

1.1.8 Acquisition and Analysis of TCGA Data 1.1.8.1 Acquisition of TCGA data

Several molecular datasets from TCGA breast cancer (BRCA) cohort were used throughout the study e.g., for validation. Clinical annotation of samples was obtained from the TCGA publication in TCGA (2012) *Nature*, 490:61-70 (Supplementary Table 1). Raw HM450K methylation data (Level 1) was obtained from TCGA data portal in January 2012. Methylation data spanned 67 normal and 354 tumor ER+ve samples, 16 normal and 105 tumor ER−ve samples, and 9 normal and 73 tumor TNBC samples.

Processed array expression data (Level 3) was obtained from TCGA data portal in March 2012. Expression data spanned 52 normal and 406 tumor ER+ve samples, 9 normal and 118 tumor ER−ve samples, and 8 normal and 89 tumor TNBC samples. Processed RNA-Seq expression data (Level 3) was obtained from TCGA data portal in December 2012. Expression data spanned 73 normal and 588 tumor ER+ve samples, 19 normal and 174 tumor ER−ve samples, and 12 normal and 119 tumor TNBC samples. TCGA BRCA mutation data was obtained from COSMIC database (http://cancer.sanger.ac.uk/cosmic/study/overview?study_id=414). Genes mutated in 2 or more patients were declared as recurrently mutated.

1.1.8.2 Analysis of HM450K Methylation Data

The raw data was pre-processed and background normalized with Bioconductor minfi package using preprocess Illumina ( . . . , bg.correct=TRUE, normalize="controls", reference=1) command; resulting M-Values were used for statistical analyses (Laird P W (2003) Nat. Rev. *Cancer,* 3:253-266). and Beta-Values for heatmap visualizations and clustering. To identify TNBC specific HM450K probes, a t-test comparison between TNBC (n=73) and non-TNBC (n=386) tumors was carried out. This analysis resulted in 282 probes having adj. p-value less than 0.05 and estimated mean difference of methylation between TNBC and non-TNBC tumors of at least 10%; these probes were declared as TNBC specific. Regions overlapping 3 or more TNBC specific probes were declared as TNBC specific.

1.1.5.3 Analysis of Array Expression Data

Differential expression analysis between normal (n=8) and tumor (n=89) TNBC samples was carried out with Bioconductor limma package. Since only subset of tumor samples had paired adjacent normal samples, patient data was treated as random effect using limma's duplicateCorrelation( . . . ) function. This analysis resulted in 3,017 down-regulated and 3,407 up-regulated genes with adj. p-value less than 0.05 out of 17,655 genes on the array. When considering genes with SssI regions in their promoter regions only, these numbers of genes on the array was reduced to 15,543, out of which 2,119 were down-regulated and 2,722 were up-regulated.

1.1.8.4 Analysis of RNA-Seq Expression Data

Figure 2:
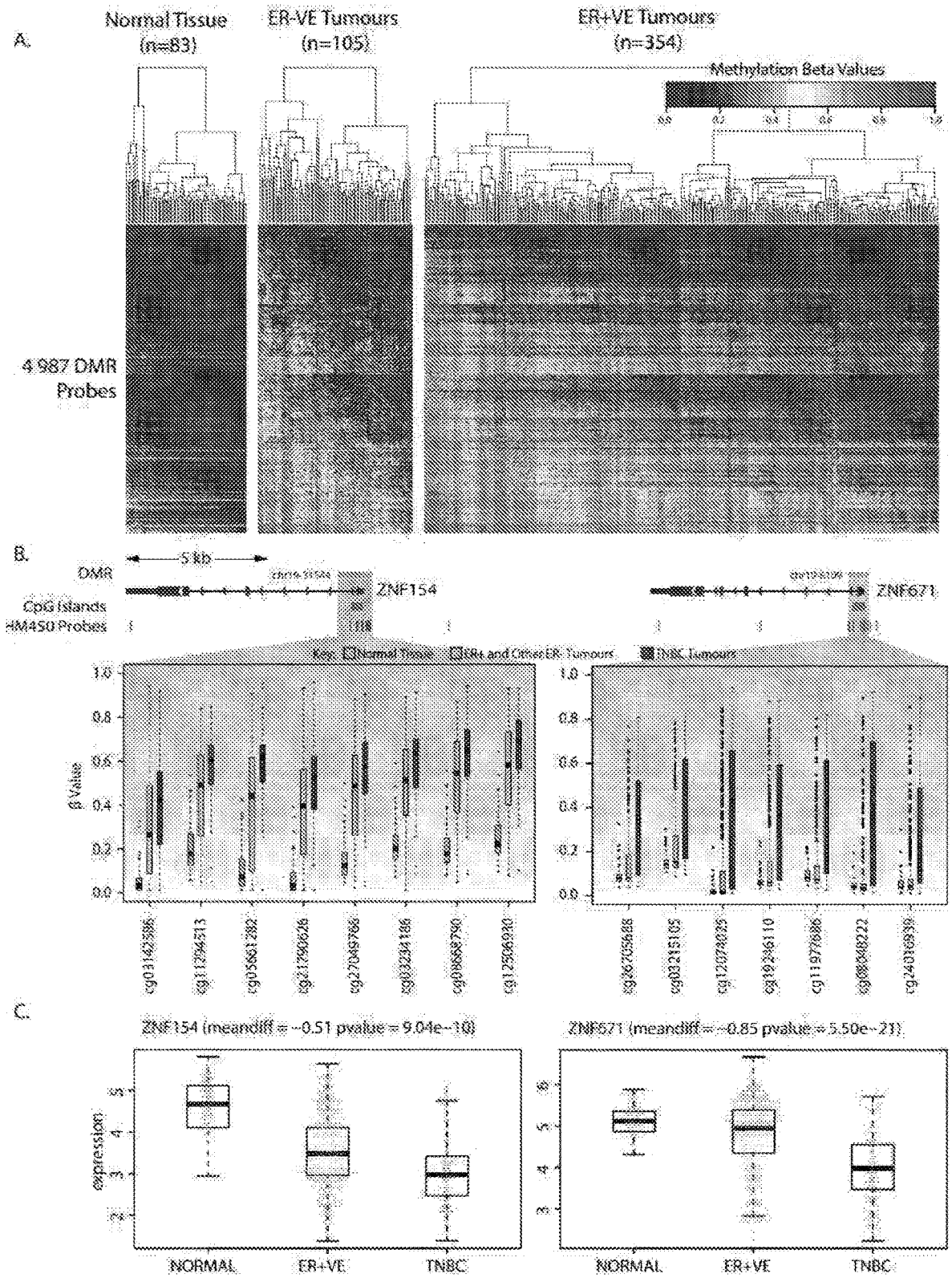
FIG. 2. Methylation profile of candidate DMRs in the TCGA breast cancer cohort. (A) A heatmap showing methylation profile of TCGA breast cancer samples across 4,987 HM450K probes overlapping hypermethylated DMRs identified in the discovery cohort. Rows are probes and columns are TCGA breast cancer samples profiled on HM450K—83 normal, 105 ER−VE tumour, and 354 ER+VE tumour samples. (B) Box plots showing distribution of methylation levels for two adjacent regions on chromosome 19 in TCGA normal, TNBC tumour, and other breast tumour samples. These two regions span the promoter of ZNF154 and the adjacent ZNF671 gene, are hypermethylated in the discovery cohort and exhibit regional TNBC specific hypermethylation in TCGA cohort, i.e. they are more heavily methylated in TNBC tumours as compared to normal and other tumour subtypes, as shown in the box plots. (C) Box plots showing distribution of expression levels of ZNF154 and ZNF671 genes in TCGA normal, TNBC tumour, and ER+VE tumour samples. The difference in expression of TNBC tumours versus ER+VE is found significant for both genes (t-test; ZNF154 mean diff. −0.51 with p-value 9.04e-10; ZNF671 mean diff. −0.85 and p-value of 5.50e-21).
Figure 11:
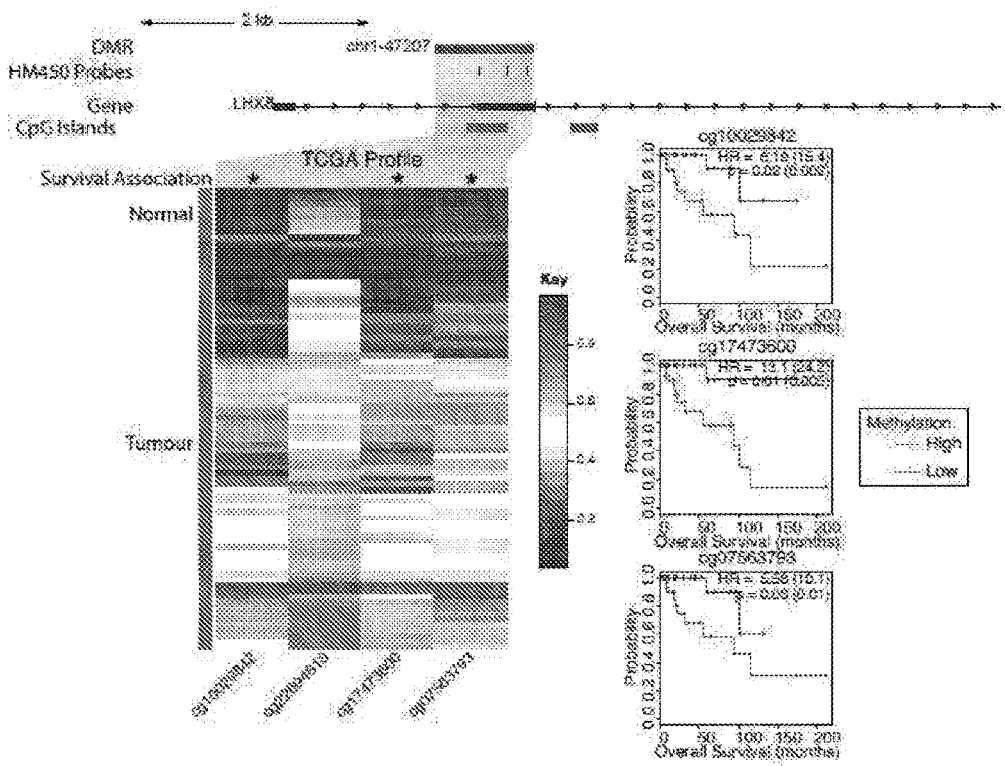
FIG. 11. Regions associated with overall survival in TCGA TNBC patients. For each of the 17 survival regions, regions overlapping 3 or more HM450K probes with statistically significant association with overall survival in TCGA TNBC cohort, we show: (i) genomic location of the region, (ii) heatmap showing methylation profile of survival probes in normal and tumour TNBC samples, and (iii) for each survival probe a Kaplan-Meier plot capturing survival curves for TNBC patients stratified based on median beta methylation value of the probe; hazard values and p-values are shown for both univariate and multivariate analyses (multivariate values are given in parentheses).
Figure 11:
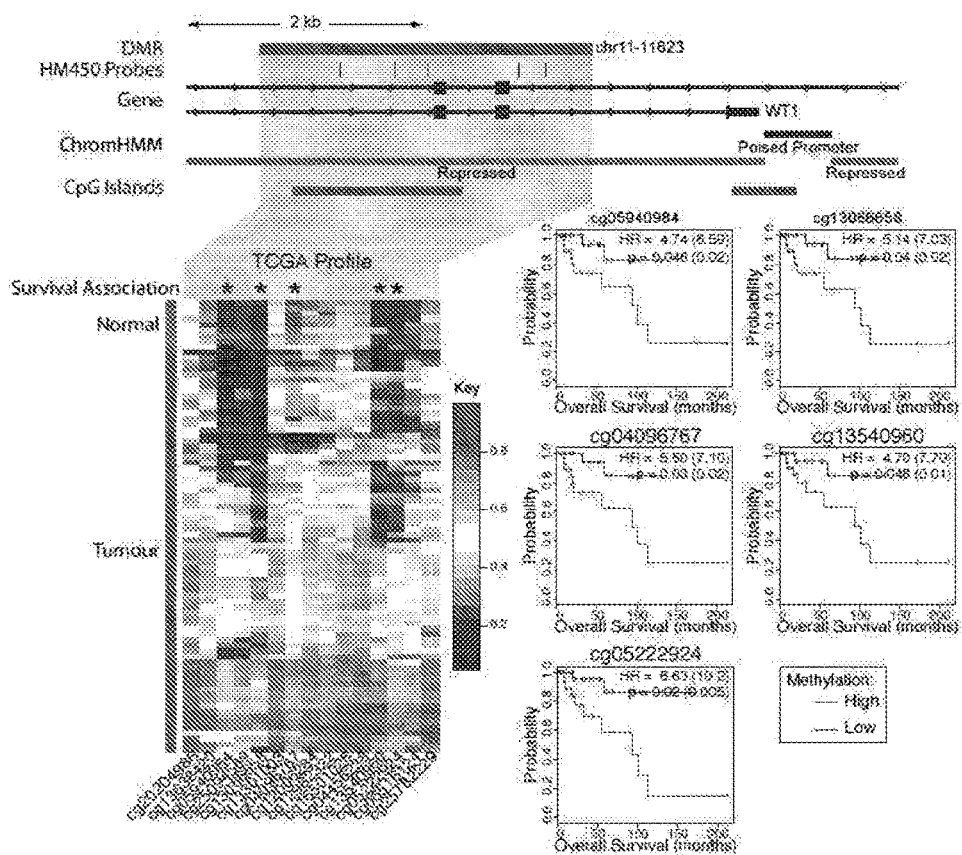
Figure 11:
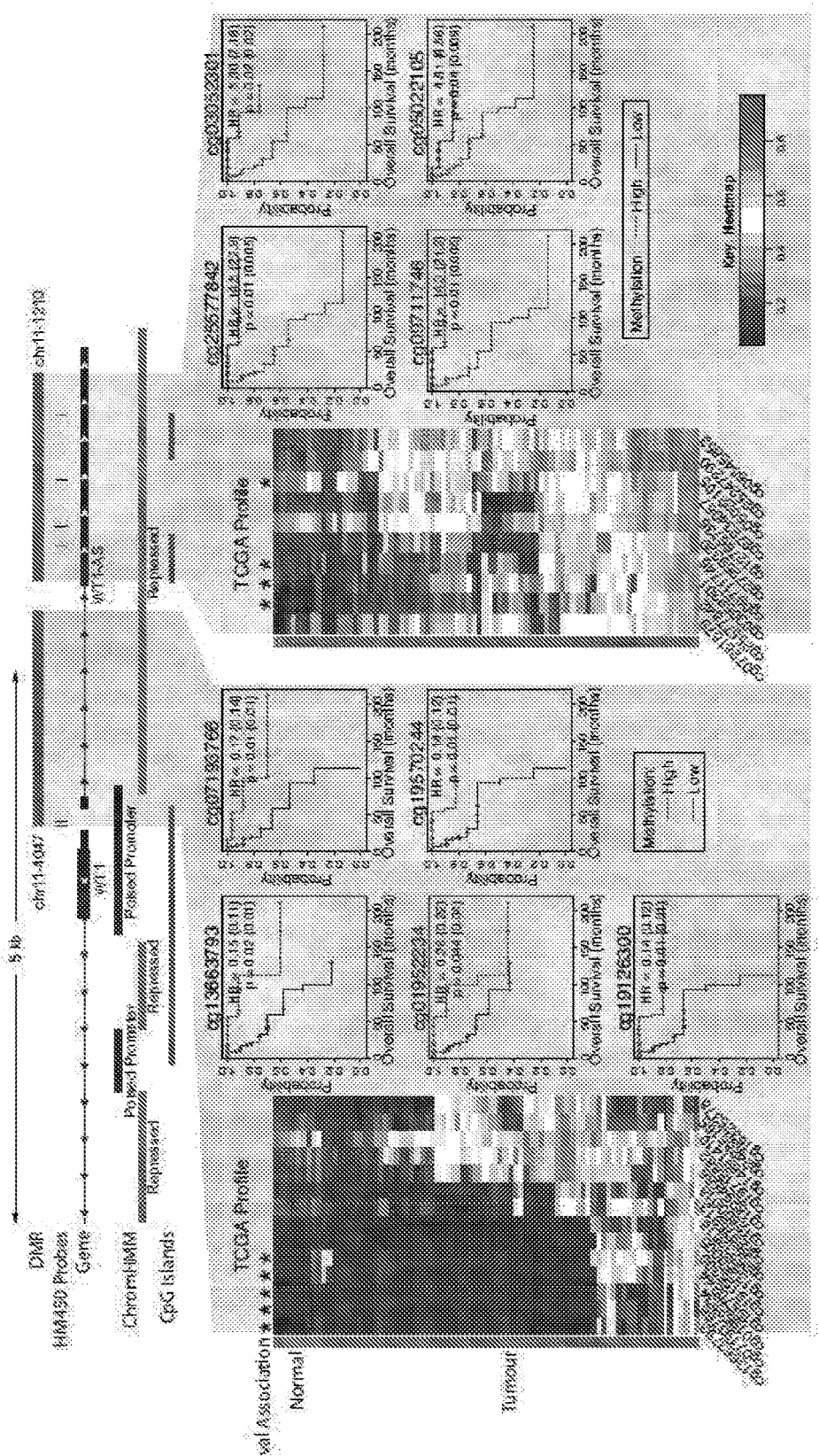
Figure 11:
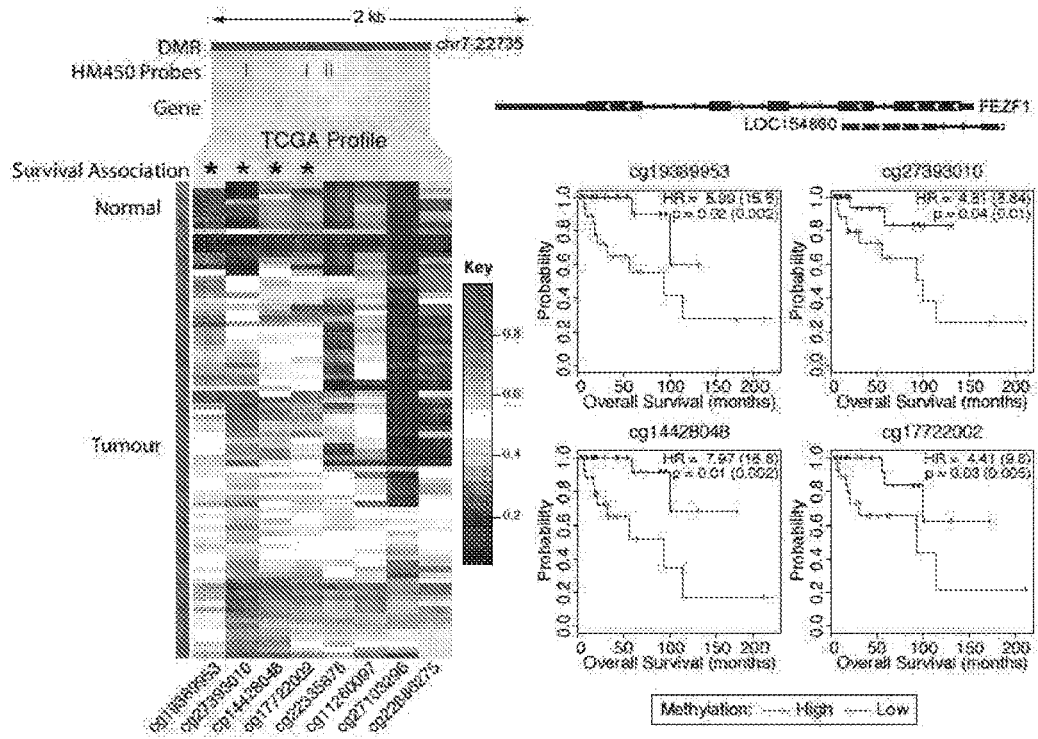
Figure 11:
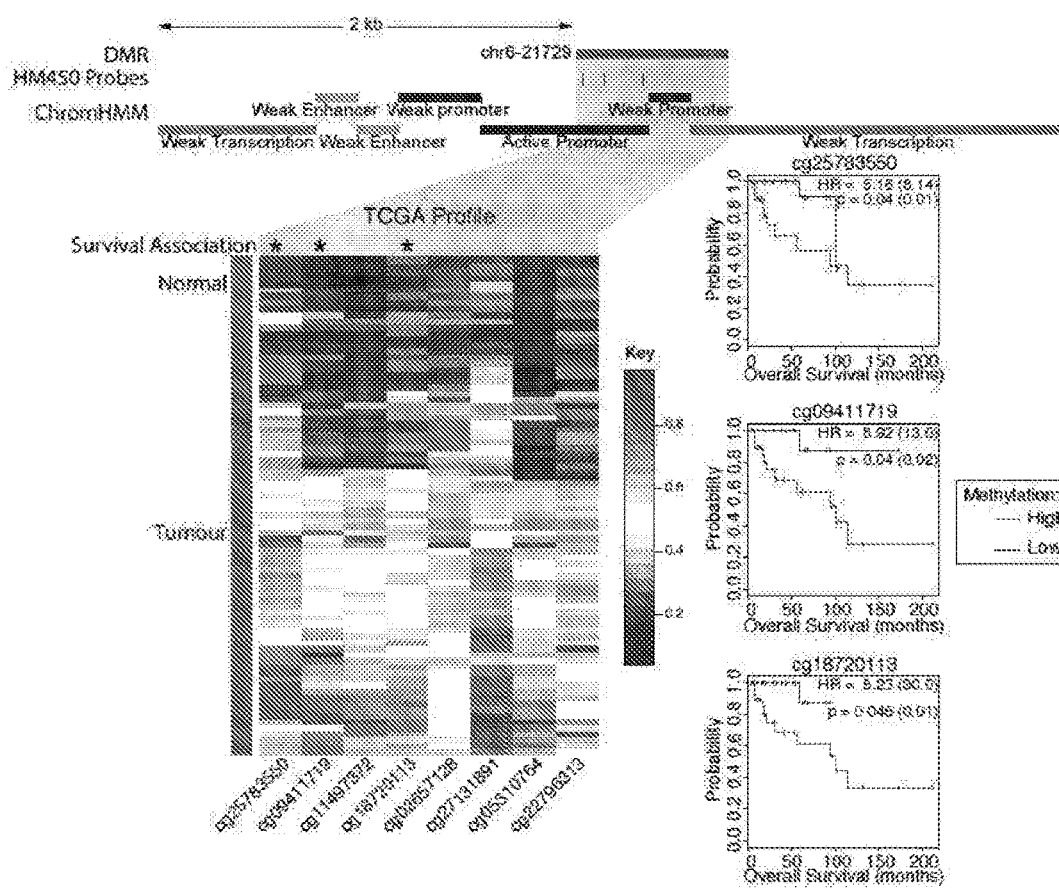
Figure 11:
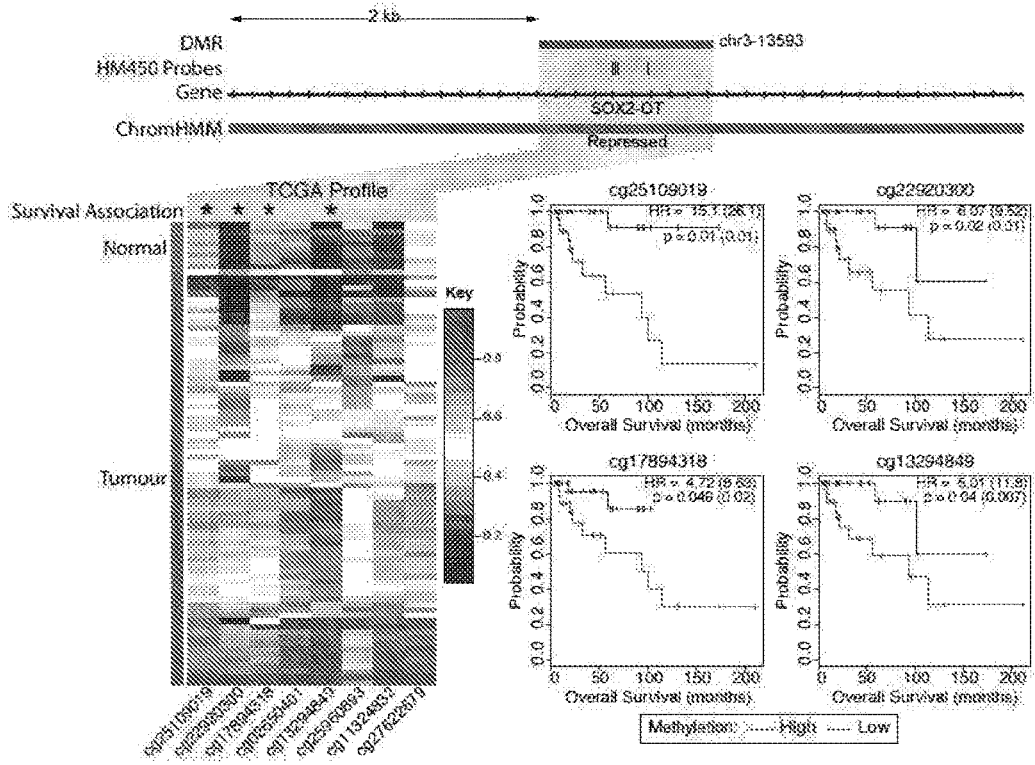
Figure 11:
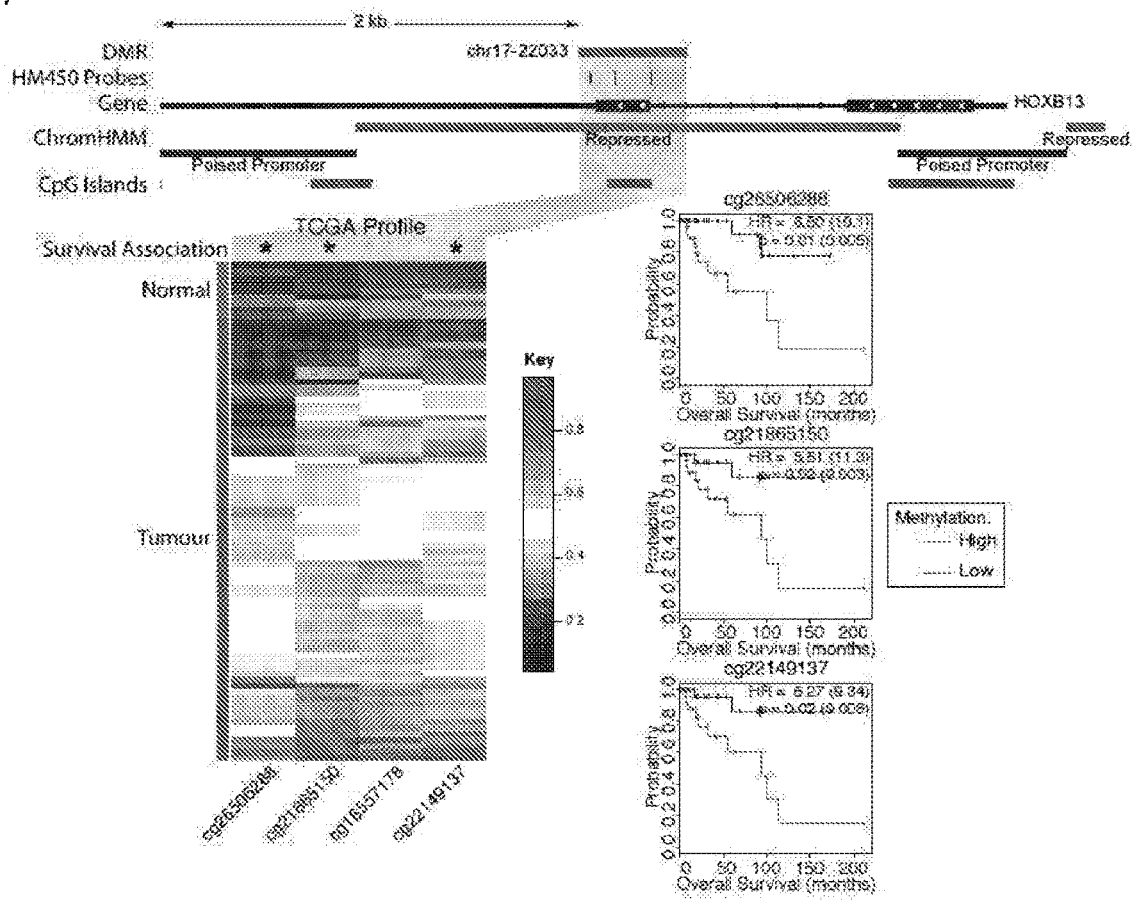
Figure 11:
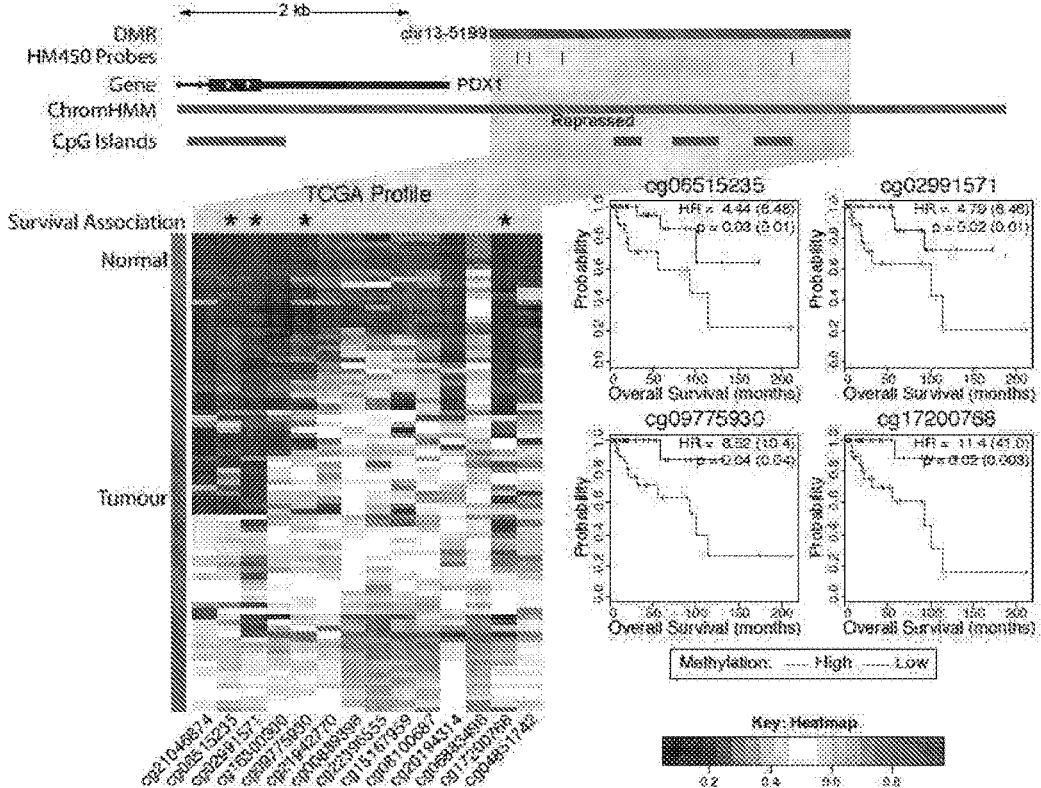
Figure 11:
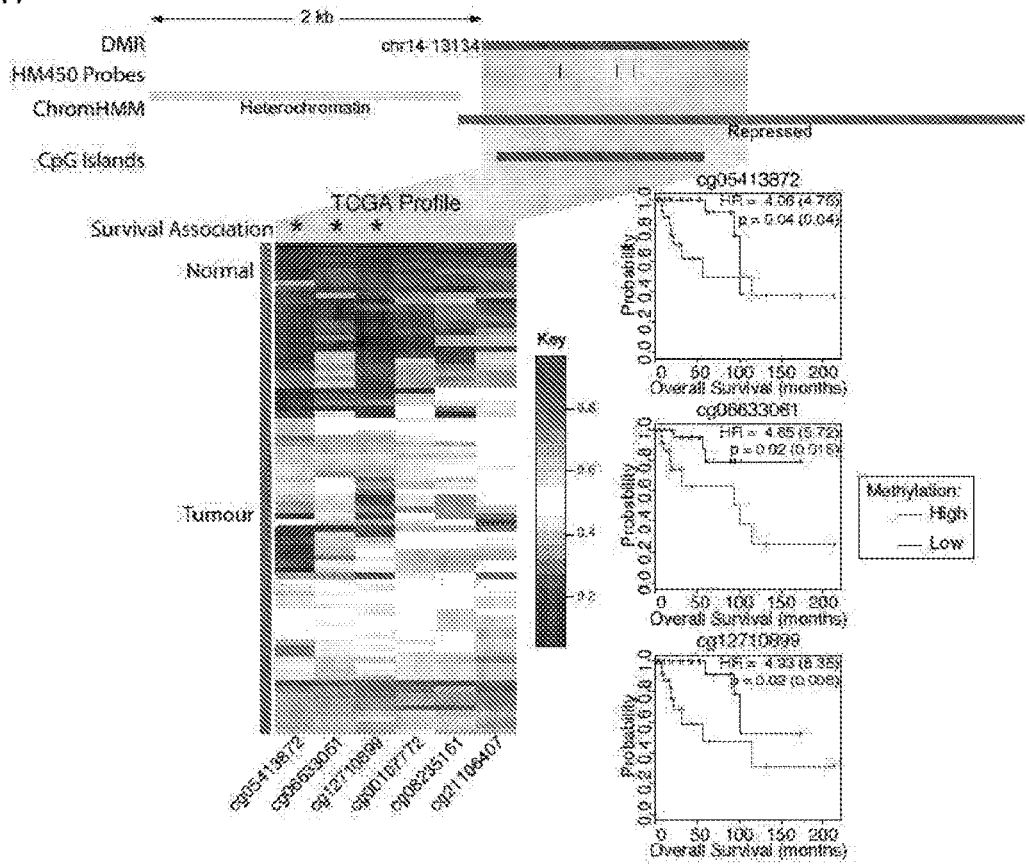
Figure 11:
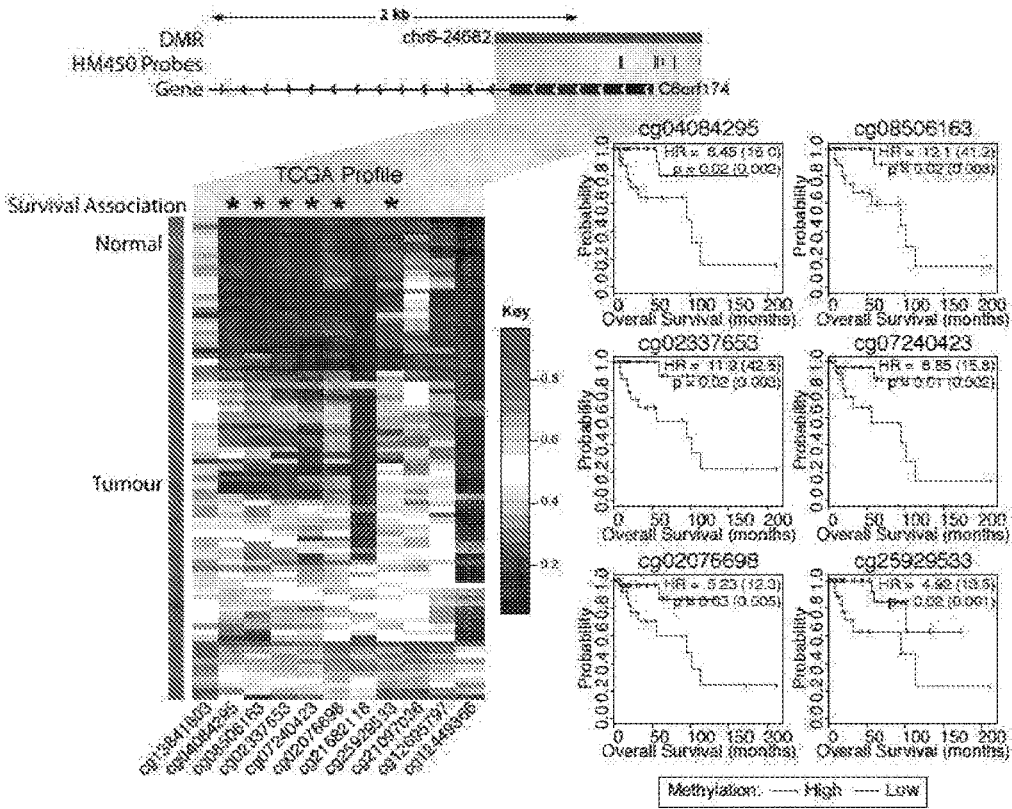
Figure 11:
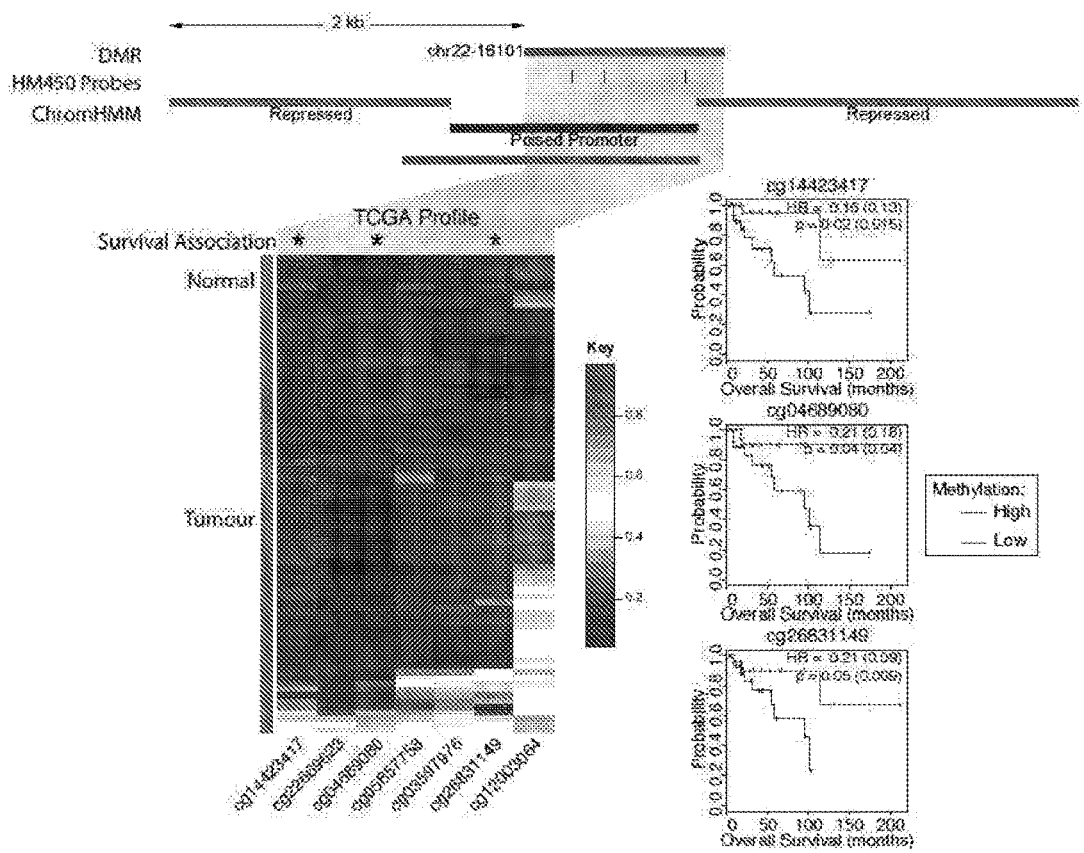
Figure 11:
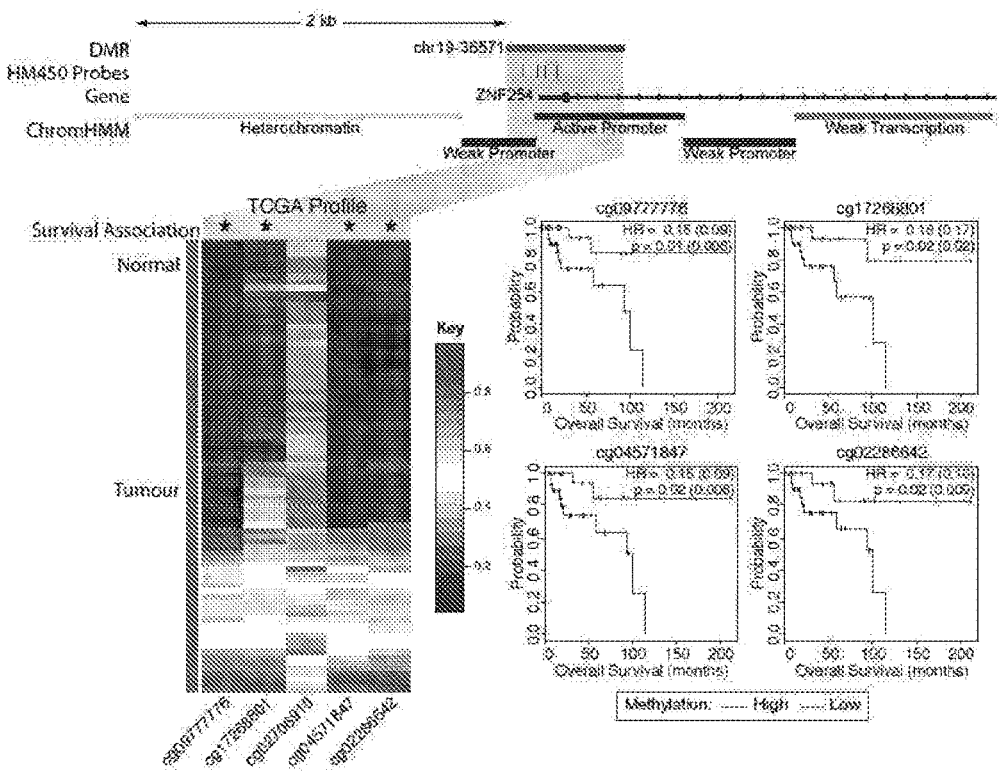
Figure 11:
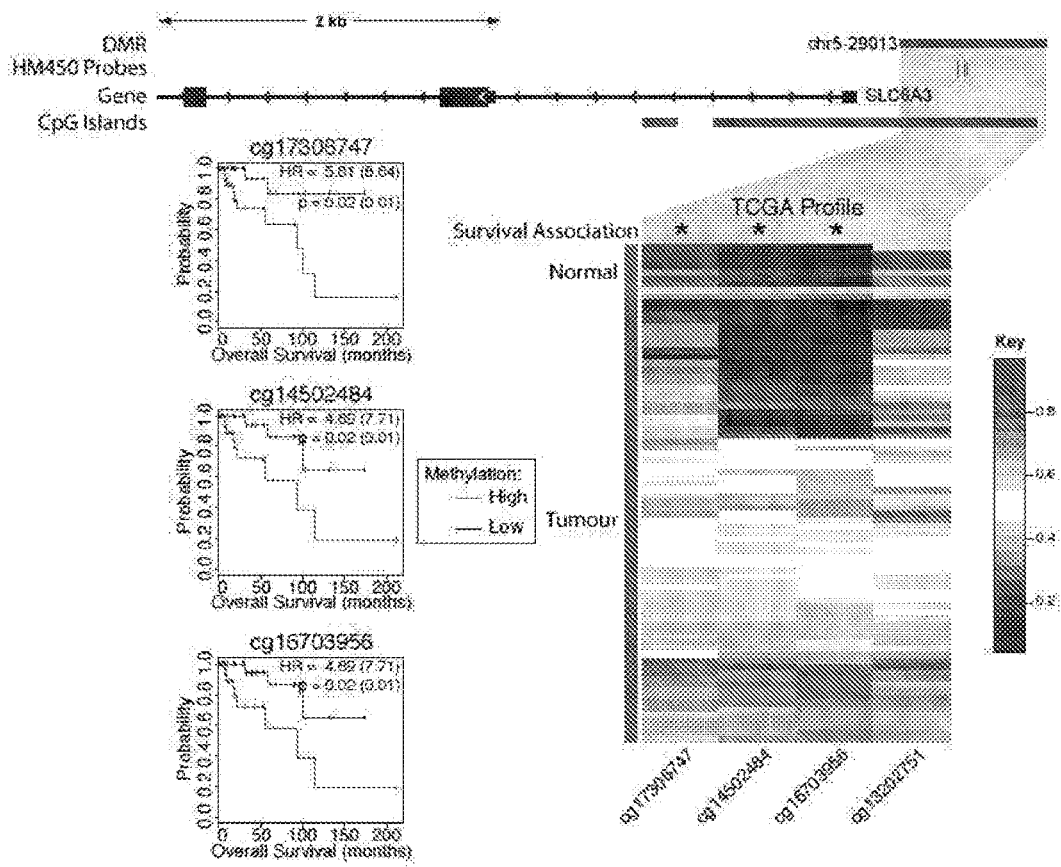
Figure 11:
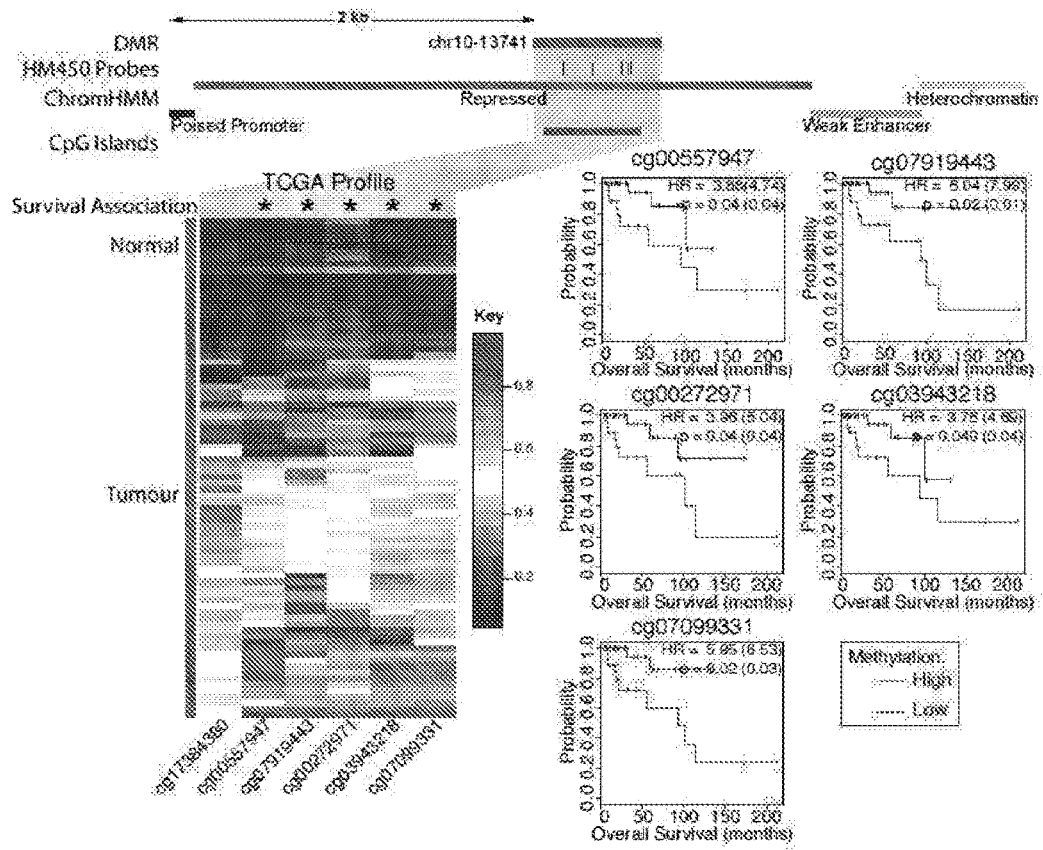
Figure 11:
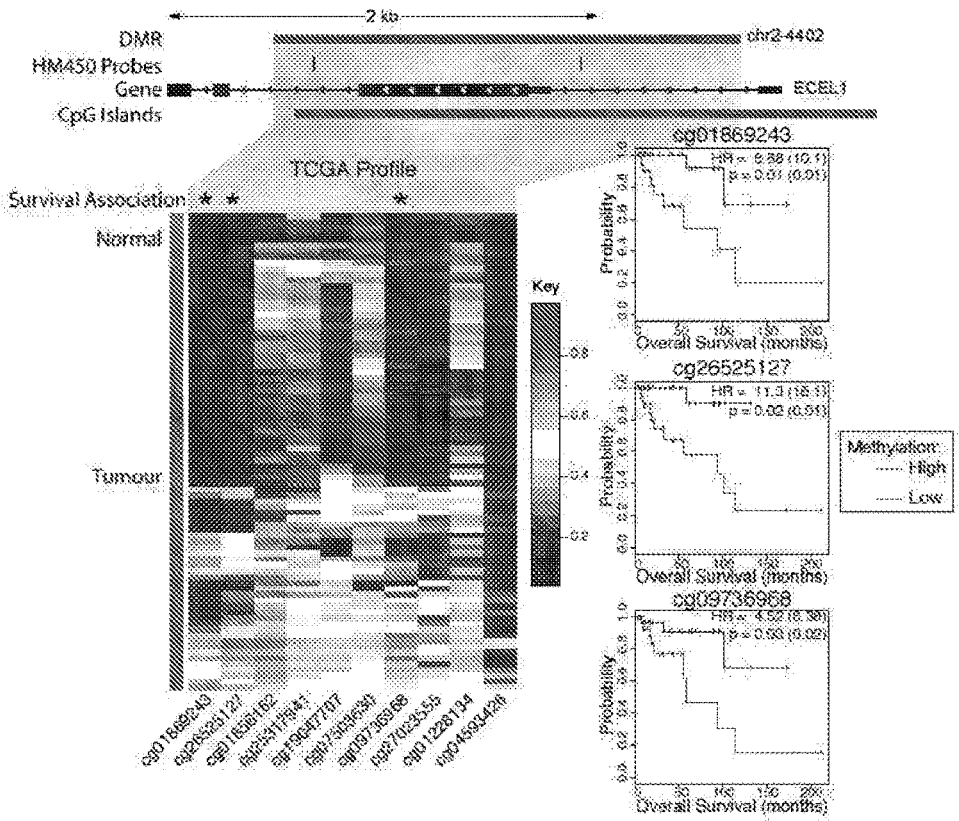
Figure 11:
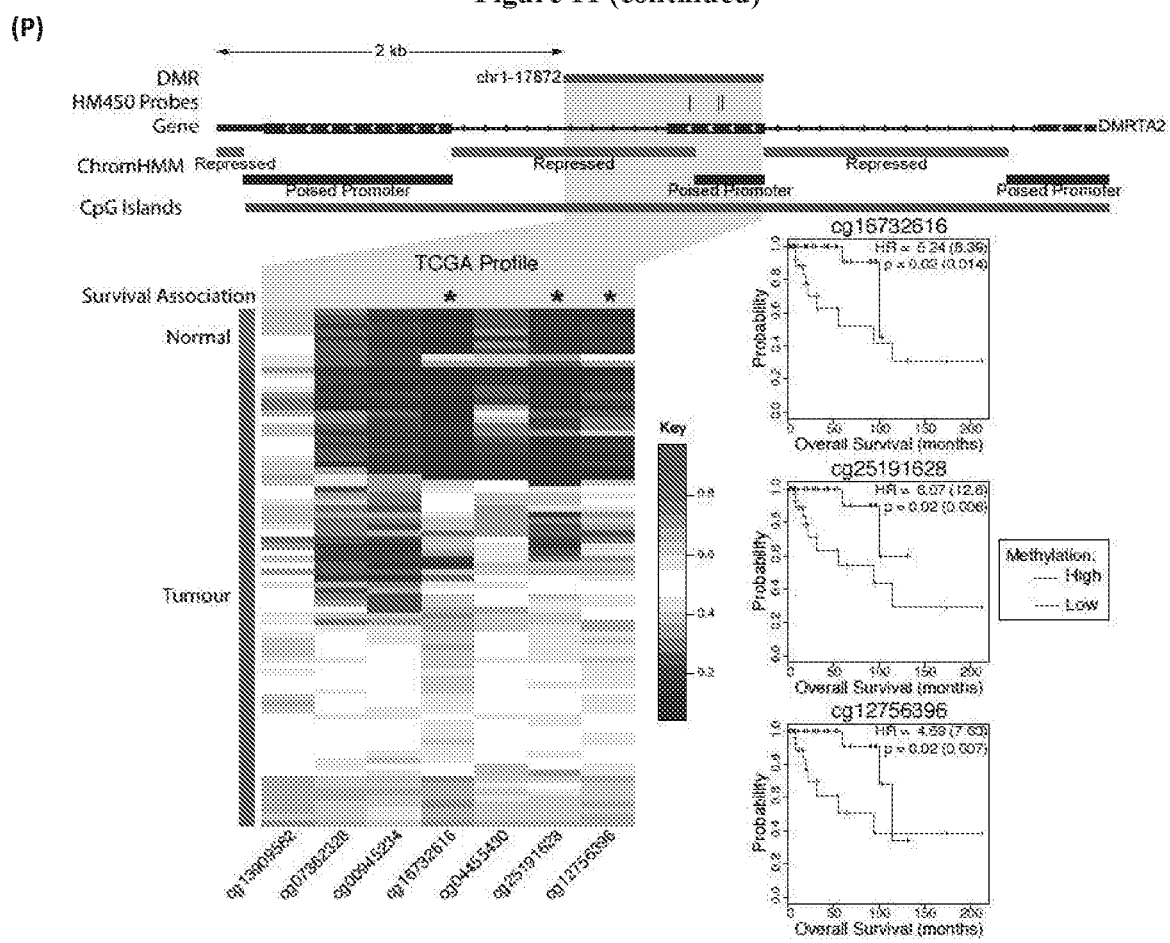

Log transformed RNA-Seq expression values were used to highlight relationship between methylation and expression for a number of candidate regions in FIG. 2C and FIG. 11.

1.2 Results 1.2.1 Genome Coverage of MBDCap-Seq

Computational analysis of SssI MBDCap-Seq revealed that MBDCap-Seq can robustly assess the methylation status of 230,655 regions spanning a total of 116 Mbp, comprising 5,012,633 CpG dinucleotides, or approximately 18% of the total number of CpG sites in the human genome (FIG. 4A). The assayed CpG sites span 91% of all CpG islands; 84% CpG island shores; 72% RefSeq promoters; 38% introns and 31% exons. Furthermore, a comparison of MBDCap-Seq with the Illumina HumanMethylation450K (HM450K) array (FIG. 4B) revealed that MBDCap-Seq is able to interrogate a further 4,740,327 CpG sites relative to the high-density HM450K array.

A major advantage of the MBDCap-Seq method is its ability to interrogate regional blocks of hypermethylation i.e., methylation spanning consecutive CpG sites, which commonly occurs in cancer. In this respect, comparison of regional MBDCap-Seq coverage to that of HM450K arrays (Supplementary FIG. S1A) showed that while MBDCap-Seq and HM450K arrays have similar regional coverage of CpG islands (91% vs. 81%) and RefSeq promoters (71% vs. 83%), MBDCap-Seq regional coverage of shores (77% vs. 28%), enhancers (12% vs. 2%) and insulators (11% vs. 1%) is much greater, highlighting the potential advantage of MBDCap-Seq in screening novel functional regions of the cancer methylome.

1.2.2 Accuracy of Methylation Analysis Using DNA from FFPE Tissue

To determine if MBDCap-Seq can provide accurate methylation analysis for DNA from FFPET, DNA methylation profiles from DNA isolated from FF and FFPET of matching tumor and lymph node samples were compared.

MBDCap-Seq from FFPET was shown to provide equivalent methylation to FF DNA (Pearson Correlation Coefficient of 0.95 and 0.86, respectively) (FIG. 5A). Furthermore, analyses using MBDCap-Seq and the HM450K array performed on the same FFPET tumor and lymph node DNA were shown to have high concordance (0.79 & 0.77 respectively) (FIGS. 5B-D).

Figure 6:
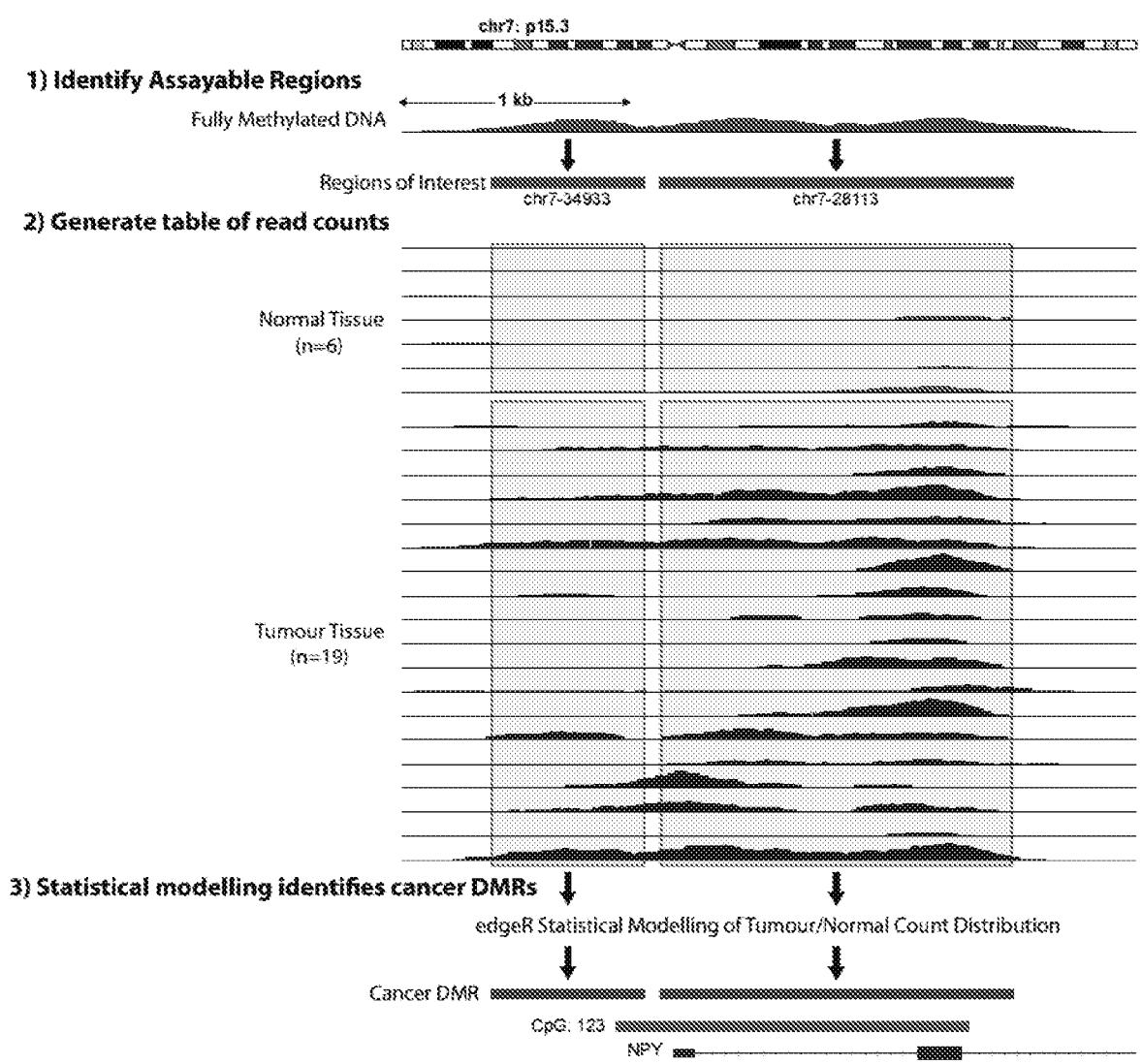
FIG. 6. This figure illustrates the MBDCap-Seq analysis pipeline at an example locus in 3 steps as follows: 1) HOMER peak detection software is applied to the fully methylated (Roche Blood SssI) sample to identify 230,655 peaks or regions of interest or SssI regions. These peaks are used as ground set of regions for subsequent comparative statistical analysis. 2) For each MBDCap-Seq sample to be analysed, the number of sequenced tags overlapping each region of interest is computed. This results in a table of counts where columns are samples (6 normal and 19 tumour) and rows are the 230,655 regions of interest. 3) Normal and tumour tag counts are analysed with the edgeR package to identify regions with statistically significant differences in tag distributions between normal and tumour group of samples. These regions are reported as DMRs.

1.2.3 Identification and Validation of Differentially Methylated Regions in TNBCs To identify differentially methylated regions (DMRs) in Triple Negative Breast Cancers (TNBCs), methylation profiles were determined for FFPET DNA from a discovery cohort of 19 Grade 3 TNBCs tumor and 6 matched normal samples (Table 4) using MBDCap-Seq according to the methods discussed previously. The data obtained was analysed using a novel computational pipeline for comparative statistical analysis of MBDCap-Seq samples as discussed previously (FIG. 6).

822 hypermethylated and 43 hypomethylated statistically significant DMRs (FDR<0.05) were identified, harboring 64,005 and 623 CpG sites respectively, compared to matched normal samples (FIGS. 1A-B and Table 1) and validated sample-specific differential methylation using Sequenom DNA methylation analysis (FIG. 7).

Of the DMRs identified, it was found that CpG islands, CpG island shores and promoters are significantly over-represented in the 822 hypermethylated regions and under-represented in the 43 regions of hypomethylation (FIG. 1C). Notably, ChromHMM annotated HMEC promoters and polycomb repressed regions were also significantly enriched for gain of methylation in the breast cancer samples. A subset of the DMRs were validated in an independent cohort of 31 TNBCs (Table 7), a panel of cell lines (Table 8), and 15 normal breast samples (Table 9), using Sequenom.

TABLE 7

Clinical samples from independent cohort of 31 TNBCs used for validation of selected DMRs with Sequenom

| Patient No. | Grade | ER status | Pr status | HER2 status | Lymph node status | Age at diagnosis | Tumour size (mm) |
|---|---|---|---|---|---|---|---|
| 08P18585 | 3 | — | — | — | 0/1 | 36 | 35 |
| 08P19084 | 3 | — | — | — | 0/1 | 44 | 24 |
| 07P09975 | 2 & 3 | — | — | — | 0/4 | 45 | 30 |
| 09P05790 | 3 | — | — | — | 0/4 | 48 | 36 |
| 09P07178 | 3 | — | — | — | 0/19 | 50 | 60 |
| 07P19869 | 3 | — | — | — | 0/3 | 51 | 46 |
| 09P14372 | 3 | — | — | — | 0/2 | 52 | 25 |
| 09P01080 | 3 | — | — | — | 0/23 | 52 | 25 |
| 09P13385 | 2 | — | — | — | No lymph nodes found | 57 | 23 |
| 07P18351 | 3 | — | — | — | 0/12 | 61 | 36 |
| 07P09663 | 3 | — | — | — | 0/15 | 69 | 35 |
| 07P10215 | 1 | — | — | — | 0/1 | 73 | 16 |
| 09P13015 | 3 | — | — | — | 0/1 | 73 | 40 |
| 08P16834 | 2 | — | — | — | 0/8 | 80 | 20 |
| 09P15105 | 3 | — | — | — | 0/4 | 84 | 43 |
| 07P18017 | 3 | — | — | — | 1/17 | 39 | 28 |
| 09P14783 | 3 | — | — | — | 1/15 | 42 | 25 |
| 08P20420 | 3 | — | — | = | 1/9 | 42 | 33 |
| 09P06626 | 3 | — | — | = | 1/1 | 45 | 20 |
| 09P15999 | 3 | — | — | — | 4/13 | 47 | 30 |
| 09P09950 | 3 | — | — | — | 1/3 | 48 | 15 |
| 09P07430 | 3 | — | — | — | 1/2 | 50 | 12 |
| 08P20600 | 3 | — | — | — | 2/4 | 50 | 45 |
| 09P04704 | 3 | — | — | = | 1/17 | 55 | 30 |
| 04P15487 | 3 | — | — | — | 23/25 | 55 | 28 |
| 08P15189 | 2 | — | — | — | 9/22 | 56 | 100 |
| 08P10459 | 3 | — | — | — | 1/3 | 64 | 15 |
| 04P7410 | 3 | — | — | — | 1/23 | 66 | 40 |
| 08P20503 | 3 | — | — | — | 2/17 | 72 | 17 |
| 09P03391 | 3 | — | — | — | 16/19 | 78 | 35 |
| 07P13965 | 3 | — | — | — | 2/18 | 78 | 38 |

TABLE 8

Cell lines used for validation of selected DMRs with Sequenom Breast Cell lines

|  | Classification |
|---|---|
| Tumour cell lines | |
| HBL-100 | Basal B |
| MDA-MB-330 | unclassified |
| BT-20 | Basal A |
| HCC-1187 | Basal A |
| HCC-1569 | Basal A |
| HCC-1937 | Basal A |
| HCC-1954 | Basal A |
| HCC-70 | Basal A |
| MDA-MB-468 | Basal A |
| BT-549 | Basal B |
| HCC-1500 | Basal B |
| HCC-38 | Basal B |
| Hs578.T | Basal B |
| MCF-12A | Basal B |
| MDA-MB-157 | Basal B |
| MDA-MB-231 | Basal B |
| MDA-MB-436 | Basal B |
| BT-483 | Luminal |
| MCF-7 | Luminal |
| MDA-MB-175 | Luminal |
| MDA-MB-361 | Luminal |
| SK-Br3 | Luminal |
| T-47D | Luminal |
| ZR-75-1 | Luminal |
| Normal cell lines | |
| 184 A1 | Normal |
| 184 B5 | Normal |
| HMEC 219-4 | Normal |

TABLE 9

Clinical samples from independent cohort of 14 non-cancer patients (normal) used for validation of selected DMRs with Sequenom

| SampleID | Sample Type |
|---|---|
| Bre12 | Normal |
| Bre13 | Normal |
| Bre67 | Normal |
| Bre71 | Normal |
| Bre76 | Normal |
| Bre78 | Normal |
| Bre85 | Normal |
| Bre88 | Normal |
| Bre97 | Normal |
| Bre98 | Normal |
| Bre101 | Normal |
| Bre103 | Normal |
| Bre113 | Normal |
| Bre117 | Normal |

Figure 10:
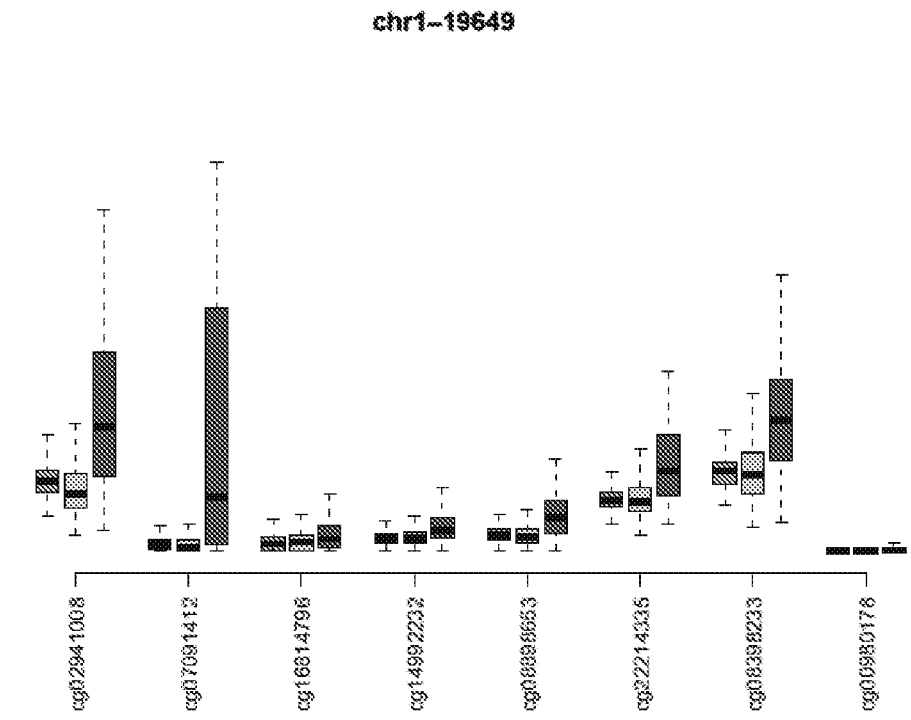
FIG. 10. Regions showing TNBC specific methylation in TCGA breast cancer cohort are provided in A-P. Boxplots showing distribution of methylation beta values in normal (pink), ER+VE (light blue), and TNBC (purple) samples in TCGA cohort across HM450K probes overlapping the 36 TNBC specific regions; one boxplot per region.
Figure 10:
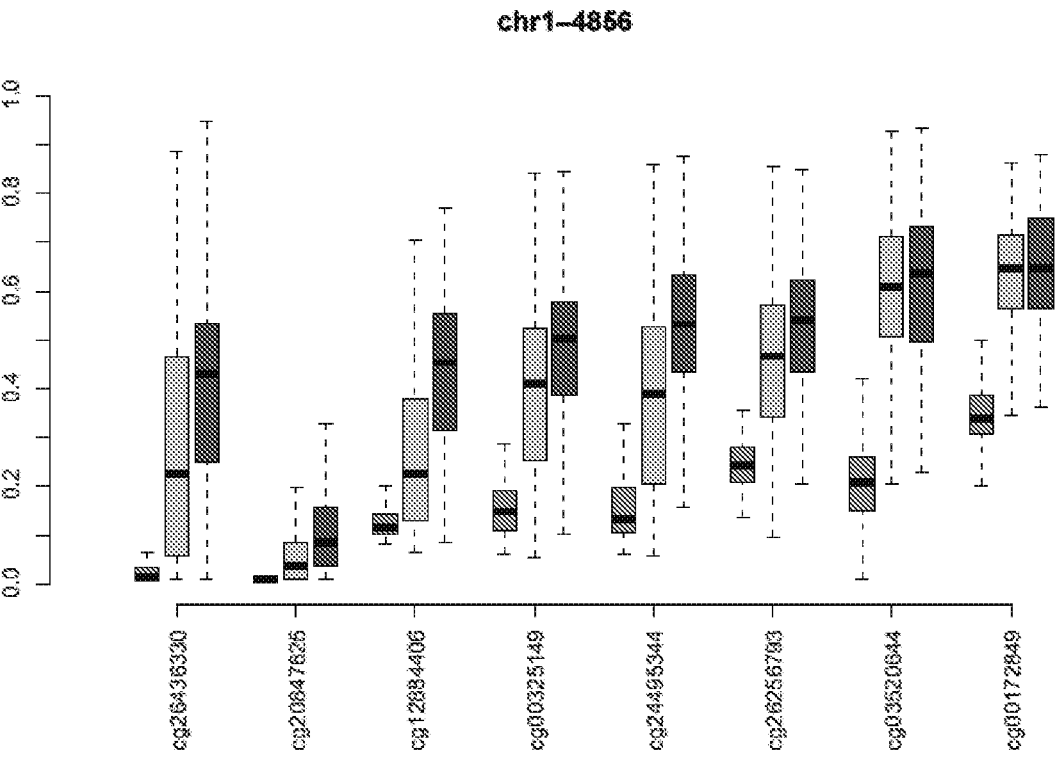
Figure 10:
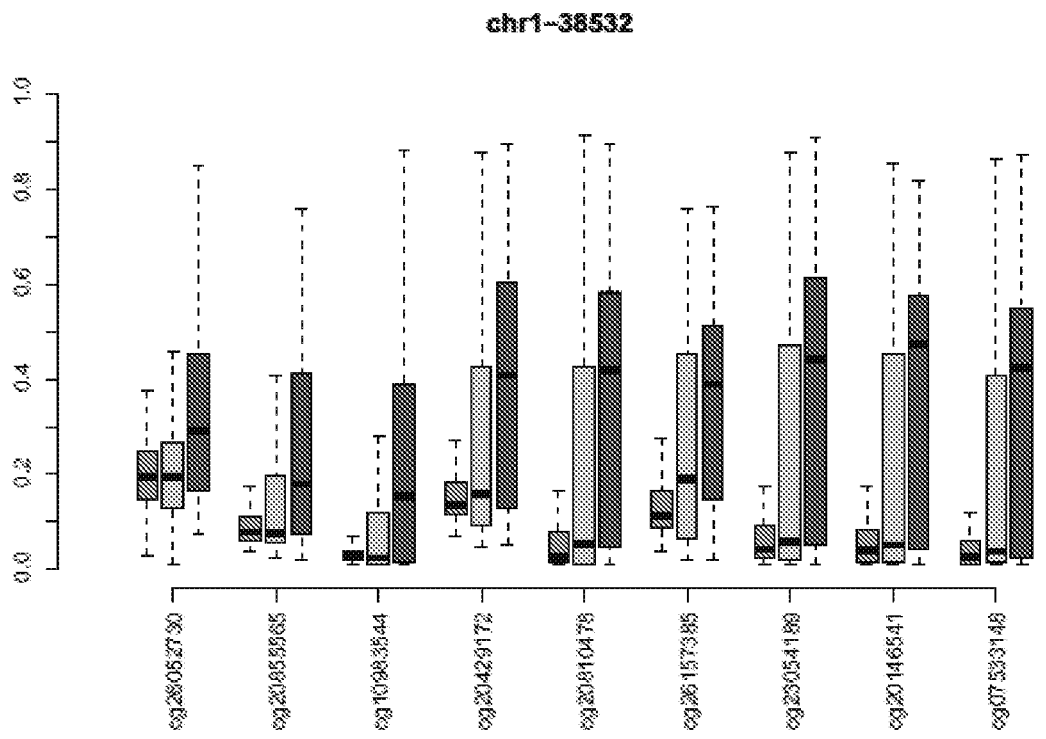
Figure 10:
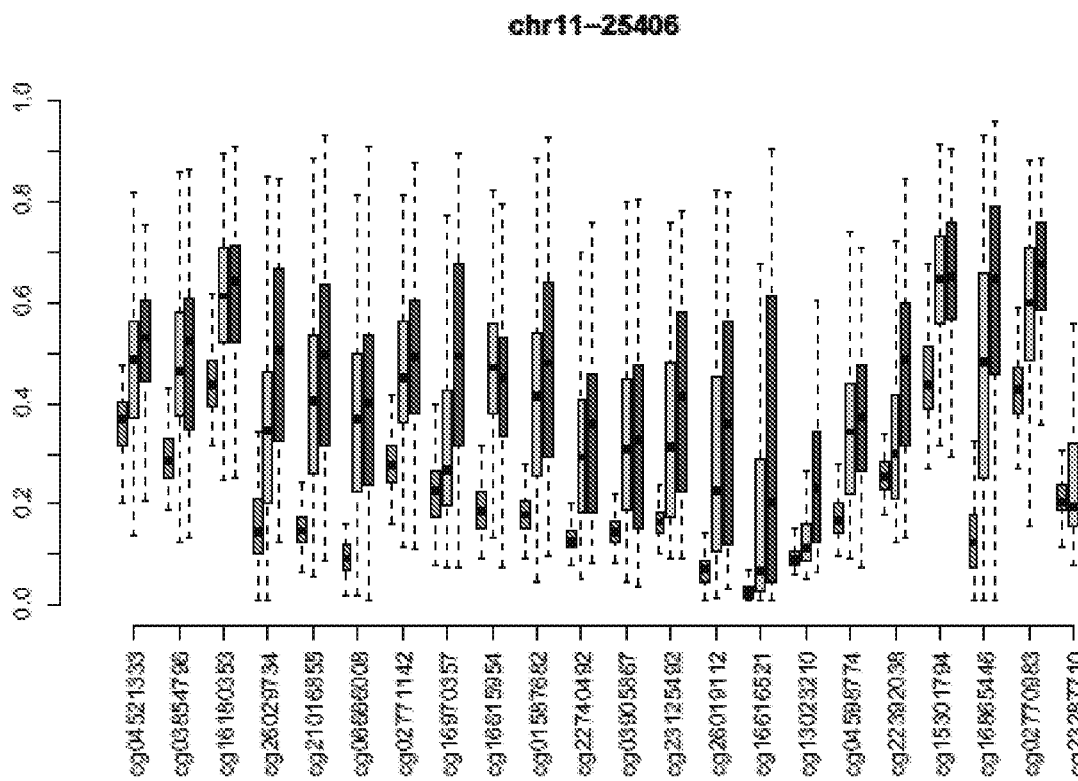
Figure 10:
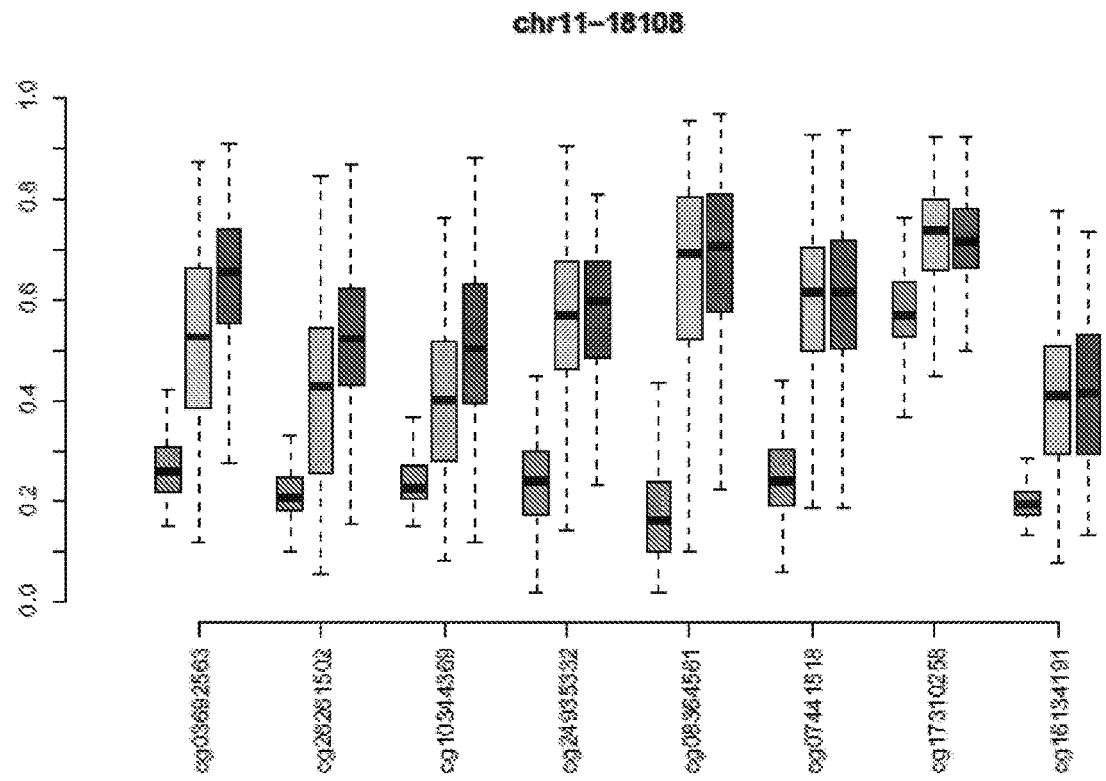
Figure 10:
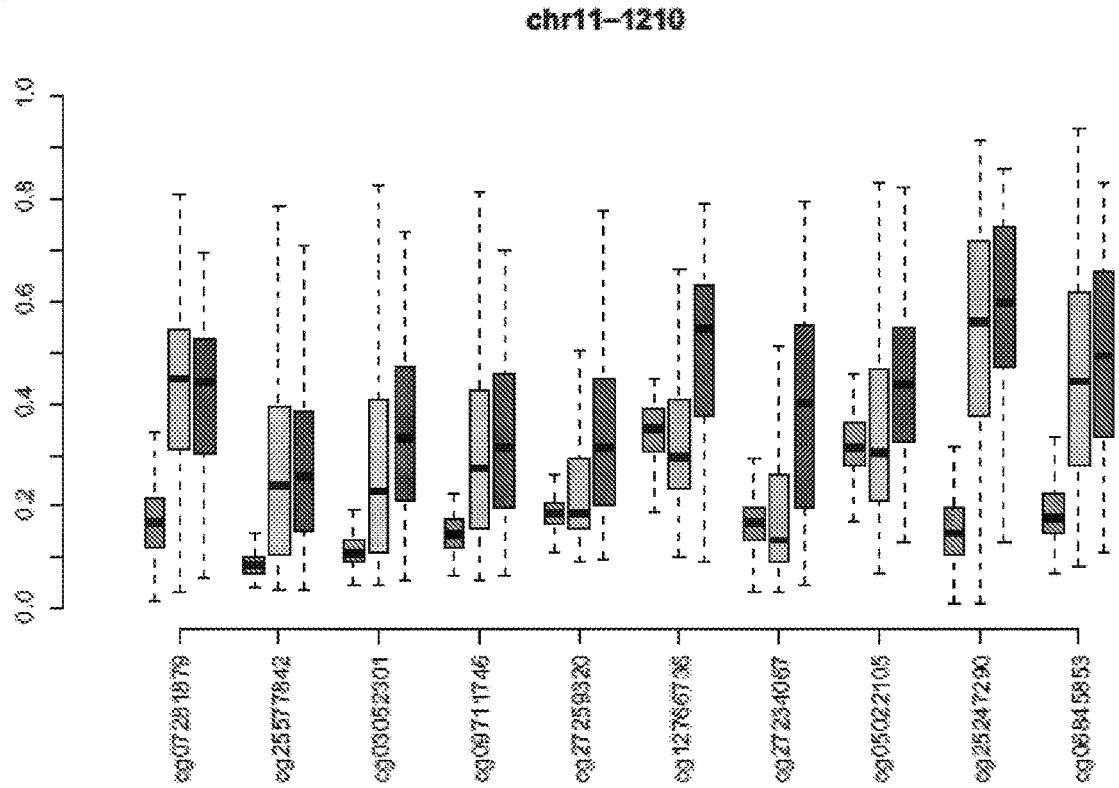
Figure 10:
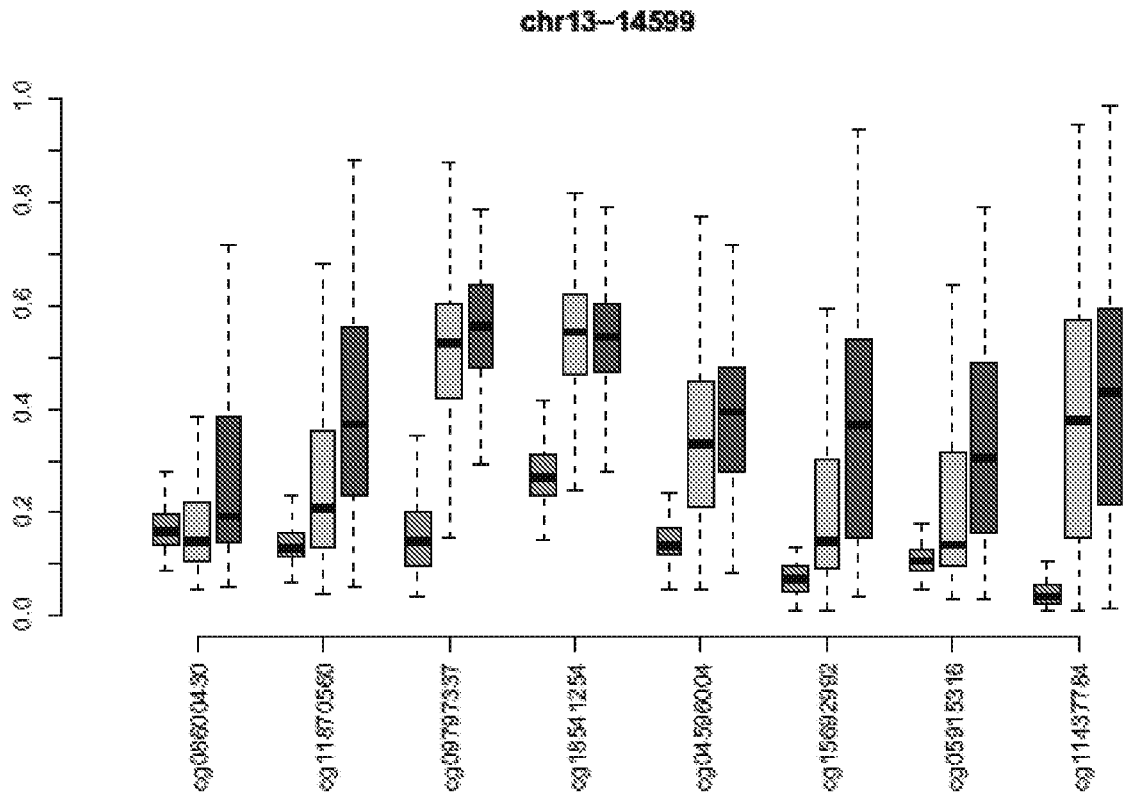
Figure 10:
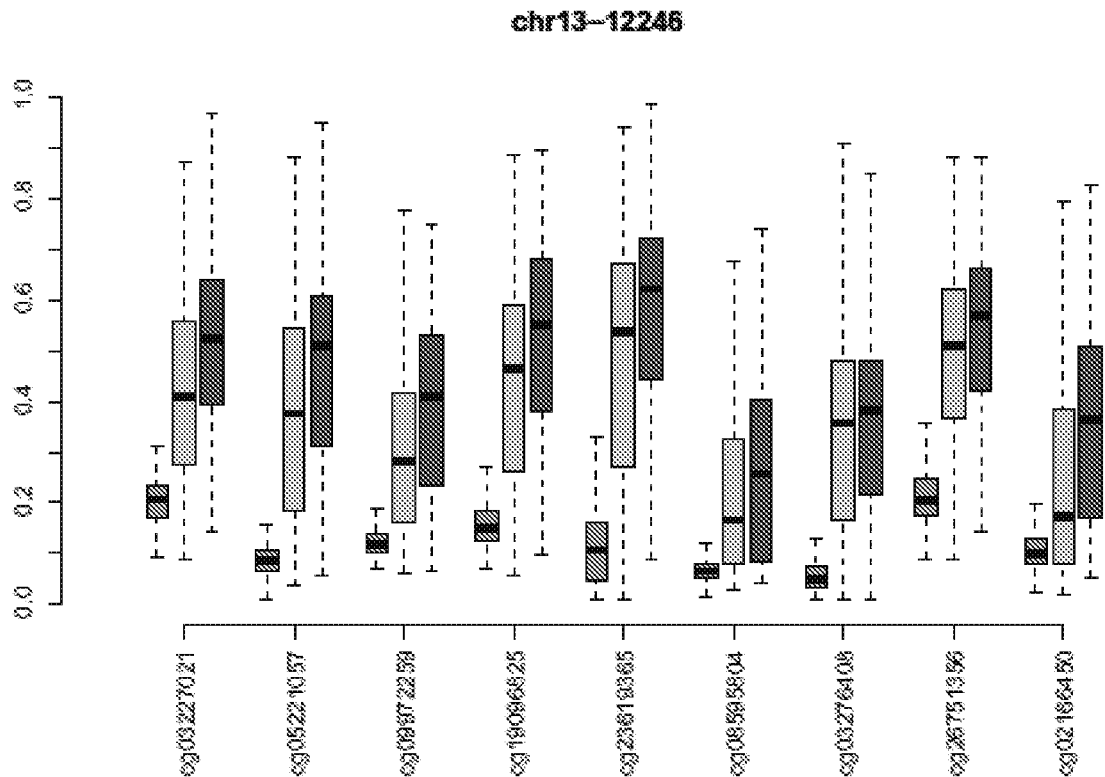
Figure 10:
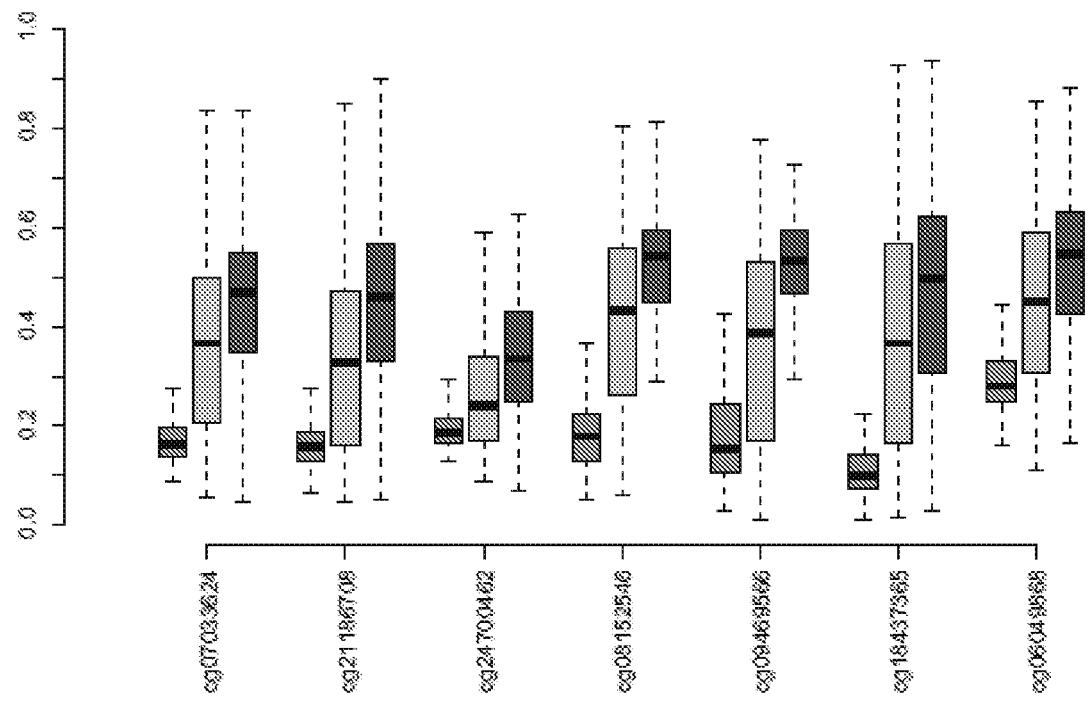
Figure 10:
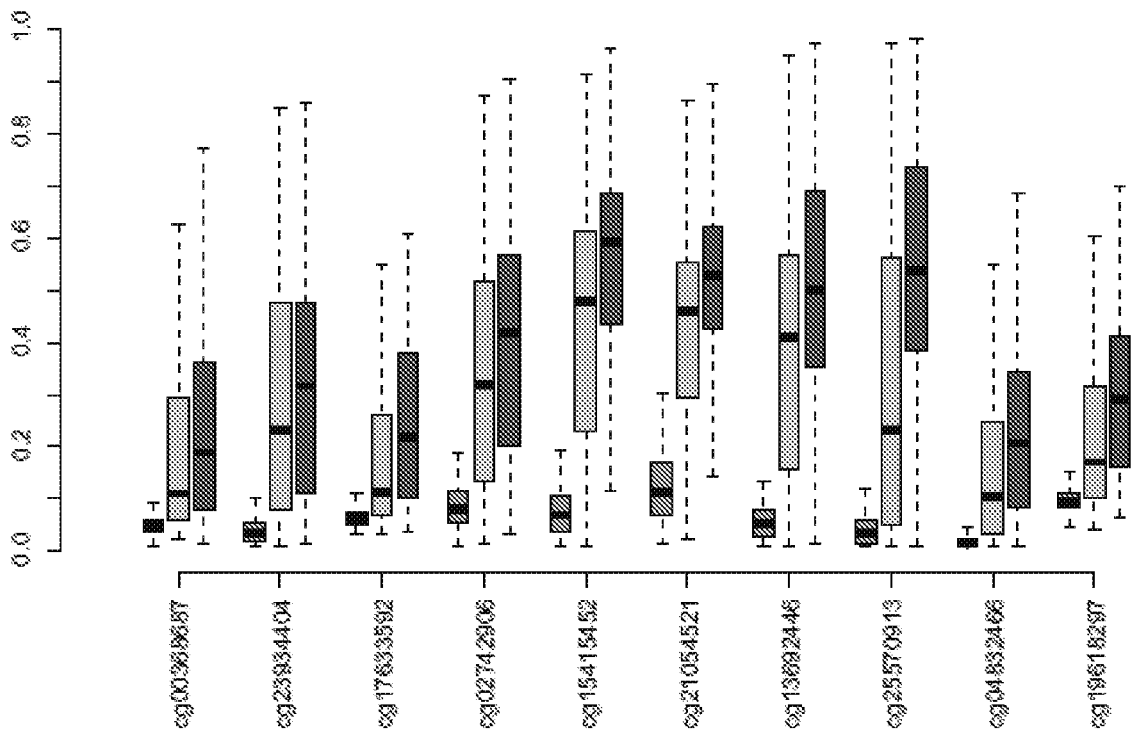
Figure 10:
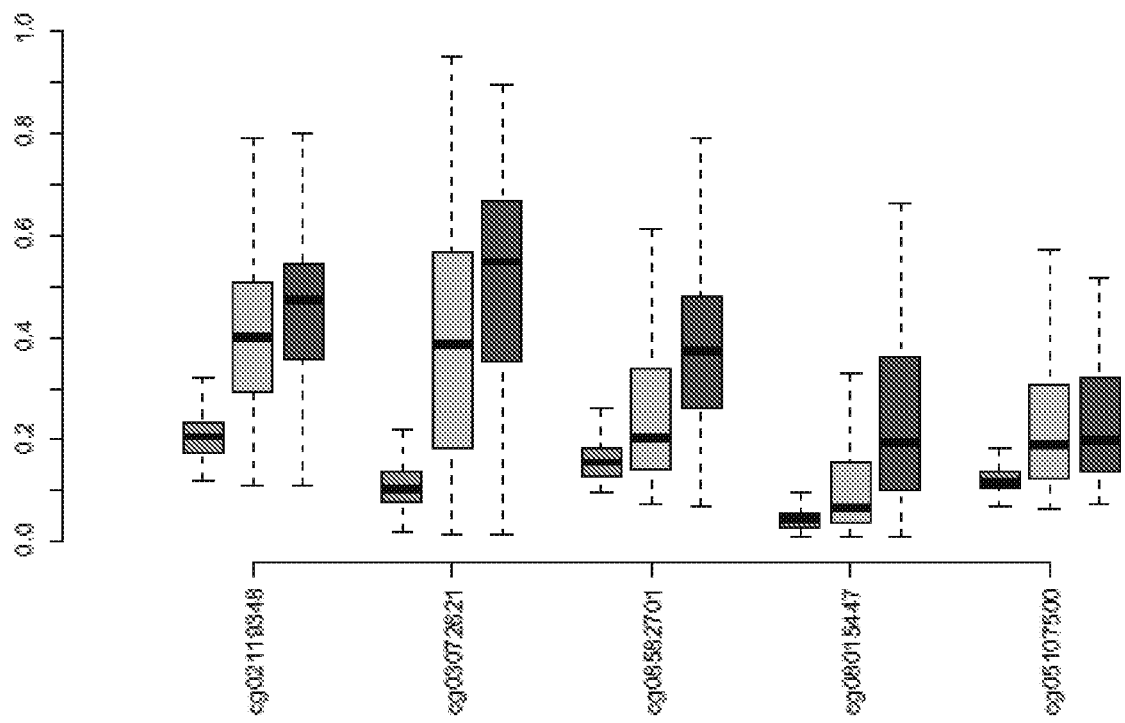
Figure 10:
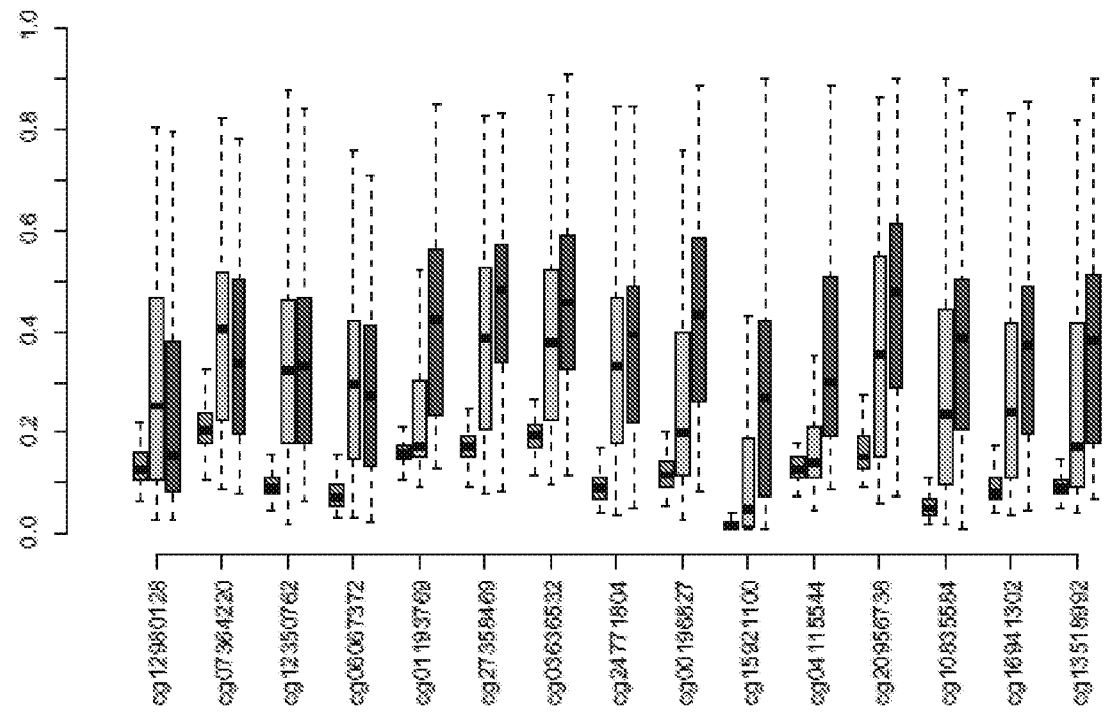
Figure 10:
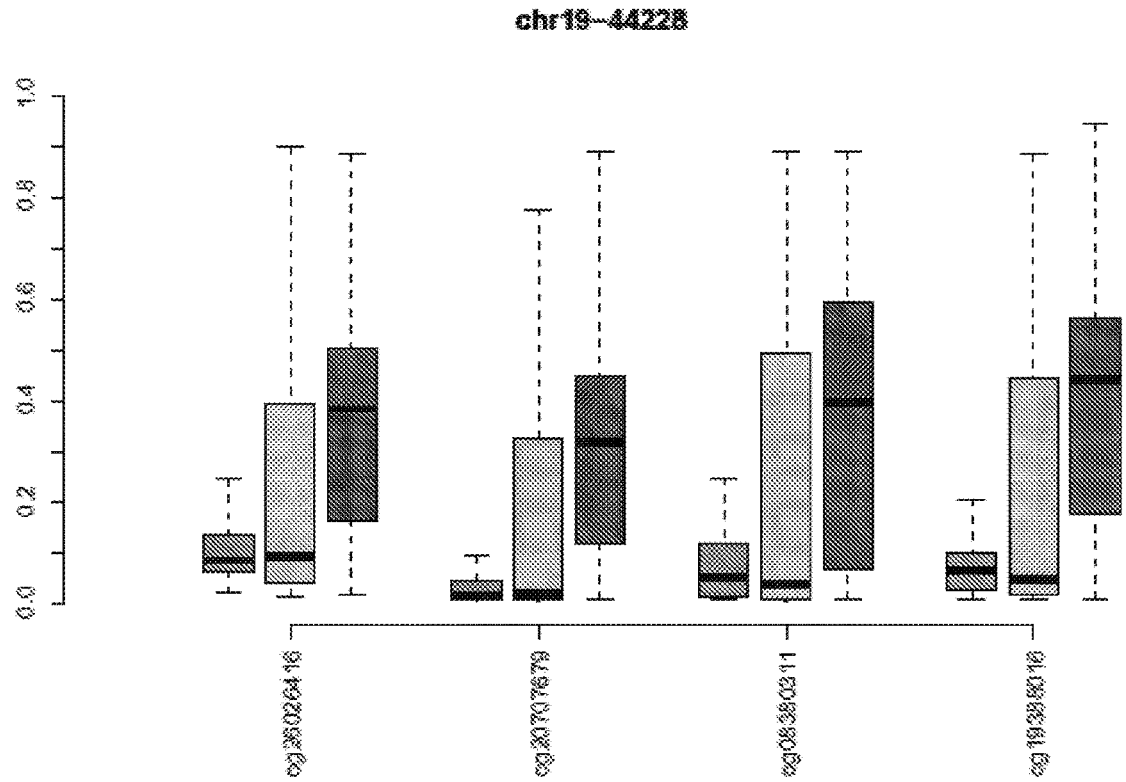
Figure 10:
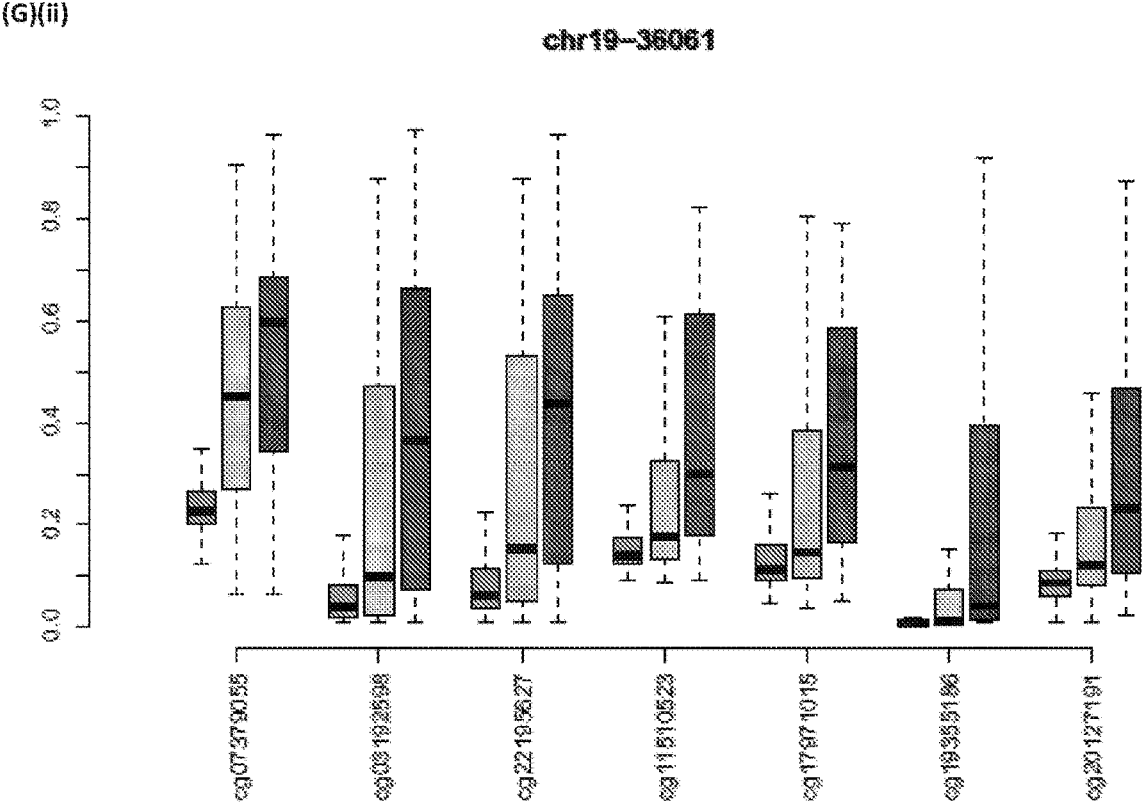
Figure 10:
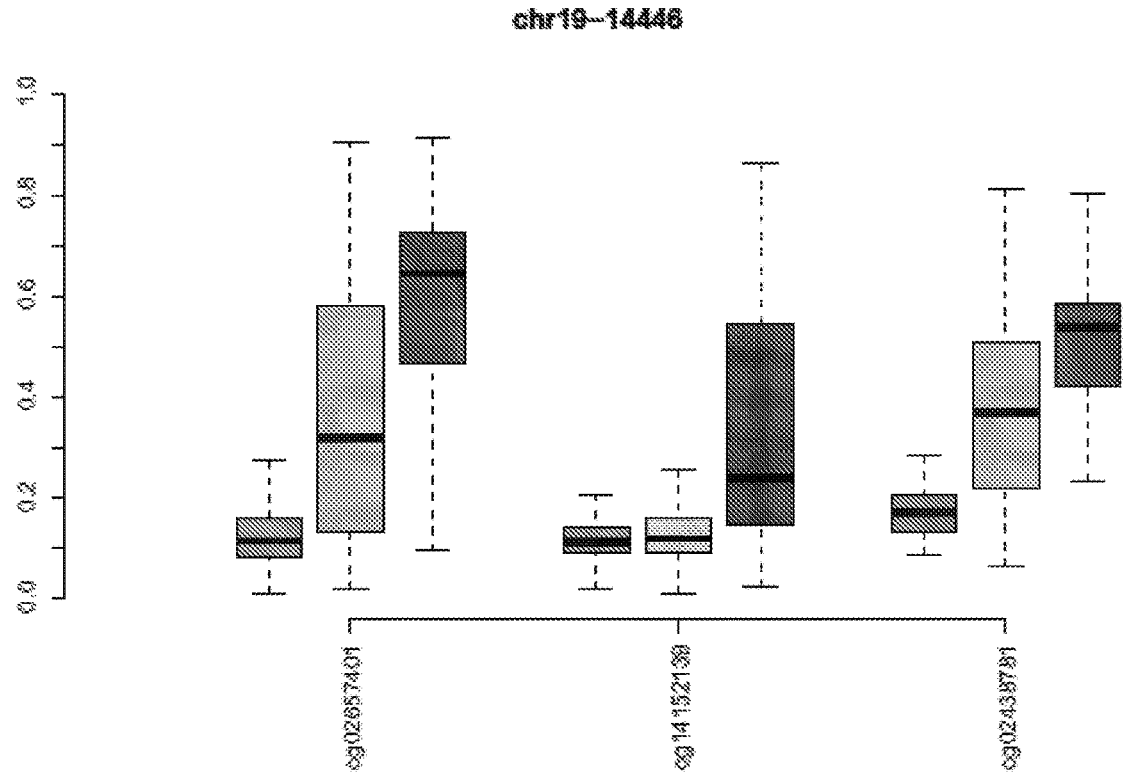
Figure 10:
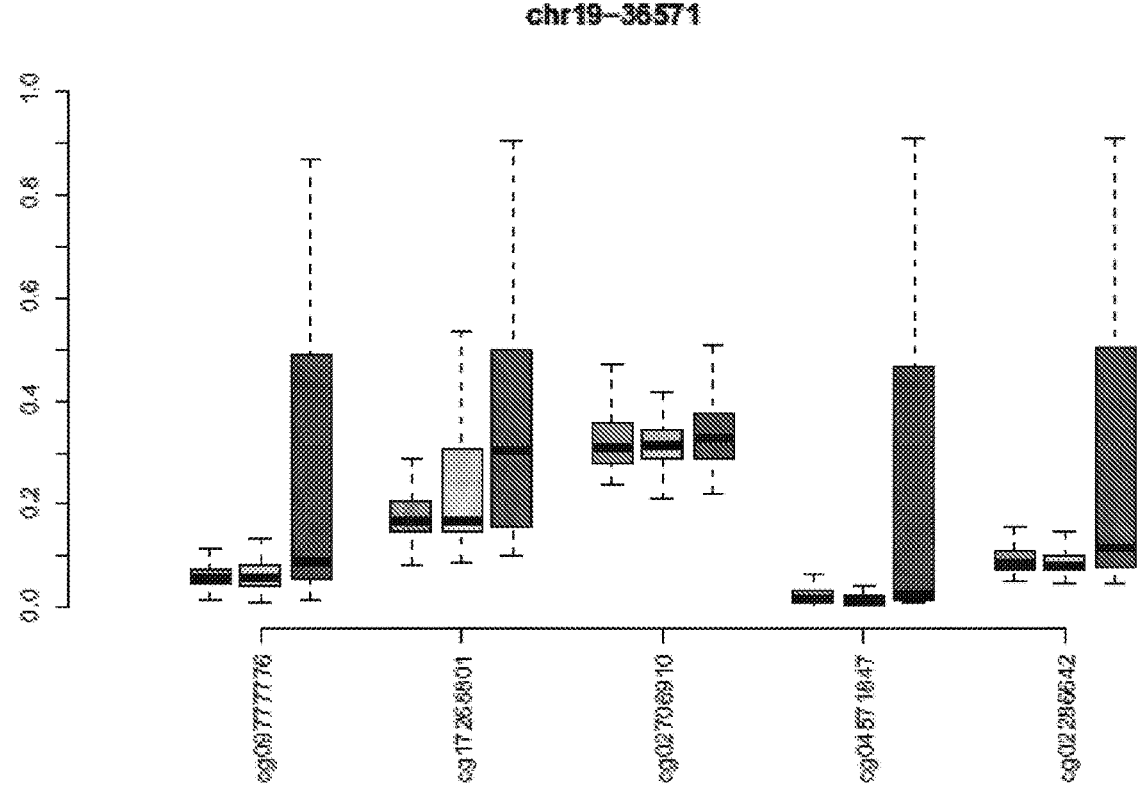
Figure 10:
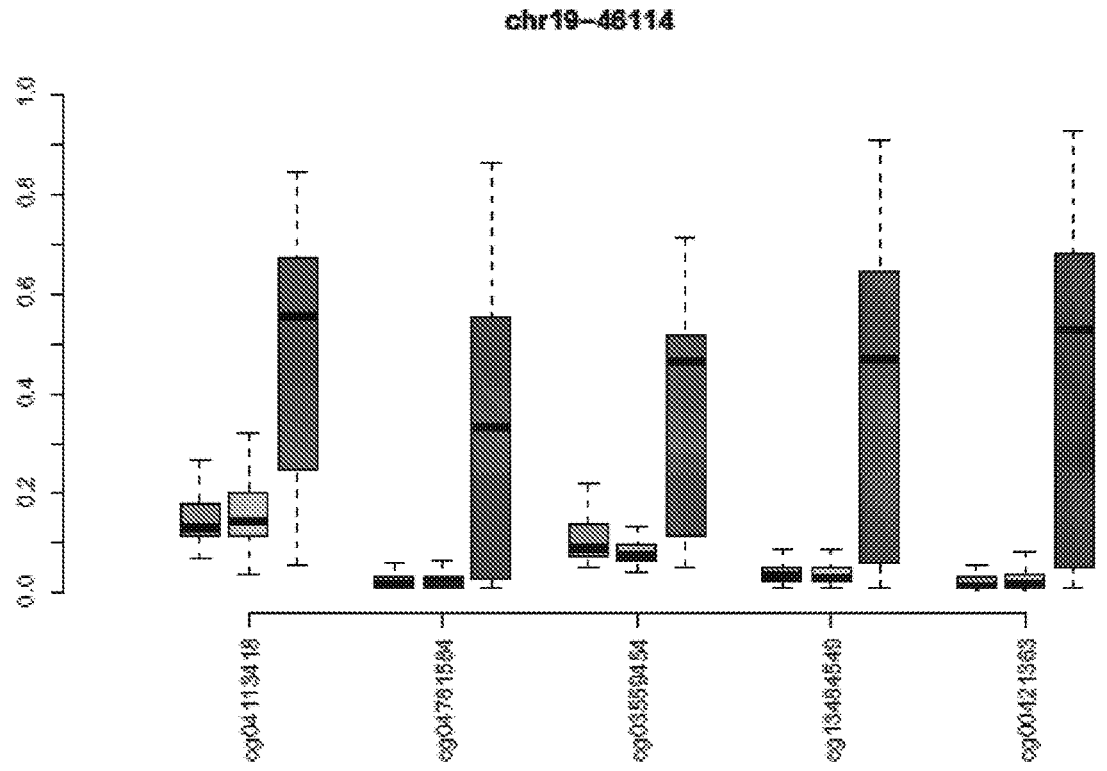
Figure 10:
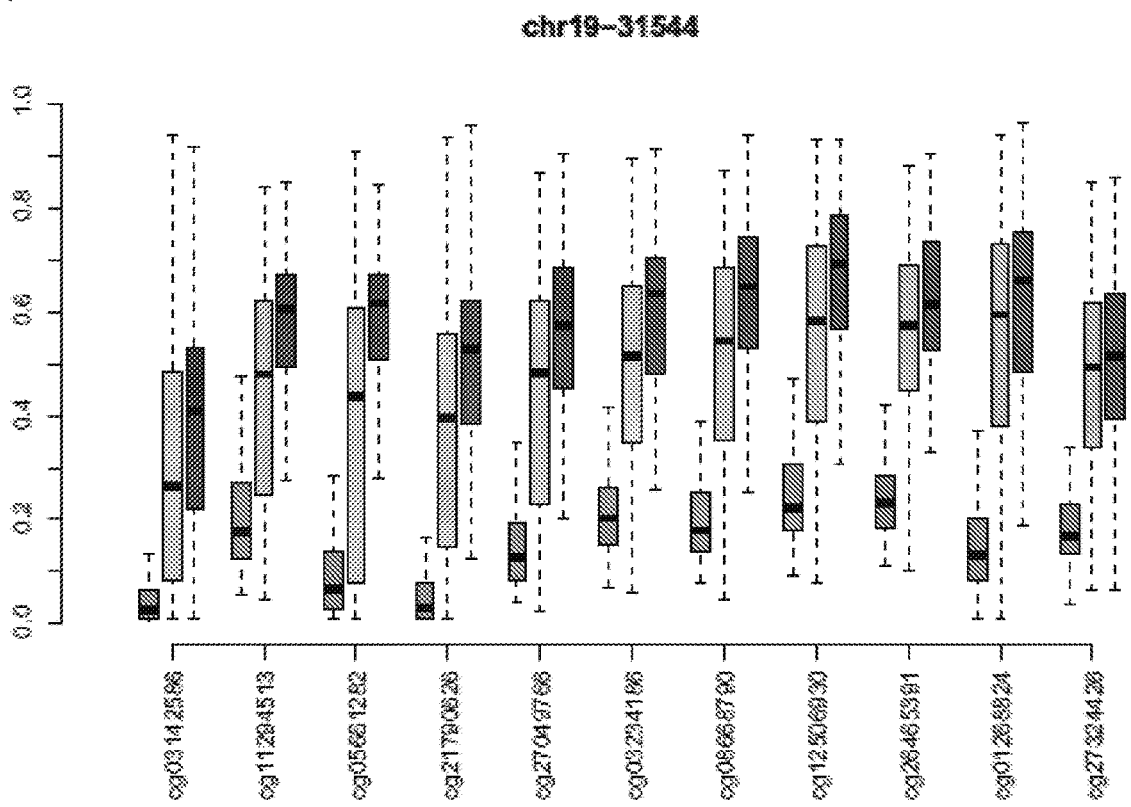
Figure 10:
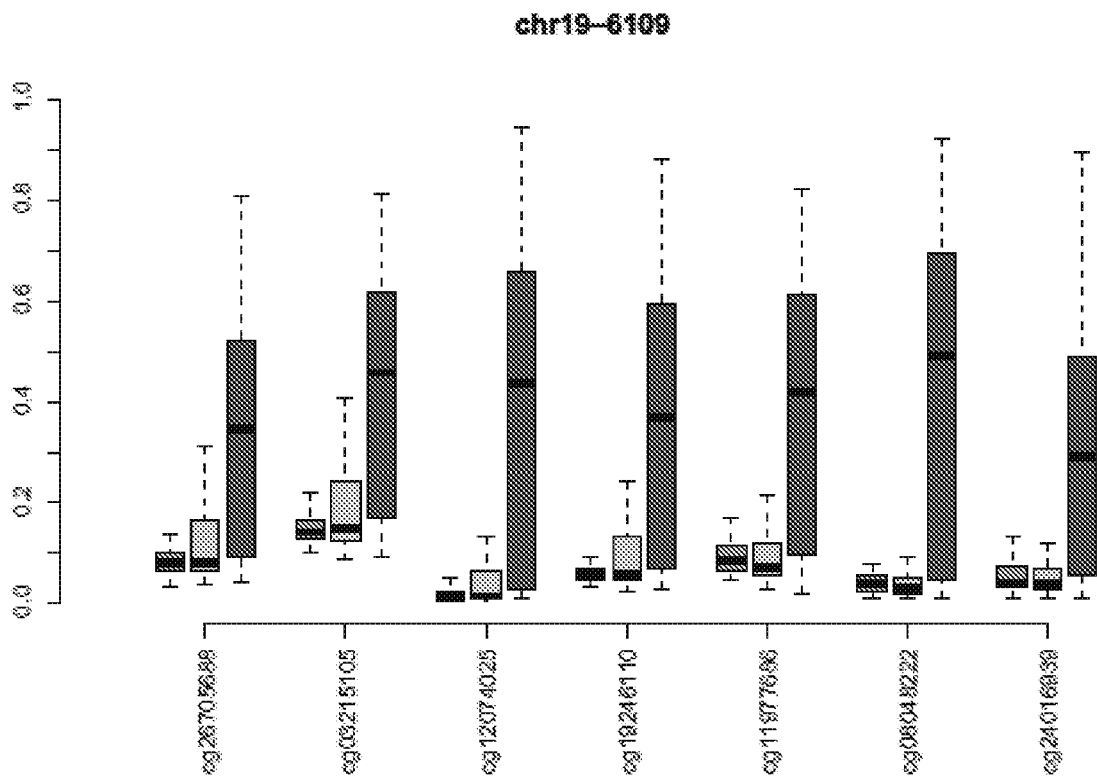
Figure 10:
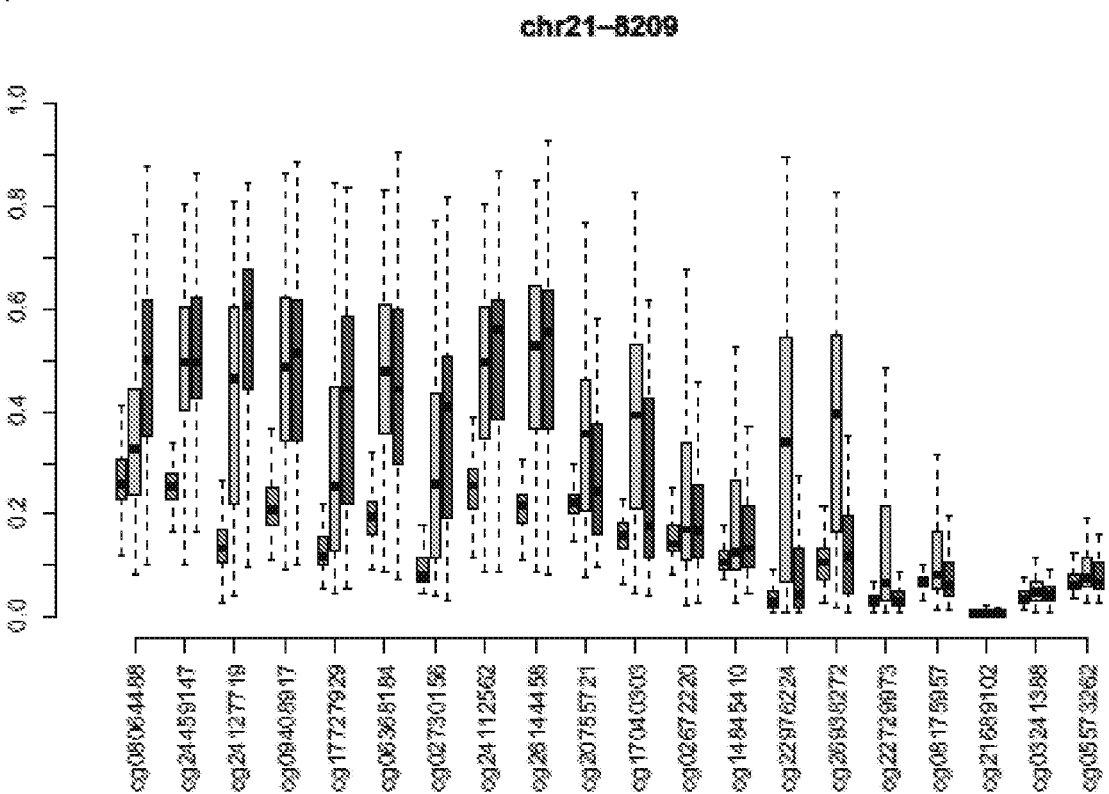
Figure 10:
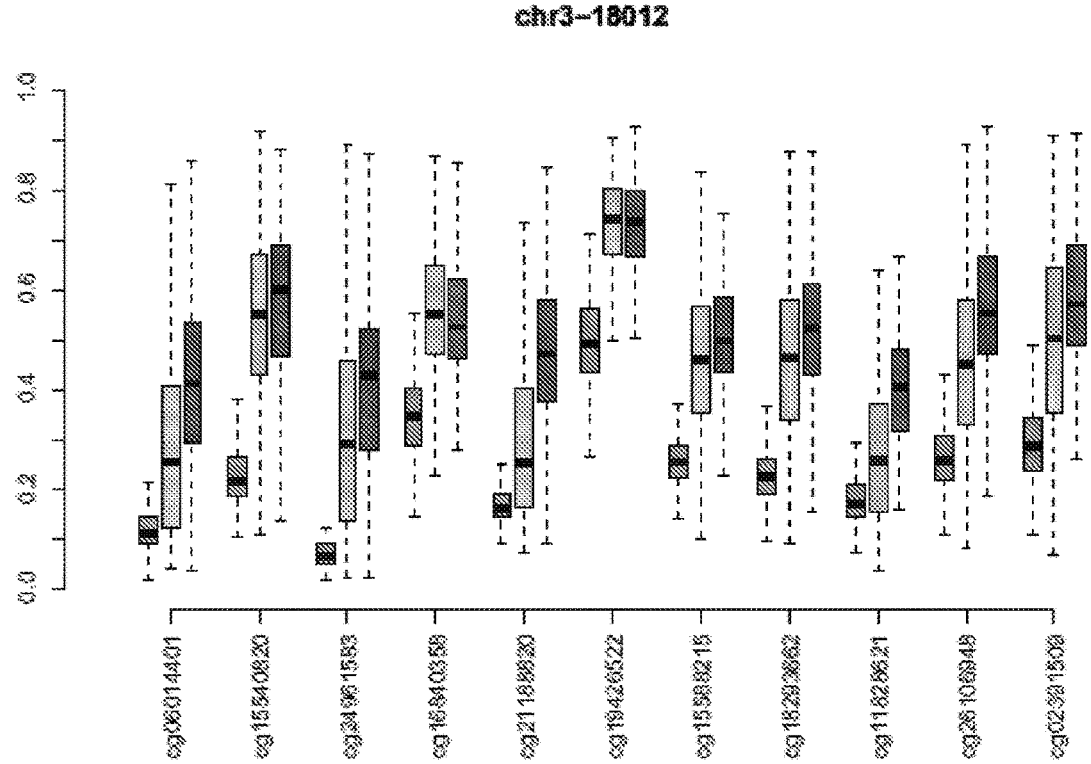
Figure 10:
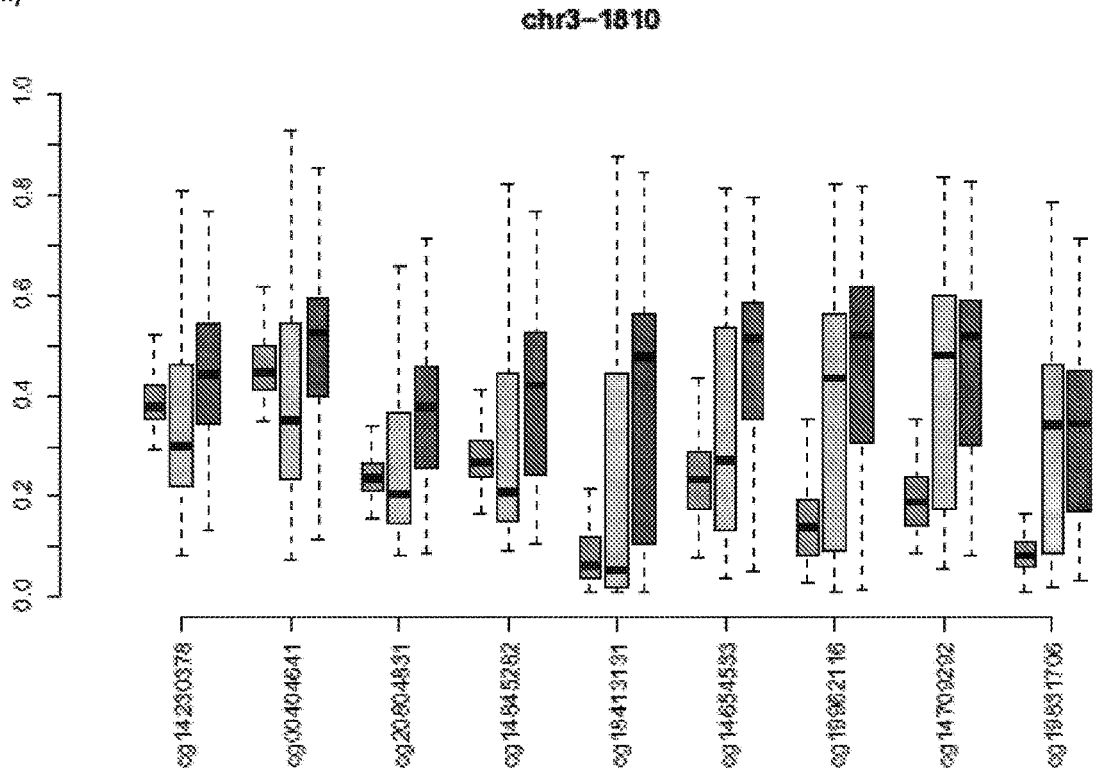
Figure 10:
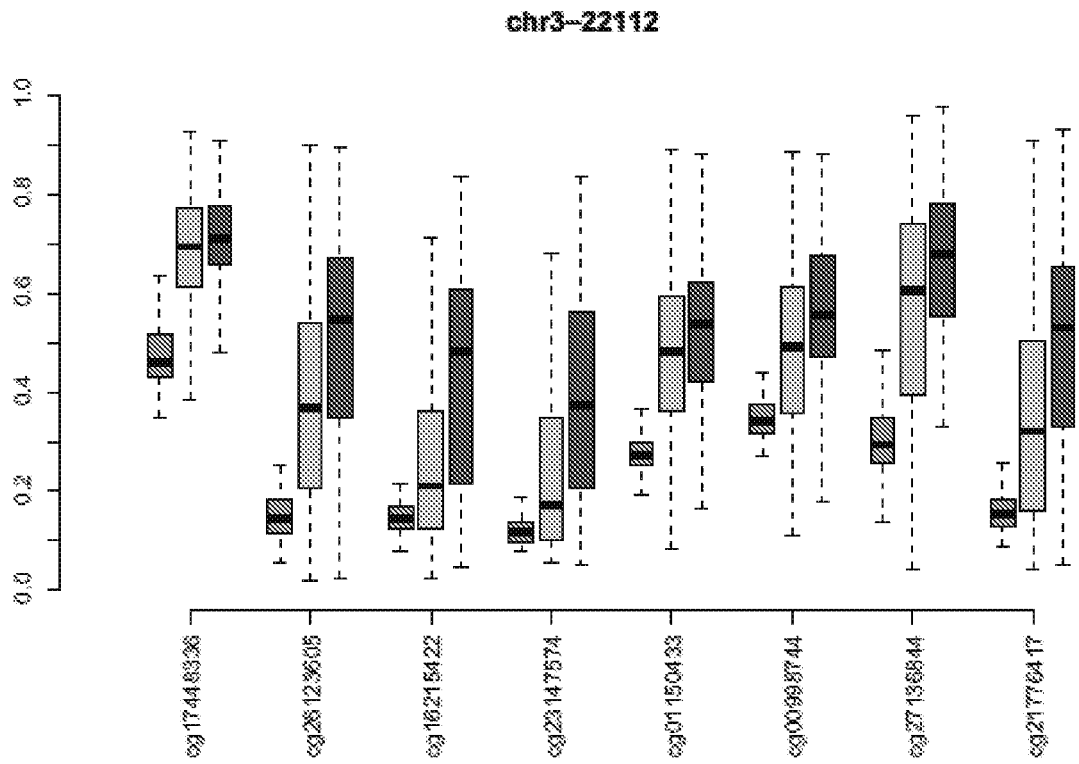
Figure 10:
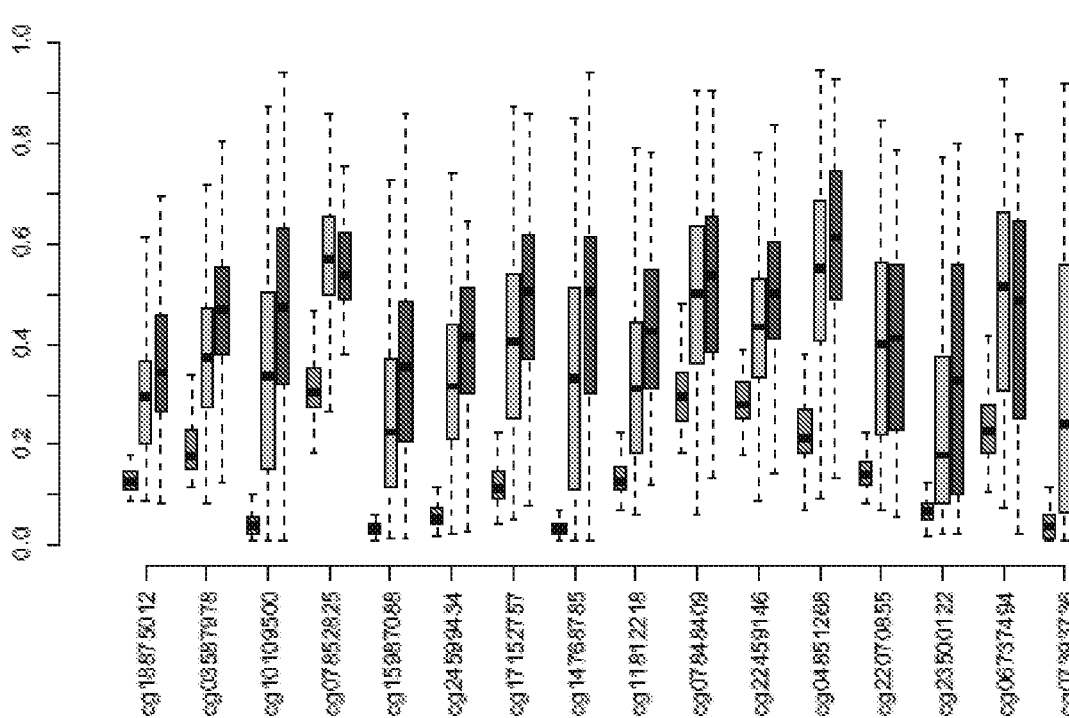
Figure 10:
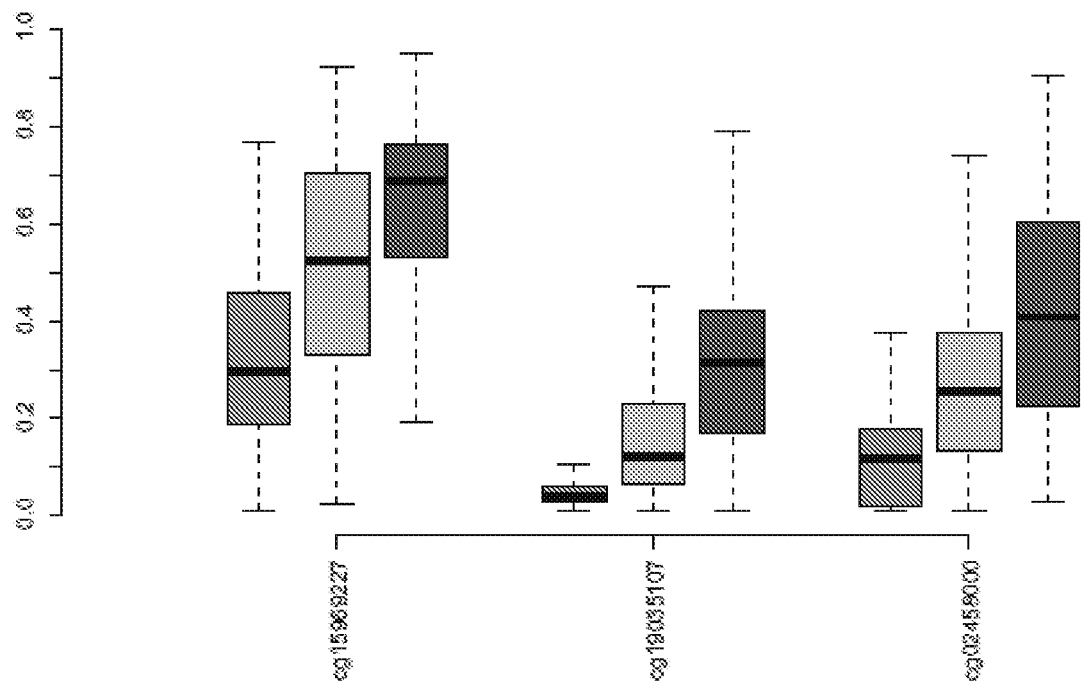
Figure 10:
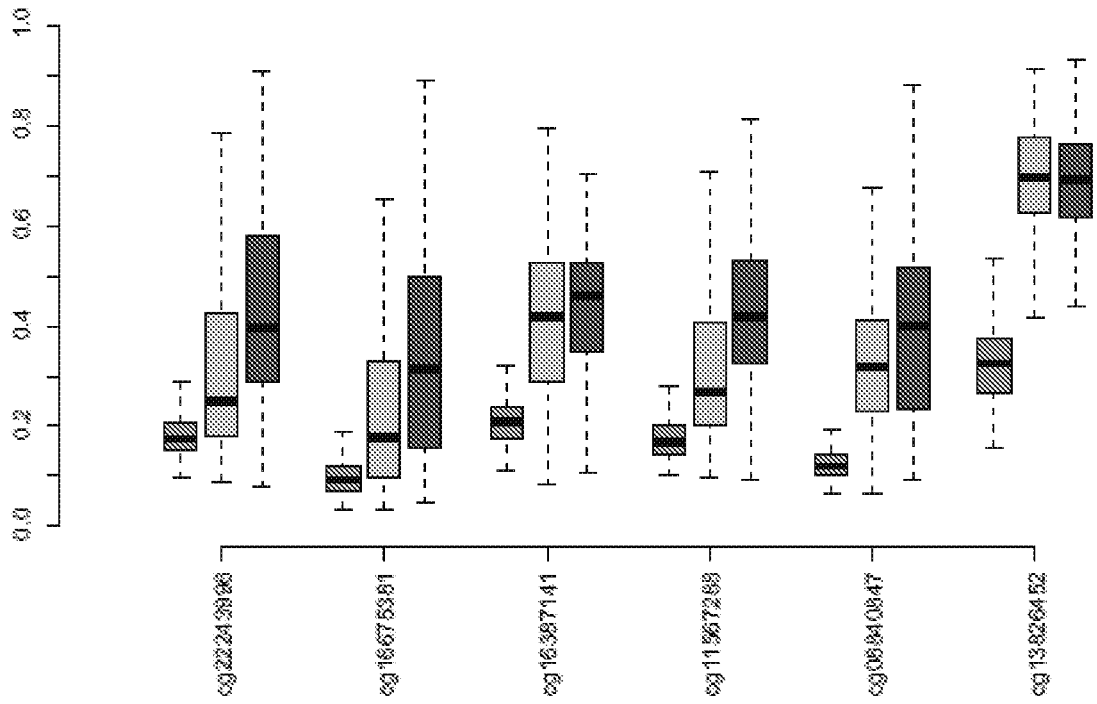
Figure 10:
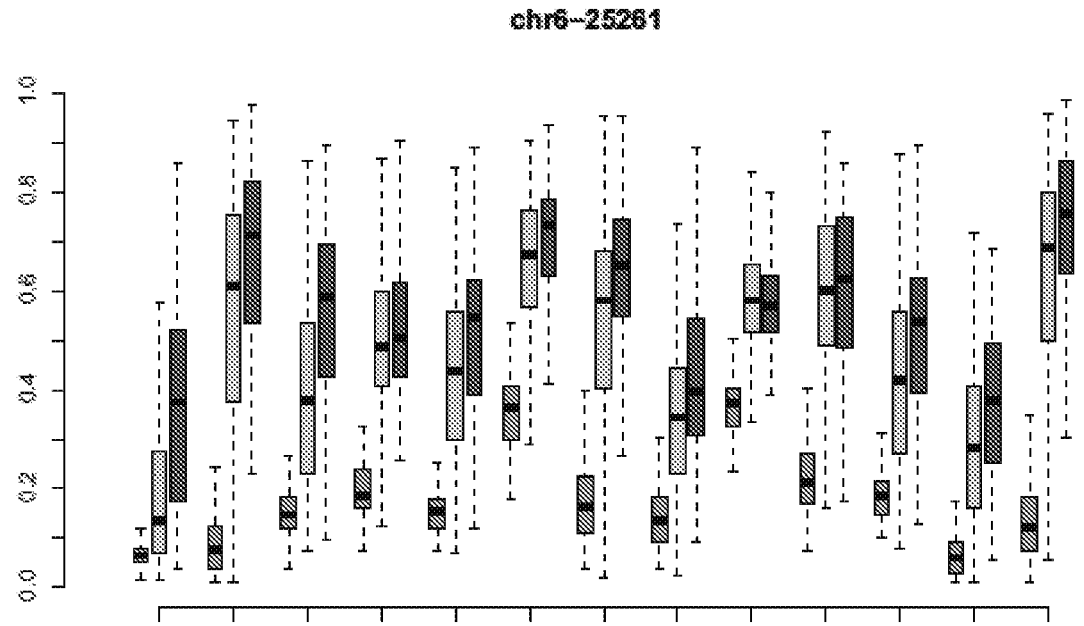
Figure 10:
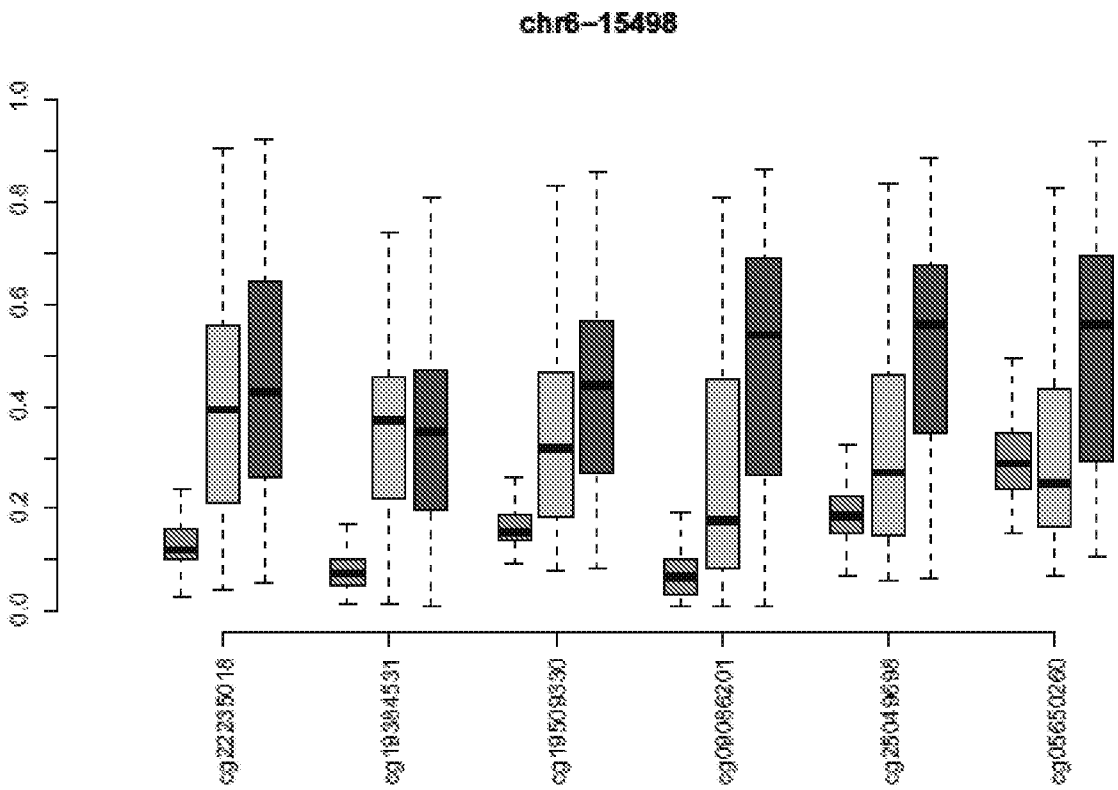
Figure 10:
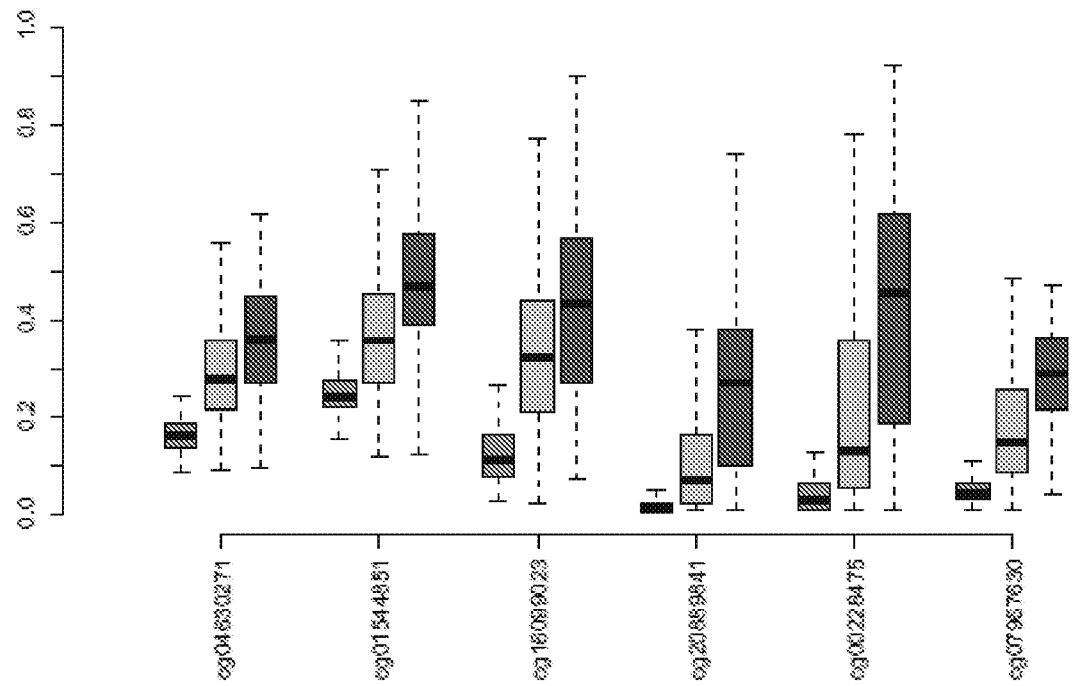
Figure 10:
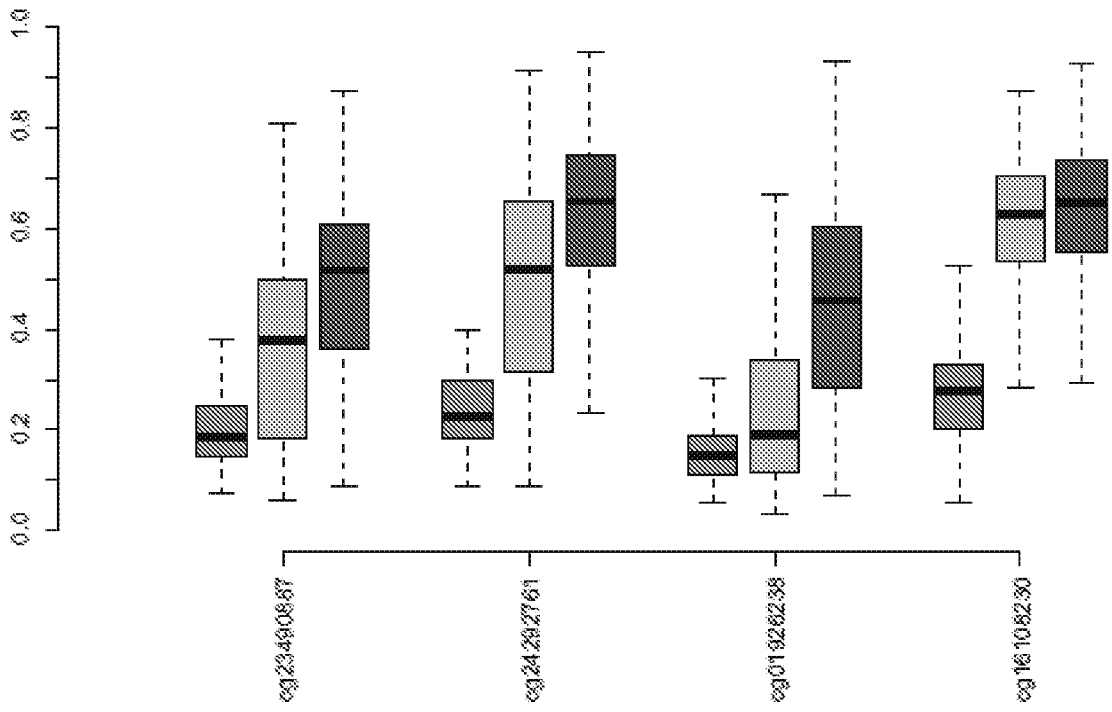
Figure 10:
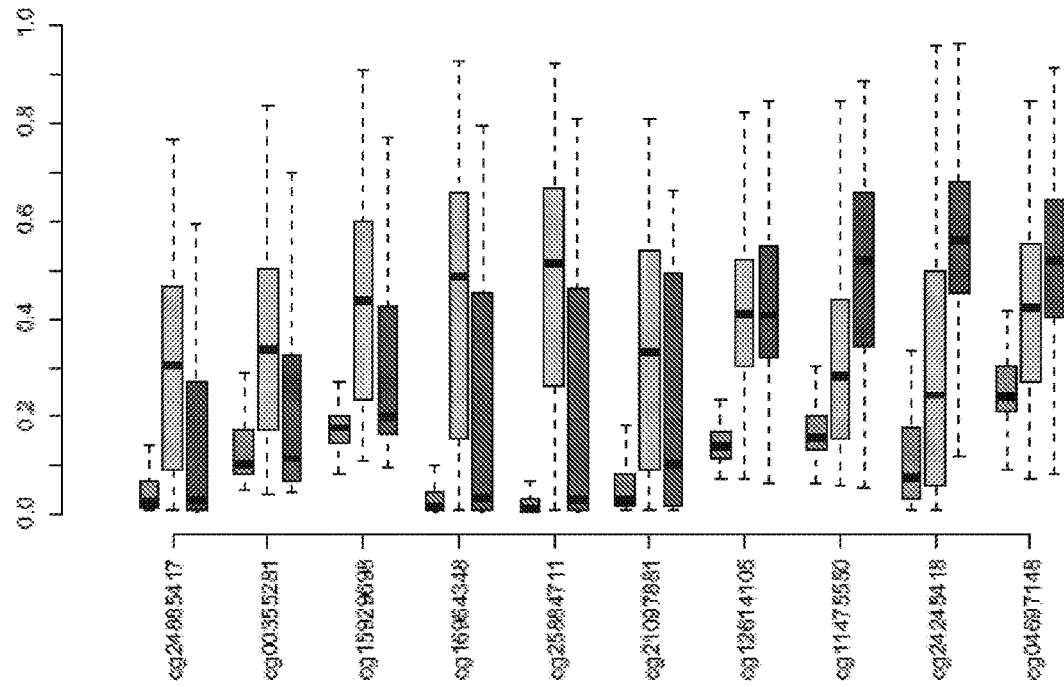
Figure 10:
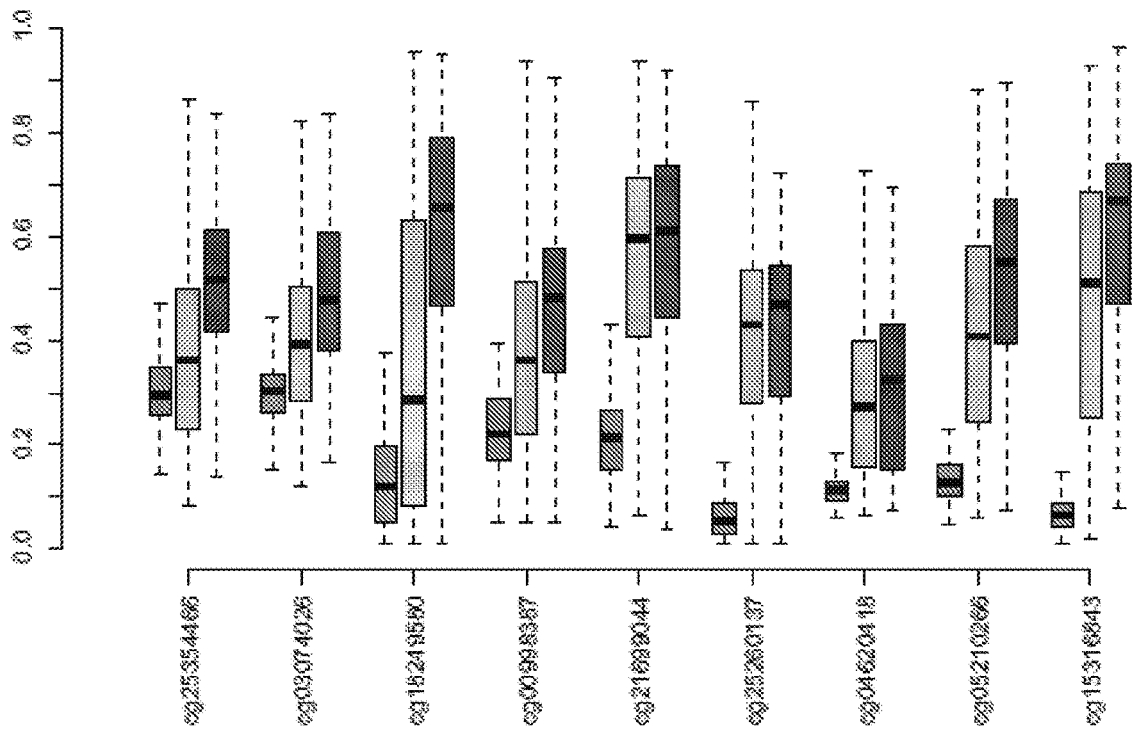
Figure 10:
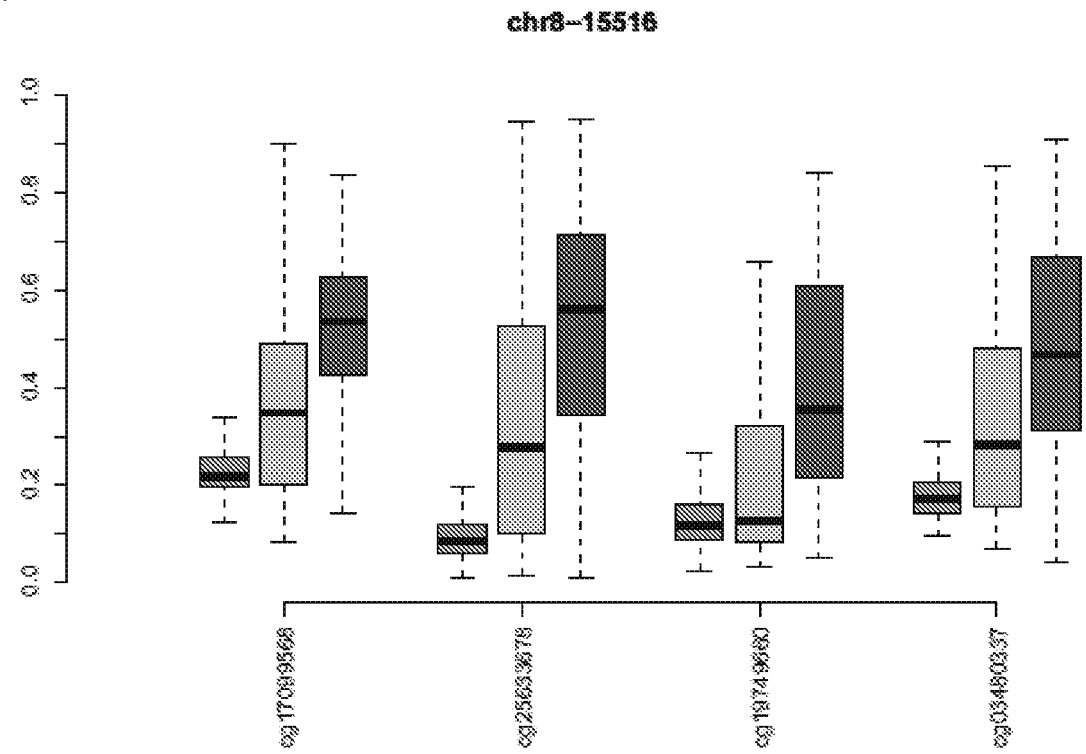
Figure 10:
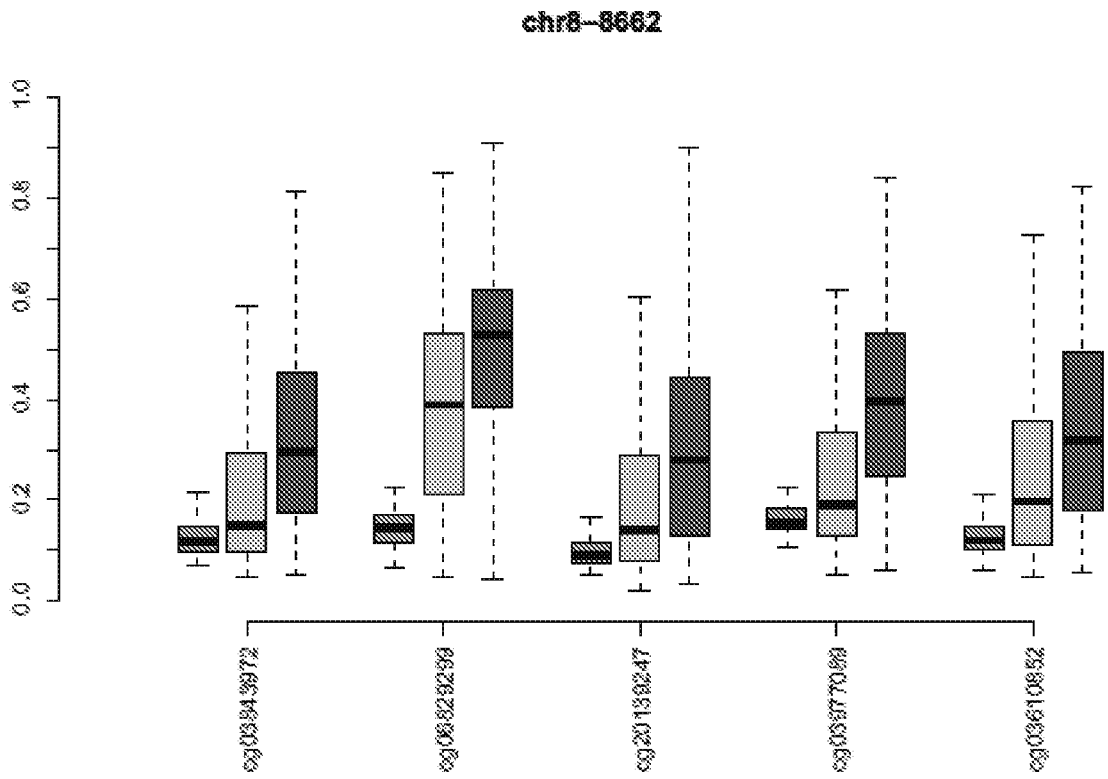
Figure 10:
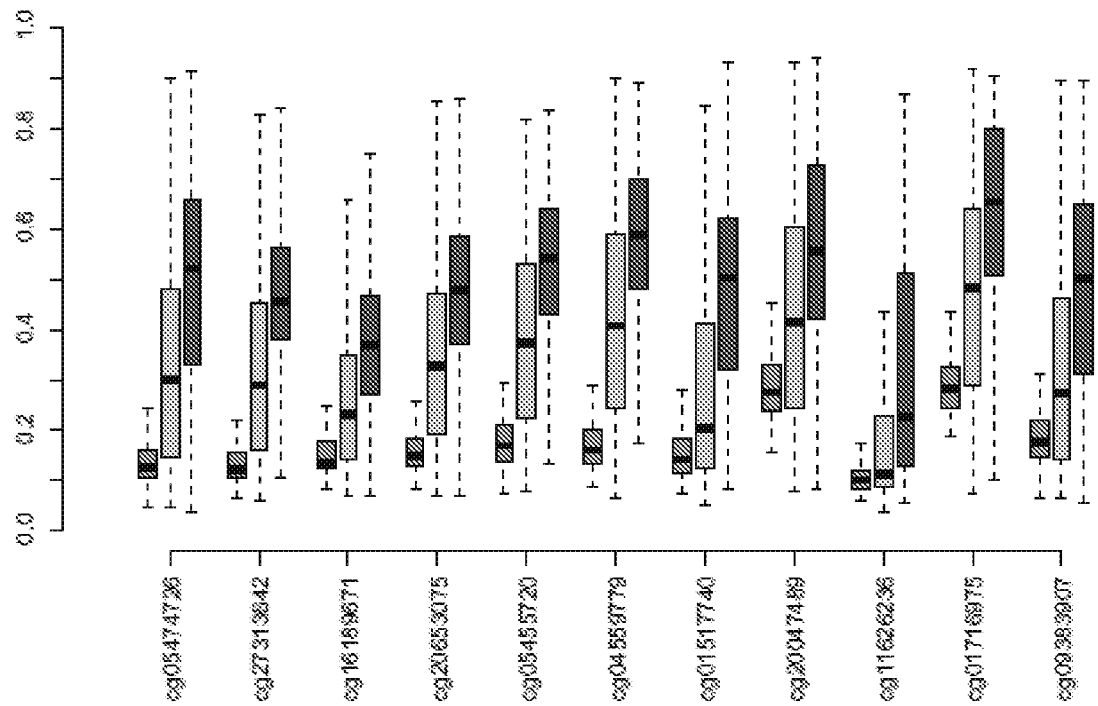
Figure 10:
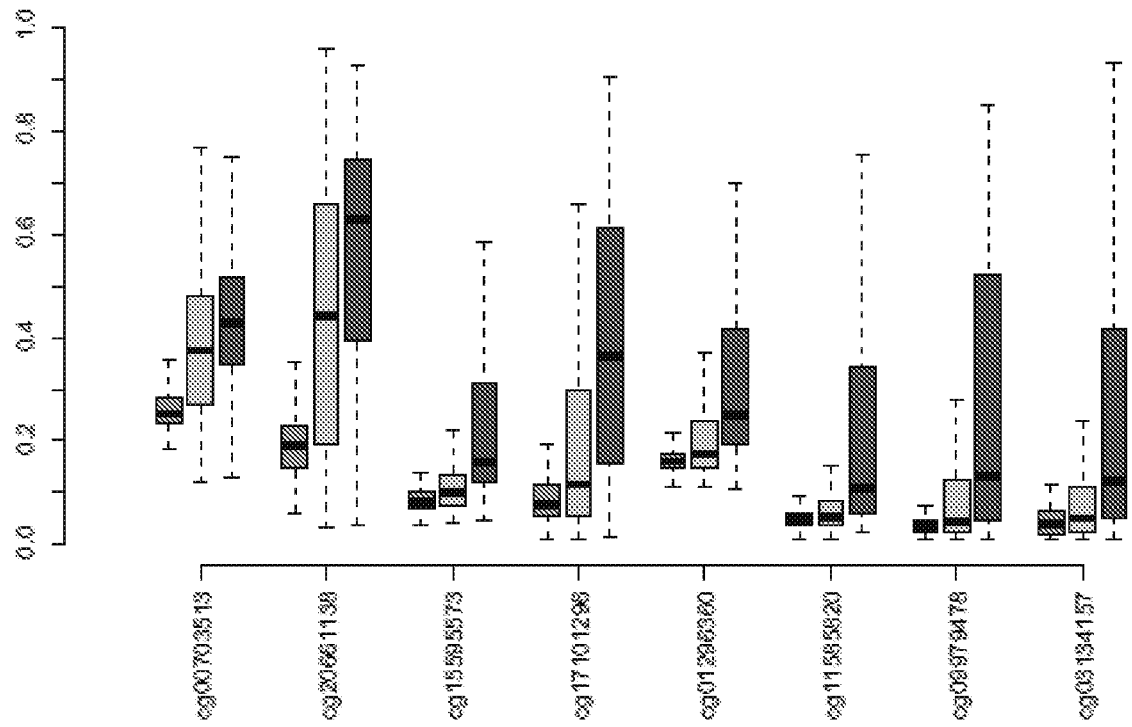

Sequenom methylation analysis performed on 5 of the 822 hypermethylated regions spanning the CpG island promoters of NPY, FERD3L, HMX2, SATB2 and C9orf125 showed that the levels of methylation in the normal samples were uniformly low, whereas the 5 DMRs showed striking hypermethylation in the TNBCs (FIG. 10), and 24 breast cancer cell lines (FIG. 1E).

1.2.4 Functional Characterization of Genes With Promoter Hypermethylation

To predict the potential functional significance of the 822 DMRs identified in the TNBC, those regions which overlapped with promoters and genes were determined. It was found that the 822 DMRs were associated with 513 RefSeq promoters, which corresponded to 308 genes. These genes can be identified using nucleotide analysis software available in the art.

TABLE 10

A list of RefSeq transcripts whose promoters overlap one or more hypermethylated DMRs. The following information is listed for each transcript: (i) promoter genomic coordinates with respect to hg18 (−2000/+100 base pairs around transcript TSS), (ii) region id of the overlapping DMR, (iii) official gene symbol, and (iv) transcript type. The table contains 513 unique transcripts which correspond to 308 unique gene symbols.

| Chromosome | Start (promoter) | End (promoter) | Transcript ID | Strand | Region ID | Gene name | Transcript type |
|---|---|---|---|---|---|---|---|
| 1 | 2,973,602 | 2,975,701 | NM_199454 | + | chr1-38247 | PRDM16 | 1 |
| 1 | 2,973,602 | 2,975,701 | NM_022114 | + | chr1-38247 | PRDM16 | 1 |
| 1 | 75,371,155 | 75,373,254 | NM_001256114 | + | chr1-53988 | NA | NA |
| 1 | 85,298,581 | 85,300,680 | NM_145172 | + | chr1-49613 | WDR63 | 1 |
| 1 | 147,192,910 | 147,195,009 | NR_027356 | + | chr1-11916 |  | 8 |
| 1 | 147,192,910 | 147,195,009 | NR_027355 | + | chr1-11916 |  | 8 |
| 1 | 147,195,029 | 147,197,128 | NR_027354 | + | chr1-11916 |  | 2 |
| 1 | 151,915,788 | 151,917,887 | NM_000906 | + | chr1-20728 | NPR1 | 1 |
| 1 | 168,897,937 | 168,900,036 | NM_006902 | + | chr1-48261 | PRRX1 | 1 |
| 1 | 168,897,937 | 168,900,036 | NM_022716 | + | chr1-48261 | PRRX1 | 1 |
| 1 | 177,976,921 | 177,979,020 | NM_173509 | + | chr1-11343 | FAM163A | 1 |
| 1 | 179,717,309 | 179,719,408 | NM_001205294 | + | chr1-48028 | CACNA1E | 1 |
| 1 | 179,717,309 | 179,719,408 | NM_001205293 | + | chr1-48028 | CACNA1E | 1 |
| 1 | 179,717,309 | 179,719,408 | NM_000721 | + | chr1-48028 | CACNA1E | 1 |
| 1 | 222,868,802 | 222,870,901 | NM_152495 | + | chr1-4629 | CNIH3 | 1 |
| 1 | 235,270,325 | 235,272,424 | NM_001035 | + | chr1-39636 | RYR2 | 1 |
| 1 | 235,270,325 | 235,272,424 | NM_001035 | + | chr1-32204 | RYR2 | 1 |
| 1 | 242,145,327 | 242,147,426 | NR_033883 | + | chr1-32857 |  | 3 |
| 1 | 246,085,124 | 246,087,223 | NM_015431 | + | chr1-38532 | TRIM58 | 1 |
| 1 | 2,974,050 | 2,976,149 | NR_015440 | − | chr1-38247 |  | 3 |
| 1 | 2,974,050 | 2,976,149 | NR_024371 | − | chr1-38247 |  | 3 |
| 1 | 37,272,332 | 37,274,431 | NM_000831 | − | chr1-29954 | GRIK3 | 1 |
| 1 | 38,003,312 | 38,005,411 | NM_001099439 | − | chr1-6836 | EPHA10 | 1 |
| 1 | 38,003,312 | 38,005,411 | NM_173641 | − | chr1-6836 | EPHA10 | 1 |
| 1 | 50,661,608 | 50,663,707 | NM_032110 | − | chr1-29436 | DMRTA2 | 1 |
| 1 | 58,488,700 | 58,490,799 | NM_021080 | − | chr1-23869 | DAB1 | 1 |
| 1 | 63,555,390 | 63,557,489 | NR_038252 | − | chr1-38653 | LINC00466 | 3 |

TABLE 10-continued

A list of RefSeq transcripts whose promoters overlap one or more hypermethylated DMRs. The following information is listed for each transcript: (i) promoter genomic coordinates with respect to hg18 (−2000/+100 base pairs around transcript TSS), (ii) region id of the overlapping DMR, (iii) official gene symbol, and (iv) transcript type. The table contains 513 unique transcripts which correspond to 308 unique gene symbols.

| Chromosome | Start (promoter) | End (promoter) | Transcript ID | Strand | Region ID | Gene name | Transcript type |
|---|---|---|---|---|---|---|---|
| 1 | 90,955,283 | 90,957,382 | NM_020063 | − | chr1-20354 | BARHL2 | 1 |
| 1 | 103,346,541 | 103,348,640 | NM_080629 | − | chr1-4856 | COL11A1 | 1 |
| 1 | 103,346,541 | 103,348,640 | NM_001190709 | − | chr1-4856 | COL11A1 | 1 |
| 1 | 103,346,541 | 103,348,640 | NM_080630 | − | chr1-4856 | COL11A1 | 1 |
| 1 | 103,346,541 | 103,348,640 | NM_001854 | − | chr1-4856 | COL11A1 | 1 |
| 1 | 152,741,051 | 152,743,150 | NM_001010846 | − | chr1-27293 | SHE | 1 |
| 1 | 154,656,746 | 154,658,845 | NR_029691 | − | chr1-41132 | MIR9-1 | 4 |
| 1 | 167,663,195 | 167,665,294 | NM_021179 | − | chr1-40928 | C1orf114 | 1 |
| 1 | 210,939,851 | 210,941,950 | NM_018664 | − | chr1-28592 | BATF3 | 1 |
| 1 | 227,636,367 | 227,638,466 | NM_001100 | − | chr1-48080 | ACTA1 | 1 |
| 1 | 240,754,522 | 240,756,621 | NM_152666 | − | chr1-24072 | PLD5 | 1 |
| 10 | 6,282,846 | 6,284,945 | NM_004566 | + | chr10-2387 | PFKFB3 | 1 |
| 10 | 22,672,380 | 22,674,479 | NM_012443 | + | chr10-6953 | SPAG6 | 1 |
| 10 | 22,672,380 | 22,674,479 | NM_172242 | + | chr10-6953 | SPAG6 | 1 |
| 10 | 22,672,380 | 22,674,479 | NM_001253854 | + | chr10-6953 | SPAG6 | 1 |
| 10 | 22,672,380 | 22,674,479 | NM_001253855 | + | chr10-6953 | SPAG6 | 1 |
| 10 | 23,519,466 | 23,521,565 | NM_178161 | + | chr10-9290 | PTF1A | 1 |
| 10 | 25,502,296 | 25,504,395 | NM_020752 | + | chr10-32739 | GPR158 | 1 |
| 10 | 26,543,242 | 26,545,341 | NM_001134366 | + | chr10-8209 | GAD2 | 1 |
| 10 | 26,543,242 | 26,545,341 | NM_000818 | + | chr10-8209 | GAD2 | 1 |
| 10 | 50,486,353 | 50,488,452 | NM_003055 | + | chr10-35571 | SLC18A3 | 1 |
| 10 | 50,489,160 | 50,491,259 | NM_020985 | + | chr10-35571 | CHAT | 1 |
| 10 | 50,489,160 | 50,491,259 | NM_020986 | + | chr10-35571 | CHAT | 1 |
| 10 | 50,490,089 | 50,492,188 | NM_001142934 | + | chr10-35571 | CHAT | 1 |
| 10 | 50,490,089 | 50,492,188 | NM_020549 | + | chr10-35571 | CHAT | 1 |
| 10 | 50,490,089 | 50,492,188 | NM_001142929 | + | chr10-35571 | CHAT | 1 |
| 10 | 50,490,089 | 50,492,188 | NM_001142933 | + | chr10-35571 | CHAT | 1 |
| 10 | 50,555,690 | 50,557,789 | NM_001042427 | + | chr10-20530 | C10orf53 | 1 |
| 10 | 50,555,690 | 50,557,789 | NM_182554 | + | chr10-20530 | C10orf53 | 1 |
| 10 | 101,280,680 | 101,282,779 | NM_145285 | + | chr10-27233 | NKX2-3 | 1 |
| 10 | 106,388,849 | 106,390,948 | NM_014978 | + | chr10-3695 | SORCS3 | 1 |
| 10 | 106,388,849 | 106,390,948 | NM_014978 | + | chr10-22036 | SORCS3 | 1 |
| 10 | 124,895,628 | 124,897,727 | NM_005519 | + | chr10-2952 | HMX2 | 1 |
| 10 | 134,899,398 | 134,901,497 | NM_014468 | + | chr10-29209 | VENTX | 1 |
| 10 | 1,769,571 | 1,771,670 | NM_018702 | − | chr10-15047 | ADARB2 | 1 |
| 10 | 15,801,677 | 15,803,776 | NM_003638 | − | chr10-20648 | ITGA8 | 1 |
| 10 | 25,505,112 | 25,507,211 | NR_027333 | − | chr10-32739 | | 3 |
| 10 | 71,003,117 | 71,005,216 | NM_020999 | − | chr10-2772 | NEUROG3 | 1 |
| 10 | 118,021,710 | 118,023,809 | NM_145793 | − | chr10-22147 | GFRA1 | 1 |
| 10 | 118,022,687 | 118,024,786 | NM_001145453 | − | chr10-22147 | GFRA1 | 1 |
| 10 | 118,023,017 | 118,025,116 | NM_005264 | − | chr10-22147 | GFRA1 | 1 |
| 10 | 118,887,703 | 118,889,802 | NM_199131 | − | chr10-19113 | VAX1 | 1 |
| 10 | 118,887,703 | 118,889,802 | NM_001112704 | − | chr10-19113 | VAX1 | 1 |
| 10 | 132,999,875 | 133,001,974 | NM_174937 | − | chr10-18957 | TCERG1L | 1 |
| 10 | 134,449,428 | 134,451,527 | NM_177400 | − | chr10-17539 | NKX6-2 | 1 |
| 11 | 6,902,230 | 6,904,329 | NM_013250 | + | chr11-12951 | ZNF215 | 1 |
| 11 | 17,695,686 | 17,697,785 | NM_002478 | + | chr11-5813 | MYOD1 | 1 |
| 11 | 20,645,693 | 20,647,792 | NM_201551 | + | chr11-13529 | NELL1 | 1 |
| 11 | 20,645,693 | 20,647,792 | NM_201551 | + | chr11-30051 | NELL1 | 1 |
| 11 | 20,645,693 | 20,647,792 | NM_006157 | + | chr11-13529 | NELL1 | 1 |
| 11 | 20,645,693 | 20,647,792 | NM_006157 | + | chr11-30051 | NELL1 | 1 |
| 11 | 32,411,861 | 32,413,960 | NR_023920 | + | chr11-24196 | WT1-AS | 5 |
| 11 | 32,411,861 | 32,413,960 | NR_023920 | + | chr11-4047 | WT1-AS | 5 |
| 11 | 46,337,721 | 46,339,820 | NM_001105540 | + | chr11-6782 | DGKZ | 1 |
| 11 | 108,796,056 | 108,798,155 | NM_207645 | + | chr11-28585 | C11orf87 | 1 |
| 11 | 113,433,641 | 113,435,740 | NM_006006 | + | chr11-7178 | ZBTB16 | 1 |
| 11 | 113,433,641 | 113,435,740 | NM_006006 | + | chr11-24352 | ZBTB16 | 1 |
| 11 | 113,434,498 | 113,436,597 | NM_001018011 | + | chr11-7178 | ZBTB16 | 1 |
| 11 | 113,434,498 | 113,436,597 | NM_001018011 | + | chr11-24352 | ZBTB16 | 1 |
| 11 | 124,238,515 | 124,240,614 | NM_022370 | + | chr11-25281 | ROBO3 | 1 |
| 11 | 125,277,482 | 125,279,581 | NM_013264 | + | chr11-24690 | DDX25 | 1 |
| 11 | 131,283,922 | 131,286,021 | NM_001144059 | + | chr11-31615 | NTM | 1 |
| 11 | 131,283,922 | 131,286,021 | NM_016522 | + | chr11-31615 | NTM | 1 |
| 11 | 131,283,922 | 131,286,021 | NM_001144058 | + | chr11-31615 | NTM | 1 |
| 11 | 133,442,030 | 133,444,129 | NM_001205329 | + | chr11-10966 | JAM3 | 1 |
| 11 | 133,442,030 | 133,444,129 | NM_032801 | + | chr11-10966 | JAM3 | 1 |
| 11 | 8,147,067 | 8,149,166 | NM_001206672 | − | chr11-27538 | RIC3 | 1 |
| 11 | 8,147,067 | 8,149,166 | NM_001206671 | − | chr11-27538 | RIC3 | 1 |
| 11 | 8,147,067 | 8,149,166 | NM_024557 | − | chr11-27538 | RIC3 | 1 |
| 11 | 8,147,067 | 8,149,166 | NM_001135109 | − | chr11-27538 | RIC3 | 1 |

TABLE 10-continued

A list of RefSeq transcripts whose promoters overlap one or more hypermethylated DMRs. The following information is listed for each transcript: (i) promoter genomic coordinates with respect to hg18 (−2000/+100 base pairs around transcript TSS), (ii) region id of the overlapping DMR, (iii) official gene symbol, and (iv) transcript type. The table contains 513 unique transcripts which correspond to 308 unique gene symbols.

| Chromosome | Start (promoter) | End (promoter) | Transcript ID | Strand | Region ID | Gene name | Transcript type |
|---|---|---|---|---|---|---|---|
| 11 | 8,147,067 | 8,149,166 | NR_045405 | − | chr11-27538 | NA | NA |
| 11 | 19,692,695 | 19,694,794 | NR_015384 | − | chr11-23818 | NA | NA |
| 11 | 20,138,347 | 20,140,446 | NM_001029865 | − | chr11-13605 | DBX1 | 1 |
| 11 | 27,697,771 | 27,699,870 | NM_001143807 | − | chr11-3267 | BDNF | 1 |
| 11 | 27,698,803 | 27,700,902 | NM_001143806 | − | chr11-3267 | BDNF | 1 |
| 11 | 27,698,803 | 27,700,902 | NM_001143805 | − | chr11-3267 | BDNF | 1 |
| 11 | 27,698,803 | 27,700,902 | NM_170732 | − | chr11-3267 | BDNF | 1 |
| 11 | 27,700,082 | 27,702,181 | NM_170731 | − | chr11-3267 | BDNF | 1 |
| 11 | 32,408,840 | 32,410,939 | NM_001198551 | − | chr11-24196 | WT1 | 1 |
| 11 | 32,408,840 | 32,410,939 | NM_001198552 | − | chr11-24196 | WT1 | 1 |
| 11 | 32,413,558 | 32,415,657 | NM_024424 | − | chr11-4047 | WT1 | 1 |
| 11 | 32,413,558 | 32,415,657 | NM_024426 | − | chr11-4047 | WT1 | 1 |
| 11 | 32,413,558 | 32,415,657 | NM_000378 | − | chr11-4047 | WT1 | 1 |
| 11 | 62,315,963 | 62,318,062 | NM_001080501 | − | chr11-22903 | TMEM223 | 1 |
| 11 | 74,119,735 | 74,121,834 | NM_015424 | − | chr11-24335 | CHRDL2 | 1 |
| 11 | 77,411,869 | 77,413,968 | NM_023930 | − | chr11-27245 | KCTD14 | 1 |
| 11 | 125,278,227 | 125,280,326 | NM_031307 | − | chr11-24690 | PUS3 | 1 |
| 11 | 132,318,148 | 132,320,247 | NM_002545 | − | chr11-30995 | OPCML | 1 |
| 11 | 133,331,991 | 133,334,090 | NM_014987 | − | chr11-24671 | IGSF9B | 1 |
| 12 | 4,251,163 | 4,253,262 | NM_001759 | + | chr12-28277 | CCND2 | 1 |
| 12 | 30,837,882 | 30,839,981 | NR_040245 | + | chr12-2820 | | 3 |
| 12 | 46,861,633 | 46,863,732 | NM_001013635 | + | chr12-7564 | C12orf68 | 1 |
| 12 | 70,950,796 | 70,952,895 | NM_013381 | + | chr12-10548 | TRHDE | 1 |
| 12 | 103,219,640 | 103,221,739 | NM_001008394 | + | chr12-26855 | EID3 | 1 |
| 12 | 118,513,647 | 118,515,746 | NM_001136534 | + | chr12-17914 | TMEM233 | 1 |
| 12 | 127,315,901 | 127,318,000 | NM_001136103 | + | chr12-23224 | TMEM132C | 1 |
| 12 | 127,315,901 | 127,318,000 | NM_001136103 | + | chr12-29205 | TMEM132C | 1 |
| 12 | 45,759,902 | 45,762,001 | NM_181847 | − | chr12-24630 | AMIGO2 | 1 |
| 12 | 45,759,902 | 45,762,001 | NM_001143668 | − | chr12-24630 | AMIGO2 | 1 |
| 12 | 70,953,457 | 70,955,556 | NR_026837 | − | chr12-10548 | | 3 |
| 12 | 70,953,457 | 70,955,556 | NR_026836 | − | chr12-10548 | | 3 |
| 12 | 73,889,679 | 73,891,778 | NM_139136 | − | chr12-10547 | KCNC2 | 1 |
| 12 | 73,889,679 | 73,891,778 | NM_153748 | − | chr12-10547 | KCNC2 | 1 |
| 12 | 73,889,679 | 73,891,778 | NM_139137 | − | chr12-10547 | KCNC2 | 1 |
| 12 | 97,812,706 | 97,814,805 | NM_001204081 | − | chr12-18252 | ANKS1B | 1 |
| 12 | 97,812,706 | 97,814,805 | NM_001204065 | − | chr12-18252 | ANKS1B | 1 |
| 12 | 97,812,706 | 97,814,805 | NM_001204080 | − | chr12-18252 | ANKS1B | 1 |
| 12 | 97,812,706 | 97,814,805 | NM_001204079 | − | chr12-18252 | ANKS1B | 1 |
| 12 | 106,821,579 | 106,823,678 | NR_037629 | − | chr12-9653 | NA | NA |
| 12 | 109,611,230 | 109,613,329 | NM_032369 | − | chr12-30179 | HVCN1 | 1 |
| 12 | 109,611,901 | 109,614,000 | NM_001040107 | − | chr12-30179 | HVCN1 | 1 |
| 12 | 112,394,161 | 112,396,260 | NM_022363 | − | chr12-894 | LHX5 | 1 |
| 12 | 128,954,066 | 128,956,165 | NM_133448 | − | chr12-2151 | TMEM132D | 1 |
| 13 | 27,262,780 | 27,264,879 | NM_145657 | + | chr13-13783 | GSX1 | 1 |
| 13 | 48,690,475 | 48,692,574 | NM_001507 | + | chr13-9261 | MLNR | 1 |
| 13 | 57,101,790 | 57,103,889 | NM_001040429 | + | chr13-10897 | PCDH17 | 1 |
| 13 | 42,464,278 | 42,466,377 | NM_033255 | − | chr13-8897 | EPSTI1 | 1 |
| 13 | 42,464,278 | 42,466,377 | NM_001002264 | − | chr13-8897 | EPSTI1 | 1 |
| 13 | 52,320,677 | 52,322,776 | NM_002590 | − | chr13-5196 | PCDH8 | 1 |
| 13 | 52,320,677 | 52,322,776 | NM_032949 | − | chr13-5196 | PCDH8 | 1 |
| 13 | 94,162,291 | 94,164,390 | NM_007084 | − | chr13-9865 | SOX21 | 1 |
| 13 | 107,317,362 | 107,319,461 | NM_001080396 | − | chr13-9410 | FAM155A | 1 |
| 14 | 56,347,654 | 56,349,753 | NR_029385 | + | chr14-13812 | | 5 |
| 14 | 91,857,905 | 91,860,004 | NM_153646 | + | chr14-12954 | SLC24A4 | 1 |
| 14 | 21,075,078 | 21,077,177 | NM_005407 | − | chr14-8228 | SALL2 | 1 |
| 14 | 36,058,555 | 36,060,654 | NM_003317 | − | chr14-10157 | NKX2-1 | 1 |
| 14 | 36,059,082 | 36,061,181 | NM_001079668 | − | chr14-10157 | NKX2-1 | 1 |
| 14 | 56,346,838 | 56,348,937 | NM_021728 | − | chr14-13812 | OTX2 | 1 |
| 14 | 60,022,418 | 60,024,517 | NM_174978 | − | chr14-7997 | C14orf39 | 1 |
| 15 | 46,955,582 | 46,957,681 | NM_014335 | + | chr15-7466 | EID1 | 1 |
| 15 | 58,081,713 | 58,083,812 | NM_012182 | + | chr15-2485 | FOXB1 | 1 |
| 15 | 32,833,882 | 32,835,981 | NM_020660 | − | chr15-5377 | GJD2 | 1 |
| 15 | 46,725,178 | 46,727,277 | NM_000138 | − | chr15-15389 | FBN1 | 1 |
| 15 | 73,792,145 | 73,794,244 | NM_001897 | − | chr15-12559 | CSPG4 | 1 |
| 15 | 87,239,675 | 87,241,774 | NM_178232 | − | chr15-6733 | HAPLN3 | 1 |
| 16 | 12,900,978 | 12,903,077 | NM_001145205 | + | chr16-39747 | SHISA9 | 1 |
| 16 | 12,900,978 | 12,903,077 | NM_001145204 | + | chr16-39747 | SHISA9 | 1 |
| 16 | 22,731,361 | 22,733,460 | NM_006043 | + | chr16-21410 | HS3ST2 | 1 |
| 16 | 29,981,101 | 29,983,200 | NM_184043 | + | chr16-39788 | ALDOA | 1 |
| 16 | 29,981,319 | 29,983,418 | NM_001127617 | + | chr16-39788 | ALDOA | 1 |

TABLE 10-continued

A list of RefSeq transcripts whose promoters overlap one or more hypermethylated DMRs. The following information is listed for each transcript: (i) promoter genomic coordinates with respect to hg18 (−2000/+100 base pairs around transcript TSS), (ii) region id of the overlapping DMR, (iii) official gene symbol, and (iv) transcript type. The table contains 513 unique transcripts which correspond to 308 unique gene symbols.

| Chromosome | Start (promoter) | End (promoter) | Transcript ID | Strand | Region ID | Gene name | Transcript type |
|---|---|---|---|---|---|---|---|
| 16 | 29,982,495 | 29,984,594 | NM_184041 | + | chr16-39788 | ALDOA | 1 |
| 16 | 29,982,495 | 29,984,594 | NM_001243177 | + | chr16-39788 | ALDOA | 1 |
| 16 | 66,118,218 | 66,120,317 | NM_024519 | + | chr16-38440 | FAM65A | 1 |
| 16 | 66,118,221 | 66,120,320 | NM_001193522 | + | chr16-38440 | FAM65A | 1 |
| 16 | 66,119,041 | 66,121,140 | NM_001193523 | + | chr16-38440 | FAM65A | 1 |
| 16 | 81,215,900 | 81,217,999 | NM_001220491 | + | chr16-10222 | CDH13 | 1 |
| 16 | 81,215,900 | 81,217,999 | NM_001220492 | + | chr16-10222 | CDH13 | 1 |
| 16 | 81,215,900 | 81,217,999 | NM_001220488 | + | chr16-10222 | CDH13 | 1 |
| 16 | 81,215,900 | 81,217,999 | NM_001257 | + | chr16-10222 | CDH13 | 1 |
| 16 | 81,215,900 | 81,217,999 | NM_001220490 | + | chr16-10222 | CDH13 | 1 |
| 16 | 81,215,900 | 81,217,999 | NM_001220489 | + | chr16-10222 | CDH13 | 1 |
| 16 | 83,726,257 | 83,728,356 | NR_033984 | + | chr16-31613 | NA | NA |
| 16 | 84,875,538 | 84,877,637 | NR_038438 | + | chr16-15120 | NA | NA |
| 16 | 85,099,634 | 85,101,733 | NM_001451 | + | chr16-19848 | FOXF1 | 1 |
| 16 | 86,192,000 | 86,194,099 | NM_020655 | + | chr16-31470 | JPH3 | 1 |
| 16 | 19,992,502 | 19,994,601 | NM_001002911 | − | chr16-10570 | GPR139 | 1 |
| 16 | 31,121,499 | 31,123,598 | NM_145182 | − | chr16-16067 | PYCARD | 1 |
| 16 | 31,121,499 | 31,123,598 | NM_013258 | − | chr16-16067 | PYCARD | 1 |
| 16 | 31,135,797 | 31,137,896 | NM_152901 | − | chr16-16055 | PYDC1 | 1 |
| 16 | 47,873,144 | 47,875,243 | NM_004352 | − | chr16-27356 | CBLN1 | 1 |
| 16 | 60,628,141 | 60,630,240 | NM_001796 | − | chr16-28483 | CDH8 | 1 |
| 17 | 43,125,629 | 43,127,728 | NM_014726 | + | chr17-35096 | TBKBP1 | 1 |
| 17 | 53,587,319 | 53,589,418 | NR_002307 | + | chr17-23838 | MSX2P1 | 6 |
| 17 | 55,580,084 | 55,582,183 | NM_000717 | + | chr17-9298 | CA4 | 1 |
| 17 | 70,176,851 | 70,178,950 | NM_175738 | + | chr17-34300 | RAB37 | 1 |
| 17 | 44,161,011 | 44,163,110 | NM_006361 | − | chr17-17561 | HOXB13 | 1 |
| 17 | 47,591,032 | 47,593,131 | NM_020178 | − | chr17-32969 | CA10 | 1 |
| 17 | 47,592,061 | 47,594,160 | NM_001082533 | − | chr17-32969 | CA10 | 1 |
| 17 | 47,592,277 | 47,594,376 | NM_001082534 | − | chr17-32969 | CA10 | 1 |
| 18 | 2,835,028 | 2,837,127 | NM_032048 | + | chr18-11204 | EMILIN2 | 1 |
| 18 | 10,442,625 | 10,444,724 | NM_153000 | + | chr18-8094 | APCDD1 | 1 |
| 18 | 53,168,719 | 53,170,818 | NM_015879 | + | chr18-11487 | ST8SIA3 | 1 |
| 18 | 65,217,264 | 65,219,363 | NM_152721 | + | chr18-12432 | DOK6 | 1 |
| 18 | 73,088,996 | 73,091,095 | NM_001480 | + | chr18-4037 | GALR1 | 1 |
| 18 | 74,839,263 | 74,841,362 | NM_171999 | + | chr18-7308 | SALL3 | 1 |
| 18 | 5,187,156 | 5,189,255 | NM_001145194 | − | chr18-1098 | C18orf42 | 1 |
| 18 | 11,138,662 | 11,140,761 | NM_022068 | − | chr18-13032 | PIEZO2 | 1 |
| 18 | 42,590,938 | 42,593,037 | NM_013305 | − | chr18-2933 | ST8SIA5 | 1 |
| 18 | 68,685,691 | 68,687,790 | NM_001201465 | − | chr18-14616 | NETO1 | 1 |
| 18 | 68,685,691 | 68,687,790 | NM_001201465 | − | chr18-4761 | NETO1 | 1 |
| 18 | 68,685,691 | 68,687,790 | NM_138966 | − | chr18-14616 | NETO1 | 1 |
| 18 | 68,685,691 | 68,687,790 | NM_138966 | − | chr18-4761 | NETO1 | 1 |
| 18 | 68,683,815 | 68,685,914 | NM_138999 | − | chr18-4761 | NETO1 | 1 |
| 18 | 72,336,035 | 72,338,134 | NM_014643 | − | chr18-5056 | ZNF516 | 1 |
| 19 | 1,399,148 | 1,401,247 | NM_005883 | + | chr19-43568 | APC2 | 1 |
| 19 | 22,259,092 | 22,261,191 | NM_001242680 | + | chr19-14446 | ZNF729 | 1 |
| 19 | 24,059,816 | 24,061,915 | NM_203282 | + | chr19-36571 | ZNF254 | 1 |
| 19 | 34,707,331 | 34,709,430 | NM_001146339 | + | chr19-49971 | VSTM2B | 1 |
| 19 | 34,707,331 | 34,709,430 | NM_001146339 | + | chr19-29086 | VSTM2B | 1 |
| 19 | 42,732,113 | 42,734,212 | NR_038249 | + | chr19-26515 | NA | NA |
| 19 | 42,732,113 | 42,734,212 | NR_038250 | + | chr19-26515 | NA | NA |
| 19 | 42,732,113 | 42,734,212 | NM_152606 | + | chr19-26515 | ZNF540 | 1 |
| 19 | 42,997,891 | 42,999,990 | NR_040013 | + | chr19-6795 | NA | NA |
| 19 | 49,145,237 | 49,147,336 | NM_013359 | + | chr19-8563 | ZNF221 | 1 |
| 19 | 57,562,982 | 57,565,081 | NM_001145434 | + | chr19-30142 | ZNF880 | 1 |
| 19 | 61,569,280 | 61,571,379 | NR_003127 | + | chr19-13959 | ZNF542 | 3 |
| 19 | 61,569,302 | 61,571,401 | NR_024057 | + | chr19-13959 | ZNF542 | 3 |
| 19 | 61,569,302 | 61,571,401 | NR_024056 | + | chr19-13959 | NA | NA |
| 19 | 61,569,302 | 61,571,401 | NR_024055 | + | chr19-13959 | ZNF542 | 3 |
| 19 | 61,569,302 | 61,571,401 | NR_033418 | + | chr19-13959 | ZNF542 | 3 |
| 19 | 61,844,339 | 61,846,438 | NM_001193628 | + | chr19-24064 | NA | NA |
| 19 | 62,701,121 | 62,703,220 | NM_198542 | + | chr19-31732 | ZNF773 | 1 |
| 19 | 62,785,440 | 62,787,539 | NM_001010879 | + | chr19-11665 | ZIK1 | 1 |
| 19 | 6,542,064 | 6,544,163 | NM_001252 | − | chr19-46269 | CD70 | 1 |
| 19 | 9,470,180 | 9,472,279 | NM_152476 | − | chr19-30352 | ZNF560 | 1 |
| 19 | 10,489,027 | 10,491,126 | NM_030760 | − | chr19-17643 | S1PR5 | 1 |
| 19 | 10,489,569 | 10,491,668 | NM_001166215 | − | chr19-17643 | S1PR5 | 1 |
| 19 | 11,549,454 | 11,551,553 | NM_001611 | − | chr19-8158 | ACP5 | 1 |
| 19 | 11,550,493 | 11,552,592 | NM_001111034 | − | chr19-8158 | ACP5 | 1 |
| 19 | 11,550,702 | 11,552,801 | NM_001111036 | − | chr19-8158 | ACP5 | 1 |

TABLE 10-continued

A list of RefSeq transcripts whose promoters overlap one or more hypermethylated DMRs. The following information is listed for each transcript: (i) promoter genomic coordinates with respect to hg18 (−2000/+100 base pairs around transcript TSS), (ii) region id of the overlapping DMR, (iii) official gene symbol, and (iv) transcript type. The table contains 513 unique transcripts which correspond to 308 unique gene symbols.

| Chromosome | Start (promoter) | End (promoter) | Transcript ID | Strand | Region ID | Gene name | Transcript type |
|---|---|---|---|---|---|---|---|
| 19 | 11,550,702 | 11,552,801 | NM_001111035 | − | chr19-8158 | ACP5 | 1 |
| 19 | 17,659,909 | 17,662,008 | NM_001080421 | − | chr19-26183 | UNC13A | 1 |
| 19 | 19,793,461 | 19,795,560 | NM_001099269 | − | chr19-28214 | ZNF506 | 1 |
| 19 | 19,793,461 | 19,795,560 | NM_001145404 | − | chr19-28214 | ZNF506 | 1 |
| 19 | 21,985,486 | 21,987,585 | NM_007153 | − | chr19-49834 | ZNF208 | 1 |
| 19 | 22,396,889 | 22,398,988 | NM_001098626 | − | chr19-31045 | ZNF98 | 1 |
| 19 | 34,708,400 | 34,710,499 | NR_040029 | − | chr19-49971 | NA | NA |
| 19 | 34,708,400 | 34,710,499 | NR_040029 | − | chr19-29086 | NA | NA |
| 19 | 36,531,931 | 36,534,030 | NM_020856 | − | chr19-24060 | TSHZ3 | 1 |
| 19 | 49,644,406 | 49,646,505 | NM_014518 | − | chr19-10652 | ZNF229 | 1 |
| 19 | 56,789,346 | 56,791,445 | NR_034159 | − | chr19-31043 | NA | NA |
| 19 | 62,912,292 | 62,914,391 | NM_001085384 | − | chr19-31544 | ZNF154 | 1 |
| 19 | 62,930,708 | 62,932,807 | NM_024833 | − | chr19-6109 | ZNF671 | 1 |
| 19 | 63,138,453 | 63,140,552 | NM_133460 | − | chr19-16291 | ZNF418 | 1 |
| 19 | 63,301,443 | 63,303,542 | NM_001145544 | − | chr19-19145 | ZSCAN18 | 1 |
| 19 | 63,301,443 | 63,303,542 | NM_023926 | − | chr19-19145 | ZSCAN18 | 1 |
| 19 | 63,301,443 | 63,303,542 | NM_001145543 | − | chr19-19145 | ZSCAN18 | 1 |
| 2 | 124,497,334 | 124,499,433 | NM_130773 | + | chr2-4092 | CNTNAP5 | 1 |
| 2 | 176,663,778 | 176,665,877 | NM_000523 | + | chr2-22578 | HOXD13 | 1 |
| 2 | 176,687,738 | 176,689,837 | NM_002148 | + | chr2-9342 | HOXD10 | 1 |
| 2 | 278,209 | 280,308 | NM_001002919 | − | chr2-45413 | FAM150B | 1 |
| 2 | 176,656,837 | 176,658,936 | NM_001080458 | − | chr2-9331 | EVX2 | 1 |
| 2 | 182,253,538 | 182,255,637 | NM_002500 | − | chr2-13825 | NEUROD1 | 1 |
| 2 | 182,253,538 | 182,255,637 | NM_002500 | − | chr2-17703 | NEUROD1 | 1 |
| 2 | 192,767,790 | 192,769,889 | NM_016192 | − | chr2-26540 | TMEFF2 | 1 |
| 2 | 200,044,135 | 200,046,234 | NM_015265 | − | chr2-27090 | SATB2 | 1 |
| 2 | 219,881,874 | 219,883,973 | NM_001199764 | − | chr2-6335 | PTPRN | 1 |
| 2 | 219,882,440 | 219,884,539 | NM_002846 | − | chr2-6335 | PTPRN | 1 |
| 2 | 219,882,440 | 219,884,539 | NM_001199763 | − | chr2-6335 | PTPRN | 1 |
| 2 | 232,959,899 | 232,961,998 | NR_028501 | − | chr2-45508 | | 3 |
| 2 | 241,408,299 | 241,410,398 | NM_004321 | − | chr2-31496 | KIF1A | 1 |
| 2 | 241,408,299 | 241,410,398 | NM_001244008 | − | chr2-31496 | KIF1A | 1 |
| 20 | 21,632,297 | 21,634,396 | NM_006192 | + | chr20-15341 | PAX1 | 1 |
| 20 | 34,601,301 | 34,603,400 | NM_006097 | + | chr20-17172 | MYL9 | 1 |
| 20 | 34,601,301 | 34,603,400 | NM_181526 | + | chr20-17172 | MYL9 | 1 |
| 20 | 61,278,297 | 61,280,396 | NR_029670 | + | chr20-20481 | MIR124-3 | 4 |
| 20 | 61,839,655 | 61,841,754 | NM_020062 | + | chr20-19704 | SLC2A4RG | 1 |
| 20 | 62,179,915 | 62,182,014 | NM_000913 | + | chr20-17950 | OPRL1 | 1 |
| 20 | 62,179,915 | 62,182,014 | NM_182647 | + | chr20-17950 | OPRL1 | 1 |
| 20 | 5,242,916 | 5,245,015 | NM_144773 | − | chr20-4787 | PROKR2 | 1 |
| 20 | 22,507,181 | 22,509,280 | NR_001558 | − | chr20-11329 | LINC00261 | 7 |
| 20 | 22,507,181 | 22,509,280 | NR_001558 | − | chr20-5927 | LINC00261 | 7 |
| 20 | 25,010,916 | 25,013,015 | NM_001256271 | − | chr20-4500 | NA | NA |
| 20 | 25,010,916 | 25,013,015 | NM_001256272 | − | chr20-4500 | NA | NA |
| 20 | 25,010,916 | 25,013,015 | NR_045948 | − | chr20-4500 | NA | NA |
| 20 | 25,010,916 | 25,013,015 | NR_045951 | − | chr20-4500 | NA | NA |
| 20 | 25,010,916 | 25,013,015 | NM_014588 | − | chr20-4500 | VSX1 | 1 |
| 20 | 25,010,916 | 25,013,015 | NM_199425 | − | chr20-4500 | VSX1 | 1 |
| 20 | 44,575,502 | 44,577,601 | NM_199441 | − | chr20-7936 | ZNF334 | 1 |
| 20 | 44,575,502 | 44,577,601 | NM_018102 | − | chr20-7936 | ZNF334 | 1 |
| 20 | 54,013,320 | 54,015,419 | NM_080617 | − | chr20-4778 | CBLN4 | 1 |
| 20 | 61,108,733 | 61,110,832 | NM_080606 | − | chr20-22989 | BHLHE23 | 1 |
| 20 | 62,181,190 | 62,183,289 | NM_005873 | − | chr20-17950 | RGS19 | 1 |
| 20 | 62,181,669 | 62,183,768 | NM_001039467 | − | chr20-17950 | RGS19 | 1 |
| 21 | 33,318,086 | 33,320,185 | NM_005806 | + | chr21-7896 | OLIG2 | 1 |
| 21 | 36,991,861 | 36,993,960 | NM_009586 | + | chr21-8209 | SIM2 | 1 |
| 21 | 36,991,861 | 36,993,960 | NM_005069 | + | chr21-8209 | SIM2 | 1 |
| 21 | 38,210,467 | 38,212,566 | NM_002240 | − | chr21-5935 | KCNJ6 | 1 |
| 21 | 38,955,389 | 38,957,488 | NM_001243432 | − | chr21-5864 | ERG | 1 |
| 21 | 38,954,362 | 38,956,461 | NM_001243428 | − | chr21-5864 | ERG | 1 |
| 21 | 38,955,475 | 38,957,574 | NM_004449 | − | chr21-5864 | ERG | 1 |
| 21 | 38,955,475 | 38,957,574 | NM_001136154 | − | chr21-5864 | ERG | 1 |
| 22 | 25,381,446 | 25,383,545 | NR_033319 | + | chr22-15317 | MIAT | 3 |
| 22 | 25,381,446 | 25,383,545 | NR_033321 | + | chr22-15317 | MIAT | 3 |
| 22 | 25,381,446 | 25,383,545 | NR_033320 | + | chr22-15317 | MIAT | 3 |
| 22 | 25,381,446 | 25,383,545 | NR_003491 | + | chr22-15317 | MIAT | 3 |
| 22 | 17,517,697 | 17,519,796 | NM_005315 | − | chr22-14473 | GSC2 | 1 |
| 22 | 43,783,439 | 43,785,538 | NM_001242450 | − | chr22-14234 | PHF21B | 1 |
| 22 | 43,784,146 | 43,786,245 | NM_138415 | − | chr22-14234 | PHF21B | 1 |
| 22 | 43,784,374 | 43,786,473 | NM_001135862 | − | chr22-14234 | PHF21B | 1 |

TABLE 10-continued

A list of RefSeq transcripts whose promoters overlap one or more hypermethylated DMRs. The following information is listed for each transcript: (i) promoter genomic coordinates with respect to hg18 (−2000/+100 base pairs around transcript TSS), (ii) region id of the overlapping DMR, (iii) official gene symbol, and (iv) transcript type. The table contains 513 unique transcripts which correspond to 308 unique gene symbols.

| Chromosome | Start (promoter) | End (promoter) | Transcript ID | Strand | Region ID | Gene name | Transcript type |
|---|---|---|---|---|---|---|---|
| 3 | 211,279 | 213,378 | NM_006614 | + | chr3-11819 | CHL1 | 1 |
| 3 | 211,279 | 213,378 | NM_001253387 | + | chr3-11819 | CHL1 | 1 |
| 3 | 212,326 | 214,425 | NR_045572 | + | chr3-11819 | CHL1 | 3 |
| 3 | 12,303,436 | 12,305,535 | NM_138711 | + | chr3-19388 | PPARG | 1 |
| 3 | 37,007,845 | 37,009,944 | NM_000249 | + | chr3-8813 | MLH1 | 1 |
| 3 | 37,008,272 | 37,010,371 | NM_001167619 | + | chr3-8813 | MLH1 | 1 |
| 3 | 37,008,272 | 37,010,371 | NM_001167618 | + | chr3-8813 | MLH1 | 1 |
| 3 | 37,008,272 | 37,010,371 | NM_001167617 | + | chr3-8813 | MLH1 | 1 |
| 3 | 44,727,139 | 44,729,238 | NM_033210 | + | chr3-7330 | ZNF502 | 1 |
| 3 | 44,727,139 | 44,729,238 | NM_001134442 | + | chr3-7330 | ZNF502 | 1 |
| 3 | 44,727,139 | 44,729,238 | NM_001134441 | + | chr3-7330 | ZNF502 | 1 |
| 3 | 44,727,139 | 44,729,238 | NM_001134440 | + | chr3-7330 | ZNF502 | 1 |
| 3 | 63,236,954 | 63,239,053 | NM_001130003 | + | chr3-4075 | SYNPR | 1 |
| 3 | 113,532,606 | 113,534,705 | NM_005944 | + | chr3-20990 | CD200 | 1 |
| 3 | 113,532,606 | 113,534,705 | NM_001004196 | + | chr3-20990 | CD200 | 1 |
| 3 | 123,383,220 | 123,385,319 | NM_000388 | + | chr3-13141 | CASR | 1 |
| 3 | 123,383,871 | 123,385,970 | NM_001178065 | + | chr3-13141 | CASR | 1 |
| 3 | 132,561,379 | 132,563,478 | NR_002949 | + | chr3-1810 | | 3 |
| 3 | 132,561,408 | 132,563,507 | NR_027766 | + | chr3-1810 | | 3 |
| 3 | 148,607,871 | 148,609,970 | NM_003412 | + | chr3-9862 | ZIC1 | 1 |
| 3 | 149,896,348 | 149,898,447 | NM_000685 | + | chr3-2993 | AGTR1 | 1 |
| 3 | 149,896,348 | 149,898,447 | NM_004835 | + | chr3-2993 | AGTR1 | 1 |
| 3 | 149,896,348 | 149,898,447 | NM_031850 | + | chr3-2993 | AGTR1 | 1 |
| 3 | 149,896,348 | 149,898,447 | NM_009585 | + | chr3-2993 | AGTR1 | 1 |
| 3 | 169,448,004 | 169,450,103 | NR_021485 | + | chr3-19953 | EGFEM1P | 3 |
| 3 | 174,596,938 | 174,599,037 | NM_014932 | + | chr3-10180 | NLGN1 | 1 |
| 3 | 13,896,520 | 13,898,619 | NM_004625 | − | chr3-16318 | WNT7A | 1 |
| 3 | 27,738,690 | 27,740,789 | NM_005442 | − | chr3-18012 | EOMES | 1 |
| 3 | 37,009,700 | 37,011,799 | NM_014805 | − | chr3-8813 | EPM2AIP1 | 1 |
| 3 | 62,334,131 | 62,336,230 | NM_018008 | − | chr3-11179 | FEZF2 | 1 |
| 3 | 79,899,650 | 79,901,749 | NM_002941 | − | chr3-9248 | ROBO1 | 1 |
| 3 | 129,689,355 | 129,691,454 | NM_001145662 | − | chr3-16920 | GATA2 | 1 |
| 3 | 129,689,964 | 129,692,063 | NM_001145661 | − | chr3-16920 | GATA2 | 1 |
| 3 | 171,786,458 | 171,788,557 | NM_020949 | − | chr3-22674 | SLC7A14 | 1 |
| 3 | 173,648,841 | 173,650,940 | NM_198407 | − | chr3-1158 | GHSR | 1 |
| 3 | 173,648,841 | 173,650,940 | NM_004122 | − | chr3-1158 | GHSR | 1 |
| 3 | 188,870,796 | 188,872,895 | NM_001048 | − | chr3-3854 | SST | 1 |
| 4 | 5,102,428 | 5,104,527 | NM_018401 | + | chr4-2546 | STK32B | 1 |
| 4 | 6,251,361 | 6,253,460 | NR_037863 | + | chr4-6479 | | 8 |
| 4 | 36,921,085 | 36,923,184 | NM_001144990 | + | chr4-2028 | KIAA1239 | 1 |
| 4 | 66,216,274 | 66,218,373 | NR_034138 | + | chr4-3545 | | 3 |
| 4 | 172,969,150 | 172,971,249 | NM_001034845 | + | chr4-2412 | GALNTL6 | 1 |
| 4 | 177,221,979 | 177,224,078 | NM_181265 | + | chr4-8602 | WDR17 | 1 |
| 4 | 177,221,979 | 177,224,078 | NM_170710 | + | chr4-8602 | WDR17 | 1 |
| 4 | 5,941,117 | 5,943,216 | NM_001313 | − | chr4-18262 | CRMP1 | 1 |
| 4 | 21,559,373 | 21,561,472 | NM_147182 | − | chr4-7295 | KCNIP4 | 1 |
| 4 | 36,919,909 | 36,922,008 | NR_039965 | − | chr4-2028 | NA | NA |
| 4 | 46,690,180 | 46,692,279 | NM_001204267 | − | chr4-25870 | GABRA4 | 1 |
| 4 | 46,690,180 | 46,692,279 | NM_001204266 | − | chr4-25870 | GABRA4 | 1 |
| 4 | 46,691,082 | 46,693,181 | NM_000809 | − | chr4-25870 | GABRA4 | 1 |
| 5 | 9,597,312 | 9,599,411 | NR_045196 | + | chr5-27730 | | 8 |
| 5 | 9,599,939 | 9,602,038 | NR_003689 | + | chr5-18793 | SNORD123 | 9 |
| 5 | 31,227,519 | 31,229,618 | NM_004932 | + | chr5-19148 | CDH6 | 1 |
| 5 | 140,765,954 | 140,768,053 | NM_032100 | + | chr5-22310 | PCDHGB6 | 1 |
| 5 | 140,765,954 | 140,768,053 | NM_018926 | + | chr5-22310 | PCDHGB6 | 1 |
| 5 | 145,696,780 | 145,698,879 | NM_002700 | + | chr5-12906 | POU4F3 | 1 |
| 5 | 1,498,444 | 1,500,543 | NM_001044 | − | chr5-29013 | SLC6A3 | 1 |
| 5 | 9,599,134 | 9,601,233 | NM_003966 | − | chr5-18793 | SEMA5A | 1 |
| 5 | 36,027,193 | 36,029,292 | NM_152404 | − | chr5-23479 | UGT3A1 | 1 |
| 5 | 37,875,440 | 37,877,539 | NM_000514 | − | chr5-12543 | GDNF | 1 |
| 5 | 63,293,203 | 63,295,302 | NM_000524 | − | chr5-5052 | HTR1A | 1 |
| 5 | 158,459,267 | 158,461,366 | NM_024007 | − | chr5-17366 | EBF1 | 1 |
| 6 | 334,739 | 336,838 | NM_001195286 | + | chr6-14328 | IRF4 | 1 |
| 6 | 334,739 | 336,838 | NM_001195286 | + | chr6-7903 | IRF4 | 1 |
| 6 | 334,739 | 336,838 | NM_002460 | + | chr6-14328 | IRF4 | 1 |
| 6 | 334,739 | 336,838 | NM_002460 | + | chr6-7903 | IRF4 | 1 |
| 6 | 334,739 | 336,838 | NR_036585 | + | chr6-14328 | NA | NA |
| 6 | 334,739 | 336,838 | NR_036585 | + | chr6-7903 | NA | NA |
| 6 | 7,050,829 | 7,052,928 | NM_001168344 | + | chr6-3985 | RREB1 | 1 |
| 6 | 7,051,085 | 7,053,184 | NM_001003699 | + | chr6-3985 | RREB1 | 1 |

TABLE 10-continued

A list of RefSeq transcripts whose promoters overlap one or more hypermethylated DMRs. The following information is listed for each transcript: (i) promoter genomic coordinates with respect to hg18 (−2000/+100 base pairs around transcript TSS), (ii) region id of the overlapping DMR, (iii) official gene symbol, and (iv) transcript type. The table contains 513 unique transcripts which correspond to 308 unique gene symbols.

| Chromosome | Start (promoter) | End (promoter) | Transcript ID | Strand | Region ID | Gene name | Transcript type |
|---|---|---|---|---|---|---|---|
| 6 | 7,051,085 | 7,053,184 | NM_001003698 | + | chr6-3985 | RREB1 | 1 |
| 6 | 7,051,085 | 7,053,184 | NM_001003700 | + | chr6-3985 | RREB1 | 1 |
| 6 | 26,290,003 | 26,292,102 | NM_003523 | + | chr6-10828 | HIST1H2BE | 1 |
| 6 | 27,912,419 | 27,914,518 | NM_003520 | + | chr6-15406 | HIST1H2BN | 1 |
| 6 | 31,889,270 | 31,891,369 | NM_005345 | + | chr6-16375 | HSPA1A | 1 |
| 6 | 43,718,745 | 43,720,844 | NM_001193341 | + | chr6-9437 | RSPH9 | 1 |
| 6 | 43,718,745 | 43,720,844 | NM_152732 | + | chr6-9437 | RSPH9 | 1 |
| 6 | 84,617,704 | 84,619,803 | NM_001009994 | + | chr6-2200 | RIPPLY2 | 1 |
| 6 | 117,691,414 | 117,693,513 | NM_153453 | + | chr6-28662 | VGLL2 | 1 |
| 6 | 117,691,414 | 117,693,513 | NM_153453 | + | chr6-19743 | VGLL2 | 1 |
| 6 | 117,691,430 | 117,693,529 | NM_182645 | + | chr6-28662 | VGLL2 | 1 |
| 6 | 117,691,430 | 117,693,529 | NM_182645 | + | chr6-19743 | VGLL2 | 1 |
| 6 | 133,602,188 | 133,604,287 | NM_172105 | + | chr6-23296 | EYA4 | 1 |
| 6 | 133,602,188 | 133,604,287 | NM_172103 | + | chr6-23296 | EYA4 | 1 |
| 6 | 133,602,188 | 133,604,287 | NM_004100 | + | chr6-23296 | EYA4 | 1 |
| 6 | 10,989,985 | 10,992,084 | NM_004752 | − | chr6-25890 | GCM2 | 1 |
| 6 | 27,913,997 | 27,916,096 | NM_003510 | − | chr6-15406 | HIST1H2AK | 1 |
| 6 | 28,475,424 | 28,477,523 | NR_028077 | − | chr6-6380 | NA | NA |
| 6 | 28,475,424 | 28,477,523 | NM_001163391 | − | chr6-6380 | ZSCAN12 | 1 |
| 6 | 28,519,159 | 28,521,258 | NM_001012455 | − | chr6-16740 | ZSCAN23 | 1 |
| 6 | 28,662,992 | 28,665,091 | NM_052923 | − | chr6-17652 | SCAND3 | 1 |
| 6 | 31,890,715 | 31,892,814 | NM_005527 | − | chr6-16375 | HSPA1L | 1 |
| 6 | 43,384,409 | 43,386,508 | NM_206922 | − | chr6-7762 | CRIP3 | 1 |
| 6 | 63,053,960 | 63,056,059 | NM_152688 | − | chr6-1661 | KHDRBS2 | 1 |
| 6 | 78,229,740 | 78,231,839 | NM_000863 | − | chr6-26510 | HTR1B | 1 |
| 6 | 85,530,519 | 85,532,618 | NM_001080508 | − | chr6-2768 | TBX18 | 1 |
| 6 | 127,882,094 | 127,884,193 | NM_001012279 | − | chr6-24682 | C6orf174 | 1 |
| 6 | 137,857,125 | 137,859,224 | NM_175747 | − | chr6-23012 | OLIG3 | 1 |
| 6 | 170,441,523 | 170,443,622 | NM_005618 | − | chr6-28480 | DLL1 | 1 |
| 7 | 8,438,110 | 8,440,209 | NM_152745 | + | chr7-4850 | NXPH1 | 1 |
| 7 | 24,288,332 | 24,290,431 | NM_000905 | + | chr7-28113 | NPY | 1 |
| 7 | 86,109,166 | 86,111,265 | NM_000840 | + | chr7-19417 | GRM3 | 1 |
| 7 | 86,810,887 | 86,812,986 | NM_001243745 | + | chr7-11427 | CROT | 1 |
| 7 | 86,810,887 | 86,812,986 | NM_001143935 | + | chr7-11427 | CROT | 1 |
| 7 | 86,810,887 | 86,812,986 | NM_021151 | + | chr7-11427 | CROT | 1 |
| 7 | 96,471,226 | 96,473,325 | NM_005222 | + | chr7-9141 | DLX6 | 1 |
| 7 | 97,197,207 | 97,199,306 | NM_003182 | + | chr7-15475 | TAC1 | 1 |
| 7 | 97,197,207 | 97,199,306 | NM_013998 | + | chr7-15475 | TAC1 | 1 |
| 7 | 97,197,207 | 97,199,306 | NM_013997 | + | chr7-15475 | TAC1 | 1 |
| 7 | 97,197,207 | 97,199,306 | NM_013996 | + | chr7-15475 | TAC1 | 1 |
| 7 | 98,082,533 | 98,084,632 | NM_002523 | + | chr7-38902 | NPTX2 | 1 |
| 7 | 103,754,340 | 103,756,439 | NM_199000 | + | chr7-28012 | LHFPL3 | 1 |
| 7 | 120,754,326 | 120,756,425 | NM_057168 | + | chr7-8399 | WNT16 | 1 |
| 7 | 136,201,939 | 136,204,038 | NM_001006630 | + | chr7-33041 | CHRM2 | 1 |
| 7 | 136,201,939 | 136,204,038 | NM_001006627 | + | chr7-33041 | CHRM2 | 1 |
| 7 | 136,202,372 | 136,204,471 | NM_000739 | + | chr7-33041 | CHRM2 | 1 |
| 7 | 136,202,372 | 136,204,471 | NM_001006632 | + | chr7-33041 | CHRM2 | 1 |
| 7 | 136,202,372 | 136,204,471 | NM_001006631 | + | chr7-33041 | CHRM2 | 1 |
| 7 | 136,202,409 | 136,204,508 | NM_001006626 | + | chr7-33041 | CHRM2 | 1 |
| 7 | 136,202,524 | 136,204,623 | NM_001006629 | + | chr7-33041 | CHRM2 | 1 |
| 7 | 136,202,533 | 136,204,632 | NM_001006628 | + | chr7-33041 | CHRM2 | 1 |
| 7 | 150,735,255 | 150,737,354 | NR_034013 | + | chr7-35552 |  | 5 |
| 7 | 150,735,255 | 150,737,354 | NR_034012 | + | chr7-35552 | NA | NA |
| 7 | 153,213,352 | 153,215,451 | NM_001039350 | + | chr7-25866 | DPP6 | 1 |
| 7 | 154,941,585 | 154,943,684 | NM_001427 | + | chr7-16609 | EN2 | 1 |
| 7 | 154,941,585 | 154,943,684 | NM_001427 | + | chr7-12439 | EN2 | 1 |
| 7 | 19,151,470 | 19,153,569 | NM_152898 | − | chr7-40510 | FERD3L | 1 |
| 7 | 27,162,722 | 27,164,821 | NM_006896 | − | chr7-23529 | HOXA7 | 1 |
| 7 | 35,260,137 | 35,262,236 | NM_001077653 | − | chr7-7931 | TBX20 | 1 |
| 7 | 35,260,137 | 35,262,236 | NM_001166220 | − | chr7-7931 | TBX20 | 1 |
| 7 | 45,094,919 | 45,097,018 | NM_001146334 | − | chr7-39912 | NACAD | 1 |
| 7 | 71,440,045 | 71,442,144 | NM_001017440 | − | chr7-37359 | CALN1 | 1 |
| 7 | 86,812,645 | 86,814,744 | NR015381 | − | chr7-11427 | TP53TG1 | 3 |
| 7 | 92,301,068 | 92,303,167 | NM_001259 | − | chr7-36853 | CDK6 | 1 |
| 7 | 93,041,879 | 93,043,978 | NM_001742 | − | chr7-3549 | CALCR | 1 |
| 7 | 93,041,879 | 93,043,978 | NM_001164737 | − | chr7-3549 | CALCR | 1 |
| 7 | 126,679,565 | 126,681,664 | NM_001127323 | − | chr7-14832 | GRM8 | 1 |
| 7 | 127,458,139 | 127,460,238 | NM_022143 | − | chr7-30884 | LRRC4 | 1 |
| 7 | 133,794,329 | 133,796,428 | NM_001628 | − | chr7-5134 | AKR1B1 | 1 |
| 7 | 150,737,958 | 150,740,057 | NM_198285 | − | chr7-35552 | WDR86 | 1 |

TABLE 10-continued

A list of RefSeq transcripts whose promoters overlap one or more hypermethylated DMRs. The following information is listed for each transcript: (i) promoter genomic coordinates with respect to hg18 (−2000/+100 base pairs around transcript TSS), (ii) region id of the overlapping DMR, (iii) official gene symbol, and (iv) transcript type. The table contains 513 unique transcripts which correspond to 308 unique gene symbols.

| Chromosome | Start (promoter) | End (promoter) | Transcript ID | Strand | Region ID | Gene name | Transcript type |
|---|---|---|---|---|---|---|---|
| 7 | 155,297,629 | 155,299,728 | NM_000193 | − | chr7-10560 | SHH | 1 |
| 7 | 158,630,311 | 158,632,410 | NM_003382 | − | chr7-27744 | VIPR2 | 1 |
| 8 | 11,597,126 | 11,599,225 | NM_002052 | + | chr8-16712 | GATA4 | 1 |
| 8 | 13,466,723 | 13,468,822 | NM_001007090 | + | chr8-27248 | C8orf48 | 1 |
| 8 | 16,927,118 | 16,929,217 | NM_181723 | + | chr8-4176 | EFHA2 | 1 |
| 8 | 24,825,179 | 24,827,278 | NM_005382 | + | chr8-4443 | NEFM | 1 |
| 8 | 24,826,360 | 24,828,459 | NM_001105541 | + | chr8-4443 | NEFM | 1 |
| 8 | 50,985,150 | 50,987,249 | NM_018967 | + | chr8-8079 | SNTG1 | 1 |
| 8 | 55,531,048 | 55,533,147 | NM_022454 | + | chr8-16602 | SOX17 | 1 |
| 8 | 56,175,571 | 56,177,670 | NM_052898 | + | chr8-10864 | XKR4 | 1 |
| 8 | 56,175,571 | 56,177,670 | NM_052898 | + | chr8-6273 | XKR4 | 1 |
| 8 | 65,446,329 | 65,448,428 | NR_034102 | + | chr8-10122 | NA | NA |
| 8 | 65,446,329 | 65,448,428 | NR_034102 | + | chr8-5087 | NA | NA |
| 8 | 65,446,329 | 65,448,428 | NR_034102 | + | chr8-15516 | NA | NA |
| 8 | 65,450,438 | 65,452,537 | NR_034103 | + | chr8-2210 | | 3 |
| 8 | 65,452,260 | 65,454,359 | NR_029669 | + | chr8-3384 | MIR124-2 | 4 |
| 8 | 65,452,260 | 65,454,359 | NR_029669 | + | chr8-2210 | MIR124-2 | 4 |
| 8 | 67,505,272 | 67,507,371 | NM_144650 | + | chr8-12141 | ADHFE1 | 1 |
| 8 | 69,025,157 | 69,027,256 | NM_025170 | + | chr8-7773 | PREX2 | 1 |
| 8 | 69,025,157 | 69,027,256 | NM_024870 | + | chr8-7773 | PREX2 | 1 |
| 8 | 72,916,905 | 72,919,004 | NR_033651 | + | chr8-26787 | | 3 |
| 8 | 79,738,837 | 79,740,936 | NM_016010 | + | chr8-29409 | FAM164A | 1 |
| 8 | 79,738,837 | 79,740,936 | NM_016010 | + | chr8-14671 | FAM164A | 1 |
| 8 | 86,536,308 | 86,538,407 | NM_005181 | + | chr8-4283 | CA3 | 1 |
| 8 | 100,023,807 | 100,025,906 | NM_001142462 | + | chr8-15618 | OSR2 | 1 |
| 8 | 100,023,807 | 100,025,906 | NM_053001 | + | chr8-15618 | OSR2 | 1 |
| 8 | 121,204,533 | 121,206,632 | NM_021110 | + | chr8-20019 | COL14A1 | 1 |
| 8 | 23,619,957 | 23,622,056 | NM_001136271 | − | chr8-13399 | NKX2-6 | 1 |
| 8 | 24,869,949 | 24,872,048 | NM_006158 | − | chr8-3960 | NA | NA |
| 8 | 37,943,242 | 37,945,341 | NM_000025 | − | chr8-13897 | ADRB3 | 1 |
| 8 | 57,188,996 | 57,191,095 | NM_005372 | − | chr8-3477 | MOS | 1 |
| 8 | 57,521,048 | 57,523,147 | NM_006211 | − | chr8-5843 | PENK | 1 |
| 8 | 57,521,048 | 57,523,147 | NM_006211 | − | chr8-15117 | PENK | 1 |
| 8 | 57,521,737 | 57,523,836 | NM_001135690 | − | chr8-5843 | PENK | 1 |
| 8 | 57,521,737 | 57,523,836 | NM_001135690 | − | chr8-15117 | PENK | 1 |
| 8 | 61,356,409 | 61,358,508 | NM_004056 | − | chr8-10610 | CA8 | 1 |
| 8 | 72,919,186 | 72,921,285 | NM_005098 | − | chr8-26787 | MSC | 1 |
| 8 | 92,066,562 | 92,068,661 | NM_001190972 | − | chr8-27696 | | 1 |
| 8 | 92,066,562 | 92,068,661 | NM_001190972 | − | chr8-20122 | | 1 |
| 8 | 93,176,567 | 93,178,666 | NM_001198630 | − | chr8-21157 | RUNX1T1 | 1 |
| 8 | 93,176,567 | 93,178,666 | NM_001198632 | − | chr8-21157 | RUNX1T1 | 1 |
| 8 | 93,176,567 | 93,178,666 | NM_175635 | − | chr8-21157 | RUNX1T1 | 1 |
| 8 | 93,176,567 | 93,178,666 | NM_001198629 | − | chr8-21157 | RUNX1T1 | 1 |
| 8 | 93,176,959 | 93,179,058 | NM_001198634 | − | chr8-21157 | RUNX1T1 | 1 |
| 8 | 93,176,959 | 93,179,058 | NM_001198626 | − | chr8-21157 | RUNX1T1 | 1 |
| 8 | 93,176,959 | 93,179,058 | NM_001198631 | − | chr8-21157 | RUNX1T1 | 1 |
| 8 | 93,176,959 | 93,179,058 | NM_001198627 | − | chr8-21157 | RUNX1T1 | 1 |
| 8 | 93,176,959 | 93,179,058 | NM_001198679 | − | chr8-21157 | RUNX1T1 | 1 |
| 8 | 93,176,959 | 93,179,058 | NM_001198625 | − | chr8-21157 | RUNX1T1 | 1 |
| 8 | 93,180,993 | 93,183,092 | NM_001198628 | − | chr8-17019 | RUNX1T1 | 1 |
| 8 | 93,184,531 | 93,186,630 | NM_001198633 | − | chr8-17019 | RUNX1T1 | 1 |
| 8 | 93,184,531 | 93,186,630 | NM_175634 | − | chr8-17019 | RUNX1T1 | 1 |
| 8 | 97,242,097 | 97,244,196 | NM_001001557 | − | chr8-10467 | GDF6 | 1 |
| 8 | 105,548,354 | 105,550,453 | NM_001385 | − | chr8-19479 | DPYS | 1 |
| 8 | 109,164,990 | 109,167,089 | NM_178565 | − | chr8-27831 | RSPO2 | 1 |
| 8 | 110,773,097 | 110,775,196 | NM_001099744 | − | chr8-18053 | SYBU | 1 |
| 8 | 110,773,097 | 110,775,196 | NM_001099743 | − | chr8-18053 | SYBU | 1 |
| 8 | 111,056,036 | 111,058,135 | NM_014379 | − | chr8-4616 | KCNV1 | 1 |
| 8 | 120,720,188 | 120,722,287 | NM_001130863 | − | chr8-16413 | ENPP2 | 1 |
| 8 | 120,720,188 | 120,722,287 | NM_001040092 | − | chr8-16413 | ENPP2 | 1 |
| 8 | 120,720,188 | 120,722,287 | NM_006209 | − | chr8-16413 | ENPP2 | 1 |
| 8 | 132,121,918 | 132,124,017 | NM_001115 | − | chr8-3407 | ADCY8 | 1 |
| 8 | 139,995,319 | 139,997,418 | NM_152888 | − | chr8-8451 | COL22A1 | 1 |
| 8 | 140,784,382 | 140,786,481 | NM_016601 | − | chr8-19164 | KCNK9 | 1 |
| 8 | 142,446,448 | 142,448,547 | NM_005293 | − | chr8-21185 | GPR20 | 1 |
| 8 | 144,312,733 | 144,314,832 | NM_002347 | − | chr8-24646 | LY6H | 1 |
| 8 | 144,313,031 | 144,315,130 | NM_001135655 | − | chr8-24646 | LY6H | 1 |
| 8 | 145,089,999 | 145,092,098 | NM_201382 | − | chr8-29731 | PLEC | 1 |
| 8 | 145,090,794 | 145,092,893 | NM_201381 | − | chr8-29731 | PLEC | 1 |
| 8 | 145,091,336 | 145,093,435 | NR_030383 | − | chr8-29731 | MIR661 | 4 |

TABLE 10-continued

A list of RefSeq transcripts whose promoters overlap one or more hypermethylated DMRs. The following information is listed for each transcript: (i) promoter genomic coordinates with respect to hg18 (−2000/+100 base pairs around transcript TSS), (ii) region id of the overlapping DMR, (iii) official gene symbol, and (iv) transcript type. The table contains 513 unique transcripts which correspond to 308 unique gene symbols.

| Chromosome | Start (promoter) | End (promoter) | Transcript ID | Strand | Region ID | Gene name | Transcript type |
|---|---|---|---|---|---|---|---|
| 8 | 145,530,652 | 145,532,751 | NM_031309 | − | chr8-25100 | SCRT1 | 1 |
| 9 | 17,123,038 | 17,125,137 | NM_001114395 | + | chr9-8090 | CNTLN | 1 |
| 9 | 17,123,038 | 17,125,137 | NM_017738 | + | chr9-8090 | CNTLN | 1 |
| 9 | 22,434,840 | 22,436,939 | NM_022160 | + | chr9-24850 | DMRTA1 | 1 |
| 9 | 32,771,497 | 32,773,596 | NM_212558 | + | chr9-11022 | TMEM215 | 1 |
| 9 | 70,976,791 | 70,978,890 | NM_001170630 | + | chr9-33024 | TJP2 | 1 |
| 9 | 70,976,791 | 70,978,890 | NM_004817 | + | chr9-33024 | TJP2 | 1 |
| 9 | 70,976,791 | 70,978,890 | NM_201629 | + | chr9-33024 | TJP2 | 1 |
| 9 | 73,952,087 | 73,954,186 | NM_004293 | + | chr9-21502 | GDA | 1 |
| 9 | 73,952,087 | 73,954,186 | NM_001242506 | + | chr9-21502 | GDA | 1 |
| 9 | 73,952,087 | 73,954,186 | NM_001242505 | + | chr9-21502 | GDA | 1 |
| 9 | 78,822,391 | 78,824,490 | NM_001013735 | + | chr9-28705 | FOXB2 | 1 |
| 9 | 94,609,714 | 94,611,813 | NR_026868 | + | chr9-9221 | ANKRD19P | 10 |
| 9 | 97,263,712 | 97,265,811 | NR_038982 | + | chr9-12742 | NA | NA |
| 9 | 16,860,687 | 16,862,786 | NM_017637 | − | chr9-28476 | BNC2 | 1 |
| 9 | 36,248,397 | 36,250,496 | NM_005476 | − | chr9-31429 | GNE | 1 |
| 9 | 36,248,397 | 36,250,496 | NM_001190384 | − | chr9-31429 | GNE | 1 |
| 9 | 36,248,397 | 36,250,496 | NM_001190383 | − | chr9-31429 | GNE | 1 |
| 9 | 93,752,166 | 93,754,265 | NM_004560 | − | chr9-25007 | ROR2 | 1 |
| 9 | 95,148,418 | 95,150,517 | NM_001098808 | − | chr9-33335 | C9orf129 | 1 |
| 9 | 103,289,197 | 103,291,296 | NM_032342 | − | chr9-7772 | C9orf125 | 1 |
| 9 | 103,540,584 | 103,542,683 | NM_133445 | − | chr9-21296 | GRIN3A | 1 |
| 9 | 132,803,961 | 132,806,060 | NM_032843 | − | chr9-18934 | FIBCD1 | 1 |
| 9 | 132,804,177 | 132,806,276 | NM_001145106 | − | chr9-18934 | FIBCD1 | 1 |

Transcript types are as follows: 1 = protein coding; 2 = unprocessing pseudogene; 3 = processed transcript; 4 = miRNA; 5 = antisense; 6 = pseudogene; 7 = ambiguous open reading frame; 8 = linRNA; 9 = snoRNA; 10 = transcribed unprocessed pseudogene.

Figure 9:
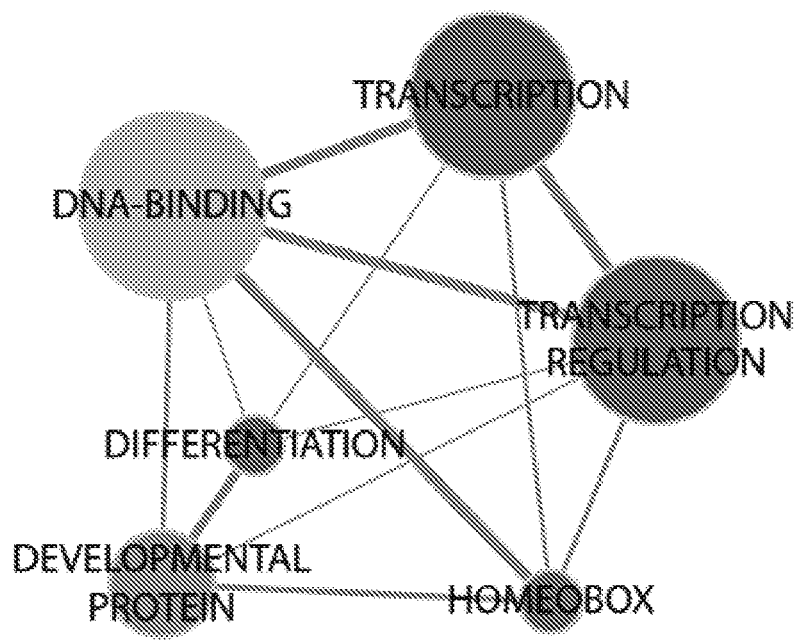
FIG. 9. Promoter hypermethylation affects actively expressed and functionally important genes. DAVID functional analysis of 308 genes with promoter hypermethylation against SP_PIR_KEYWORDS annotation identifies 12 significantly enriched (FDR<0.05) gene sets. Network representation with EnrichmentMap of enriched gene sets are provided in A-B, where nodes represent gene sets and edges represent overlap between gene sets. Node sizes are proportional to the number of genes and edge widths are proportional to the amount of overlap. Node colours encode various types of SP_PIR_KEYWORDS annotation—biological process (red), molecular function (salmon), post-translation modification (light green), domain (dark green), ligand (light cyan), and cellular component (dark cyan).
Figure 9:
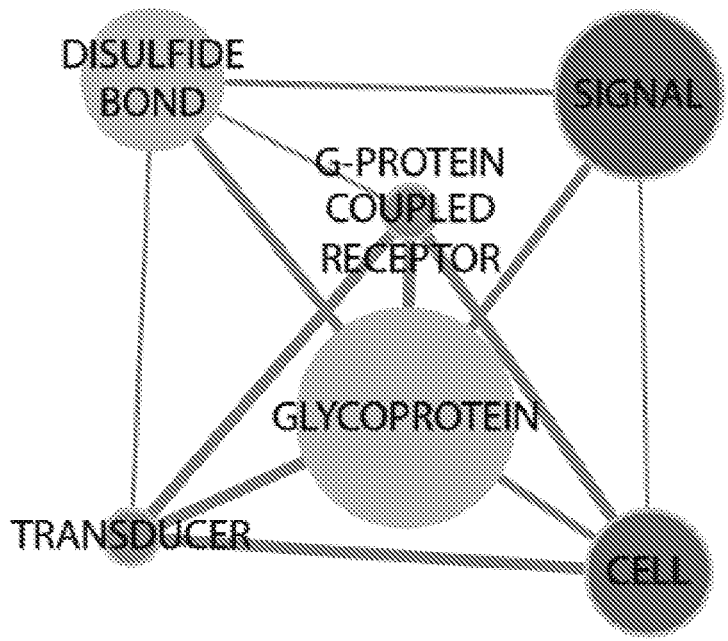

Using the DAVID functional annotation tool to annotate this set of genes, two largely non-overlapping groups of genes were identified (FIGS. 9A and 9B).

One group is annotated with keywords "DNA-BINDING", "TRANSCRIPTION", "TRANSCRIPTION REGULATION", "HOMEOBOX", "DEVELOPMENTAL PROTEIN", and "DIFFERENTIATIONS" and contains around 100 genes, mostly transcription factors, such as BARHL2, DLX6, OTX2, RUNX1T1 and TAC1. The second group is annotated with keywords "SIGNAL", "CELL MEMBRANE", "TRANSDUCER", "GLYCOPROTEIN", "G-PROTEIN COUPLED RECEPTOR" and contains genes involved in signaling pathways such as ADRB3, GHSR, NPY and ROBO3. These groups of genes are listed in Table 11.

To determine if promoter hypermethylation was potentially involved in gene silencing, TCGA expression data was assessed for the 308 genes affected by promoter hypermethylation as discussed previously. In doing so, it was shown that genes with promoter hypermethylation are enriched in down-regulated genes (71 out of 245 genes for which expression data is available are down-regulated; fold change (FC) of 1.73; p-value 1e-06) and are depleted in up-regulated genes (28 out of 245 genes are up-regulated; FC of 0.53; p-value 1e-05) (FIG. 1F).

The 308 hypermethylated genes were then overlapped with genes recurrently mutated in breast cancer in TCGA [TCGA (2012) Nature, 490:61-70] (FIG. 1G) to identify potential driver events. Of the 308 genes with promoter methylation, 51 were identified as being mutated (FC of 1.92; p-value 4.12e-06) and 12 (C9orf125, COL14A1, ENPP2, ERG2, PLD5, ROBO3, RUNX1T1, SEMA5A, TBX18, TSHZ3, ZBTB16, and ZNF208) were both mutated and down-regulated. Notably, of these gene subset which are both mutated and down-regulated, ROBO3 and SEMA5 are part of the axon guidance pathway recently implicated in tumor initiation and progression (Mehlen et al., (2011) Nat. Rev. Cancer 2011, 11:188-197; Neufeld and Kessler (2008) Nat. Rev. Cancer, 8:632-645). Interestingly, promoter hypermethylation affects, in total, seven members of the axon guidance pathway (CRMP1, GDNF, GFRA1, MYL9, ROBO1, ROBO3 and SEMA5A) with four members (GFRA1, MYL9, ROBO3, and SEMA5A) being down-regulated.

TABLE 11

DAVID functional analysis of genes with promoter hypermethylation

| Category | Term | Count | % | PValue | Genes | List Total | Pop Hits | Pop Total | Fold Enrichment | Bonferroni | Benjamini | FDR |
|---|---|---|---|---|---|---|---|---|---|---|---|---|
| SP_PIR_KEYWORDS | dna-binding | 86 | 29 | 9.35E-18 | BARHL2, BATF3, BHLHE23, DLX6, DMRTA1, DMRTA2, EBF1, EN2, EOMES, ERG, EVX2, FERD3L, FE2F2, FOXB1, FOXB2, FOXF1, GATA2, GATA4, GOM2, GSC2, GSX1, HIST1H2AX, HIST1H2BE, HIST1H2BN, HMX2, HOXA7, HOXB13, HOXD10, HOXD13, IRF4, LHX5, M5C, MYOD1, NEUROD1, NEUROG3, NKX2-1, NKX2-3, NKX2-6, OLIG2, OLIG3, OTX3, PAX1, POU4F3, PPARG, PROM16, PRRX1, PTF1A, RREB1, RUNXIT1, SALL2, SALL3, SATB2, SCRT1, SIM2, SLC2A4RG, SOX17, SOX21, TBX18, TBX20, TSHZ3, VAX1, VENTX, VSX1, WT1, ZBTB16, ZIC1, ZIK1, ZNF154, ZNF215, ZNF221, ZNF229, ZNF254, ZNF334, ZNF418, ZNF502, ZNF506, ZNF516, ZNF540, ZNF542, ZNF560, ZNF671, ZNF773, ZNF98, ZSCAN18, ZSCAN23 | 284 | 1628 | 14208 | 2.64 | 2.65E-15 | 2.65E-15 | 1.24E-14 |
| SP_PIR_KEYWORDS | developmental protein | 46 | 15 | 5.88E-13 | C140RF39, CHL1, CHRDL2, CSPG4, DAB1, DDX25, DLL1, DLX6, EBF1, EN2, EOMES, EVX2, EYA4, FEZF2, GCM2, GSX1, HMX2, HOXA7, HOXB13, HOXD10, HOXD13, ITGA5, MYOD1, NEUROD1, NEUROG3, NKX6-2, OLIG2, OTX2, PAX1, PRRX1, PTF1A, RIPPLY2, ROBO1, ROBO3, ROR2, SATB2, SEMA5A, SHH, SIM2, TSHZ3, VAX1, VENTX, VSX1, WNT16, WNT7A, ZIC1 | 284 | 671 | 14208 | 3.43 | 1.66E-10 | 8.32E-11 | 7.79E-10 |
| SP_PIR_KEYWORDS | Homeobox | 24 | 8 | 1.16E-11 | BARHL2, DLX6, EN2, EVX2, GSC2, GSX1, HMXZ, HOXA7, HOXB13, HOXO10, HOXD13, UHX5, NKX2-1, NKX2-3, NKX2-6, NKX6-2, OTX2, POU4F3, PRRX1, SATB2, TSHZ3, VAX1, VENTZ, VSK1 | 284 | 200 | 14208 | 6.00 | 3.29E-09 | 1.10E-09 | 1.54E-08 |
| SP_PIR_KEYWORDS | transcription regulation | 77 | 26 | 4.13E-11 | BARHL2, BATF3, BHLHE23, BNC2, DMRTA1, EBF1, EID1, EN2, EOMES, ERG, EYA4, FERDJL, FEZF2, FOXB2, FOXF1, GATA2, GATA4, GCM2, GSX1, HMX2, HOXA7, HOXB13, HOXD10, HOXD13, IRF4, KHDRBS2, LHXS, MSC, MYOD1, NEUROD1, NEUROG3, NKX2-1, NKX2-3, OLIG2, OLIG3, PAX1, PPARG, PRDM16, PTF1A, RREB1, RUNX1T1, SALL1, SALL2, SALL3, SATB2, SCRT1, SIM2, SLC2A4RG, SOX17, SOX21, TBX18, TBX20, TSHZ3, VAX1, VGLL2, VSX1, WT1, ZBTB16, ZIK1, ZNF154, ZNF215, ZNF221, ZNF229, ZNF254, ZNF334, ZNF418, ZNF502, ZNF506, ZNF516, ZNF540, ZNF542, ZNF560, ZNF671, ZNF773, ZNF98, ZSCAN18, ZSCAN23 | 284 | 1780 | 14208 | 2.16 | 1.17E-08 | 2.93E-09 | 5.48E-08 |
| SP_PIR_KEYWORDS | Transcription | 76 | 25 | 3.18E-10 | BARHL2, BATF3, BHLHE23, BNC2, DMRTA1, EBF1, EID1, EOMES, ERG, EYA4, FERD3L, FEZF2, FOXB2, FOXF1, GATA2, GATA4, GCM2, GSX1, HMX2, HOXA7, HOXB13, HOXD10, HOXD13, IRF4, KHDRBS2, LHXS, MSC, MYOD1, NEUROG3, NEUROG3, NKX2-1, NKX2-3, OLIG2, OLIG3, PAX1, PPARG, PRDM16, PTF1A, RREB1, RUNX1T1, SALL1, SALL3, SATB2, SCRT1, SIM2, SLC2A4RG, SOX17, TBX18, TBX20, TSHZ3, VAK1, VGLL2, VSX1, WT1, ZBTB16, ZIK1, ZNF154, ZNF215, ZNF221, ZNF229, ZNF254, ZNF334, ZNF418, ZNF502, ZNF506, ZNF516, ZNF540, ZNF542, ZNF560, ZNF671, ZNF773, ZNF98, ZSCAN18, ZSCAN23 | 284 | 1821 | 14208 | 2.09 | 9.01E-08 | 1.80E-08 | 4.22E-07 |
| SP_PIR_KEYWORDS | glycoprotein | 99 | 33 | 6.00E-10 | ACP5, ADCY3, ADRB3, AGTR1, AMIGO2, APCDD1, BONF, C11ORF87, CA4, CACNA1E, CALCR, CASR, CBLN1, CBLN4, CD200, CD70, CDH13, CDH6, CDH8, CHL1, CHRDL2, CHRM2, CNTNAP5, COL11A1, COL14A1, COL22A1, CSPG4, DLL1, OPP6, EMILIN2, ENPP2, EPHA10, FAM155A, FBN1, GABRA4, GALNTL6, GALRI, GDF6, GDNF, GFRA1, GHSR, GPR139, GPR158, GPR20, GRIK3, GRIN3A, GRM3, GRM8, HAPLN3, HS3ST2, HTR1A, HTR1B, IGSF9B, ITGA8, JAM3, KCNC2, KCNK9, LRRC4, LV6H, MLNR, NEFM, NELL1, NETO1, NLGN1, NPR1, NFTX2, NTM, NXPH1, | 284 | 2739 | 14208 | 1.81 | 1.70E-07 | 2.83E-08 | 7.95E-07 |

TABLE 11-continued

DAVID functional analysis of genes with promoter hypermethylation

| Category | Term | Count | % | PValue | Genes | List Total | Pop Hits | Pop Total | Fold Enrichment | Bonferroni | Benjamini | FDR |
|---|---|---|---|---|---|---|---|---|---|---|---|---|
| SP_PIR_KEY WORDS | signal | 75 | 25 | 3.57E-07 | OPCML, OPRL1, PCDH17, PCCH8, PLD5, PROKR2, PTPRN, ROBO1, ROBO3, ROR2, RSPO2, RYR2, S1PR5, SEMA5A, SHH, SLC18A3, SLC24A4, SLC6A3, SLC7A14, SORCS3, ST8SIA5, SYNPR, TMEFF2, TMEM132C, TMEM132D, TRHDE, UGT3A1, VIPR2, WNT16, WNT7A ACP5, AMIGO2, APCDD1, BDNF, C11ORF87, C6ORF174, CA4, CALCR, CASR, CBLN1, CBLN4, CD200, CDH13, CDH6, CDH8, CHL1, CHRDK2, CNTNAP5, COL11A1, COL14A1, CSPG4, DLL1, EMILIN2, ENPP2, EPHA10, FAM150B, FBN1, GABRA4, GDF6, GDNF, GFRA1, GPR158, GRIK3, GRIN3A, GRM3, GRM8, HAPLN3, IG5F9B, ITGA8, JAM3, LRRC4, LY6H, NELL1, NETO1, NLGN1, NPR1, NPTX2, NPY, NTM, NXFH1, OPCML, PCDH17, PCDH8, PENK, PTPRN, RIC3, ROBO1, ROBO3, ROR2, RSPOZ, SEMA54, SHH, SLC24A4, SDRCS3, SST, TAC1, TMEFF2, TMEM132C, TMEM132D, UGT3A1, VIPR2, VSTM2B, WNT16, WNT7A | 284 | 2101 | 14208 | 1.79 | 1.01E-04 | 1.44E-05 | 4.73E-04 |
| SP_PIR_KEY WORDS | cell membrane | 54 | 18 | 9.43E-07 | ADRB3, AGTR1, AMIGO2, ANK51B, APC2, CA4, CALCR, CALN1, CA5R, CD200, CDH13, CDH6, CDH8, CHL1, CHRM2, CSPG4, DGKZ, EPHA10, GABRA4, GAD2, GALR1, GFRA1, GH5R, GID2, GPR139, GPR158, GPR20, GRIK3, GRIN3A, GRM3, GRM8, HTR1A, HTR1B, IG5F9B, JAM3, JPH3, KCNIP4, KCNV1, LRRC4, LY8H, MLNR, NETO1, NLGN1, NTM, OPCML, OPRL1, PCDH17, PCDH8, PROKR2, S1PR5, SHH, T3P2, UNC13A, VIPR2 | 284 | 1344 | 14208 | 2.01 | 2.67E-04 | 3.33E-05 | 1.25E-03 |
| SP_PIR_KEY WORDS | disulfide bond | 61 | 20 | 1.49E-06 | ACP5, ADRB3, AGTR1, AMIGO2, BDNF, CA4, CACNA1E, CBLN1, CBLN4, CD200, CD70, CHL1, CHRM2, CNTNAP5, CDL14A1, CSPG4, DLL1, DPP6, EMILN2, ENPP2, FBN1, GABRA4, GALNTL5, GALR1, GDF6, GDNF, GFRA1, GHSR, HAPLN1, H53ST2, HTR1A, HTR1B, IG5F9B, ITGA8, JAM3, LRRC4, LY6H, MLNR, NELL1, NETO1, NLGN1, NPR1, NPTX2, NTM, OPCML, OPRL1, PENK, PROKR2, ROBO1, ROBO3, ROR2, RSPO2, SEMA54, SLC6A3, SST, ST51A3, ST85IA3, TMEFF2, TRHDE, VIPR2, VSTM2B | 284 | 1628 | 14208 | 1.87 | 4.22E-04 | 4.69E-05 | 1.97E-03 |
| SP_PIR_KEY WORDS | g-protein coupled receptor | 19 | 6 | 7.21E-06 | ADRB3, AGTR1, CALCR, CASR, CHRM2, GALR1, GHSR, GPR139, GPR158, GPR20, GRM3, GRM8, HTR1A, HTR1B, MLNR, OPRL1, PROKR2, S1PR5, VIPR2 | 284 | 268 | 14208 | 3.55 | 2.04E-03 | 2.04E-04 | 9.55E-03 |
| SP_PIR_KEY WORDS | transducer | 20 | 7 | 1.79E-05 | ADRB3, AGTR1, CALCR, CASR, CHRM2, CSPG4, GALR1, GHSR, GPR139, GPR158, GPR20, GRM3, GRM8, HTR1A, HTR1B, MLNR, OPRL1, PROKR2, S1PR5, VIPR2 | 284 | 314 | 14208 | 3.19 | 5.05E-03 | 4.60E-04 | 2.37E-02 |
| SP_PIR_KEY WORDS | differentiation | 22 | 7 | 2.71E-05 | CHL1, CHRDL2, CSPG4, DAB1, DOX25, DLL1, DMRTA1, EID1, EDMES, FEZF2, HMX2, ITGAB, MYDDI, NEURDD1, NEURDG3, PRDM16, PTF14, ROBO1, ROBO3, SEMA5A, SIM2, ZIC3 | 284 | 362 | 14208 | 2.88 | 7.54E-03 | 6.39E-04 | 3.59E-02 |

1.2.5 Differentially Methylated Regions Specific to TNBCs

To determine if any of the 822 DMRs were also found in ER−ve or ER+ve breast cancer, the TCGA breast cancer methylation cohort, which comprises HM450K data for 354 ER+ve and 105 ER−ve breast tumors (73 of which are TNBCs) and 83 normal breast samples, was interrogated. Of the 822 hypermethylated DMRs identified using MBDCap-Seq, it was determined that 770 are interrogated by a total of 4,987 HM450K probes. It was also determined that whilst the majority of these probes are not methylated in breast normal tissue, they were hypermethylated to various degrees in both ER+ve and ER−ve breast cancers (FIG. 2A). Both ER+ve and ER−ve subtypes were also found to contain samples with minimal methylation across all probes, as well as those that displayed extensive methylation more representative of a CpG island methylator phenotype (CIMP) (Hughes et al., (2013) *Cancer Research*).

Out of 4,987 HM450K probes, it was determined that 5% (282/4,987) were significantly hypermethylated in TNBCs (t-test adjusted p-value less than 0.05) compared to the ER+ve tumors and the rest of the ER−ve tumors. From the 282 TNBC-specific probes, 36 TNBC-specific regions (harbouring at least 3 or more 450K TNBC-specific probes) were identified, that primarily overlap promoters and/or gene bodies (Table 2 and FIG. 10). These regions are enriched in genes encoding zinc fingers and transcription factors and intergenic regions that are commonly marked by polycomb in HMECs. An example of two such TNBC specific regions, are located in the promoters of genes encoding zinc finger proteins ZNF154 and ZNF671 on chromosome 9 (FIG. 2B). Both promoters have low methylation levels in normal breast and increased levels of methylation in TNBC samples as compared to ER+ve cancer. It was also found that the distribution of expression values mirrors the methylation status, with normal samples showing the highest levels of expression and TNBC tumors showing the lowest levels of expression (FIG. 2C), suggesting silencing by methylation of both ZNF154 and ZNF671 in TNBC tumors.

Example 2: Prognostic Markers of Patient Outcome

2.1 Methods

To identify DMRs that potentially stratify TNBCs, unsupervised cluster analysis was performed on methylation data for the 4,987 HM450K probes. A survival analysis was then performed to determine to what extent regional methylation stratifies TNBCs into good and bad prognosis groups.

2.1.1. Unsupervised Clustering

The TCGA TNBC (n=73) tumor samples were clustered based on methylation beta-values of 4,987 HM450K probes overlapping the 822 hypermethylated regions. A consensus clustering algorithm (Monti et. al., Machine Learning 2003) i.e., as implemented in Bioconductor Consensus Cluster Plus package to the 4,987×73 methylation matrix with parameters max K=4, reps=1000, pItem=0.8, pFeature=0.8, clusterAlg="km", distance="euclidean", was then applied. SVD decomposition was used to reduce the dimension of the methylation matrix to $R^{10}$ prior to clustering. A three-cluster configuration was chosen for downstream survival analysis.

2.1.2 Survival Analysis

Survival analysis was carried out using Cox proportional hazards model as implemented in R survival package against overall survival data. The BRCA TNBC cohort consists of 73 patients with HM450K methylation data and 12 events. Survival analysis of cluster data was carried out with cluster membership as an explanatory variable. Survival analysis of individual probes was carried out with probe methylation status as explanatory variable (univariate analysis) and age, stage and probe methylation status (multivariate analysis). Methylation status was represented by a binary variable, high (higher that the median beta-value for the probe) and low (smaller or equal to the median beta-value for the probe). Stage was derived from AJCC stage in the clinical annotation of samples. Due to moderate size the cohort we reduced the number of values of the stage variable to two by collapsing stages I, IA, IB, II, IIA, and IIB into one state and stages III, IIIA, IIIB, IIIC, and IV into one state.

2.2 Results

2.2.1 Stratification of TNBCs

Figure 3:
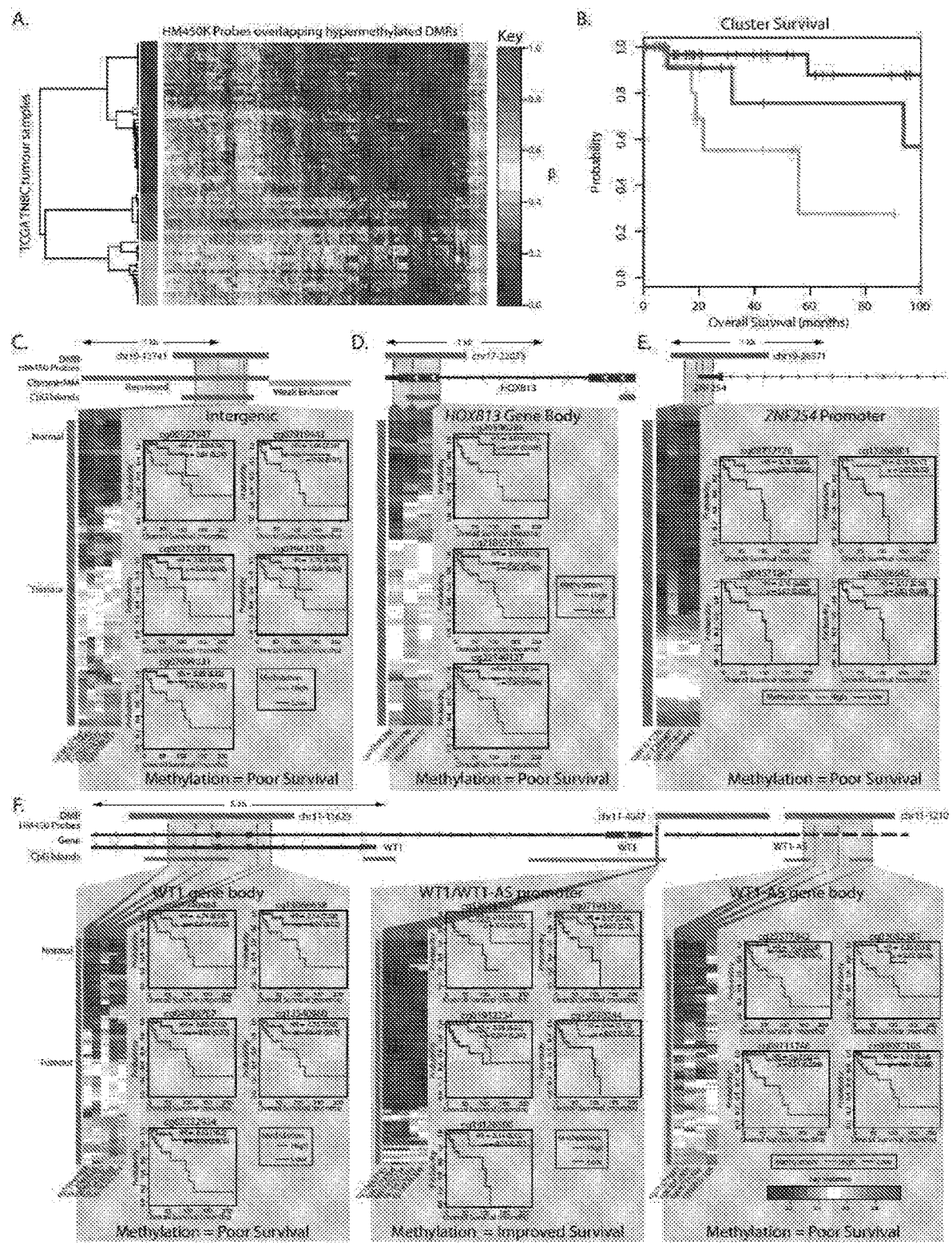
FIG. 3. Methylation profile stratifies TNBC tumours into survival subgroups. (A) Unsupervised clustering with 4,987 HM450K probes overlapping hypermethylated DMRs identified in the discovery cohort separates TCGA TNBC tumours into three main clusters. The heatmap shows methylation profile of TCGA TNBC tumours and cluster dendrogram. The three clusters are color-coded in red, orange, and blue. (B) A Kaplan-Meier plot showing survival curves for the patients in the three clusters from (A). Additionally, individual regions of hypermethylation in the discovery cohort overlap with survival associated probes in the TCGA cohort; including (C) intergenic loci, (D) intragenic loci (e.g. the HOXB13 gene body) and (E) promoter associate loci (e.g. ZNF254 promoter). (F) Association with survival for three adjacent regions—chr11-11623, chr11-4047, and chr11-1210—spanning the WT1/WT1-AS locus is shown. These three regions are hypermethylated in the discovery cohort and overlap several probes showing statistically significant association with overall survival in both univariate and multivariate analyses. For each region the methylation profile of TCGA TNBC tumour and adjacent normal samples across overlapping survival probes is shown as a heatmap. The Kaplan-Meyer plots for each of the overlapping survival probes is shown as well with corresponding hazard ratios and p-values; values in parentheses correspond to multivariate analysis.

The unsupervised clustering analysis identified three distinct groups of TNBC tumors from the TCGA data sets (FIG. 3A).

Survival analysis revealed that the largely hypomethylated cluster (blue cluster) was associated with better prognosis as compared to the other two more highly methylated clusters (orange and red clusters) (FIG. 3B). In particular, the medium methylated cluster (orange cluster) comprises samples with the worst prognosis (hazard ratio of 8.64 and p-value of 0.005) as compared to the good prognosis cluster (blue cluster).

2.2.2 TNBC Methylation Prognostic Signature(s)

Survival analysis of the 4,987 HM450K probes overlapping 822 hyper-methylated DMRs identified 190 probes with methylation status statistically significantly (p-value<0.05 in both univariate and multivariate analyses Cox Proportional Hazard models) associated with overall survival in TCGA TNBC samples. Furthermore, regional aggregation of survival probes identified 17 hyper-methylated DMRs overlapping three or more survival probes i.e., at least three concordantly located survival probes. In particular, fourteen DMRs were associated with poor prognosis, these regions overlapped probes for which high methylation corresponded to lower probability of survival, and three regions were associated with good prognosis (Table 3 and FIG. 11). Each of the individual Kaplan Meier plots showed excellent survival separation, highlighting the potential value of probes overlapping the 17 hyper-methylated DMRs as prognostic biomarkers for TNBC (FIGS. 3C-E and FIG. 11). Critically, our classifiers paralleled the biologically relevant time-dependent pattern of patient outcome, whereby TNBC patients are most vulnerable to disease associated death within the first 5 years following diagnosis, further highlighting their potential use in prognostic applications for TNBC.

The genomic location of the 17 hyper-methylated DMRs vary, with four regions located in a promoter (SLC6A3, C6orf174, WT1-AS and ZNF254), seven in the gene body only (DMRTA2, LHX8, WT1, WT1-AS, HOXB13, ECEL1, SOX2-OT) and five in intergenic regions (Table 3).

Figure 12:
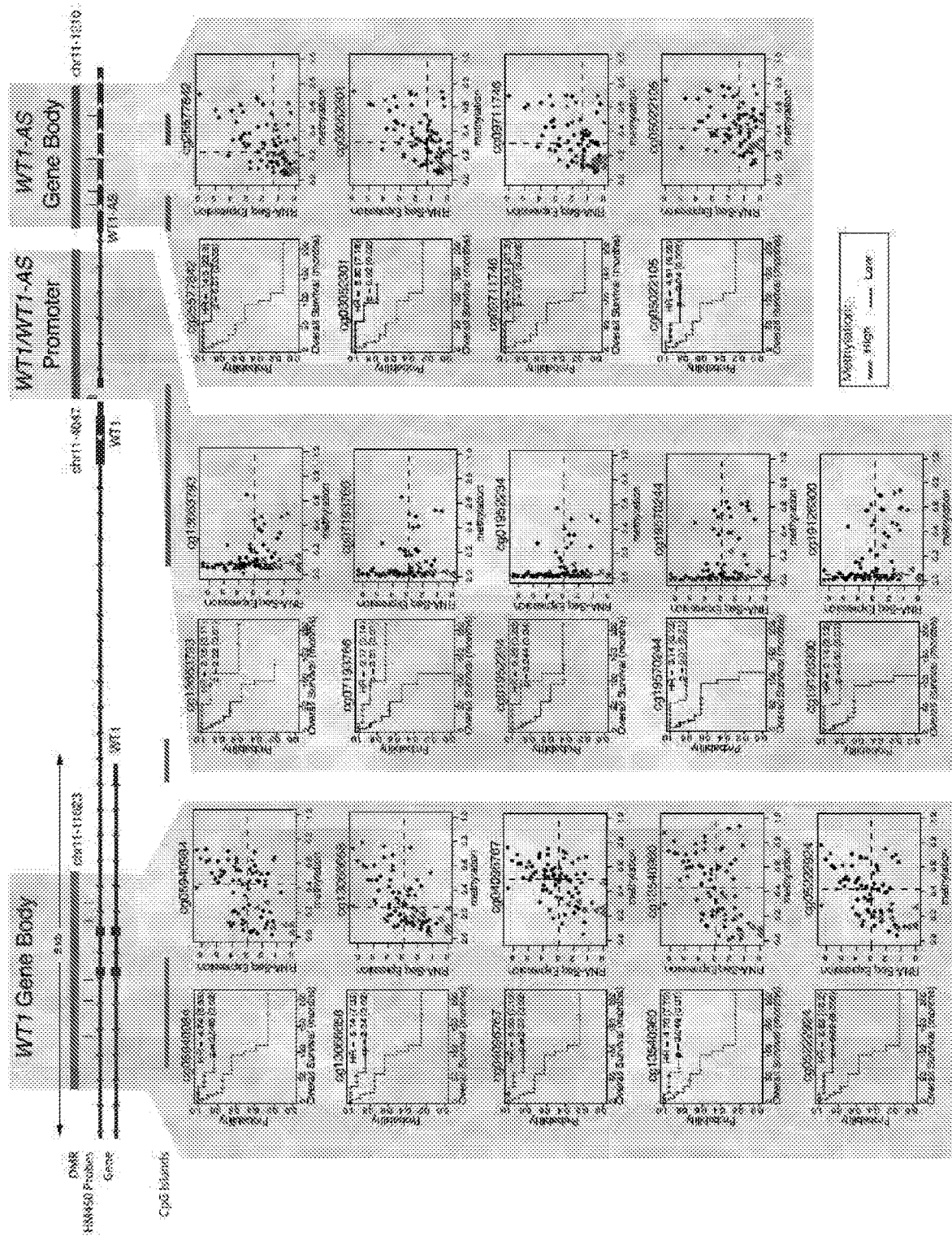
FIG. 12. This figure illustrates methylation versus expression for survival probes spanning WT1/WT1-AS locus. Scatter plots showing relationship between methylation and expression for survival probes in WT1 locus across TCGA TNBC normal (n=7; green triangles) and tumour (n=70; black circles) samples for which both RNA-Seq expression and HM450K methylation data is available. For each of the three survival regions in WT1/WT1-AS locus, the following is also provided: (i) genomic location of the region, and (ii) for each survival probe a Kaplan-Meier plot capturing survival curves for TNBC patients stratified based on median beta methylation value of the probe; hazard values and p-values are shown for both univariate and multivariate analyses (multivariate values are given in parentheses).

A striking example of regional hyper-methylation across consecutive CpG probes that provides statistical significance as a prognostic marker of survival are the DMRs spanning the bidirectional promoter and gene bodies of WT1 gene and its antisense counter-part, WT1-AS (FIG. 3F). Wilms tumour protein (WT1) is a zinc finger transcription factor over-expressed in several tumour types including breast (reviewed in Yang et al., (2007) *Leukemia*, 21:868-876). In the present study, an association was observed between a high level of methylation in chr11-11623 and chr11-1210 i.e., regions spanning the gene bodies of WT1 and WT1-AS respectively, and poor survival in TCGA TNBC cohort (FIG. 3F). Moreover, increased levels of methylation in these regions was also found to be associated with increased expression of WT1 (chr11-11623) and WT1-AS (chr11-1210) in TNBC patients (FIG. 12). Conversely, TNBC patients with high methylation in chr11-4047 i.e., a region spanning bi-directional promoter of WT1 and WT1-AS, were found to survive longer than TNBC patients with low methylation in this region.

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features. It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive. Functionally-equivalent products, compositions and methods are clearly within the scope of the disclosure, as described herein.

Example 3: TNBC-Specific Methylation 3.1 Methods

ROC curve analyses were performed using methylation data obtained for the 282 TNBC-specific probes (identified in Example 1) in the TCGA HM450K cohort to determine the accuracy with which those probes can be used to classify tumour samples into TNBC and non-TNBC.

The TCGA HM450K cohort was randomly split into training set (TNBC n=37; non-TNBC n=193) and testing set (TNBC n=36; non-TNBC n=193). The model was trained on training set and prediction accuracy assessed on testing set.

3.2 Results

Figure 13:
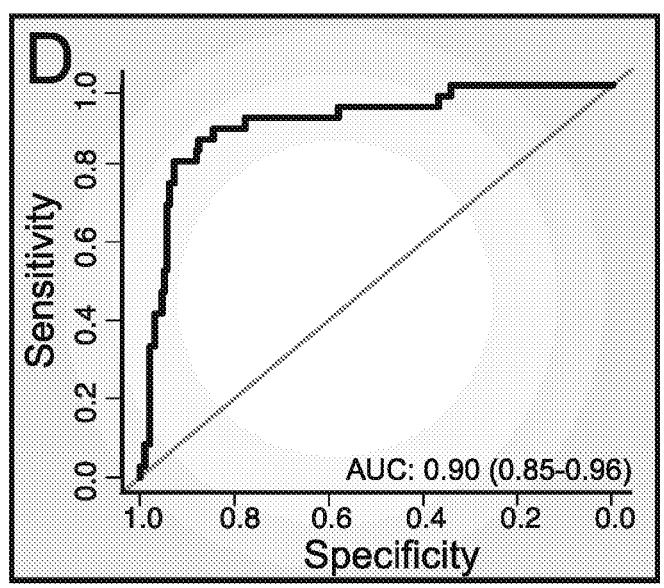
FIG. 13. This figure provides a ROC curve of the Diagnostic Methylation Signature based on methylation values for the 282 TNBC-specific probes FIG. 14. This figure shows average methylation values for the 282 TNBC-specific probes in TCGA cohort normal tissues, TCGA cohort non-TNBC tissues, TCGA cohort TNBC tissue and NBFC cohort TNBC tissues.

ROC curve analysis showed that the diagnostic methylation signature for the 282 TNBC-specific probes can classify TCGA HM450K tumour samples into TNBC and non-TNBC with high accuracy i.e., sensitivity of 0.72, specificity of 0.94 and AUC of 0.90 (FIG. 13).

Example 4: Validation of the TNBC Diagnostic Methylation Signature on an Independent Cohort of Clinical Samples 4.1 Methods Methylation signatures of an independent cohort of TNBC clinical samples obtained from The Garvan Institute, The University of Queensland (UQ) and The University of Newcastle (The NBCF cohort) were determined using HM450K arrays and methodologies described in Example 1. The NBCF cohort comprised 47 patient samples which passed quality control (QC); 24 events and 23 non-events.

4.2 Results

Figure 14:
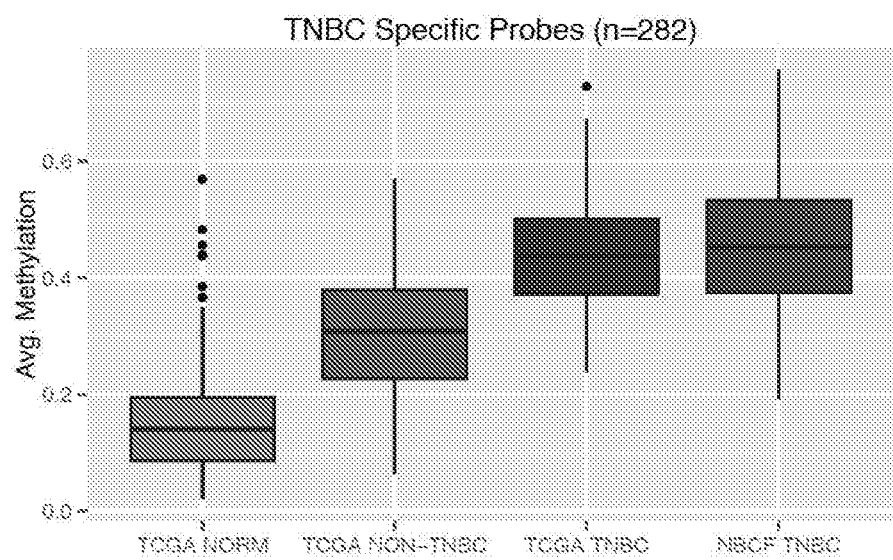
Figure 15:
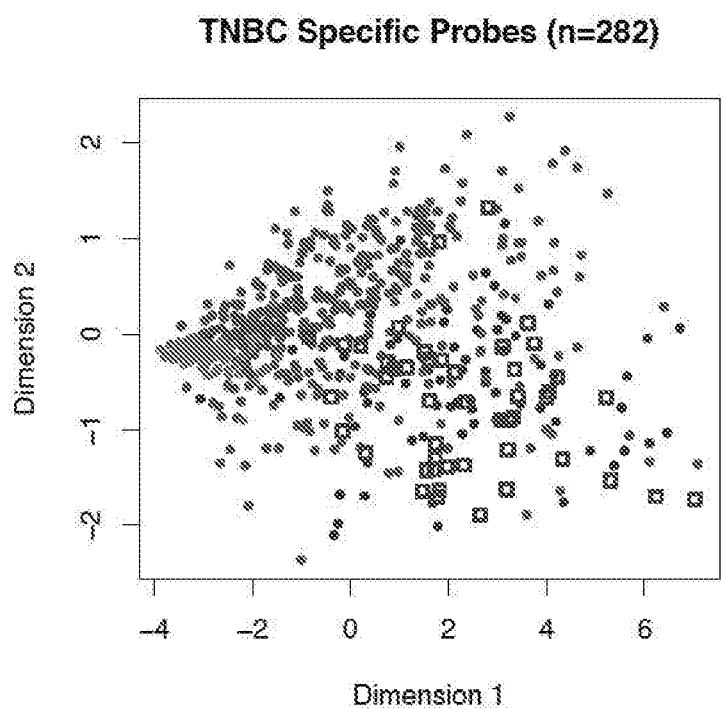
FIG. 15. This figure provides a diagnostic methylation signature for the 282 TNBC-specific probes.

Based on the HM450K methylation data obtained for the NBCF cohort, the diagnostic methylation signature of the 282 TNBC-specific probes trained on TCGA data was able to classify 93% (44/47) samples from the NBCF cohort as TNBC (FIGS. 14 and 15).

Example 5: Enumerating Diagnostic Signatures 5.1 Methods

Based on the 282 TNBC-specific probes identified in Example 1 as having higher average methylation in TNBC tumours relative to non-TNBC tumours, the inventors then sought to identify small subsets of probes that could be used in combination with Machine Learning Techniques to achieve accurate separation between TNBC and non-TNBC tumours.

5.1.1 Modelling Approach

A Partial Least Squares (PLS) family of models was selected for classification and caret R package (https://cran.r-project.org/web/packages/caret/index.html; Max Kuhn and Kjell Johnson, Adaptive Predictive Modeling, Springer 2013) used to train and evaluate the PLS models.

Model selection and parameter estimation was performed on the train dataset and final model evaluation was performed on the test dataset. The train dataset included all TCGA TNBC tumour samples (n=73) and half of TCGA non-TNBC tumour samples (n=193; 117 ER+ve and 16 non-TNBC ER−ve samples). The test dataset included all NBCF TNBC tumour samples (n=47) and the other half of TCGA non-TNBC tumour samples (n=193; 117 ER+ve and 16 non-TNBC ER−ve samples). In some plots information from TCGA normal samples (n=83) and whole blood samples (n=11; GSE48472) was also included.

5.1.2 Signature Enumeration Strategy

Figure 16:
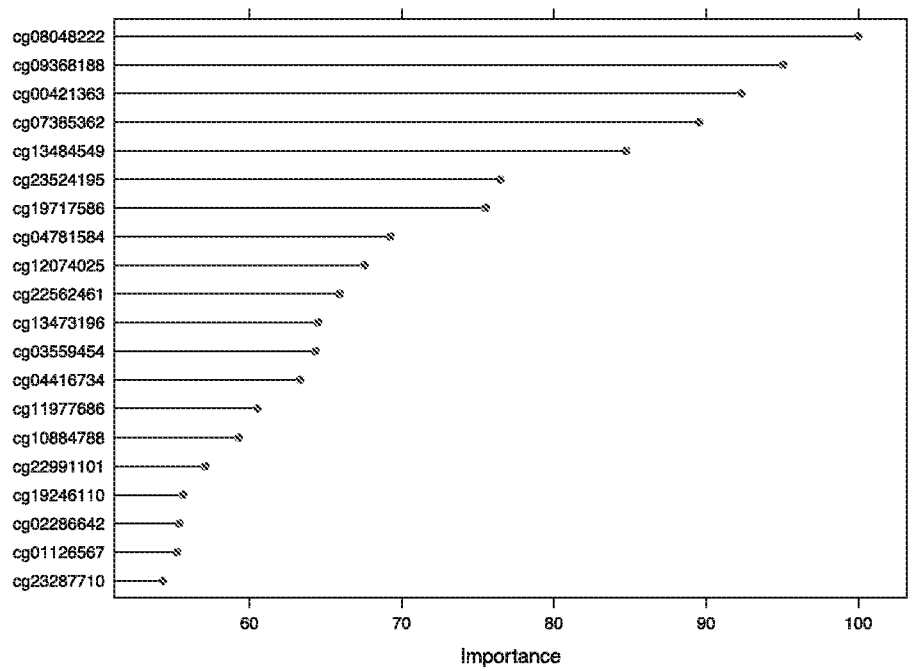
FIG. 16. This figure provides PLS estimates of variable Importance for representative probes in the full subset of 256 TNBC-specific probes.

A simple greedy strategy was devised to enumerate a large number of probe combinations (two to four probes per panel) resulting in PLS models with good performance on the train dataset. We first trained a PLS model on full subset of 256 probes (26 of the 282 probes were removed from the analyses due to the presence of missing values in some of the samples) and ranked the probes using PLS in-built variable importance estimates (function caret::varImp) (FIG. 16).

Two-probe signatures were formed by training PLS models on all three possible combinations of two probes out of three most important probes. The two-probe signatures were then extended to three-probe signatures by adding one probe at a time and keeping solutions that resulted in statistically significant improvement of AUC on train dataset (function pROC::roc.test). To reduce the amount of computation, only the twenty most important probes were considered during the extension step. Using this approach, four-probe signatures were also created by extending three-probe signatures in a similar manner. This procedure resulted in 56 possible signatures as shown in FIG. 17.

5.2 Results

Figure 17:
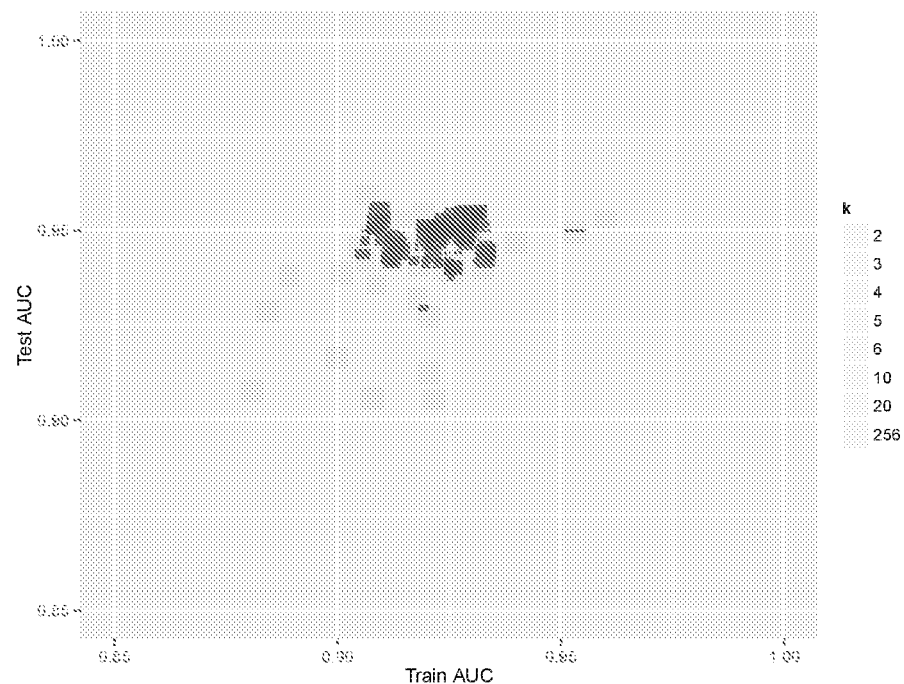
FIG. 17. This figure provides a performance evaluation for the fifty-six signatures with each data point corresponding to a unique signature. Each data point is represented with respect to its corresponding model AUC on train (Train AUC) and test (Test AUC) datasets. The signatures are color-coded by the number of variables (i.e., probes) in the model. The plot also shows the performance of PLS model trained on the whole dataset as well as on 5, 6, 10, and 20 most important probes.

Based on the data presented in FIG. 17, it is apparent that some three-probe and four-probe signatures performed as well as full PLS model on test dataset.

A summary of the 56 possible signatures is provided in Table 12.

TABLE 12

Summary of different probe subsets evaluated

| Subset ID | Probes in subsets | AUC | No. of Probes | FIG. |
|---|---|---|---|---|
| 1 | cg08048222 + cg09368188 | 0.938 | 2 | 18 |
| 2 | cg00421363 + cg09368188 | 0.929 | 2 | 19 |

TABLE 12-continued

Summary of different probe subsets evaluated

| Subset ID | Probes in subsets | AUC | No. of Probes | FIG. |
|---|---|---|---|---|
| 3 | cg00421363 + cg08048222 | 0.908 | 2 | 20 |
| 4 | cg04781584 + cg08048222 + cg09368188 | 0.959 | 3 | 21 |
| 5 | cg03559454 + cg08048222 + cg09368188 | 0.955 | 3 | 22 |
| 6 | cg08048222 + cg09368188 + cg23524195 | 0.952 | 3 | 23 |
| 7 | cg08048222 + cg09368188 + cg10884788 | 0.952 | 3 | 24 |
| 8 | cg08048222 + cg09368188 + cg13473196 | 0.951 | 3 | 25 |
| 9 | cg00421363 + cg08048222 + cg09368188 | 0.949 | 3 | 26 |
| 10 | cg00421363 + cg09368188 + cg09777776 | 0.949 | 3 | 27 |
| 11 | cg01126567 + cg08048222 + cg09368188 | 0.948 | 3 | 28 |
| 12 | cg00421363 + cg09368188 + cg23524195 | 0.948 | 3 | 29 |
| 13 | cg00421363 + cg09368188 + cg10884788 | 0.947 | 3 | 30 |
| 14 | cg00421363 + cg02286642 + cg09368188 | 0.945 | 3 | 31 |
| 15 | cg07385362 + cg08048222 + cg09368188 | 0.945 | 3 | 32 |
| 16 | cg08048222 + cg09368188 + cg22562461 | 0.944 | 3 | 33 |
| 17 | cg01926238 + cg08048222 + cg09368188 | 0.943 | 3 | 34 |
| 18 | cg05650260 + cg08048222 + cg09368188 | 0.943 | 3 | 35 |
| 19 | cg00421363 + cg04416734 + cg09368188 | 0.942 | 3 | 36 |
| 20 | cg00421363 + cg05650260 + cg09368188 | 0.942 | 3 | 37 |
| 21 | cg00421363 + cg01126567 + cg09368188 | 0.940 | 3 | 38 |
| 22 | cg04416734 + cg08048222 + cg09368188 | 0.940 | 3 | 39 |
| 23 | cg00421363 + cg07385362 + cg09368188 | 0.939 | 3 | 40 |
| 24 | cg00421363 + cg01926238 + cg09368188 | 0.936 | 3 | 41 |
| 25 | cg00421363 + cg08048222 + cg23524195 | 0.917 | 3 | 42 |
| 26 | cg00421363 + cg04416734 + cg08048222 | 0.906 | 3 | 43 |
| 27 | cg01926238 + cg03559454 + cg08048222 + cg09368188 | 0.954 | 4 | 44 |
| 28 | cg03559454 + cg05650260 + cg08048222 + cg09368188 | 0.954 | 4 | 45 |
| 29 | cg04416734 + cg04781584 + cg08048222 + cg09368188 | 0.953 | 4 | 46 |
| 30 | cg04416734 + cg08048222 + cg09368188 + cg23524195 | 0.953 | 4 | 47 |
| 31 | cg00421363 + cg05650260 + cg09368188 + cg23524195 | 0.951 | 4 | 48 |
| 32 | cg00421363 + cg09368188 + cg09777776 + cg23524195 | 0.951 | 4 | 49 |
| 33 | cg00421363 + cg05650260 + cg09368188 + cg10884788 | 0.950 | 4 | 50 |
| 34 | cg05650260 + cg08048222 + cg09368188 + cg13473196 | 0.950 | 4 | 51 |
| 35 | cg00421363 + cg02286642 + cg09368188 + cg23524195 | 0.949 | 4 | 52 |
| 36 | cg01926238 + cg08048222 + cg09368188 + cg13473196 | 0.949 | 4 | 53 |
| 37 | cg00421363 + cg04416734 + cg08048222 + cg09368188 | 0.949 | 4 | 54 |
| 38 | cg00421363 + cg07385362 + cg08048222 + cg09368188 | 0.949 | 4 | 55 |
| 39 | cg00421363 + cg09368188 + cg09777776 + cg10884788 | 0.949 | 4 | 56 |
| 40 | cg00421363 + cg05650260 + cg08048222 + cg09368188 | 0.948 | 4 | 57 |
| 41 | cg00421363 + cg08048222 + cg09368188 + cg22562461 | 0.948 | 4 | 58 |
| 42 | cg08048222 + cg09368188 + cg13473196 + cg22562461 | 0.948 | 4 | 59 |
| 43 | cg04416734 + cg08048222 + cg09368188 + cg13473196 | 0.948 | 4 | 60 |
| 44 | cg01126567 + cg05650260 + cg08048222 + cg09368188 | 0.947 | 4 | 61 |
| 45 | cg00421363 + cg02286642 + cg09368188 + cg10884788 | 0.947 | 4 | 62 |
| 46 | cg00421363 + cg01926238 + cg09368188 + cg23524195 | 0.945 | 4 | 63 |
| 47 | cg00421363 + cg01126567 + cg05650260 + cg09368188 | 0.944 | 4 | 64 |
| 48 | cg00421363 + cg01126567 + cg09368188 + cg09777776 | 0.943 | 4 | 65 |
| 49 | cg00421363 + cg05650260 + cg09368188 + cg13473196 | 0.941 | 4 | 66 |
| 50 | cg00421363 + cg01126567 + cg02286642 + cg09368188 | 0.940 | 4 | 67 |
| 51 | cg00421363 + cg04416734 + cg05650260 + cg09368188 | 0.939 | 4 | 68 |
| 52 | cg04416734 + cg07385362 + cg08048222 + cg09368188 | 0.939 | 4 | 69 |
| 53 | cg00421363 + cg01926238 + cg09368188 + cg13473196 | 0.932 | 4 | 70 |
| 54 | cg00421363 + cg01926238 + cg08048222 + cg23524195 | 0.927 | 4 | 71 |
| 55 | cg00421363 + cg04416734 + cg08048222 + cg23524195 | 0.912 | 4 | 72 |
| 56 | cg00421363 + cg04416734 + cg08048222 + cg20095233 | 0.905 | 4 | 73 |
| 57 | s5 | 0.950 | 4 | 74 |
| 58 | s6 | 0.953 | 6 | 75 |
| 59 | s10 | 0.954 | 10 | 76 |
| 60 | s20 | 0.950 | 20 | 77 |
| 61 | full | 0.952 | 256 | 78 |

Figure 18:
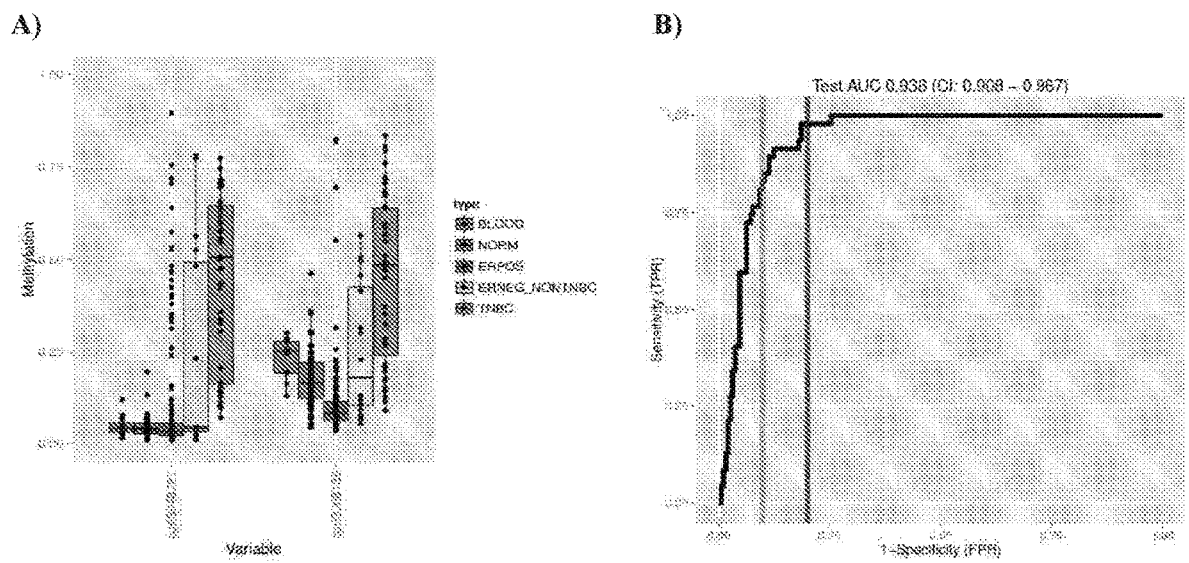
FIG. 18. This figure a) illustrates the distribution of methylation for each of the probes in subset 1 as detailed in Table 12, and b) provides a ROC curve and associated AUC statistics for diagnosing TNBC using probe subset 1.
Figure 19:
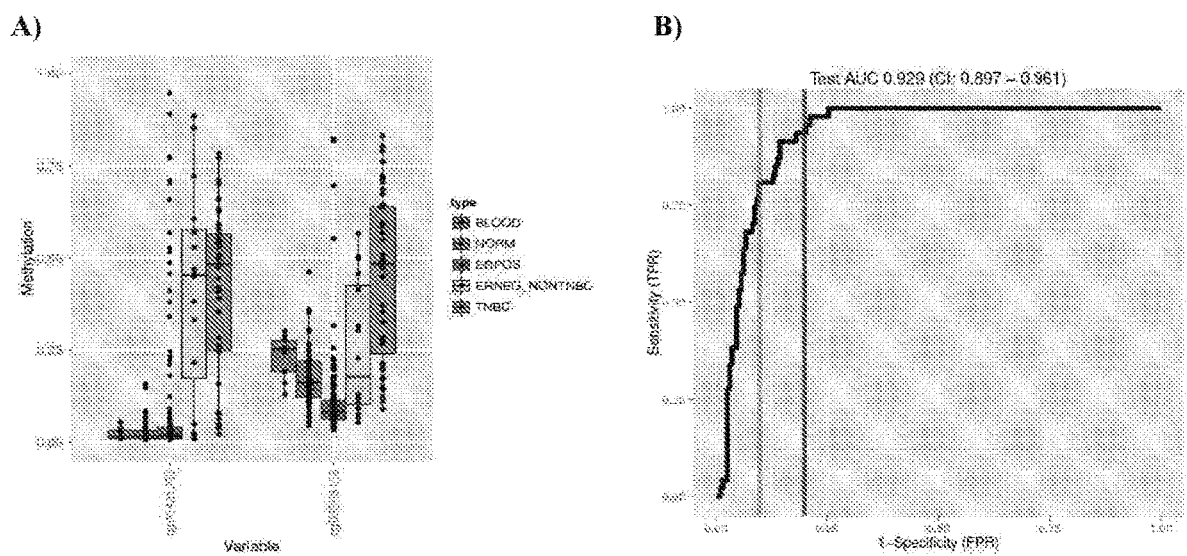
FIG. 19. This figure a) illustrates the distribution of methylation for each of the probes in subset 2 as detailed in Table 12, and b) provides a ROC curve and associated AUC statistics for diagnosing TNBC using probe subset 2.
Figure 20:
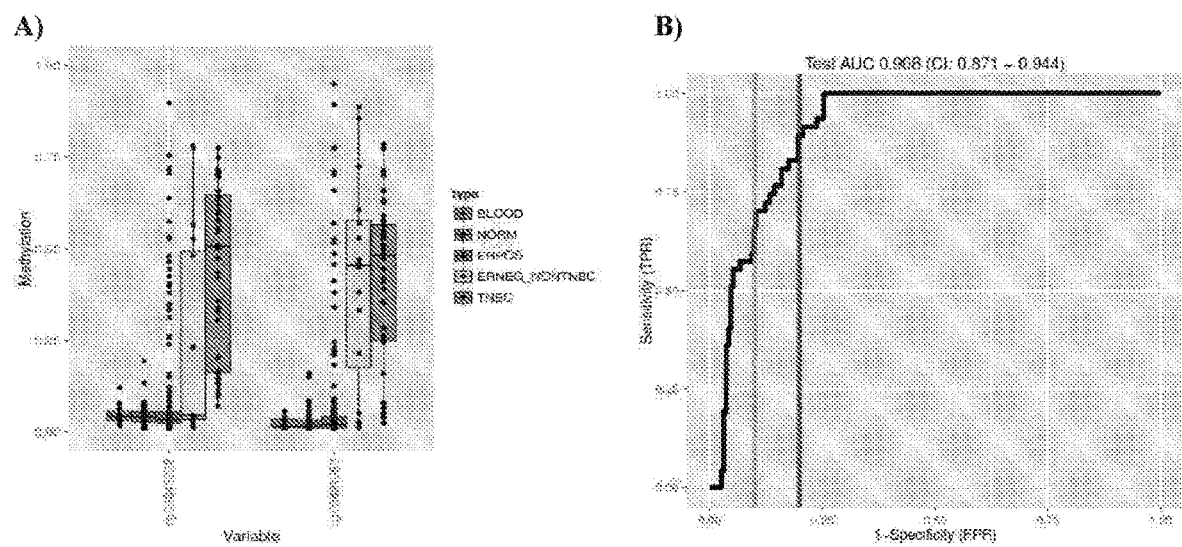
FIG. 20. This figure a) illustrates the distribution of methylation for each of the probes in subset 3 as detailed in Table 12, and b) provides a ROC curve and associated AUC statistics for diagnosing TNBC using probe subset 3.
Figure 21:
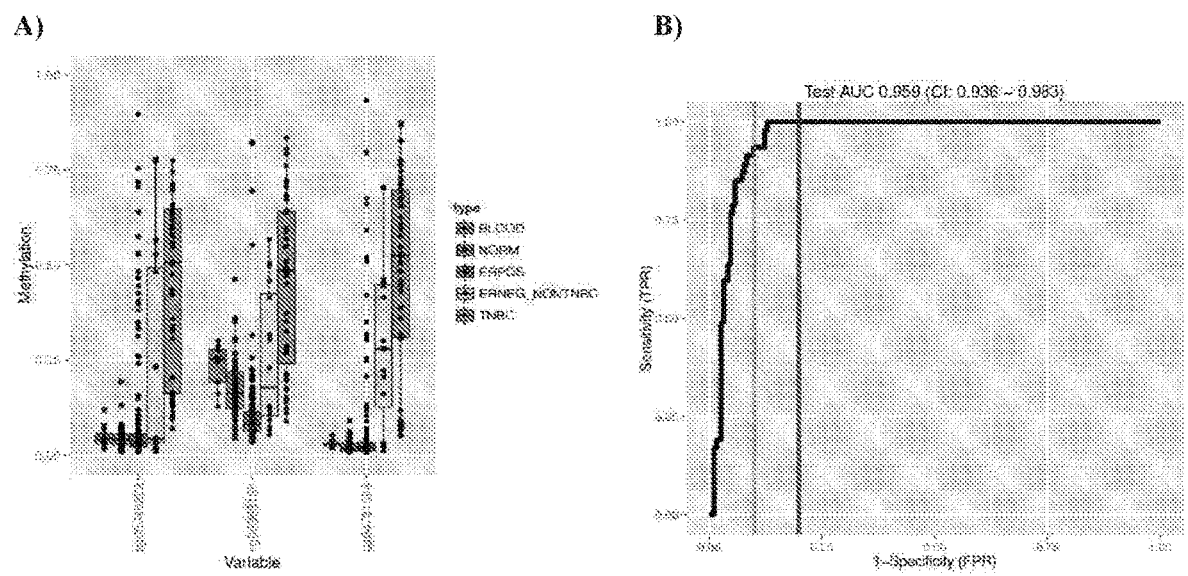
FIG. 21. This figure a) illustrates the distribution of methylation for each of the probes in subset 4 as detailed in Table 12, and b) provides a ROC curve and associated AUC statistics for diagnosing TNBC using probe subset 4.
Figure 22:
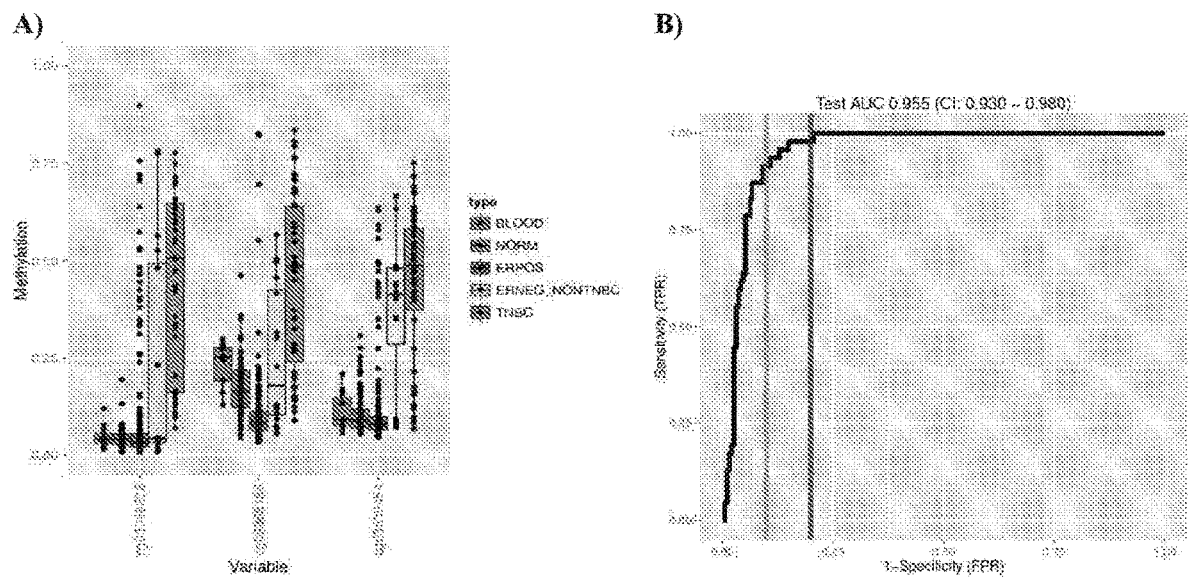
FIG. 22. This figure a) illustrates the distribution of methylation for each of the probes in subset 5 as detailed in Table 12, and b) provides a ROC curve and associated AUC statistics for diagnosing TNBC using probe subset 5.
Figure 23:
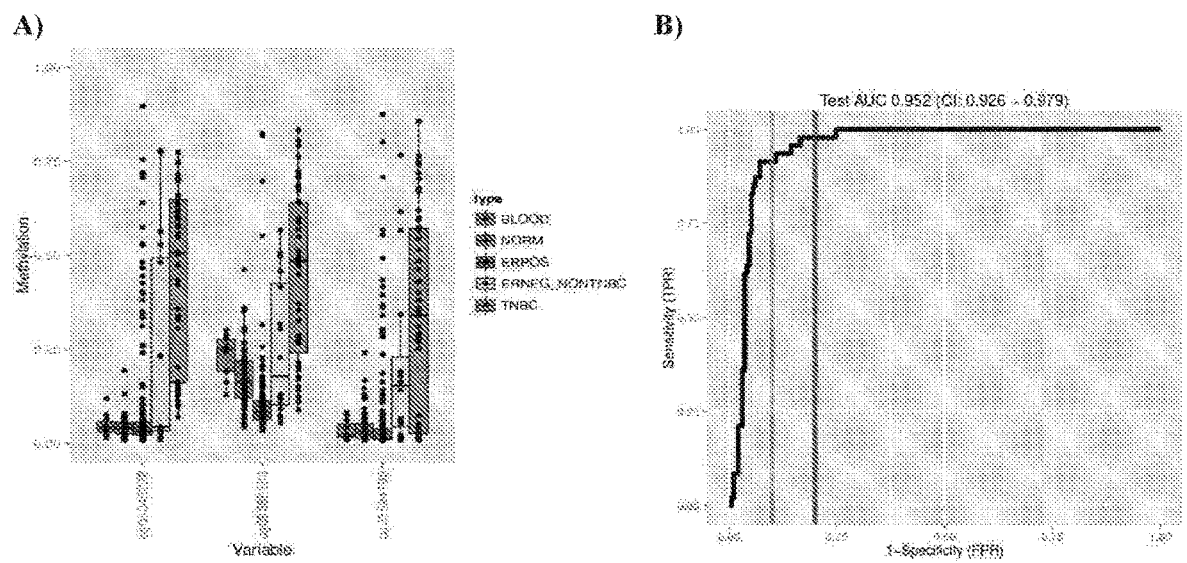
FIG. 23. This figure a) illustrates the distribution of methylation for each of the probes in subset 6 as detailed in Table 12, and b) provides a ROC curve and associated AUC statistics for diagnosing TNBC using probe subset 6.
Figure 24:
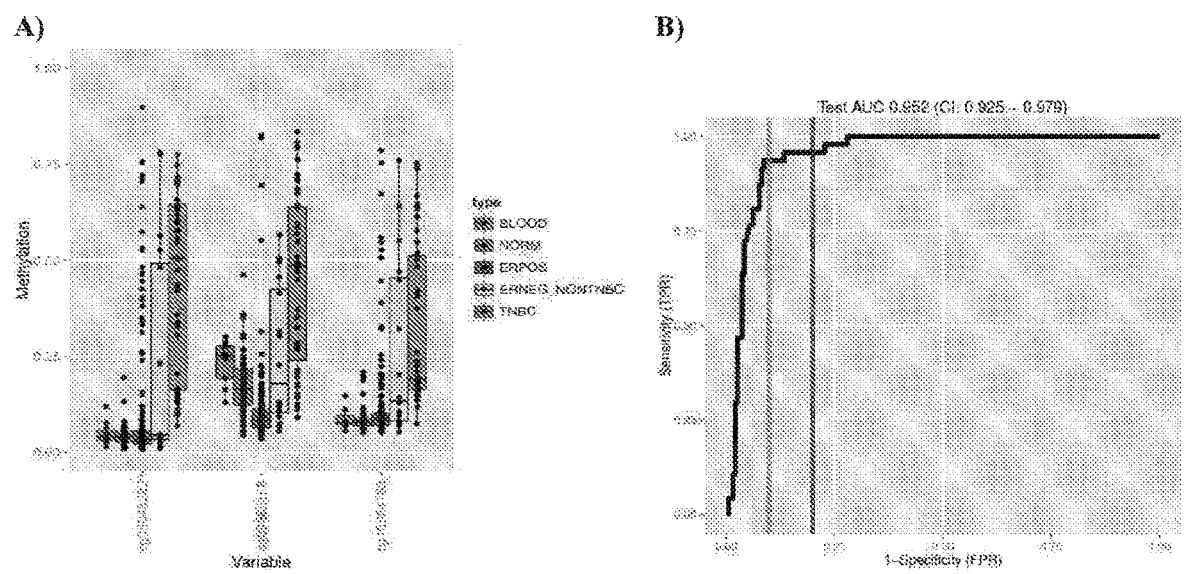
FIG. 24. This figure a) illustrates the distribution of methylation for each of the probes in subset 7 as detailed in Table 12, and b) provides a ROC curve and associated AUC statistics for diagnosing TNBC using probe subset 7.
Figure 25:
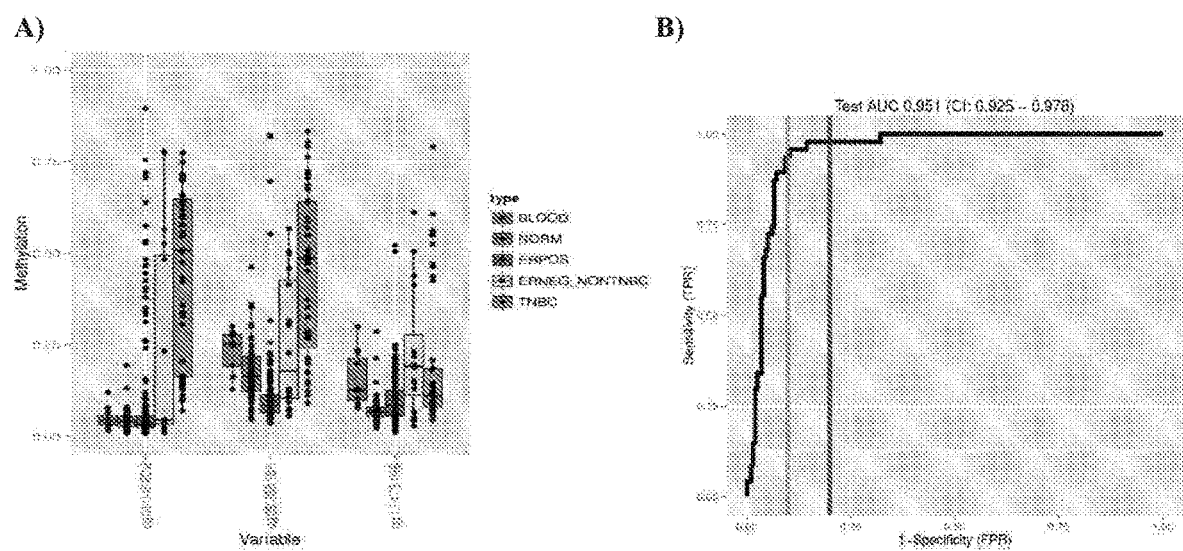
FIG. 25. This figure a) illustrates the distribution of methylation for each of the probes in subset 8 as detailed in Table 12, and b) provides a ROC curve and associated AUC statistics for diagnosing TNBC using probe subset 8.
Figure 26:
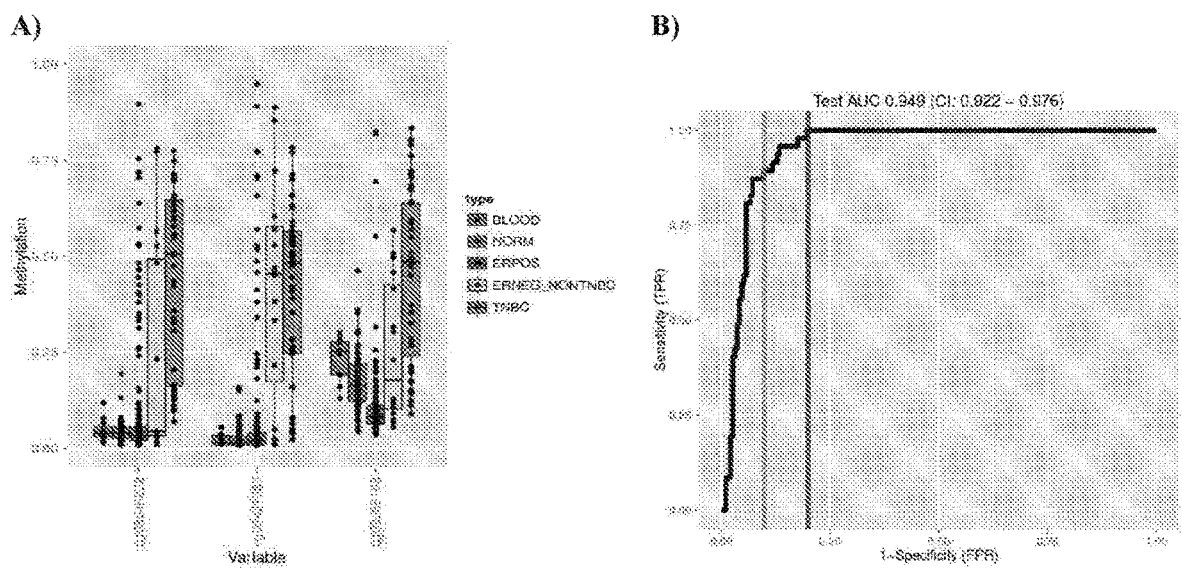
FIG. 26. This figure a) illustrates the distribution of methylation for each of the probes in subset 9 as detailed in Table 12, and b) provides a ROC curve and associated AUC statistics for diagnosing TNBC using probe subset 9.
Figure 27:
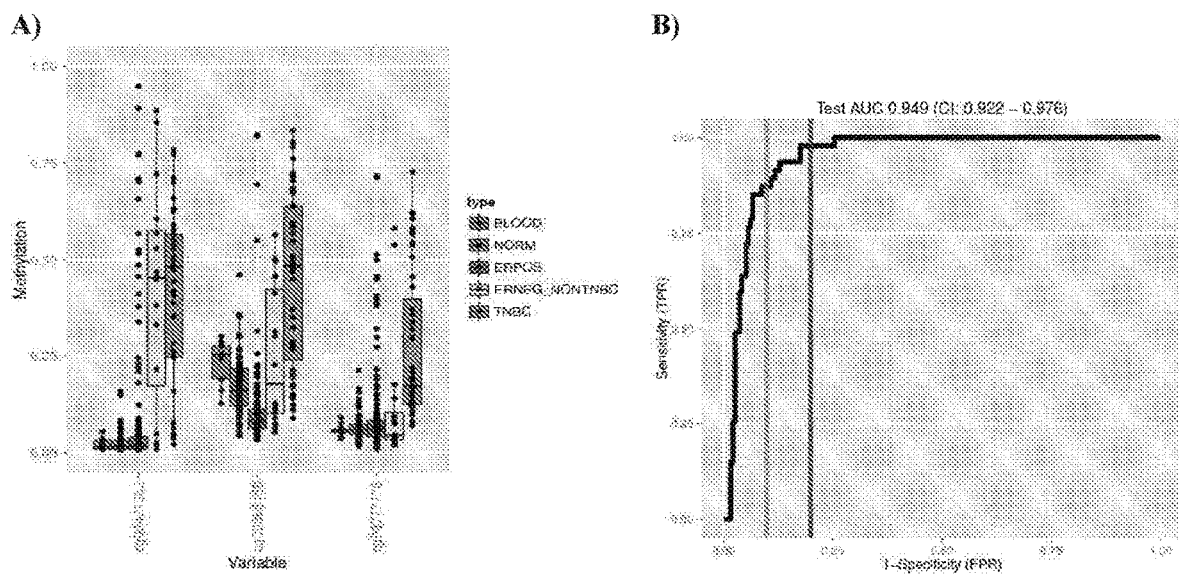
FIG. 27. This figure a) illustrates the distribution of methylation for each of the probes in subset 10 as detailed in Table 12, and b) provides a ROC curve and associated AUC statistics for diagnosing TNBC using probe subset 10.
Figure 28:
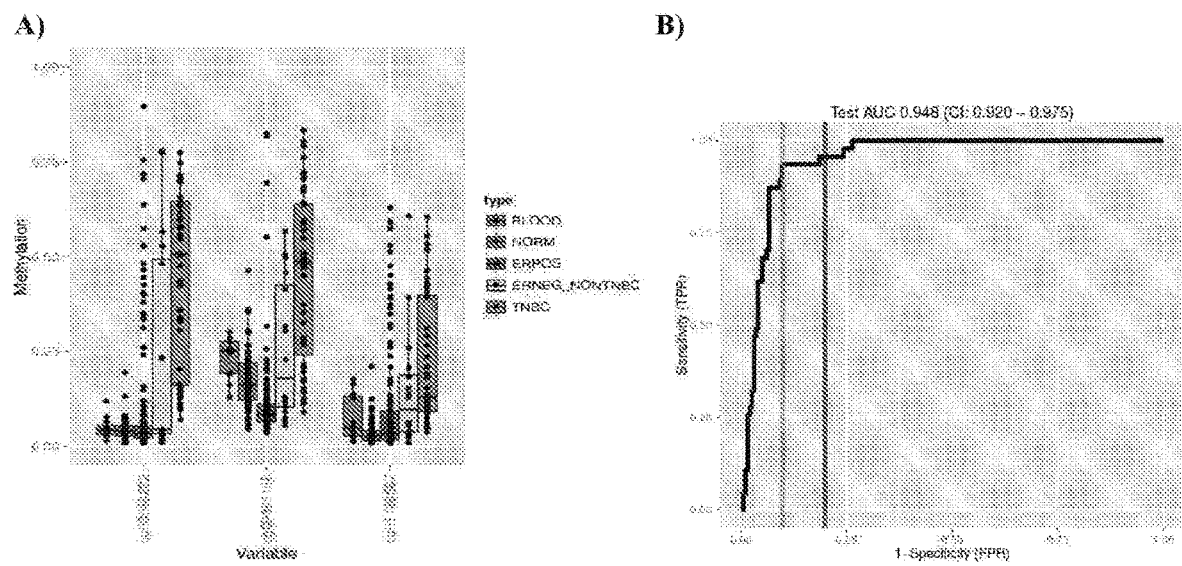
FIG. 28. This figure a) illustrates the distribution of methylation for each of the probes in subset 11 as detailed in Table 12, and b) provides a ROC curve and associated AUC statistics for diagnosing TNBC using probe subset 11.
Figure 29:
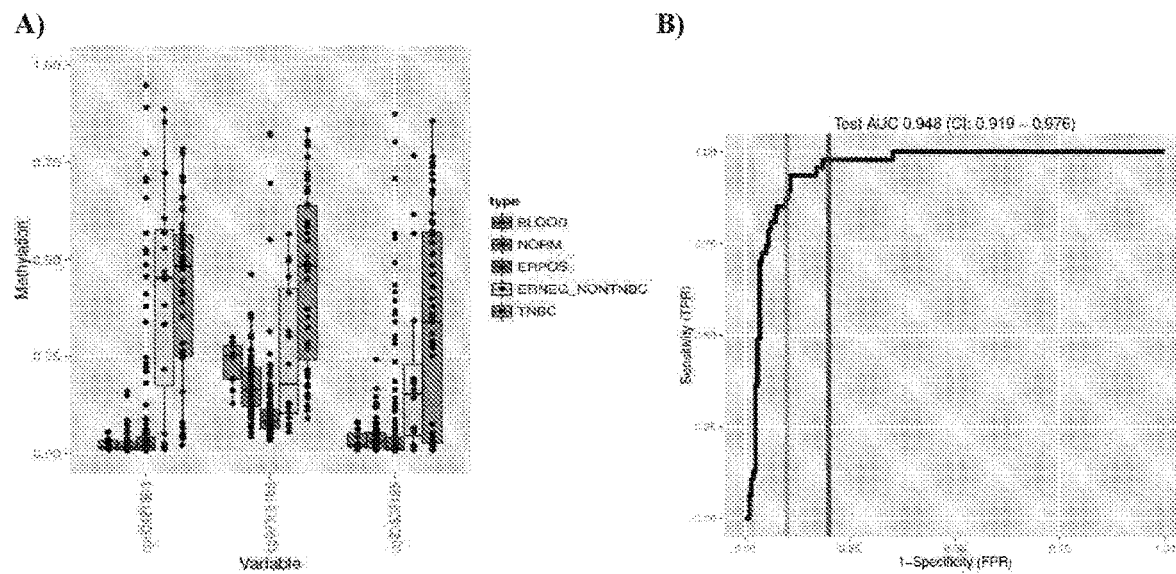
FIG. 29. This figure a) illustrates the distribution of methylation for each of the probes in subset 12 as detailed in Table 12, and b) provides a ROC curve and associated AUC statistics for diagnosing TNBC using probe subset 12.
Figure 30:
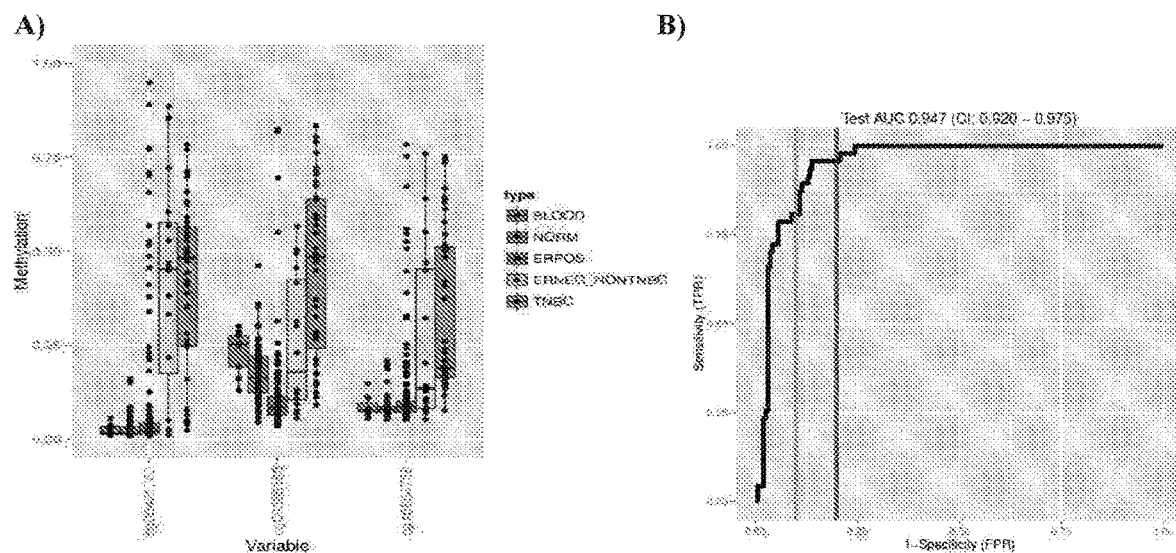
FIG. 30. This figure a) illustrates the distribution of methylation for each of the probes in subset 13 as detailed in Table 12, and b) provides a ROC curve and associated AUC statistics for diagnosing TNBC using probe subset 13.
Figure 31:
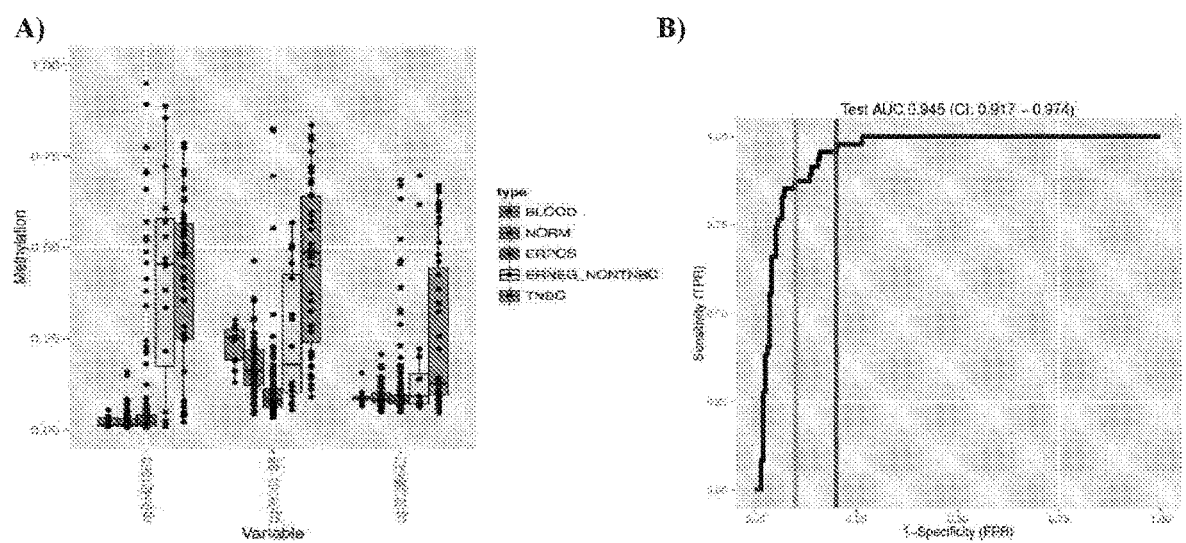
FIG. 31. This figure a) illustrates the distribution of methylation for each of the probes in subset 14 as detailed in Table 12, and b) provides a ROC curve and associated AUC statistics for diagnosing TNBC using probe subset 14.
Figure 32:
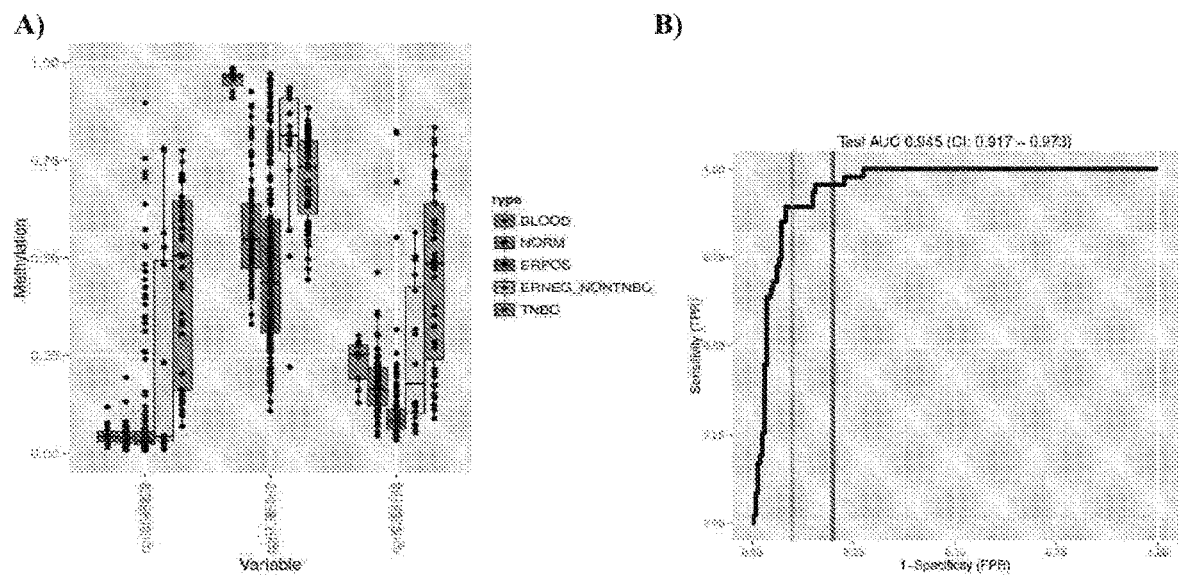
FIG. 32. This figure a) illustrates the distribution of methylation for each of the probes in subset 15 as detailed in Table 12, and b) provides a ROC curve and associated AUC statistics for diagnosing TNBC using probe subset 15.
Figure 33:
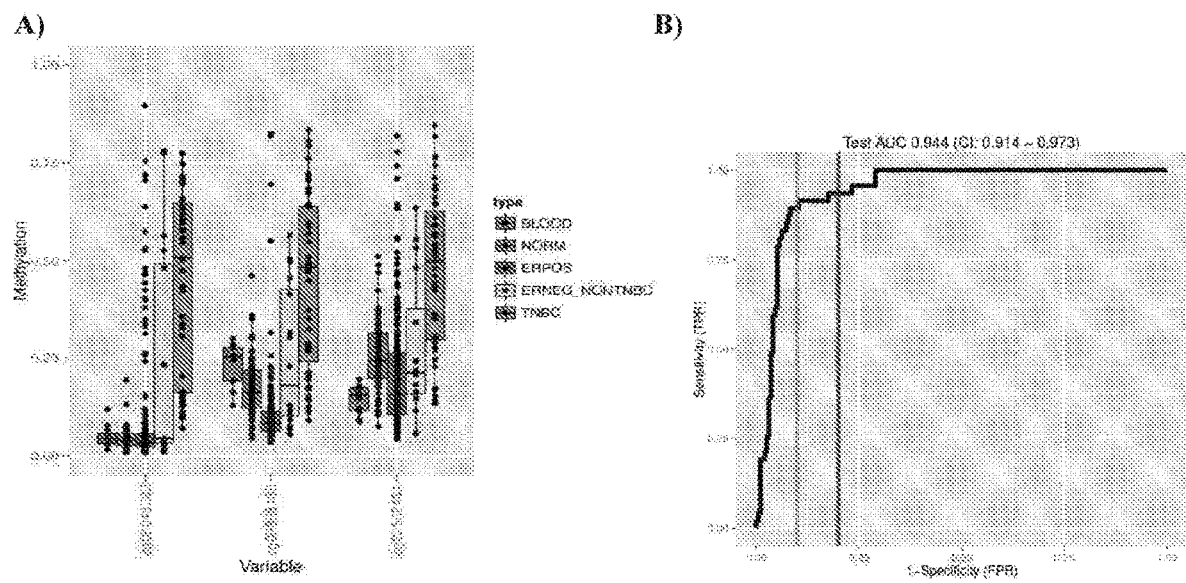
FIG. 33. This figure a) illustrates the distribution of methylation for each of the probes in subset 16 as detailed in Table 12, and b) provides a ROC curve and associated AUC statistics for diagnosing TNBC using probe subset 16.
Figure 34:
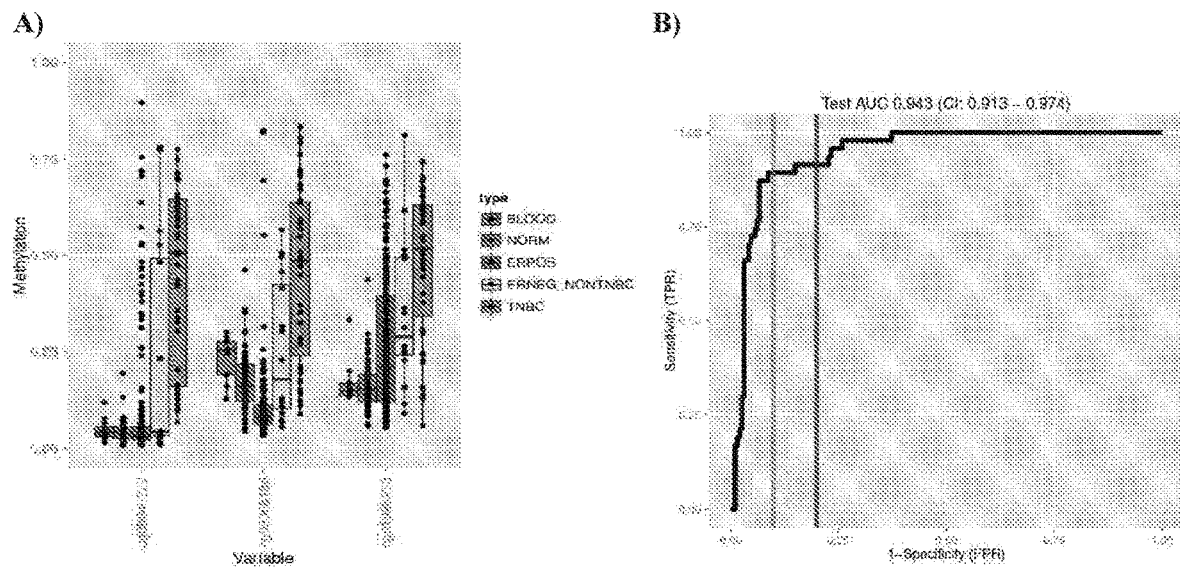
FIG. 34. This figure a) illustrates the distribution of methylation for each of the probes in subset 17 as detailed in Table 12, and b) provides a ROC curve and associated AUC statistics for diagnosing TNBC using probe subset 17.
Figure 35:
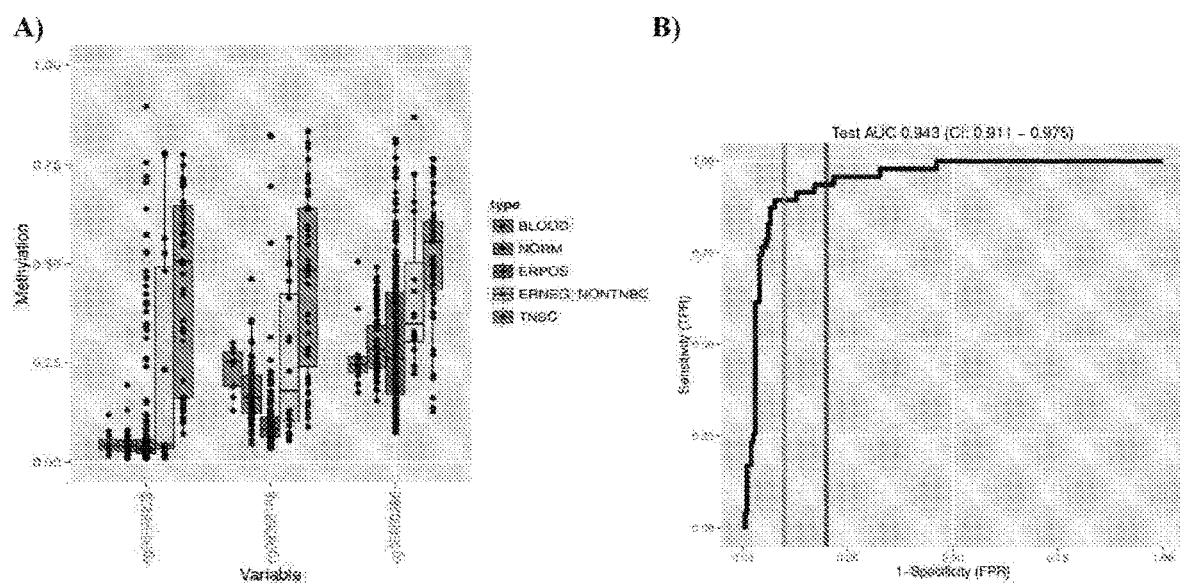
FIG. 35. This figure a) illustrates the distribution of methylation for each of the probes in subset 18 as detailed in Table 12, and b) provides a ROC curve and associated AUC statistics for diagnosing TNBC using probe subset 18.
Figure 36:
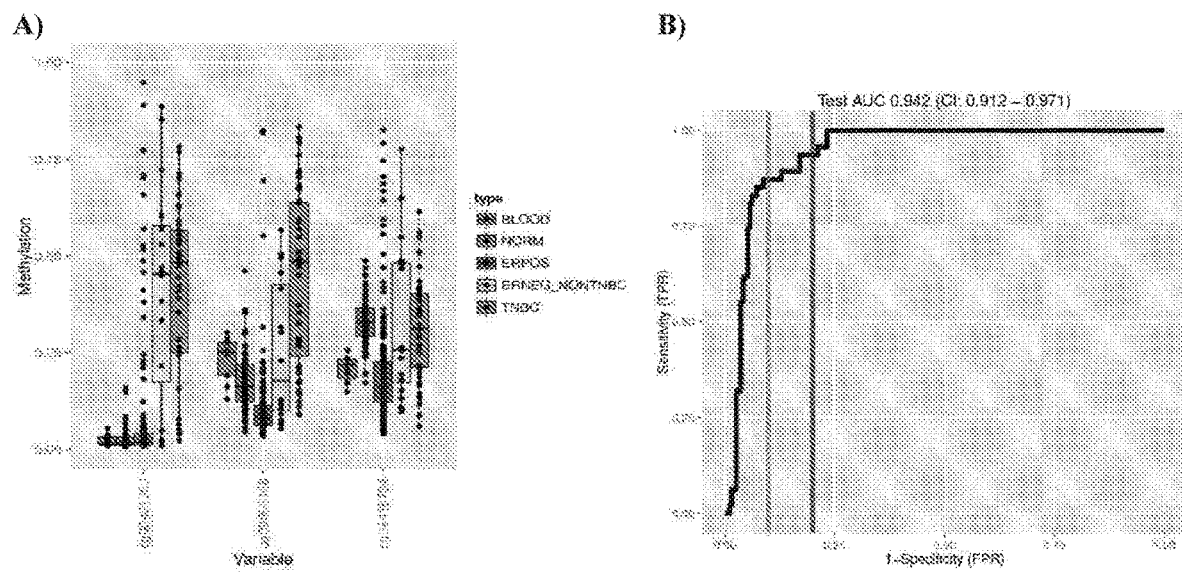
FIG. 36. This figure a) illustrates the distribution of methylation for each of the probes in subset 19 as detailed in Table 12, and b) provides a ROC curve and associated AUC statistics for diagnosing TNBC using probe subset 19.
Figure 37:
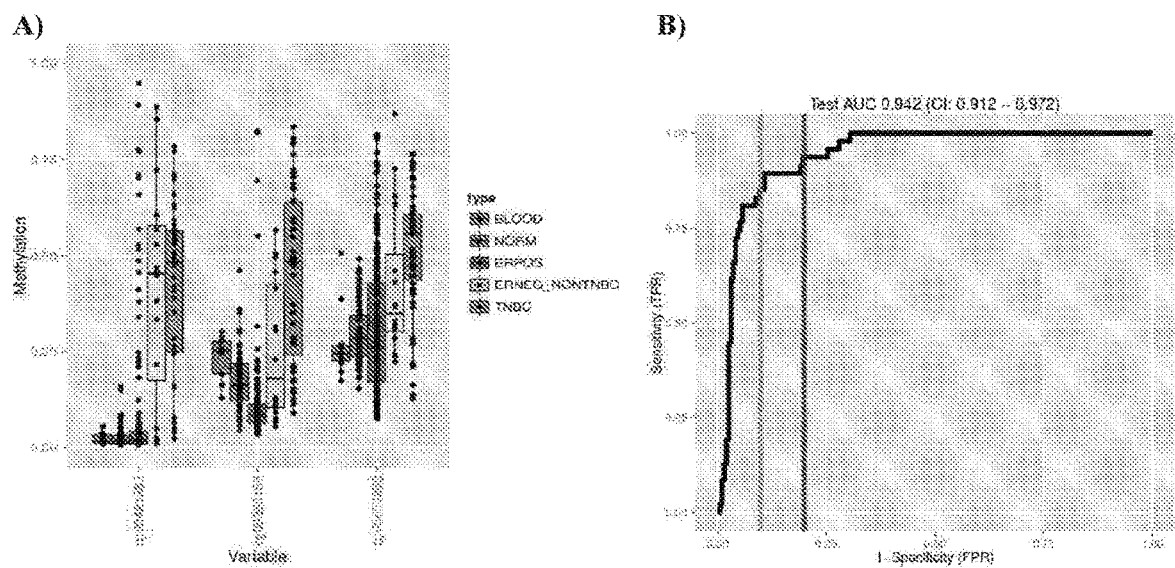
FIG. 37. This figure a) illustrates the distribution of methylation for each of the probes in subset 20 as detailed in Table 12, and b) provides a ROC curve and associated AUC statistics for diagnosing TNBC using probe subset 20.
Figure 38:
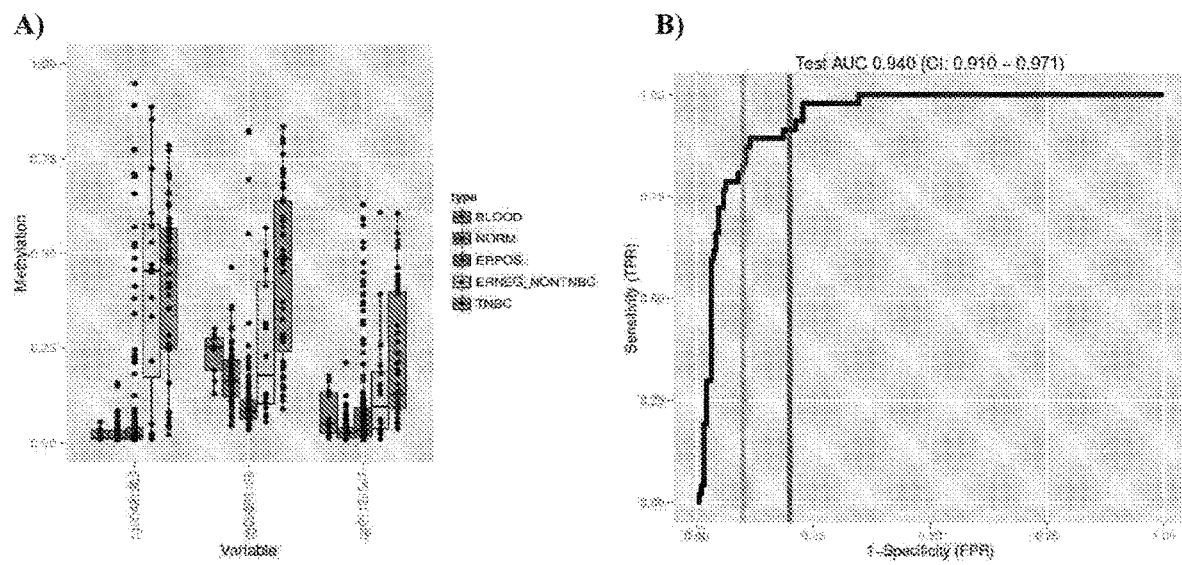
FIG. 38. This figure a) illustrates the distribution of methylation for each of the probes in subset 21 as detailed in Table 12, and b) provides a ROC curve and associated AUC statistics for diagnosing TNBC using probe subset 21.
Figure 39:
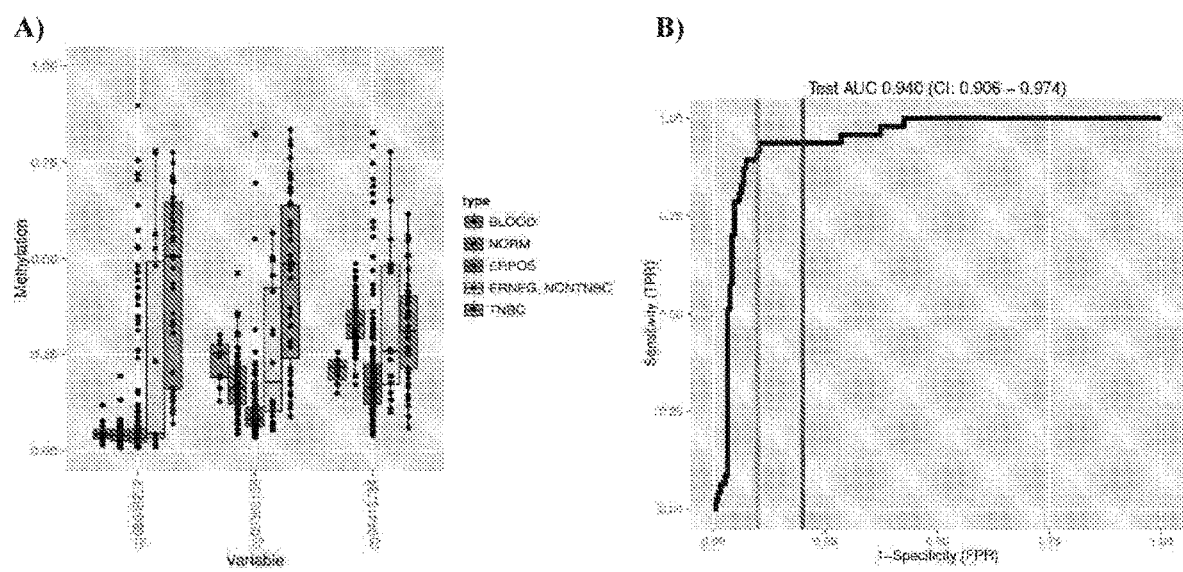
FIG. 39. This figure a) illustrates the distribution of methylation for each of the probes in subset 22 as detailed in Table 12, and b) provides a ROC curve and associated AUC statistics for diagnosing TNBC using probe subset 22.
Figure 40:
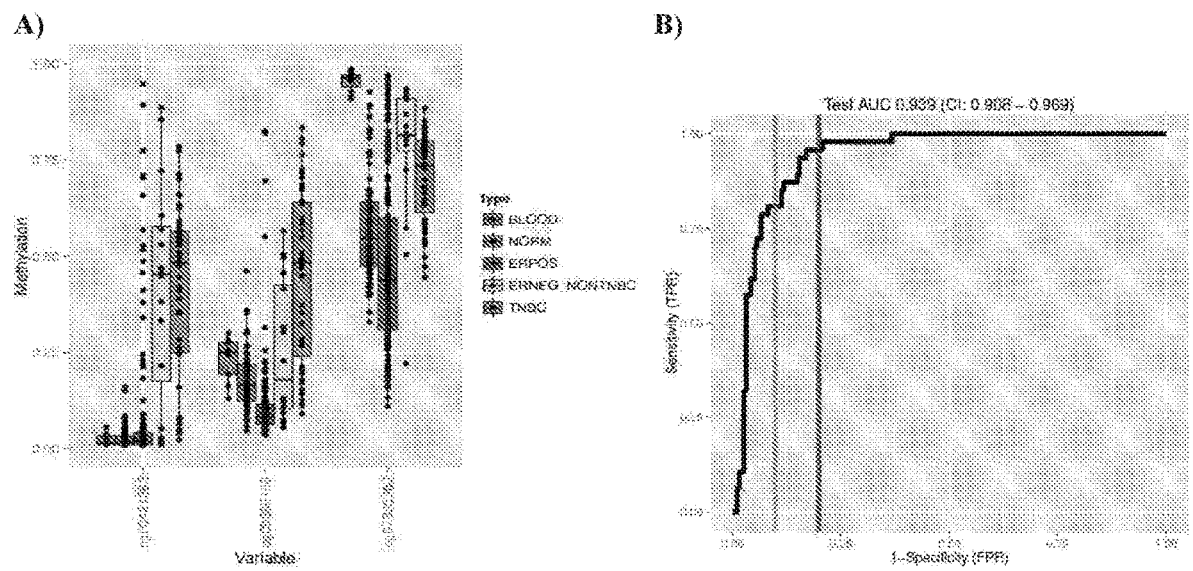
FIG. 40. This figure a) illustrates the distribution of methylation for each of the probes in subset 23 as detailed in Table 12, and b) provides a ROC curve and associated AUC statistics for diagnosing TNBC using probe subset 23.
Figure 41:
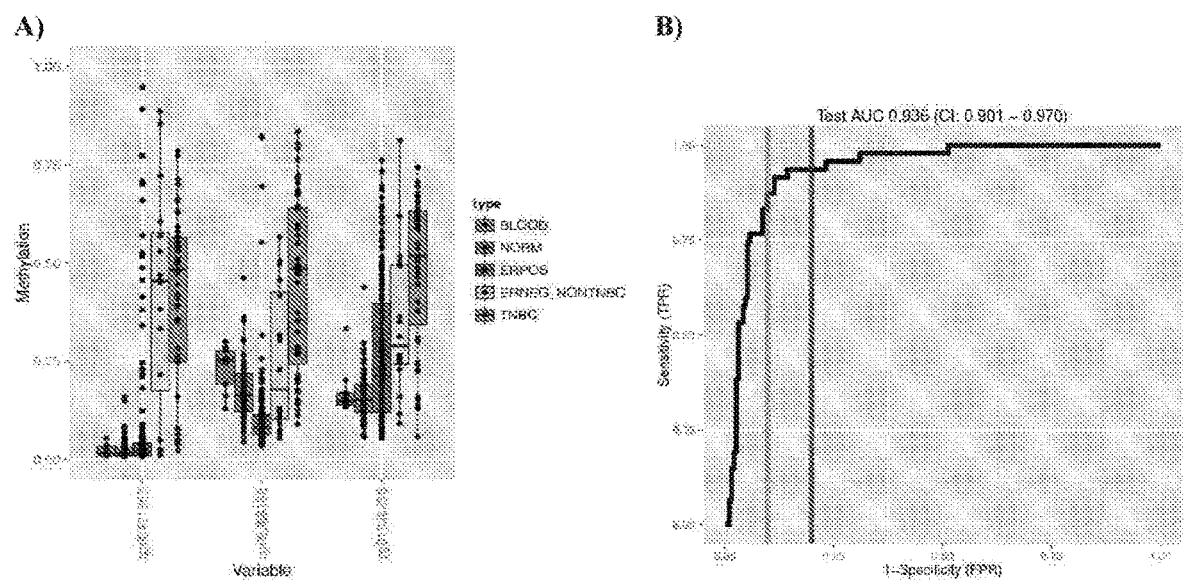
FIG. 41. This figure a) illustrates the distribution of methylation for each of the probes in subset 24 as detailed in Table 12, and b) provides a ROC curve and associated AUC statistics for diagnosing TNBC using probe subset 24.
Figure 42:
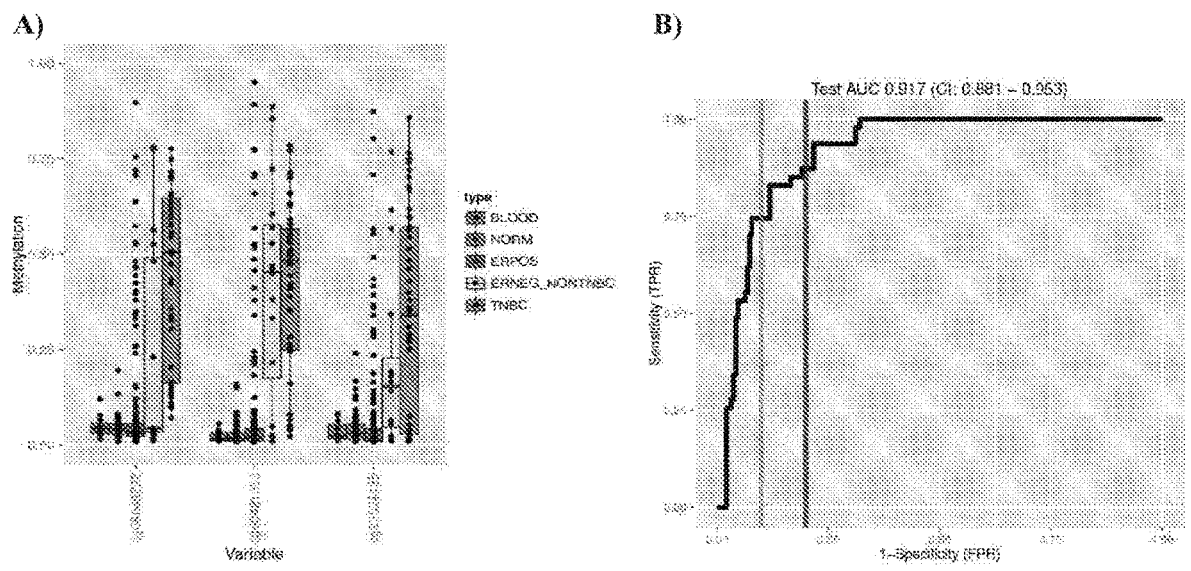
FIG. 42. This figure a) illustrates the distribution of methylation for each of the probes in subset 25 as detailed in Table 12, and b) provides a ROC curve and associated AUC statistics for diagnosing TNBC using probe subset 25.
Figure 43:
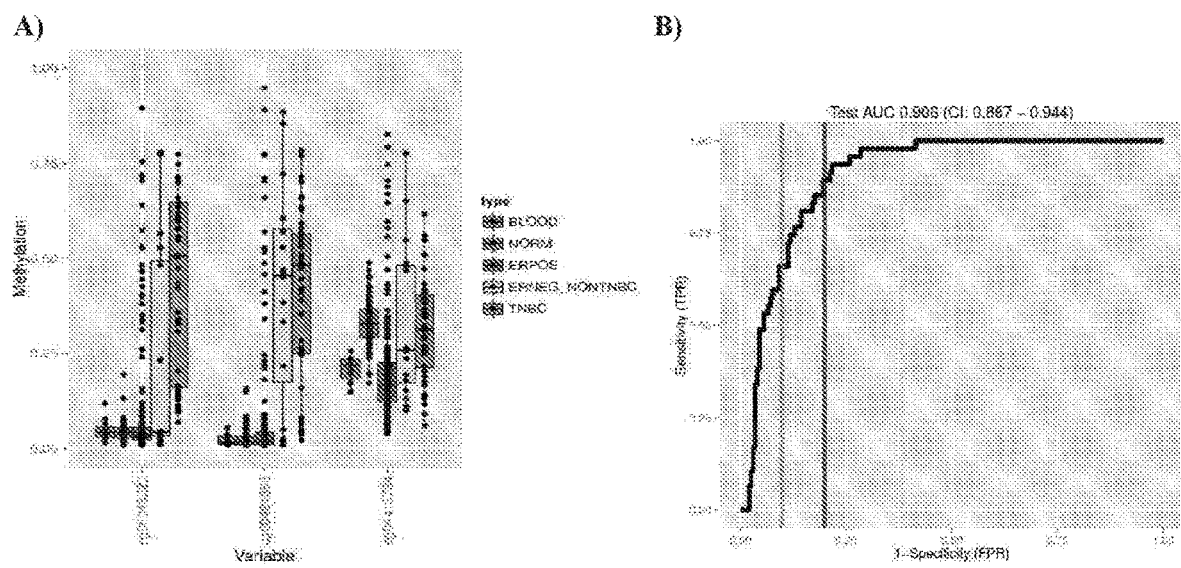
FIG. 43. This figure a) illustrates the distribution of methylation for each of the probes in subset 26 as detailed in Table 12, and b) provides a ROC curve and associated AUC statistics for diagnosing TNBC using probe subset 26.
Figure 44:
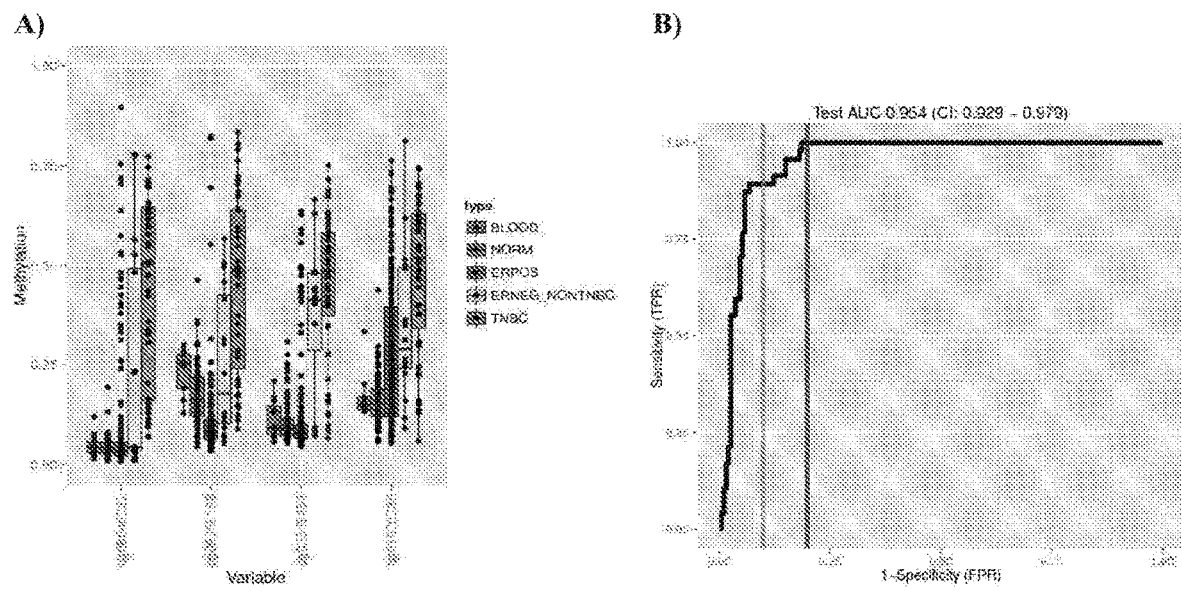
FIG. 44. This figure a) illustrates the distribution of methylation for each of the probes in subset 27 as detailed in Table 12, and b) provides a ROC curve and associated AUC statistics for diagnosing TNBC using probe subset 27.
Figure 45:
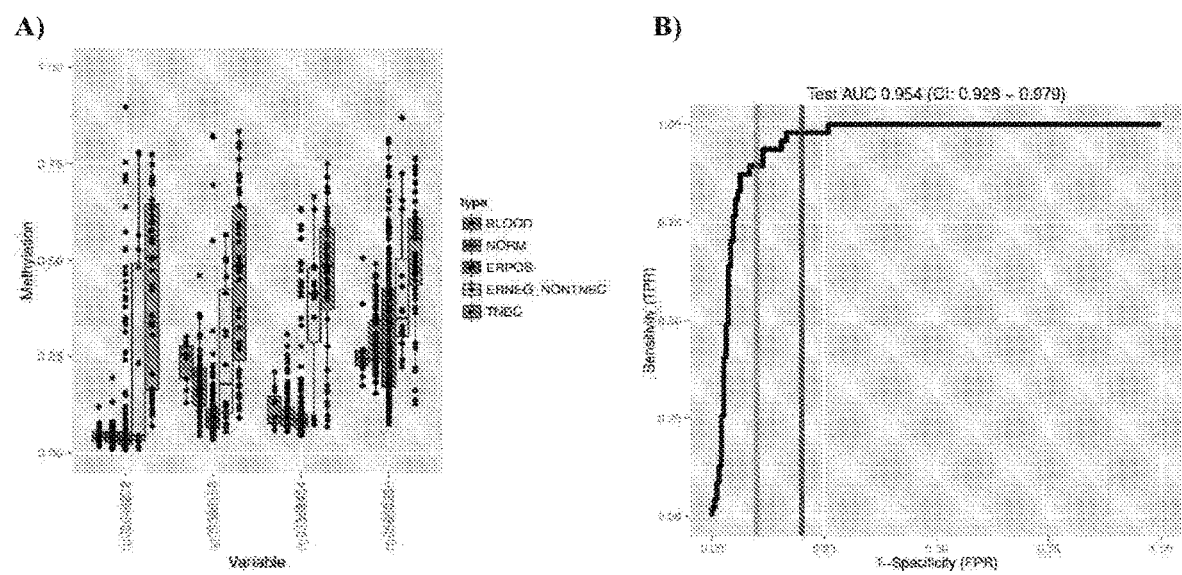
FIG. 45. This figure a) illustrates the distribution of methylation for each of the probes in subset 28 as detailed in Table 12, and b) provides a ROC curve and associated AUC statistics for diagnosing TNBC using probe subset 28.
Figure 46:
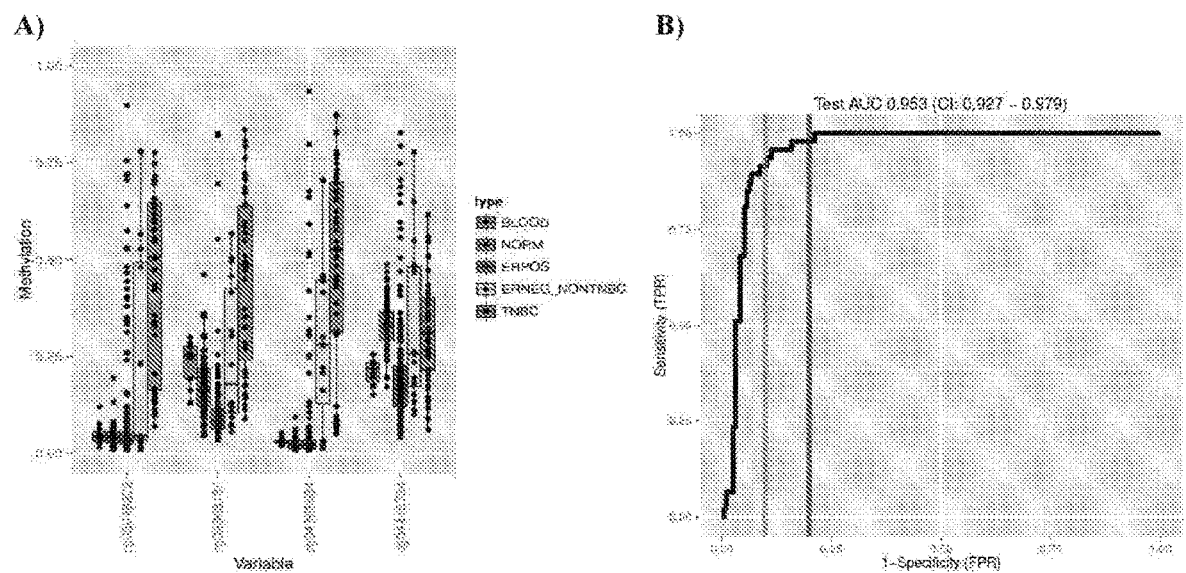
FIG. 46. This figure a) illustrates the distribution of methylation for each of the probes in subset 29 as detailed in Table 12, and b) provides a ROC curve and associated AUC statistics for diagnosing TNBC using probe subset 29.
Figure 47:
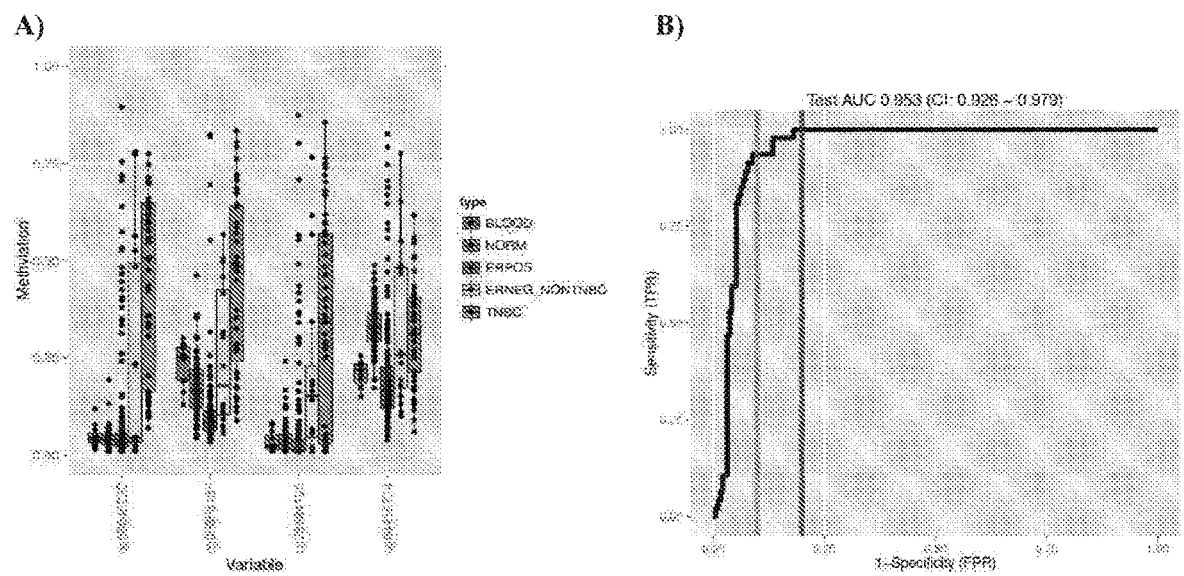
FIG. 47. This figure a) illustrates the distribution of methylation for each of the probes in subset 30 as detailed in Table 12, and b) provides a ROC curve and associated AUC statistics for diagnosing TNBC using probe subset 30.
Figure 48:
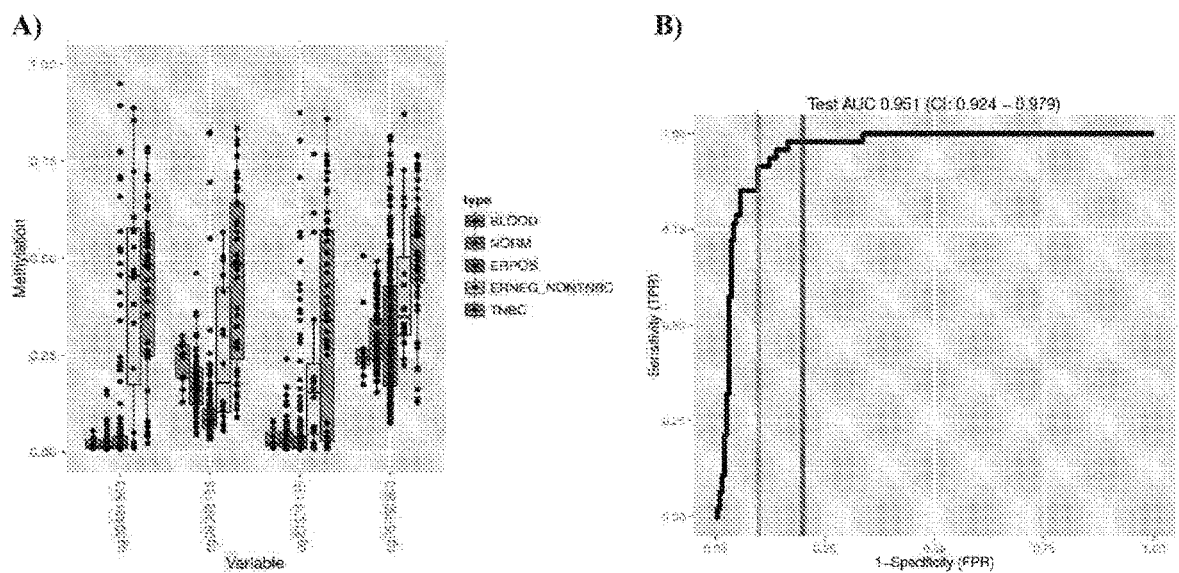
FIG. 48. This figure a) illustrates the distribution of methylation for each of the probes in subset 31 as detailed in Table 12, and b) provides a ROC curve and associated AUC statistics for diagnosing TNBC using probe subset 31.
Figure 49:
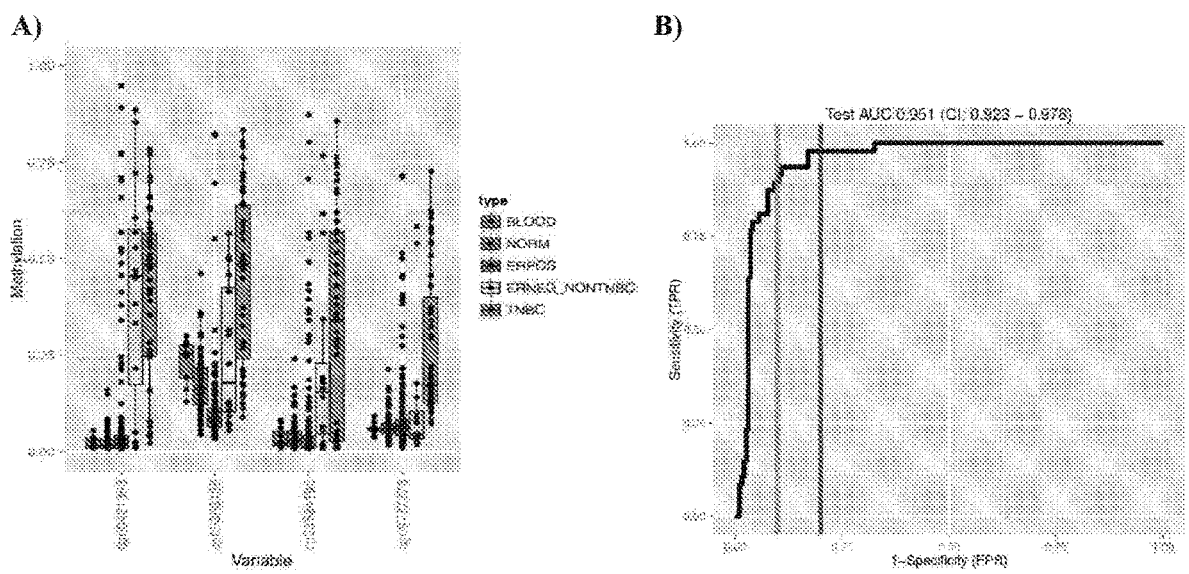
FIG. 49. This figure a) illustrates the distribution of methylation for each of the probes in subset 32 as detailed in Table 12, and b) provides a ROC curve and associated AUC statistics for diagnosing TNBC using probe subset 32.
Figure 50:
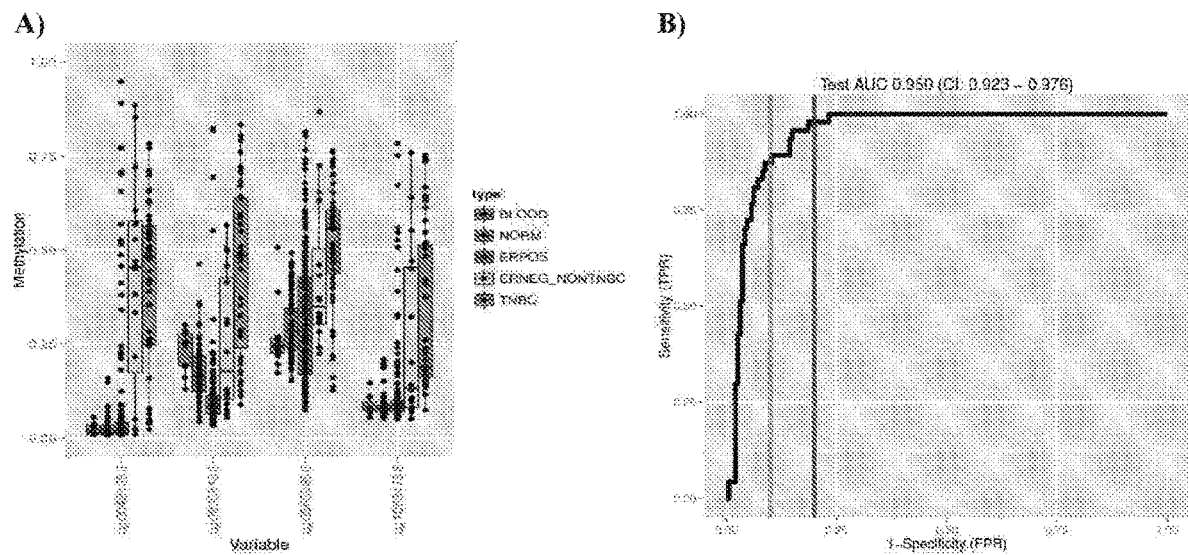
FIG. 50. This figure a) illustrates the distribution of methylation for each of the probes in subset 33 as detailed in Table 12, and b) provides a ROC curve and associated AUC statistics for diagnosing TNBC using probe subset 33.
Figure 51:
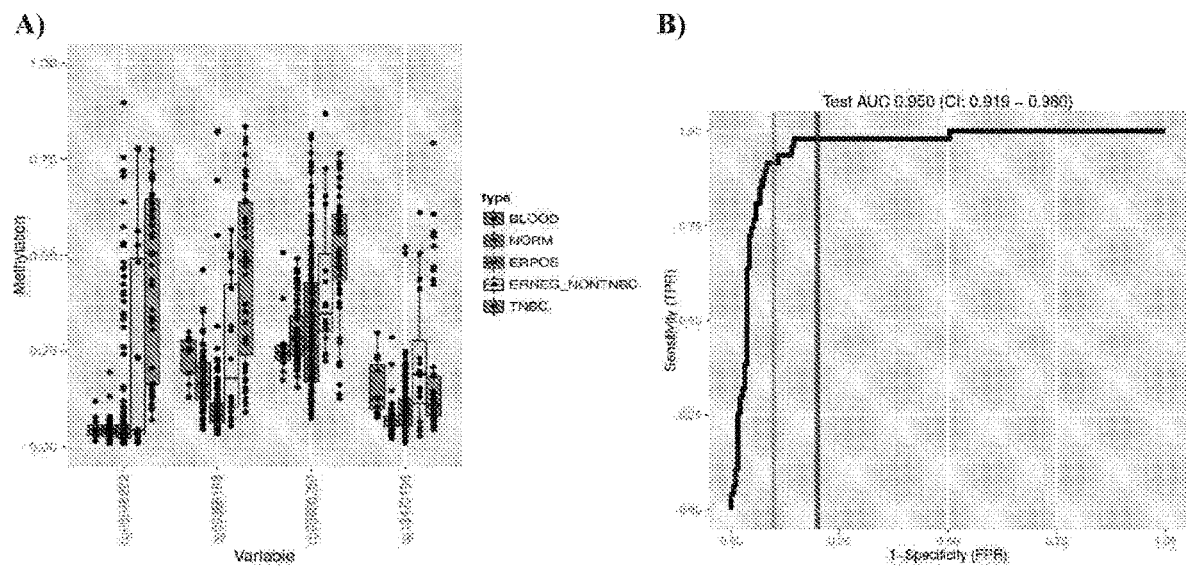
FIG. 51. This figure a) illustrates the distribution of methylation for each of the probes in subset 34 as detailed in Table 12, and b) provides a ROC curve and associated AUC statistics for diagnosing TNBC using probe subset 34.
Figure 52:
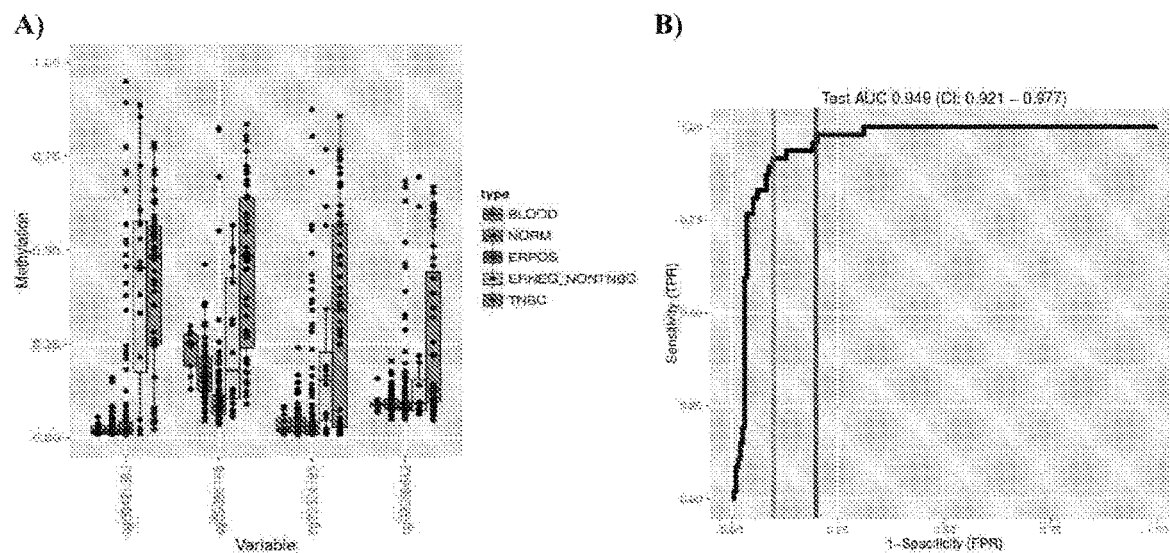
FIG. 52. This figure a) illustrates the distribution of methylation for each of the probes in subset 35 as detailed in Table 12, and b) provides a ROC curve and associated AUC statistics for diagnosing TNBC using probe subset 35.
Figure 53:
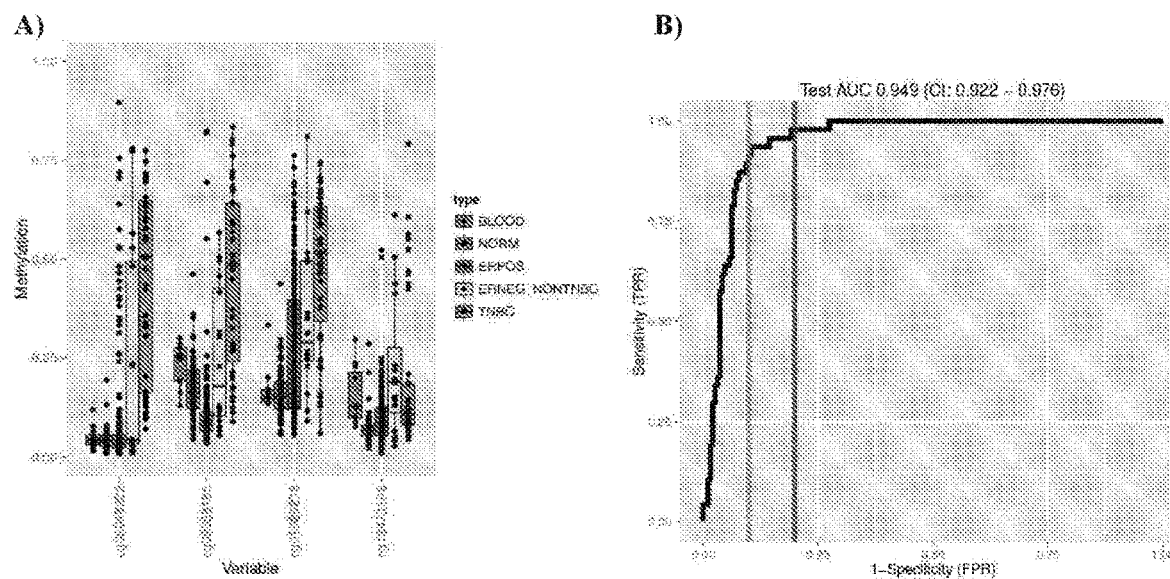
FIG. 53. This figure a) illustrates the distribution of methylation for each of the probes in subset 36 as detailed in Table 12, and b) provides a ROC curve and associated AUC statistics for diagnosing TNBC using probe subset 36.
Figure 54:
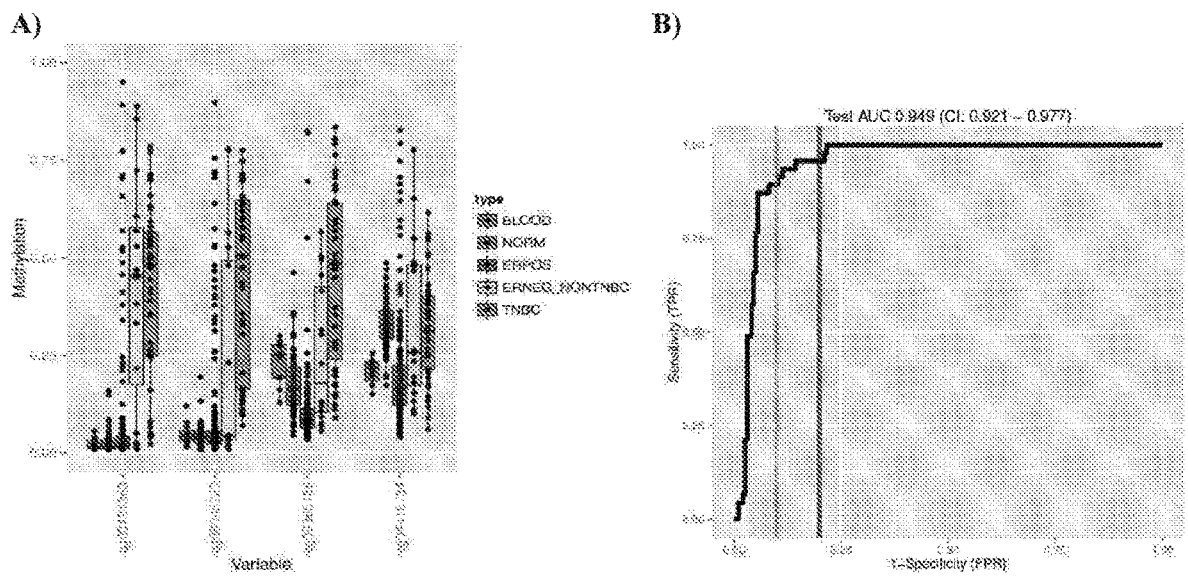
FIG. 54. This figure a) illustrates the distribution of methylation for each of the probes in subset 37 as detailed in Table 12, and b) provides a ROC curve and associated AUC statistics for diagnosing TNBC using probe subset 37.
Figure 55:
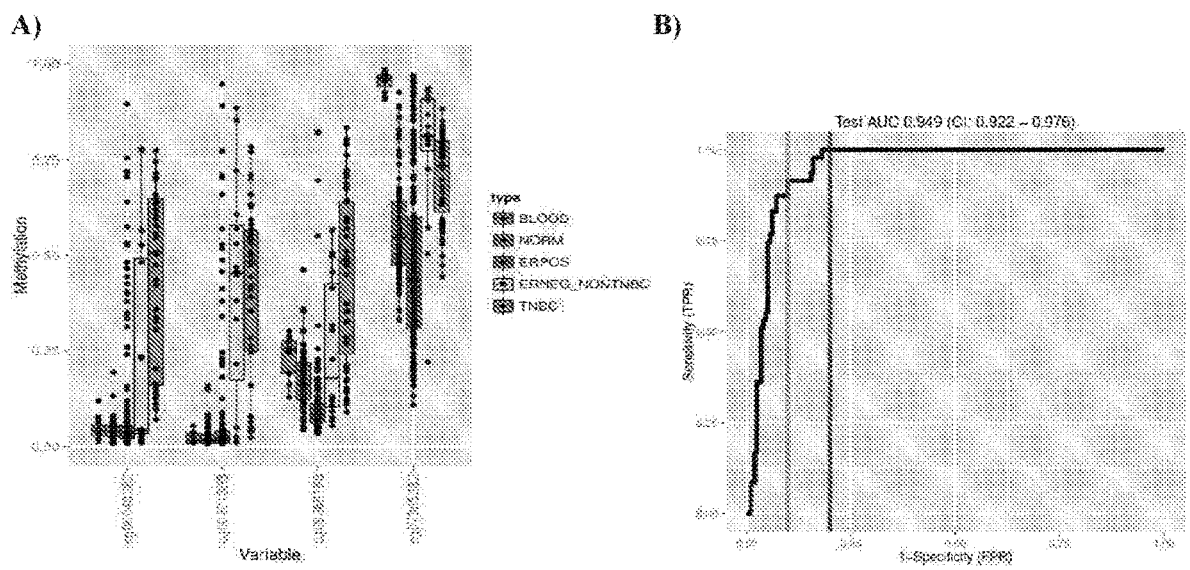
FIG. 55. This figure a) illustrates the distribution of methylation for each of the probes in subset 38 as detailed in Table 12, and b) provides a ROC curve and associated AUC statistics for diagnosing TNBC using probe subset 38.
Figure 56:
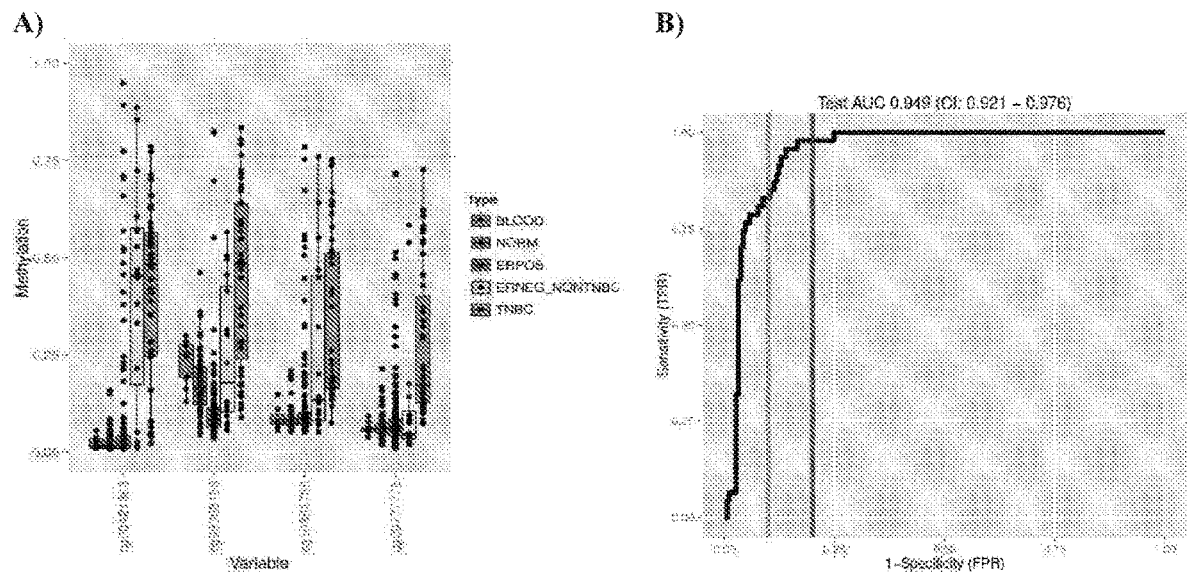
FIG. 56. This figure a) illustrates the distribution of methylation for each of the probes in subset 39 as detailed in Table 12, and b) provides a ROC curve and associated AUC statistics for diagnosing TNBC using probe subset 39.
Figure 57:
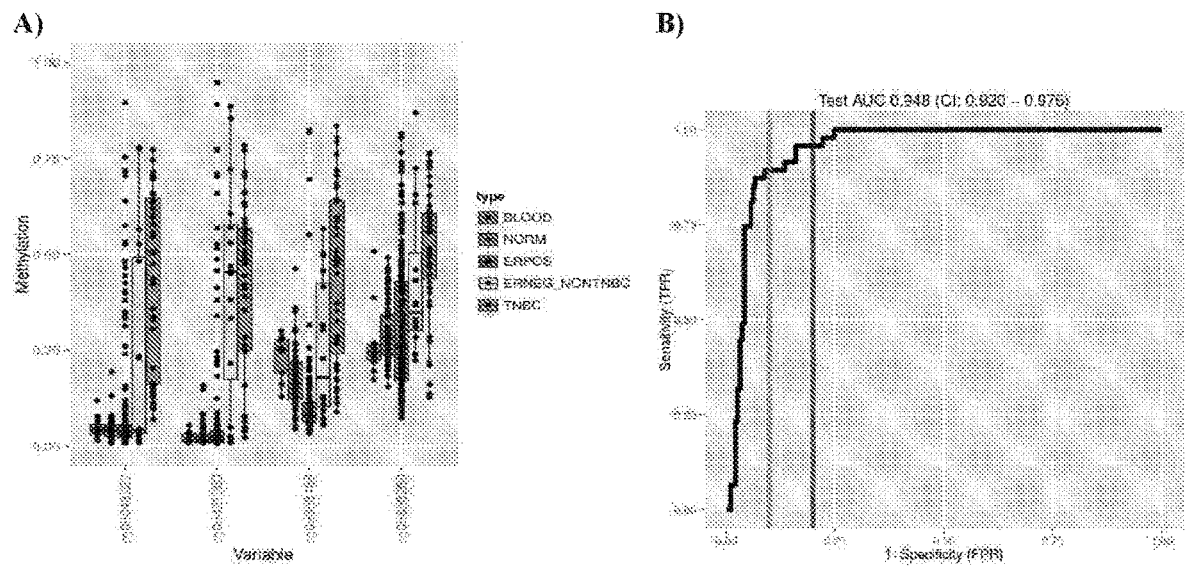
FIG. 57. This figure a) illustrates the distribution of methylation for each of the probes in subset 40 as detailed in Table 12, and b) provides a ROC curve and associated AUC statistics for diagnosing TNBC using probe subset 40.
Figure 58:
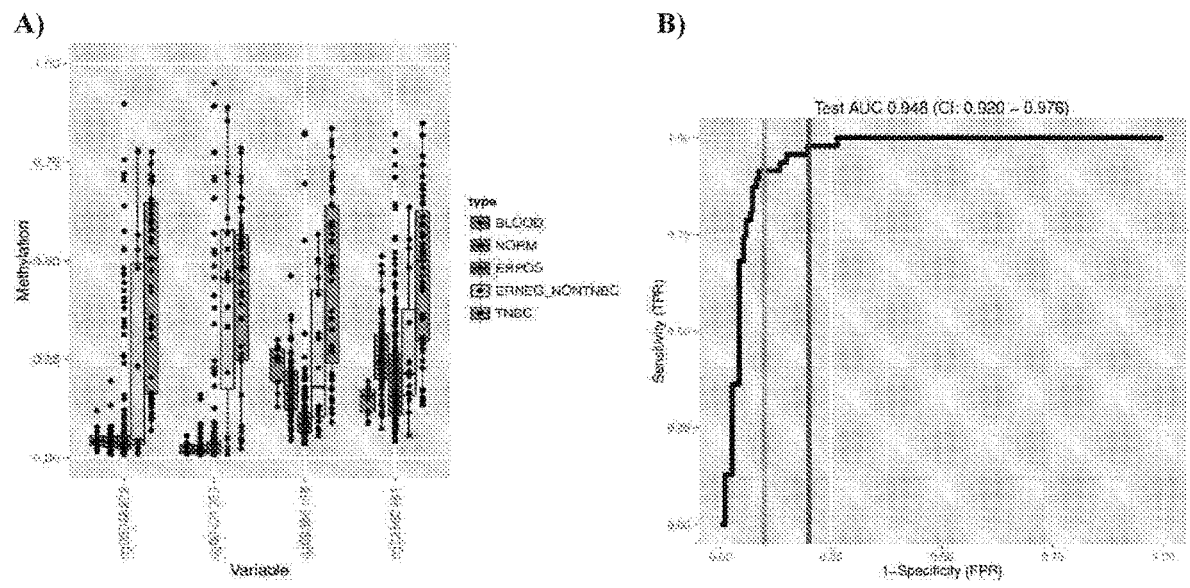
FIG. 58. This figure a) illustrates the distribution of methylation for each of the probes in subset 41 as detailed in Table 12, and b) provides a ROC curve and associated AUC statistics for diagnosing TNBC using probe subset 41.
Figure 59:
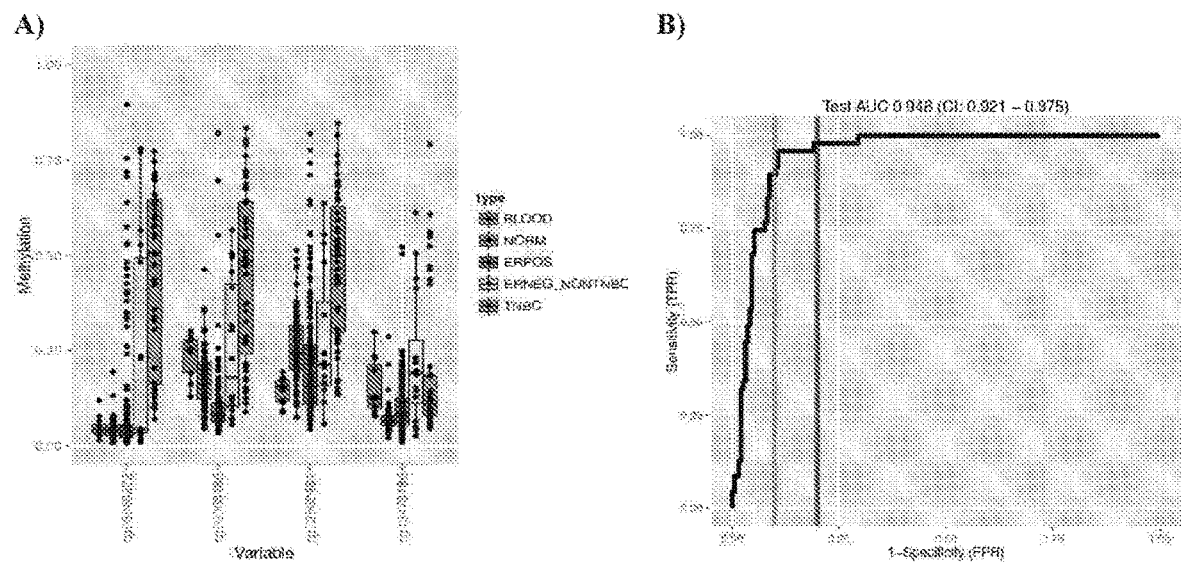
FIG. 59. This figure a) illustrates the distribution of methylation for each of the probes in subset 42 as detailed in Table 12, and b) provides a ROC curve and associated AUC statistics for diagnosing TNBC using probe subset 42.
Figure 60:
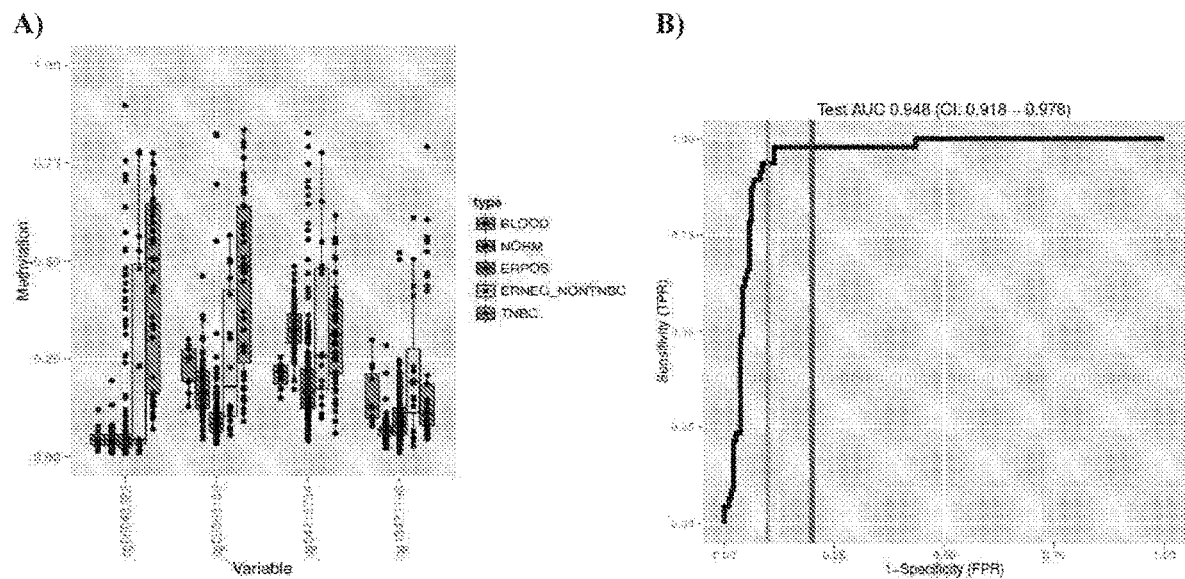
FIG. 60. This figure a) illustrates the distribution of methylation for each of the probes in subset 43 as detailed in Table 12, and b) provides a ROC curve and associated AUC statistics for diagnosing TNBC using probe subset 43.
Figure 61:
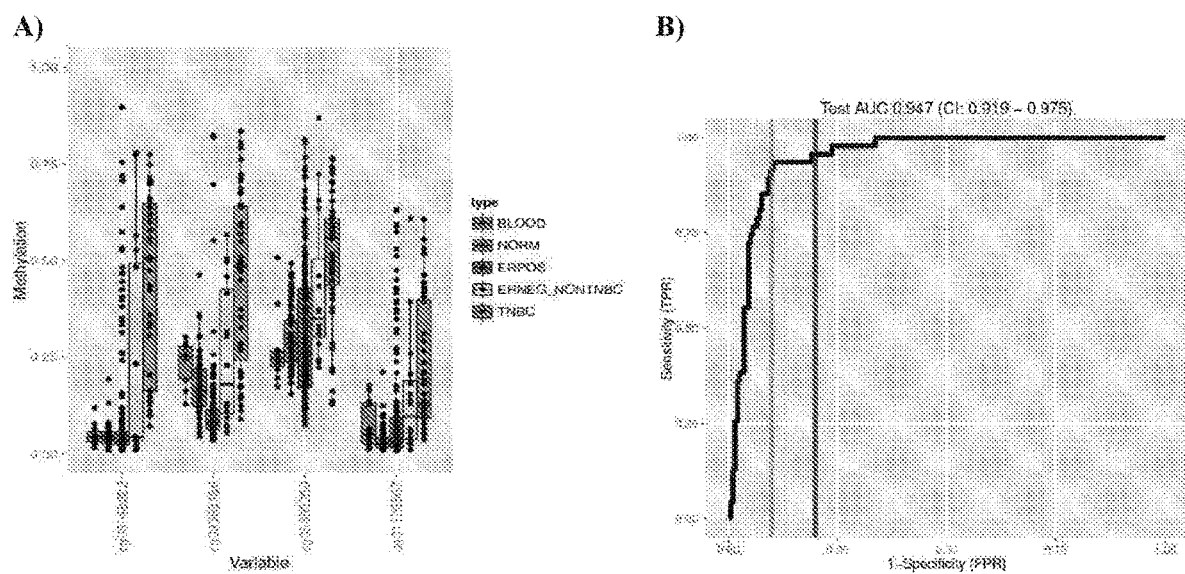
FIG. 61. This figure a) illustrates the distribution of methylation for each of the probes in subset 44 as detailed in Table 12, and b) provides a ROC curve and associated AUC statistics for diagnosing TNBC using probe subset 44.
Figure 62:
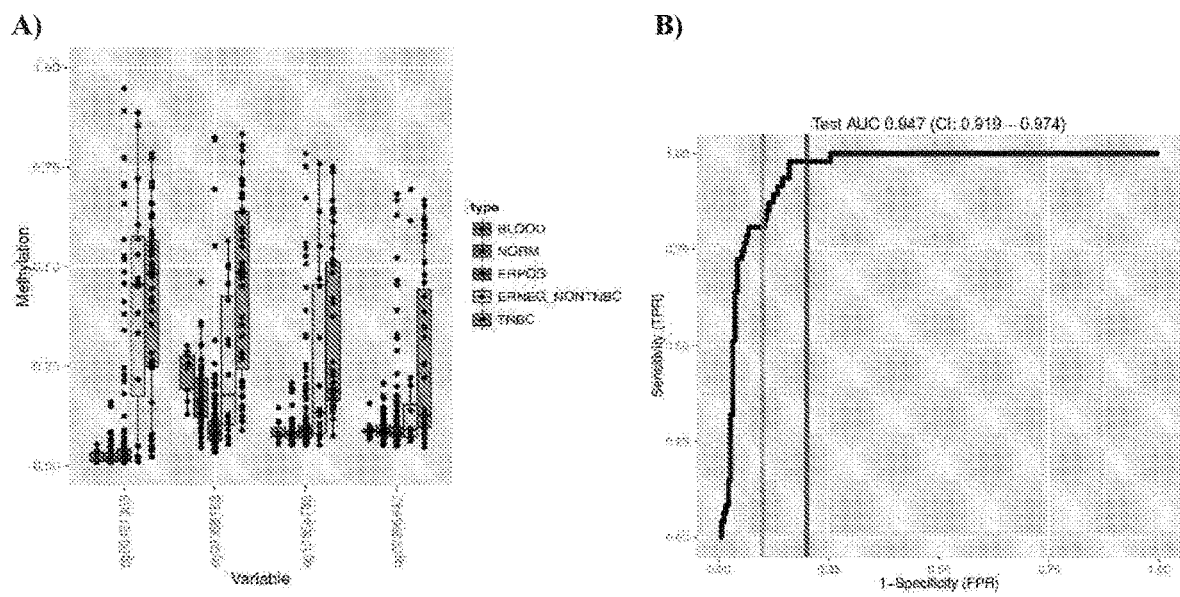
FIG. 62. This figure a) illustrates the distribution of methylation for each of the probes in subset 45 as detailed in Table 12, and b) provides a ROC curve and associated AUC statistics for diagnosing TNBC using probe subset 45.
Figure 63:
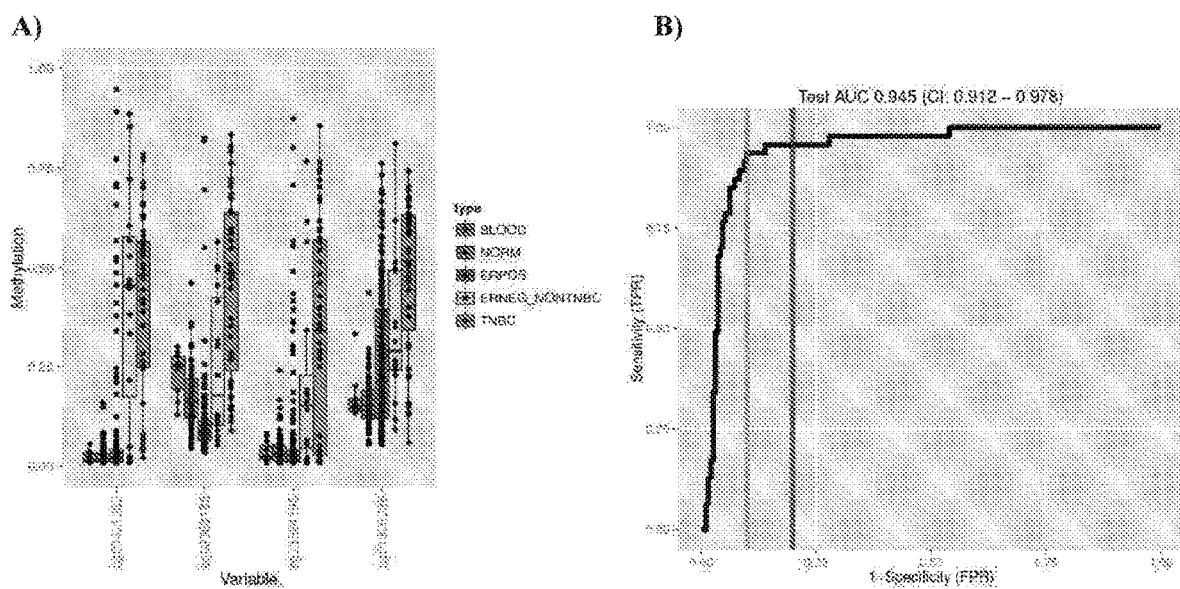
FIG. 63. This figure a) illustrates the distribution of methylation for each of the probes in subset 46 as detailed in Table 12, and b) provides a ROC curve and associated AUC statistics for diagnosing TNBC using probe subset 46.
Figure 64:
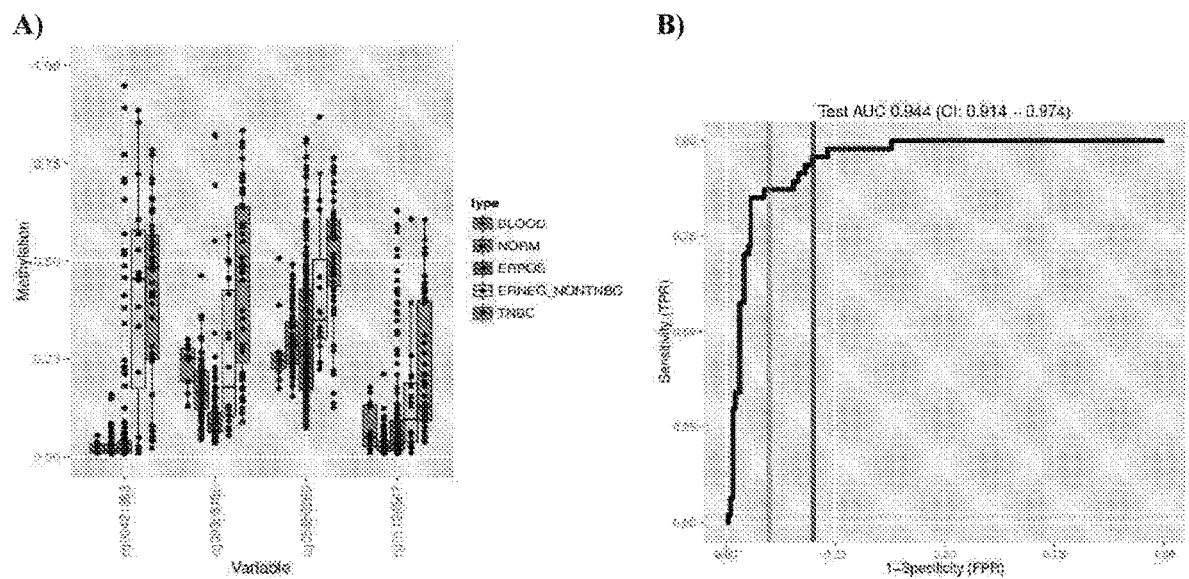
FIG. 64. This figure a) illustrates the distribution of methylation for each of the probes in subset 47 as detailed in Table 12, and b) provides a ROC curve and associated AUC statistics for diagnosing TNBC using probe subset 47.
Figure 65:
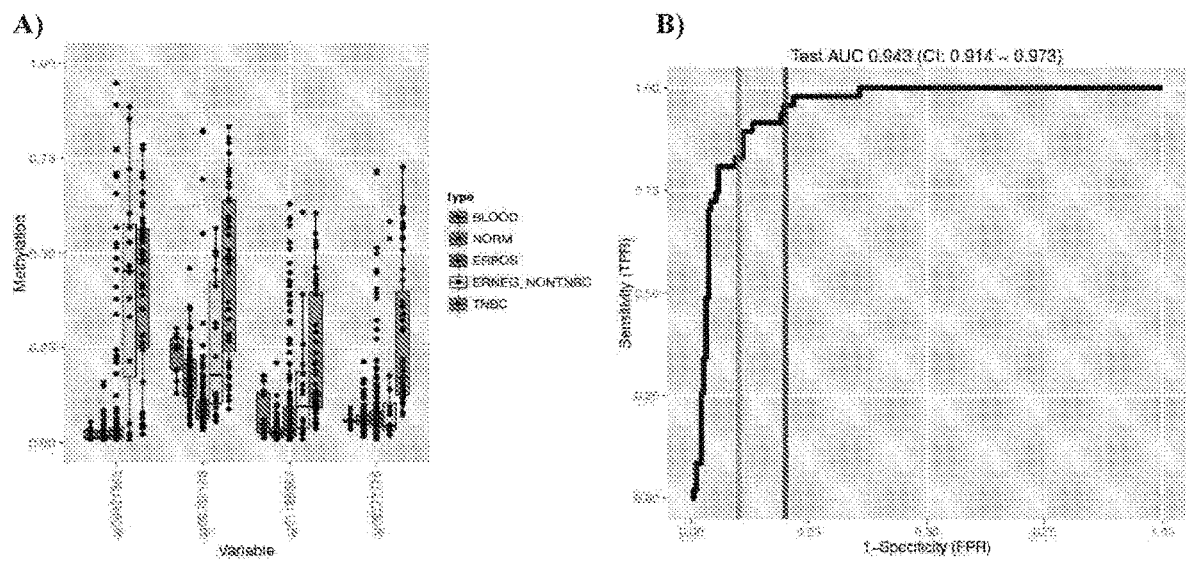
FIG. 65. This figure a) illustrates the distribution of methylation for each of the probes in subset 48 as detailed in Table 12, and b) provides a ROC curve and associated AUC statistics for diagnosing TNBC using probe subset 48.
Figure 66:
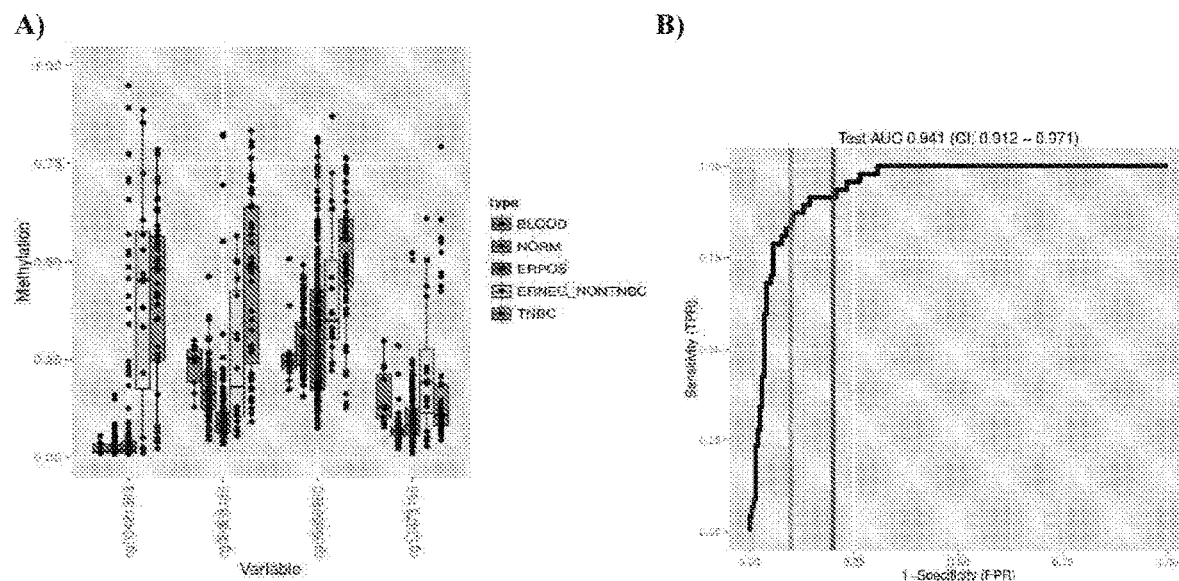
FIG. 66. This figure a) illustrates the distribution of methylation for each of the probes in subset 49 as detailed in Table 12, and b) provides a ROC curve and associated AUC statistics for diagnosing TNBC using probe subset 49.
Figure 67:
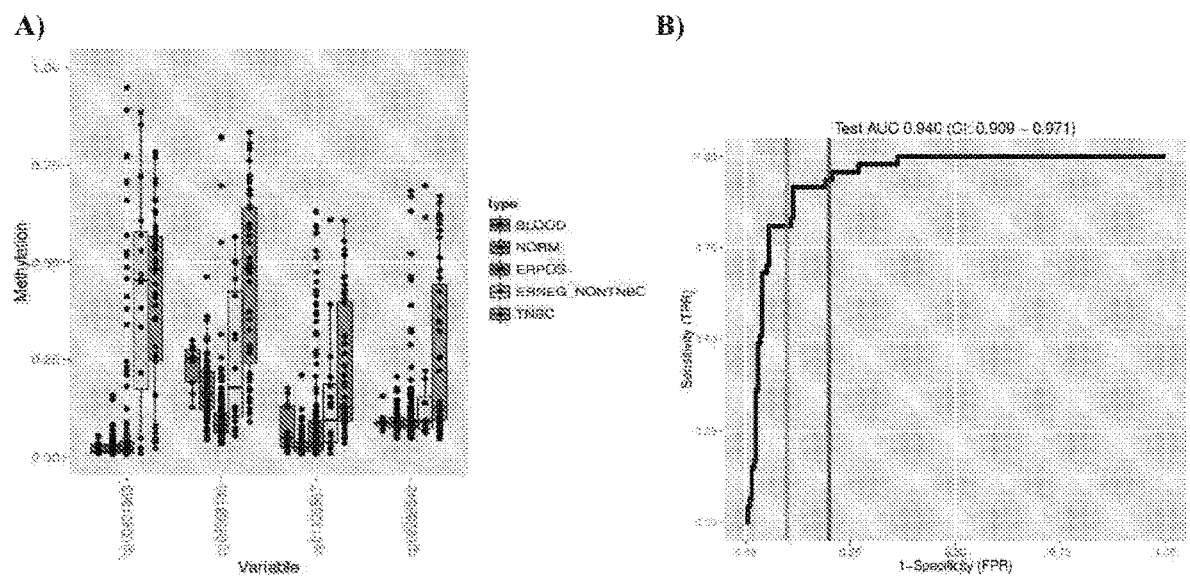
FIG. 67. This figure a) illustrates the distribution of methylation for each of the probes in subset 50 as detailed in Table 12, and b) provides a ROC curve and associated AUC statistics for diagnosing TNBC using probe subset 50.
Figure 68:
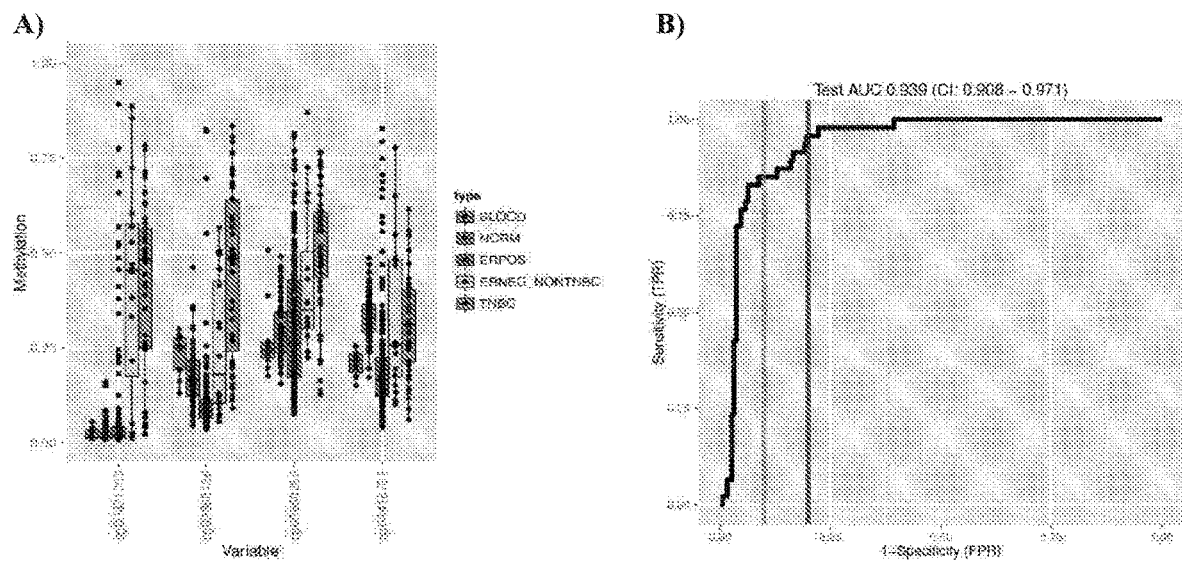
FIG. 68. This figure a) illustrates the distribution of methylation for each of the probes in subset 51 as detailed in Table 12, and b) provides a ROC curve and associated AUC statistics for diagnosing TNBC using probe subset 51.
Figure 69:
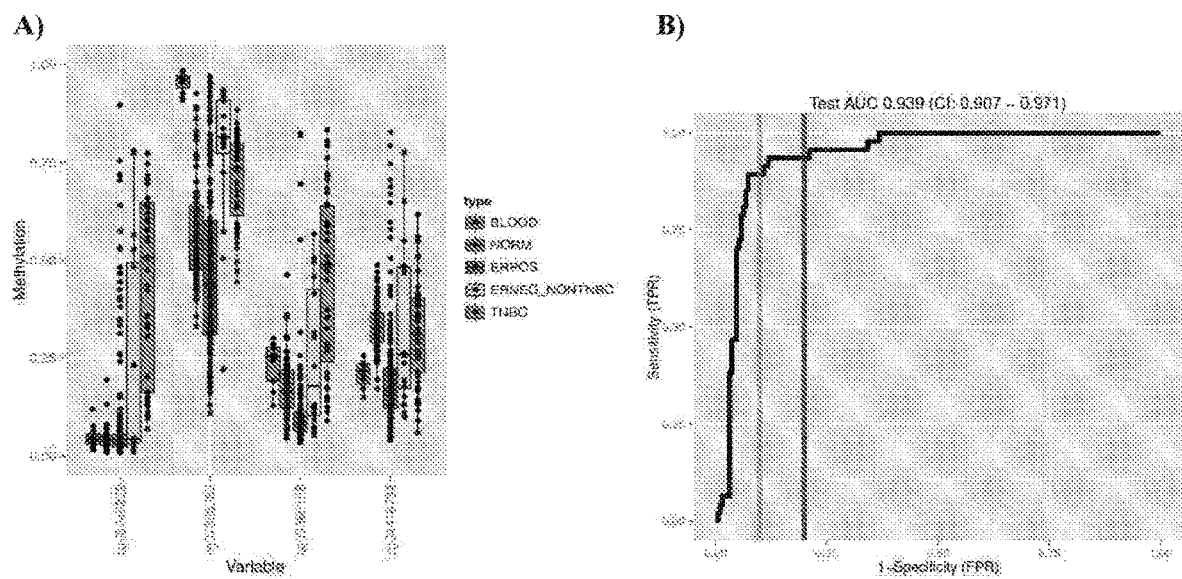
FIG. 69. This figure a) illustrates the distribution of methylation for each of the probes in subset 52 as detailed in Table 12, and b) provides a ROC curve and associated AUC statistics for diagnosing TNBC using probe subset 52.
Figures 70, 71:
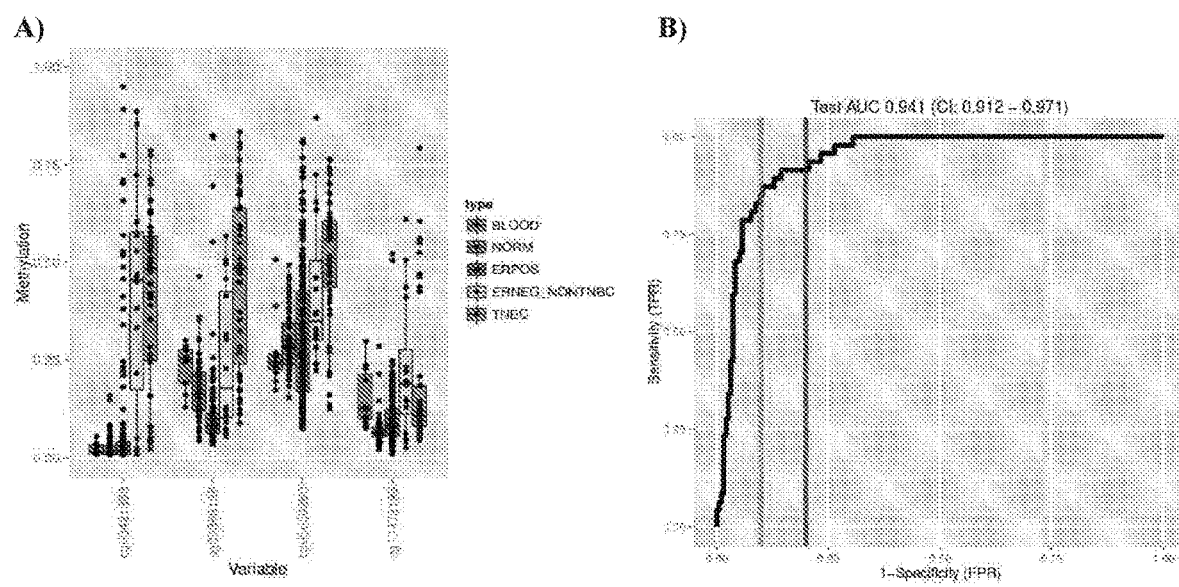
FIG. 70. This figure a) illustrates the distribution of methylation for each of the probes in subset 53 as detailed in Table 12, and b) provides a ROC curve and associated AUC statistics for diagnosing TNBC using probe subset 53.
FIG. 71. This figure a) illustrates the distribution of methylation for each of the probes in subset 54 as detailed in Table 12, and b) provides a ROC curve and associated AUC statistics for diagnosing TNBC using probe subset 54.
Figure 72:
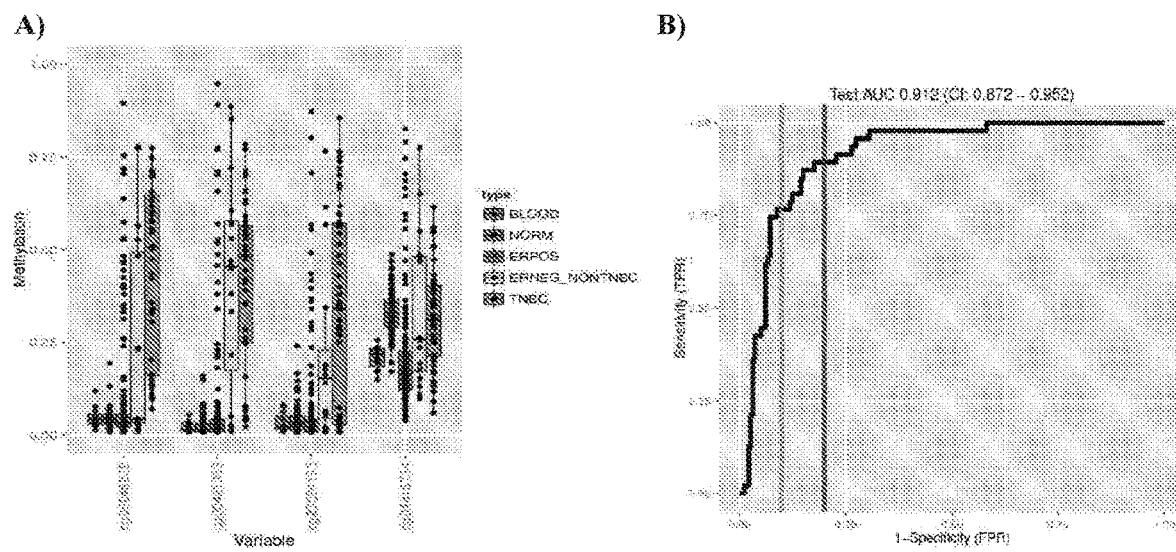
FIG. 72. This figure a) illustrates the distribution of methylation for each of the probes in subset 55 as detailed in Table 12, and b) provides a ROC curve and associated AUC statistics for diagnosing TNBC using probe subset 55.
Figure 73:
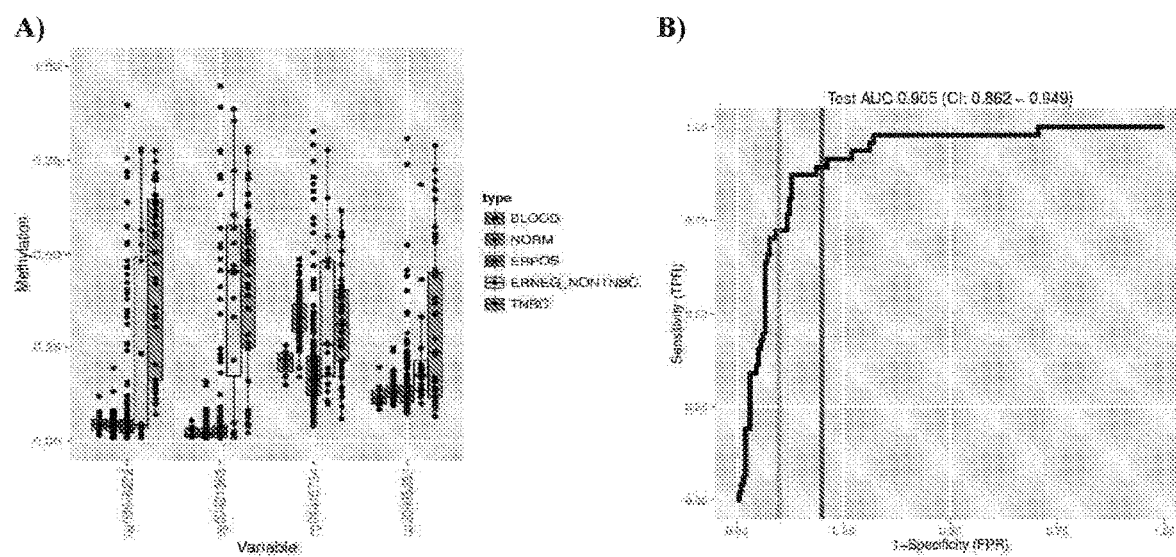
FIG. 73. This figure a) illustrates the distribution of methylation for each of the probes in subset 56 as detailed in Table 12, and b) provides a ROC curve and associated AUC statistics for diagnosing TNBC using probe subset 56.
Figure 74:
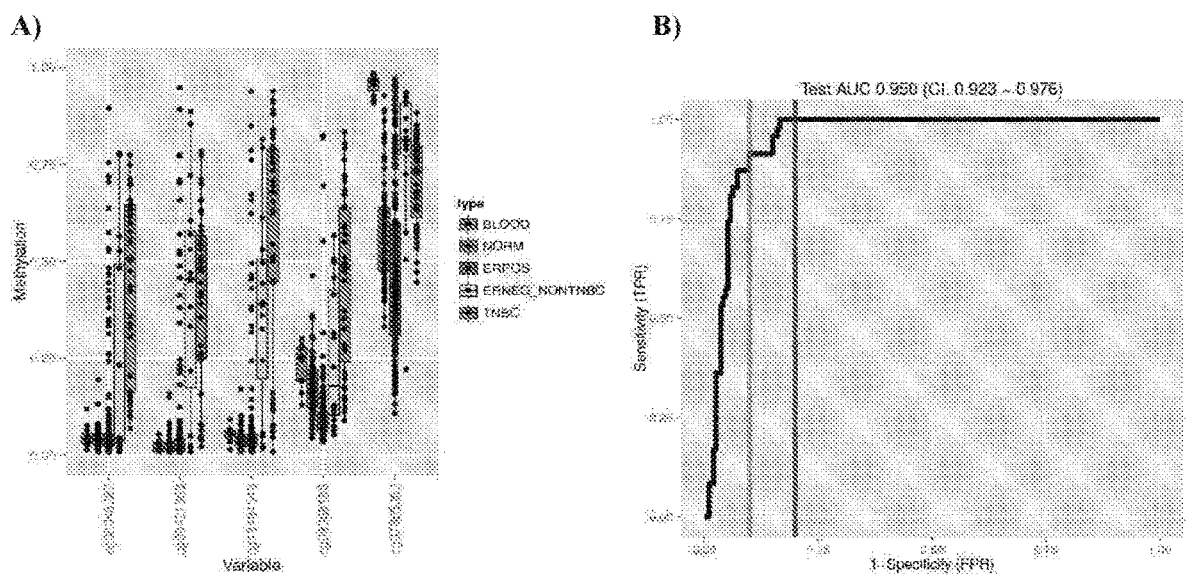
FIG. 74. This figure a) illustrates the distribution of methylation for each of the probes in subset 57 as detailed in Table 12, and b) provides a ROC curve and associated AUC statistics for diagnosing TNBC using probe subset 57.
Figure 75:
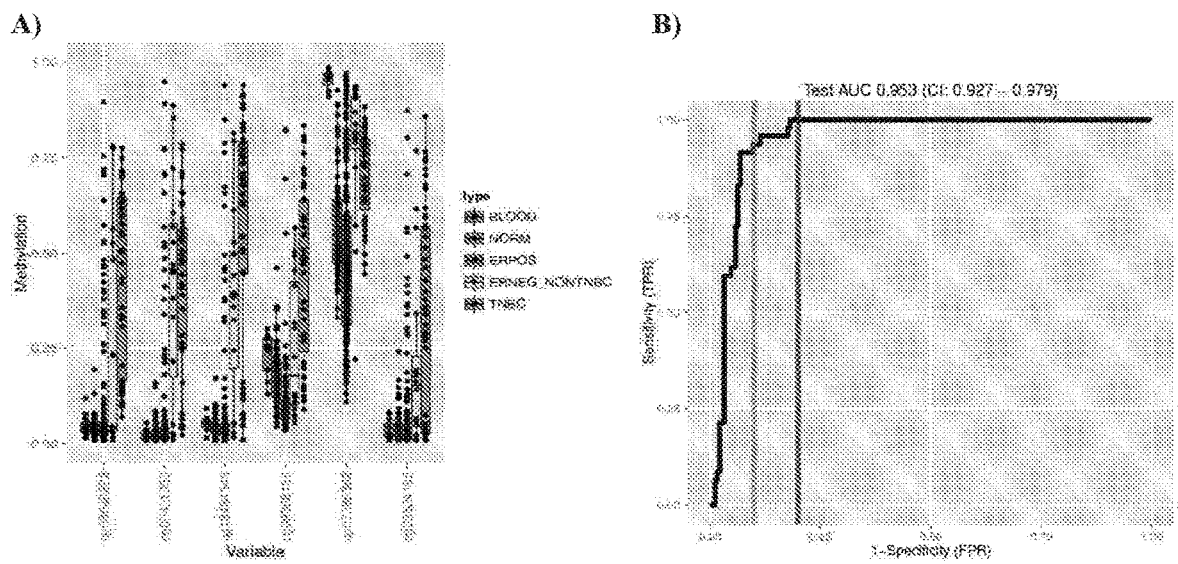
FIG. 75. This figure a) illustrates the distribution of methylation for each of the probes in subset 58 as detailed in Table 12, and b) provides a ROC curve and associated AUC statistics for diagnosing TNBC using probe subset 58.
Figure 76:
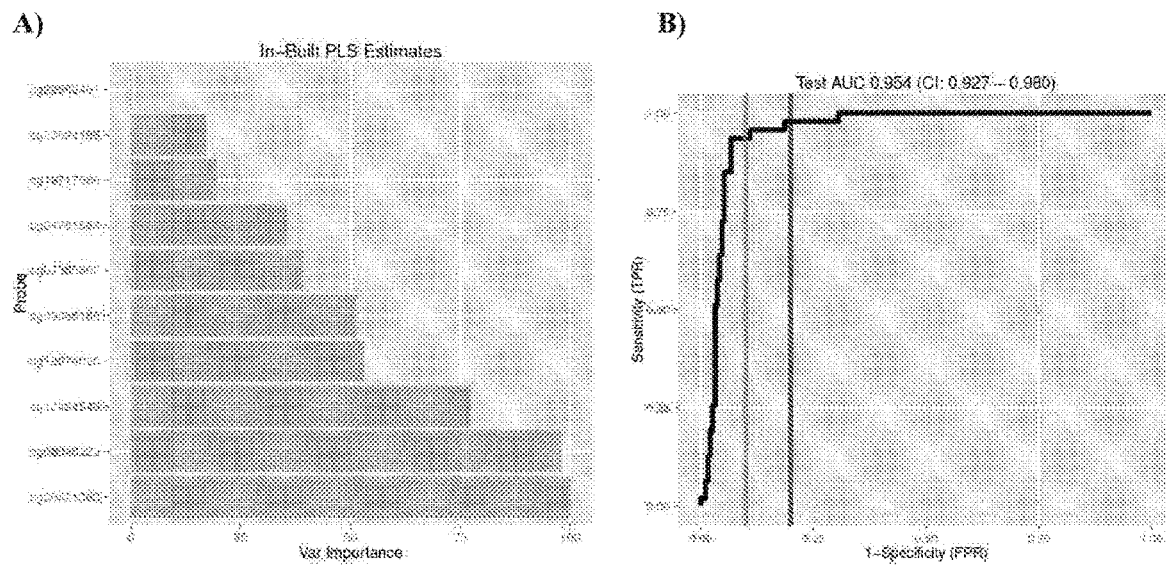
FIG. 76. This figure a) shows the importance of probes in subset 59 (s detailed in Table 12) to the diagnostic methylation signature of that subset based on In-built PLS estimates, and b) provides a ROC curve and associated AUC statistics for diagnosing TNBC using probe subset 59.
Figure 77:
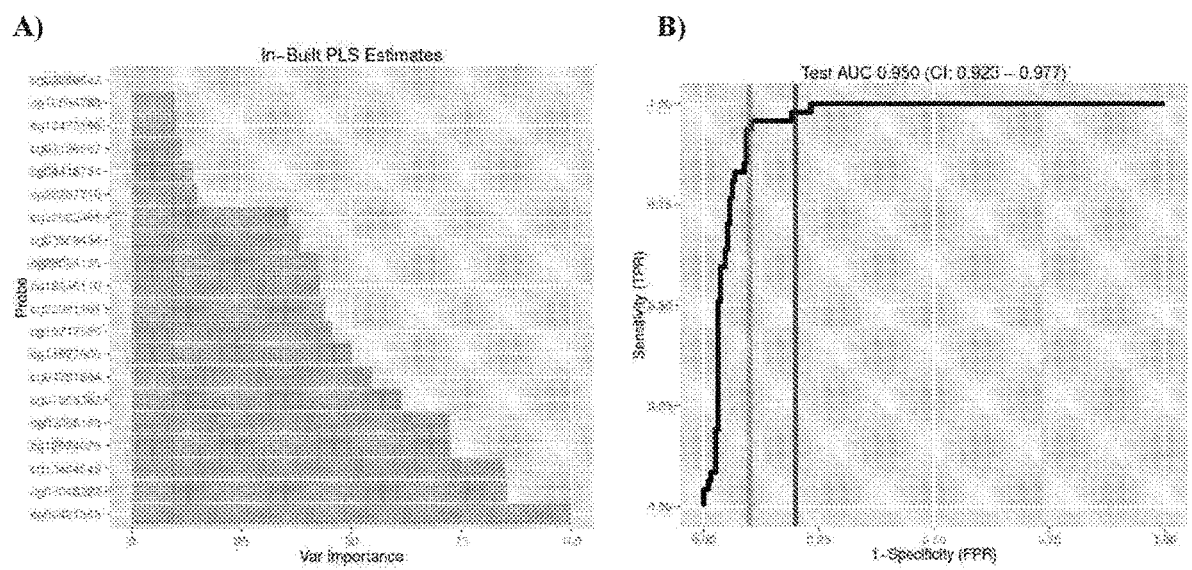
FIG. 77. This figure a) shows the importance of probes in subset 60 (s detailed in Table 12) to the diagnostic methylation signature of that subset based on In-built PLS estimates, and b) provides a ROC curve and associated AUC statistics for diagnosing TNBC using probe subset 60.
Figure 78:
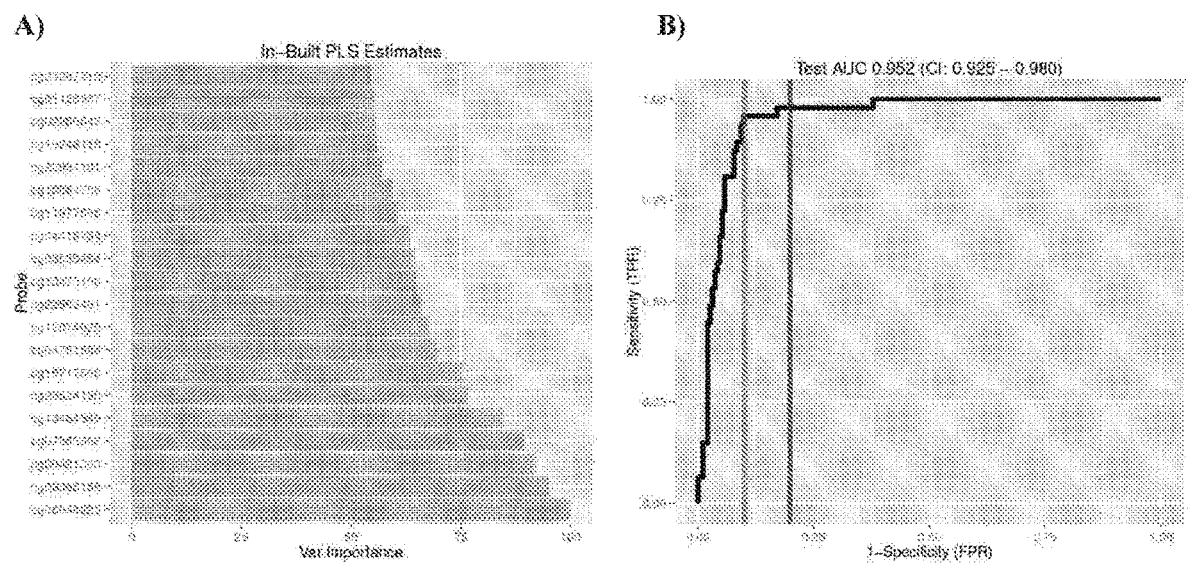
FIG. 78. This figure a) shows the importance of probes in subset 60 (s detailed in Table 12) to the diagnostic methylation signature of that subset based on In-built PLS estimates, and b) provides a ROC curve and associated AUC statistics for diagnosing TNBC using probe subset 61.

Detailed performance summaries of (i) three representative two-probe signatures which performed particularly well are provided in FIGS. 18-20, respectively, (ii) three representative three-probe signatures which performed particularly well are provided in FIGS. 21-23, respectively, and (iii) three representative four-probe signatures which performed particularly well are provided in FIGS. 44-46, respectively. Each of FIGS. 18-23 and 44-46 show the distribution of methylation values across the probes in the model, as well as ROC curves and associated AUC statistics for diagnosing TNBC using the respective probe subset. Similar performance summaries for the remaining unique diagnostic signatures described in Table 12 are provided in FIGS. 24-43 and 45-78.

Models which performed particularly well comprised the following HM450K probes:

cg0804822—promoter of ZNF671
cg09368188—intronic region of KIF26B
cg00421363—promoter region of PPFIA3
cg04781584—promoter region of PPFIA3
cg03559454—promoter region of PPFIA3
cg01926238—distant promoter of VGLL2
cg05650260—intronic region of TFAP2D
cg04416734—exonic region of ALDOA

Example 6: Enumerating Diagnostic Signatures With Discrete Methylation Values 6.1 Method In this example, the inventors determined whether the numerical methylation values (fraction of methylated molecules which is between 0 and 1) could be reduced from the HM450K array to three methylation categories (Category_1: 0.00-0.25, Category_2: 0.25-0.50, and Category_3: 0.50-1.00) to increase the applicability in the clinical setting.

6.1.1 Modelling and Signature Enumeration Strategies

Computational approaches similar to those described in Example 5 were used to model and enumerate the diagnostic signatures. The only modification to the approach previously described is that probes that showed methylation values greater than 25% in 10 or more tissue normal samples were also excluded. This further exclusion resulted in subset of 181 probes.

Figure 79:
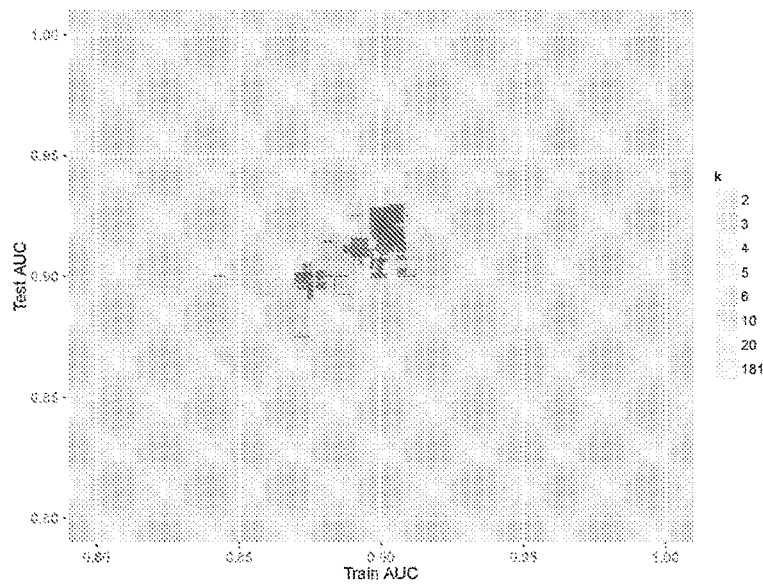
FIG. 79. This figure provides a performance evaluation for 40 methylation signatures, with each data point corresponding to a unique methylation signature. Each data point is represented with respect to its corresponding model AUC on train (Train AUC) and test (Test AUC) datasets. The signatures are color-coded by the number of variables (i.e., probes) in the model. The plot also shows the performance of PLS model trained on the whole dataset as well as on 5, 6, 10, and 20 most important probes.

6.2 Results 40 unique diagnostic signatures were identified using the approach described (FIG. 79). Based on the data presented in FIG. 79, it is apparent that a number of the three-probe and four-probe diagnostic signatures performed almost as well as the full PLS model on the test dataset.

A summary of the 40 possible diagnostic CpG methylation signatures is provided in Table 13.

TABLE 13

Summary of different diagnostic CpG methylation signatures

| Subset ID | Probes in subset | AUC | No of Probes | FIG. |
|---|---|---|---|---|
| 1 | cg11977686 + cg13484549 | 0.897 | 2 | 80 |
| 2 | cg08048222 + cg13484549 | 0.895 | 2 | 81 |
| 3 | cg00421363 + cg08048222 | 0.868 | 2 | 82 |
| 4 | cg00421363 + cg11977686 | 0.867 | 2 | 83 |
| 5 | cg00421363 + cg13484549 | 0.825 | 2 | 84 |
| 6 | cg08048222 + cg11977686 | 0.798 | 2 | 85 |
| 7 | cg01926238 + cg08048222 + cg13484549 | 0.927 | 3 | 86 |
| 8 | cg08048222 + cg08398233 + cg13484549 | 0.911 | 3 | 87 |
| 9 | cg00421363 + cg01926238 + cg08048222 | 0.908 | 3 | 88 |
| 10 | cg08048222 + cg13484549 + cg20095233 | 0.902 | 3 | 89 |
| 11 | cg08048222 + cg13484549 + cg23524195 | 0.901 | 3 | 90 |
| 12 | cg00421363 + cg08048222 + cg17268801 | 0.898 | 3 | 91 |
| 13 | cg08048222 + cg13473196 + cg13484549 | 0.898 | 3 | 92 |
| 14 | cg00421363 + cg08048222 + cg20095233 | 0.894 | 3 | 93 |
| 15 | cg00421363 + cg08048222 + cg23524195 | 0.892 | 3 | 94 |
| 16 | cg00421363 + cg08048222 + cg08398233 | 0.889 | 3 | 95 |
| 17 | cg00421363 + cg08048222 + cg13473196 | 0.873 | 3 | 96 |
| 18 | cg01926238 + cg07802350 + cg08048222 + cg13484549 | 0.926 | 4 | 97 |
| 19 | cg01926238 + cg08048222 + cg13484549 + cg20095233 | 0.924 | 4 | 98 |
| 20 | cg01926238 + cg08048222 + cg13473196 + cg13484549 | 0.924 | 4 | 99 |
| 21 | cg01926238 + cg07091412 + cg08048222 + cg13484549 | 0.924 | 4 | 100 |
| 22 | cg01926238 + cg08048222 + cg13484549 + cg23524195 | 0.921 | 4 | 101 |
| 23 | cg01926238 + cg02809746 + cg08048222 + cg13484549 | 0.921 | 4 | 102 |
| 24 | cg02286642 + cg08048222 + cg13484549 + cg20095233 | 0.919 | 4 | 103 |
| 25 | cg08048222 + cg08398233 + cg13484549 + cg19717586 | 0.917 | 4 | 104 |
| 26 | cg00421363 + cg02286642 + cg08048222 + cg20095233 | 0.914 | 4 | 105 |
| 27 | cg00421363 + cg01926238 + cg08048222 + cg20095233 | 0.914 | 4 | 106 |
| 28 | cg08048222 + cg08398233 + cg13473196 + cg13484549 | 0.913 | 4 | 107 |
| 29 | cg00421363 + cg01926238 + cg08048222 + cg23524195 | 0.912 | 4 | 108 |
| 30 | cg00421363 + cg08048222 + cg17268801 + cg20095233 | 0.912 | 4 | 109 |
| 31 | cg01926238 + cg08048222 + cg08398233 + cg13484549 | 0.911 | 4 | 110 |
| 32 | cg00421363 + cg01926238 + cg07091412 + cg08048222 | 0.910 | 4 | 111 |
| 33 | cg00421363 + cg08048222 + cg17268801 + cg23524195 | 0.909 | 4 | 112 |
| 34 | cg08048222 + cg08398233 + cg13484549 + cg23524195 | 0.907 | 4 | 113 |
| 35 | cg00421363 + cg01926238 + cg08048222 + cg13473196 | 0.905 | 4 | 114 |
| 36 | cg00421363 + cg01926238 + cg02809746 + cg08048222 | 0.904 | 4 | 115 |
| 37 | cg08048222 + cg08398233 + cg13484549 + cg20095233 | 0.903 | 4 | 116 |
| 38 | cg00421363 + cg01926238 + cg08048222 + cg08398233 | 0.899 | 4 | 117 |
| 39 | cg00421363 + cg08048222 + cg08398233 + cg20095233 | 0.897 | 4 | 118 |
| 40 | cg00421363 + cg08048222 + cg13473196 + cg20095233 | 0.896 | 4 | 119 |

TABLE 13-continued

Summary of different diagnostic CpG methylation signatures

| Subset ID | Probes in subset | AUC | No of Probes | FIG. |
|---|---|---|---|---|
| 41 | s5 | 0.918 | 5 | 120 |
| 42 | s6 | 0.918 | 6 | 121 |
| 43 | s10 | 0.916 | 10 | 122 |
| 44 | s20 | 0.917 | 20 | 123 |
| 45 | full | 0.934 | 181 | 124 |

Figure 80:
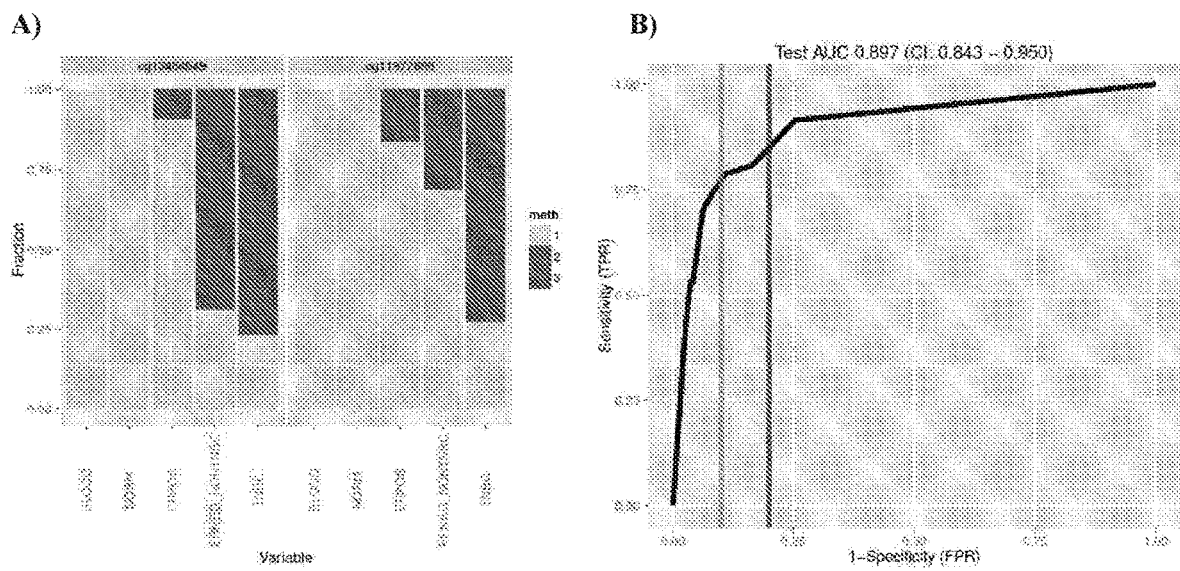
FIG. 80. This figure a) illustrates the distribution of methylation for each of the probes in subset 1 as detailed in Table 13, and b) provides a ROC curve and associated AUC statistics for diagnosing TNBC using probe subset 1.
Figure 81:
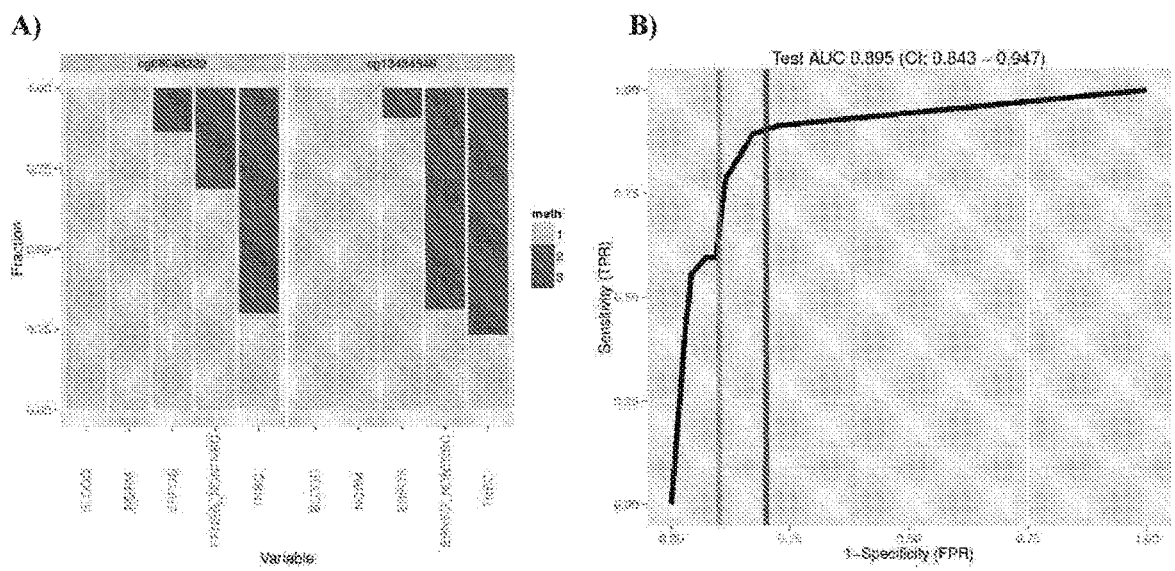
FIG. 81. This figure a) illustrates the distribution of methylation for each of the probes in subset 2 as detailed in Table 13, and b) provides a ROC curve and associated AUC statistics for diagnosing TNBC using probe subset 2.
Figure 82:
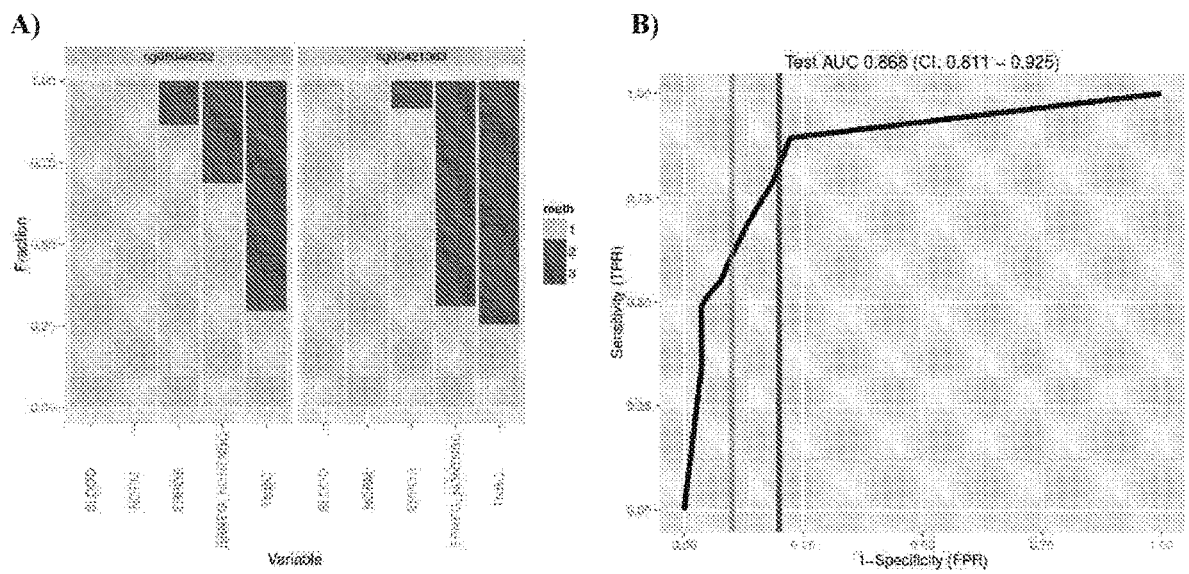
FIG. 82. This figure a) illustrates the distribution of methylation for each of the probes in subset 3 as detailed in Table 13, and b) provides a ROC curve and associated AUC statistics for diagnosing TNBC using probe subset 3.
Figure 83:
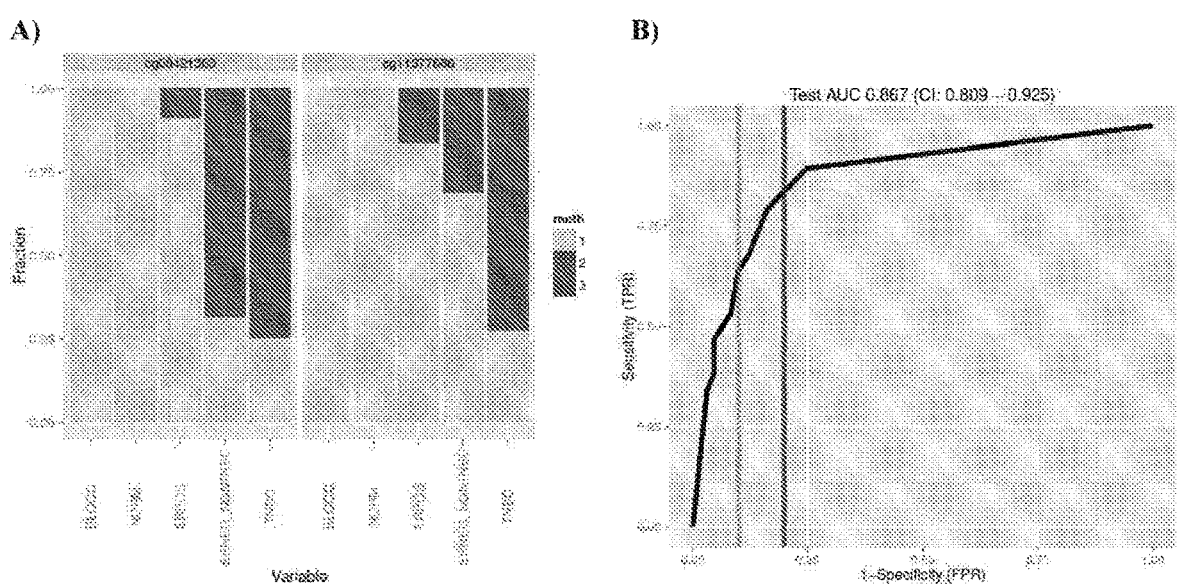
FIG. 83. This figure a) illustrates the distribution of methylation for each of the probes in subset 4 as detailed in Table 13, and b) provides a ROC curve and associated AUC statistics for diagnosing TNBC using probe subset 4.
Figure 84:
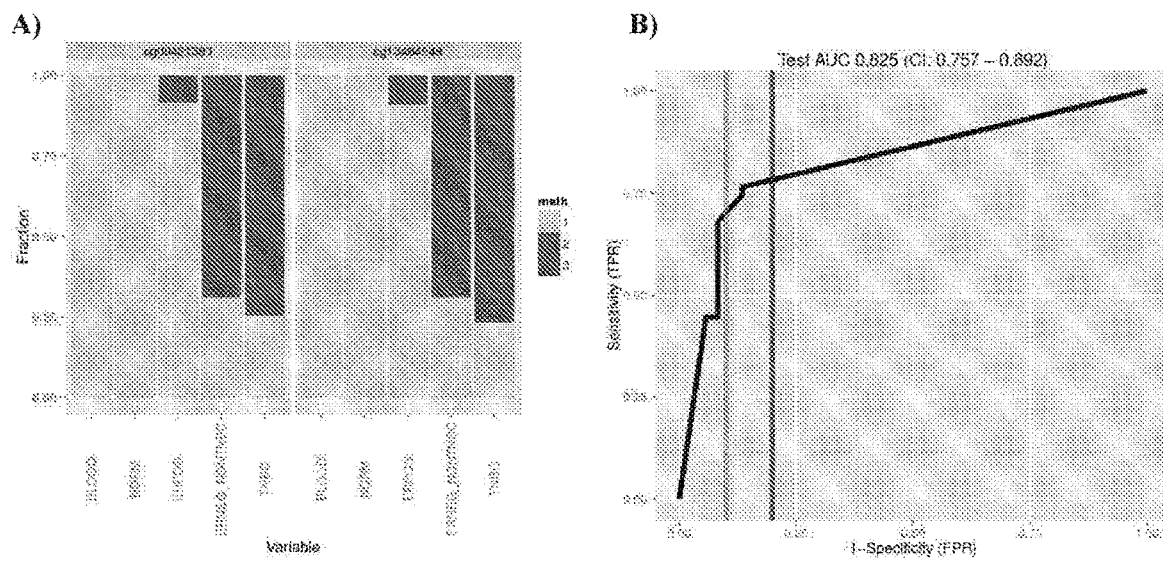
FIG. 84. This figure a) illustrates the distribution of methylation for each of the probes in subset 5 as detailed in Table 13, and b) provides a ROC curve and associated AUC statistics for diagnosing TNBC using probe subset 5.
Figure 85:
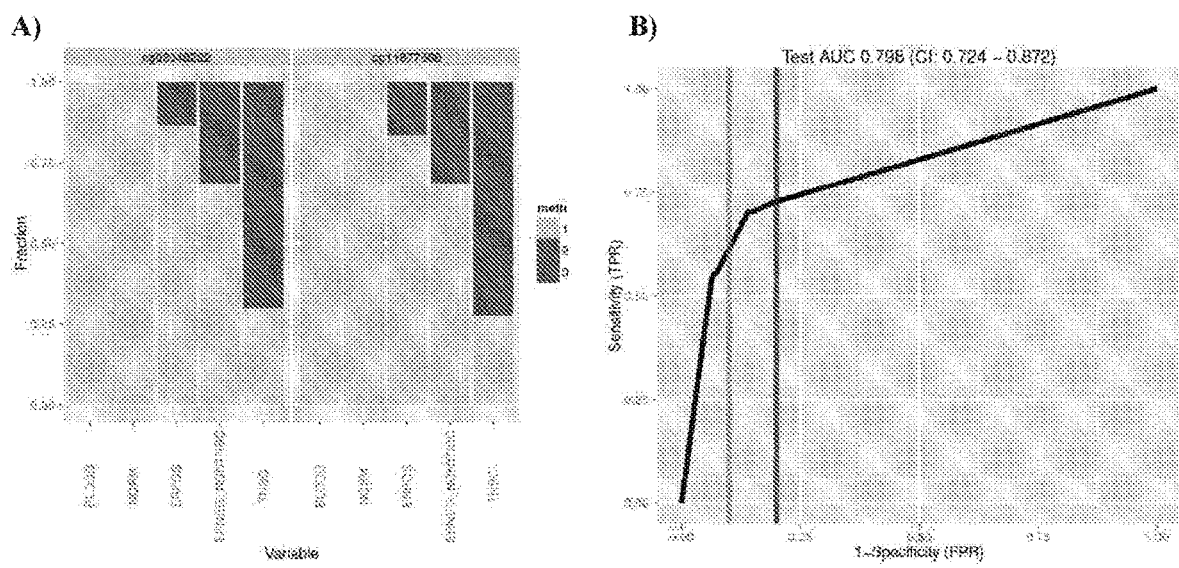
FIG. 85. This figure a) illustrates the distribution of methylation for each of the probes in subset 6 as detailed in Table 13, and b) provides a ROC curve and associated AUC statistics for diagnosing TNBC using probe subset 6.
Figure 86:
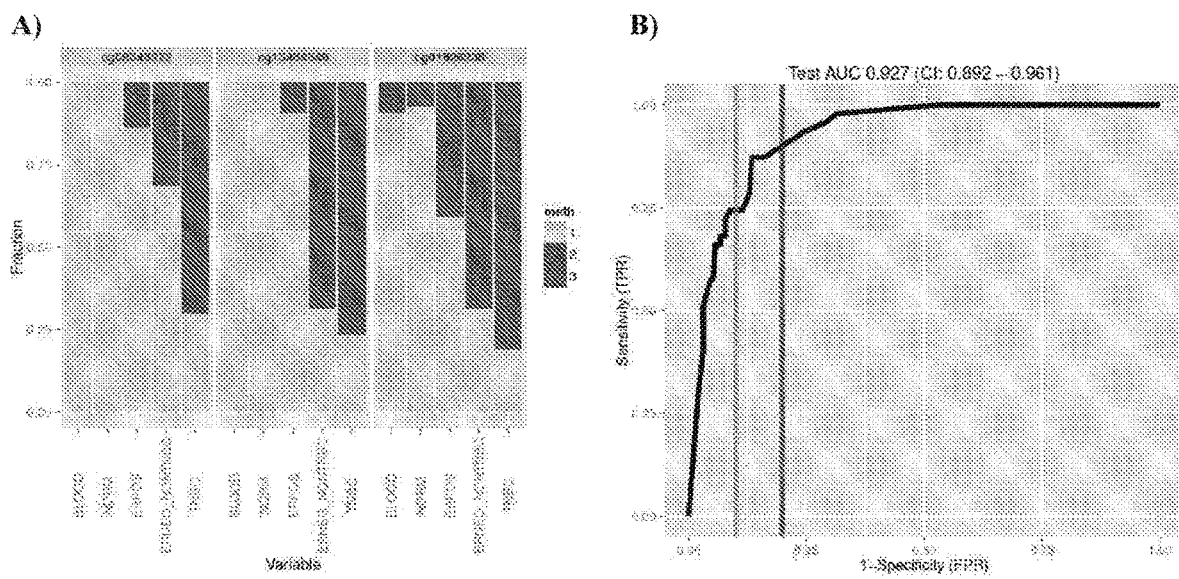
FIG. 86. This figure a) illustrates the distribution of methylation for each of the probes in subset 7 as detailed in Table 13, and b) provides a ROC curve and associated AUC statistics for diagnosing TNBC using probe subset 7.
Figure 87:
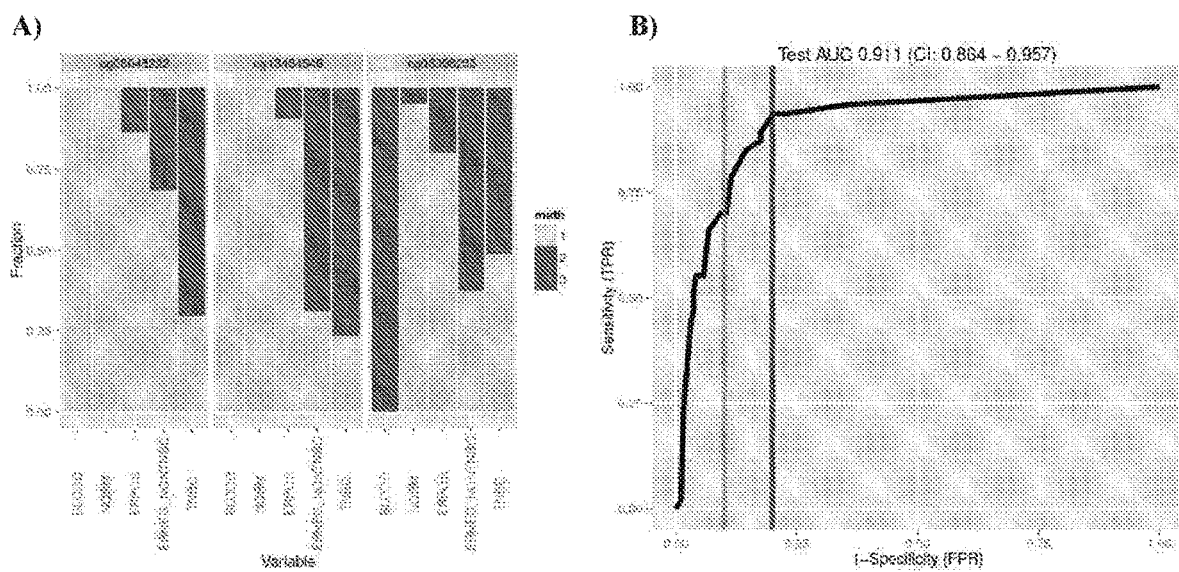
FIG. 87. This figure a) illustrates the distribution of methylation for each of the probes in subset 8 as detailed in Table 13, and b) provides a ROC curve and associated AUC statistics for diagnosing TNBC using probe subset 8.
Figure 88:
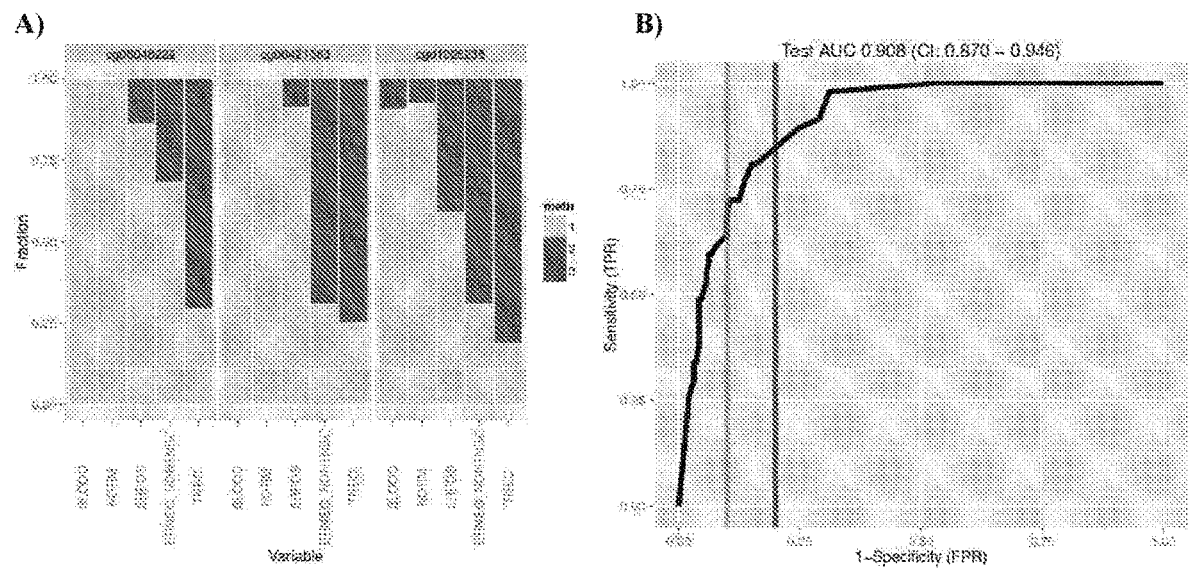
FIG. 88. This figure a) illustrates the distribution of methylation for each of the probes in subset 9 as detailed in Table 13, and b) provides a ROC curve and associated AUC statistics for diagnosing TNBC using probe subset 9.
Figure 89:
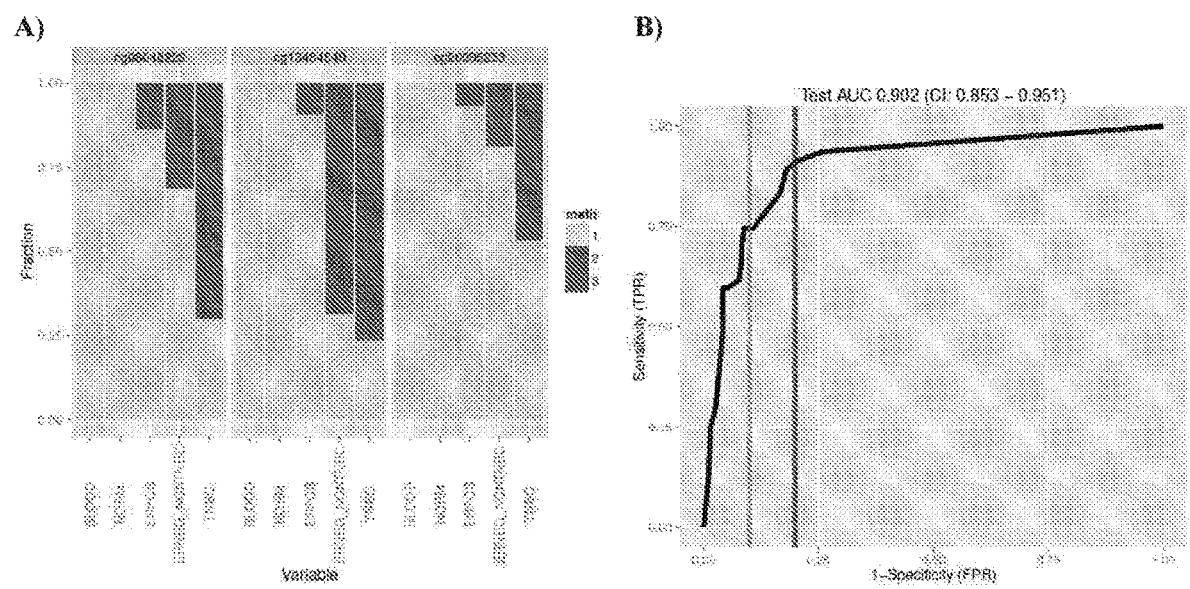
FIG. 89. This figure a) illustrates the distribution of methylation for each of the probes in subset 10 as detailed in Table 13, and b) provides a ROC curve and associated AUC statistics for diagnosing TNBC using probe subset 10.
Figure 90:
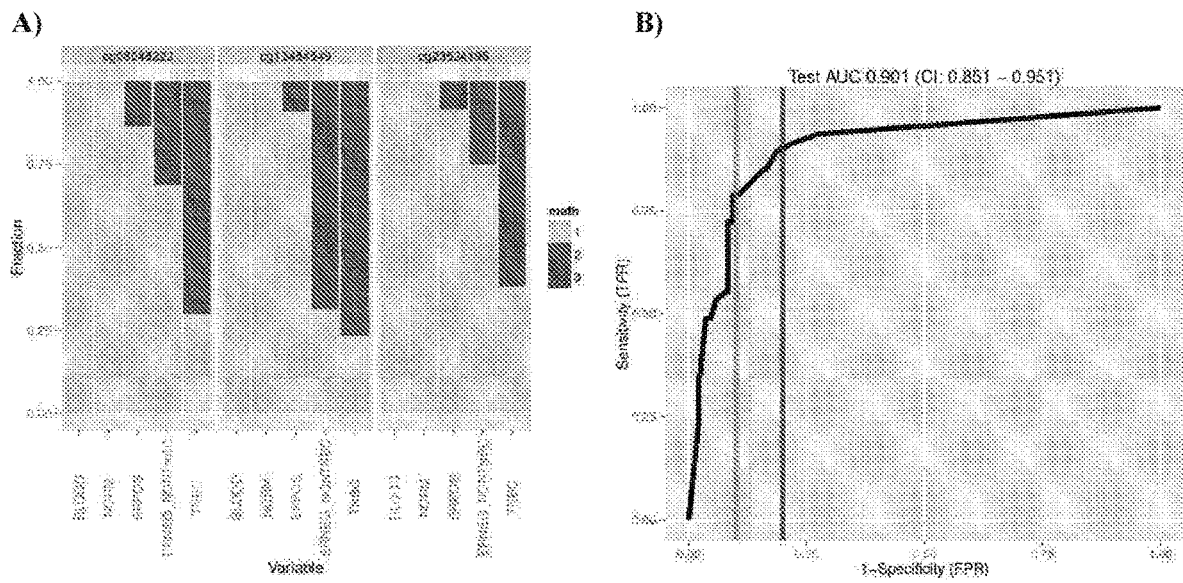
FIG. 90. This figure a) illustrates the distribution of methylation for each of the probes in subset 11 as detailed in Table 13, and b) provides a ROC curve and associated AUC statistics for diagnosing TNBC using probe subset 11.
Figure 91:
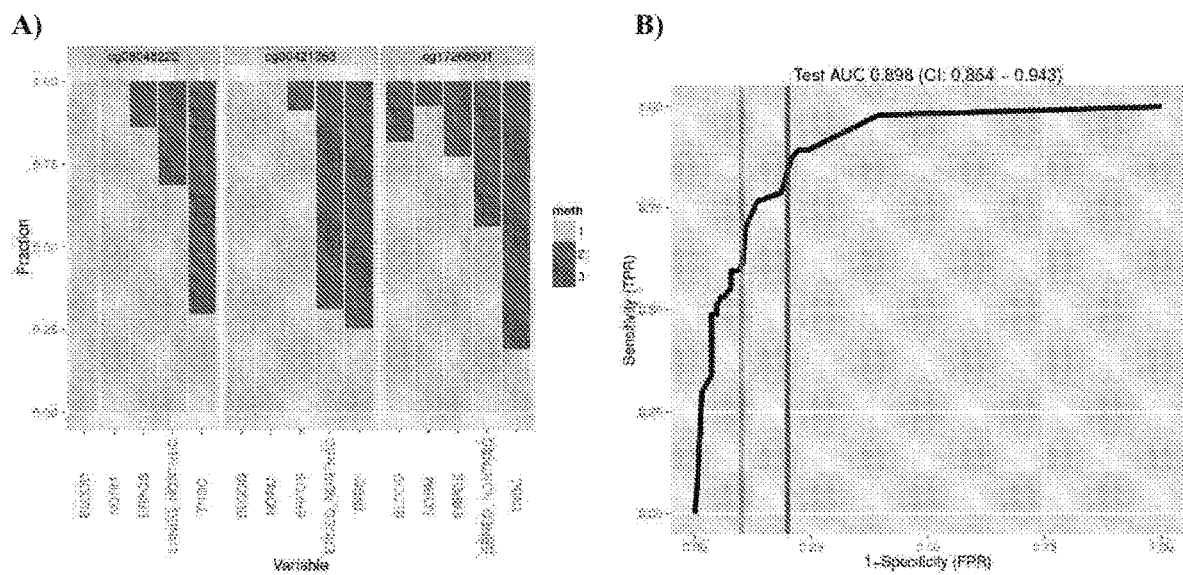
FIG. 91. This figure a) illustrates the distribution of methylation for each of the probes in subset 12 as detailed in Table 13, and b) provides a ROC curve and associated AUC statistics for diagnosing TNBC using probe subset 12.
Figure 92:
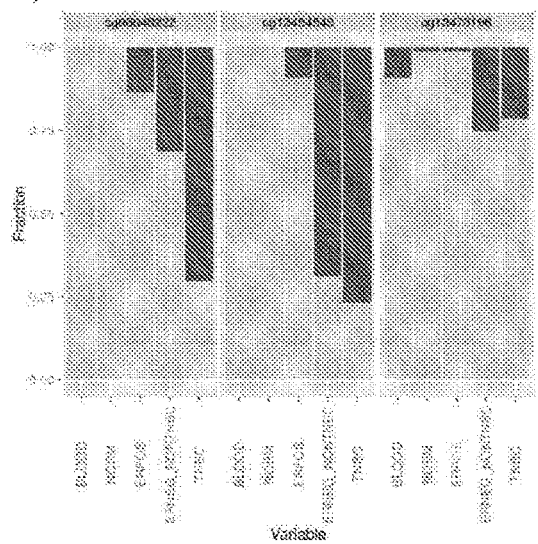
FIG. 92. This figure a) illustrates the distribution of methylation for each of the probes in subset 13 as detailed in Table 13, and b) provides a ROC curve and associated AUC statistics for diagnosing TNBC using probe subset 13.
Figure 92:
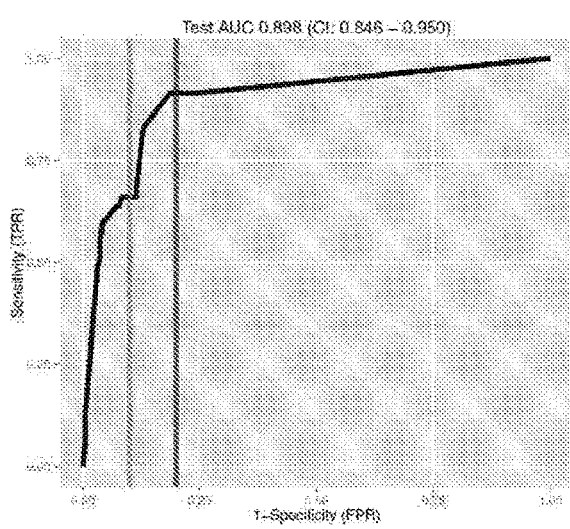
Figure 93:
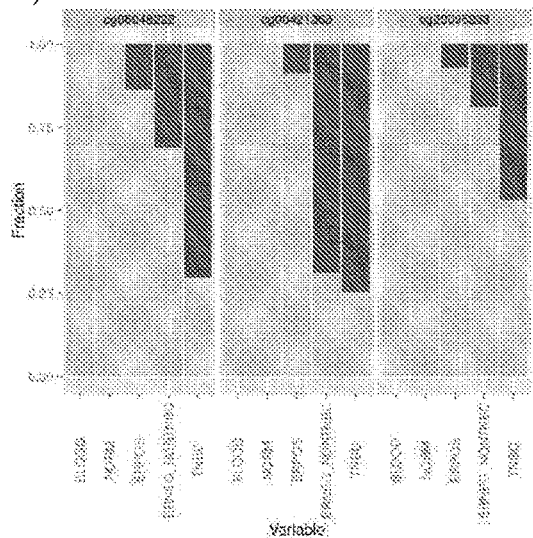
FIG. 93. This figure a) illustrates the distribution of methylation for each of the probes in subset 14 as detailed in Table 13, and b) provides a ROC curve and associated AUC statistics for diagnosing TNBC using probe subset 14.
Figure 93:
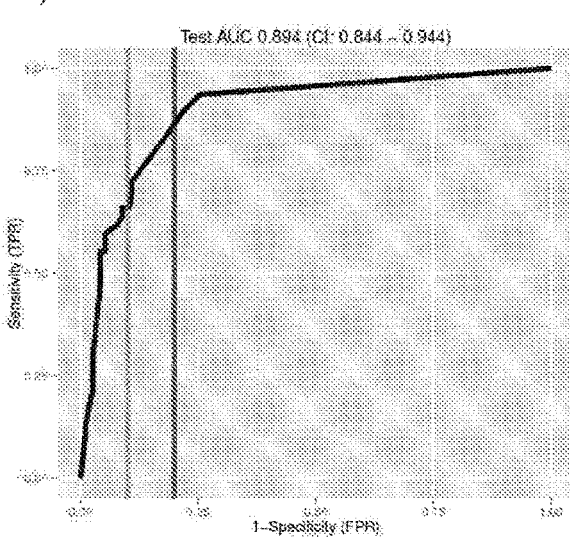
Figure 94:
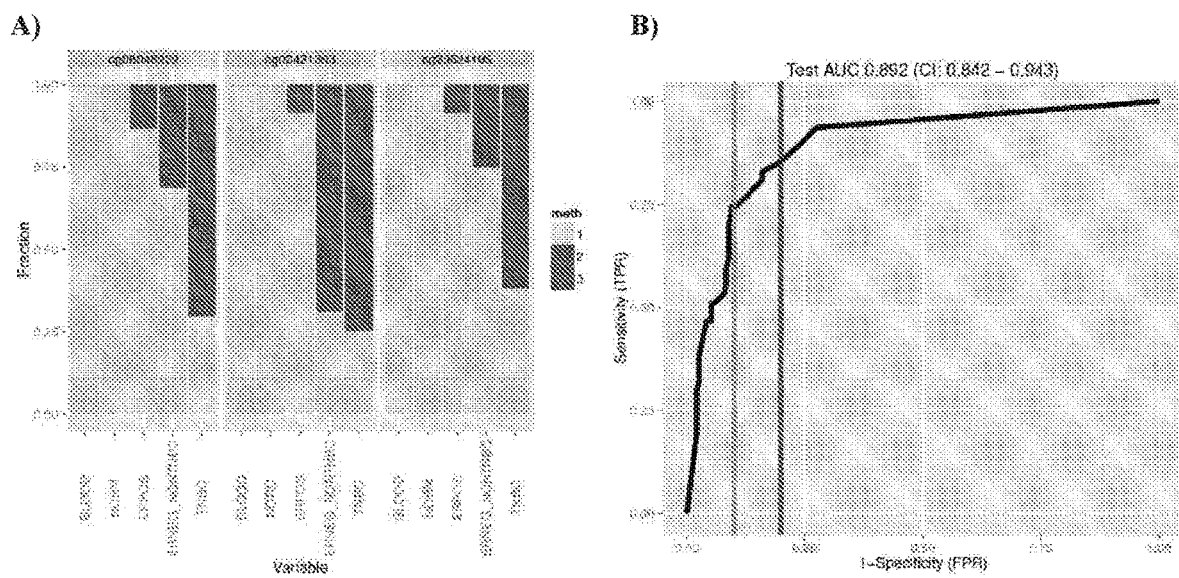
FIG. 94. This figure a) illustrates the distribution of methylation for each of the probes in subset 15 as detailed in Table 13, and b) provides a ROC curve and associated AUC statistics for diagnosing TNBC using probe subset 15.
Figure 95:
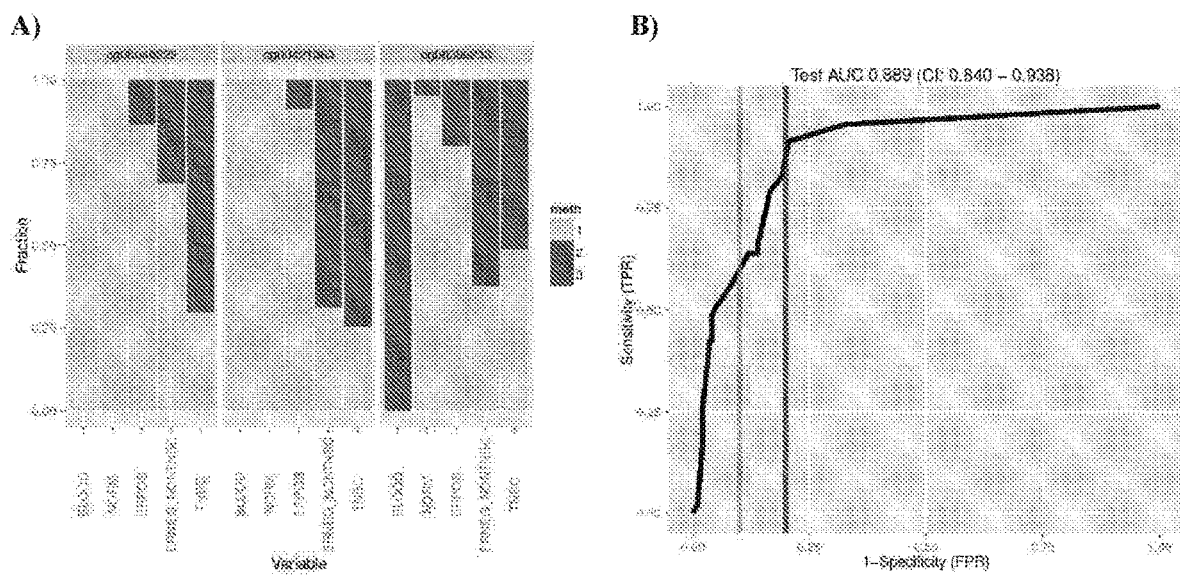
FIG. 95. This figure a) illustrates the distribution of methylation for each of the probes in subset 16 as detailed in Table 13, and b) provides a ROC curve and associated AUC statistics for diagnosing TNBC using probe subset 16.
Figure 96:
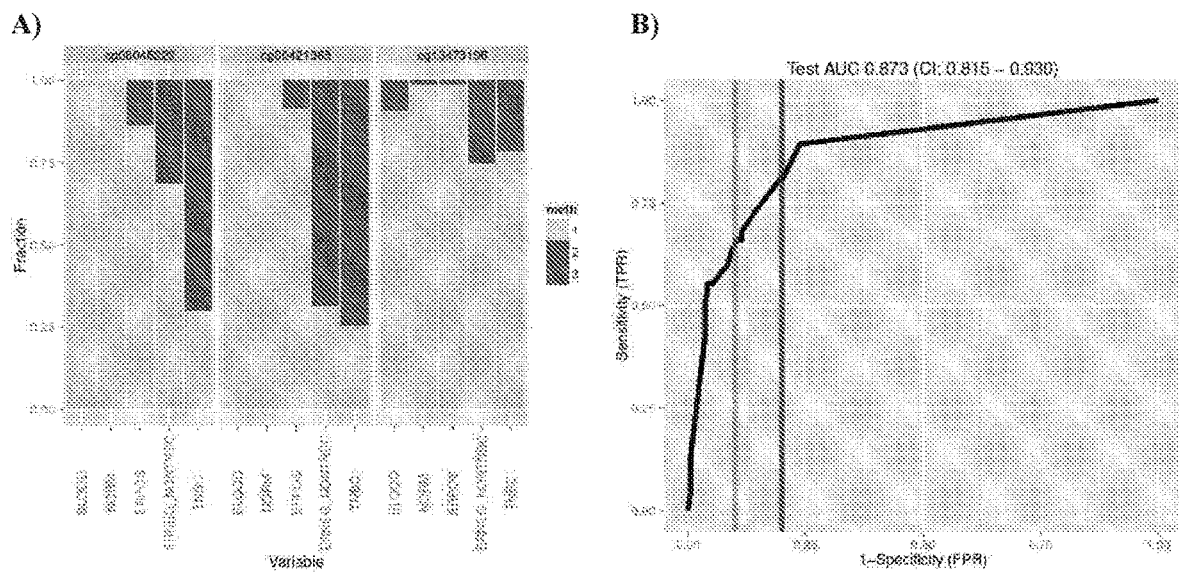
FIG. 96. This figure a) illustrates the distribution of methylation for each of the probes in subset 17 as detailed in Table 13, and b) provides a ROC curve and associated AUC statistics for diagnosing TNBC using probe subset 17.
Figure 97:
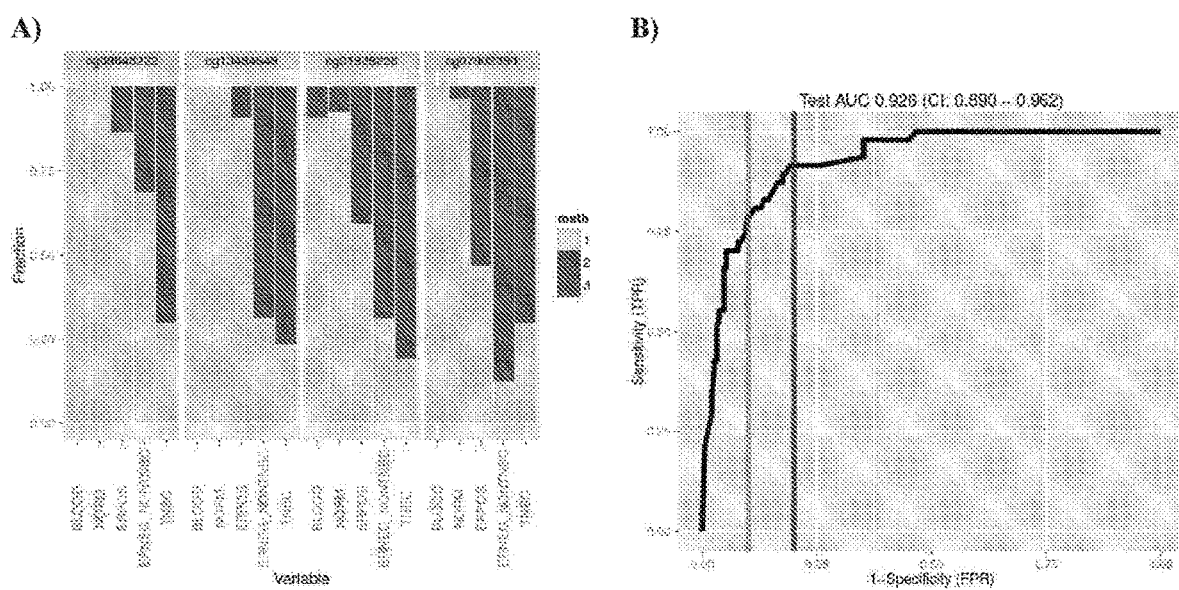
FIG. 97. This figure a) illustrates the distribution of methylation for each of the probes in subset 18 as detailed in Table 13, and b) provides a ROC curve and associated AUC statistics for diagnosing TNBC using probe subset 18.
Figure 98:
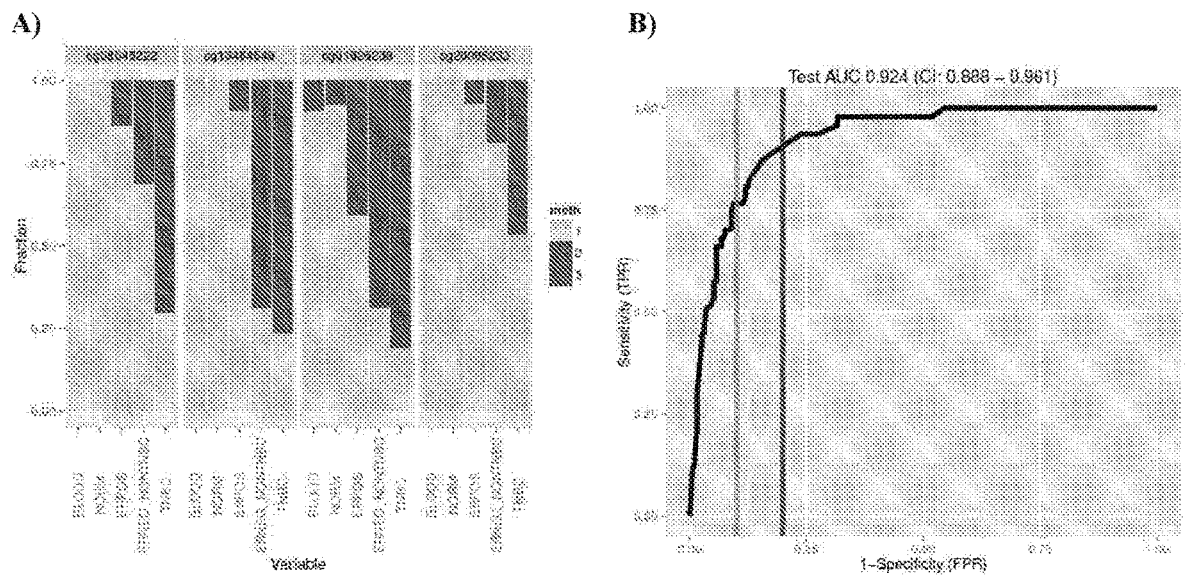
FIG. 98. This figure a) illustrates the distribution of methylation for each of the probes in subset 19 as detailed in Table 13, and b) provides a ROC curve and associated AUC statistics for diagnosing TNBC using probe subset 19.
Figure 99:
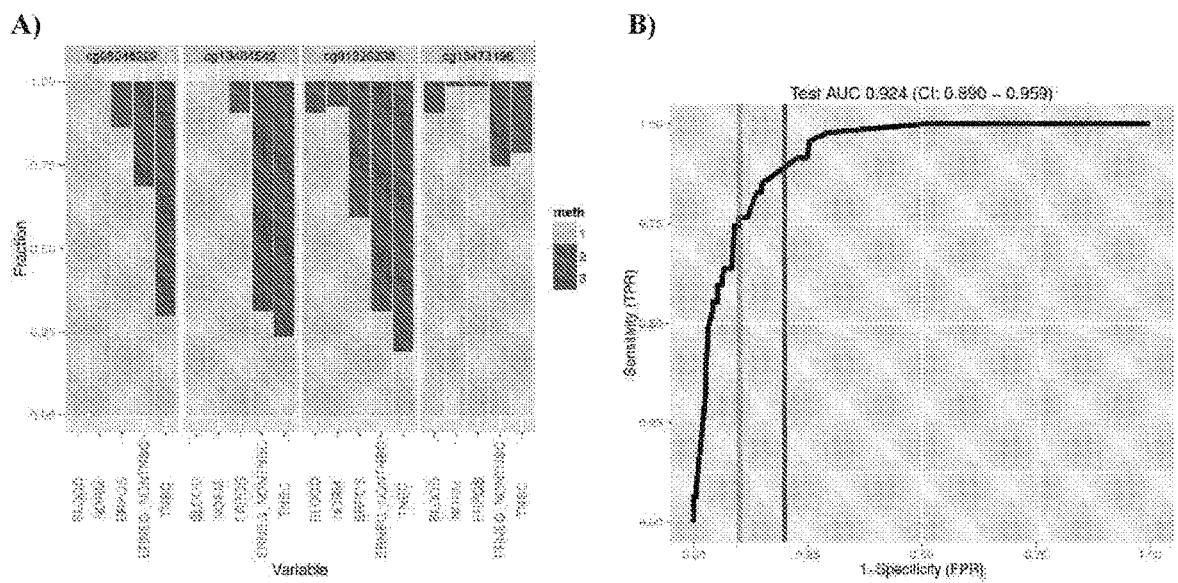
FIG. 99. This figure a) illustrates the distribution of methylation for each of the probes in subset 20 as detailed in Table 13, and b) provides a ROC curve and associated AUC statistics for diagnosing TNBC using probe subset 20.
Figure 100:
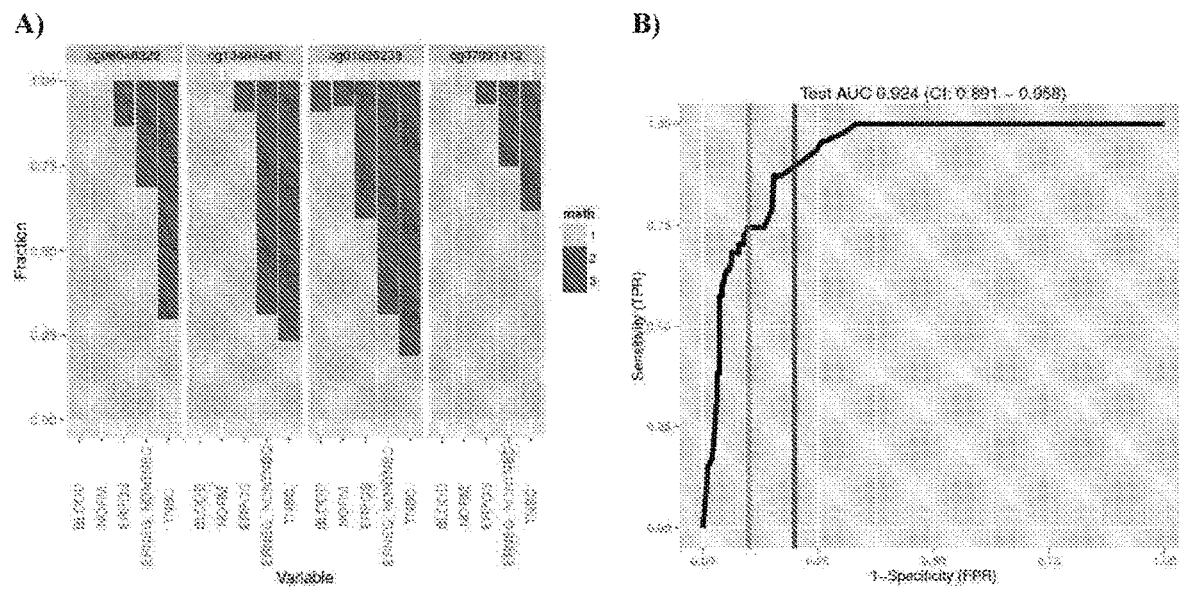
FIG. 100. This figure a) illustrates the distribution of methylation for each of the probes in subset 21 as detailed in Table 13, and b) provides a ROC curve and associated AUC statistics for diagnosing TNBC using probe subset 21.
Figure 101:
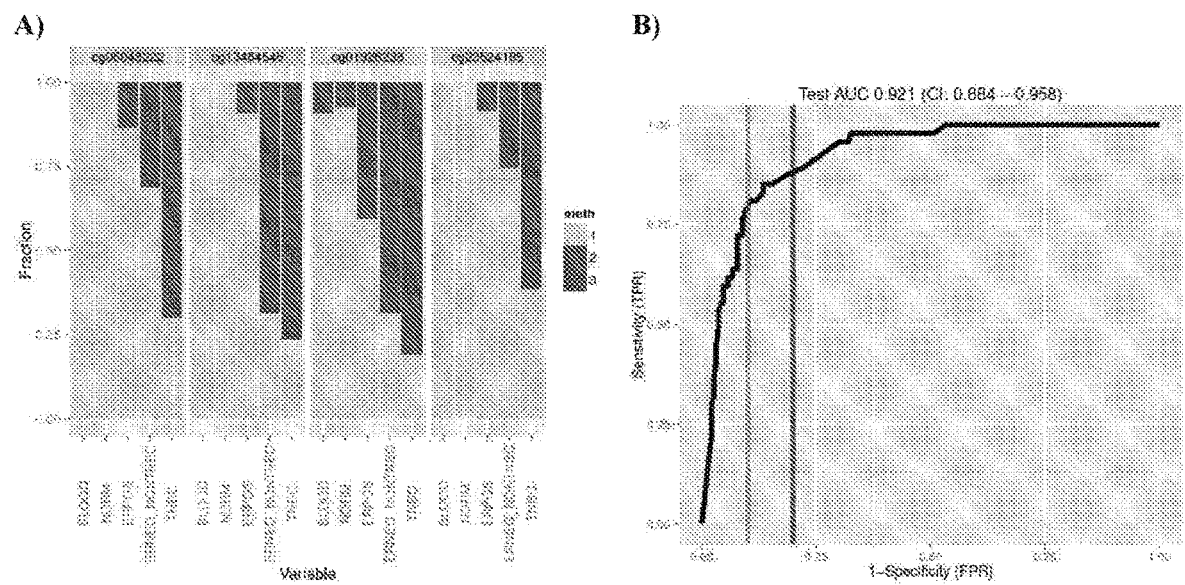
FIG. 101. This figure a) illustrates the distribution of methylation for each of the probes in subset 22 as detailed in Table 13, and b) provides a ROC curve and associated AUC statistics for diagnosing TNBC using probe subset 22.
Figure 102:
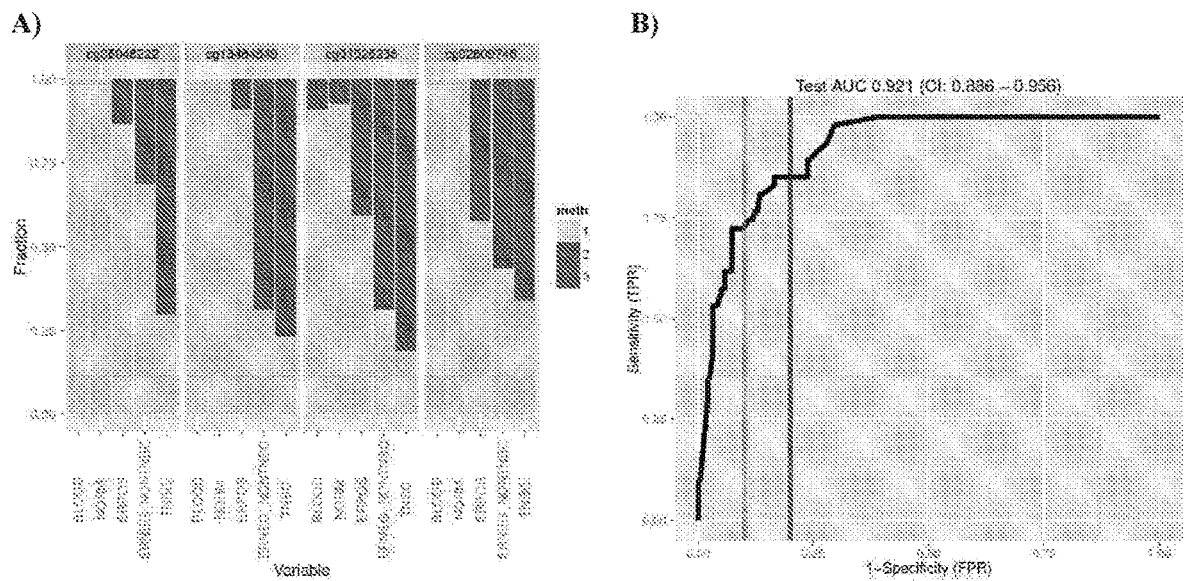
FIG. 102. This figure a) illustrates the distribution of methylation for each of the probes in subset 23 as detailed in Table 13, and b) provides a ROC curve and associated AUC statistics for diagnosing TNBC using probe subset 23.
Figure 103:
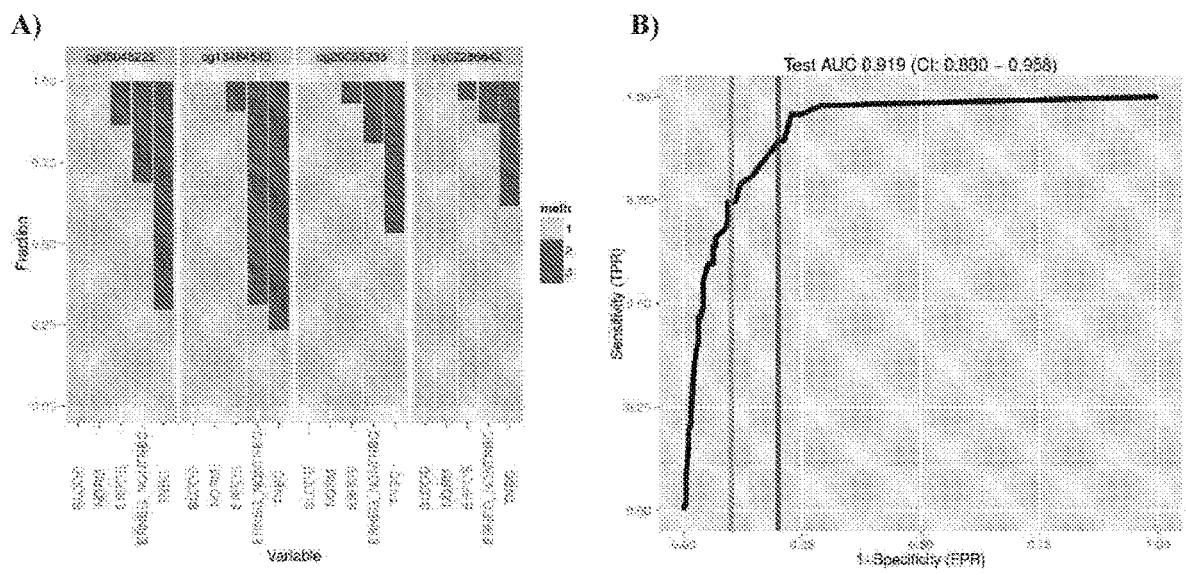
FIG. 103. This figure a) illustrates the distribution of methylation for each of the probes in subset 24 as detailed in Table 13, and b) provides a ROC curve and associated AUC statistics for diagnosing TNBC using probe subset 24.
Figure 104:
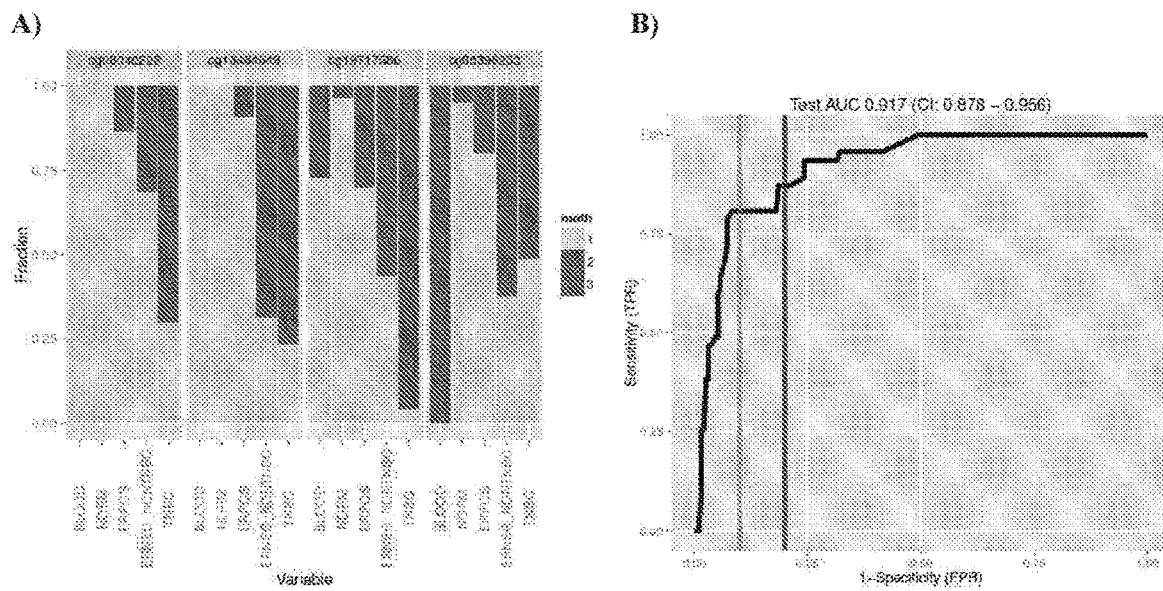
FIG. 104. This figure a) illustrates the distribution of methylation for each of the probes in subset 25 as detailed in Table 13, and b) provides a ROC curve and associated AUC statistics for diagnosing TNBC using probe subset 25.
Figure 105:
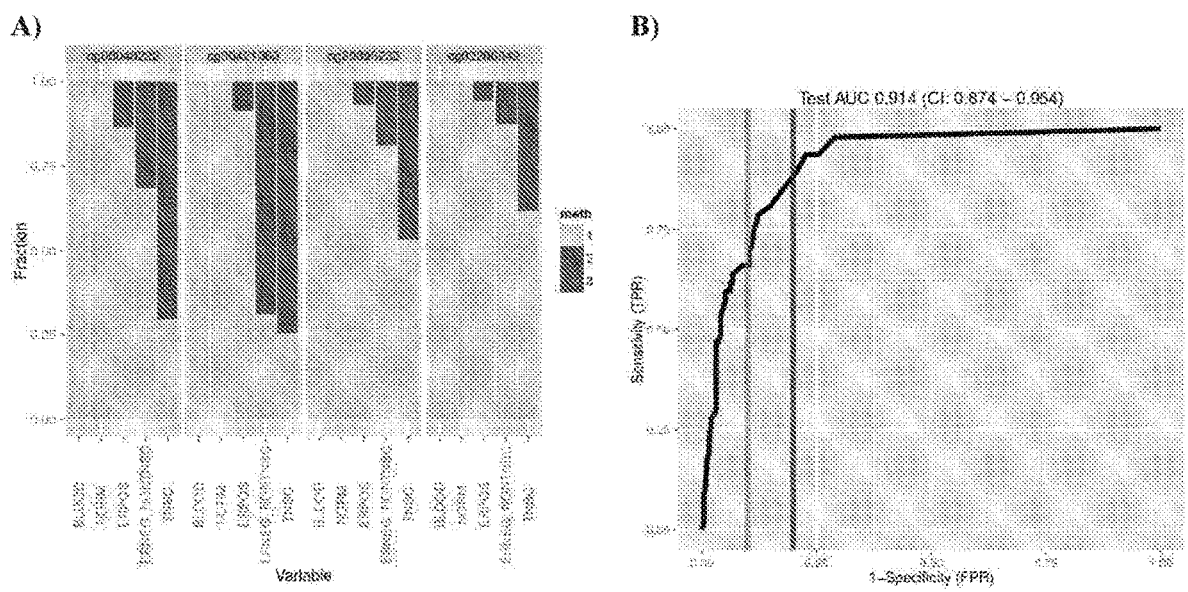
FIG. 105. This figure a) illustrates the distribution of methylation for each of the probes in subset 26 as detailed in Table 13, and b) provides a ROC curve and associated AUC statistics for diagnosing TNBC using probe subset 26.
Figure 106:
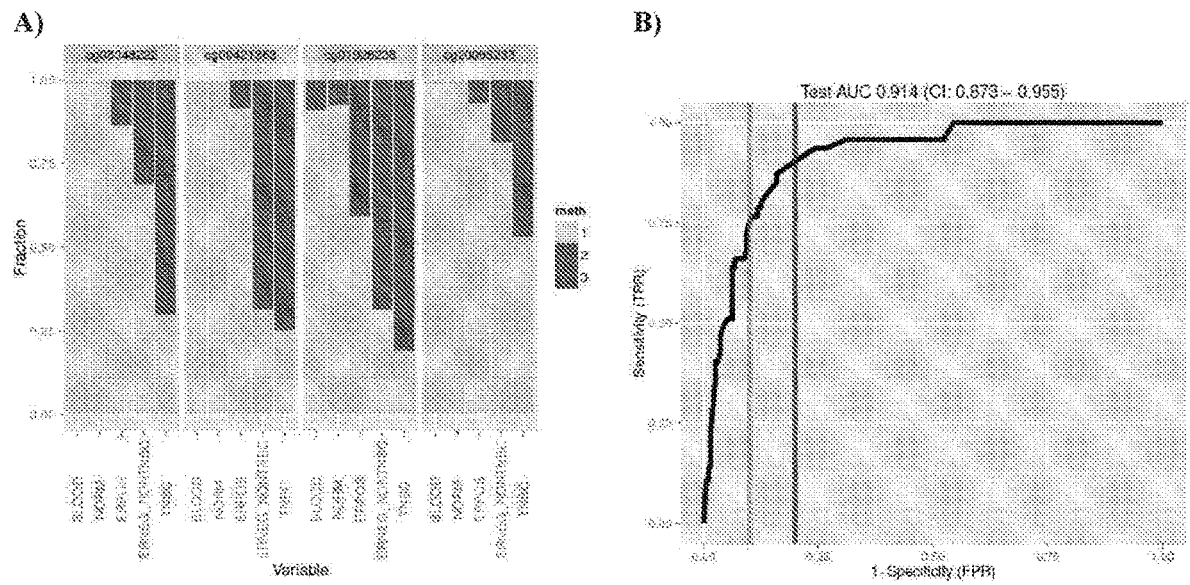
FIG. 106. This figure a) illustrates the distribution of methylation for each of the probes in subset 27 as detailed in Table 13, and b) provides a ROC curve and associated AUC statistics for diagnosing TNBC using probe subset 27.
Figure 107:
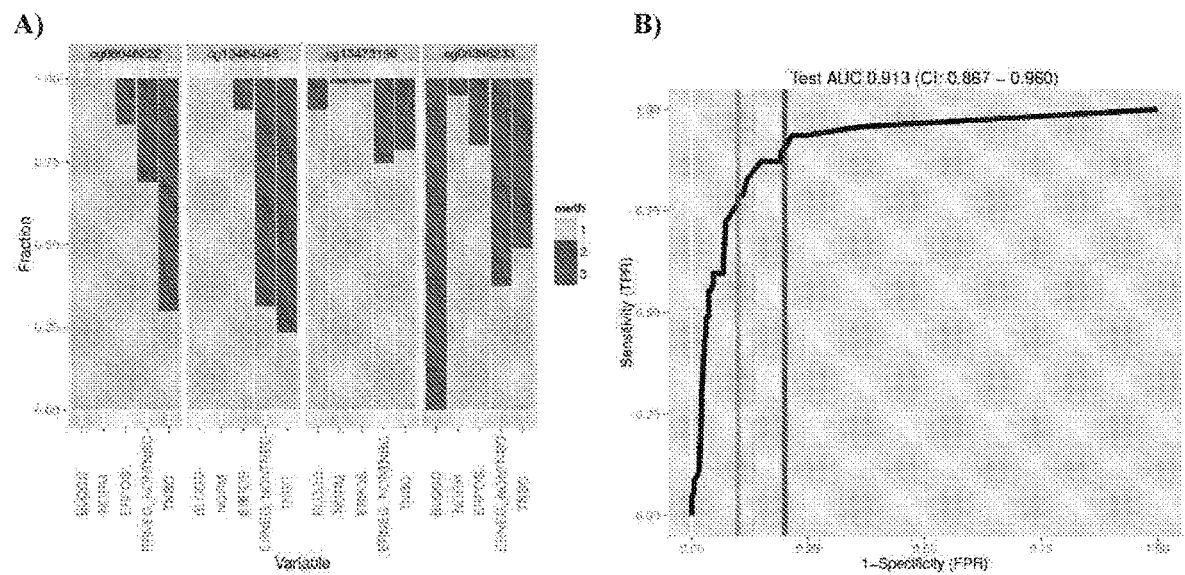
FIG. 107. This figure a) illustrates the distribution of methylation for each of the probes in subset 28 as detailed in Table 13, and b) provides a ROC curve and associated AUC statistics for diagnosing TNBC using probe subset 28.
Figure 108:
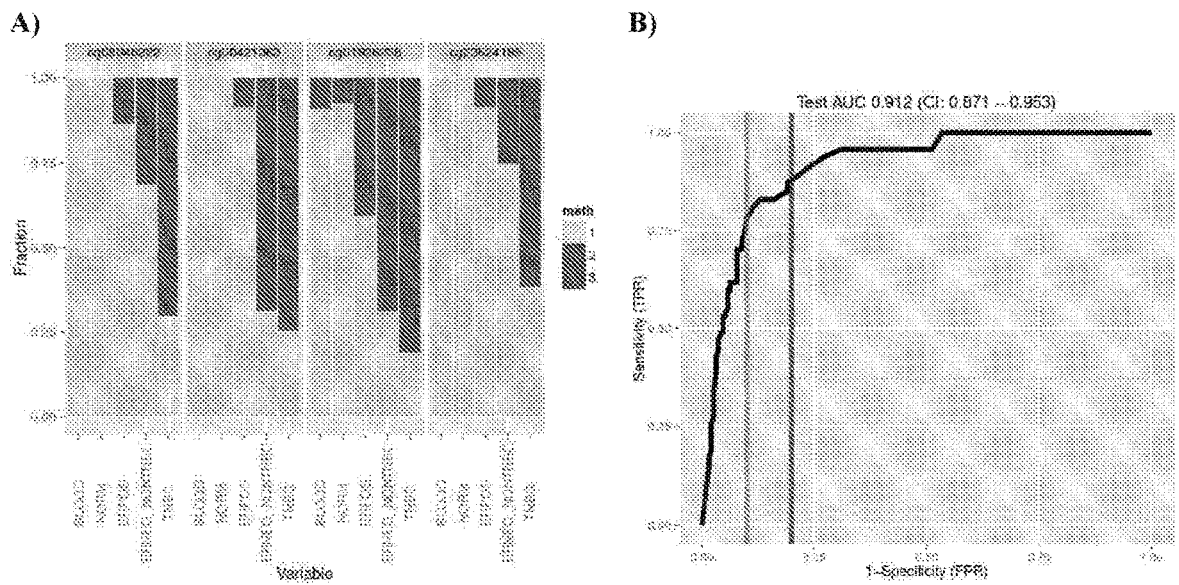
FIG. 108. This figure a) illustrates the distribution of methylation for each of the probes in subset 29 as detailed in Table 13, and b) provides a ROC curve and associated AUC statistics for diagnosing TNBC using probe subset 29.
Figure 109:
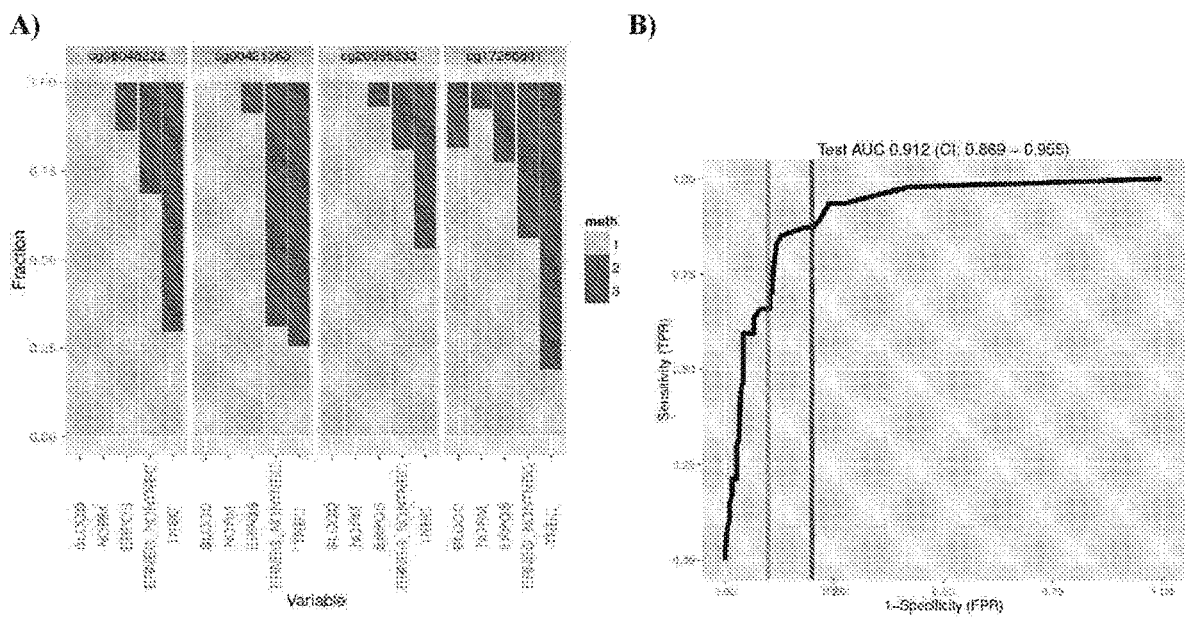
FIG. 109. This figure a) illustrates the distribution of methylation for each of the probes in subset 30 as detailed in Table 13, and b) provides a ROC curve and associated AUC statistics for diagnosing TNBC using probe subset 30.
Figure 110:
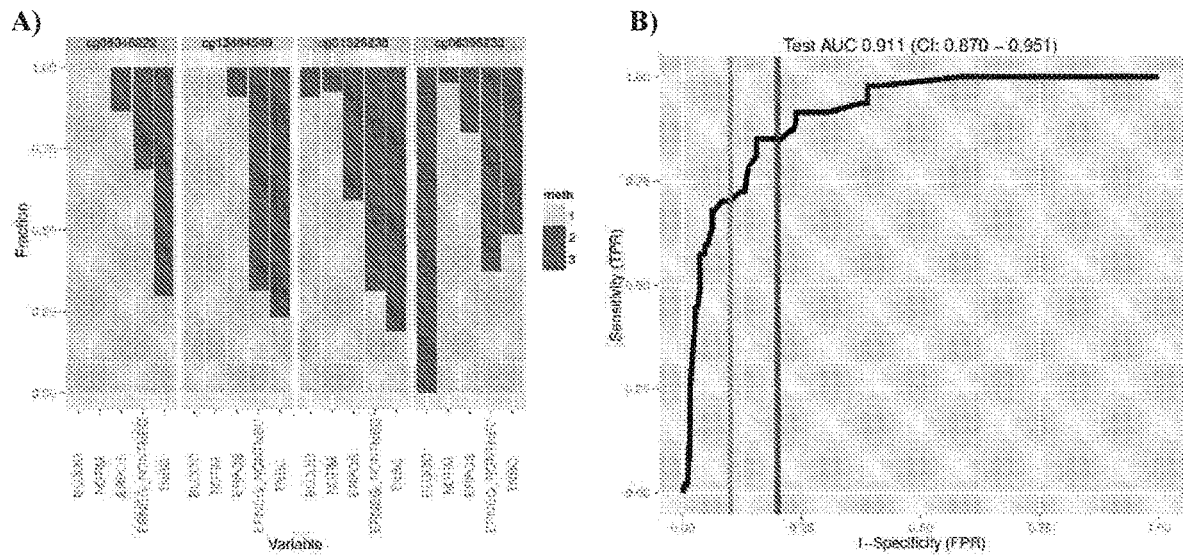
FIG. 110. This figure a) illustrates the distribution of methylation for each of the probes in subset 31 as detailed in Table 13, and b) provides a ROC curve and associated AUC statistics for diagnosing TNBC using probe subset 31.
Figure 111:
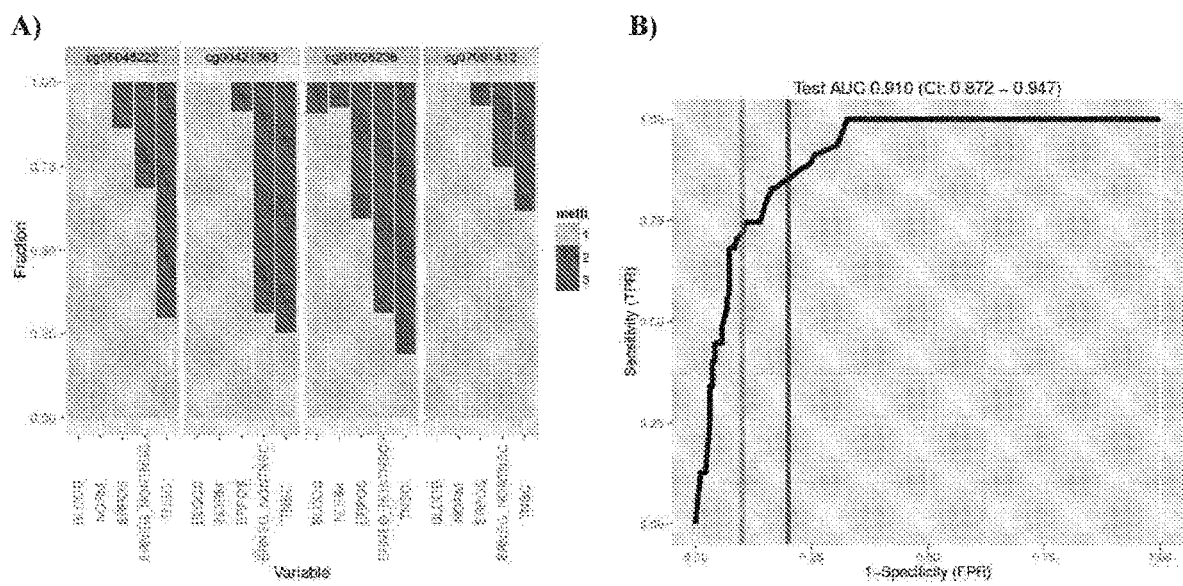
FIG. 111. This figure a) illustrates the distribution of methylation for each of the probes in subset 32 as detailed in Table 13, and b) provides a ROC curve and associated AUC statistics for diagnosing TNBC using probe subset 32.
Figure 112:
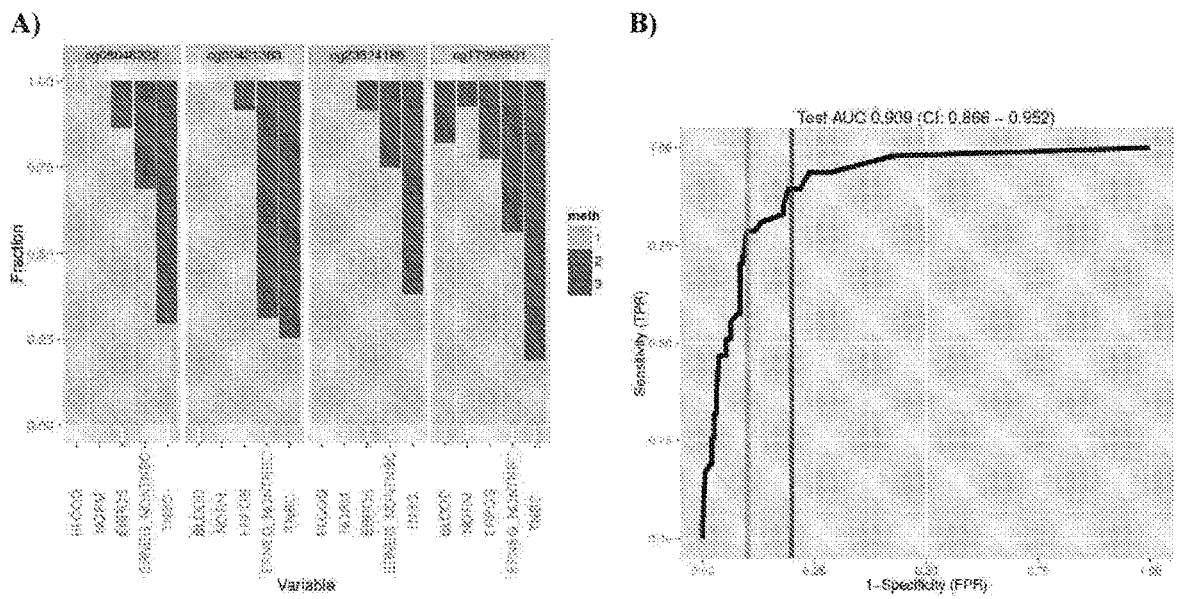
FIG. 112. This figure a) illustrates the distribution of methylation for each of the probes in subset 33 as detailed in Table 13, and b) provides a ROC curve and associated AUC statistics for diagnosing TNBC using probe subset 33.
Figure 113:
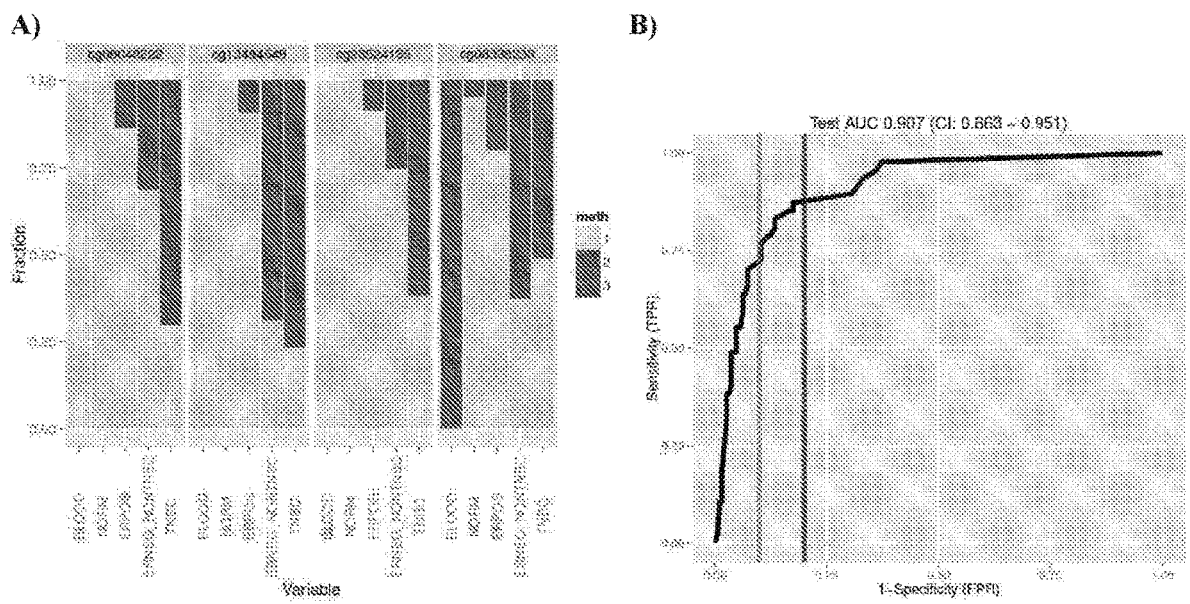
FIG. 113. This figure a) illustrates the distribution of methylation for each of the probes in subset 34 as detailed in Table 13, and b) provides a ROC curve and associated AUC statistics for diagnosing TNBC using probe subset 34.
Figure 114:
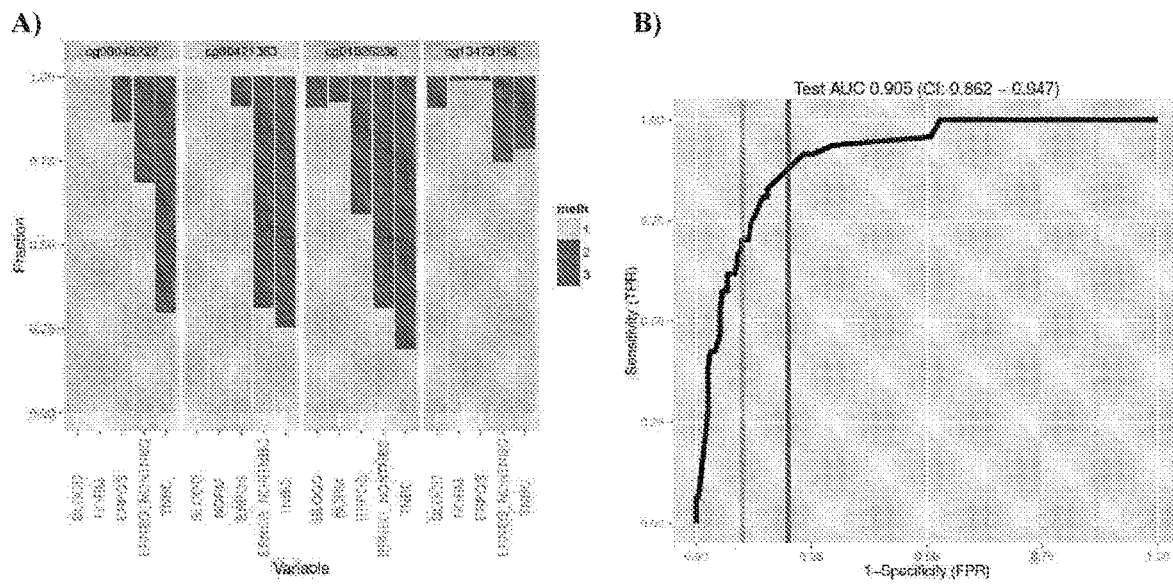
FIG. 114. This figure a) illustrates the distribution of methylation for each of the probes in subset 35 as detailed in Table 13, and b) provides a ROC curve and associated AUC statistics for diagnosing TNBC using probe subset 35.
Figure 115:
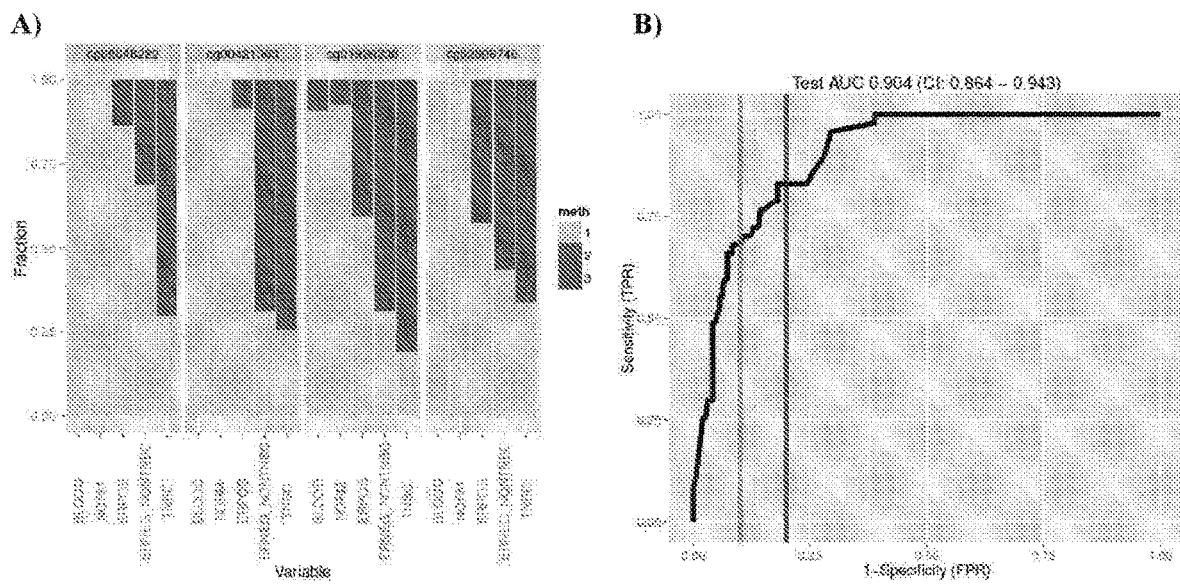
FIG. 115. This figure a) illustrates the distribution of methylation for each of the probes in subset 36 as detailed in Table 13, and b) provides a ROC curve and associated AUC statistics for diagnosing TNBC using probe subset 36.
Figure 116:
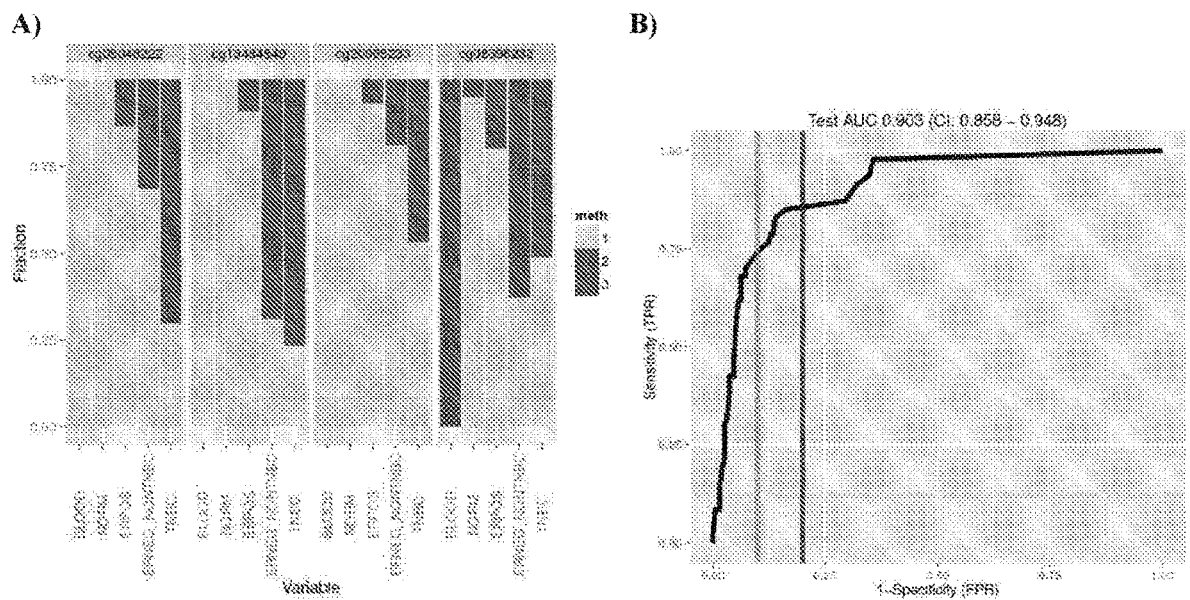
FIG. 116. This figure a) illustrates the distribution of methylation for each of the probes in subset 37 as detailed in Table 13, and b) provides a ROC curve and associated AUC statistics for diagnosing TNBC using probe subset 37.
Figure 117:
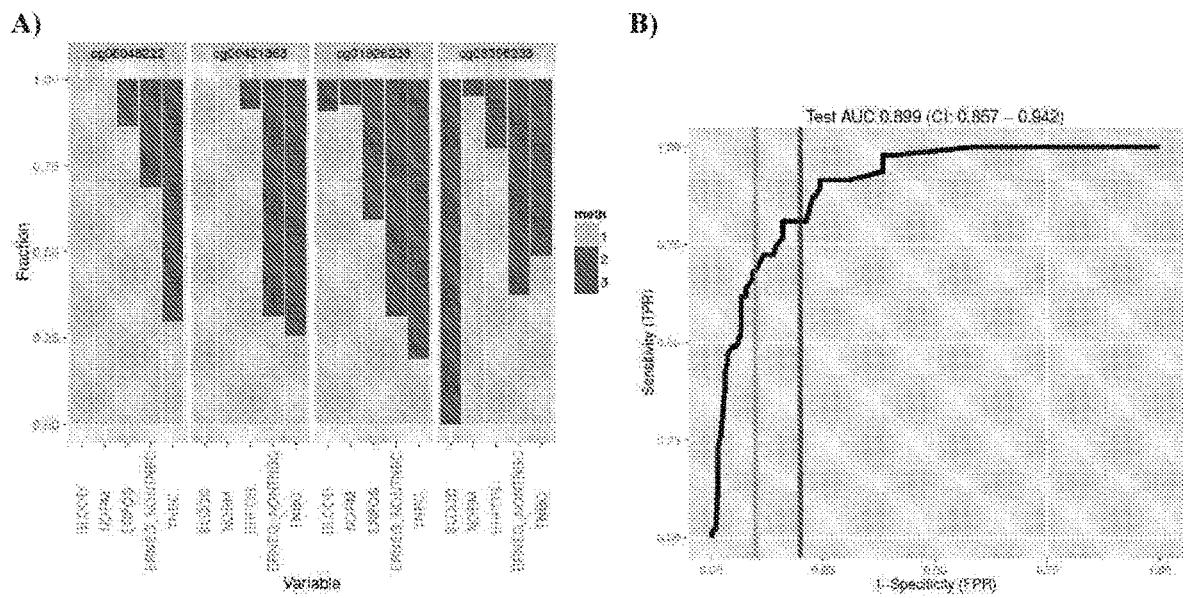
FIG. 117. This figure a) illustrates the distribution of methylation for each of the probes in subset 38 as detailed in Table 13, and b) provides a ROC curve and associated AUC statistics for diagnosing TNBC using probe subset 38.
Figure 118:
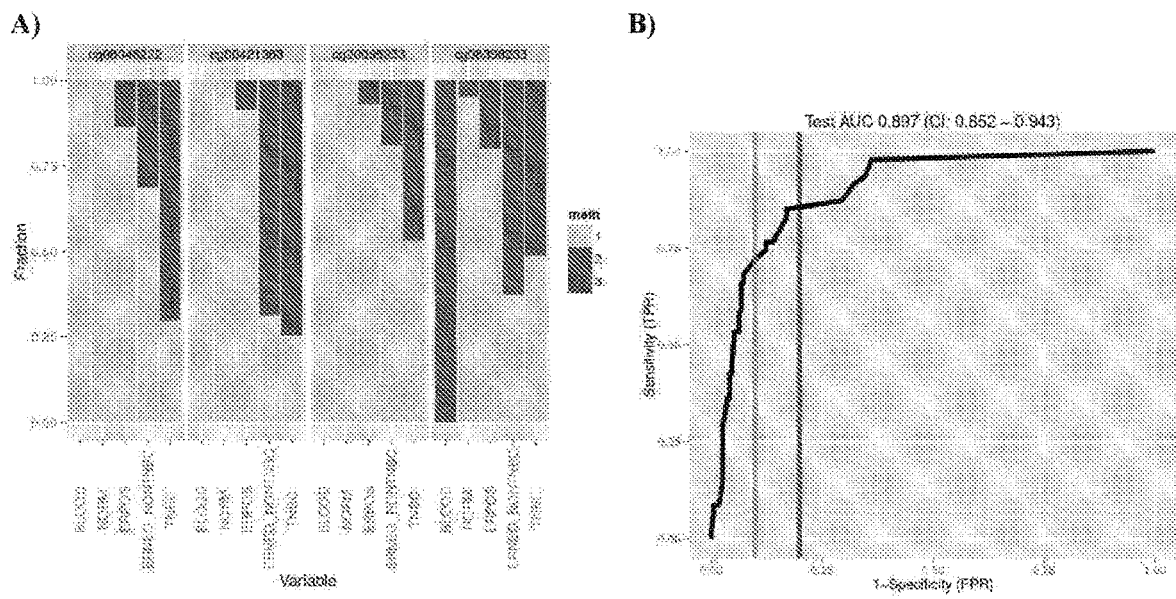
FIG. 118. This figure a) illustrates the distribution of methylation for each of the probes in subset 39 as detailed in Table 13, and b) provides a ROC curve and associated AUC statistics for diagnosing TNBC using probe subset 39.
Figure 119:
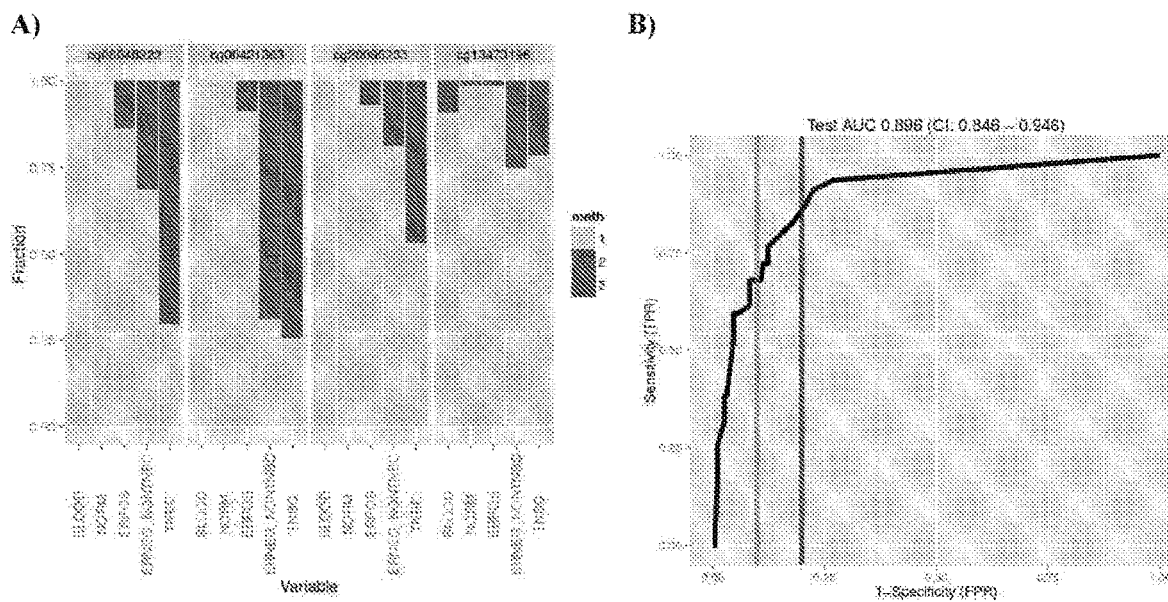
FIG. 119. This figure a) illustrates the distribution of methylation for each of the probes in subset 40 as detailed in Table 13, and b) provides a ROC curve and associated AUC statistics for diagnosing TNBC using probe subset 40.

Detailed performance summaries of the (i) three representative two-probe diagnostic signatures which performed particularly well are provided in FIGS. 80-82, respectively, (ii) three representative three-probe diagnostic signatures which performed particularly well are provided in FIGS. 86-88, respectively, and (iii) three representative four-probe diagnostic signatures which performed particularly well are provided in FIGS. 97-99, respectively. Each of FIGS. 80-82, 86-88 and 97-99 provides the distribution of methylation values across probes in the respective model, as well as ROC curves and associated AUC statistics for diagnosing TNBC using the respective probe subset. Similar performance summaries for the remaining unique diagnostic signatures described in Table 13 are provided in FIGS. 83-85, 89-96 and 100-118.

Models which performed particularly well comprised the following HM450K probes:
cg11977686—promoter of ZNF671
cg13484549—promoter of PPFIA3
cg08048222—promoter of ZNF671
cg00421363—promoter of PPFIA3
cg01926238—distant promoter of VGLL2
cg08398233—intronic region of CAMK2N1
cg07802350—distant promoter of HOXD13
cg20095233—distant promoter of GFRA1
cg13473196—intronic region of CKAP5

Example 7: Validation of the TNBC Prognostic Methylation Signature on an Independent Cohort of Clinical Samples 7.1 Method
7.1.1 Methylation Signature for NBCF Cohort
Methylation signatures were determined for the NBCF cohort using HM450K arrays and methodologies described in Example 1. The NBCF cohort used to validate TNBC prognostic methylation signatures comprised a total of 62 patients which passed HM450 array QC and had a complete set of clinical data. Events had a median time to death of 28.5 months (range 7-82 months) and non-events had a median follow up time of 61.5 months (range 7-194 months) (FIG. 125).

7.1.2 Survival Analysis
Survival analysis was performed in accordance with methods described previously at Example section 2.1.2 for all MBDCap regions that contained at least one HM450 probe that was prognostically significant in the discovery cohort.

7.1.3 Validation and Filtering of Survival Regions in the NBCF Cohort
From the discovery cohort, there were 190 significant probes that mapped to 118 MBDCap regions. In the NBCF Cohort, 60 HM450 probes from 34 of the 118 regions were statistically significantly associated with survival (cox proportional hazards model univariate p value<0.05). To ensure that these 60 probes exhibited biologically relevant levels of differential methylation between survival groups, a subset of the NBCF cohort that exhibited good prognosis (non-event with >5 years follow up, n=18) was identified and a group with poor prognosis (event with <2.5 years survival, n=15) was identified, and the methylation levels across all regions were compared in these two populations. Probes showing <10% difference in median methylation between the good and poor prognosis groups were removed. The validation and filtering process is represented in FIG. 126.

7.2 Results
Following validation and filtering of survival regions, the prognostic regions were limited to a set of 20 loci (Table 14). This final set of prognostic regions contained 39 probes that were statistically significant in the discovery cohort and 35 probes significant in the NBCF cohort. FIGS. 127-146 show methylation levels in the good and poor prognosis groups for each of the probes in the prognostic regions identified in Table 14. FIGS. 147-166 provide Kaplan Meier plots for each of the probes in the prognostic regions based on methylation between survival groups in the NBCF cohort. Detailed performance summaries are provided in Table 15 for the 35 probes showing significant differential methylation between survival groups in the NBCF cohort. The Figures providing Kaplan Meier plots for those 35 probes are also identified in Table 15. All significant probes in the NBCF cohort exhibited an association between increased methylation and poorer prognosis.

TABLE 14

Validated Survival regions

| Chromosome | Start (hg18) | End (hg18) | Region name | FIG. |
|---|---|---|---|---|
| 3 | 131718242 | 131718973 | chr3-1415 | 128 |
| 7 | 100732591 | 100733729 | chr7-12819 | 129 |
| 11 | 125278717 | 125279989 | chr11-24690 | 130 |
| 2 | 182253383 | 182254903 | chr2-13825 | 131 |
| 7 | 24290275 | 24291795 | chr7-28113 | 132 |
| 15 | 50873927 | 50875994 | chr15-2568 | 133 |
| 20 | 36786620 | 36791737 | chr20-11674 | 134 |
| 11 | 32404535 | 32407465 | chr11-11623 | 135 |
| 2 | 104846206 | 104847327 | chr2-26887 | 136 |
| 13 | 27398788 | 27401867 | chr13-5199 | 137 |
| 13 | 52321726 | 52322229 | chr13-5196 | 138 |
| 8 | 23618273 | 23621219 | chr8-13399 | 139 |
| 11 | 31802820 | 31804364 | chr11-18108 | 140 |
| 11 | 32410931 | 32413157 | chr11-24196 | 141 |
| 13 | 27263290 | 27268058 | chr13-13783 | 142 |
| 18 | 53170434 | 53170733 | chr18-11487 | 143 |
| 2 | 124498663 | 124500373 | chr2-4092 | 144 |
| 6 | 27755606 | 27757375 | chr6-25261 | 145 |
| 11 | 32413697 | 32415714 | chr11-4047 | 146 |
| 2 | 176653510 | 176657430 | chr2-9331 | 147 |

TABLE 15

Summary Statistics of NBCF Cohort Survival Associated Probes

| Chromosome | start (hg18) | end (hg18) | Illumina Probe ID | hazard Ratio (uni-variate) | z score (uni-variate) | p value (uni-variate) | hazard (multi-variate) | z score (multi-variate) | p value (multi-variate) |
|---|---|---|---|---|---|---|---|---|---|
| 2 | 176654145 | 176654146 | cg01658421 | 2.272 | 2.128 | 0.033 | 1.977 | 1.722 | 0.085 |
| 2 | 176656939 | 176656940 | cg01749491 | 2.162 | 2.011 | 0.044 | 2.209 | 2.008 | 0.045 |
| 2 | 104847180 | 104847181 | cg07112473 | 2.499 | 2.390 | 0.017 | 2.191 | 1.938 | 0.053 |
| 2 | 176657005 | 176657006 | cg07411620 | 2.301 | 2.163 | 0.031 | 2.201 | 2.019 | 0.043 |
| 2 | 176656945 | 176656946 | cg11359133 | 2.576 | 2.406 | 0.016 | 2.241 | 1.990 | 0.047 |
| 2 | 176656842 | 176656843 | cg12074182 | 2.618 | 2.438 | 0.015 | 2.410 | 2.173 | 0.030 |
| 2 | 176656974 | 176656975 | cg14118515 | 2.730 | 2.511 | 0.012 | 2.777 | 2.497 | 0.013 |
| 2 | 124499724 | 124499725 | cg16198087 | 2.338 | 2.202 | 0.028 | 2.355 | 2.186 | 0.029 |
| 2 | 182253807 | 182253808 | cg19711579 | 2.286 | 2.122 | 0.034 | 1.955 | 1.615 | 0.106 |
| 2 | 176656032 | 176656033 | cg23242052 | 2.372 | 2.215 | 0.027 | 2.289 | 2.100 | 0.036 |
| 2 | 176656186 | 176656187 | cg27116912 | 2.845 | 2.603 | 0.009 | 2.469 | 2.178 | 0.029 |
| 3 | 131718727 | 131718728 | cg09685182 | 2.200 | 2.024 | 0.043 | 1.851 | 1.544 | 0.123 |
| 6 | 27757099 | 27757100 | cg03161803 | 2.567 | 2.461 | 0.014 | 2.202 | 1.975 | 0.048 |
| 7 | 24291604 | 24291605 | cg04697148 | 2.513 | 2.422 | 0.015 | 2.263 | 2.067 | 0.039 |
| 7 | 100732831 | 100732832 | cg20713092 | 2.670 | 2.556 | 0.011 | 2.112 | 1.691 | 0.091 |
| 8 | 23619127 | 23619128 | cg01336781 | 2.345 | 2.262 | 0.024 | 2.171 | 2.031 | 0.042 |
| 8 | 23619517 | 23619518 | cg03330710 | 2.724 | 2.549 | 0.011 | 2.584 | 2.427 | 0.015 |
| 8 | 23618863 | 23618864 | cg14451926 | 2.454 | 2.355 | 0.019 | 2.356 | 2.206 | 0.027 |
| 8 | 23619915 | 23619916 | cg15854847 | 2.474 | 2.356 | 0.018 | 2.529 | 2.318 | 0.020 |
| 11 | 32406214 | 32406215 | cg12006284 | 2.281 | 2.155 | 0.031 | 1.883 | 1.579 | 0.114 |
| 11 | 32415633 | 32415634 | cg16325378 | 2.190 | 2.048 | 0.041 | 1.690 | 1.250 | 0.211 |
| 11 | 32411294 | 32411295 | cg16463460 | 2.267 | 2.169 | 0.030 | 1.817 | 1.471 | 0.141 |
| 11 | 31803749 | 31803750 | cg17310258 | 2.403 | 2.170 | 0.030 | 2.326 | 2.079 | 0.038 |
| 11 | 125279521 | 125279522 | cg22097425 | 2.145 | 1.991 | 0.047 | 1.881 | 1.587 | 0.113 |
| 11 | 32415542 | 32415543 | cg24286165 | 2.483 | 2.307 | 0.021 | 2.033 | 1.720 | 0.085 |
| 11 | 32407268 | 32407269 | cg25782229 | 2.349 | 2.230 | 0.026 | 1.888 | 1.521 | 0.128 |
| 13 | 27401235 | 27401236 | cg06883496 | 2.341 | 2.246 | 0.025 | 2.004 | 1.770 | 0.077 |
| 13 | 52322033 | 52322034 | cg10323552 | 2.351 | 2.236 | 0.025 | 1.990 | 1.725 | 0.085 |
| 13 | 52322128 | 52322129 | cg10484958 | 2.092 | 1.970 | 0.049 | 1.792 | 1.510 | 0.131 |
| 13 | 27263587 | 27263588 | cg11444278 | 2.508 | 2.347 | 0.019 | 2.181 | 1.954 | 0.051 |
| 13 | 27267080 | 27267081 | cg20562678 | 2.160 | 2.022 | 0.043 | 1.699 | 1.292 | 0.196 |
| 15 | 50874608 | 50874609 | cg09481404 | 2.330 | 2.222 | 0.026 | 1.923 | 1.620 | 0.105 |
| 15 | 50874360 | 50874361 | cg21038785 | 2.187 | 2.074 | 0.038 | 1.819 | 1.522 | 0.128 |
| 18 | 53170709 | 53170710 | cg24811864 | 2.632 | 2.458 | 0.014 | 2.190 | 1.916 | 0.055 |
| 20 | 36790258 | 36790259 | cg05936441 | 2.150 | 2.004 | 0.045 | 1.798 | 1.425 | 0.154 |

The invention claimed is:

1. A method for indicating to a user whether or not a subject has triple negative breast cancer (TNBC), the method comprising:
  (a) producing sample methylation data by determining a level of methylation at one or more CpG dinucleotides within one or more genomic regions set forth in Table 1 for a test sample from the subject using one or more techniques selected from the group consisting of nucleic acid amplification, polymerase chain reaction (PCR), methylation specific PCR, bisulfate pyrosequencing, single-strand conformation polymorphism (SSCP) analysis, restriction analysis, microarray technology, next generation methylation sequencing and proteomics;
  (b) a processor receiving the sample methylation data which is indicative of the level of methylation at one or more CpG dinucleotides within one or more genomic regions set forth in Table 1 for the test sample from the subject;
  (c) the processor receiving reference level methylation data for the one or more CpG dinucleotides within the one or more genomic regions set forth in Table 1;
  (d) the processor generating differential methylation data for the one or more CpG dinucleotides within the one or more genomic regions set forth in Table 1 for the test sample from the subject by comparing the sample methylation data to the reference level methylation data;
  (e) the processor processing the differential methylation data using a univariate and/or multivariate analysis to provide a disease index value;
  (f) determining by the processor a disease status of the subject based on the disease index value, the disease status being an indication of whether or not the subject has TNBC; and
  (g) transferring an indication of the disease status of the subject to the user via a communications network.

2. The method of claim 1, further comprising:
  (a) determining the methylation data using a remote end station; and
  (b) transferring the methylation data from the end station to the base station via the communications network.

3. The method of claim 2, wherein the base station comprises first and second processing systems, and wherein the method comprises:
  (a) transferring the methylation data to the first processing system;
  (b) transferring the methylation data to the second processing system; and
  (c) causing the first processing system to perform the univariate or multivariate analysis function to generate the disease index value based on the differential methylation data.

4. The method of claim 3, comprising:
  (a) transferring the results of the univariate or multivariate analysis function to the first processing system; and
  (b) causing the first processing system to determine the disease status of the subject.

5. The method of claim 4, wherein the second processing system is coupled to a database adapted to store predetermined reference level methylation data and/or the univariate or multivariate analysis function, and the method comprises:
  (a) querying the database to obtain at least selected predetermined reference level methylation data or access to the multivariate analysis function from the database; and
  (b) comparing the selected predetermined reference level methylation data to the sample methylation data for the subject or generating a predicted probability index.

6. The method of claim 5, wherein the second processing system is coupled to a database, and the method comprises storing the data in the database.

7. The method of claim 1, comprising:
  (a) the processor processing the differential methylation data using a univariate and/or multivariate analysis to provide a disease index value, wherein said processing comprises determining that the level of methylation at one or more CpG dinucleotides within one or more genomic regions set forth in Table 1 for the test sample from the subject is decreased relative to the reference level of methylation for the one or more CpG dinucleotides;
  (b) in response to the processor determining that the level of methylation at one or more CpG dinucleotides within one or more genomic regions set forth in Table 1 for the test sample from the subject is decreased relative to the reference level of methylation for the one or more CpG dinucleotides, the processor making a determination that the subject has TNBC as the disease status; and
  (c) transferring an indication of the status of the subject to the user via the communications network.

8. The method of claim 1, comprising:
(a) the processor processing the differential methylation data using a univariate and/or multivariate analysis to provide a disease index value, wherein said processing comprises determining that the level of methylation at one or more CpG dinucleotides within one or more genomic regions set forth in Table 1 for the test sample from the subject is increased relative to the reference level of methylation for the one or more CpG dinucleotides;
(b) in response to the processor determining that the level of methylation at one or more CpG dinucleotides within one or more genomic regions set forth in Table 1 for the test sample from the subject is increased relative to the reference level of methylation for the one or more CpG dinucleotides, the processor making a determination that the subject has TNBC as the disease status; and
(c) transferring an indication of the status of the subject to the user via the communications network.

9. The method of claim 1, comprising:
(a) the processor processing the differential methylation data using a univariate and/or multivariate analysis to provide a disease index value, wherein said processing comprises determining that the level of methylation at one or more CpG dinucleotides within one or more genomic regions set forth in Table 1 for the test sample from the subject is not significantly different to the reference level of methylation for the one or more CpG dinucleotides;
(b) in response to the processor determining that the level of methylation at one or more CpG dinucleotides within one or more genomic regions set forth in Table 1 for the test sample from the subject is not significantly different to the reference level of methylation for the one or more CpG dinucleotides, the processor making a determination that the subject does not have TNBC as the disease status; and
(c) transferring an indication of the status of the subject to the user via the communications network.

10. The method of claim 1, comprising:
(a) the processor receiving sample methylation data which is indicative of a level of methylation at one or more CpG dinucleotides within one or more genomic regions set forth in Table 2 for the test sample from the subject;
(b) the processor receiving reference level methylation data for the one or more CpG dinucleotides within the one or more genomic regions set forth in Table 2;
(c) the processor generating differential methylation data for the one or more CpG dinucleotides within the one or more genomic regions set forth in Table 2 for the test sample from the subject by comparing the sample methylation data to the reference level methylation data;
(d) the processor processing the differential methylation data using a univariate and/or multivariate analysis to provide a disease index value;
(e) determining by the processor a disease status of the subject based on the disease index value, the disease status being an indication of whether or not the subject has TNBC; and
(f) transferring an indication of the disease status of the subject to the user via a communications network.

11. The method of claim 1, wherein the test sample from the subject comprises tissue and/or a body fluid comprising, or suspected of comprising, a breast cancer cell or components of a breast cancer cell.

12. The method of claim 11, wherein the test sample comprises tissue, a cell and/or an extract thereof taken from a breast or lymph node.

13. The method of claim 11, wherein the body fluid is selected from the group consisting of whole blood, a fraction of blood such as blood serum or plasma, urine, saliva, breast milk, pleural fluid, sweat, tears and mixtures thereof.

14. The method of claim 1, wherein the reference level methylation data comprises a level of methylation determined for the one or more CpG dinucleotide sequences within a corresponding genomic region of a sample selected from the group consisting of:
(i) a sample from a normal or healthy tissue;
(ii) a sample comprising a non-cancerous cell;
(iii) a sample comprising a cancerous cell other than a TNBC cell;
(iv) an extract of any one of (i) to (iii);
(v) a data set comprising levels of methylation for the one or more CpG dinucleotide sequences within the corresponding genomic region in a normal or healthy individual or a population of normal or healthy individuals;
(vi) a data set comprising levels of methylation for the one or more CpG dinucleotide sequences within the corresponding genomic region in an individual or a population of individuals having cancer of a non-TNBC subtype; and
(vii) a data set comprising levels of methylation for the one or more CpG dinucleotide sequences within the corresponding genomic region in the subject being tested wherein the levels of methylation are determined for a matched sample having normal cells.

15. The method of claim 14, wherein the likelihood of survival of the subject is a likelihood that the subject will survive at least 3 years after being diagnosed with TNBC.

16. The method of claim 14, wherein the likelihood of survival of the subject is a likelihood that the subject will survive at least 5 years after being diagnosed with TNBC.

17. The method of claim 14, wherein the test sample from the subject comprises tissue and/or a body fluid comprising, or suspected of comprising, a breast cancer cell or components of a breast cancer cell.

18. The method of claim 17, wherein the test sample comprises tissue, a cell and/or an extract thereof taken from a breast or lymph node.

19. The method of claim 17, wherein the body fluid is selected from the group consisting of whole blood, a fraction of blood such as blood serum or plasma, urine, saliva, breast milk, pleural fluid, sweat, tears and mixtures thereof.

20. The method of claim 1, wherein the level of methylation at one or more CpG dinucleotides within one or more genomic regions set forth in Table 1 for the test sample from the subject is determined using one or more methods selected from the group consisting of:
(i) performing methylation-sensitive endonuclease digestion of DNA from the subject;
(ii) treating a nucleic acid from the subject with an amount of a compound that selectively mutates non-methylated cytosine residues in the nucleic acid under conditions sufficient to induce mutagenesis thereof and produce a mutant nucleic acid and amplifying the mutant nucleic acid using at least one primer that selectively hybridizes to the mutant nucleic acid;
(iii) treating a nucleic acid from the subject with an amount of a compound that selectively mutates non-methylated cytosine residues in the nucleic acid under conditions sufficient to induce mutagenesis thereof and produce a mutant nucleic acid, hybridizing a nucleic acid probe or primer capable of specifically hybridizing to the mutant nucleic acid and detecting the hybridized probe or primer;
(iv) treating a nucleic acid from the subject with an amount of a compound that selectively mutates non-methylated cytosine residues in the nucleic acid under conditions sufficient to induce mutagenesis thereof and produce a mutant nucleic acid, amplifying the mutant nucleic acid with promoter-tagged primers, transcribing the mutant nucleic acid in vitro to produce a transcript, subjecting the transcript to an enzymatic base-specific cleavage, and determining differences in mass and/or size of any cleaved fragments resulting from mutated cysteine residues; and
(v) treating a nucleic acid from the subject with an amount of a compound that selectively mutates non-methylated cytosine residues in the nucleic acid under conditions sufficient to induce mutagenesis thereof, thereby producing a mutant nucleic acid, and determining the nucleotide sequence of the mutant nucleic acid.

21. The method of claim 1, further comprising treating the subject with a chemotherapy drug, or a combination of chemotherapy drugs, effective for treating TNBC if the subject is determined as having TNBC.

22. A method for indicating to a user whether or not a subject has triple negative breast cancer (TNBC) and treating the subject if they have TNBC, the method comprising:
(a) a processor receiving sample methylation data which is indicative of a level of methylation at one or more CpG dinucleotides within one or more genomic regions set forth in Table 1 for a test sample from the subject;
(b) the processor receiving reference level methylation data for the one or more CpG dinucleotides within the one or more genomic regions set forth in Table 1;
(c) the processor generating differential methylation data for the one or more CpG dinucleotides within the one or more genomic regions set forth in Table 1 for the test sample from the subject by comparing the sample methylation data to the reference level methylation data;
(d) the processor processing the differential methylation data using a univariate and/or multivariate analysis to provide a disease index value;
(e) determining by the processor a disease status of the subject based on the disease index value, the disease status being an indication of whether or not the subject has TNBC;
(f) transferring an indication of the disease status of the subject to the user via a communications network; and
(g) treating the subject with a chemotherapy drug, or a combination of chemotherapy drugs, effective for treating TNBC if the subject is determined as having TNBC.

23. The method of claim 22, wherein the reference level methylation data comprises a level of methylation determined for the one or more CpG dinucleotide sequences within a corresponding genomic region of a sample selected from the group consisting of:
(i) a sample from a normal or healthy tissue;
(ii) a sample comprising a non-cancerous cell;
(iii) a sample comprising a cancerous cell other than a TNBC cell;
(iv) an extract of any one of (i) to (iii);
(v) a data set comprising levels of methylation for the one or more CpG dinucleotide sequences within the corresponding genomic region in a normal or healthy individual or a population of normal or healthy individuals;
(vi) a data set comprising levels of methylation for the one or more CpG dinucleotide sequences within the corresponding genomic region in an individual or a population of individuals having cancer of a non-TNBC subtype; and
(vii) a data set comprising levels of methylation for the one or more CpG dinucleotide sequences within the corresponding genomic region in the subject being tested wherein the levels of methylation are determined for a matched sample having normal cells.

\* \* \* \* \*